US008288425B2

(12) United States Patent
Edwards et al.

(10) Patent No.: US 8,288,425 B2
(45) Date of Patent: Oct. 16, 2012

(54) BENZIMIDAZOLES

(75) Inventors: Michael L. Edwards, Morristown, NJ (US); Paul J. Cox, Millington, NJ (US); Shelley Amendola, Bedminster, NJ (US); Stephanie D. Deprets, Paris (FR); Timothy A. Gillespy, Hillsboro, NJ (US); Christopher D. Edlin, Newark (GB); Andrew D. Morley, Macclesfield (GB); Charles J. Gardner, Royersford, NJ (US); Brian Pedgrift, Flemington, NJ (US); Herve Bouchard, Thiais (FR); Didier Babin, Montigny (FR); Laurence Gauzy, Paris (FR); Alain Le-Brun, Vigneux (FR); Tahir N. Majid, Hoboken, NJ (US); John C. Reader, Cambridge (GB); Lloyd J. Payne, Cambridgeshire (GB); Nawaz M. Khan, Cambridge (GB); Michael Cherry, Stuffolk (GB)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 569 days.

(21) Appl. No.: 11/029,064

(22) Filed: Jan. 4, 2005

(65) Prior Publication Data

US 2006/0014756 A1      Jan. 19, 2006

Related U.S. Application Data

(63) Continuation of application No. 10/279,834, filed on Oct. 24, 2002, now Pat. No. 6,897,208.

(60) Provisional application No. 60/395,060, filed on Jul. 11, 2002, provisional application No. 60/395,151, filed on Jul. 11, 2002.

(30) Foreign Application Priority Data

Oct. 26, 2001  (FR) .................................... 01 13868
Mar. 22, 2002  (GB) .................................... 0206893.0
Mar. 22, 2002  (GB) .................................... 0206895.5

(51) Int. Cl.
    *A61K 31/4184*    (2006.01)
    *C07D 235/18*    (2006.01)
(52) U.S. Cl. ................... 514/397; 548/304.7; 548/305.1
(58) Field of Classification Search ............... 548/304.7, 548/305.1
    See application file for complete search history.

(56) References Cited

U.S. PATENT DOCUMENTS 3,549,754 A *  12/1970  Egerton et al. ............. 514/224.8
3,711,608 A *   1/1973  Campbell ..................... 514/361
3,839,575 A *  10/1974  Gauss et al. .................. 514/395
4,027,032 A *   5/1977  Frohberger et al. ......... 514/395
5,958,950 A     9/1999  Padia et al.
6,136,831 A *  10/2000  Aotsuka et al. ............... 514/367
6,358,978 B1    3/2002  Ritzeler
6,555,539 B2 *  4/2003  Reich et al. .............. 514/252.02
2005/0009894 A1  1/2005  Babin et al.

FOREIGN PATENT DOCUMENTS

DE  2130029       12/1972
DE  2263878        7/1979
EP  1006114        6/2000
EP  1020447        7/2000
WO  WO01/02389     1/2001
WO  WO01/53268     7/2001
WO  WO03/004488    1/2003

OTHER PUBLICATIONS

Rangarajan, et al. Bioorganic &Medicinal Chemistry (2000), 8, pp. 1371-1382.*
Prodrug [online]; [retrieved on Mar. 26, 2007]. Retrieved from the Internet, URL; http://en.wikipedia.org/wiki/Prodrug>.*
Vippagunta, et al. Advanced Drug Delivery Reviews. 48 (2001) 3-26.*
RN 221276-12-6, retrieved from CAPLUS; retrieved on Feb. 28, 2009.*
RN 58113-10-3, retrieved from CAPLUS; retrieved on Feb. 28, 2009.*
RN 214854-79-2, retrieved from CAPLUS; retrieved on Feb. 28, 2009.*
RN 40341-04-6,retrieved from CAPLUS; retrieved on Feb. 28, 2009.*
Andreichikov, Yu. S. et al., Dihydro-1,2-diazaphenazines, Khim. Geterotsild. Soedin., No. 12, 1974, pp. 1690-1694, Abstract only— XP-002204303.
Essassi, E.M. el al., Syntheee at HererocyclIsatIon des (Pyrazolyl-3(5))-2 Benzimidazoles en Catalyse par Transfert de Phase, Bulletin des Societes Chimiques Beiges. vol. 98, No. 1, 1987, pp. 65-67, XP-008005414.

(Continued)

*Primary Examiner* — Shawquia Young
(74) *Attorney, Agent, or Firm* — Brian R. Morrill

(57) ABSTRACT

The invention is directed to physiologically active compounds of the general formula (Ix)

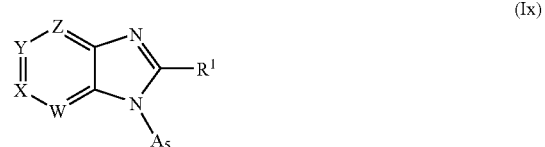

and compositions containing such compounds, and their prodrugs, and pharmaceutically acceptable salts and solvates of such compounds and their prodrugs, as well as to novel compounds within the scope of formula (Ix), and to processes for their preparation. Such compounds and compositions have valuable pharmaceutical properties, in particular the ability to inhibit kinases.

18 Claims, No Drawings

OTHER PUBLICATIONS

Farag, Ahmad M. et al., Regioselective Synthesis of Novel 1-Methyl-2-(4-aryl-5-eyano-1,3-diphenyl-4,5-dihydropyrazol-6-yl)benzimidazoles and 2-(4-aryl-5-oyano-1,3-diphenyl-4,5-dihydropyrazol-5-yl)benzothiazoles via benzonitrilium N-phenylimide, J. Chem. Res., Synop., No. 7, 1994, pp. 286-287, Abstract only—XP-002204304.

Finar, I. L et al., The Preparation and Some Reactions of 4-Formyl-1-phenyl-pyrazoles, Journal of the Chemical Society, 1981, pp. 2733-2738, XP-002204301.

Gopal et al., Topoisomerase II poisoning by Indazole and Imidazole Complexes of Ruthenium, PubMed Abstract 1142608.also cited as Journal Biosci.; Jun;26(2); 2001; pp. 271-278.

Hubert, Andre J. et al., Thermolyee von v-Triazolyl-Derivaten, Chemische Berichte. vol. 103, No. 12, 1970, pp. 3911-3816, XP-002204297.

Joshi, Krishna C. et al., Investigation of the Reactions of 2-Hydrazino-Banzimidazoles with B-diketones: Synthesis of 2-(3,5-Disubstituted-1 H-pyraxole-1-yl)benzimidazoles, Journal of Heterocyclic Chemistry, vol. 25, No. 6, 1988, pp. 1641-1643, XP-002204298.

Saha, Nityananda et al., Synthesis, Characterization and Coordinating Properties of a New Benzimidazolylpyrazole: cobalt (II), nickel (II) and copper (II) complexes of 5-methyl-3-(2'-benzimidazotyl) pyrazole, J. Indian Chem. Soc., vol. 70, No. 11-12, 1993, pp. 1035-1042, Abstract only—XP-002204302.

Senga, Keitaro et al., Synthesis of Pyrazolo(1',5':1,2)-1,3,5-triazno[5,6,-a]benzimidazoles, Journal of Heterocyclic Chemistry, vol. 12, No. 5, 1975, pp. 899-901, XP-002204300.

Singh, Shiv P. et al., Formation and Dehydration of a Series of 5-hydroxy-5-trifluoromentyl-4,5-dihydropyrazoles, Journal of Fluorine Chemistry, vol. 94, No. 2, 1999, pp. 199-203, XP-004163162.

Soos, T. et al., Novel Thermal Rearrangement of Fused Diaryi-v-Triazolium Salts to Neutral Indazole Derivatives. Fused Azolium Salts. 10, Journal of Organic Chemistry, vol. 62, No. 4, 1997, pp. 1136-1138, XP-002204298.

Takagi, Kaname et al., Synthesis of Pyrimidino[4,5-b][1,5]benzodiazepin-2-ones and Pyrimidino[1,6-a]benzimidezol-1-ones from 4-Ethoxycarbonylamino-1H-1,5-benzodiazpine-S-carbonitrite via 4-(2-Aminoanillno)pytlmidln-2(1H)-one-5-carbonitrilee, Journal of Heterocyclic Chemistry, vol. 23, No. 5, 1986, pp. 1443-1449, XP-002204299.

Vereshchagina et al., Chemical Name: 2-(5-methyl-1H[1,2,4]triazol-3-yl)-1H-benzoimidazole, Khim. Farm, Zh., vol. 7, No. 6, 1973, p. 18, Abstract only—XP-002204305.

Berger, G.A., Antitumor Activity of Some Ruthenium Derivatives in Human Colon Cancer Cell Lines in Vitro, PubMed Abstract 1418038, also cited as Arzneimitleforschung; Jun. ;42(6), 1992; pp. 821-824.

Damasio, A.R., Alzheimer's Disease and Related Dementias, Cecil Textbook of Medicine, 20th Edition; vol. 2; 1996; pp. 1992-1996.

Fossa, et al., Toward the Identification of the Cardiac cGMP Inhibited-phosphodiesterase Catalytic Site, J. of Computer-Aided Molecular Design; 1998; 12(4): pp. 361-372.

Simone, J., Oncology, Cecil Textbook of Medicine, 20th Edition; vol. 1, 1996: pp. 1004-1010.

Uckun, et al., Structure-Based Design of Novel Anticancer Agents, Current Cancer Drug Targets; vol. 1; 2001 pp. 59-71.

Wong, et al., Combined Therapy of Local and Metastatic 4T1 Breats Tumor in Mice Using SU6658, an Inhibitor of Angiogenic Receptor Tyrosine Kinases, and the Immunostimulator B7, 2-IgG Fusion Protein, PubMed Abstract 12384531, also cited as Cancer Research: Oct. 15;62(20); 2002: pp. 5727-5735.

* cited by examiner

BENZIMIDAZOLES

This application is entitled to the benefit of earlier filed French Application No. 0113868 filed Oct. 26, 2001, British Application No. 0206893.0 filed Mar. 22, 2002, British Application No. 0206895.5 filed Mar. 22, 2002, U.S. Provisional Application No. 60/395,060 filed Jul. 11, 2002, and U.S. Provisional Application No. 60/395,151 filed Jul. 11, 2002.

This invention is directed to benzimidazoles of formula (Ix), their preparation, pharmaceutical compositions containing these compounds, and their pharmaceutical use in the treatment of disease states capable of being modulated by the inhibition of the protein kinases. Such protein kinases belong especially to the following group: EGFR, Fak, FLK-1, FGFR1, FGFR2, FGFR3, FGFR4, FGFR5, flt-1, IGF-1R, KDR, PDGFR, tie2, VEGFR, ITK and SYK.

Protein kinases are a family of enzymes that participate in the signalling events which control the activation, growth and differentiation of cells in response to extracellular mediators and to changes in the environment. In general, these kinases fall into several groups; those which preferentially catalyse the phosphorylation of hydroxy groups of serine and/or threonine residues and those which preferentially catalyse the phosphorylation of hydroxy groups of tyrosine residues [S. K. Hanks and T. Hunter, FASEB. J., 1995, 9, pages 576-596]. Such phosphorylations may greatly modify the function of the proteins; thus, protein kinases play an important role in regulating a wide variety of cell processes including, especially, metabolism, cell proliferation, cell differentiation or cell survival. Among the various cellular functions in which the activity of a kinase protein is involved, certain processes represent attractive targets for treating certain diseases. As an example, mention may be made especially of angiogenesis and the control of the cell cycle, in which kinase proteins can play an essential role. These processes are essential for the growth of solid tumours and also for other diseases.

Angiogenesis or the formation of new blood vessels by sprouting from the preexisting vasculature is of central importance for embryonic development and organogenesis. Should the need arise, the vascular system has the potential to generate a network of new vessels so as to maintain the correct functioning of the tissues and organs. Angiogenesis is a complex multistage process which includes activation, migration, proliferation and survival of endothelial cells. In adults, angiogenesis is fairly limited, appearing mainly only in the processes of repair after an injury or of vascularization of the endometrium. (Merenmies et al., Cell Growth & Differentiation, 8, 3-10, 1997). However, uncontrolled angiogenesis is found in certain pathologies such as retinopathy, psoriasis, rheumatoid arthritis, diabetes, muscle degeneration or cancer (solid tumours) (Folkman, Nature Med., 1, 27-31, 1995). The kinase proteins whose involvement it has been possible to demonstrate in the angiogenesis process include three members of the family of growth factor receptor tyrosine kinases: VEGF-R2 (vascular endothelial growth factor receptor 2, also known as KDR, kinase insert domain receptor, or FLK-1), FGF-R (fibroblast growth factor receptor) and TEK (also known as Tie-2).

In conjunction with other systems, the Vascular Endothelial Growth Factor receptors (VEGFRs) transmit signals involved in the migration, proliferation and survival of endothelial cells. The family VEGFR includes VEGFR-1 (Flt-1), VEGFR-2 (KDR) and VEGFR3 (Flt4). The receptor VEGF-R2, which is expressed only in the endothelial cells, binds to the angiogenic growth factor VEGF, and thus serves as a transduction signal mediator via the activation of its intracellular kinase domain. Thus, the direct inhibition of the kinase activity of VEGF-R2 makes it possible to reduce the phenomenon of angiogenesis in the presence of exogenous VEGF (Strawn et al., Cancer Research, 56, 3540-3545, 1996), this process being demonstrated especially with the aid of VEGF-R2 mutants (Millauer et al., Cancer Research, 56, 1615-1620, 1996). The VEGF-R2 receptor appears to have no other function in adults than that associated with the angiogenic activity of VEGF. Thus, a selective inhibitor of the kinase activity of VEGF-R2 should show only little toxicity.

In addition to this central role in the dynamic angiogenic process, recent results suggest that the expression of VEGF contributes towards the survival of tumoral cells after chemotherapy and radiotherapy, underlining the potential synergism of KDR inhibitors with other agents (Lee C. G., Heijn M. et al., (2000), Cancer Research, 60 (19), 5565-70). The KDR inhibitors thus especially constitute anti-angiogenic agents and such agents might be used as a first line treatment against the emergence or regrowth of malignant tumours. The inhibition or regulation of VEGFR-2 (KDR) thus provides a powerful new mechanism of action for the treatment of a large number of solid tumours.

Extensive studies in the field of tumor angiogenesis in the past two decades have identified a number of therapeutic targets including kinases, proteases and integrins resulting in the discovery of many new anti-angiogenic agents, including KDR inhibitors some of which are currently under clinical evaluation (Jekunen, et al Cancer Treatment Rev. 1997, 23, pages 263-286.).

The present patent application thus relates particularly to novel inhibitors of the VEGFR-2 (KDR) receptor that may be used especially for anti-angiogenic treatment in oncology.

The protein kinases which preferentially catalyse the phosphorylation of hydroxy groups of serine and/or threonine residues include for example, protein kinase C isoforms [A. C. Newton, J. Biol. Chem., 1995, 270, pages 28495-28498] and a group of cyclin-dependent kinases such as cdk2 [J. Pines, Trends in Biochemical Sciences, 1995, 18, pages 195-197]. The protein kinases which preferentially catalyse the phosphorylation of hydroxy groups of serine and/or threonine residues include membrane-spanning growth factor receptors such as the epidermal growth factor receptor [S. Iwashita and M. Kobayashi, Cellular Signalling, 1992, 4, pages 123-132], and cytosolic non-receptor kinases such as p56lck, p59fYn, ZAP-70 and csk kinases [C. Chan et. al., Ann. Rev. Immunol., 1994, 12, pages 555-592].

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream of the kinase. In all of these instances, selective inhibition of the action of the kinase might be expected to have a beneficial effect.

SYK (Spleen Tyrosine Kinase) is a 72-kDa cytoplasmic protein tyrosine kinase that is expressed in a variety of hematopoietic cells and is an essential element in several cascades that couple antigen receptors to cellular responses. Thus, SYK plays a pivotal role in signalling of the high affinity IgE receptor, FcεR1, in mast cells and in receptor antigen signalling in T and B lymphocytes. The signal transduction pathways present in mast, T and B cells have common features. The ligand binding domain of the receptor lacks intrinsic tyrosine kinase activity. However, they interact with transducing subunits that contain immunoreceptor tyrosine based activation motifs (ITAMs) [M. Reth, Nature, 1989, 338, pages 383-384]. These motifs are present in both the β and γ subunits of the FcεR1, in the ξ-subunit of the T cell receptor (TCR) and in the IgGα and IgG β subunits of the B cell receptor (BCR). [N. S. van Oers and A. Weiss, Seminars in Immunology, 1995, 7, pages 227-236] Upon binding of antigen and multimerization, the ITAM residues are phosphorylated by protein tyrosine kinases of the Src family. SYK belongs to a unique class of tyrosine kinases that have two tandem Src homology 2 (SH2) domains and a C terminal catalytic domain. These SH2 domains bind with high affinity to ITAMs and this SH2-mediated association of SYK with an activated receptor stimulates SYK kinase activity and localises SYK to the plasma membrane.

In SYK deficient mice, mast cell degranulation is inhibited, suggesting that this is an important target for the development of mast cell stabilising agents [P. S. Costello, Oncogene, 1996, 13, pages 2595-2605]. Similar studies have demonstrated a critical role for SYK in BCR and TCR signalling [A. M. Cheng, Nature, 1995, 378, pages 303-306, (1995) and D. H. Chu et al., Immunological Reviews, 1998, 165, pages 167-180]. SYK also appears to be involved in eosinophil survival in response to IL-5 and GM-CSF [S. Yousefi et al., J. Exp. Med., 1996, 183, pages 1407-1414]. Despite the key role of SYK in mast cell, BCR and T cell signalling, little is known about the mechanism by which SYK transmits downstream effectors. Two adaptor proteins, BLNK (B cell Linker protein, SLP-65) and SLP-76 have been shown to be substrates of SYK in B cells and mast cells respectively and have been postulated to interface SYK with downstream effectors [M. Ishiai et al., Immunity, 1999, 10, pages 117-125 and L. R. Hendricks-Taylor et al., J. Biol. Chem, 1997, 272, pages 1363-1367]. In addition SYK appears to play an important role in the CD40 signalling pathway, which plays an important role in B cell proliferation [M. Faris et al., J. Exp. Med., 1994, 179, pages 1923-1931].

SYK is further involved in the activation of platelets stimulated via the low-affinity IgG receptor (Fc gamma-RIIA) or stimulated by collagen [F. Yanaga et al., Biochem. J., 1995, 311, (Pt. 2) pages 471-478].

ITK, is a T cell specific tyrosine kinase of the Tec family that is required for normal Th2 function. Asthma is a disease characterised by increased Th2 cytokine production including IL-4. An inhibitor of ITK should therefore have an impact on disease progression in asthma through inhibition of Th2 cytokine production.

We have now found a novel group of benzimidazoles, which have valuable pharmaceutical properties, in particular, the ability to inhibit protein kinases, more particularly, the ability to inhibit the protein kinase SYK, the protein kinase KDR, the protein kinase tie2 or the protein kinase ITK.

Thus, in one aspect, the present invention is directed to pharmaceutical compositions comprising compounds of general formula (Ix):—

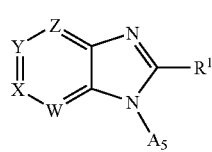

wherein, for the purposes of (Ix):—
X represents C—$R^2$ and W, Y and Z, which may be identical or different, represent CH or $CR^3$; or
W represents CH, X represents N, Y represents CH or $CR^3$, and Z represents CH or $CR^3$; or
W represents N, X represents CH or $CR^2$, Y represents CH and $CR^3$, and Z represents CH or $CR^3$; or
W represents N, X represents CH or $CR^2$, Y represents N, and Z is CH or $CR^3$; or
W represents N, X represents CH or $CR^2$, Y represents CH or $CR^3$, and Z represents N; or
W represents N, X represents N, Y represents CH or $CR^3$, and Z represents CH or $CR^3$;
$A_5$ represents H or alkyl;
$R^1$ represents aryl or heteroaryl, each optionally substituted by one or more groups selected from carboxy, cyano, halo, haloalkyl, hydroxy, nitro, $R^4$, —C(=O)$R^4$, —C(=O)N$Y^1Y^2$, —C(=O)O$R^4$, —N($R^6$)C(=O)$R^4$, —N($R^6$)C(=O)N$Y^1Y^2$, —N($R^6$)C(=O)O$R^4$, —N($R^6$)$SO_2R^4$, —N($R^6$)$SO_2$N$Y^1Y^2$, —N$Y^1Y^2$, —O$R^4$, —OC$F_2$H, —OC$F_3$, —OC(=O)$R^4$, —OC(=O)N$Y^1Y^2$, —OS(O)$_n$$R^4$, —S(O)$_n$$R^4$, —S(O)$_n$N$Y^1Y^2$ and —S(O)$_n$O$R^4$;
$R^2$ and $R^3$ are such that:
$R^2$ and $R^3$, which may be identical or different, represent H, carboxy, cyano, halo, haloalkyl, hydroxy, nitro, $R^4$, —C(=O)$R^4$, —C(=O)N$Y^1Y^2$, —C(=O)O$R^4$, —N$Y^1Y^2$, —N($R^6$)C(=O)$R^4$, —N($R^6$)C(=O)N$Y^1Y^2$, —N($R^6$)C(=O)O$R^4$, —N($R^6$)$SO_2R^4$, —N($R^6$)$SO_2$N$Y^1Y^2$, —O$R^4$, —OC$F_2$H, —OC$F_3$, —OC(=O)$R^4$, —OC(=O)N$Y^1Y^2$, —S(O)$_n$$R^4$, —S(O)$_n$N$Y^1Y^2$ or —S(O)$_n$O$R^4$; or
$R^2$ represents H, carboxy, cyano, halo, haloalkyl, hydroxy, nitro, $R^4$, —C(=O)$R^4$, —C(=O)N$Y^1Y^2$, —C(=O)O$R^4$, —N$Y^1Y^2$, —N($R^6$)C(=O)$R^4$, —N($R^6$)C(=O)N$Y^1Y^2$, —N($R^6$)C(=O)O$R^4$, —N($R^6$)$SO_2R^4$, —N($R^6$)$SO_2$N$Y^1Y^2$, —O$R^4$, —OC$F_2$H, —OC$F_3$, —OC(=O)$R^4$, —OC(=O)N$Y^1Y^2$, —S(O)$_n$$R^4$, —S(O)$_n$N$Y^1Y^2$ or —S(O)$_n$O$R^4$ and $R^3$ represents alkyl, haloalkyl, halogen and O$R^6$; or
$R^2$ and $R^3$ groups on adjacent carbon atoms may form a 5- to 6-membered carbon-based ring containing one or more heteroatoms, which may be identical or different, chosen from O, N and S, and which may be optionally substituted by alkyl [examples include those where $R^2$ and $R^3$ form a group selected from —O—$CH_2$—O—, —O—$CH_2$—$CH_2$—O—; —$CH_2$—O—$CH_2$—, —$CH_2$—N($R^{14}$)—$CH_2$—, —$CH_2$—$CH_2$—$CH_2$—, —$CH_2$—C($CH_3$)$_2$—$CH_2$—, —$CH_2$—O—$CH_2$—$CH_2$—, —$CH_2$—N($R^{14}$)—$CH_2$—$CH_2$—, —$CH_2$—$CH_2$—$CH_2$—$CH_2$—, —$CH_2$—C($CH_3$)$_2$—$CH_2$—$CH_2$—, —CH=CH—CH=CH—, —N=CH—CH=CH—, —CH=N—CH=CH—, —CH=CH—N=CH— or —CH=CH—CH=N, in which $R^{14}$ is H or alkyl)];
$R^4$ is alkyl, alkenyl, alkynyl, cycloalkyl, heterocycloalkyl, aryl or heteroaryl, each optionally substituted with one or more substituents selected from alkyl, aryl, cycloalkyl, heteroaryl, heterocycloalkyl, halo, hydroxy, hydroxyalkyl, —C(=O)N$Y^3Y^4$, —C(=O)O$R^6$, —N($R^6$)C(=O)N$Y^1Y^2$, —N$Y^1Y^2$, —O$R^5$ or alkyl substituted by —N$Y^3Y^4$;
$R^5$ is alkyl, alkenyl, aryl, arylalkyl, cycloalkyl, cycloalkylalkyl, heteroaryl, heteroarylalkyl, heterocycloalkyl or heterocycloalkylalkyl;
$R^6$ is chosen from the values of $R^5$;
n is zero or an integer 1 or 2;
$Y^1$ and $Y^2$ are independently hydrogen, alkenyl, aryl, cycloalkyl, heteroaryl, heterocycloalkyl, heterocycloalkylalkyl or alkyl optionally substituted by one or more groups selected from cyano, aryl, heteroaryl, hydroxy, —C(=O)OR$^6$, —C(=O)NY$^3$Y$^4$, —NY$^3$Y$^4$ or —OR$^5$, or the group —NY$^1$Y$^2$ may form a cyclic amine;

Y$^3$ and Y$^4$ are independently hydrogen, alkenyl, alkyl, aryl, arylalkyl, cycloalkyl, heteroaryl or heteroarylalkyl; or the group —NY$^3$Y$^4$ may form a cyclic amine; all the alkyl (or alk, which represents alkyl), alkenyl, cycloalkyl, heterocycloalkyl, aryl, arylalkyl, heteroaryl and heteroarylalkyl radicals present in the above radicals furthermore being optionally substituted with one or more radicals chosen from halogen atoms and hydroxyl, cyano, alkyl, alkoxy, acylamino(NH—COalk), —C(=O)OR$^6$, —C(=O)R$^6$, hydroxyalkyl, carboxyalkyl, S(O)$_n$-alk S(O)$_n$—NH$_2$, S(O)$_n$—NH(alk), S(O)$_n$—N(alk)$_2$, CF$_3$, OCF$_3$, NO$_2$, arylalkoxy, aryl, heteroaryl, aryloxy, aryloxyalkyl, —C(=O)—NY$^3$Y$^4$ and NY$^3$Y$^4$ radicals, the latter radicals containing alkyl, aryl and heteroaryl being themselves optionally substituted with one or more radicals chosen from halogen atoms and alkyl radicals, free, salified or esterified carboxyl radicals and acylamino radicals NH—C(O)R$^5$;

and their corresponding N-oxides, and their prodrugs, and their acid bioisosteres; and pharmaceutically acceptable salts and solvates (e.g. hydrates) of such compounds and their N-oxides and their prodrugs, and their acid bioisosteres; together with one or more pharmaceutically acceptable carriers or excipients.

In another aspect, the invention concerns the compounds of formula (Ix) as defined above wherein R$^1$ is a pyrazolyl moiety

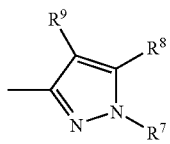

in which R$^7$ is hydrogen or alkyl, and R$^8$ and R$^9$ are independently selected from hydrogen, carboxy, cyano, halo, haloalkyl, hydroxy, nitro, R$^4$, —C(=O)R$^4$, —C(=O)NY$^1$Y$^2$, —C(=O)OR$^4$, —N(R$^6$)C(=O)R$^4$, —N(R$^6$)C(=O)NY$^1$Y$^2$, —N(R$^6$)C(=O)OR$^4$, —N(R$^6$)SO$_2$R$^4$, —N(R$^6$)SO$_2$NY$^1$Y$^2$, —NY$^1$Y$^2$, —OR$^4$, —OC(=O)R$^4$, —OC(=O)NY$^1$Y$^2$, —S(O)$_n$R$^4$ and —S(O)$_2$NY$^1$Y$^2$; or R$^8$ and R$^9$ together with the carbon atoms to which they are attached form (i) a 5 to 8 membered carbocyclic ring optionally substituted by one or more carbocyclic ring substituents; (ii) a phenyl ring optionally substituted by one or more aryl group substituents; (iii) a 5 or 6 membered heteroaromatic ring in which one or more of the ring members is/are nitrogen, oxygen or sulfur (examples of such groups include furyl, imidazolyl, isoxazolyl, isothiazolyl, oxadiazolyl, pyrazinyl, pyridazinyl, pyrazolyl, pyridyl, pyrimidinyl, pyrrolyl, 1,3,4-thiadiazolyl, thiazolyl, thienyl and triazolyl groups) and which is optionally substituted by one or more groups selected from haloalkyl, hydroxy, halo, cyano, nitro, R$^4$, —C(=O)NY$^1$Y$^2$, —N(R$^6$)C(=O)R$^4$, —N(R$^6$)C(=O)NY$^1$Y$^2$, —N(R$^6$)SO$_2$R$^4$, —NY$^1$Y$^2$ and —OR$^5$; or (iv) a 5 or 6 membered heterocyclic ring optionally substituted by alkyl or oxo, and containing a heteroatom-containing group selected from O, S, SO$_2$, or NY$^5$ (where Y$^5$ is hydrogen, R$^4$, —C(=O)R$^4$, —C(=O)NY$^1$Y$^2$, —C(=O)OR$^4$ or —SO$_2$R$^4$); but excluding the compounds: 2-(2H-pyrazol-3-yl)-1H-benzoimidazole; 2-(5-methyl-2H-pyrazol-3-yl)-1H-benzoimidazole; 5-methyl-6-[2-(2H-pyrazol-3-yl)-3H-benzoimidazol-5-yl]-4,5-dihydro-2H-pyridazin-3-one; 5-methyl-6-[2-(2H-pyrazol-3-yl)-1H-benzoimidazol-4-yl]4,5-dihydro-2H-pyridazin-3-one; 3,5-bis(benzimidazol-2-yl)-1H-pyrazole; 5,6-dimethyl-2-(5-methyl-1H-pyrazol-3-yl)-1H-benzoimidazole; 6-methyl-2-(5-methyl-1H-pyrazol-3-yl)-1H-benzoimidazole; 5,6-dichloro-2-(5-methyl-1H-pyrazole-3-yl)-1H-benzoimidazole; 5-nitro-2-(5-methyl-1H-pyrazole-3-yl)-1H-benzoimidazole; 2-(5-methyl-1H-pyrazole-3-yl)-1H-benzoimidazole-5-carboxylic acid; 2-(5-phenyl-1H-pyrazole-3-yl)-1H-benzoimidazole; 5,6-dimethyl-2-(5-phenyl-1H-pyrazole-3-yl)-1H-benzoimidazole; 5-methyl-2-(5-phenyl-1H-pyrazole-3-yl)-1H-benzoimidazole; 6-chloro-2-(5-methyl-1H-pyrazole-3-yl)-1H-benzoimidazole; 5-chloro-2-(5-phenyl-1H-pyrazole-3-yl)-1H-benzoimidazole; 5,6-dichloro-2-(5-phenyl-1H-pyrazole-3-yl)-1H-benzoimidazole; N-[2-(5-isoquinolin-4-yl-1H-indazol-3-yl)-3H-benzoimidazol-5-yl]-methanesulfonamide; 3-(1H-benzoimidazol-2-yl)-5-(1H-indazol-4-yl)-1H-indazole, 3-[3-(1H-benzoimidazol-2-yl)-1H-indazol-5-yl]-2-methoxyphenol; 4-[3-(1H-benzoimidazol-2-yl)-1H-indazol-5-yl]isoquinoline; 4-{3-[6-(4-methyl-piperazin-1-yl)-1H-benzoimidazol-2-yl]-1H-indazol-5-yl}-isoquinoline; 4-[3-(4-chloro-1H-benzoimidazol-2-yl)-1H-indazol-5-yl]-isoquinoline; 4-[2-(1H-indazol-3-yl)-1H-benzoimidazol-5-yl]-phenol; 3-[5-(4-methoxy-phenyl)-1H-benzoimidazol-2-yl]-1H-indazole; 3-[5-(4-methoxy-phenyl)-1H-benzoimidazol-2-yl]-1H-indazole; 3-[5-(3-methoxy-phenyl)-1H-benzoimidazol-2-yl]-1H-indazole; 3-(1H-benzoimidazol-2-yl)-5-phenyl-1H-indazole; 2-(4-bromo-1-methyl-1H-pyrazol-3-yl)-1H-benzoimidazole; 2-(5-tert-butyl-1H-pyrazol-3-yl)-1H-benzoimidazole; 3-(1H-benzoimidazol-2-yl)-6-(3-methoxyphenyl)-1H-indazole; 3-(1H-benzoimidazol-2-yl)-1H-indazole-6-carboxylic acid; 5-{[3-(1H-benzoimidazol-2-yl)-1H-indazole-6-carbonyl]-amino}-2-hydroxy-benzoic acid methyl ester; 5-{[3-(1H-benzoimidazol-2-yl)-1H-indazole-6-carbonyl]-amino}-furan-2-carboxylic acid methyl ester; 3-(1H-benzoimidazol-2-yl)-1H-indazole-6-carboxylic acid (3-hydroxy-4-methoxy-phenyl)-amide; 3-(1H-benzoimidazol-2-yl)-1H-indazole-6-carboxylic acid (5-hydroxy-1H-pyrazol-3-yl)-amide; 3-(1H-benzoimidazol-2-yl)-1H-indazole-6-carboxylic acid (1H-pyrazol-3-yl)-amide; [3-(1H-benzoimidazol-2-yl)-1H-indazol-6-yl]-[4-(2-hydroxy-ethyl)-piperidin-1-yl]-methanone; 3-(1H-benzoimidazol-2-yl)-1H-indazole-6-carboxylic acid (9H-purin-6-yl)-amide; 3-(1H-benzoimidazol-2-yl)-1H-indazole-6-carboxylic acid dimethylamide; [3-(1H-benzoimidazol-2-yl)-1H-indazol-6-yl]-morpholin-4-yl-methanone; 3-(1H-benzoimidazol-2-yl)-1H-indazole-6-carboxylic acid pyrazin-2-ylamide; 3-(1H-benzoimidazol-2-yl)-1H-indazole-6-carboxylic acid cyclohexylamide; 3-(1H-benzoimidazol-2-yl)-1H-indazole-6-carboxylic acid (1H-indazol-5-yl)-amide; [3-(1H-benzoimidazol-2-yl)-1H-indazol-6-yl]-pyrrolidin-1-yl-methanone; 3-(1H-benzoimidazol-2-yl)-1H-indazole-6-carboxylic acid (1H-indazol-5-yl)-amide; [3-(1H-benzoimidazol-2-yl)-1H-indazol-6-yl]-[4-(furan-2-carbonyl)-piperazin-1-yl]-methanone; [3-(1H-benzoimidazol-2-yl)-1H-indazol-6-yl]-(4-methyl-piperazin-1-yl)-methanone; 1-{4-[3-(1H-benzoimidazol-2-yl)-1H-indazole-6-carbonyl]-piperazin-1-yl}-ethanone; 3-(1H-benzoimidazol-2-yl)-1H-indazole-6-carboxylic acid (6-methoxy-pyridin-3-yl)-amide; 3-(1H-benzoimidazol-2-yl)-1H-indazole-6-carboxylic acid (3-hydroxy-phenyl)-amide; 3-(1H-benzoimidazol-2-yl)-1H-indazole-6-carboxylic acid pyridin-4-ylamide; 3-(1H-benzoimidazol-2-yl)-1H-indazole-6-carboxylic acid (2-morpholin-4-yl-ethyl)-amide; 3-(1H-benzoimidazol-2-yl)-1H- indazole-6-carboxylic acid (2-hydroxy-ethyl)-methyl-amide; 3-{[3-(1H-benzoimidazol-2-yl)-1H-indazole-6-carbonyl]-amino}-butyric acid ethyl ester; 3-(1H-benzoimidazol-2-yl)-1H-indazole-6-carboxylic acid (3-hydroxy-propyl)-amide; 3-(1H-benzoimidazol-2-yl)-1H-indazole-6-carboxylic acid phenylamide; 3-(1H-benzoimidazol-2-yl)-1H-indazole-6-carboxylic acid pyridin-3-ylamide; 3-(6-methoxy-1H-benzoimidazol-2-yl)-1H-indazole-6-carboxylic acid (4-hydroxy-phenyl)-amide; 3-(1H-benzoimidazol-2-yl)-6-pyridin-4-yl-1H-indazole; 3-(5-chloro-1H-benzoimidazol-2-yl)-1H-indazole-6-carboxylic acid (4-hydroxy-phenyl)-amide; 3-(5,6-dimethoxy-1H-benzoimidazol-2-yl)-1H-indazole-6-carboxylic acid (4-hydroxy-phenyl)-amide; 3-(5-fluoro-1H-benzoimidazol-2-yl)-1H-indazole-6-carboxylic acid (4-hydroxy-phenyl)-amide; 3-(6-trifluoromethyl-1H-benzoimidazol-2-yl)-1H-indazole-6-carboxylic acid (4-hydroxy-phenyl)-amide; 3-(6-tert-butyl-1H-benzoimidazol-2-yl)-1H-indazole-6-carboxylic acid (4-hydroxy-phenyl)-amide; 3-(6,7-dimethyl-1H-benzoimidazol-2-yl)-1H-indazole-6-carboxylic acid (4-hydroxy-phenyl)-amide; 3-(5,6-dichloro-1H-benzoimidazol-2-yl)-1H-indazole-6-carboxylic acid (4-hydroxy-phenyl)-amide; 3-(5,6-difluoro-1H-benzoimidazol-2-yl)-1H-indazole-6-carboxylic acid (4-hydroxy-phenyl)-amide; 3-(1H-benzoimidazol-2-yl)-1H-indazole-6-carboxylic acid (3-fluoro-4-hydroxy-phenyl)-amide; 3-(1H-benzoimidazol-2-yl)-1H-indazole-6-carboxylic acid amide; 3-(1H-benzoimidazol-2-yl)-1H-indazole-6-carboxylic acid (4-hydroxy-2,3-dimethyl-phenyl)-amide; 3-(1H-benzoimidazol-2-yl)-1H-indazole-6-carboxylic acid (4-hydroxy-2-methyl-phenyl)-amide; 3-(1H-benzoimidazol-2-yl)-1H-indazole-6-carboxylic acid (4-hydroxy-phenyl)-amide; 3-(1H-benzoimidazol-2-yl)-1H-indazole-6-carboxylic acid cyclopropylamide; 2-[6-(4-hydroxy-2-methoxy-phenyl)-1H-indazol-3-yl]-3H-benzoimidazole-5-sulfonic acid amide; 4-[3-(6-dimethylamino-1H-benzoimidazol-2-yl)-1H-indazol-6-yl]-3-methoxy-phenol; 2-[6-(4-hydroxy-2-methoxy-phenyl)-1H-indazol-3-yl]-3H-benzoimidazole-5-carboxylic acid methylamide; 3-methoxy-4-{3-[6-(4-methyl-piperazin-1-yl)-1H-benzoimidazol-2-yl]-1H-indazol-6-yl}-phenol; 2-[6-(4-hydroxy-2-methoxy-phenyl)-1H-indazol-3-yl]-3H-benzoimidazole-5-carboxylic acid (2-morpholin-4-yl-ethyl)-amide; 4-[3-(1H-imidazo[4,5-c]pyridin-2-yl)-1H-indazol-6-yl]-3-methoxy-phenol; 3-[3-(1H-benzoimidazol-2-yl)-1H-indazol-6-yl]-2-methoxy-phenol; 3-[3-(1H-benzoimidazol-2-yl)-1H-indazol-6-yl]-phenol; 4-[3-(1H-benzoimidazol-2-yl)-1H-indazol-6-yl]-3,5-dimethyl-phenol; 4-[3-(1H-benzoimidazol-2-yl)-1H-indazol-6-yl]-3-phenoxy-phenol; 4-[3-(1H-benzoimidazol-2-yl)-1H-indazol-6-yl]-benzene-1,3-diol; 4-[3-(1H-benzoimidazol-2-yl)-1H-indazol-6-yl]-3-methoxy-phenol; 4-[3-(1H-benzoimidazol-2-yl)-1H-indazol-6-yl]-2-methoxy-phenol; N-{3-[3-(1H-benzoimidazol-2-yl)-1H-indazole-6-carbonyl]-phenyl}-benzamide; 6-[2-(1,5-dimethyl-1H-pyrazol-3-yl)-3H-benzoimidazol-5-yl]-5-methyl-4,5-dihydro-2H-pyridazin-3-one; 5-methyl-6-[2-(1-methyl-1H-pyrazol-3-yl)-3H-benzoimidazol-5-yl]-4,5-dihydro-2H-pyridazin-3-one; 8-(1,5-dimethyl-1H-pyrazol-3-yl)-7H-purine; 2-(1,5-dimethyl-1H-pyrazol-3-yl)-1H-imidazo[4,5-b]pyridine and 2-(5-methyl-1H-pyrazol-3-yl)-1H-imidazo[4,5-b]pyridine.

In the present specification, the term "compounds of the invention", and equivalent expressions, are meant to embrace compounds of general formula (Ix) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above for compounds of formula (Ix), and throughout the description of the invention hereinafter, the following terms unless otherwise indicated, shall be understood to have the following meanings:—

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, p283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 "Bioisosteric Replacement And Development Of Lead Compounds In Drug Design"; Graham, Theochem, 1995, 343, pages 105-109 "Theoretical Studies Applied To Drug Design: ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" denotes a radical R—C(=O)— in which R represents a radical chosen from a hydrogen atom, linear or branched alkyl radicals containing not more than 6 carbon atoms; optionally substituted amino; aryl, heteroaryl, cycloalkyl or heterocycloalkyl radicals, for example phenyl or pyrrolidinyl radicals: the term "acyl" thus especially denotes, for example, formyl radicals and acetyl, propionyl, butanoyl, pentanoyl, hexanoyl, benzoyl and pyrrolidinylcarbonyl radicals.

"Acylamino" denotes —C(=O)—NH$_2$, —C(O)—NH(alk) and —C(O)—N(alk)(alk) radicals: in these radicals, NH(alk) and N(alk)(alk) have the meanings given hereinafter defined.

"Alkenyl" means an aliphatic hydrocarbon group containing a carbon-carbon double bond and which may be straight or branched having about 2 to about 15 carbon atoms in the chain and containing one or more double bonds. Preferred alkenyl groups have 2 to about 12 carbon atoms in the chain; and more preferably 2 to about 6 carbon atoms (e.g. 2 to 4 carbon atoms) in the chain. "Branched," as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain, which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl, decenyl, and 3,7-dimethyl-octa-2,6-dienyl.

"Alkoxy" means an alkyl-O— group in which the alkyl group is as described herein. Exemplary alkoxy groups include difluoromethoxy, methoxy, trifluoromethoxy, ethoxy, n-propoxy, i-propoxy, n-butoxy, s-butoxy, t-butoxy, pentoxy, hexoxy and heptoxy, and also the linear or branched positional isomers thereof.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched chain having about 1 to about 15 carbon atoms in the chain, optionally substituted by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be a straight or branched chain having 1 to about 4 carbon atoms in the chain. Exemplary alkyl groups include methyl, ethyl, n-propyl, i-propyl, n-butyl, isobutyl, s-butyl, t-butyl, n-pentyl, 3-pentyl, hexyl, isohexyl, heptyl, octyl, nonyl, decyl and dodecyl, and also the linear or branched positional isomers thereof. Exemplary alkyl groups substituted by one or more halogen atoms include trifluoromethyl, difluoromethyl, trifluoroethyl and difluoroethyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-SO$_2$— group in which the alkyl group is as previously described. Preferred alkylsulfonyl groups are those in which the alkyl group is $C_{1-4}$alkyl.

"Alkylsulfonylcarbamoyl" means an alkyl-SO$_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, propylthio, isopropylthio, butylthio, isobutylthio, sec-butylthio, tert-butylthio, pentylthio, isopentylthio, hexylthio, isohexylthio and heptylthio, and also the linear or branched positional isomers thereof. Preferred alkylthio groups have not more than 4 carbon atoms.

"Alkynyl" means an aliphatic hydrocarbon group containing a carbon-carbon triple bond and which group may be a straight or branched chain having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Aroyl" means an aryl-CO— group in which the aryl group is as described herein. Exemplary aroyl groups include-benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which a monocyclic aromatic carbocyclic moiety and a cycloalkyl or cycloalkenyl group are fused together to form a cyclic structure, such as a tetrahydronaphthyl, indenyl or indanyl ring. Except where otherwise defined, aryl groups may be substituted with one or more aryl group substituents, which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, cycloalkyl, halo, heteroaroyl, heteroaryl, heteroarylalkyloxy, heteroarylamino, heteroaryloxy, heterocycloalkyl, hydroxy, nitro, trifluoromethyl, —C(=O)NY$^1$Y$^2$, —NY$^1$—C(=O)alkyl, —NY$^1$SO$_2$alkyl, —NY$^1$Y$^2$, —SO$_2$NY$^1$Y$^2$ or alkyl, alkenyl or alkynyl each optionally substituted with aryl, cycloalkyl, heteroaryl, hydroxy, —C(=O)OR$^6$, —C(=O)NY$^1$Y$^2$, —NY$^1$Y$^2$ or —OR$^5$.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl group is as previously described. Exemplary arylalkyloxy groups include benzyloxy and 1- or 2-naphthalenemethoxy.

"Arylalkyloxycarbonyl" means an arylalkyl-O—CO— group in which the arylalkyl group is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Aryloxy" means an aryl-O— group in which the aryl group is as previously described. Exemplary aryloxy groups include phenoxy and naphthoxy, each optionally substituted.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-SO$_2$— group in which the aryl group is as previously described.

"Arylsulfonylcarbamoyl" means an aryl-SO$_2$—NH—C(=O)— group in which the aryl group is as previously described.

"Arylthio" means an aryl-S— group in which the aryl group is as previously described. Exemplary arylthio groups include phenylthio and naphthylthio.

"Carbocyclic" means a saturated ring system comprising carbon atoms.

"Carbocyclic group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, cycloalkyl, halo, heteroaroyl, heteroaryl, heteroarylalkyloxy, heteroaroylamino, heteroaryloxy, heterocycloalkyl, hydroxy, nitro, trifluoromethyl, —C(=O)NY$^1$Y$^2$, —NY$^1$—C(=O)alkyl, —NY$^1$SO$_2$alkyl, —NY$^1$Y$^2$, —SO$_2$NY$^1$Y$^2$ or alkyl, alkenyl or alkynyl each optionally substituted with aryl, cycloalkyl, heteroaryl, hydroxy, —C(=O)OR$^6$, —C(=O)NY$^1$Y$^2$, —NY$^1$Y$^2$ or —OR$^5$.

"Cyclic amine" means a 3 to 8 membered monocyclic cycloalkyl ring system wherein one of the ring carbon atoms is replaced by nitrogen and which (i) may also contain a further heteroatom-containing group selected from O, S, SO$_2$, or NY$^6$ (where Y$^6$ is hydrogen, alkyl, aryl, arylalkyl, —C(=O)R$^5$, —C(=O)OR$^5$, —C(=O)NY$^1$Y$^2$ or —SO$_2$R$^5$); and (ii) may be fused to additional aryl (e.g. phenyl), heteroaryl (e.g. pyridyl), heterocycloalkyl or cycloalkyl rings to form a bicyclic or tricyclic ring system. Exemplary cyclic amines include pyrrolidine, piperidine, morpholine, piperazine, indoline, pyrindoline, tetrahydroquinoline and the like groups.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl and cycloheptenyl.

"Cycloalkyl" means a saturated monocyclic or bicyclic ring system of about 3 to about 10 carbon atoms, optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkyl" means a cycloalkyl-alkyl- group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Halo" or "halogen" means fluoro, chloro, bromo, or iodo. Preferred are fluoro, bromo and chloro.

"Haloalkyl" means an alkyl group having about 1 to about 6 carbon atoms in the chain and substituted by one or more halo atoms. Exemplary haloalkyl groups include trifluoromethyl.

"Heteroaroyl" means a heteroaryl-C(=O)— group in which the heteroaryl group is as described herein. Exemplary heteroaryl groups include pyridylcarbonyl.

"Heteroaroylamino" means a heteroaroyl-NH— group in which the heteroaryl moiety is as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzoimidazolyl, benzothiazolyl, furyl, imidazolyl, indazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above except where otherwise defined); (ii) an optionally substituted partially saturated multicyclic heterobicyclic moiety in which a monocyclic heteroaromatic moiety and a cycloalkyl, cycloalkenyl or heterocycloalkyl group are fused together to form a cyclic structure (examples of such groups include tetrahydro-indazole, tetrahydro-pyrazolopyridine, 5-oxo-1,4,5,6,7,8,9,9a-octahydro-1,2,4,5a-tetraza-cyclopenta[a]naphthyl, optionally substituted by one or more "aryl group substituents" as defined above, except where otherwise defined). Optional substituents include one or more "aryl group substituents" as defined above, except where otherwise defined. When $R^1$ is heteroaryl this may particularly represent pyrazolyl, triazolyl, isoxazolyl, isothiazolyl, thiazolyl, oxazolyl, imidazolyl, pyrrolyl, furanyl, thiophenyl, phenyl, pyridinyl, oxodihydropyridinyl, pyrimidinyl, indolyl, indazolyl, thienopyrazolyl, tetrahydroindazolyl, tetrahydrocyclopentapyrazolyl, dihydrofuropyrazolyl, oxodihydropyridazinyl, tetrahydropyrrolopyrazolyl, oxotetrahydropyrrolopyrazolyl, tetrahydropyranopyrazolyl, tetahydropyridinopyrazolyl, or oxodihydropyridinopyrazolyl.

"Heteroarylalkyl" means a heteroaryl-alkyl- group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroaryloxy" means an heteroaryl-O— group in which the heteroaryl group is as previously described. Exemplary heteroaryloxy groups include optionally substituted pyridyloxy.

"Heteroarylsulfonylcarbamoyl" means a heteroaryl-$SO_2$—NH—C(=O)— group in which the heteroaryl group is as previously described.

"Heterocycloalkyl" means: (i) a cycloalkyl group of about 3 to 10 ring members which contains one or more heteroatoms or heteroatom-containing groups selected from O, S and $NY^6$ and may be optionally substituted by oxo (examples of such groups include hexahydropyran, pyrrolidinyl, piperidinyl, tetrahydropyranyl and octahydro-pyrido[1,2-c]pyrimidin-1-one); (ii) a partially saturated multicyclic heterocarbocyclic moiety in which an aryl (or heteroaryl) ring, each optionally substituted by one or more "aryl group substituents," and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl- group in which the heterocycloalkyl and alkyl moieties are as previously described.

"Hydroxyalkyl" means an alkyl group substituted by one or hydroxy groups.

"NH(alk)" and "N(alk)(alk)" denote an amino radical substituted, respectively, with one or two alkyl radicals, such alkyl radicals being linear or branched and chosen from alkyl radicals as defined above, preferably containing not more than 4 carbon atoms.

"Prodrug" means a compound which is convertible in vivo by metabolic means (e.g. by hydrolysis) to a compound of formula (Ix), including N-oxides thereof. For example an ester of a compound of formula (Ix) containing a hydroxy group may be convertible by hydrolysis in vivo to the parent molecule. Alternatively, an ester of a compound of formula (Ix) containing a carboxy group may be convertible by hydrolysis in vivo to the parent molecule.

Suitable esters of compounds of formula (Ix) containing a hydroxy group are, for example acetates, citrates, lactates, tartrates, malonates, oxalates, salicylates, propionates, succinates, fumarates, maleates, methylene-bis-p-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (Ix) containing a carboxy group are, for example, those described by F. J. Leinweber, Drug Metab. Res., 1987, 18, page 379.

An especially useful class of esters of compounds of formula (Ix) containing a hydroxy group, may be formed from acid moieties selected from those described by Bundgaard et. al., J. Med. Chem., 1989, 32, pages 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention of formula (Ix) contains a carboxy group, or a sufficiently acidic bioisostere, base addition salts may be formed and are simply a more convenient form for use; in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide, and the like.

Some of the compounds of the present invention of formula (Ix) are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention of compounds of formula (Ix) are useful for the purposes of purification of the compounds, for example by exploitation of the solubility differences between the salts and the parent compounds, side products and/or starting materials by techniques well known to those skilled in the art.

It will be appreciated that compounds of the present invention of formula (Ix) may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (Ix) hereinabove. Such isomers can be separated from their mixtures, by the application or adaptation of known methods, for example chromatographic techniques and recrystallisation techniques, or they are separately prepared from the appropriate isomers of their intermediates. Additionally, tautomers of the compounds of formula (Ix) are possible, and the present invention is intended to include all tautomeric forms of the compounds.

One subject of the present invention is thus the compounds of formula (I):

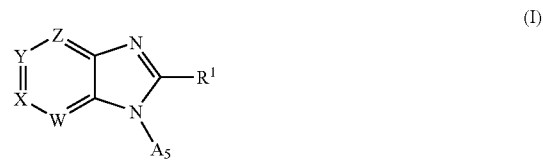

in which:

X represents C—$R^2$ and W, Y and Z, which may be identical or different, represent CH or $CR^3$;

$R^1$ represents aryl or heteroaryl chosen from pyrazolyl, triazolyl, imidazolyl, indolyl, indazolyl, thieno-pyrazolyl, tetrahydroindazolyl, tetrahydrocyclopentapyrazolyl, dihydrofuropyrazolyl, oxodihydropyridazinyl, tetrahydropyrrolopyrazolyl, oxotetrahydropyrrolopyrazolyl, tetrahydropyranopyrazolyl, tetrahydropyridinopyrazolyl, and oxodihydropyridinopyrazolyl radicals, all these radicals being optionally substituted with one or more radicals $X^1$, $X^2$ or $X^3$ chosen from H, halogen, haloalkyl, OH, $R^4$, $NO_2$, CN, $S(O)_nR^4$, $OR^4$, $NY^1Y^2$, $COR^4$, —C(=O)$NY^1Y^2$, —C(=O)$OR^4$, —C(=O)OH, —N($R^6$)C(=O)$R^4$, —N($R^6$)$SO_2R^4$, —N($R^6$)C(=O)$NY^1Y^2$, —N($R^6$)C(=O)OR, —S(O)n$OR^4$, —S(O)$_n$$NY^1Y^2$, —OC(=O)$NY^1Y^2$, —OS(O)$_nR^4$, —OC(=O)$R^4$ and optionally substituted thienyl, $R^2$ and $R^3$ are such that:

either $R^2$ and $R^3$, which may be identical or different, represent H, $R^4$, halogen, haloalkyl, OH, $NO_2$, CN, $OR^4$, $COR^4$, $S(O)_nR^4$—C(=O)$NY^1Y^2$, —C(=O)$OR^4$, —C(=O)OH, —$NY^1Y^2$, —N($R^6$)C(=O)$R^4$, —N($R^6$)$SO_2R$, —N(R)C(=O)$NY^1Y^2$, —N($R^6$)C(=O)$OR^4$, —S(O)$_nOR^4$, —S(O)$_nNY^1Y^2$, —OC(=O)$NY^1Y^2$ and —OC(=O)$R^4$ or $R^2$ represents H, $R^4$, halogen, haloalkyl, OH, $NO_2$, CN, $OR^4$, $COR^4S(O)_nR^4$, —C(=O)$NY^1Y^2$, —C(=O)$OR^4$, —C(=O)OH, —$NY^1Y^2$, —N($R^6$)C(=O)$R^4$, —N($R^6$)$SO_2R^4$, —N($R^6$)C(=O)$NY^1Y^2$, —N($R^6$)C(=O)$OR^4$, —S(O)$_nOR^4$, —S(O)$_nNY^1Y^2$, —OC(=O)$NY^1Y^2$ and —OC(=O)$R^4$ and $R^3$ represents alkyl, haloalkyl, halogen and $OR^6$ or $R^2$ and $R^3$ together form a 5- to 6-membered carbon-based ring containing one or more hetero atoms, which may be identical or different, chosen from O, N and S, $R^4$ represents alkyl, alkenyl, alkynyl, cycloalkyl, aryl, heteroaryl, cycloalkylalkyl, heterocycloalkyl, heteroarylalkyl and arylalkyl, all these radicals being optionally substituted with one or more radicals chosen from aryl (optionally substituted), halogen, alkyl, hydroxyalkyl, OH, $OR^5$, C(=O)$NY^3Y^4$, $NY^3Y^4$, alk-$NY^3Y^4$ and C(=O)$OR^6$, $R^5$ represents alkyl, alkenyl, cycloalkyl, heterocycloalkyl, aryl, heteroaryl, arylalkyl, cycloalkylalkyl, heteroarylalkyl and heterocycloalkylalkyl.

$Y^1$ and $Y^2$ are such that: either $Y^1$ and $Y^2$, which may be identical or different, represent H and optionally substituted alkyl, alkenyl, cycloalkyl, heterocycloalkyl, heterocycloalkylalkyl, aryl, arylalkyl, heteroaryl and heteroarylalkyl, or Y$^1$ and Y$^2$ form, together with the nitrogen atom to which they are attached, a cyclic amino radical, Y$^3$ and Y$^4$ are such that: either Y$^3$ and Y$^4$, which may be identical or different, represent hydrogen, alkenyl, alkyl, aryl, arylalkyl, cycloalkyl, heteroaryl or heteroarylalkyl or Y$^3$ and Y$^4$ form, together with the nitrogen atom to which they are attached, an optionally substituted cyclic amino radical, A$_5$ represents H or alkyl, R$^6$ is chosen from the values of R$^5$, all the alkyl (or alk, which represents alkyl), alkenyl, cycloalkyl, heterocycloalkyl, aryl, arylalkyl, heteroaryl and heteroarylalkyl radicals present in the above radicals furthermore being optionally substituted with one or more radicals chosen from halogen atoms and hydroxyl, cyano, alkyl, alkoxy, acylamino(NH—COalk), —C(=O)OR$^6$, acyl —C(=O)R$^6$, hydroxyalkyl, carboxyalkyl, S(O)$_n$-alk, S(O)$_n$—NH$_2$, S(O)$_n$—NH(alk), S(O), —N(alk)$_2$, CF$_3$, OCF$_3$, NO$_2$, arylalkoxy, aryl, heteroaryl, aryloxy, aryloxyalkyl, —C(=O)—NY$^3$Y$^4$ and NY$^3$Y$^4$ radicals, the latter radicals containing alkyl, aryl and heteroaryl being themselves optionally substituted with one or more radicals chosen from halogen atoms and alkyl radicals, free, salified or esterified carboxyl radicals and acylamino radicals NH—C(O)R$^5$, the phenyl radicals furthermore being optionally substituted with a dioxole radical, n represents an integer from 0 to 2, it being understood that when R$^1$ represents an indazolyl radical to give the compounds of formula (F) below:

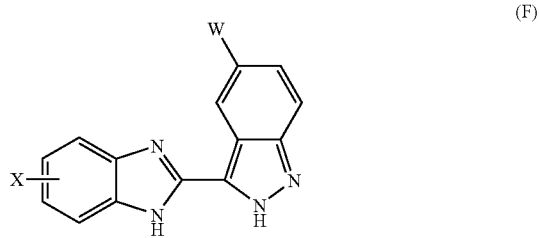

(F)

with X representing H, R$^2$ or R$^3$ as defined above, then W necessarily represents H or unsubstituted alkyl, the said compounds of formula (I) being in any possible racemic, enantiomeric or diastereoisomeric isomer form, and also the addition salts with mineral and organic acids or with mineral bases.

One subject of the present invention is thus the compoundss of formula (I) as defined above corresponding to the formula (Ia):

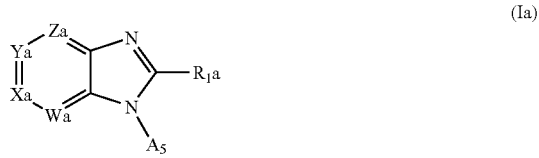

(Ia)

in which:

Xa represents C—R$^2$a and Wa, Ya and Za, which may be identical or different, represent CH or CR$^3$a;

R$_1$a represents aryl or heteroaryl chosen from pyrazolyl, triazolyl and indazolyl radicals, all these radicals being optionally substituted with one or more radicals X$^1$a, X$^2$a or X$^3$a chosen from H, halogen, OH, R$^4$a, OR$^4$a, NY$^1$aY$^2$a, S(O)$_n$Ra, —C(=O)NY$^1$aY$^2$a, —C(=O)OR$^4$a, —N(R$^6$a)C(=O)R$^4$a, —N(R$^6$a)SO$_2$R$^4$a, —N(R$^6$a)C(=O)NY$^1$aY$^2$a, —N(R$^6$a)C(=O)OR$^4$a, —OC(=O)NY$^1$aY$^2$a, —OC(=O)R$^4$a, —OS(O)$_n$R$^4$a and thienyl optionally substituted with an alkyl radical, R$^2$a and R$^3$a are such that:

either R$^2$a and R$^3$a, which may be identical or different, represent H, R$^4$a, halogen, OH, OR$^4$a, C(=O)NY$^1$aY$^2$a, —C(=O)OR$^4$a and —C(=O)OH, and R$^3$a represents alkyl, halogen and OR$^6$a, or R$^2$a represents H, R$^4$a, halogen, OH, OR$^4$a, C(=O)NY$^1$aY$^2$a, —C(=O)OR$^4$a and —C(=O)OH, and R$^3$a represents alkyl, halogen and OR$^6$a, or R$^2$a and R$^3$a together form an —O—CH$_2$—O— or —O—CH$_2$—CH$_2$—O— ring, R$^4$a represents alkyl, alkenyl, cycloalkyl, aryl, heteroaryl, cycloalkylalkyl, heterocycloalkyl, heteroarylalkyl and arylalkyl, all these radicals being optionally substituted with one or more radicals chosen from aryl (optionally substituted), halogen, alkyl, hydroxyalkyl, OH, OR$^5$a, C(=O)NY$^3$aY$^4$a, NY$^3$aY$^4$a, alk-NY$^3$aY$^4$a and C(=O)OR$^6$a, R$^5$a represents alkyl, alkenyl, cycloalkyl, heterocycloalkyl, aryl, heteroaryl, arylalkyl, cycloalkylalkyl, heteroarylalkyl and heterocycloalkylalkyl, all these radicals being optionally substituted, Y$^1$a and Y$^2$a are such that: either Y$^1$a and Y$^2$a, which may be identical or different, represent H, alkyl, alkoxyalkyl, aryloxyalkyl, arylalkyl, heteroarylalkyl, heterocycloalkylalkyl, cycloalkyl, aryl and heteroaryl, all these radicals being optionally substituted, or Y$^1$a and Y$^2$a form, together with the nitrogen atom to which they are attached, an optionally substituted cyclic amino radical, Y$^3$a and Y$^4$a are such that: either Y$^3$a and Y$^4$a, which may be identical or different, represent hydrogen, alkyl, aryl, arylalkyl, cycloalkyl, heteroaryl or heteroarylalkyl, or Y$^3$a and Y$^4$a form, together with the nitrogen atom to which they are attached, a cyclic amino radical, A$_5$ represents H or alkyl, all the alkyl, alkenyl, cycloalkyl, heterocycloalkyl, aryl, arylalkyl, heteroaryl and heteroarylalkyl radicals present in the above radicals furthermore being optionally substituted with one or more radicals chosen from halogen atoms and hydroxyl, cyano, alkyl, alkoxy, acylamino(NH—C(O)R$^6$a), —C(=O)OR$^6$a, acyl —C(=O)R$^6$a, hydroxyalkyl, carboxyalkyl, S(O)$_n$-alk, S(O)$_n$—NH$_2$, S(O), —NH(alk), S(O)$_n$—N(alk)$_2$, CF$_3$, OCF$_3$, NO$_2$, arylalkoxy, aryl, heteroaryl, aryloxy, aryloxyalkyl, —C(=O)—NY$^3$aY$^4$a and NY$^3$aY$^4$a radicals, the latter radicals containing alkyl, aryl and heteroaryl themselves being optionally substituted with one or more radicals chosen from halogen atoms and alkyl radicals, alkoxy radicals, free, salified or esterified carboxyl radicals and acylamino radicals NH—C(O)R$^6$a, the phenyl radicals furthermore being optionally substituted with a dioxole radical, R$^6$a is chosen from the values of R$^5$a, n represents an integer from 0 to 2, the said compounds of formula (Ia) being in any possible racemic, enantiomeric or diastereoisomeric isomer form, and also the addition salts with mineral and organic acids or with mineral bases.

One subject of the present invention is thus the compounds of formula (I):

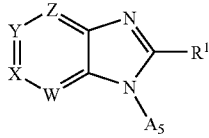

(I)

in which:

X represents C—R² and W, Y and Z, which may be identical or different, represent CH or CR³;

R¹ represents aryl or heteroaryl chosen from pyrazolyl, triazolyl, imidazolyl, indolyl, indazolyl, thieno-pyrazolyl, tetrahydroindazolyl, tetrahydrocyclopentapyrazolyl, dihydrofuropyrazolyl, oxodihydropyridazinyl, tetrahydropyrrolopyrazolyl, oxotetrahydropyrrolopyrazolyl, tetrahydropyranopyrazolyl, tetrahydropyridinopyrazolyl, and oxodihydro-pyridinopyrazolyl radicals, all these radicals optionally being substituted with one or more radicals $X^1$, $X^2$ or $X^3$ chosen from H, halogen, haloalkyl, OH, R⁴, NO₂, CN, S(O)$_n$R, OR⁴, NY¹Y², COR⁴, —C(=O)NY¹Y², —C(=O)OR⁴, —C(=O)OH, —N(R⁶)C(=O)R⁴, —N(R⁶)SO₂R⁴, —N(R⁶)C(=O)NY¹Y², —N(R⁶)C(=O)OR⁴, —S(O)$_n$OR⁴, —S(O)$_n$NY¹Y², —OC(=O)NY¹Y², —OS(O)$_n$R⁴, —OC(=O)R⁴ and optionally substituted thienyl, R² and R³ are such that:

either R² and R³, which may be identical or different, represent H, R⁴, halogen, haloalkyl, OH, NO², CN, OR⁴, COR⁴, S(O)$_n$R⁴, —C(=O)NY¹Y², —C(=O)OR⁴, —C(=O)OH, —NY¹Y², —N(R⁶)C(=O)R⁴, —N(R6)SO2R4, —N(R6)C(=O)NY1Y2, —N(R6)C(=O)OR4, —S(O)nOR4, —S(O)nNY1Y2, —OC(=O)NY¹Y² and —OC(=O)R⁴ or R² represents H, R⁴, halogen, haloalkyl, OH, NO₂, CN, OR⁴, COR⁴, S(O)$_n$R⁴, —C(=O)NY¹Y², —C(=O)OR⁴, —C(=O)OH, —NY¹Y², —N(R⁶)C(=O)R⁴, —N(R⁶)SO₂R⁴, —N(R⁶)C(=O)NY¹Y², —N(R⁶)C(=O)OR⁴, —S(O)$_n$OR⁴, S(O)$_n$NY¹Y², —OC(=O)NY¹Y² and —OC(=O)R⁴ and R³ represents alkyl, haloalkyl, halogen and OR⁶ or R² and R³ together form a 5- to 6-membered carbon-based ring containing one or more hetero atoms, which may be identical or different, chosen from O, N and S, R⁴ represents alkyl, alkenyl, cycloalkyl, aryl, heteroaryl, cycloalkylalkyl, heterocycloalkyl, hetero-arylalkyl and arylalkyl, all these radicals being optionally substituted with one or more radicals chosen from aryl, OH, OR⁵, C(=O)NY³Y⁴, NY³Y⁴ and C(=O)OR⁶, R⁵ represents alkyl, alkenyl, cycloalkyl, heterocycloalkyl, aryl, heteroaryl, arylalkyl, cycloalkylalkyl, heteroarylalkyl and heterocycloalkylalkyl.

R⁶ represents H and C1-C4 alkyl, n represents an integer from 0 to 2

Y¹ and Y² are such that: either Y¹ and Y², which may be identical or different, represent H, alkyl, alkenyl, cycloalkyl, aryl, arylalkyl, heteroaryl or heteroarylalkyl, all these radicals being optionally substituted with one or more radicals chosen from hydroxyl, —C(=O)—NY³Y⁴, —C(=O)OR⁶ and NY³Y⁴, or Y¹ and Y² form, together with the nitrogen atom to which they are attached, a cyclic amino radical, Y³ and Y⁴ are such that: either Y³ and Y⁴, which may be identical or different, represent hydrogen, alkenyl, alkyl, aryl, arylalkyl, cycloalkyl, heteroaryl or heteroarylalkyl or Y³ and Y⁴ form, together with the nitrogen atom to which they are attached, a cyclic amino radical, A₅ represents H or alkyl, it being understood that when R¹ represents an indazolyl radical to give the compounds of formula (F) below:

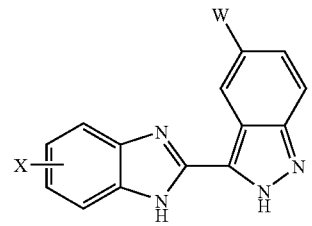

(F)

with X representing H, R² or R³ as defined above, then W necessarily represents H or unsubstituted alkyl, the said compounds of formula (F) being in any possible racemic, enantiomeric or diastereoisomeric isomer form, and also the addition salts with mineral and organic acids or with mineral bases.

It is obvious that, according to the ring represented by R¹ and its number of members, R¹ can comprise one, two or three substituents represented by X¹, X² and X³.

One subject of the present invention is thus the compounds of formula (I) as defined above corresponding to the formula (Ia):

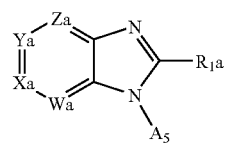

(Ia)

in which:

Xa represents C—R²a and Wa, Ya and Za, which may be identical or different, represent CH or CR³a;

R¹a represents aryl or heteroaryl chosen from pyrazolyl, triazolyl or indazolyl radicals, all these radicals being optionally substituted with one or more radicals X¹a, X²a or X³a chosen from H, halogen, OH, R⁴a, OR⁴a, NY¹aY²a, S(O)$_n$R⁴a, —C(=O)NY¹aY²a, —C(=O)OR⁴a, —N(R⁶a)C(=O)R⁴a, —N(R⁶a)SO₂R⁴a, —N(R⁶a)C(=O)NY¹aY²a, —N(R⁶a)C(=O)OR⁴a, —OC(=O)NY¹aY²a and —OC(=O)R⁴a, —OS(O)$_n$R⁴a and thienyl optionally substituted with an alkyl radical, R²a and R³a are such that:

either R²a and R³a, which may be identical or different, represent H, R⁴a, halogen, OH, OR⁴a, C(=O)NY¹aY²a, —C(=O)OR⁴a, —C(=O)OH, and R³a represents alkyl, halogen and OR⁶a, or R²a represents H, R⁴a, halogen, OH, OR⁴a, C(=O)NY¹aY²a, —C(=O)OR⁴a, —C(=O)OH, and R³a represents alkyl, halogen and OR⁶, or R²a and R³a together form an —O—CH₂—O or —O—CH₂—CH₂—O— ring, R⁴a represents alkyl, cycloalkyl, aryl, heteroaryl, heterocycloalkyl, heteroarylalkyl or arylalkyl, all these radicals being optionally substituted with one or more radicals chosen from aryl, OH, OR⁵a, C(=O)NY³aY⁴a, NY³aY⁴a and C(=O)OR⁶a, R5a represents alkyl, alkenyl, cycloalkyl, heterocycloalkyl, aryl, heteroaryl, arylalkyl, cycloalkylalkyl, heteroarylalkyl and heterocycloalkylalkyl, $R^6$a represents H and C1-C4 alkyl, n represents an integer from 0 to 2, $Y^1$a and $Y^2$a are such that: either $Y^1$a and $Y^2$a, which may be identical or different, represent H, alkyl, cycloalkyl, aryl and heteroaryl, all these radicals being optionally substituted with one or more radicals chosen from hydroxyl, —C(=O)—$NY^3Y^4$, —C(=O)$OR^6$ and $NY^3Y^4$, or $Y^1$a and $Y^2$a form, together with the nitrogen atom to which they are attached, a cyclic amino radical, $Y^3$a and $Y^4$a are such that: either $Y^3$a and $Y^4$a, which may be identical or different, represent hydrogen, alkyl, aryl, arylalkyl, cycloalkyl, heteroaryl or heteroarylalkyl, or $Y^3$a and $Y^4$a form, together with the nitrogen atom to which they are attached, a cyclic amino radical, $A_5$ represents H or alkyl, the said compounds of formula (Ia) being in any possible racemic, enantiomeric or diastereoisomeric isomer form, and also the addition salts with mineral and organic acids or with mineral bases.

One subject of the present invention is thus the compounds of formula (I) as defined above corresponding to the formula (IA):

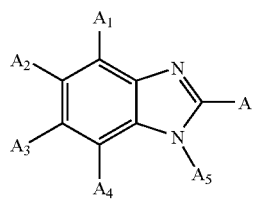

(IA)

in which A represents a saturated heterocyclic radical which is either a 5- or 6-membered monocyclic radical or a bicyclic radical that is not more than 10-membered, these members being such that at least two of them represent a nitrogen atom and the others, which may be identical or different, represent a carbon member or a hetero atom member chosen from O, N and S, this heterocycle A being optionally substituted with one or more radicals $XA^1$, $XA^2$ or $XA^3$ chosen from the values indicated hereinabove for the radicals $X^1$, $X^2$ or $X^3$, $A_1$, $A_2$, $A_3$ and $A_4$, which may be identical or different, are chosen from a hydrogen atom, halogen atoms and hydroxyl, alkyl, alkenyl, alkoxy, nitro, cyano, aryl, heteroaryl and aryloxy radicals, a carboxyl radical which is free, salified, esterified with an alkyl radical or amidated with a radical $NA^6A^7$ such that either $A^6$ and $A^7$, which may be identical or different, are chosen from a hydrogen atom and optionally substituted alkyl, alkoxyalkyl, phenoxyalkyl, aryl, arylalkyl, cycloalkyl, cycloalkylalkyl, heterocycloalkylalkyl and heteroarylalkyl radicals, or $A^6$ and $A^7$ form, together with the nitrogen atom to which they are attached, an optionally substituted 5- or 6-membered cyclic radical, it being understood that two consecutive radicals among $A_1$, $A_2$, $A_3$ and $A_4$ can form, with the benzimidazole radical to which they are attached, a 5- to 6-membered carbon-based ring containing one or more hetero atoms, which may be identical or different, chosen from O, N and S, $A_5$ represents a hydrogen atom or an alkyl radical, $R^6$b represents hydrogen, alkyl, alkenyl, cycloalkyl, phenyl, phenylalkyl and cycloalkylalkyl, all the alkyl, alkenyl, aryl, heteroaryl, aryloxy, cycloalkyl and heterocycloalkyl radicals present in the above radicals being optionally substituted with one or more radicals chosen from halogen atoms and hydroxyl, cyano, alkyl, alkoxy, amino, alkylamino, dialkylamino, phenylamino, phenylalkylamino, acylamino(NH—$COR^6$), —C(=O)$OR^6$b, acyl —C(=O) $R^6$b, hydroxyalkyl, carboxyalkyl, phenoxyalkyl, $S(O)_n$-alk, $S(O)_n$—$NH_2$, $S(O)_n$—NH(alk), $S(O)_n$—N(alk)$_2$, $CF_3$, $OCF_3$, $NO_2$, CN, phenyl, itself optionally substituted with one or more halogen atoms, thienyl, phenoxy, phenylalkoxy, —C(=O)—$NH_2$, —C(=O)—NH(alk) and C(=O)—N (alk)$_2$ radicals, all the above alkyl, alkenyl, alkoxy and alkylthio radicals being linear or branched and containing not more than 4 carbon atoms, all the phenyl radicals of the above radicals furthermore being optionally substituted with a dioxole radical, n represents an integer from 0 to 2, the said compounds of formula (IA) being in any possible racemic, enantiomeric or diastereoisomeric isomer form, and also the addition salts with mineral and organic acids or with mineral and organic bases of the said compounds of formula (IA).

A subject of the present invention is thus the compounds of formula (I) as defined above, corresponding to the formula (IAa):

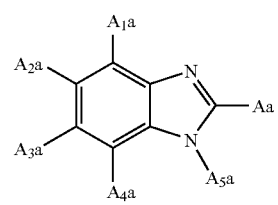

(IAa)

in which Aa represents a pyrazolyl, triazolyl or indazolyl radical, this heterocycle Aa being optionally substituted with one or more radicals $XA^1$, $XA^2$ or $XA^3$ chosen from the values indicated hereinabove for the radicals $X^1$, $X^2$ or $X^3$, $A_1$a, $A_2$a, $A_3$a and $A_4$a, which may be identical or different, are chosen from a hydrogen atom, halogen atoms, hydroxyl, alkyl, alkoxy, nitro, cyano, phenyl and phenoxy radicals, and a carboxyl radical which is free, salified, esterified with an alkyl radical or amidated with a radical $NA^6aA^7a$ such that either $A^6$a and $A^7$a, which may be identical or different, are chosen from a hydrogen atom and alkyl, phenyl, phenylalkyl, cycloalkylalkyl, cycloalkyl, furylalkyl, thienylalkyl and pyridylalkyl radicals, or A6a and A7a form, together with the nitrogen atom to which they are attached, a pyrrolidinyl, pyrazolidinyl, pyrazolinyl, piperidyl, morpholino or piperazinyl radical optionally substituted on the second nitrogen atom with an alkyl or phenyl radical, which are themselves optionally substituted, it being understood that two consecutive radicals from among $A_1$a, $A_2$a, $A_3$a and $A_4$a may form, with the benzimidazole radical to which they are attached, an optionally substituted 5- to 6-membered carbon-based ring containing one or two oxygen atoms, $A_5a$ represents a hydrogen atom or an alkyl radical, the phenyl and phenoxy radicals above being optionally substituted with one or more radicals chosen from halogen atoms and hydroxyl, cyano, trifluoromethyl, trifluoromethoxy, alkyl, alkoxy, amino, alkylamino, dialkylamino, phenylamino, phenylalkylamino, free, salified or esterified carboxyl, and dioxole radicals, all the alkyl, alkoxy and alkylthio radicals above being linear or branched and containing not more than 6 carbon atoms, the said compounds of formula (IAa) being in any possible racemic, enantiomeric or diastereoisomeric isomer form, and also the addition salts with mineral and organic acids or with mineral and organic bases of the said compounds of formula (IAa).

The substituents $X^1$, $X^2$ and $X^3$ as defined above are in particular such that one represents a hydrogen atom and the other two, which may be identical or different, are chosen from halogen atoms and OH, $R^4a$, $OR^4a$, $CF_3$, $OCF_3$, $NO_2$, CN, $NY^1aY^2a$, acylamino(NH—$COR^6b$), $S(O)_n$-alk, $S(O)_n$—$NH_2$, $S(O)_n$—NH(alk), $S(O)_n$—N(alk)$_2$, —C(=O)—$NH_2$, —C(=O)—NH(alk), C(=O)—N(alk)$_2$, —C(=O)$OR^4a$, —N($R^6b$)C(=O)$R^4a$, —N($R^6b$)$SO_2R^4a$, —N($R^6b$)C(=O)$NY^1aY^2a$, —N($R^6b$)C(=O)$OR^4a$, —OC(=O)$NY^1aY^2a$ and thienyl radicals, the thienyl radical being optionally substituted with an alkyl radical, $R^4a$, $Y^1a$, $Y^2a$ and $R^6b$ having the values defined above and alk representing a linear or branched alkyl radical including not more than 6 carbon atoms and optionally substituted as indicated above.

All the alkylthio radicals are such that the sulfur atom is optionally oxidized to sulfone or sulfoxide with one or two oxygen atoms.

Tables I, II and III described below give examples of compounds illustrating the present invention, with in particular substituents chosen from the values of $X^1$, $X^2$ and $X^3$ as defined above.

TABLE I

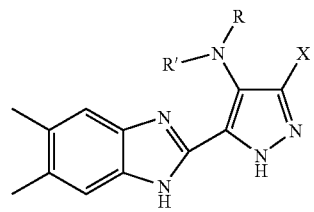

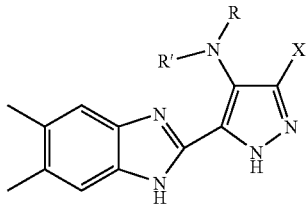

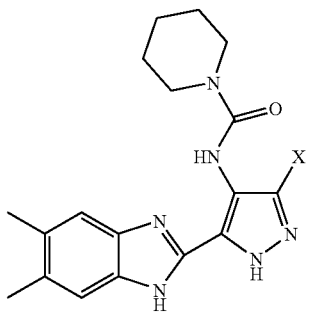

TABLE I-continued

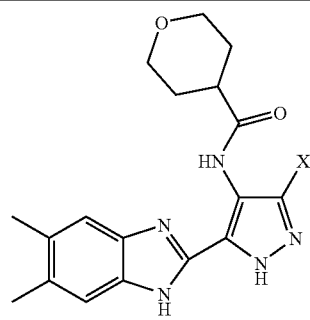

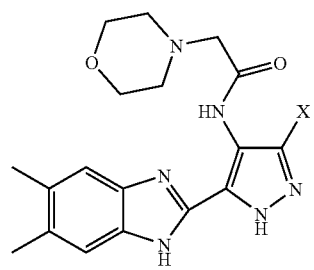

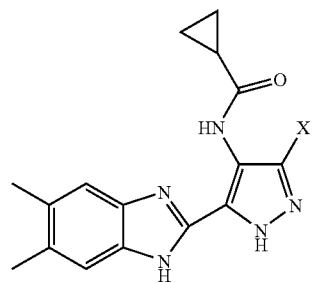

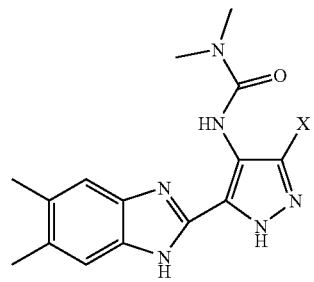

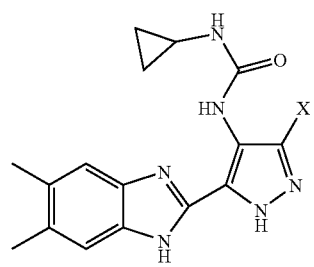

TABLE I-continued
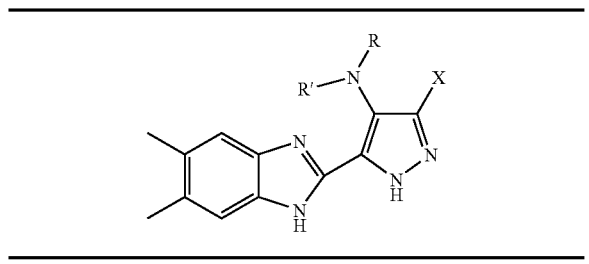
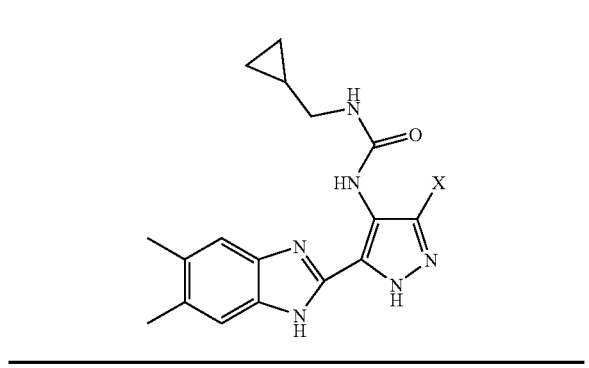
with X represents hydrogen, halogen or alkoxy as defined above.
TABLE II
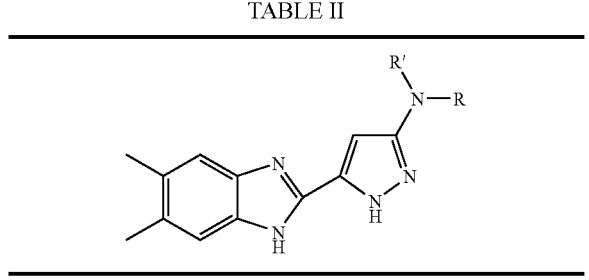
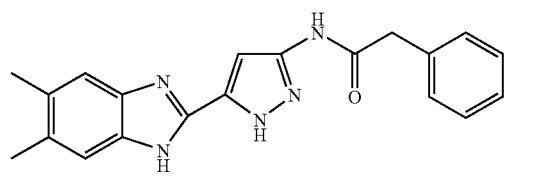
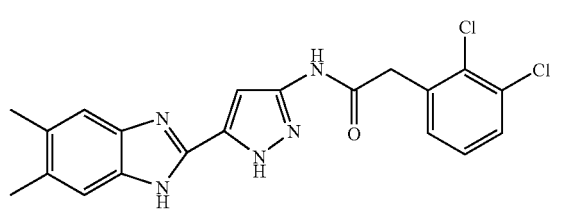
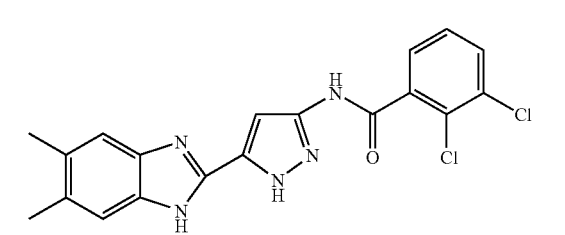
TABLE II-continued
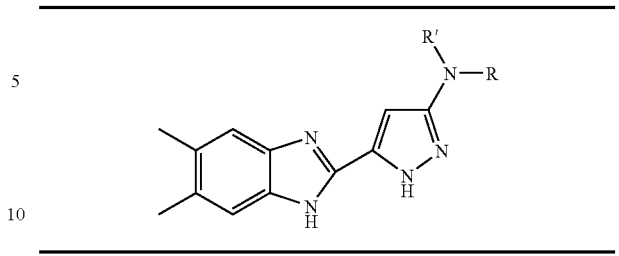
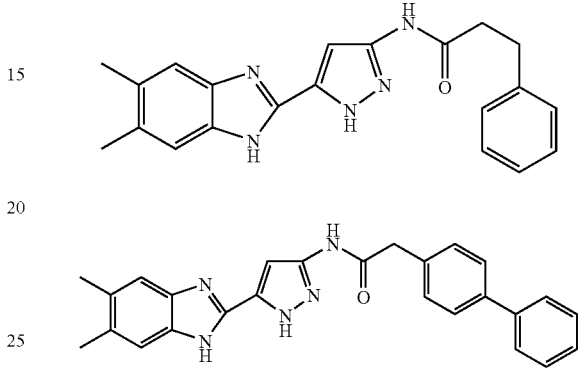
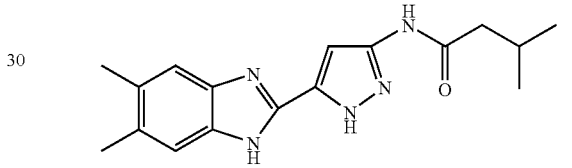
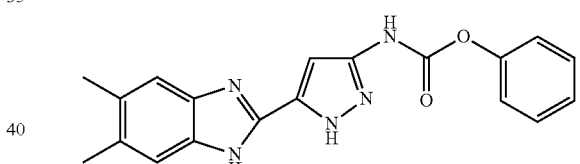
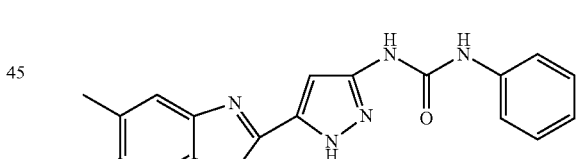
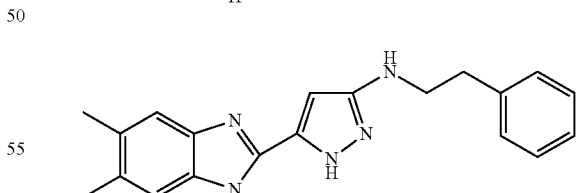
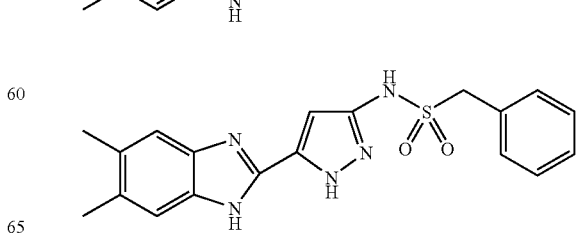

TABLE II-continued
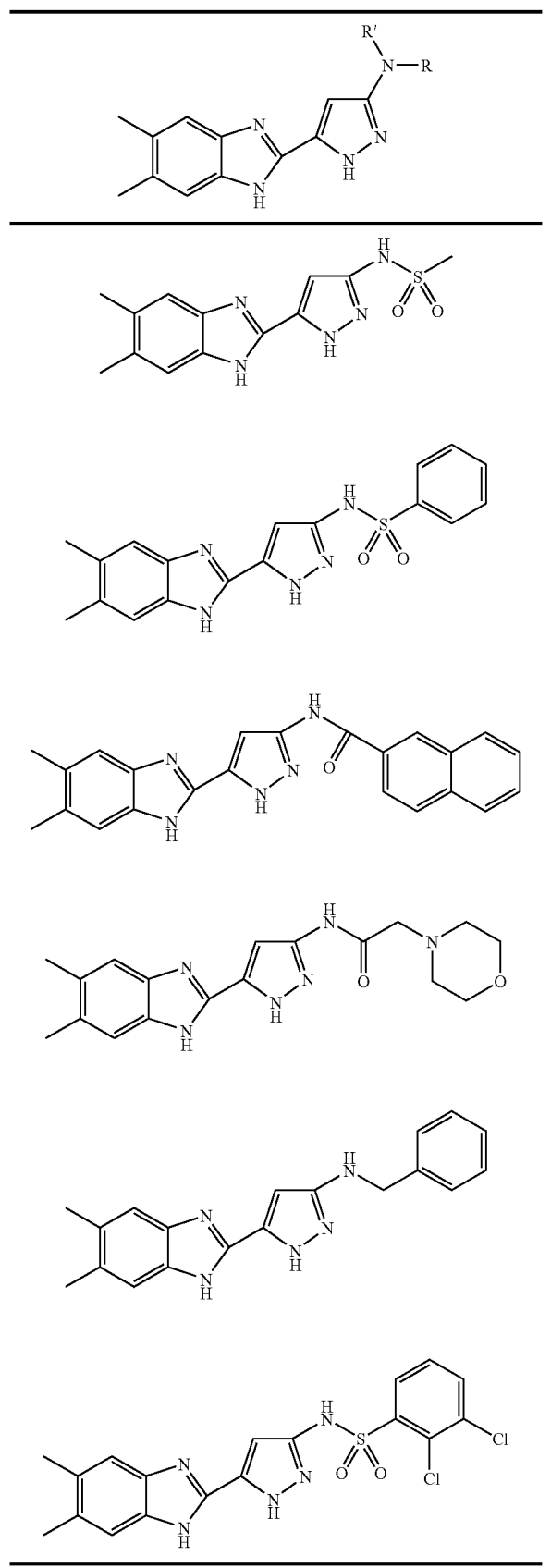
in which NR'R represents NY$^1$Y$^2$ as defined above.
TABLE III
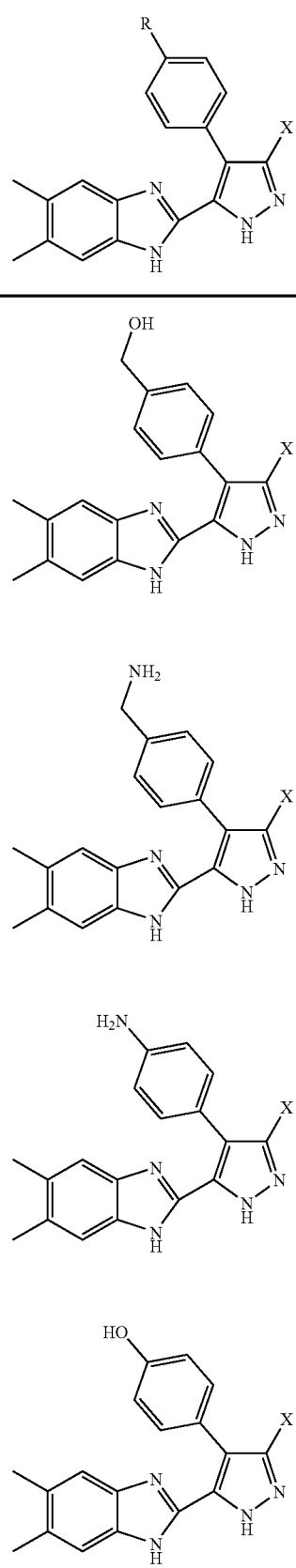

TABLE III-continued

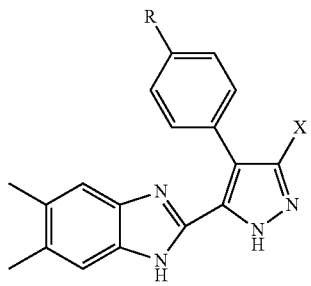

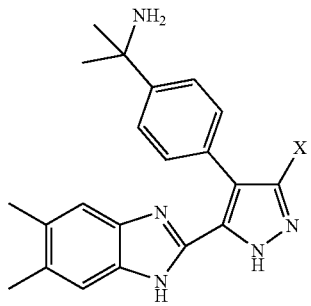

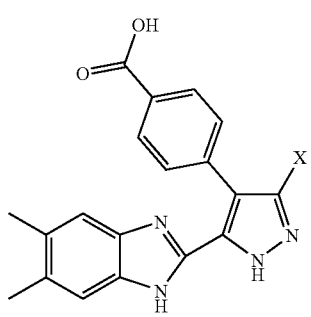

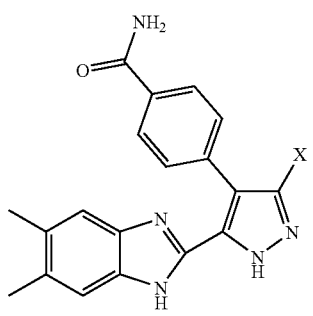

in which X represents hydrogen, alkynyl or NHCOCH$_2$Ph which is optionally substituted.

The subject of the present invention is thus the compounds of formula (I) as defined above in which the substituents of the said compounds of formula (I) have the any of the values indicated as defined hereinabove and in which the aryl radicals represent the phenyl and naphthyl radicals; the heteroaryl radicals represent the furyl, thienyl, benzothienyl, thianthrenyl, pyridyl, pyrazolyl, benzimidazolyl, benzofuran, isobenzofuran and dihydrobenzofuran radicals; the cycloalkyl radicals represent a cyclopropyl, cyclobutyl, cyclopentyl or cyclohexyl radical; the heterocycloalkyl radicals represent the hexahydropyran, piperidyl or morpholino radicals; the heterocycloalkylalkyl radicals represent the hexahydropyranylalkyl, piperidylalkyl and morpholinoalkyl radicals; the arylalkyl radicals represent the phenylalkyl, ethylenedioxyphenylalkyl and naphthylalkyl radicals; the heteroarylalkyl radicals represent the thienylalkyl, pyridylalkyl, furylalkyl, pyrazolylalkyl, benzothienylalkyl, dihydrobenzofuranylalkyl and benzimidazolylalkyl radicals; the aryloxy radicals represent the phenoxy and naphthyloxy radicals; the arylalkoxy radicals represent the phenylalkoxy and naphthylalkoxy radicals; and the aryloxyalkyl radicals represent the phenoxyalkyl radical; all these radicals being optionally substituted as indicated hereinabove.

One subject of the present invention is, more particularly, the compounds of formula (I) as defined above corresponding to the formula (IA):

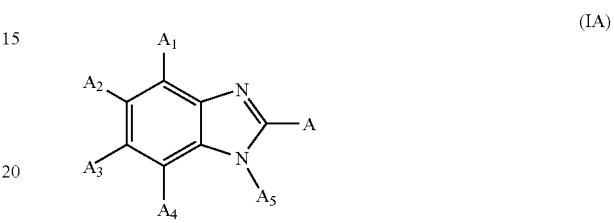

(IA)

in which A represents a saturated heterocyclic radical which is either a 5- or 6-membered monocyclic radical or a bicyclic radical that is not more than 10-membered, these members being such that at least two of them represent a nitrogen atom and the others, which may be identical or different, represent a carbon member or a hetero atom member chosen from O, N and S, this heterocycle A optionally being substituted with one or more radicals $XA^1$, $XA^2$ or $XA^3$ chosen from halogen atoms, alkyl, alkoxy or alkylthio radicals or thienyl radicals optionally substituted with an alkyl radical, $A_1$, $A_2$, $A_3$ and $A_4$, which may be identical or different, are chosen from a hydrogen atom, halogen atoms and hydroxyl, alkyl, alkoxy, nitro, cyano, phenyl and phenoxy radicals, a carboxyl radical which is free, salified, esterified with an alkyl radical or amidated with a radical $NA^6A^7$ such that either $A^6$ and $A^7$, which may be identical or different, are chosen from a hydrogen atom and alkyl, phenyl, phenylalkyl, cycloalkylalkyl, cycloalkyl and heteroarylalkyl radicals, or $A^6$ and $A^7$ form, together with the nitrogen atom to which they are attached, a 5- or 6-membered cyclic radical, it being understood that two consecutive radicals among $A_1$, $A_2$, $A_3$ and $A_4$ can form, with the benzimidazole radical to which they are attached, a 5- to 6-membered carbon-based ring containing one or more hetero atoms, which may be identical or different, chosen from O, N and S, $A_5$ represents a hydrogen atom or an alkyl radical, all the phenyl, phenoxy, cycloalkyl and heteroarylalkyl radicals above being optionally substituted with one or more radicals chosen from halogen atoms and hydroxyl, cyano, trifluoromethyl, trifluoromethoxy, alkyl, alkoxy, amino, alkylamino, dialkylamino, phenylamino, phenylalkylamino, free, salified or esterified carboxyl, and dioxole radicals, all the alkyl, alkoxy and alkylthio radicals above being linear or branched and containing not more than 6 carbon atoms, the said compounds of formula (IA) being in any possible racemic, enantiomeric or diastereoisomeric isomer form, and also the addition salts with mineral and organic acids or with mineral and organic bases of the said compounds of formula (IA).

A subject of the present invention is also, more particularly, the compounds of formula (D) as defined above, corresponding to the formula (IAb):

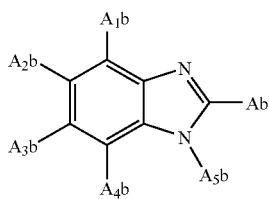

(IAb)

in which Ab represents a pyrazolyl or indazolyl radical optionally substituted with one or two radicals chosen from halogen atoms and OH, alkyl, alkynyl, —$OR^6b$ (including alkoxy), —$COR^6b$, —O—$COR^6b$, —$OS(O)_nR^6b$, —$O(CH_2)_n$—CO—$R^6b$, phenyl, phenylalkyl, $CF_3$, $OCF_3$, $NO_2$, CN, $NY^1bY^2b$, —NH—C(=O)$NY^1bY^2b$, acylamino (NH—CO—$R^6b$), $S(O)_n$-alk, $S(O)_n$—$NY^1bY^2b$, —C(=O)—$NY^1bY^2b$, —C(=O)$OR^6b$, —NH—C(=O)$R^6b$, —NH—$S(O)_nR^6b$, —NH—C(=O)$OR^6b$, —N($R^6b$)C(=O)$NY^1bY^2b$, —OC(=O)$NY^1bY^2b$ and thienyl radicals, all these radicals being optionally substituted, with $NY^1bY^2b$ such that either $Y^1b$ and $Y^2b$, which may be identical or different, are chosen from hydrogen and optionally substituted alkyl, cycloalkyl, cycloalkylalkyl, phenyl, naphthyl, phenoxy, phenylalkyl, phenylalkylthio and naphthylalkyl or $Y^1b$ and $Y^2b$ form, together with the nitrogen atom to which they are attached, a piperidyl, hexahydrofuran, morpholinyl or morpholinylalkyl radical, $A_1b$, $A_2b$, $A_3b$ and $A_4b$, which may be identical or different, are chosen from a hydrogen atom, halogen atoms, hydroxyl, alkyl, alkenyl, —$OR^6b$ (including alkoxy), —CO—$R^6b$, —O—$COR^6b$, —$OS(O)_nR^6b$, —O($CH_2)_n$—CO—$R^6b$, nitro, cyano, furyl, thienyl, benzothienyl, naphthyl, thianthrenyl, phenyl and phenoxy radicals and a carboxyl radical which is free, salified, esterified with an alkyl radical or amidated with a radical $NA^6bA^7b$ such that either $A^6b$ and $A^7b$, which may be identical or different, are chosen from hydrogen and alkyl, alkoxyalkyl, phenoxyalkyl, phenyl, phenylalkyl, cycloalkylalkyl, cycloalkyl, furylalkyl, naphthylalkyl, thienylalkyl, piperidylalkyl, pyridylalkyl, benzothienylalkyl, pyrazolylalkyl, dihydrobenzofuranylalkyl, hexahydropyranylalkyl, ethylenedioxyphenylalkyl and benzimidazolylalkyl radicals, all these radicals being optionally substituted, or $A^6b$ and $A^7b$ form, together with the nitrogen atom to which they are attached, a pyrrolidinyl, morpholino or piperazinyl radical, the piperazinyl radical being optionally substituted on the second nitrogen atom with an alkyl radical itself optionally substituted, it being understood that two consecutive radicals among $A_1b$, $A_2b$, $A_3b$ and $A_4b$ can form, with the benzimidazole radical to which they are attached, an optionally substituted 4,5-ethylenedioxybenzimid-azole radical or an optionally substituted 4,5-methylenedioxybenzimidazole radical, $A_5b$ represents a hydrogen atom, all the above radicals containing alkyl, alkenyl, phenyl, phenoxy, furyl, thienyl, piperidyl, pyridyl, pyrazolyl and benzimidazolyl being optionally substituted with one or more radicals chosen from halogen atoms and hydroxyl, cyano, alkyl, alkoxy, amino, alkylamino, dialkylamino, phenylamino, phenylalkylamino, acylamino(NH—$COR^6b$), —C(=O)$OR^6b$, acyl —C(=O)$R^6b$, hydroxyalkyl, carboxyalkyl, phenoxyalkyl, $S(O)_n$-alk, $S(O)_n$—$NH_2$, $S(O)_n$—NH(alk), $S(O)_n$—N(alk)$_2$, $CF_3$, $OCF_3$, $NO_2$, CN, phenyl, itself optionally substituted with one or more halogen atoms, thienyl, phenoxy, phenylalkoxy, —C(=O)—$NH_2$, —C(=O)—NH(alk) and C(=O)—N(alk)$_2$ radicals, with n representing an integer from 0 to 2, and $R^6b$ representing hydrogen, alkyl, alkenyl, cycloalkyl, phenyl, pyridyl, thienyl, naphthyl, isoxazole, adamentyl, quinoline, quinolone, dihydroquinolone, —NH-phenyl, phenylalkyl and cycloalkylalkyl, all these radicals being optionally substituted with a morpholino, piperidyl or phenyl radical itself optionally substituted with one or more radicals chosen from halogen atoms and the cyano, $CF_3$, $OCF_3$, alkyl, phenyl-$S(O)_n$-alk-phenyl, alkoxy, $NH_2$, NHalk, N(alk)$_2$, $SO_2NH_2$, $SO_2$Nalk or $SO_2$N(alk)$_2$ radical, all the alkyl, alkenyl, alkoxy and alkylthio radicals above being linear or branched and containing not more than 10 carbon atoms, all the phenyl radicals of the above radicals furthermore being optionally substituted with a dioxole radical, the said compounds of formula (IAb) being in any possible racemic, enantiomeric or diastereomeric isomer form, and also the addition salts with mineral and organic acids or with mineral and organic bases of the said compounds of formula (IAb).

One subject of the present invention is thus in particular the compounds of formula (I) as defined above corresponding to the formula (IAb) in which Ab represents a pyrazolyl or indazolyl radical optionally substituted with one or two radicals chosen from halogen atoms and OH, alkyl, alkynyl, alkoxy, phenyl, phenylalkyl, $CF_3$, $OCF_3$, $NO_2$, CN, $NY^1bY^2b$, —NH—C(=O)$NY^1bY^2b$, acylamino (NH—CO—$R^6b$), $S(O)_n$-alk, $S(O)_n$—$NY^1bY^2b$, —C(=O)—$NY^1bY^2b$, —C(=O)$OR^6b$, —NH—C(=O)$R^5b$, —NH—S(O)$_nR^6b$, —NH—C(=O)$OR^6b$, —N($R^6b$)C(=O)$NY^1bY^2b$, —OC(=O)$NY^1bY^2b$ and thienyl radicals which are optionally substituted, with $NY^1bY^2b$ such that either $Y^1b$ and $Y^2b$, which may be identical or different, are chosen from hydrogen and optionally substituted alkyl, cycloalkyl, cycloalkylalkyl, phenyl, naphthyl, phenoxy, phenylalkyl, phenylalkylthio and naphthylalkyl or $Y^1b$ and $Y^2b$ form, together with the nitrogen atom to which they are attached, a piperidyl, hexahydrofuran, morpholinyl or morpholinylalkyl radical, $A_1b$, $A_2b$, $A_3b$ and $A_4b$, which may be identical or different, are chosen from a hydrogen atom, halogen atoms, hydroxyl, alkyl, alkenyl, alkoxy, nitro, cyano, furyl, thienyl, benzothienyl, naphthyl, thianthrenyl, phenyl and phenoxy radicals and a carboxyl radical which is free, salified, esterified with an alkyl radical or amidated with a radical $NA^6bA^7b$ such that either $A^6b$ and $A^7b$, which may be identical or different, are chosen from hydrogen and alkyl, alkoxyalkyl, phenoxyalkyl, phenyl, phenylalkyl, cycloalkylalkyl, cycloalkyl, furylalkyl, naphthylalkyl, thienylalkyl, piperidylalkyl, pyridylalkyl, benzothienylalkyl, pyrazolylalkyl, dihydrobenzofuranylalkyl, hexahydropyranylalkyl, ethylenedioxyphenylalkyl and benzimidazolylalkyl radicals, all these radicals being optionally substituted, or $A^6b$ and $A^7b$ form, together with the nitrogen atom to which they are attached, a pyrrolidinyl, morpholino or piperazinyl radical, the piperazinyl radical being optionally substituted on the second nitrogen atom with an alkyl radical itself optionally substituted, it being understood that two consecutive radicals among $A_1b$, $A_2b$, $A_3b$ and $A_4b$ can form, with the benzimidazole radical to which they are attached, an optionally substituted 4,5-ethylenedioxybenzimidazole radical or an optionally substituted
4,5-methylenedioxybenzimidazole radical, $A_5b$ represents a hydrogen atom, all the above radicals containing alkyl, alkenyl, phenyl, phenoxy, furyl, thienyl, piperidyl, pyridyl, pyrazolyl and benzimidazolyl being optionally substituted with one or more radicals chosen from halogen atoms and hydroxyl, cyano, alkyl, alkoxy, amino, alkylamino, dialkylamino, phenylamino, phenylalkylamino, acylamino(NH—$COR^6b$), —C(=O)$OR^6b$, acyl —C(=O)$R^6b$, hydroxyalkyl, carboxyalkyl, phenoxyalkyl, S(O)$_n$-alk, S(O)$_n$—$NH_2$, S(O)$_n$—NH(alk), S(O)$_n$—N(alk)$_2$, $CF_3$, $OCF_3$, $NO_2$, CN, phenyl, itself optionally substituted with one or more halogen atoms, thienyl, phenoxy, phenylalkoxy, —C(=O)—$NH_2$, —C(=O)—NH(alk) and C(=O)N(alk)$_2$ radicals, with n representing an integer from 0 to 2, and $R^6b$ representing hydrogen, alkyl, alkenyl, cycloalkyl, phenyl, phenylalkyl and cycloalkylalkyl, all the alkyl, alkenyl, alkoxy and alkylthio radicals above being linear or branched and containing not more than 10 carbon atoms, all the phenyl radicals of the above radicals furthermore being optionally substituted with a dioxole radical, the said compounds of formula (IAb) being in any possible racemic, enantiomeric or diastereoisomeric isomer form, and also the addition salts with mineral and organic acids or with mineral and organic bases of the said compounds of formula (IAb).

A subject of the present invention is thus in particular the compounds of formula (I) as defined above corresponding to the formula (IAb) in which Ab represents a pyrazolyl radical substituted with one or two radicals such that one is chosen from hydrogen, halogen atoms and alkyl, alkynyl, —$COR^6b$, phenyl, phenylalkyl, $CF_3$, $NO_2$, CN, $NY^1bY^2b$, —NH—C(=O)$NY^1bY^2b$, NH—CO—$R^6b$, S(O)$_n$-alk, S(O)$_n$—$NY^1bY^2b$, —C(=O)—$NY^1bY^2b$, —C(=O)$OR^6b$, —NH—C(=O)$R^6b$, —NH—S(O)$_nR^6b$, —NH—C(=O)$OR^6b$, —N($R^6b$)C(=O)$NY^1bY^2b$ and thienyl radicals, all these radicals being optionally substituted, and the other is chosen from OH, —$OR^6b$, —O—$COR^6b$, —OS(O)$_nR^6b$, —O(CH$_2$)$_n$—CO—$R^6b$ and —OC(=O)$NY^1bY^2b$ radicals, all these radicals being optionally substituted, with $NY^1bY^2b$ such that $Y^1b$ and $Y^2b$, which may be identical or different, are chosen from hydrogen and optionally substituted alkyl, cycloalkyl, cycloalkylalkyl, phenyl, naphthyl, phenoxy, phenylalkyl, phenylalkylthio and naphthylalkyl or $Y^1b$ and $Y^2b$ form, together with the nitrogen atom to which they are attached, a piperidyl, hexahydrofuran, morpholinyl or morpholinylalkyl radical, $A_1b$, $A_2b$, $A_3b$ and $A_4b$, which may be identical or different, are such that two of them represent hydrogen and the other two, which may be identical or different, are chosen from a hydrogen atom, halogen atoms, hydroxyl, alkyl, alkenyl, —$OR^6b$ (including alkoxy), —CO—$R^6b$, —O—$COR^6b$, —OS(O)$_nR^6b$, —O(CH$_2$)$_n$—CO—$R^6b$, nitro, cyano, furyl, thienyl, benzothienyl, naphthyl, thianthrenyl, phenyl and phenoxy radicals and a carboxyl radical which is free, salified, esterified with an alkyl radical or amidated with a radical $NA^6bA^7b$ such that either $A^6b$ and $A^7b$, which may be identical or different, are chosen from hydrogen and alkyl, alkoxyalkyl, phenoxyalkyl, phenyl, phenylalkyl, cycloalkylalkyl, cycloalkyl, furylalkyl, naphthylalkyl, thienylalkyl, piperidylalkyl, pyridylalkyl, benzothienylalkyl, pyrazolylalkyl, dihydrobenzofuranylalkyl, hexahydropyranylalkyl, ethylenedioxyphenylalkyl and benzimidazolylalkyl radicals, all these radicals being optionally substituted, or $A^6b$ and $A^7b$ form, together with the nitrogen atom to which they are attached, a pyrrolidinyl, morpholino or piperazinyl radical, the piperazinyl radical being optionally substituted on the second nitrogen atom with an alkyl radical itself optionally substituted, $A_5b$ represents a hydrogen atom, all the above radicals containing alkyl, alkenyl, phenyl, phenoxy, furyl, thienyl, piperidyl, pyridyl, pyrazolyl and benzimidazolyl being optionally substituted with one or more radicals chosen from halogen atoms and hydroxyl, cyano, alkyl, alkoxy, amino, alkylamino, dialkylamino, phenylamino, phenylalkylamino, acylamino(NH—$COR^6b$), —C(=O)$OR^6b$, acyl —C(=O)$R^6b$, hydroxyalkyl, carboxyalkyl, phenoxyalkyl, S(O)$_n$-alk, S(O)$_n$—$NH_2$, S(O)—NH(alk), S(O)$_n$—N(alk)$_2$, $CF_3$, $OCF_3$, $NO_2$, CN, phenyl, itself optionally substituted with one or more halogen atoms, thienyl, phenoxy, phenylalkoxy, —C(=O)—$NH_2$, —C(=O)—NH(alk) and C(=O)—N(alk)$_2$ radicals, with n representing an integer from 0 to 2, and $R^6b$ representing hydrogen, alkyl, alkenyl, cycloalkyl, phenyl, pyridyl, thienyl, naphthyl, isoxazole, adamentyl, quinoline, quinolone, dihydroquinolone, —NH-phenyl, phenylalkyl and cycloalkylalkyl, all these radicals being optionally substituted with a morpholino, piperidyl or phenyl radical itself optionally substituted with one or more radicals chosen from halogen atoms and the cyano, $CF_3$, $OCF_3$, alkyl, phenyl-S(O)n-alk-phenyl, alkoxy, $NH_2$, NHalk, N(alk)$_2$, $SO_2NH_2$, $SO_2$Nalk or $SO_2$N(alk)$_2$ radical, all the alkyl, alkenyl, alkoxy and alkylthio radicals above being linear or branched and containing not more than 10 carbon atoms, all the phenyl radicals of the above radicals furthermore being optionally substituted with a dioxole radical, the said compounds of formula (IAb) being in any possible racemic, enantiomeric or diastereoisomeric isomer form, and also the addition salts with mineral and organic acids or with mineral and organic bases of the said compounds of formula (IAb).

A subject of the present invention is thus in particular the compounds of formula (I) as defined above corresponding to the formula (IAb) in which Ab represents a pyrazolyl or indazolyl radical optionally substituted with one or more radicals chosen from halogen atoms and alkyl, alkoxy and thienyl radicals, $A_1b$, $A_2b$, $A_3b$ and $A_4b$, which may be identical or different, are chosen from a hydrogen atom; halogen atoms; radicals of the following types: hydroxyl, alkyl, alkenyl optionally substituted with phenyl itself optionally substituted with one or more halogen atoms, alkoxy, nitro, cyano, furyl, thienyl optionally substituted with acyl COalk, benzothienyl, naphthyl, thianthrenyl, phenyl and phenoxy which are optionally substituted; and a carboxyl radical which is free, salified, esterified with an alkyl radical or amidated with a radical $NA^6bA^7b$ such that either $A^6b$ and $A^7b$, which may be identical or different, are chosen from hydrogen and radicals of the following types: alkyl, alkoxyalkyl containing not more than 6 carbon atoms, phenoxyalkyl optionally substituted with acylamino NH—C(O)alk, phenyl, optionally substituted phenylalkyl, cycloalkylalkyl, cycloalkyl, furylalkyl optionally substituted with one or more alkyl radicals, naphthylalkyl, thienylalkyl optionally substituted with alkyl or thienyl, piperidylalkyl optionally substituted with a carboxyl radical which is free, salified or esterified with an alkyl radical, pyridylalkyl optionally substituted with one or more radicals chosen from halogen and CF3, benzothienylalkyl, pyrazolylalkyl optionally substituted with one or more alkyl radicals, dihydrobenzofuranylalkyl, hexahydropyranylalkyl, ethylenedioxyphenylalkyl, and benzimidazolylalkyl optionally substituted with one or more alkyl radicals, or $A^6b$ and $A^7b$ form, together with the nitrogen atom to which they are attached, a pyrrolidinyl, morpholino or piperazinyl radical, the piperazinyl radical being optionally substituted on the second nitrogen atom with an alkyl radical, it being understood that two consecutive radicals among $A_1b, A_2b, A_3b$ and $A_4b$ can form, with the benzimidazole radical to which they are attached, an optionally substituted 4,5-ethylenedioxybenzimidazole radical or an optionally substituted 4,5-methylenedioxybenzimidazole radical, $A_5a$ represents a hydrogen atom, the phenyl, phenoxy and phenylalkyl radicals above being optionally substituted with one or more radicals chosen from halogen atoms, hydroxyl, cyano, alkyl, alkoxy, amino, alkylamino, dialkylamino, phenylamino, phenylalkylamino and NH—COalk radicals, a carboxyl radical which is free, salified or esterified with an alkyl radical, and hydroxyalkyl, carboxyalkyl, phenoxyalkyl, alkylthio, $SO_2$alk, $SO_2NH_2$, $SO_2$—NH(alk), $SO_2$—N(alk)$_2$, $CF_3$, $OCF_3$, $NO_2$, CN, phenyl, itself optionally substituted with one or more halogen atoms, thienyl, phenoxy, phenylalkoxy, —C(=O)—NH$_2$, —C(=O)—NH(alk), C(=O)—N(alk)$_2$ and C(O)CH$_3$ radicals, all the alkyl or alk, alkenyl, alkoxy and alkylthio radicals above being linear or branched and containing not more than 4 carbon atoms, all the phenyl radicals of the above radicals furthermore being optionally substituted with a dioxole radical, the said compounds of formula (IAb) being in any possible racemic, enantiomeric or diastereoisomeric isomer form, and also the addition salts with mineral and organic acids or with mineral and organic bases of the said compounds of formula (IAb).

A subject of the present invention is thus in particular the compounds of formula (I) as defined above corresponding to the formula (IAb) in which Ab, $A_1b, A_2b, A_3b, A_4b$ and $A_5b$ have any of the meanings indicated hereinabove, and when one of $A_1b, A_2b, A_3b$ and $A_4b$ represents a carboxyl radical amidated with a radical $NA^6bA^7b$, then either one of $A^6b$ and $A^7b$ represents a hydrogen atom or an alkyl radical and the other of $A^6b$ and $A^7b$ is chosen from the values defined for $A^6b$ and $A^7b$, or $A^6b$ and $A^7b$ form, together with the nitrogen atom to which they are attached, a 5- or 6-membered cyclic radical, the other substituents of the said compounds of formula (I) having the any of the values indicated hereinabove, the said compounds of formula (IAb) being in any possible racemic, enantiomeric or diastereoisomeric isomer form, and also the addition salts with mineral and organic acids or with mineral and organic bases of the said compounds of formula (IAb).

A subject of the present invention is thus in particular the compounds of formula (I) as defined above in which X, W, Y and Z are such that two or three of them represent CH and the others are chosen from the values of $CR^2$ or $CR^3$ and, if appropriate, i.e., when two of them represent CH and $CR^2$ and $CR^3$ are adjacent to each other, can form a dioxole radical, $R^2$, $R^3$ and the other substituents of the said compounds of formula (I) having any of the values as defined hereinabove, the said compounds of formula (I) being in any possible racemic, enantiomeric or diastereoisomeric isomer form, and also the addition salts with mineral and organic acids or with mineral and organic bases of the said compounds of formula (I).

The present invention thus relates in particular to the compounds of formula (IA) as defined above in which $A_1, A_2, A_3$ and $A_4$ are such that two or three of them represent a hydrogen atom and the others are chosen from the values of $A_1, A_2, A_3$ and $A_4$ and, if appropriate, i.e., when two of them represent a hydrogen atom and the other two are on adjacent carbons, can form a dioxole radical, the other substituents of the compounds of formula (IA) having any of the values as defined hereinabove, the said compounds of formula (IA) being in any possible racemic, enantiomeric or diastereoisomeric isomer form, and also the addition salts with mineral and organic acids or with mineral and organic bases of the said compounds of formula (IA).

A subject of the present invention is also, more particularly, the compounds of formula (I) as defined above, corresponding to the formula (IAa):

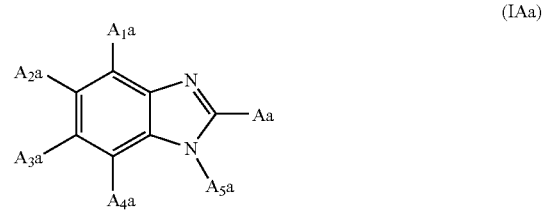

(IAa)

in which Aa represents a pyrazolyl, triazolyl or indazolyl radical, this heterocycle Aa being optionally substituted with one or more radicals $XA^1, XA^2$ or $XA^3$ chosen from halogen atoms, alkyl, alkoxy or alkylthio radicals and thienyl radicals optionally substituted with an alkyl radical, $A_1a, A_2a, A_3a$ and $A_4a$, which may be identical or different, are chosen from a hydrogen atom, halogen atoms, hydroxyl, alkyl, alkoxy, nitro, cyano, phenyl and phenoxy radicals, and a carboxyl radical which is free, salified, esterified with an alkyl radical or amidated with a radical $NA^6aA^7a$ such that either $A^6a$ and $A^7a$, which may be identical or different, are chosen from a hydrogen atom and alkyl, phenyl, phenylalkyl, cycloalkylalkyl, cycloalkyl, furylalkyl, thienylalkyl and pyridylalkyl radicals, or $A^6a$ and $A^7a$ form, together with the nitrogen atom to which they are attached, a pyrrolidinyl, pyrazolidinyl, pyrazolinyl, piperidyl, morpholino or piperazinyl radical optionally substituted on the second nitrogen atom with an alkyl or phenyl radical, which are themselves optionally substituted, it being understood that two consecutive radicals from among $A_1a, A_2a, A_3a$ and $A_4a$ may form, with the benzimidazole radical to which they are attached, an optionally substituted 5- to 6-membered carbon-based ring containing one or two oxygen atoms, A5a represents a hydrogen atom or an alkyl radical, the phenyl and phenoxy radicals above being optionally substituted with one or more radicals chosen from halogen atoms and hydroxyl, cyano, trifluoromethyl, trifluoromethoxy, alkyl, alkoxy, amino, alkylamino, dialkylamino, phenylamino, phenylalkylamino, free, salified or esterified carboxyl, and dioxole radicals, all the alkyl, alkoxy and alkylthio radicals above being linear or branched and containing not more than 6 carbon atoms, the said compounds of formula (IAa) being in any possible racemic, enantiomeric or diastereoisomeric isomer form, and also the addition salts with mineral and organic acids or with mineral and organic bases of the said compounds of formula (IAa).

One subject of the present invention is, more particularly, the compounds of formula (I) as defined above in which $R^1$ represents a pyrazolyl or indazolyl radical, the other substituents having the values indicated above or below.

Among the preferred compounds that are particularly noted are the compounds of formula (I) in which Aa represents a pyrazolyl or indazolyl radical optionally substituted as indicated above and below, $A_1a$, $A_2a$, $A_3a$ and $A_4a$ are chosen from the following values:

$A_1a$ represents hydrogen or carboxyl or forms a ring with the adjacent member $A_2a$ $A_4a$ represents hydrogen or carboxyl or forms a ring with the adjacent member $A_3a$ $A_2a$ represents a carboxyl radical that is free, salified, esterified with an optionally substituted alkyl radical or an amidated carboxyl as indicated above or below, $A_2a$ and $A_3a$ represent two optionally substituted alkyl radicals, $A_5a$ represents hydrogen.

One subject of the present invention is, even more particularly, the compounds of formula (I) as defined above, corresponding to the formula (IAb):

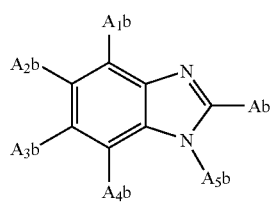

(IAb)

in which Ab represents a pyrazolyl or indazolyl radical optionally substituted with one or more radicals chosen from halogen atoms and alkyl, alkoxy and thienyl radicals, $A_1b$, $A_2b$, $A_3b$ and $A_4b$, which may be identical or different, are chosen from a hydrogen atom, halogen atoms, hydroxyl, alkyl and alkoxy, nitro, cyano, phenyl and phenoxy radicals, and a carboxyl radical that is free, salified, esterified with an alkyl radical or amidated with a radical $NA^6bA^7b$ such that either $A^6b$ and $A^7b$, which may be identical or different, are chosen from alkyl, phenyl, phenylalkyl, cycloalkylalkyl, cycloalkyl and furylalkyl radicals, or $A^6b$ and $A^7b$ form, together with the nitrogen atom to which they are attached, a pyrrolidinyl, morpholino or piperazinyl radical optionally substituted on the second nitrogen atom with an alkyl radical, it being understood that two consecutive radicals from among $A_1b$, $A_2b$, $A_3b$ and $A_4b$ may form, with the benzimidazole radical to which they are attached, an optionally substituted 4,5-ethylenedioxybenzimidazole radical or 4,5-methylenedioxybenzimidazole radical, $A_5b$ represents a hydrogen atom, the phenyl and phenoxy radicals above being optionally substituted with one or more radicals chosen from halogen atoms and hydroxyl, cyano, alkyl, alkoxy, amino, alkylamino, dialkylamino, phenylamino, phenylalkylamino and free, salified or esterified carboxyl radicals, all the alkyl, alkoxy and alkylthio radicals above being linear or branched and containing not more than 4 carbon atoms, the said compounds of formula (IAb) being in any possible racemic, enantiomeric or diastereoisomeric isomer from, and also the addition salts with mineral and organic acids or with mineral and organic bases of the said compounds of formula (IAb).

With reference to formula (Ix) above, the following are particular and preferred groupings:

$R^1$ may particularly represent optionally substituted heteroaryl. Exemplary optionally substituted heteroaryls include dihydrofuropyrazolyl, imidazolyl, indazolyl, indolyl, isoxazolyl, oxodihydropyridazinyl, oxodihydropyridinopyrazolyl, oxodihydropyridinyl, oxotetrahydropyrrolopyrazolyl, pyrazolyl, thiazolyl, thienopyrazolyl, tetrahydrocyclopentapyrazolyl, tetrahydroindazolyl, tetrahydropyranopyrazolyl, tetrahydropyridinopyrazolyl, tetrahydropyrrolopyrazolyl or triazolyl. Optional substituents include one or more groups selected from carboxy, cyano, halo, haloalkyl, hydroxy, nitro, $R^4$, —C(=O)$R^4$, —C(=O)N$Y^1Y^2$, —C(=O)O$R^4$, —N($R^6$)C(=O)$R^4$, —N($R^6$)C(=O)N$Y^1Y^2$, —N($R^6$)C(=O)O$R^4$, —N($R^6$SO$_2R^4$, —N($R^6$)SO$_2$N$Y^1Y^2$, —N$Y^1Y^2$, —O$R^4$, —OCF$_2$H, —OCF$_3$, —OC(=O)$R^4$, —OC(=O)N$Y^1Y^2$, —S(O)$_nR^4$ and —S(O)$_2$N$Y^1Y^2$. $R^1$ more preferably represents a heteroaryl moiety

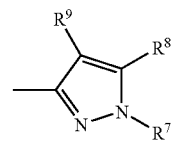

in which $R^7$, $R^8$ and $R^9$ are as hereinbefore defined. It will be appreciated that compounds of formula (Ix) in which $R^1$ represents a heteroaryl moiety

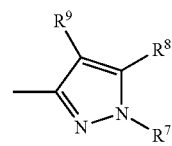

and $R^7$ is hydrogen can exist in the tautomeric forms

W may particularly represent CH when X is CR², Y is CH or CR³ and Z are CH or CR³.

W may also particularly represent CH when X is N, Y is CH or CR³ and Z is CH or CR³.

W may also particularly represent N when X is CH or CR², Y is CH or CR³ and Z is CH or CR³.

W may also particularly represent N when X is CH or CR², Y is CH or CR³ and Z is N.

It is to be understood that this invention covers all appropriate combinations of the particular and preferred groupings referred to herein.

A particular group of compounds of the invention are compounds of formula (Ixa):—

(Ixa)

in which W, X, Y, Z and R⁷ are as hereinbefore defined for compounds of formula (Ix), and R⁸ and R⁹ are independently selected from hydrogen, carboxy, cyano, halo, haloalkyl, hydroxy, nitro, R⁴, —C(=O)R⁴, —C(=O)NY¹Y², —C(=O)OR⁴, —N(R⁶)C(=O)R⁴, —N(R⁶)C(=O)NY¹Y², —N(R⁶)C(=O)OR⁴, —N(R⁶)SO₂R⁴, —NY¹Y², —OR⁴, —OC(=O)R⁴, —OC(=O)NY¹Y², —S(O)ₙR⁴ and —S(O)₂NY¹Y²; and their corresponding N-oxides, and their prodrugs, and their acid bioisosteres; and pharmaceutically acceptable salts and solvates (e.g. hydrates) of compounds of formula (Ixa) and their N-oxides and their prodrugs, and their acid bioisosteres.

Compounds of formula (Ixa) in which W represents CH, X represents CH, Y represents CH and Z represents CH or C—CH₃ are preferred.

Compounds of formula (Ixa) in which W represents CH, X represents CH, Z represents CH and Y represents:

(i) C₁—C₄alkyl [e.g. C—CH₃, C—CH₂CH₃, C—CH₂CH₂CH₃ or C—CH(CH₃)₂];

(ii) C-aryl [e.g. ...];

(iii) C—CN;
(iv) C—NO₂;
(v) C-halo [e.g. C—Br, C—Cl or C—F];
(vi) C-haloalkyl [e.g. C—CF₃];
(vii) C-heteroaryl [e.g. ...];
(viii) C—OR⁴ [e.g. C—OCH₃, C—OCH₂CH₃, C—OCHF₂, C—OCF₃, C—O—phenyl, C—O—CH₂—phenyl or C—O—(CH₂)₂—N(morpholino)];
(ix) C—C(=O)R⁴ [e.g. C—C(=O)—phenyl];
(x) C—C(=O)NY¹Y² [e.g. C—C(=O)—NH—CH₃, C—C(=O)—N(CH₃)₂, C—C(=O)—NH—CH₂CH₃, C—C(=O)—NH—CH(CH₃)₂, C—C(=O)—NH—C(CH₃)₂—CH₂OH, C—C(=O)—NH—CH₂CH₂CN, C—C(=O)—NH—CH₂CH₂OCH₃, C—C(=O)—NH—CH₂—phenyl, C—C(=O)—NH—CH₂—(2-methylphenyl), C—C(=O)—NH—CH₂—(3-methylphenyl), C—C(=O)—NH—CH₂—(4-methylphenyl), -continued

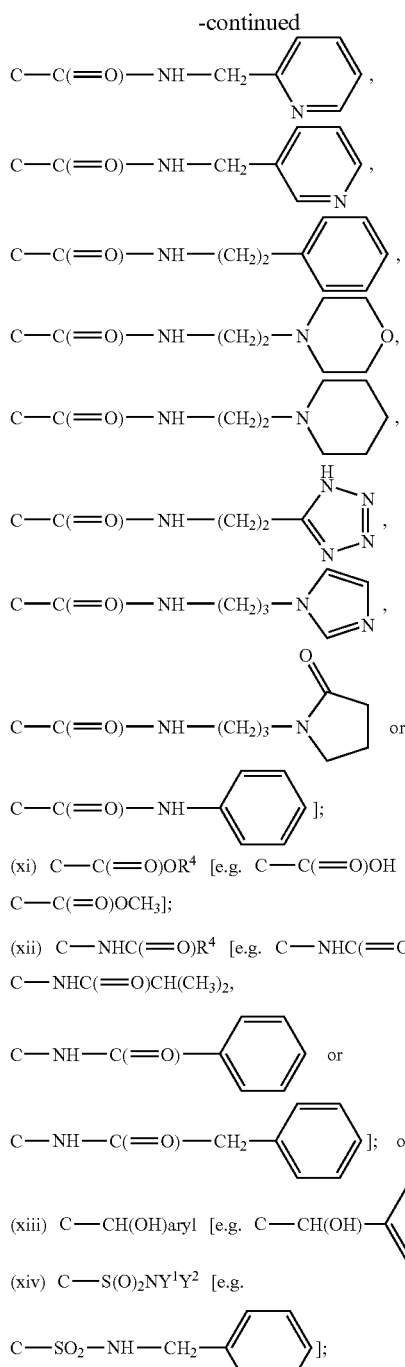

(xi) C—C(=O)OR⁴ [e.g. C—C(=O)OH or C—C(=O)OCH₃];

(xii) C—NHC(=O)R⁴ [e.g. C—NHC(=O)CH₃, C—NHC(=O)CH(CH₃)₂,

C—NH—C(=O)—[phenyl] or

C—NH—C(=O)—CH₂—[phenyl]; or (xiii) C—CH(OH)aryl [e.g. C—CH(OH)—[phenyl]];

(xiv) C—S(O)₂NY¹Y² [e.g.

C—SO₂—NH—CH₂—[phenyl]];

(xv) C—S(O)$_n$R⁴ [e.g. C—SO₂CH₃];

are also preferred.

Compounds of formula (Ixa) in which W represents CH, X represents C—CH₃, C—CH₂CH₃, C—CH(CH₃)₂, C—OCH₃, C—OCH₂CH₃, C—Br or C—Cl, Y represents C—CH₃, C—CH₂CH₃, C—OCH₃, C—Br, C—Cl, C—F, C—[phenyl] or

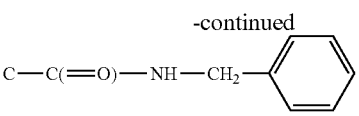

and Z represents CH are also preferred.

Compounds of formula (Ixa) in which W represents CH, X represents CH, Y represents C—CH₃ and Z represents C—CH₃ are also preferred.

Compounds of formula (Ixa) in which W represents CH, X represents CR² and Y represents CR³ where R² and R³ form the group —CH₂—O—CH₂—, and Z represents CH are also preferred.

Compounds of formula (Ixa) in which W represents CH, X represents CR² and Y represents CR³ where R² and R³ form the group —CH₂—CH₂—CH₂—, and Z represents CH are also preferred.

Compounds of formula (Ixa) in which R⁷ represents hydrogen are preferred.

Compounds of formula (Ixa) in which R⁸ represents:

(i) hydrogen;

(ii) C$_{1-4}$alkyl [e.g. CH₃, CH₂CH₃, CH(CH₃)₂ or CH(CH₃)CH₂CH₃];

(iii) —SR⁴ [e.g. —S—CH₃, —S—CH₂CH₃ or

—S—CH₂—[cyclopropyl], —S—CH₂—[phenyl],

—S—CH₂—[phenyl]—OCH₃,

—S—CH₂—CH₂—[phenyl],

—S—CH₂—[pyridyl] or —S—CH₂—[thienyl]];

(iv) —NY¹Y² [e.g. —N[morpholino]]; or (v) —OR⁵ [e.g. —OCH₂CH₃]

are preferred.

Compounds of formula (Ixa) in which R⁹ represents:

(i) hydrogen;

(ii) C$_{1-7}$alkyl [e.g. —CH₃, —CH₂CH₂CH₃, —CH(CH₃)₂ or —CH₂—CH₂—CH(CH₃)₂];

(iii) aryl [e.g. phenyl];

(iv) —C(=O)NY¹Y² [e.g.

—C(=O)—NH—CH₂CH₃,

—C(=O)—NH—CH₂CH₂CH₃,

—C(=O)—NH—CH₂CH(CH₃)₂,

—C(=O)—NH—CH(CH₃)₂,

—C(=O)—NH—C(CH₃)₃,

—C(=O)—NH—C(CH₃)₂CH₂OH,

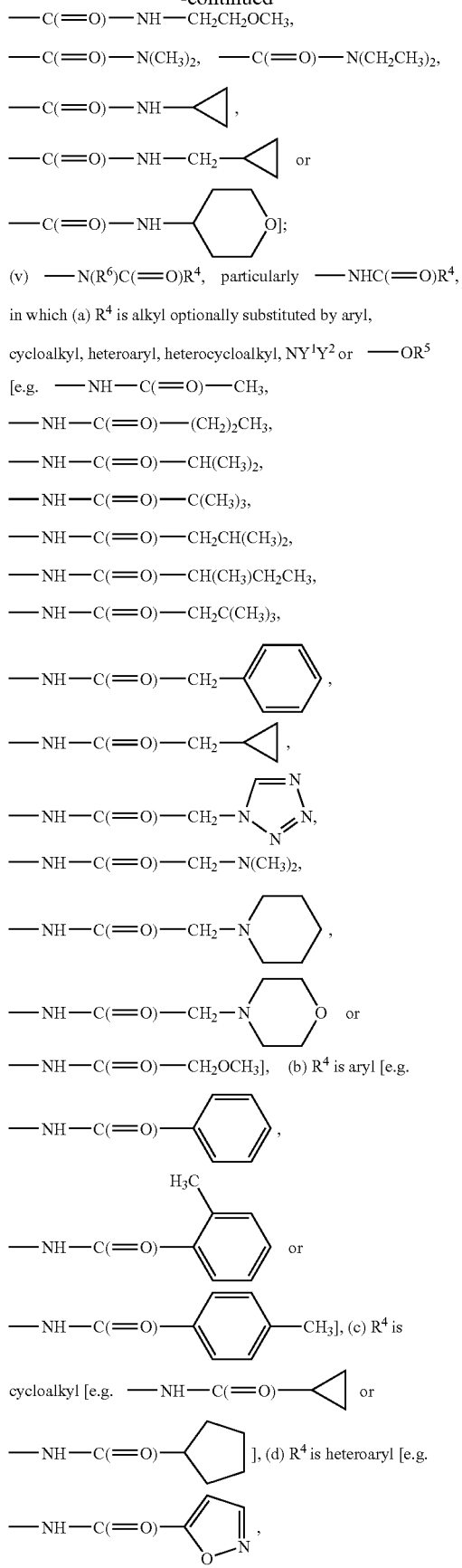
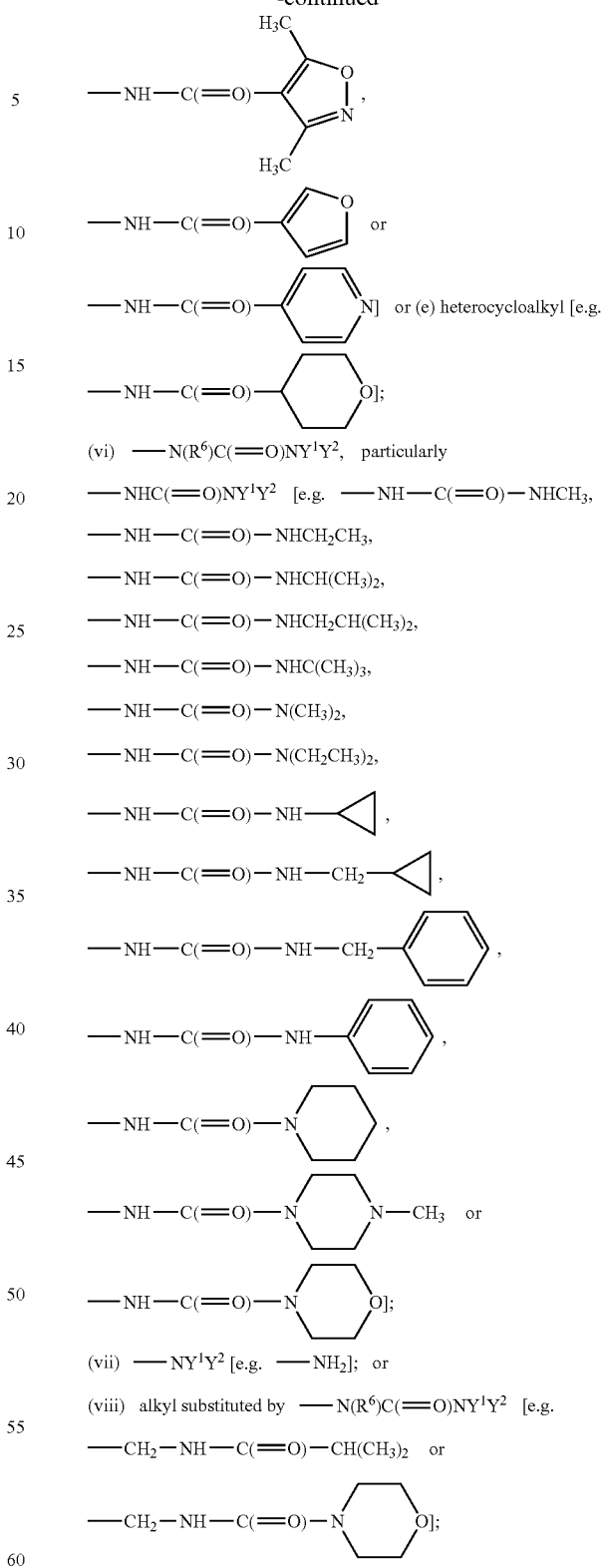
are preferred.
A preferred group of compounds of the invention are compounds of formula (Ixa) in which:—W represents CH; X represents CH; Y represents CH; Z represents CH or C—CH$_3$; R$^7$ represents hydrogen; R$^8$ represents (i) hydrogen, (ii) C$_{1-4}$alkyl [e.g. CH$_3$, CH$_2$CH$_3$, CH(CH$_3$)$_2$ or CH(CH$_3$)CH$_2$CH$_3$], (iii) —SR$^4$ [e.g. —S—CH$_3$, —S—CH$_2$CH$_3$ or

, 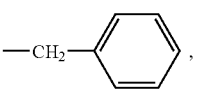,

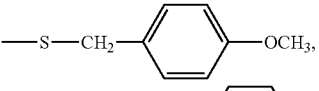,

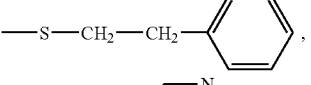,

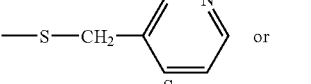 or

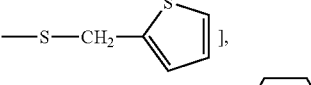], (iv) —NY$^1$Y$^2$ [e.g. ] or (v) —OR$^5$ [e.g. —OCH$_2$CH$_3$]; R$^9$ represents (i) hydrogen;

(ii) C$_{1-7}$alkyl [e.g. —CH$_3$, —CH$_2$CH$_2$CH$_3$, —CH(CH$_3$)$_2$ or —CH$_2$—CH$_2$—CH(CH$_3$)$_2$];

(iii) aryl [e.g. phenyl];

(iv) —C(=O)NY$^1$Y$^2$ [e.g.
—C(=O)—NH—CH$_2$CH$_3$,
—C(=O)—NH—CH$_2$CH$_2$CH$_3$,
—C(=O)—NH—CH$_2$CH(CH$_3$)$_2$,
—C(=O)—NH—CH(CH$_3$)$_2$,
—C(=O)—NH—C(CH$_3$)$_3$,
—C(=O)—NH—C(CH$_3$)$_2$CH$_2$OH,
—C(=O)—NH—CH$_2$CH$_2$OCH$_3$,
—C(=O)—N(CH$_3$)$_2$,  —C(=O)—N(CH$_2$CH$_3$)$_2$,
—C(=O)—NH—,
—C(=O)—NH—CH$_2$— or
—C(=O)—NH—];

(v) —N(R$^6$)C(=O)R$^4$, particularly —NHC(=O)R$^4$, in which (a) R$^4$ is alkyl optionally substituted by aryl, cycloalkyl, heteroaryl, heterocycloalkyl, NY$^1$Y$^2$ or —OR$^5$ [e.g. —NH—C(=O)—CH$_3$,
—NH—C(=O)—(CH$_2$)$_2$CH$_3$,
—NH—C(=O)—CH(CH$_3$)$_2$,
—NH—C(=O)—C(CH$_3$)$_3$,
—NH—C(=O)—CH$_2$CH(CH$_3$)$_2$, —NH—C(=O)—CH(CH$_3$)CH$_2$CH$_3$,
—NH—C(=O)—CH$_2$C(CH$_3$)$_3$,
—NH—C(=O)—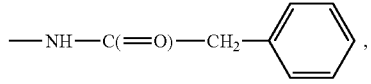,
—NH—C(=O)—CH$_2$—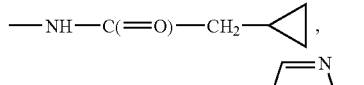,
—NH—C(=O)—CH$_2$—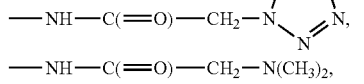,
—NH—C(=O)—CH$_2$—N(CH$_3$)$_2$,
—NH—C(=O)—CH$_2$—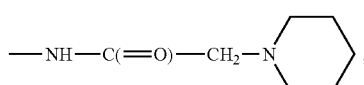,
—NH—C(=O)—CH$_2$—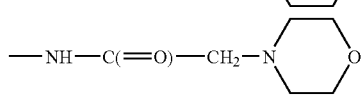 or
—NH—C(=O)—CH$_2$OCH$_3$], (b) R$^4$ is aryl [e.g.
—NH—C(=O)—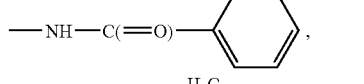,
—NH—C(=O)—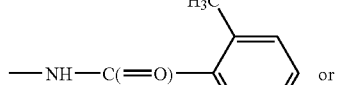 or
—NH—C(=O)—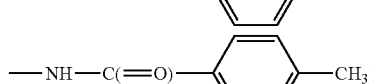], (c) R$^4$ is cycloalkyl [e.g. —NH—C(=O)—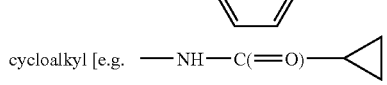 or
—NH—C(=O)—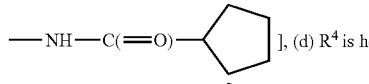], (d) R$^4$ is heteroaryl [e.g.
—NH—C(=O)—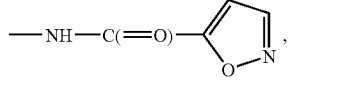,
—NH—C(=O)—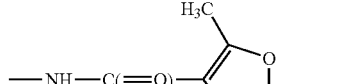,
—NH—C(=O)—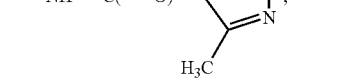 or
—NH—C(=O)—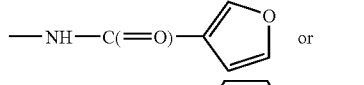] or (e) heterocycloalkyl [e.g.
—NH—C(=O)—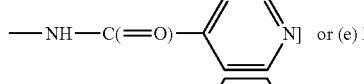];

(vi) —N(R$^6$)C(=O)NY$^1$Y$^2$, particularly —NHC(=O)NY$^1$Y$^2$ [e.g. —NH—C(=O)—NHCH$_3$,
—NH—C(=O)—NHCH$_2$CH$_3$,
—NH—C(=O)—NHCH(CH$_3$)$_2$,
—NH—C(=O)—NHCH$_2$CH(CH$_3$)$_2$,
—NH—C(=O)—NHC(CH$_3$)$_3$,

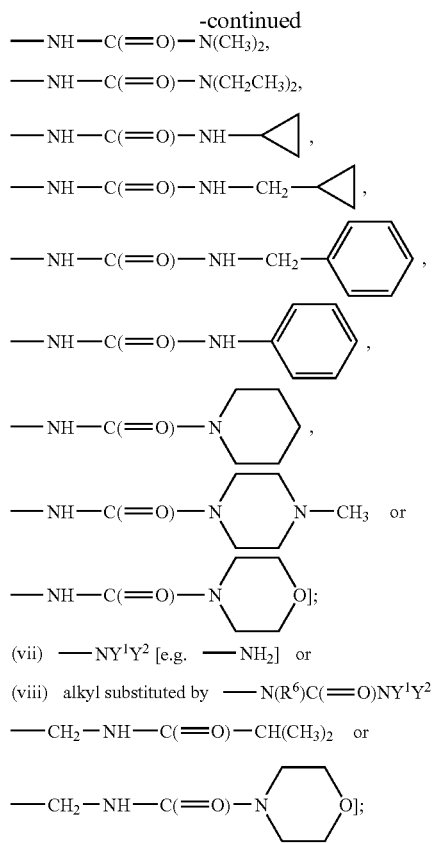

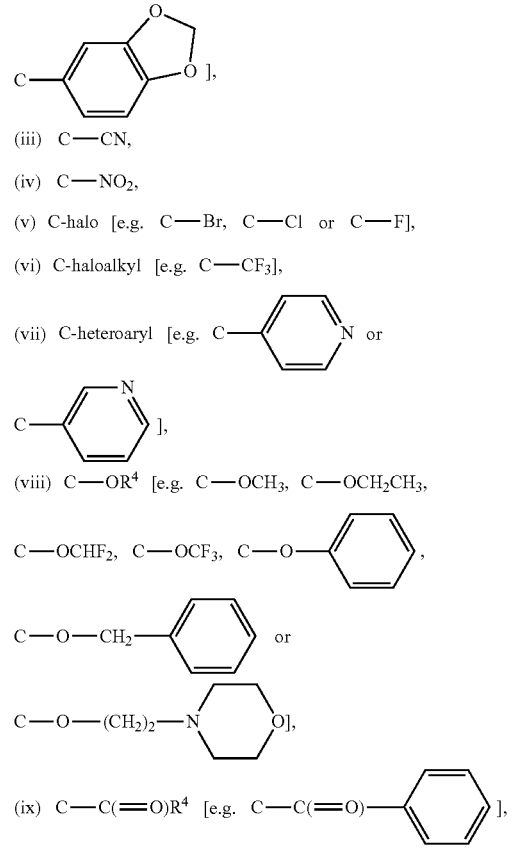

and their corresponding N-oxides, and their prodrugs, and their acid bioisosteres; and pharmaceutically acceptable salts and solvates (e.g. hydrates) of compounds of formula (Ixa) and their N-oxides and their prodrugs, and their acid bioisosteres.

A further preferred group of compounds of the invention are compounds of formula (Ixa) in which:—W represents CH; X represents CH; Z represents CH; Y represents -continued

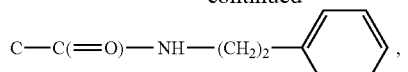,

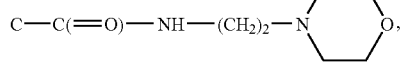,

,

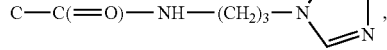,

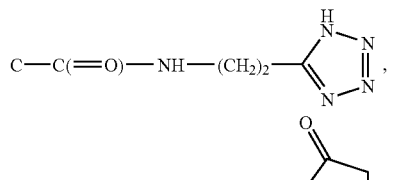,

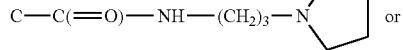];

(xi) C—C(=O)OR$^4$ [e.g. C—C(=O)OH or C—C(=O)OCH$_3$], (xii) C—NHC(=O)R$^4$ [e.g. C—NHC(=O)CH$_3$ or C—NHC(=O)CH(CH$_3$)$_2$,

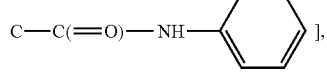 or

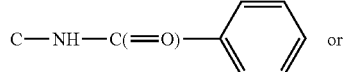], (xiii) C—CH(OH)aryl [e.g. C—CH(OH)—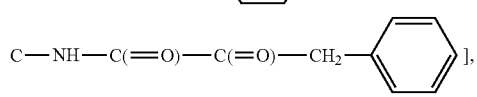], (xiv) C—S(O)$_2$NY$^1$Y$^2$ [e.g.

] or (xv) C—S(O)$_n$R$^4$ [e.g. C—SO$_2$CH$_3$];

R$^7$ represents hydrogen; R$^8$ represents (i) hydrogen, (ii) C$_{1-4}$alkyl [e.g. CH$_3$, CH$_2$CH$_3$, CH(CH$_3$)$_2$ or CH(CH$_3$)CH$_2$CH$_3$], (iii) —SR$^4$ [e.g. —S—CH$_3$, —S—CH$_2$CH$_3$ or

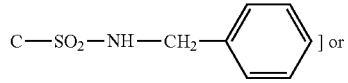,

-continued

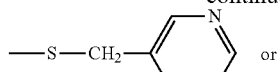 or

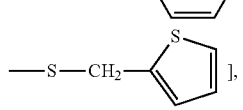], (iv) —NY$^1$Y$^2$ [e.g. ] or (v) —OR$^5$ [e.g. —OCH$_2$CH$_3$]; R$^9$ represents (i) hydrogen;

(ii) C$_{1-7}$alkyl [e.g. —CH$_3$, —CH$_2$CH$_2$CH$_3$, —CH(CH$_3$)$_2$ or —CH$_2$—CH$_2$—CH(CH$_3$)$_2$];

(iii) aryl [e.g. phenyl];

(iv) —C(=O)NY$^1$Y$^2$ [e.g.

—C(=O)—NH—CH$_2$CH$_3$,

—C(=O)—NH—CH$_2$CH$_2$CH$_3$,

—C(=O)—NH—CH$_2$CH(CH$_3$)$_2$,

—C(=O)—NH—CH(CH$_3$)$_2$,

—C(=O)—NH—C(CH$_3$)$_3$,

—C(=O)—NH—C(CH$_3$)$_2$CH$_2$OH,

—C(=O)—NH—CH$_2$CH$_2$OCH$_3$,

—C(=O)—N(CH$_3$)$_2$, —C(=O)—N(CH$_2$CH$_3$)$_2$,

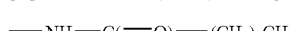,

 or

];

(v) —N(R$^6$)C(=O)R$^4$, particularly —NHC(=O)R$^4$, in which (a) R$^4$ is alkyl optionally substituted by aryl, cycloalkyl, heteroaryl, heterocycloalkyl, NY$^1$Y$^2$ or —OR$^5$ [e.g. —NH—C(=O)—CH$_3$,

—NH—C(=O)—(CH$_2$)$_2$CH$_3$,

—NH—C(=O)—CH(CH$_3$)$_2$,

—NH—C(=O)—C(CH$_3$)$_3$,

—NH—C(=O)—CH$_2$CH(CH$_3$)$_2$,

—NH—C(=O)—CH(CH$_3$)CH$_2$CH$_3$,

—NH—C(=O)—CH$_2$C(CH$_3$)$_3$,

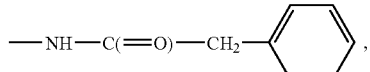,

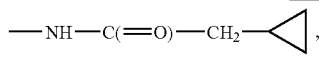,

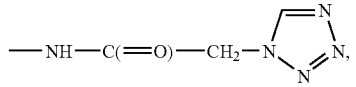,

—NH—C(=O)—CH$_2$—N(CH$_3$)$_2$,

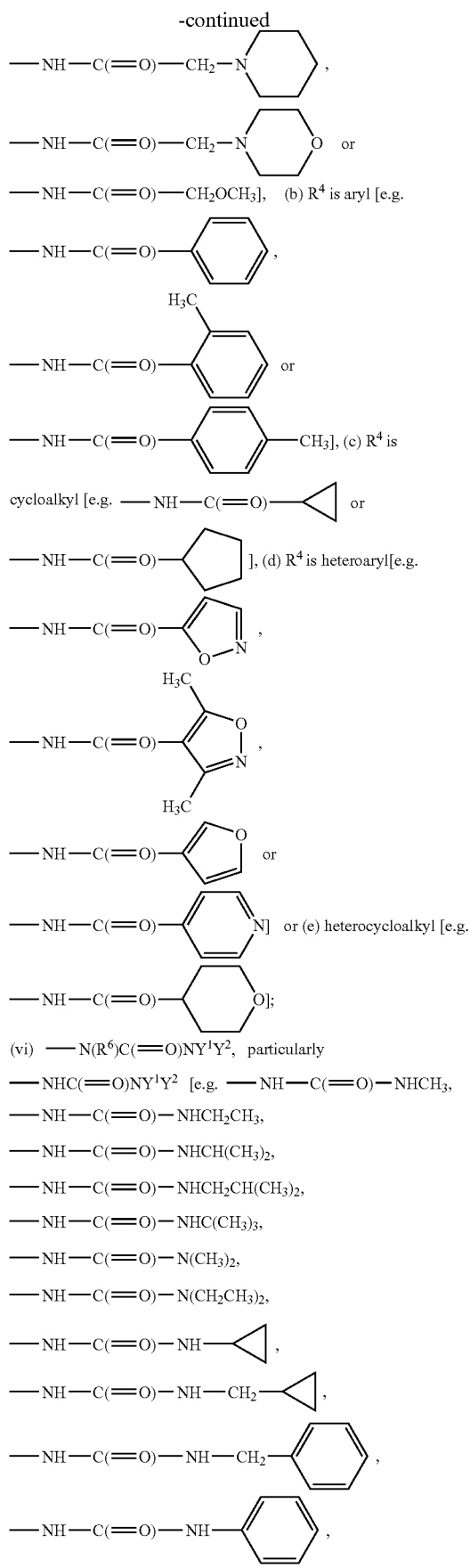
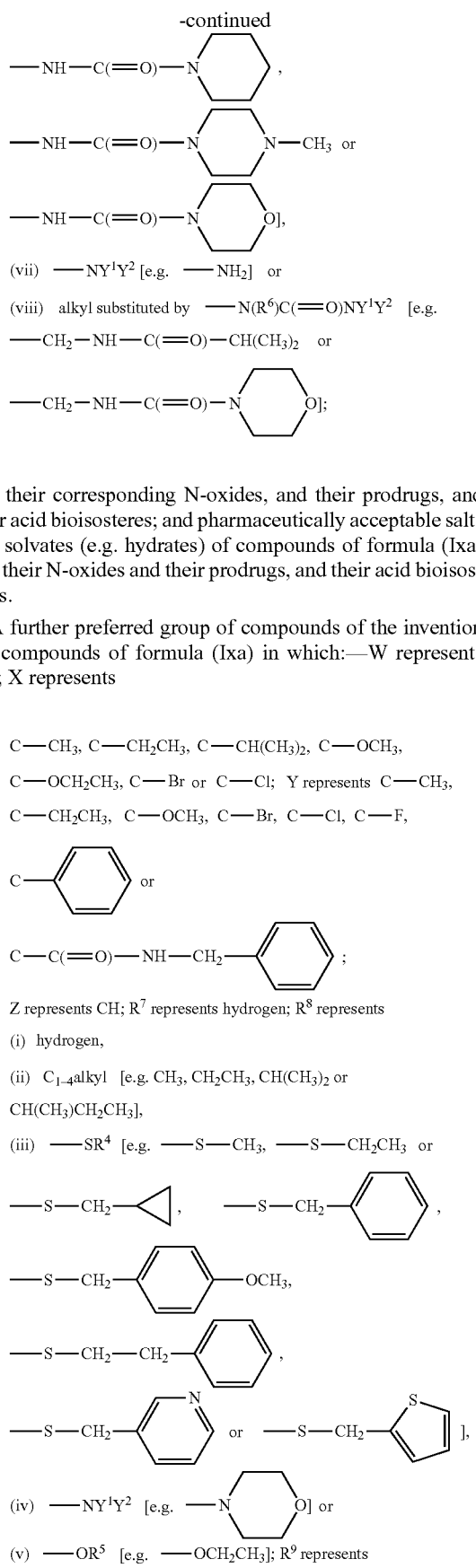

-continued (i) hydrogen;

(ii) C$_{1-7}$alkyl [e.g. —CH$_3$, —CH$_2$CH$_2$CH$_3$, —CH(CH$_3$)$_2$ or —CH$_2$—CH$_2$—CH(CH$_3$)$_2$];

(iii) aryl [e.g. phenyl];

(iv) —C(=O)NY$^1$Y$^2$ [e.g.

—C(=O)—NH—CH$_2$CH$_3$,

—C(=O)—NH—CH$_2$CH$_2$CH$_3$,

—C(=O)—NH—CH$_2$CH(CH$_3$)$_2$,

—C(=O)—NH—CH(CH$_3$)$_2$,

—C(=O)—NH—C(CH$_3$)$_3$,

—C(=O)—NH—C(CH$_3$)$_2$CH$_2$OH,

—C(=O)—NH—CH$_2$CH$_2$OCH$_3$,

—C(=O)—N(CH$_3$)$_2$, —C(=O)—N(CH$_2$CH$_3$)$_2$,

—C(=O)—NH—,

—C(=O)—NH—CH$_2$— or

—C(=O)—NH—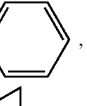];

(v) —N(R$^6$)C(=O)R$^4$, particularly —NHC(=O)R$^4$, in which (a) R$^4$ is alkyl optionally substituted by aryl, cycloalkyl, heteroaryl, heterocycloalkyl, NY$^1$Y$^2$ or —OR$^5$ [e.g. —NH—C(=O)—CH$_3$,

—NH—C(=O)—(CH$_2$)$_2$CH$_3$,

—NH—C(=O)—CH(CH$_3$)$_2$,

—NH—C(=O)—C(CH$_3$)$_3$,

—NH—C(=O)—CH$_2$CH(CH$_3$)$_2$,

—NH—C(=O)—CH(CH$_3$)CH$_2$CH$_3$,

—NH—C(=O)—CH$_2$C(CH$_3$)$_3$,

—NH—C(=O)—CH$_2$—,

—NH—C(=O)—CH$_2$—,

—NH—C(=O)—CH$_2$—,

—NH—C(=O)—CH$_2$—N(CH$_3$)$_2$,

—NH—C(=O)—CH$_2$—,

—NH—C(=O)—CH$_2$—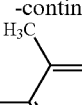 or

—NH—C(=O)—CH$_2$OCH$_3$], (b) R$^4$ is aryl [e.g.

—NH—C(=O)—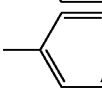,

—NH—C(=O)— or

—NH—C(=O)—], (c) R$^4$ is cycloalkyl [e.g. —NH—C(=O)— or

—NH—C(=O)—], (d) R$^4$ is heteroaryl [e.g.

—NH—C(=O)—,

—NH—C(=O)—,

—NH—C(=O)—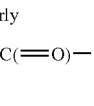 or

—NH—C(=O)—] or (e) heterocycloalkyl [e.g.

—NH—C(=O)—];

(vi) —N(R$^6$)C(=O)NY$^1$Y$^2$, particularly —NHC(=O)NY$^1$Y$^2$ [e.g. —NH—C(=O)—NHCH$_3$,

—NH—C(=O)—NHCH$_2$CH$_3$,

—NH—C(=O)—NHCH(CH$_3$)$_2$,

—NH—C(=O)—NHCH$_2$CH(CH$_3$)$_2$,

—NH—C(=O)—NHC(CH$_3$)$_3$,

—NH—C(=O)—N(CH$_3$)$_2$,

—NH—C(=O)—N(CH$_2$CH$_3$)$_2$,

—NH—C(=O)—NH—,

—NH—C(=O)—NH—CH$_2$—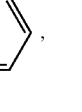,

—NH—C(=O)—NH—CH$_2$—,

—NH—C(=O)—NH—,

—NH—C(=O)—N,

—NH—C(=O)—NN—CH$_3$ or

—NH—C(=O)—NO], (vii) —NY$^1$Y$^2$ [e.g. —NH$_2$] or

-continued (viii) alkyl substituted by —N(R⁶)C(═O)NY¹Y² [e.g.

—CH₂—NH—C(═O)—CH(CH₃)₂ or

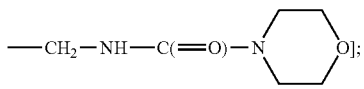];

and their corresponding N-oxides, and their prodrugs, and their acid bioisosteres; and pharmaceutically acceptable salts and solvates (e.g. hydrates) of compounds of formula (Ixa) and their N-oxides and their prodrugs, and their acid bioisosteres.

A further preferred group of compounds of the invention are compounds of formula (Ixa) in which:—W represents CH; X represents CH; Y represents C—CH₃; Z represents C—CH₃; R⁷ represents hydrogen; R⁸ represents (i) hydrogen, (ii) C₁₋₄alkyl [e.g. CH₃, CH₂CH₃, CH(CH₃)₂ or CH(CH₃)CH₂CH₃], (iii) —SR⁴ [e.g. —S—CH₃, —S—CH₂CH₃ or

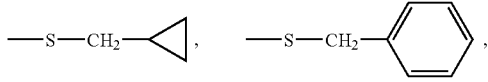

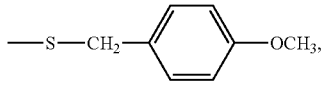

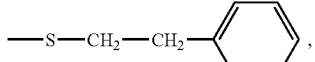

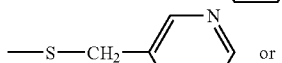

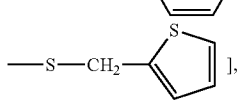], (iv) —NY¹Y² [e.g. 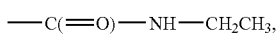] or (v) —OR⁵ [e.g. —OCH₂CH₃]; R⁹ represents (i) hydrogen;

(ii) C₁₋₇alkyl [e.g. —CH₃, —CH₂CH₂CH₃, —CH(CH₃)₂ or —CH₂—CH₂—CH(CH₃)₂];

(iii) aryl [e.g. phenyl];

(iv) —C(═O)NY¹Y² [e.g.

—C(═O)—NH—CH₂CH₃,

—C(═O)—NH—CH₂CH₂CH₃,

—C(═O)—NH—CH₂CH(CH₃)₂,

—C(═O)—NH—CH(CH₃)₂,

—C(═O)—NH—C(CH₃)₃,

—C(═O)—NH—C(CH₃)₂CH₂OH,

—C(═O)—NH—CH₂CH₂OCH₃,

—C(═O)—N(CH₃)₂, —C(═O)—N(CH₂CH₃)₂,

-continued

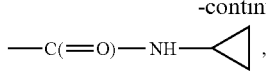,

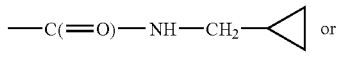 or

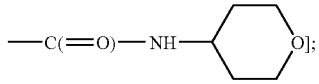];

(v) —N(R⁶)C(═O)R⁴, particularly —NHC(═O)R⁴, in which (a) R⁴ is alkyl optionally substituted by aryl, cycloalkyl, heteroaryl, heterocycloalkyl, NY¹Y² or —OR⁵

[e.g. —NH—C(═O)—CH₃,

—NH—C(═O)—(CH₂)₂CH₃,

—NH—C(═O)—CH(CH₃)₂,

—NH—C(═O)—C(CH₃)₃,

—NH—C(═O)—CH₂CH(CH₃)₂,

—NH—C(═O)—CH(CH₃)CH₂CH₃,

—NH—C(═O)—CH₂C(CH₃)₃,

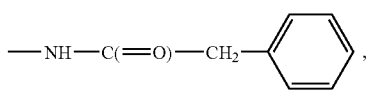,

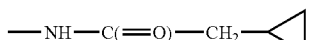,

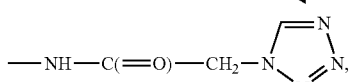,

—NH—C(═O)—CH₂—N(CH₃)₂,

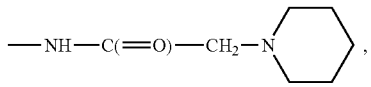,

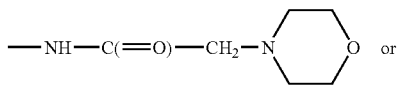

—NH—C(═O)—CH₂OCH₃], (b) R⁴ is aryl [e.g.

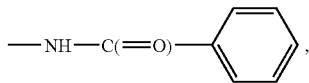,

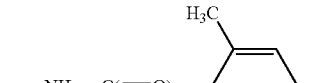 or

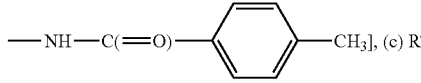], (c) R⁴ is cycloalkyl [e.g. —NH—C(═O)—◁ or

—NH—C(═O)—⬠], (d) R⁴ is heteroaryl [e.g.

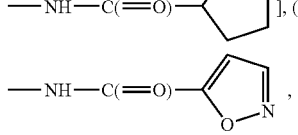,

-continued

—NH—C(=O)— 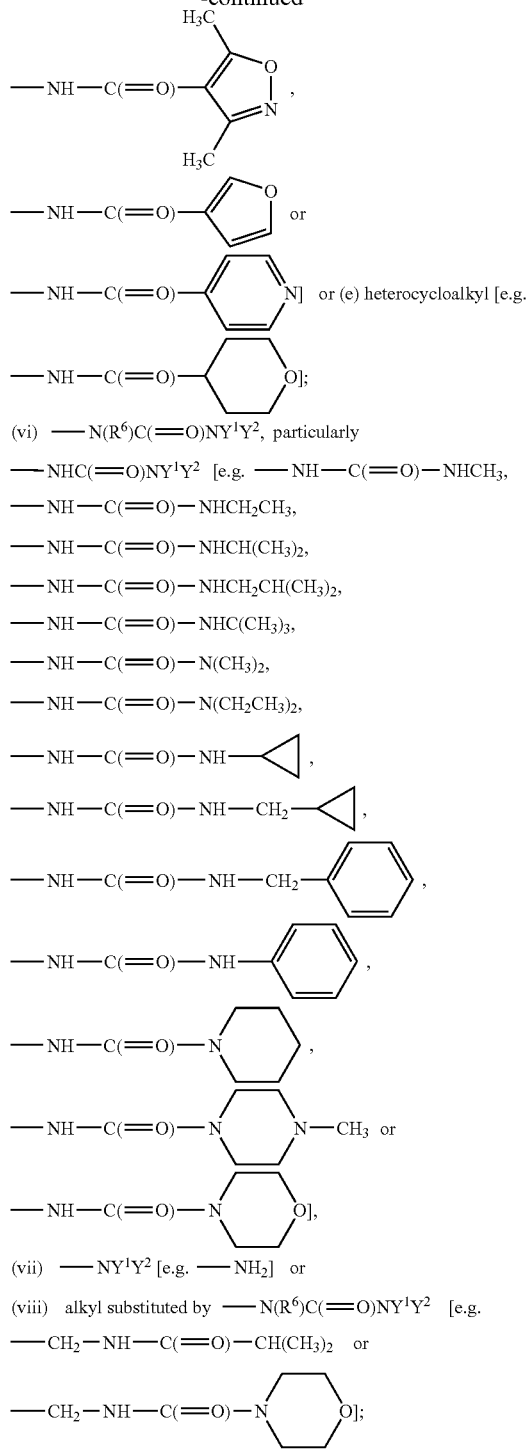

—NH—C(=O)— (furan) or

—NH—C(=O)— (pyridine) N] or (e) heterocycloalkyl [e.g.

—NH—C(=O)— (tetrahydropyran O)];

(vi) —N(R⁶)C(=O)NY¹Y², particularly

—NHC(=O)NY¹Y² [e.g. —NH—C(=O)—NHCH₃,

—NH—C(=O)—NHCH₂CH₃,

—NH—C(=O)—NHCH(CH₃)₂,

—NH—C(=O)—NHCH₂CH(CH₃)₂,

—NH—C(=O)—NHC(CH₃)₃,

—NH—C(=O)—N(CH₃)₂,

—NH—C(=O)—N(CH₂CH₃)₂,

—NH—C(=O)—NH—(cyclopropyl),

—NH—C(=O)—NH—CH₂—(cyclopropyl),

—NH—C(=O)—NH—CH₂—(phenyl),

—NH—C(=O)—NH—(phenyl),

—NH—C(=O)—N(piperidine),

—NH—C(=O)—N(piperazine)—CH₃ or

—NH—C(=O)—N(morpholine O)], (vii) —NY¹Y² [e.g. —NH₂] or (viii) alkyl substituted by —N(R⁶)C(=O)NY¹Y² [e.g.

—CH₂—NH—C(=O)—CH(CH₃)₂ or

—CH₂—NH—C(=O)—N(morpholine O)];

and their corresponding N-oxides, and their prodrugs, and their acid bioisosteres; and pharmaceutically acceptable salts and solvates (e.g. hydrates) of compounds of formula (Ixa) and their N-oxides and their prodrugs, and their acid bioisosteres.

A further preferred group of compounds of the invention are compounds of formula (Ixa) in which:—W represents CH; X represents CR² and Y represents CR³ where R² and R³ form the group —CH₂—O—CH₂—; Z represents CH; R⁷ represents hydrogen; R⁸ represents (i) hydrogen, (ii) $C_{1-4}$alkyl [e.g. CH₃, CH₂CH₃, CH(CH₃)₂ or CH(CH₃)CH₂CH₃], (iii) —SR⁴ [e.g. —S—CH₃, —S—CH₂CH₃ or —S—CH₂—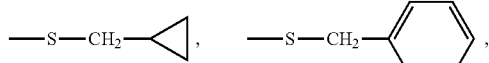, —S—CH₂—(phenyl-OCH₃), —S—CH₂—CH₂—(phenyl), —S—CH₂—(pyridine) or —S—CH₂—(thiophene)], (iv) —NY¹Y² [e.g. —N(morpholine O)] or (v) —OR⁵ [e.g. —OCH₂CH₃]; R⁹ represents (i) hydrogen;

(ii) $C_{1-7}$alkyl [e.g. —CH₃, —CH₂CH₂CH₃, —CH(CH₃)₂ or —CH₂—CH₂—CH(CH₃)₂];

(iii) aryl [e.g. phenyl];

(iv) —C(=O)NY¹Y² [e.g. —C(=O)—NH—CH₂CH₃,

—C(=O)—NH—CH₂CH₂CH₃,

—C(=O)—NH—CH₂CH(CH₃)₂,

—C(=O)—NH—CH(CH₃)₂,

—C(=O)—NH—C(CH₃)₃,

—C(=O)—NH—C(CH₃)₂CH₂OH,

—C(=O)—NH—CH₂CH₂OCH₃,

—C(=O)—N(CH₃)₂, —C(=O)—N(CH₂CH₃)₂,

—C(=O)—NH—(cyclopropyl),

—C(=O)—NH—CH₂—(cyclopropyl) or

—C(=O)—NH—(tetrahydropyran O)];

(v) —N(R⁶)C(=O)R⁴, particularly —NHC(=O)R⁴, in which (a) R⁴ is alkyl optionally substituted by aryl, cycloalkyl, heteroaryl, heterocycloalkyl, NY¹Y² or —OR⁵ [e.g. —NH—C(=O)—CH₃,

—NH—C(=O)—(CH₂)₂CH₃,

—NH—C(=O)—CH(CH₃)₂,

—NH—C(=O)—C(CH₃)₃,

—NH—C(=O)—CH₂CH(CH₃)₂,

—NH—C(=O)—CH(CH₃)CH₂CH₃,

—NH—C(=O)—CH₂C(CH₃)₃,

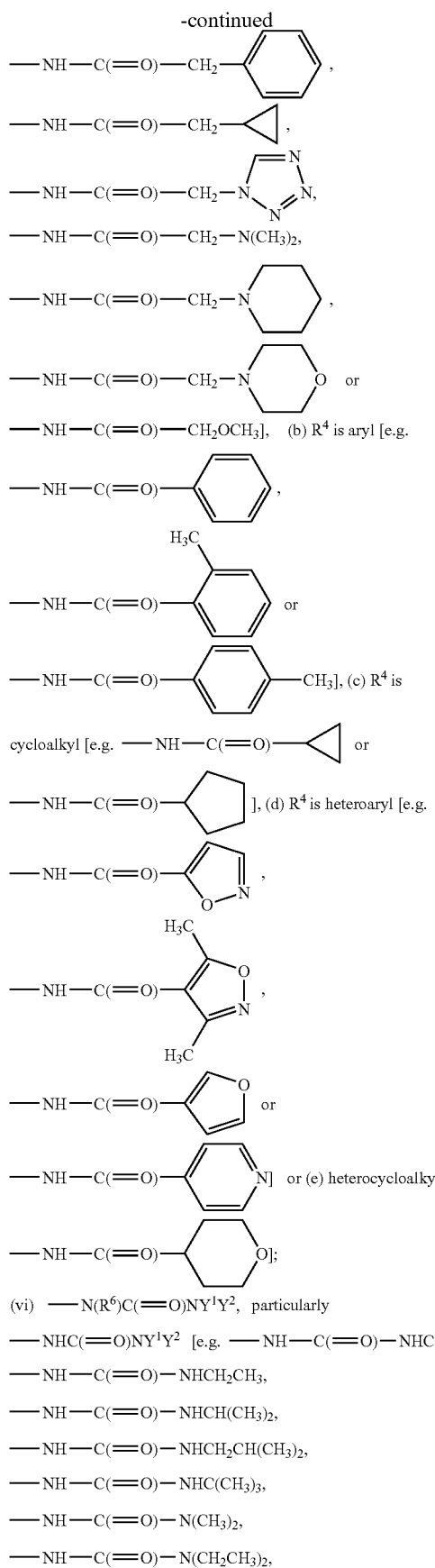
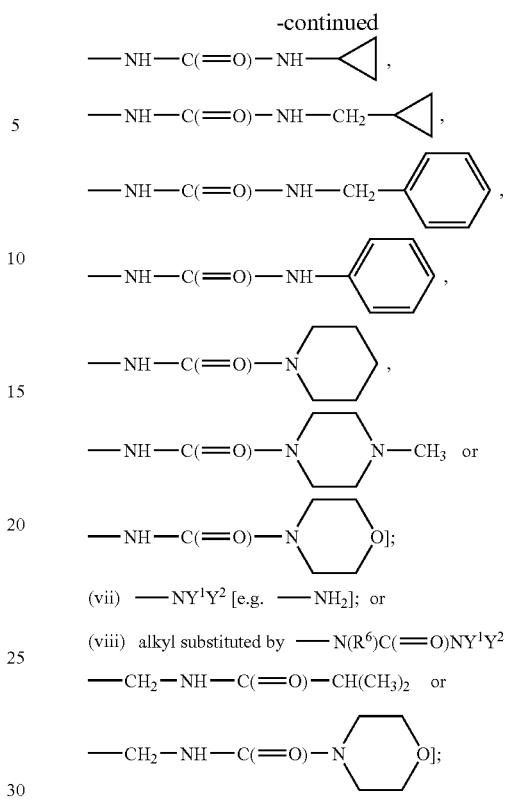

and their corresponding N-oxides, and their prodrugs, and their acid bioisosteres; and pharmaceutically acceptable salts and solvates (e.g. hydrates) of compounds of formula (Ixa) and their N-oxides and their prodrugs, and their acid bioisosteres.

A further preferred group of compounds of the invention are compounds of formula (Ixa) in which:—W represents CH; X represents $CR^2$ and Y represents $CR^3$ where $R^2$ and $R^3$ form the group —$CH_2$—$CH_2$—$CH_2$—; Z represents CH; $R^7$ represents hydrogen; $R^8$ represents (i) hydrogen, (ii) $C_{1-4}$alkyl [e.g. $CH_3$, $CH_2CH_3$, $CH(CH_3)_2$ or $CH(CH_3)CH_2CH_3$], (iii) —$SR^4$ [e.g. —S—$CH_3$, —S—$CH_2CH_3$ or

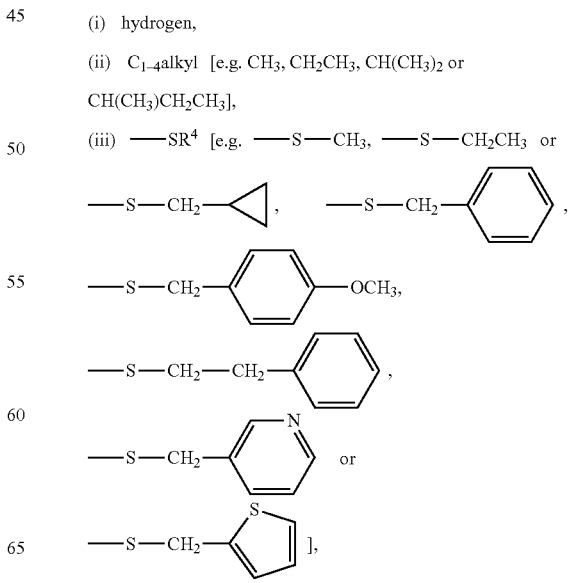

-continued (iv) —NY¹Y² [e.g. —N(morpholino)] or (v) —OR⁵ [e.g. —OCH₂CH₃]; R⁹ represents (i) hydrogen;

(ii) C₁₋₇alkyl [e.g. —CH₃, —CH₂CH₂CH₃, —CH(CH₃)₂ or —CH₂—CH₂—CH(CH₃)₂];

(iii) aryl [e.g. phenyl];

(iv) —C(=O)NY¹Y² [e.g. —C(=O)—NH—CH₂CH₃, —C(=O)—NH—CH₂CH₂CH₃, —C(=O)—NH—CH₂CH(CH₃)₂, —C(=O)—NH—CH(CH₃)₂, —C(=O)—NH—C(CH₃)₃, —C(=O)—NH—C(CH₃)₂CH₂OH, —C(=O)—NH—CH₂CH₂OCH₃, —C(=O)—N(CH₃)₂, —C(=O)—N(CH₂CH₃)₂, —C(=O)—NH—cyclopropyl, —C(=O)—NH—CH₂—cyclopropyl or —C(=O)—NH—tetrahydropyranyl];

(v) —N(R⁶)C(=O)R⁴, particularly —NHC(=O)R⁴, in which (a) R⁴ is alkyl optionally substituted by aryl, cycloalkyl, heteroaryl, heterocycloalkyl, NY¹Y² or —OR⁵ [e.g. —NH—C(=O)—CH₃, —NH—C(=O)—(CH₂)₂CH₃, —NH—C(=O)—CH(CH₃)₂, —NH—C(=O)—C(CH₃)₃, —NH—C(=O)—CH₂CH(CH₃)₂, —NH—C(=O)—CH(CH₃)CH₂CH₃, —NH—C(=O)—CH₂C(CH₃)₃, —NH—C(=O)—CH₂—phenyl, —NH—C(=O)—CH₂—cyclopropyl, —NH—C(=O)—CH₂—tetrazolyl, —NH—C(=O)—CH₂—N(CH₃)₂, —NH—C(=O)—CH₂—piperidinyl, —NH—C(=O)—CH₂—morpholino or —NH—C(=O)—CH₂OCH₃], (b) R⁴ is aryl [e.g. —NH—C(=O)—phenyl, —NH—C(=O)—(2-methylphenyl) or —NH—C(=O)—(4-methylphenyl)], (c) R⁴ is cycloalkyl [e.g. —NH—C(=O)—cyclopropyl or —NH—C(=O)—cyclopentyl], (d) R⁴ is heteroaryl [e.g. —NH—C(=O)—isoxazolyl, —NH—C(=O)—(dimethylisoxazolyl), —NH—C(=O)—furyl or —NH—C(=O)—pyridyl] or (e) heterocycloalkyl [e.g. —NH—C(=O)—tetrahydropyranyl];

(vi) —N(R⁶)C(=O)NY¹Y², particularly —NHC(=O)NY¹Y² [e.g. —NH—C(=O)—NHCH₃, —NH—C(=O)—NHCH₂CH₃, —NH—C(=O)—NHCH(CH₃)₂, —NH—C(=O)—NHCH₂CH(CH₃)₂, —NH—C(=O)—NHC(CH₃)₃, —NH—C(=O)—N(CH₃)₂, —NH—C(=O)—N(CH₂CH₃)₂, —NH—C(=O)—NH—cyclopropyl, —NH—C(=O)—NH—CH₂—cyclopropyl, —NH—C(=O)—NH—CH₂—phenyl, —NH—C(=O)—NH—phenyl, —NH—C(=O)—piperidinyl, —NH—C(=O)—(4-methylpiperazinyl) or -continued —NH—C(=O)—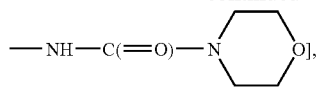, (vii) —NY¹Y² [e.g. —NH₂] or (viii) alkyl substituted by —N(R⁶)C(=O)NY¹Y² [e.g.

—CH₂—NH—C(=O)—CH(CH₃)₂ or

—CH₂—NH—C(=O)—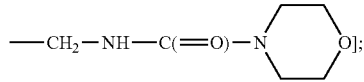];

and their corresponding N-oxides, and their prodrugs, and their acid bioisosteres; and pharmaceutically acceptable salts and solvates (e.g. hydrates) of compounds of formula (Ixa) and their N-oxides and their prodrugs, and their acid bioisosteres.

Compounds of formula (Ixa) in which R⁸ is hydrogen or —CH₃ and R⁹ is

—CH₂—CH₂—CH(CH₃)₂,
—C(=O)—NH—CH₂CH₃,
—C(=O)—NH—CH₂CH₂CH₃,
—C(=O)—NH—CH(CH₃)₂,
—C(=O)—NH—C(CH₃)₃,
—C(=O)—NH—C(CH₃)₂CH₂OH,
—C(=O)—NH—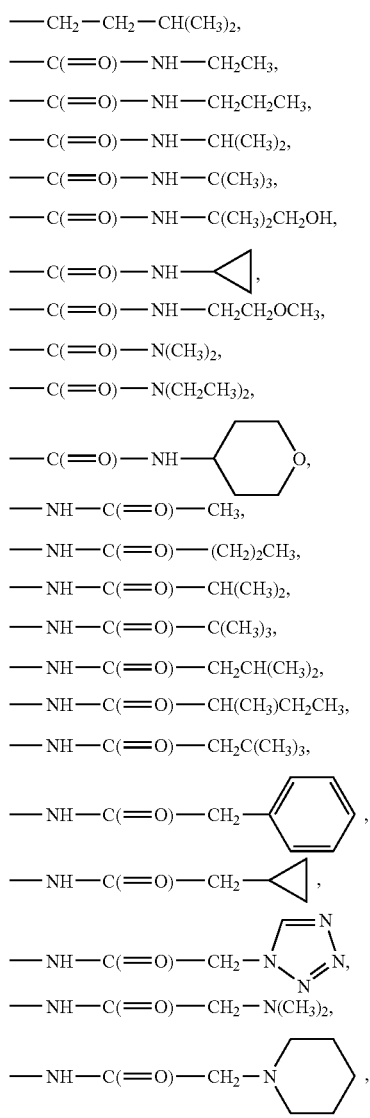,
—C(=O)—NH—CH₂CH₂OCH₃,
—C(=O)—N(CH₃)₂,
—C(=O)—N(CH₂CH₃)₂,
—C(=O)—NH—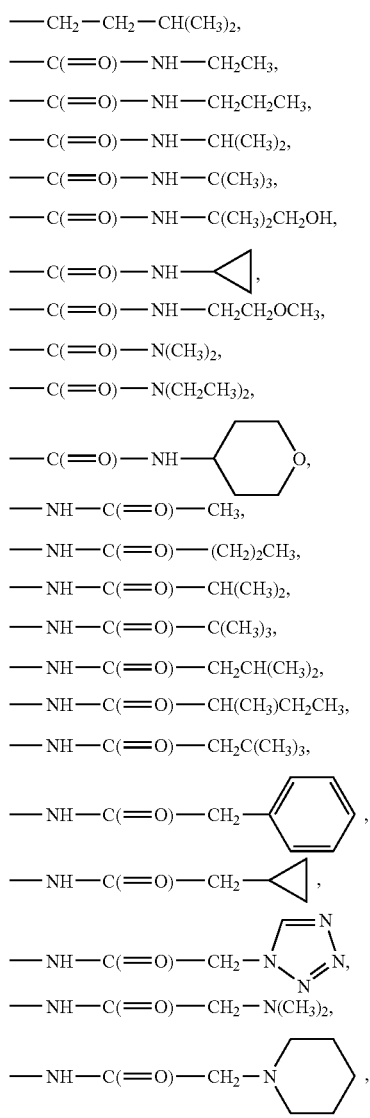,
—NH—C(=O)—CH₃,
—NH—C(=O)—(CH₂)₂CH₃,
—NH—C(=O)—CH(CH₃)₂,
—NH—C(=O)—C(CH₃)₃,
—NH—C(=O)—CH₂CH(CH₃)₂,
—NH—C(=O)—CH(CH₃)CH₂CH₃,
—NH—C(=O)—CH₂C(CH₃)₃,
—NH—C(=O)—CH₂—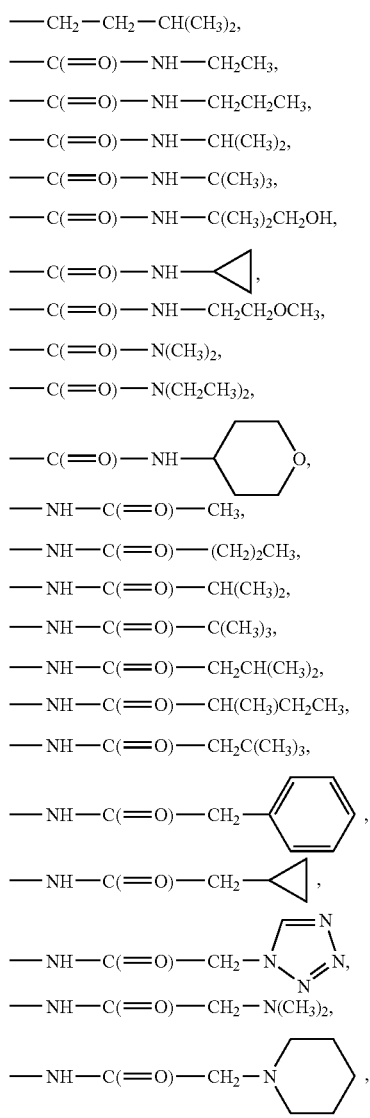,
—NH—C(=O)—CH₂—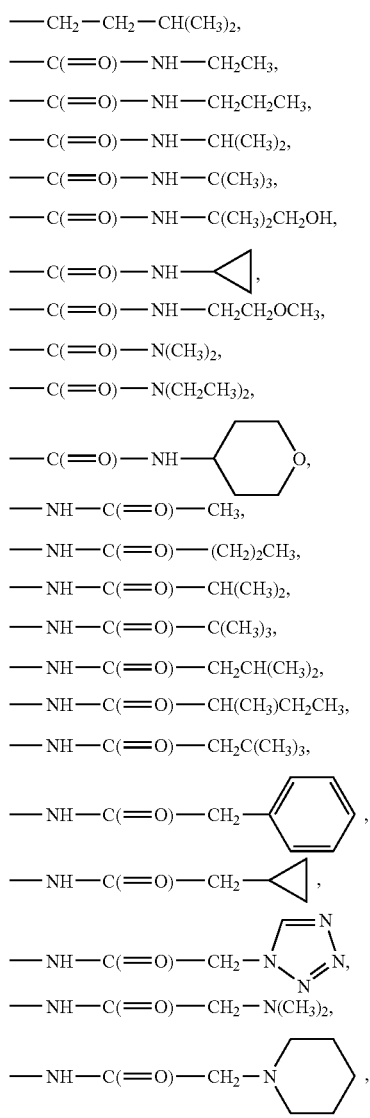,
—NH—C(=O)—CH₂—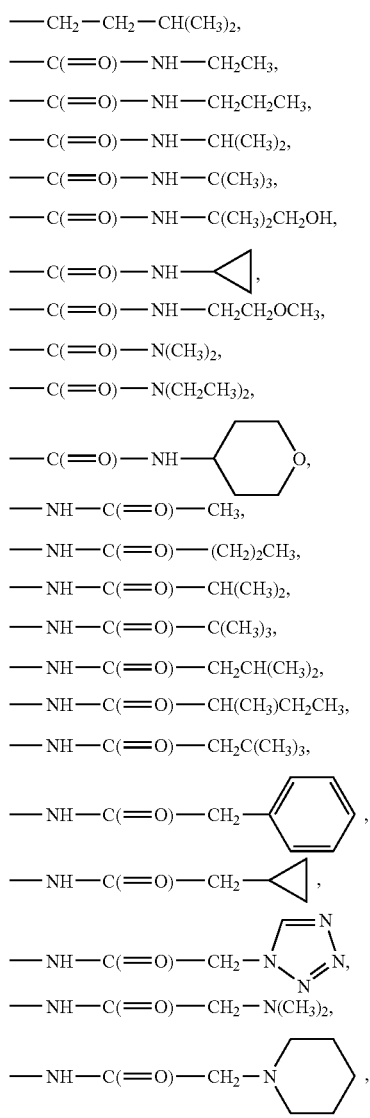,
—NH—C(=O)—CH₂—N(CH₃)₂,
—NH—C(=O)—CH₂—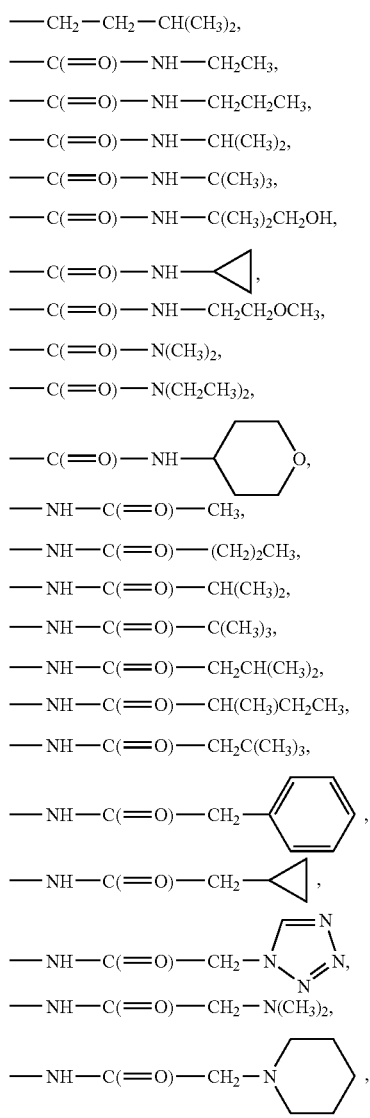, —NH—C(=O)—CH₂—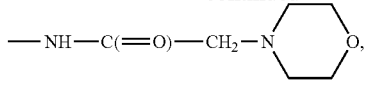,
—NH—C(=O)—CH₂OCH₃,
—NH—C(=O)—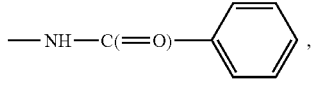,
—NH—C(=O)—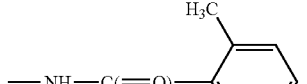,
—NH—C(=O)—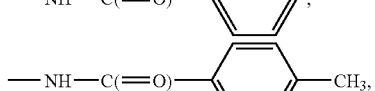,
—NH—C(=O)—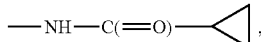,
—NH—C(=O)—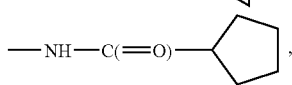,
—NH—C(=O)—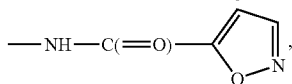,
—NH—C(=O)—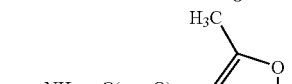,
—NH—C(=O)—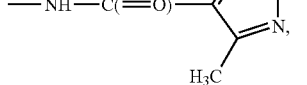,
—NH—C(=O)—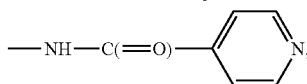,
—NH—C(=O)—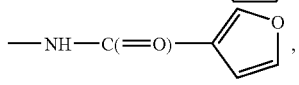,
—NH—C(=O)—NHCH₃,
—NH—C(=O)—NHCH₂CH₃,
—NH—C(=O)—NHCH(CH₃)₂,
—NH—C(=O)—NHC(CH₃)₃,
—NH—C(=O)—N(CH₃)₂,
—NH—C(=O)—N(CH₂CH₃)₂,
—NH—C(=O)—NH—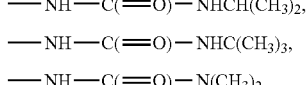,
—NH—C(=O)—NH—CH₂—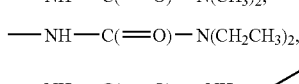,
—NH—C(=O)—NH—CH₂—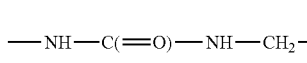,
—NH—C(=O)—NH—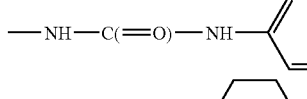,
—NH—C(=O)—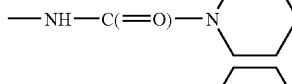,
—NH—C(=O)—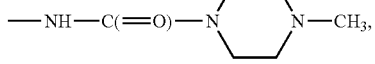,
—NH—C(=O)—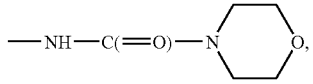, -continued

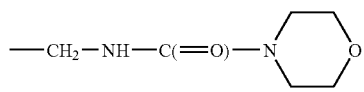

are particularly preferred.

Compounds of formula (Ixa) in which $R^9$ represents hydrogen and $R^8$ represents

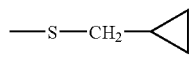

are also particularly preferred.

Compounds of formula (Ixa) in which W is CH, X is CH, Y is

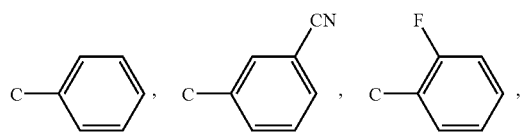
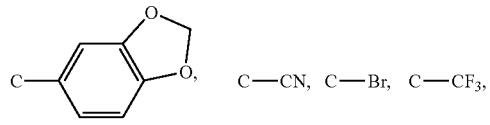
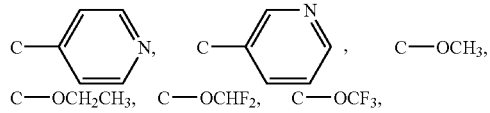
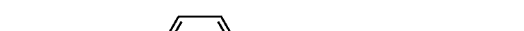
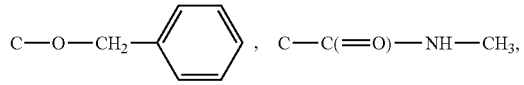
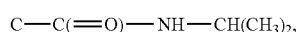
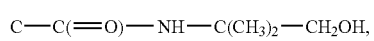
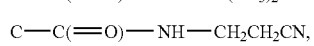
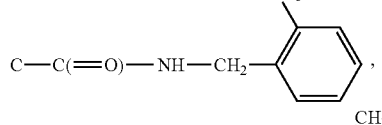
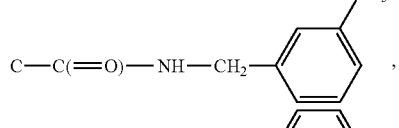
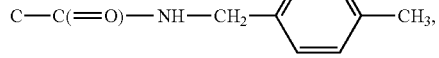

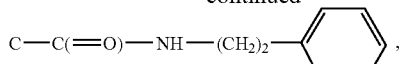
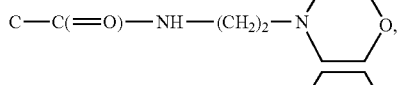
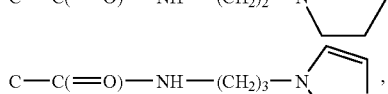
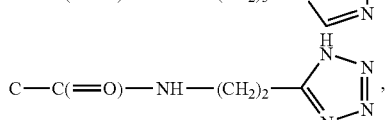
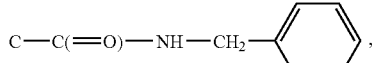
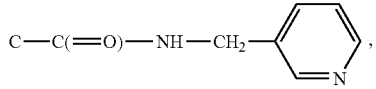
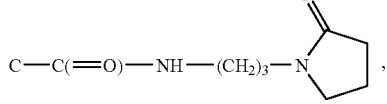
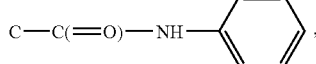
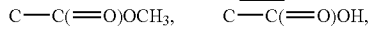
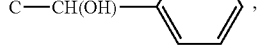
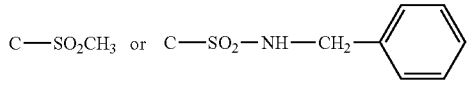

and Z is CH are particularly preferred.

Compounds of formula (Ixa) in which W is CH, X is C—CH₃ or C—CH₂CH₃, Y is

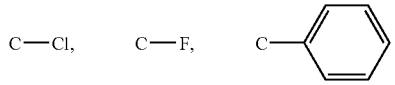
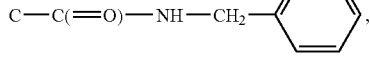

and Z is CH are also particularly preferred.

Compounds of formula (Ixa) in which W is CH, X is C—OCH₃, Y is CH, C—CH₃, C—CH₂CH₃, C—Cl or C—OCH₃ and Z is CH are also particularly-preferred.

Compounds of formula (Ixa) in which W is CH, X is C—OCH₂CH₃, Y is C—F and Z is CH are also particularly preferred.

Compounds of formula (Ixa) in which W represents CH, X represents $CR^2$ and Y represents $CR^3$ where $R^2$ and $R^3$ atoms form the group —CH₂—CH₂—CH₂—, and Z represents CH are also particularly preferred.

Compounds of formula (Ixa) in which W represents CH, X represents $CR^2$ and Y represents $CR^3$ where $R^2$ and $R^3$ form the group —$CH_2$—O—$CH_2$—, and Z represents CH are also particularly preferred.

Compounds of formula (Ixa) in which $R^8$ is hydrogen or —$CH_3$ and $R^9$ is

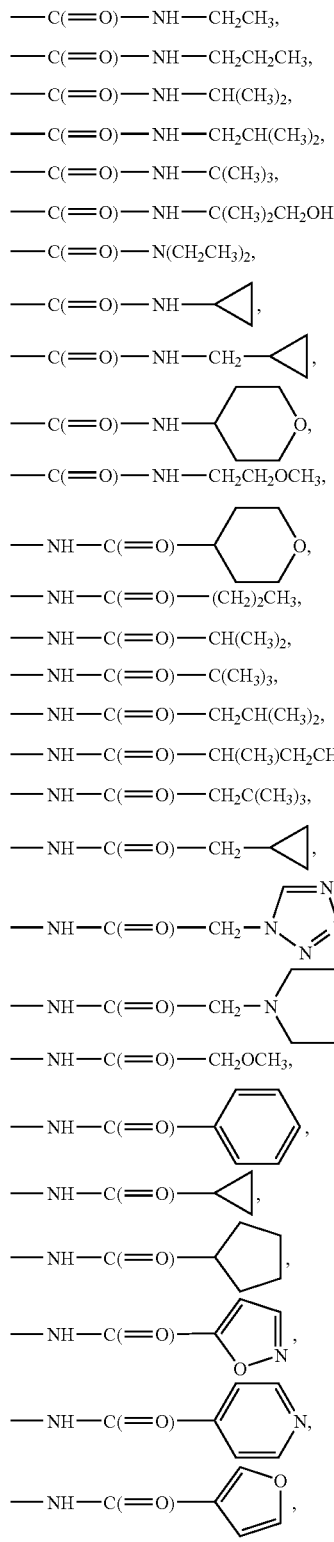

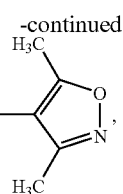,

—NH—C(=O)—$NHCH_3$,

—NH—C(=O)—$NHCH_2CH_3$,

—NH—C(=O)—$NHCH(CH_3)_2$,

—NH—C(=O)—$NHC(CH_3)_3$,

—NH—C(=O)—$N(CH_3)_2$,

—NH—C(=O)—$N(CH_2CH_3)_2$,

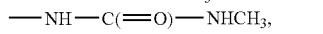,

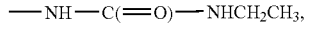,

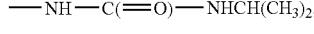,

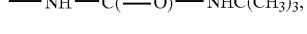,

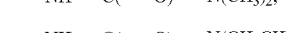

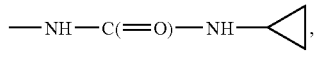 or

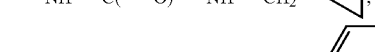

are especially preferred.

Compounds of formula (Ixa) in which W is CH, X is CH, Y is

C—$OCH_3$,  C—$OCH_2CH_3$,  C—$OCHF_2$,  C—$CF_3$,

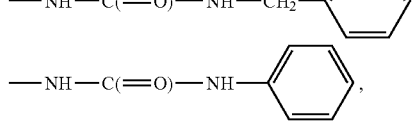 or

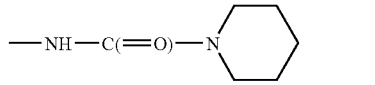

and Z is CH are especially preferred.

Compounds of formula (Ixa) in which W is CH, X is C—$CH_3$ or C—$CH_2CH_3$, Y is C—$CH_3$ or C—$CH_2CH_3$, C—Cl or C—F and Z is CH are also especially preferred.

Compounds of formula (Ixa) in which W is CH, X is C—$OCH_3$, Y is C—$CH_3$, C—$CH_2CH_3$, C—Cl, C—F or C—$OCH_3$ and Z is CH are also especially preferred.

Compounds of formula (Ixa) in which W is CH, X is C—$OCH_2CH_3$, Y is C—Cl or C—F and Z is CH are also especially preferred.

Compounds of formula (Ixa) in which W represents CH, X represents $CR^2$ and Y represents $CR^3$ where $R^2$ and $R^3$ form the group —$CH_2$—$CH_2$—$CH_2$—, and Z represents CH are also especially preferred.

Compounds of formula (Ixa) in which W represents CH, X represents CR² and Y represents CR³ where R² and R³ form the group —CH₂—O—CH₂—, and Z represents CH are also especially preferred.

Another particular group of compounds of the invention are compounds of formula (Ix) wherein R¹ is a heteroaryl moiety

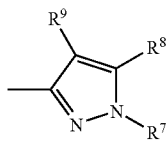

in which R⁸ and R⁹ together with the carbon atoms to which they are attached form an optionally substituted phenyl ring, i.e. compounds of formula (Ixb):—

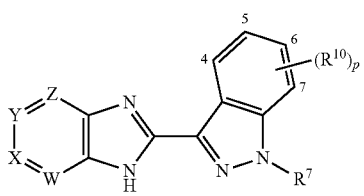

(Ixb)

in which W, X, Y, Z and R⁷ are as hereinbefore defined for compounds of formula (Ix); R¹⁰ is carboxy, cyano, halo, haloalkyl, hydroxy, nitro, R⁴, —C(=O)R⁴, —C(=O)NY¹Y², —C(=O)OR⁴, —N(R⁶)C(=O)R⁴, —N(R⁶)C(=O)NY¹Y², —N(R⁶)C(=O)OR⁴, —N(R⁶)SO₂R⁴, —N(R⁶)SO₂NY¹Y², —NY¹Y², —OR⁴, —OCF₂H, —OCF₃, —OC(=O)R⁴, —OC(=O)NY¹Y², —S(O)ₙR⁴ or —S(O)₂NY¹Y²; and p is zero, or an integer 1; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

Compounds of formula (Ixb) in which W represents CH, X represents CH, Y represents CH and Z represents CH or C—CH₃ are preferred.

Compounds of formula (Ixb) in which W represents CH, X represents CH, Z represents CH and Y represents:

(i) C—C₁₋₄alkyl [e.g. C—CH₃, C—CH₂CH₃, C—CH₂CH₂CH₃ or C—CH(CH₃)₂];

(ii) C-aryl [e.g. 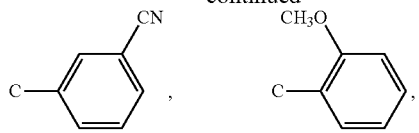

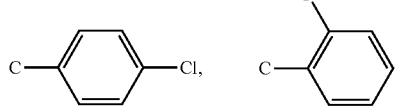,

-continued

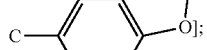

(iii) C—CN;

(iv) C—NO₂;

(v) C-halo [e.g. C—Br, C—Cl or C—F];

(vi) C-haloalkyl [e.g. C—CF₃];

(vii) C-heteroaryl [e.g. ];

(viii) C—OR⁴ [e.g. C—OCH₃, C—OCH₂CH₃, C—OCHF₂, 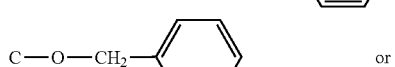

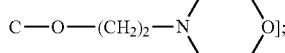];

(ix) C—C(=O)R⁴ [e.g. 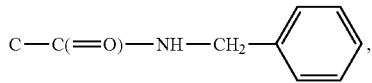];

(x) C—C(=O)NY¹Y² [e.g. C—C(=O)—NH—CH₃, C—C(=O)—N(CH₃)₂, C—C(=O)—NH—CH₂CH₃, C—C(=O)—NH—CH(CH₃)₂, C—C(=O)—NH—C(CH₃)₂—CH₂OH, C—C(=O)—NH—CH₂CH₂CN, C—C(=O)—NH—CH₂CH₂OCH₃,

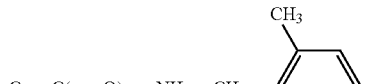

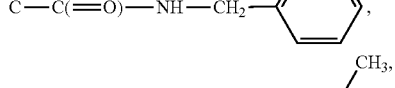

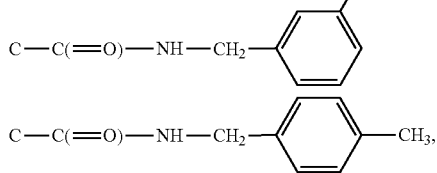

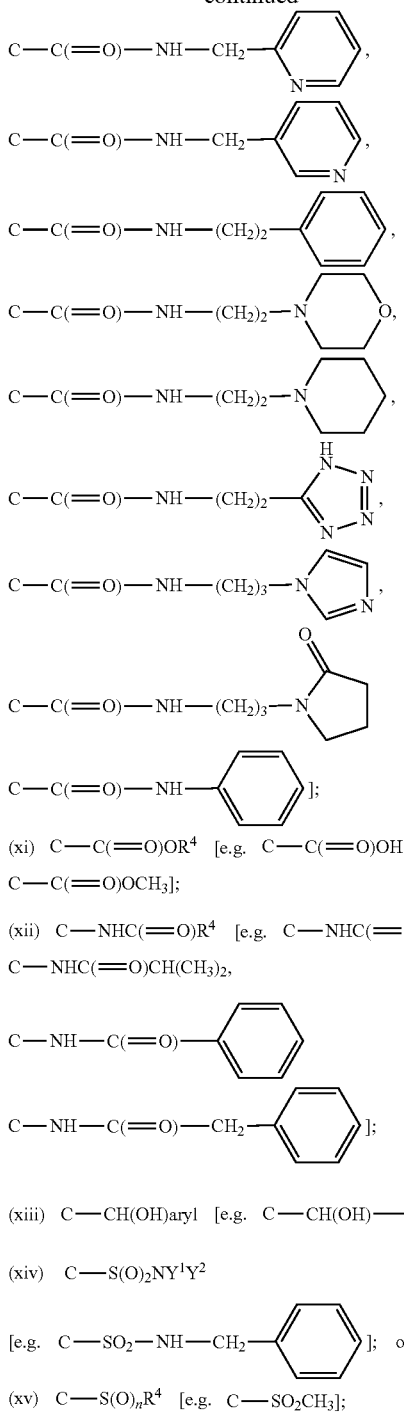

(xi)  C—C(=O)OR⁴  [e.g.  C—C(=O)OH  or
      C—C(=O)OCH₃];

(xii) C—NHC(=O)R⁴  [e.g.  C—NHC(=O)CH₃,
      C—NHC(=O)CH(CH₃)₂,

C—NH—C(=O)—[phenyl]  or

C—NH—C(=O)—CH₂—[phenyl]];

(xiii) C—CH(OH)aryl  [e.g.  C—CH(OH)—[phenyl]];

(xiv) C—S(O)₂NY¹Y²
      [e.g.  C—SO₂—NH—CH₂—[phenyl]];  or (xv)  C—S(O)ₙR⁴  [e.g.  C—SO₂CH₃];

are also preferred.

Compounds of formula (Ixb) in which W represents CH, X represents

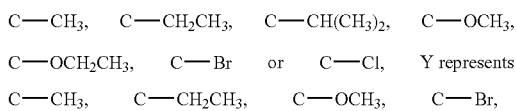

-continued

C—Cl,   C—F,   C—[phenyl]   or

C—C(=O)—NH—CH₂—[phenyl]

and Z represents CH are also preferred.

Compounds of formula (Ixb) in which W represents CH, X represents CH, Y represents C—CH₃ and Z represents C—CH₃ are also preferred.

Compounds of formula (Ixb) in which W represents CH, X represents CR² and Y represents CR³ where R² and R³ form the group —CH₂—O—CH₂—, and Z represents CH are also preferred.

Compounds of formula (Ixb) in which W represents CH, X represents CR² and Y represents CR³ where R² and R³ form the group —CH₂—CH₂—CH₂—, and Z represents CH are also preferred.

Compounds of formula (Ixb) in which R⁷ represents hydrogen are preferred.

Compounds of formula (Ixb) in which p is zero or one are preferred.

Compounds of formula (Ixb) in which R¹⁰ represents:
(i) cyano
(ii) halo [e.g. chloro, fluoro];
(iii) $C_{1-4}$alkyl [e.g. methyl,
(iv) —OR⁴ [e.g. —OCH₃, —OCH₂CH₃]; or
(v) —C(=O)NY¹Y² [e.g. —C(=O)—NH₂, —C(=O)—NHCH(CH₃)₂, —C(=O)—N(CH₃)₂ are preferred.

A preferred group of compounds of the invention are compounds of formula (Ixb) in which:—W represents CH; X represents CH; Y represents CH; Z represents CH or C—CH₃; R⁷ represents hydrogen; R¹⁰ represents (i) cyano, (ii) halo [e.g. chloro, fluoro], (iii) $C_{1-4}$alkyl [e.g. methyl], (iv) —OR⁴ [e.g. —OCH₃ or —OCH₂CH₃] or (v) —C(=O)NY¹Y² [e.g. —C(=O)—NH₂, —C(=O)—NHCH(CH₃)₂ or —C(=O)—N(CH₃)₂]; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

A further preferred group of compounds of the invention are compounds of formula (Ixb) in which:—W represents CH; X represents CH; Z represents CH; Y represents (i)  C—$C_{1-4}$alkyl  [e.g.  C—CH₃,  C—CH₂CH₃,
     C—CH₂CH₂CH₃  or  C—CH(CH₃)₂], (ii) C-aryl [e.g.

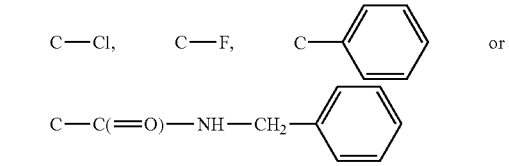

]

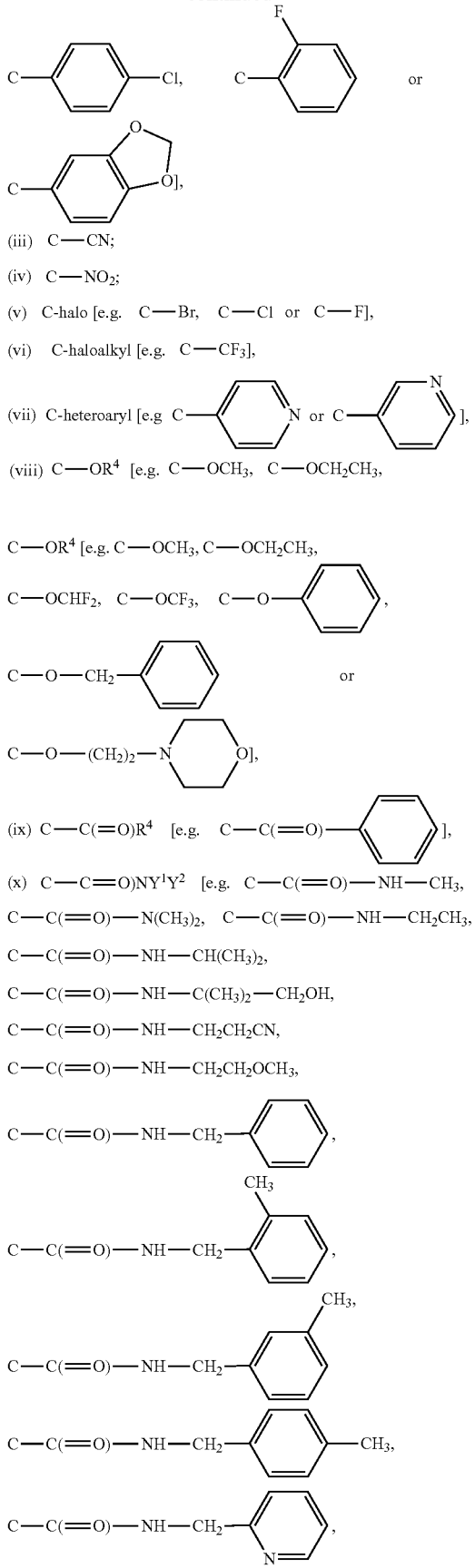

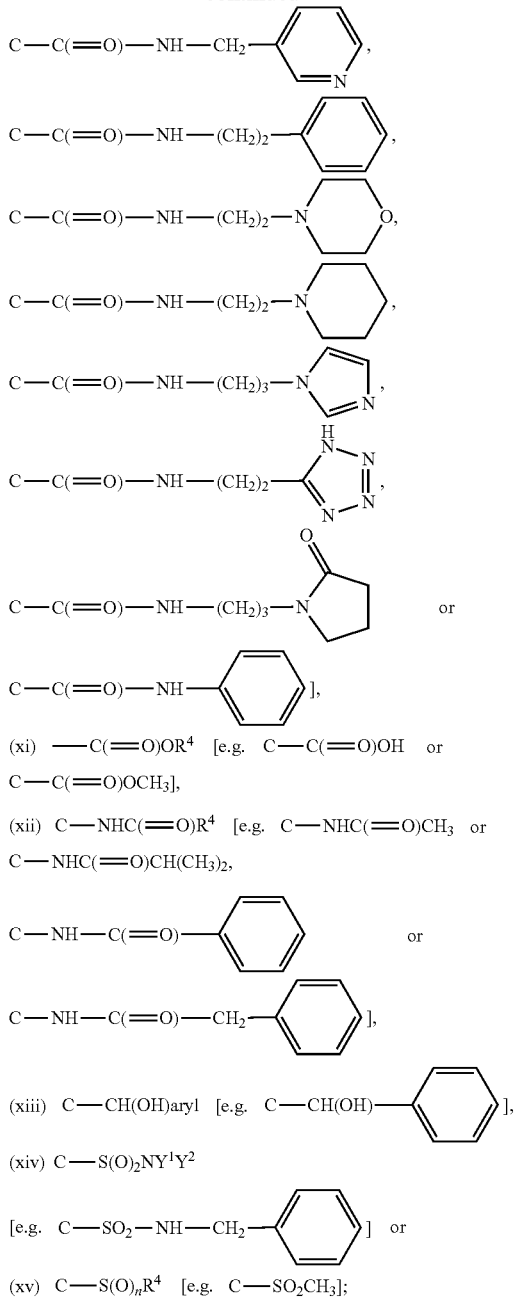

represents hydrogen; p is zero or one; $R^{10}$ represents (i) cyano, (ii) halo [e.g. chloro, fluoro], (iii) $C_{1-4}$alkyl [e.g. methyl], (iv) —$OR^4$ [e.g. —$OCH_3$ or —$OCH_2CH_3$] or (v) —C(=O)$NY^1Y^2$ [e.g. —C(=O)—$NH_2$, —C(=O)—NHCH($CH_3$)$_2$ or —C(=O)—N($CH_3$)$_2$]; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

A further preferred group of compounds of the invention are compounds of formula (Ixb) in which:—W represents CH; X represents C—$CH_3$, C—$CH_2CH_3$, C—CH($CH_3$)$_2$, C—$OCH_3$, C—$OCH_2CH_3$, C—Br or C—Cl; Y represents C—$CH_3$, C—$CH_2CH_3$,

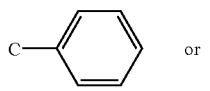 or

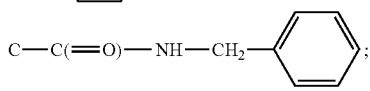

Z represents CH; R⁷ represents hydrogen; p is zero or one; R¹⁰ represents (i) cyano, (ii) halo [e.g. chloro, fluoro], (iii) C₁₋₄alkyl [e.g. methyl], (iv) —OR⁴ [e.g. —OCH₃ or —OCH₂CH₃] or (v) —C(═O)NY¹Y² [e.g. —C(═O)—NH₂, —C(═O)—NHCH(CH₃)₂ or —C(═O)—N(CH₁₃)₂]; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

A further preferred group of compounds of the invention are compounds of formula (Ixb) in which:—W represents CH; X represents CH; Y represents C—CH₃; Z represents C—CH₃; R⁷ represents hydrogen; p is zero or one; R¹⁰ represents (i) cyano, (ii) halo [e.g. chloro, fluoro], (iii) C₁₋₄alkyl [e.g. methyl], (iv) —OR⁴ [e.g. —OCH₃ or —OCH₂CH₃] or (v) —C(═O)NY¹Y² [e.g. —C(═O)—NH₂, —C(═O)—NHCH(CH₃)₂ or —C(═O)—N(CH₃)₂]; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

A further preferred group of compounds of the invention are compounds of formula (Ixb) in which:—W represents CH; X represents CR² and Y represents CR³ where R² and R³ form the group —CH₂—O—CH₂—; Z represents CH; R⁷ represents hydrogen; p is zero or one; R¹⁰ represents (i) cyano, (ii) halo [e.g. chloro, fluoro], (iii) C1-4alkyl [e.g. methyl], (iv) —OR⁴ [e.g. —OCH₃ or —OCH₂CH₃] or (v) —C(═O)NY¹Y² [e.g. —C(═O)—NH₂, —C(═O)—NHCH(CH₃)₂ or —C(═O)—N(CH₃)₂]; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

A further preferred group of compounds of the invention are compounds of formula (Ixb) in which:—W represents CH; X represents CR² and Y represents CR³ where R² and R³ form the group —CH₂—CH₂—CH₂—; Z represents CH; R⁷ represents hydrogen; p is zero or one; R¹⁰ represents (i) cyano, (ii) halo [e.g. chloro, fluoro], (iii) C₁₋₄alkyl [e.g. methyl], (iv) —OR⁴ [e.g. —OCH₃ or —OCH₂CH₃] or (v) —C(═O)NY¹Y² [e.g. —C(═O)—NH₂, —C(═O)—NHCH(CH₃)₂ or —C(═O)—N(CH₃)₂]; and their corresponding N-oxides, and their prodrugs, and their acid bioisosteres; and pharmaceutically acceptable salts and solvates (e.g. hydrates) of compounds of formula (Ixb) and their N-oxides and their prodrugs, and their acid bioisosteres.

Compounds of formula (Ixb) in which R⁷ represents hydrogen and p is zero are particularly preferred.

Compounds of formula (Ixb) in which R⁷ represents hydrogen; p is one and R¹⁰ represents cyano, chloro, fluoro, methyl, —OCH₃, —OCH₂CH₃, —C(═O)—NH₂, —C(═O)—NHCH(CH₃)₂ or —C(═O)—N(CH₃)₂ are also particularly preferred.

Compounds of formula (Ixb) in which W is CH, X is CH, Y is CH,  C—CH₂CH₃,  C—CH₂CH₂CH₃,

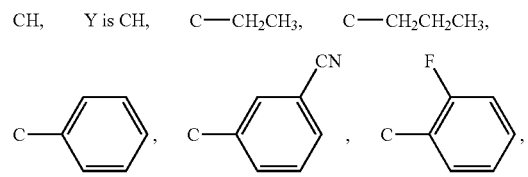

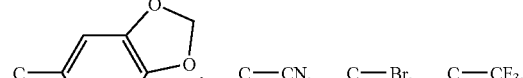

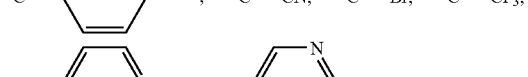

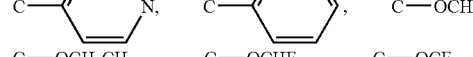

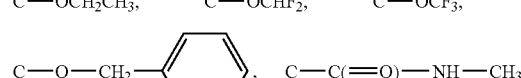

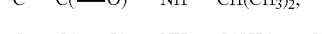

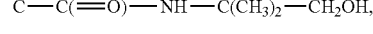

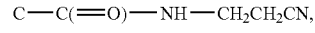

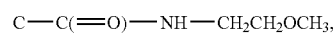

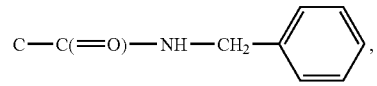


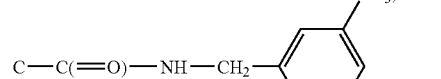

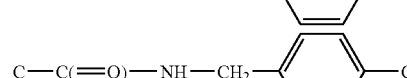

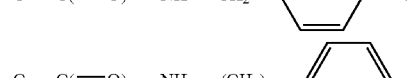

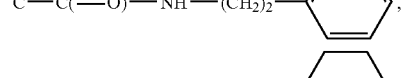

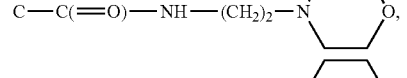

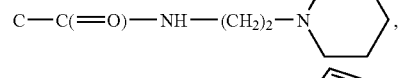

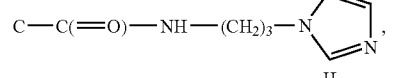

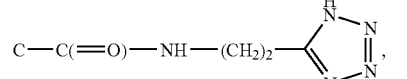

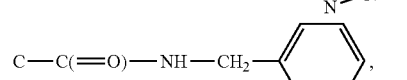

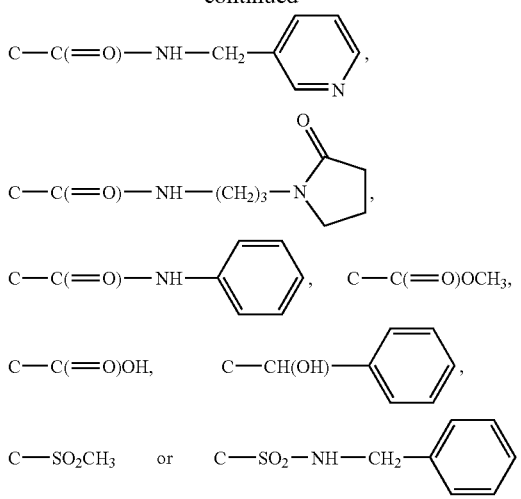

and Z is CH are particularly preferred.

Compounds of formula (Ixb) in which W is CH, X is C—CH₃ or C—CH₂CH₃, Y is

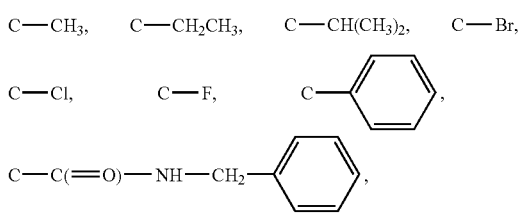

and Z is CH are also particularly preferred.

Compounds of formula (Ixb) in which W is CH, X is C—OCH₃, Y is CH, C—CH₃, C—CH₂CH₃, C—Cl or C—OCH₃ and Z is CH are also particularly preferred.

Compounds of formula (Ixb) in which W is CH, X is C—OCH₂CH₃, Y is C—F and Z is CH are also particularly preferred.

Compounds of formula (Ixb) in which W represents CH, X represents CR² and Y represents CR³ where R² and R³ form the group —CH₂—CH₂—CH₂—, and Z represents CH are also particularly preferred.

Compounds of formula (Ixb) in which W represents CH, X represents CR² and Y represents CR³ where R² and R³ form the group —CH₂—O—CH₂—, and Z represents CH are also particularly preferred.

Compounds of formula (Ixb) in which R⁷ represents hydrogen and p is zero are especially preferred.

Compounds of formula (Ixb) in which R⁷ represents hydrogen; p is one and R¹⁰ represents —OCH₃, —OCH₂CH₃ or —C(=O)—NHCH(CH₃)₂ attached to position 5 of the indazolyl ring are also especially preferred.

Compounds of formula (Ixb) in which W is CH, X is C—CH₃ or C—CH₂CH₃, Y is C—CH₃ or C—CH₂CH₃ and Z is CH are also especially preferred.

Another particular group of compounds of the invention are compounds of formula (Ix) wherein R¹ is a pyrazolyl moiety

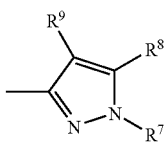

in which R⁸ and R⁹ together with the carbon atoms to which they are attached form an optionally substituted $C_{5-8}$cycloalkyl ring, i.e. compounds of formula (Ixc):—

(Ixc)

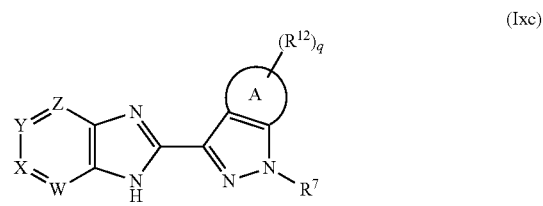

in which W, X, Y, Z, X and p are as hereinbefore defined for compounds of formula (Ix),

is a $C_{5-8}$cycloalkyl ring and R¹² is acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy (or an acid bioisostere), cyano, cycloalkyl, halo, heteroaroyl, heteroaryl, heteroarylalkyloxy, heteroaroylamino, heteroaryloxy, heterocycloalkyl, hydroxy, nitro, trifluoromethyl, —C(=O)NY¹Y², —NY¹—C(=O)alkyl, —NY¹SO₂alkyl, —NY¹Y², —SO₂NY¹Y² or alkyl, alkenyl or alkynyl each optionally substituted with aryl, cycloalkyl, heteroaryl, hydroxy, —C(=O)OR⁶, —C(=O)NY¹Y², —NY¹Y² or —OR⁵; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

Compounds of formula (Ixc) in which W represents CH, X represents CH, Y represents CH and Z represents CH or C—CH₃ are preferred.

Compounds of formula (Ixc) in which W represents CH, X represents CH, Z represents CH and Y represents:

(i) C—$C_{1-4}$alkyl [e.g. C—CH₃, C—CH₂CH₃, C—CH₂CH₂CH₃ or C—CH(CH₃)₂];

(ii) C-aryl [e.g. , , , ,

-continued

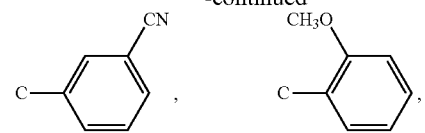,

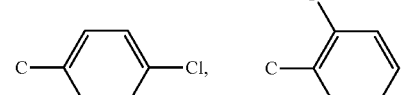

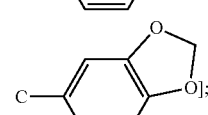];

(iii)  C—CN;

(iv)  C—NO₂;

(v)  C-halo [e.g.  C—Br,  C—Cl or C—F];

(vi)  C-haloalkyl [e.g.  C—CF₃];

(vii)  C-heteroaryl [e.g. 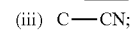 or 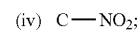];

(viii)  C—OR⁴ [e.g.  C—OCH₃,  C—OCH₂CH₃, 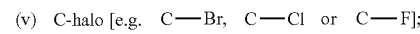

C—OCHF₂,  C—OCF₃, 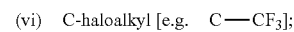,

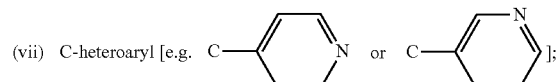 or

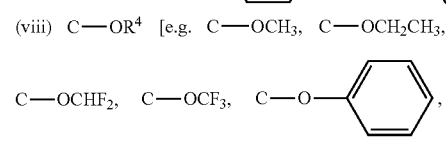];

(ix)  C—C(=O)R⁴ [e.g. 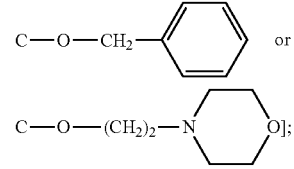];

(x)  C—C(=O)NY¹Y² [e.g.  C—C(=O)—NH—CH₃,
C—C(=O)—N(CH₃)₂,  C—C(=O)—NH—CH₂CH₃,
C—C(=O)—NH—CH(CH₃)₂,
C—C(=O)—NH—C(CH₃)₂—CH₂OH,
C—C(=O)—NH—CH₂CH₂CN,
C—C(=O)—NH—CH₂CH₂OCH₃,

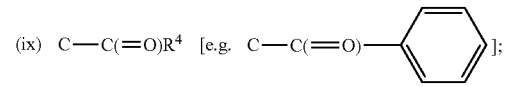,

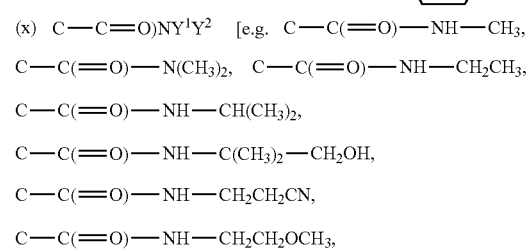,

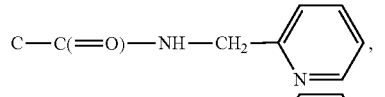,

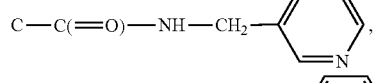,

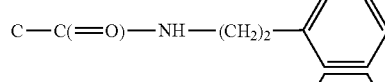,

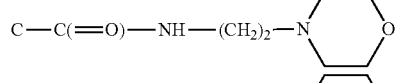,

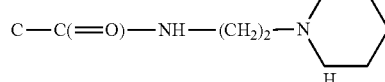,

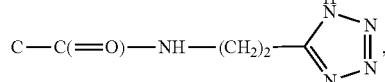,

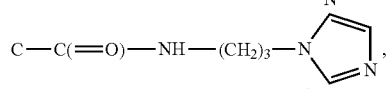,

 or

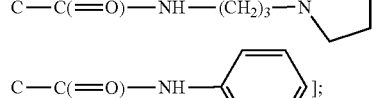];

(xi)  C—C(=O)OR⁴ [e.g.  C—C(=O)OH or
C—C(=O)OCH₃];

(xii)  C—NHC(=O)R⁴ [e.g.  C—NHC(=O)CH₃,
C—NHC(=O)CH(CH₃)₂,

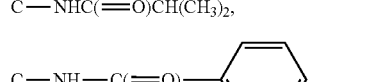 or

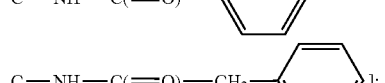]; or (xiii)  C—CH(OH)aryl [e.g 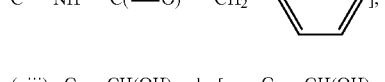];

(xiv)  C—S(O)₂NY¹Y²

[e.g. 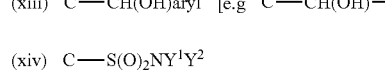];

(xv)  C—S(O)ₙR⁴ [e.g.  C—SO₂CH₃];

are also preferred.

Compounds of formula (Ixc) in which W represents CH, X represents  C—CH₃,  C—CH₂CH₃,  C—CH(CH₃)₂,
C—OCH₃, C—OCH₂CH₃, C—Br or C—Cl, Y represents C—CH₃,  C—CH₂CH₃,  C—OCH₃,  C—Br, C—Cl, C—F, 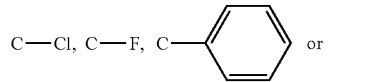 or

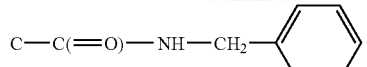

and Z represents CH are also preferred.

Compounds of formula (Ixc) in which W represents CH, X represents CH, Y represents C—CH₃ and Z represents C—CH₃ are also preferred.

Compounds of formula (Ixc) in which W represents CH, X represents $CR^2$ and Y represents $CR^3$ where $R^2$ and $R^3$ form the group —CH₂—O—CH₂—, and Z represents CH are also preferred.

Compounds of formula (Ixc) in which W represents CH, X represents $CR^2$ and Y represents $CR^3$ where $R^2$ and $R^3$ form the group —CH₂—CH₂—CH₂—, and Z represents CH are also preferred.

Compounds of formula (Ixc) in which $R^7$ represents hydrogen are preferred.

Compounds of formula (Ixc) in which

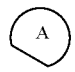

represents a cyclopentyl, cyclohexyl and cycloheptyl, especially cyclohexyl, ring are preferred.

Compounds of formula (Ixc) in which q is zero are preferred.

A preferred group of compounds of the invention are compounds of formula (Ixc) in which:—W represents CH; X represents CH; Y represents CH; Z represents CH or C—CH₃; $R^7$ represents hydrogen;

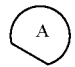

represents a cyclopentyl, cyclohexyl or cycloheptyl ring; q is zero; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

A further preferred group of compounds of the invention are compounds of formula (Ixc) in which:—W represents CH; X represents CH; Z represents CH; Y represents (i) C—C₁₋₄alkyl [e.g C—CH₃, C—CH₂CH₃, C—CH₂CH₂CH₃ or C—CH(CH₃)₂], (ii) C-aryl [e.g. 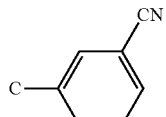, 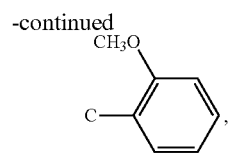,

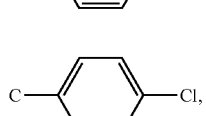, 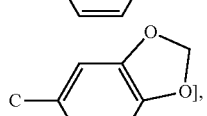,

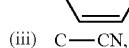,

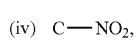], (iii) C—CN, (iv) C—NO₂, (v) C-halo [e.g. C—Br, C—Cl or C—F], (vi) C-haloalkyl [e.g. C—CF₃], (vii) C-heteroaryl [e.g. 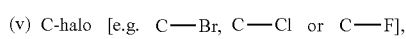 or

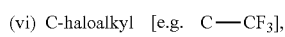], (viii) C—OR⁴ [e.g. C—OCH₃, C—OCH₂CH₃,

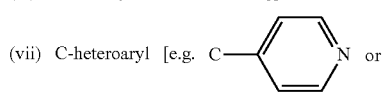

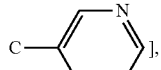 or

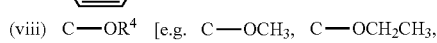], (ix) C—C(=O)R⁴ [e.g. 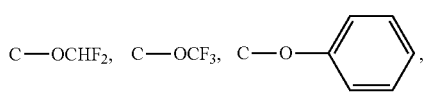], (x) C—C(=O)NY¹Y² [e.g. C—C(=O)—NH—CH₃,

C—C(=O)—N(CH₃)₂, C—C(=O)—NH—CH₂CH₃,

C—C(=O)—NH—CH(CH₃)₂,

C—C(=O)—NH—C(CH₃)₂—CH₂OH,

C—C(=O)—NH—CH₂CH₂CN,

C—C(=O)—NH—CH₂CH₂OCH₃,

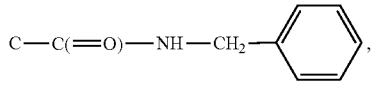

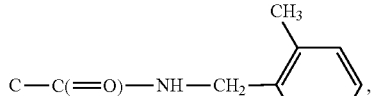

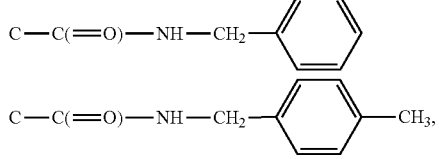

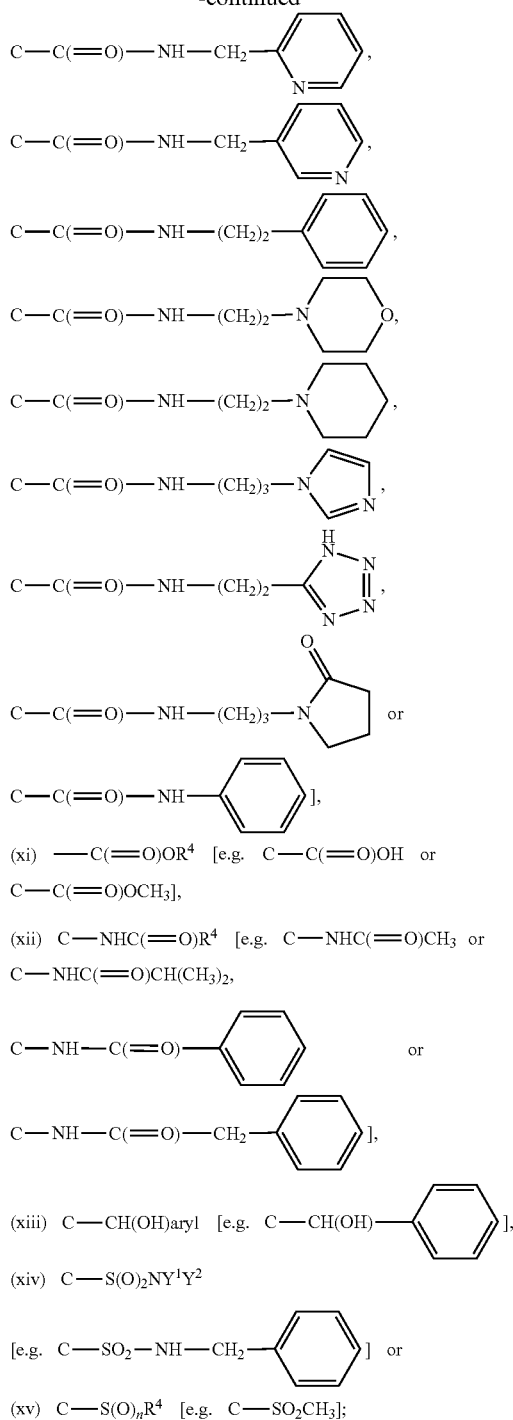

(xi) —C(=O)OR⁴ [e.g. C—C(=O)OH or C—C(=O)OCH₃], (xii) C—NHC(=O)R⁴ [e.g. C—NHC(=O)CH₃ or C—NHC(=O)CH(CH₃)₂,

(xiii) C—CH(OH)aryl [e.g. C—CH(OH)—⌬ ], (xiv) C—S(O)₂NY¹Y²

[e.g. C—SO₂—NH—CH₂—⌬ ] or (xv) C—S(O)ₙR⁴ [e.g. C—SO₂CH₃];

R⁷ represents hydrogen;

represents a cyclopentyl, cyclohexyl or cycloheptyl ring; q is zero; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

A further preferred group of compounds of the invention are compounds of formula (Ixc) in which:—W represents CH; X represents C—CH₃, C—CH₂CH₃, C—CH(CH₃)₂, C—OCH₃, C—OCH₂CH₃, C—Br or C—Cl; Y represents

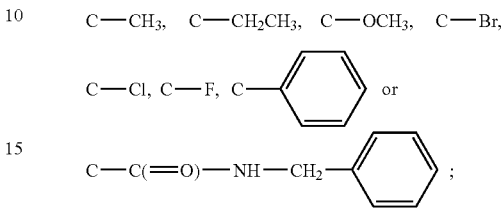

Z represents CH; R⁷ represents hydrogen;

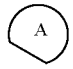

represents a cyclopentyl, cyclohexyl or cycloheptyl ring; q is zero; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

A further preferred group of compounds of the invention are compounds of formula (Ixc) in which:—W represents CH; X represents CH; Y represents C—CH₃; Z represents C—CH₃; R⁷ represents hydrogen;

represents a cyclopentyl, cyclohexyl or cycloheptyl ring; q is zero; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

A further preferred group of compounds of the invention are compounds of formula (Ixb) in which:—W represents CH; X represents CR² and Y represents CR³ where R² and R³ form the group —CH₂—O—CH₂—; Z represents CH; R⁷ represents hydrogen;

represents a cyclopentyl, cyclohexyl or cycloheptyl ring; q is zero; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

A further preferred group of compounds of the invention are compounds of formula (Ixb) in which:—W represents CH; X represents CR² and Y represents CR³ where R² and R³ form the group —CH₂—CH₂—CH₂—; Z represents CH; R⁷ represents hydrogen;

represents a cyclopentyl, cyclohexyl or cycloheptyl ring; q is zero; and their corresponding N-oxides, and their prodrugs, and their acid bioisosteres; and pharmaceutically acceptable salts and solvates (e.g. hydrates) of compounds of formula (Ixc) and their N-oxides and their prodrugs, and their acid bioisosteres.

Compounds of formula (Ixc) in which R⁷ represents hydrogen and p is zero are particularly preferred.

Compounds of formula (Ixc) in which W is CH, X is C—CH₃, Y is C—CH₃ and Z is CH are also particularly preferred.

Compounds of formula (Ixc) in which

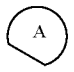

is a cyclopentyl ring are particularly preferred.

Another particular group of compounds of the invention are compounds of formula (Ix) wherein R¹ is a pyrazolyl moiety

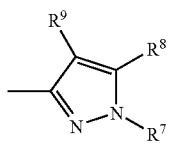

in which R⁸ and R⁹ together with the carbon atoms to which they are attached form an optionally substituted heterocycloalkyl ring, i.e. compounds of formula (Ixd):—

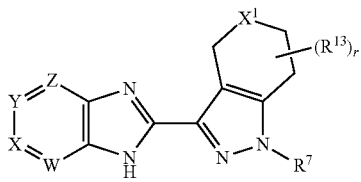

in which W, X, Y, Z and X are as hereinbefore defined for compounds of formula (Ix), $X^1$ is O, S, SO₂, or NY⁵ (where Y⁵ is hydrogen, R⁴, —C(=O)R⁴, —C(=O)NY¹Y², —C(=O)OR⁴ or —SO₂R⁴), r is zero or an integer one or two and $R^{13}$ is alkyl or two $R^{13}$ groups attached to the same carbon atom form an oxo group; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

Compounds of formula (Ixd) in which W represents CH, X represents CH, Y represents CH and Z represents CH or C—CH₃ are preferred.

Compounds of formula (Ixd) in which W represents CH, X represents CH, Z represents CH and Y represents:

(i) C—C₁₋₄alkyl [e.g C—CH₃, C—CH₂CH₃, C—CH₂CH₂CH₃ or C—CH(CH₃)₂], (ii) C-aryl [e.g. structures shown including phenyl, o-tolyl, m-tolyl, p-tolyl, cyanophenyl, methoxyphenyl, chlorophenyl, fluorophenyl, or benzodioxole], (iii) C—CN, (iv) C—NO₂, (v) C-halo [e.g. C—Br, C—Cl or C—F], (vi) C-haloalkyl [e.g. C—CF₃], (vii) C-heteroaryl [e.g. C-pyridyl structures], (viii) C—OR⁴ [e.g. C—OCH₃, C—OCH₂CH₃, C—OCHF₂, C—OCF₃, C—O-phenyl, C—O—CH₂-phenyl or C—O—(CH₂)₂—N-morpholino], (ix) C—C(=O)R⁴ [e.g. C—C(=O)-phenyl], (x) C—C(=O)NY¹Y² [e.g. C—C(=O)—NH—CH₃, C—C(=O)—N(CH₃)₂, C—C(=O)—NH—CH₂CH₃, C—C(=O)—NH—CH(CH₃)₂, C—C(=O)—NH—C(CH₃)₂—CH₂OH, C—C(=O)—NH—CH₂CH₂CN, C—C(=O)—NH—CH₂CH₂OCH₃,

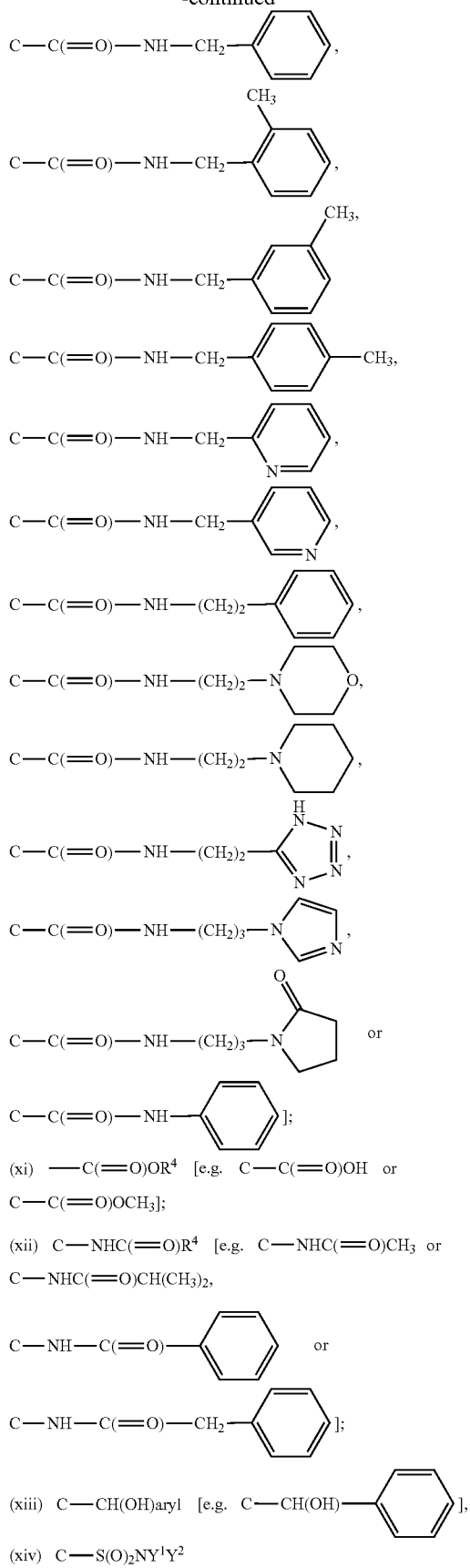

(xi) —C(=O)OR$^4$ [e.g. C—C(=O)OH or C—C(=O)OCH$_3$];

(xii) C—NHC(=O)R$^4$ [e.g. C—NHC(=O)CH$_3$ or C—NHC(=O)CH(CH$_3$)$_2$,

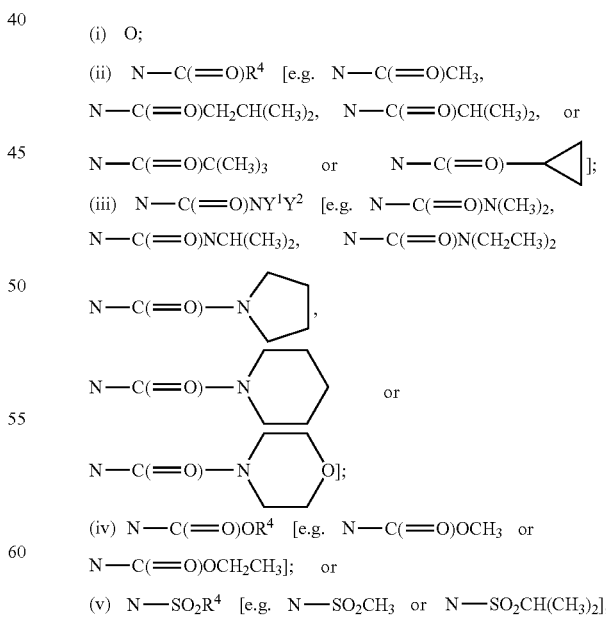

(xiii) C—CH(OH)aryl [e.g. C—CH(OH)—Ph], (xiv) C—S(O)$_2$NY$^1$Y$^2$

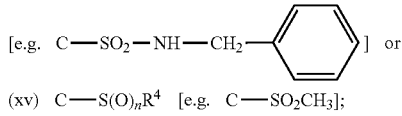

(xv) C—S(O)$_n$R$^4$ [e.g. C—SO$_2$CH$_3$];

are also preferred.

Compounds of formula (Ixd) in which W represents CH, X represents C—CH$_3$, C—CH$_2$CH$_3$, C—CH(CH$_3$)$_2$, C—OCH$_3$, C—OCH$_2$CH$_3$, C—Br or C—Cl, Y represents C—CH$_3$, C—CH$_2$CH$_3$, C—OCH$_3$, C—Br, C—Cl, C—F, 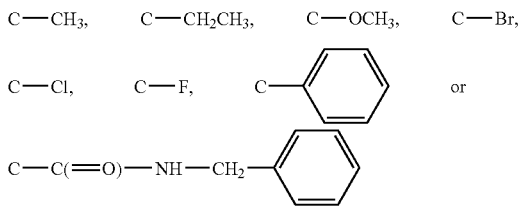 or C—C(=O)—NH—CH$_2$—Ph and Z represents CH are also preferred.

Compounds of formula (Ixa) in which W represents CH, X represents CH, Y represents C—CH$_3$ and Z represents C—CH$_3$ are also preferred.

Compounds of formula (Ixd) in which W represents CH, X represents CR$^2$ and Y represents CR$^3$ where R$^2$ and R$^3$ form the group —CH$_2$—O—CH$_2$—, and Z represents CH are also preferred.

Compounds of formula (Ixd) in which W represents CH, X represents CR$^2$ and Y represents CR$^3$ where R$^2$ and R$^3$ form the group —CH$_2$—CH$_2$—CH$_2$—, and Z represents CH are also preferred.

Compounds of formula (Ixd) in which R$^7$ represents hydrogen are preferred.

Compounds of formula (Ixd) in which X$^1$ is:

(i) O;

(ii) N—C(=O)R$^4$ [e.g. N—C(=O)CH$_3$, N—C(=O)CH$_2$CH(CH$_3$)$_2$, N—C(=O)CH(CH$_3$)$_2$, or N—C(=O)C(CH$_3$)$_3$ or N—C(=O)-cyclopropyl];

(iii) N—C(=O)NY$^1$Y$^2$ [e.g. N—C(=O)N(CH$_3$)$_2$, N—C(=O)NCH(CH$_3$)$_2$, N—C(=O)N(CH$_2$CH$_3$)$_2$ N—C(=O)—pyrrolidinyl, N—C(=O)—piperidinyl or N—C(=O)—morpholinyl];

(iv) N—C(=O)OR$^4$ [e.g. N—C(=O)OCH$_3$ or N—C(=O)OCH$_2$CH$_3$]; or (v) N—SO$_2$R$^4$ [e.g. N—SO$_2$CH$_3$ or N—SO$_2$CH(CH$_3$)$_2$];

are preferred.

Compounds of formula (Ixd) in which r is zero are preferred.

A preferred group of compounds of the invention are compounds of formula (Ixd) in which:—W represents CH; X represents CH; Y represents CH; Z represents CH or C—CH₃; R⁷ represents hydrogen; X¹ is (i) O;

(ii) N—C(=O)R⁴ [e.g. N—C(=O)CH₃, N—C(=O)CH₂CH(CH₃)₂, N—C(=O)CH(CH₃)₂, or N—C(=O)C(CH₃)₃ or N—C(=O)—];

(iii) N—C(=O)NY¹Y² [e.g. N—C(=O)N(CH₃)₂, N—C(=O)NCH(CH₃)₂, N—C(=O)N(CH₂CH₃)₂

N—C(=O)—,

N—C(=O)— or

N—C(=O)—];

(iv) N—C(=O)OR⁴ [e.g. N—C(=O)OCH₃ or N—C(=O)OCH₂CH₃]; or (v) N—SO₂R⁴ [e.g. N—SO₂CH₃ or N—SO₂CH(CH₃)₂]

and r is zero; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

A further preferred group of compounds of the invention are compounds of formula (Ixd) in which:—W represents CH; X represents CH; Z represents CH; Y represents (i) C—C₁₋₄alkyl [e.g C—CH₃, C—CH₂CH₃, C—CH₂CH₂CH₃ or C—CH(CH₃)₂], (ii) C-aryl [e.g. C—, C—, C—, C—, C—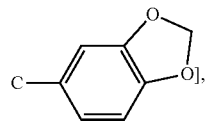, C—, C—, C— or C—], (iii) C—CN, (iv) C—NO₂, (v) C-halo [e.g. C—Br, C—Cl or C—F], (vi) C-haloalkyl [e.g. C—CF₃], (vii) C-heteroaryl [e.g. C—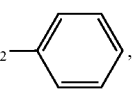 or C—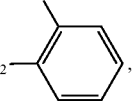], (viii) C—OR⁴ [e.g. C—OCH₃, C—OCH₂CH₃, C—OCHF₂, C—OCF₃, C—O—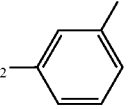, C—O—CH₂—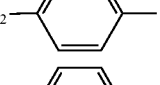 or C—O—(CH₂)₂—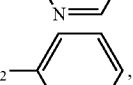], (ix) C—C(=O)R⁴ [e.g. C—C(=O)—], (x) C—C(=O)NY¹Y² [e.g. C—C(=O)—NH—CH₃, C—C(=O)—N(CH₃)₂, C—C(=O)—NH—CH₂CH₃,

C—C(=O)—NH—CH(CH₃)₂,

C—C(=O)—NH—C(CH₃)₂—CH₂OH,

C—C(=O)—NH—CH₂CH₂CN,

C—C(=O)—NH—CH₂CH₂OCH₃,

C—C(=O)—NH—CH₂—⌬,

C—C(=O)—NH—CH₂—⌬ CH₃,

C—C(=O)—NH—CH₂—⌬ CH₃,

C—C(=O)—NH—CH₂—⌬—CH₃,

C—C(=O)—NH—CH₂—⌬ₙ,

C—C(=O)—NH—CH₂—⌬ₙ,

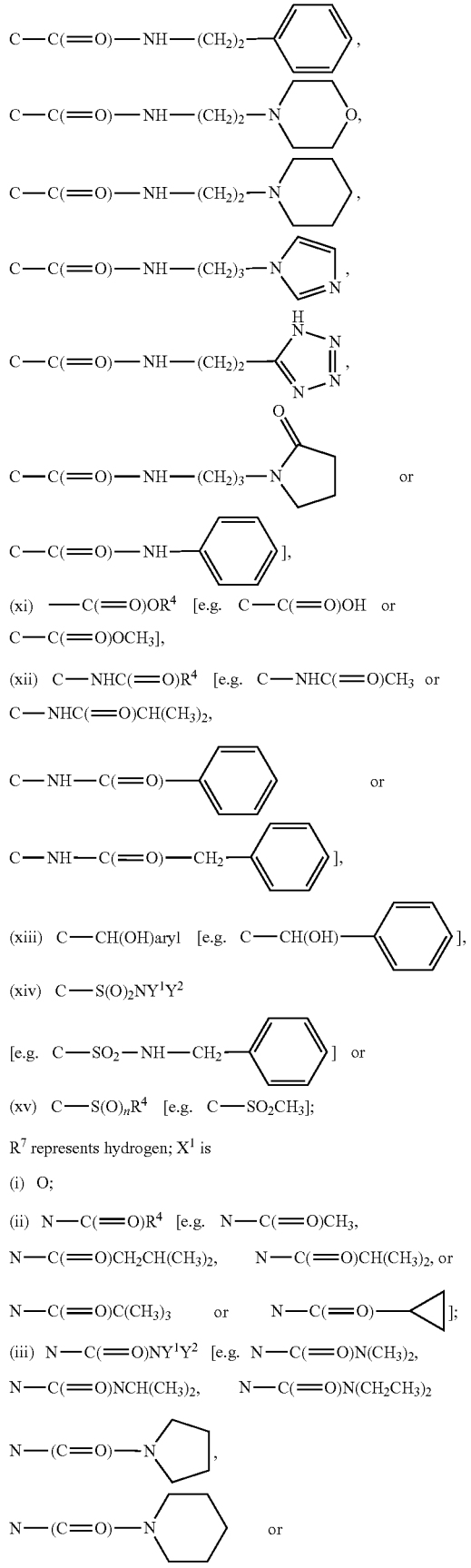

(xi) —C(=O)OR⁴ [e.g. C—C(=O)OH or C—C(=O)OCH₃], (xii) C—NHC(=O)R⁴ [e.g. C—NHC(=O)CH₃ or C—NHC(=O)CH(CH₃)₂, C—NH—C(=O)—⌬  or

C—NH—C(=O)—CH₂—⌬ ], (xiii) C—CH(OH)aryl [e.g. C—CH(OH)—⌬ ], (xiv) C—S(O)₂NY¹Y²

[e.g. C—SO₂—NH—CH₂—⌬ ] or (xv) C—S(O)$_n$R⁴ [e.g. C—SO₂CH₃];

R⁷ represents hydrogen; X¹ is (i) O;

(ii) N—C(=O)R⁴ [e.g. N—C(=O)CH₃, N—C(=O)CH₂CH(CH₃)₂, N—C(=O)CH(CH₃)₂, or N—C(=O)C(CH₃)₃  or  N—C(=O)—▷ ];

(iii) N—C(=O)NY¹Y² [e.g. N—C(=O)N(CH₃)₂, N—C(=O)NCH(CH₃)₂, N—C(=O)N(CH₂CH₃)₂

N—(C=O)—N⌬ ,

N—(C=O)—N⌬   or

N—(C=O)—N⌬O];

(iv) N—C(=O)OR⁴ [e.g. N—C(=O)OCH₃ or N—C(=O)OCH₂CH₃];  or (v) N—SO₂R⁴ [e.g. N—SO₂CH₃ or N—SO₂CH(CH₃)₂]

and r is zero; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

A further preferred group of compounds of the invention are compounds of formula (Ixd) in which:—W represents CH; X represents C—CH₃, C—CH₂CH₃, C—CH(CH₃)₂, C—OCH₃, C—OCH₂CH₃, C—Br or C—Cl; Y represents


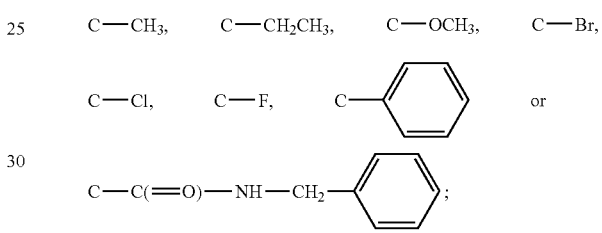

Z represents CH; R⁷ represents hydrogen; X¹ is (i) O;

(ii) N—C(=O)R⁴ [e.g. N—C(=O)CH₃, N—C(=O)CH₂CH(CH₃)₂, N—C(=O)CH(CH₃)₂, or N—C(=O)C(CH₃)₃  or  N—C(=O)—▷ ];

(iii) N—C(=O)NY¹Y² [e.g. N—C(=O)N(CH₃)₂, N—C(=O)NCH(CH₃)₂, N—C(=O)N(CH₂CH₃)₂

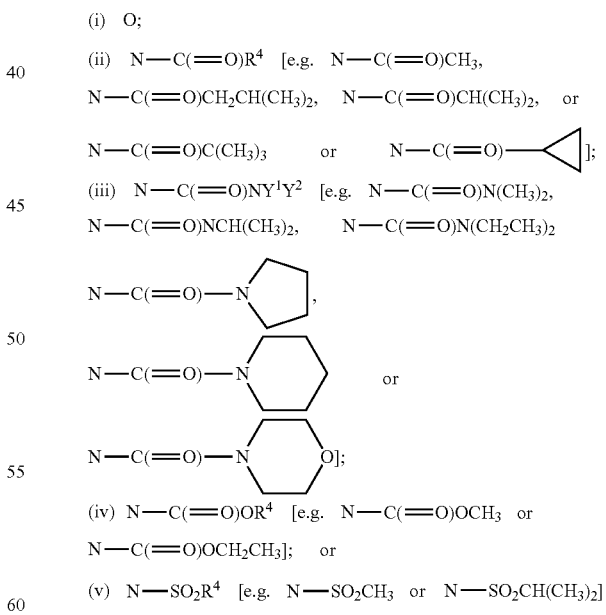

(iv) N—C(=O)OR⁴ [e.g. N—C(=O)OCH₃ or N—C(=O)OCH₂CH₃]; or (v) N—SO₂R⁴ [e.g. N—SO₂CH₃ or N—SO₂CH(CH₃)₂]

and r is zero; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

A further preferred group of compounds of the invention are compounds of formula (Ixd) in which:—W represents CH; X represents CH; Y represents C—CH$_3$; Z represents C—CH$_3$; R$^7$ represents hydrogen; X$^1$ is (i) O;

(ii) N—C(=O)R$^4$ [e.g. N—C(=O)CH$_3$, N—C(=O)CH$_2$CH(CH$_3$)$_2$, N—C(=O)CH(CH$_3$)$_2$, or N—C(=O)C(CH$_3$)$_3$ or N—C(=O)—◁];

(iii) N—C(=O)NY$^1$Y$^2$ [e.g. N—C(=O)N(CH$_3$)$_2$, N—C(=O)NCH(CH$_3$)$_2$, N—C(=O)N(CH$_2$CH$_3$)$_2$ N—C(=O)—N⟨pyrrolidine⟩, N—C(=O)—N⟨piperidine⟩ or N—C(=O)—N⟨morpholine⟩O];

(iv) N—C(=O)OR$^4$ [e.g. N—C(=O)OCH$_3$ or N—C(=O)OCH$_2$CH$_3$]; or (v) N—SO$_2$R$^4$ [e.g. N—SO$_2$CH$_3$ or N—SO$_2$CH(CH$_3$)$_2$]

and r is zero; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

A further preferred group of compounds of the invention are compounds of formula (Ixd) in which:—W represents CH; X represents CR$^2$ and Y represents CR$^3$ where R$^2$ and R$^3$ form the group —CH$_2$—O—CH$_2$—; Z represents CH; R$^7$ represents hydrogen; X$^1$ is (i) O;

(ii) N—C(=O)R$^4$ [e.g. N—C(=O)CH$_3$, N—C(=O)CH$_2$CH(CH$_3$)$_2$, N—C(=O)CH(CH$_3$)$_2$, or N—C(=O)C(CH$_3$)$_3$ or N—C(=O)—◁];

(iii) N—C(=O)NY$^1$Y$^2$ [e.g. N—C(=O)N(CH$_3$)$_2$, N—C(=O)NCH(CH$_3$)$_2$, N—C(=O)N(CH$_2$CH$_3$)$_2$ N—C(=O)—N⟨pyrrolidine⟩, N—C(=O)—N⟨piperidine⟩ or N—C(=O)—N⟨morpholine⟩O];

(iv) N—C(=O)OR$^4$ [e.g. N—C(=O)OCH$_3$ or N—C(=O)OCH$_2$CH$_3$]; or (v) N—SO$_2$R$^4$ [e.g. N—SO$_2$CH$_3$ or N—SO$_2$CH(CH$_3$)$_2$]

and r is zero; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

A further preferred group of compounds of the invention are compounds of formula (Ixd) in which:—W represents CH; X represents CR$^2$ and Y represents CR$^3$ where R$^2$ and R$^3$ form the group —CH$_2$—CH$_2$—CH$_2$—; Z represents CH; R$^7$ represents hydrogen; X$^1$ is (i) O;

(ii) N—C(=O)R$^4$ [e.g. N—C(=O)CH$_3$, N—C(=O)CH$_2$CH(CH$_3$)$_2$, N—C(=O)CH(CH$_3$)$_2$, or N—C(=O)C(CH$_3$)$_3$ or N—C(=O)—◁];

(iii) N—C(=O)NY$^1$Y$^2$ [e.g. N—C(=O)N(CH$_3$)$_2$, N—C(=O)NCH(CH$_3$)$_2$, N—C(=O)N(CH$_2$CH$_3$)$_2$ N—C(=O)—N⟨pyrrolidine⟩, N—C(=O)—N⟨piperidine⟩ or N—C(=O)—N⟨morpholine⟩O];

(iv) N—C(=O)OR$^4$ [e.g. N—C(=O)OCH$_3$ or N—C(=O)OCH$_2$CH$_3$]; or (v) N—SO$_2$R$^4$ [e.g. N—SO$_2$CH$_3$ or N—SO$_2$CH(CH$_3$)$_2$]

and r is zero; and their corresponding N-oxides, and their prodrugs, and their acid bioisosteres; and pharmaceutically acceptable salts and solvates (e.g. hydrates) of compounds of formula (Ixd) and their N-oxides and their prodrugs, and their acid bioisosteres.

Compounds of formula (Ixd) in which X$^1$ is

N—C(=O)CH(CH$_3$)$_2$,    N—C(=O)CH$_2$CH(CH$_3$)$_2$,

N—C(=O)C(CH$_3$)$_3$;    N—C(=O)—◁,

N—C(=O)N(CH$_3$)$_2$,    N—C(=O)NCH(CH$_3$)$_2$,

N—C(=O)N(CH$_2$CH$_3$)$_2$,    N—(C=O)—N⟨pyrrolidine⟩,

N—(C=O)—N⟨piperidine⟩,

N—(C=O)—N⟨morpholine⟩O,

N—C(=O)OCH$_3$ or N—C(=O)OCH$_2$CH$_3$ and r is zero are particularly preferred.

Compounds of formula (Ixd) in which W is CH, X is CH, Y is

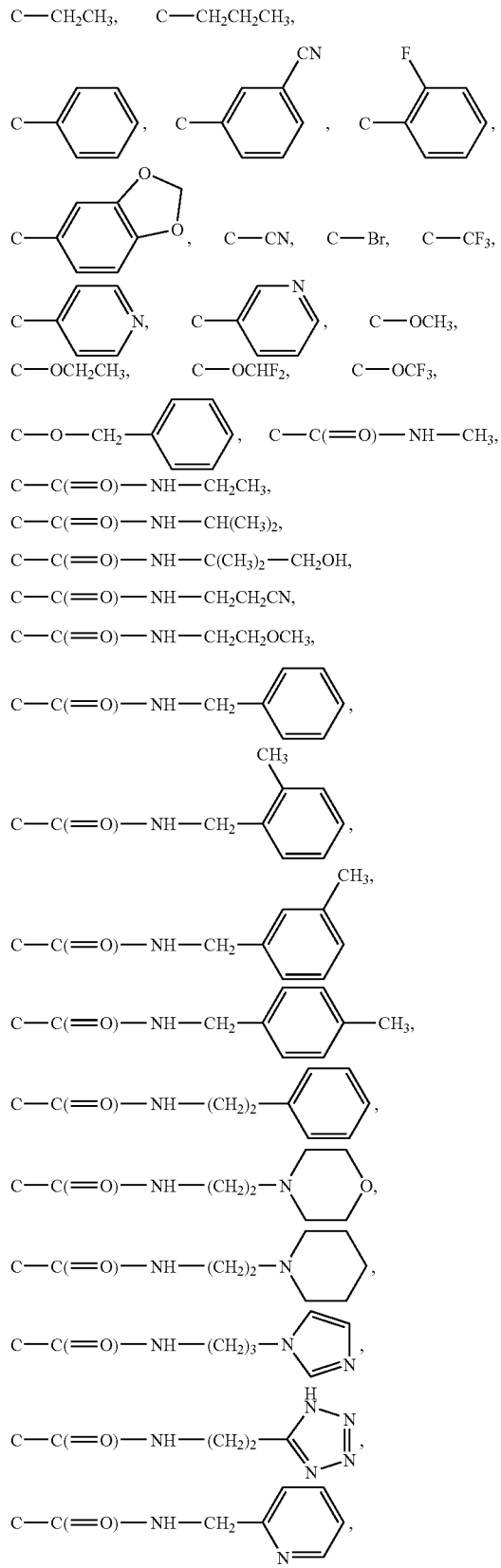

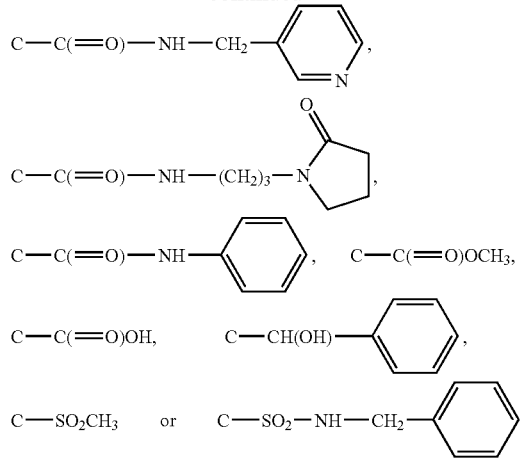

and Z is CH are particularly preferred.

Compounds of formula (Ixd) in which W is CH, X is C—CH₃ or C—CH₂CH₃, Y is

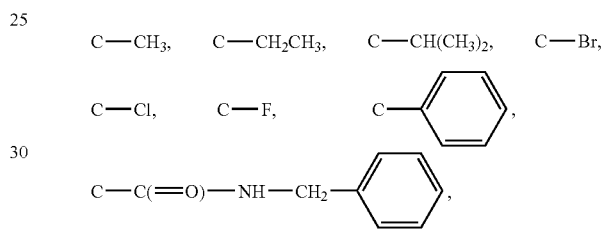

and Z is CH are also particularly preferred.

Compounds of formula (Ixa) in which W is CH, X is C—OCH₃, Y is CH, C—CH₃, C—CH₂CH₃, C—Cl or C—OCH₃ and Z is CH are also particularly preferred.

Compounds of formula (Ixd) in which W is CH, X is C—OCH₂CH₃, Y is C—F and Z is CH are also particularly preferred.

Compounds of formula (Ixd) in which W represents CH, X represents CR² and Y represents CR³ where R² and R³ form the group —CH₂—CH₂—CH₂—, and Z represents CH are also particularly preferred.

Compounds of formula (Ixd) in which W represents CH, X represents CR² and Y represents CR³ where R² and R³ form the group —CH₂—O—CH₂—, and Z represents CH are also particularly preferred.

Compounds of formula (Ixd) in which X¹ is

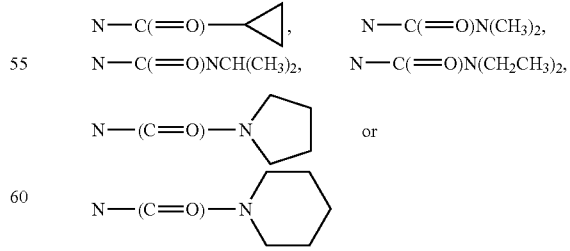

and r is zero are especially preferred.

Compounds of formula (Ixd) in which W represents CH, X represents C—CH₃, Y represents C—CH₃ or C—Cl and Z represents CH are especially preferred.

Particular compounds of the invention of formula (Ix) are selected from the compounds formed by joining the carbon atom (C*) of one of the benzoimidazole, imidazo[4,5-b]pyridine, imidazo[4,5-c]pyridine or imidazo[4,5-b]pyrazine fragments (A1 to A110) shown in Table 1 to the carbon atom (*C) in the heteroaryl moiety of one of the fragments (B1 to B168) shown in Table 2.

Particular compounds of the invention of formula (Ixa) are selected from the compounds formed by joining the carbon atom (C*) of one of the benzoimidazole, imidazo[4,5-b]pyridine, imidazo[4,5-c]pyridine or imidazo[4,5-b]pyrazine fragments (A1 to A110) shown in Table 1 to the carbon atom (*C) in the pyrazole ring of one of the fragments (B1 to B48, B74 to B107, B124 to B127, 130 to 142 or 144 to 150) shown in Table 2.

Particular compounds of the invention of formula (Ixb) are also selected from the compounds formed by joining the carbon atom (C*) of one of the benzoimidazole, imidazo[4,5-b]pyridine, imidazo[4,5-c]pyridine or imidazo[4,5-b]pyrazine fragments (A1 to A110) shown in Table 1 to the carbon atom (*C) in the five membered ring of one of the fragments (B63 to B73, B108 to B114, B128 or B151) shown in Table 2.

Particular compounds of the invention of formula (Ixc) are selected from the compounds formed by joining the carbon atom (C*) of one of the benzoimidazole, imidazo[4,5-b]pyridine, imidazo[4,5-c]pyridine or imidazo[4,5-b]pyrazine fragments (A1 to A110) shown in Table 1 to the carbon atom (*C) in the five membered ring of one of the fragments (B56, B59 or B129) shown in Table 2.

Particular compounds of the invention of formula (Ixd) are selected from the compounds formed by joining the carbon atom (C*) of one of the benzoimidazole, imidazo[4,5-b]pyridine, imidazo[4,5-c]pyridine or imidazo[4,5-b]pyrazine fragments (A1 to A110) shown in Table 1 to the carbon atom (*C) in the five membered ring of one of the fragments (B115 to B123 or B157) shown in Table 2.

TABLE 1-continued
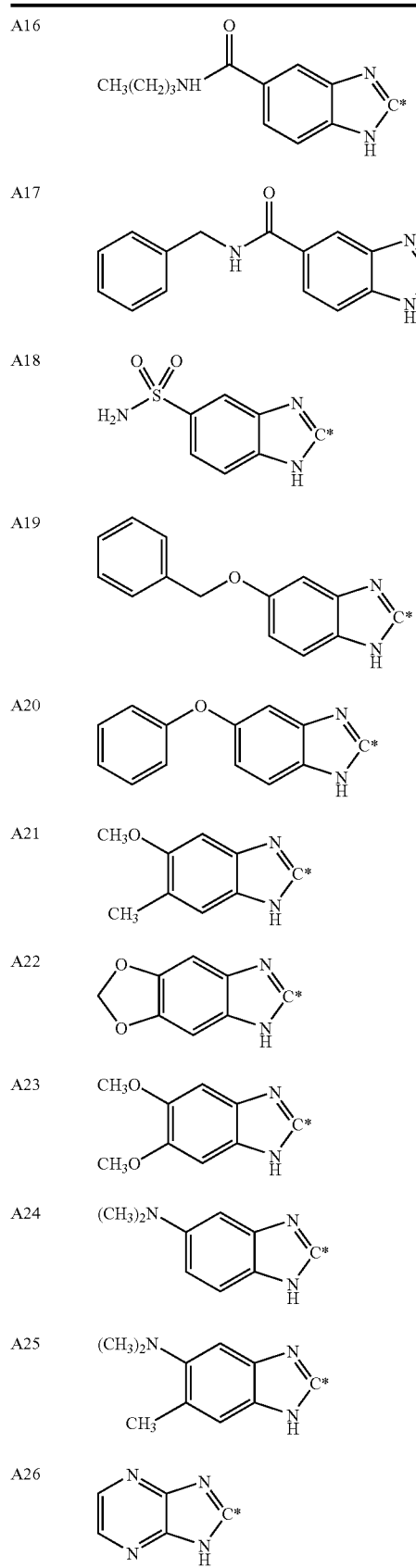
TABLE 1-continued
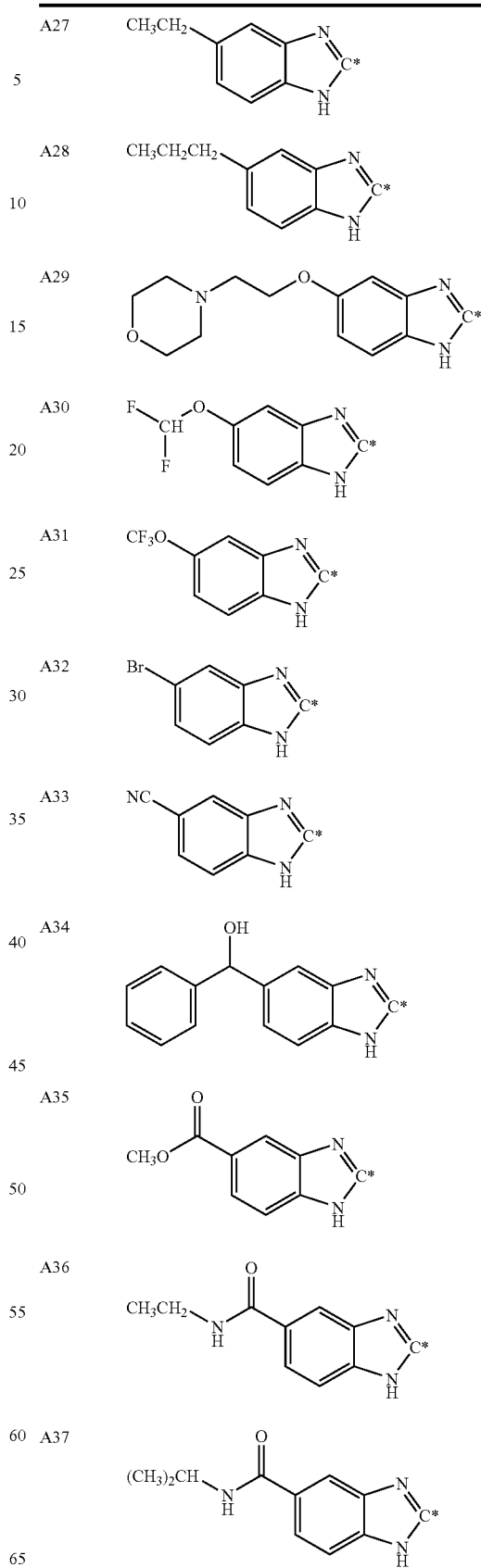

TABLE 1-continued
A38 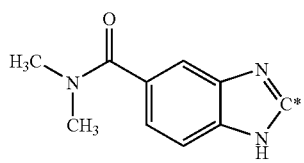
A39 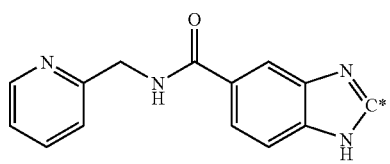
A40 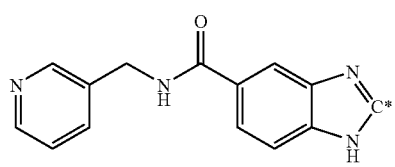
A41 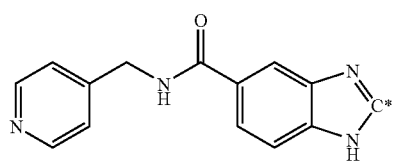
A42 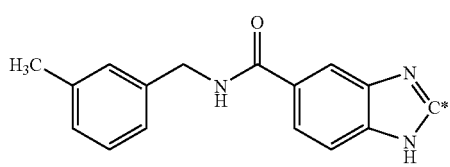
A43 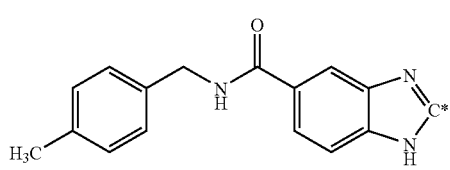
A44 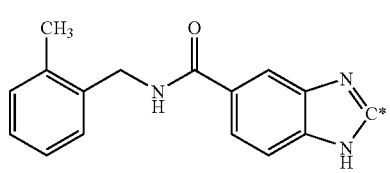
A45 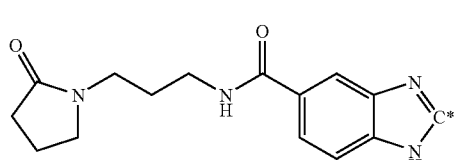
A46 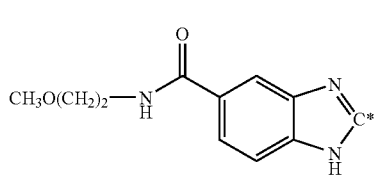
TABLE 1-continued
A47 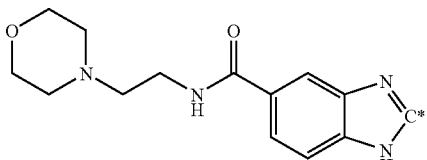
A48 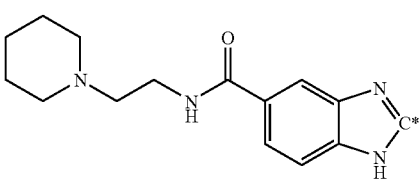
A49 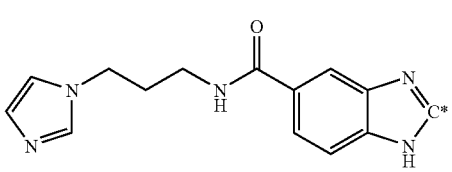
A50 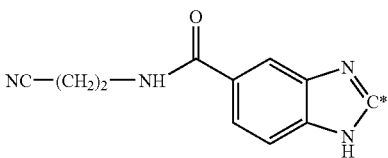
A51 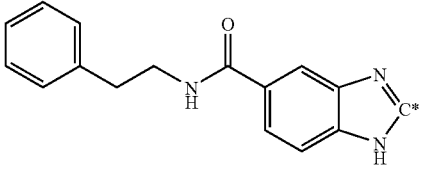
A52 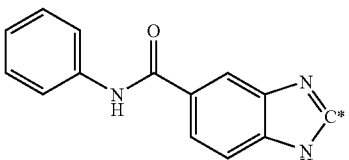
A53 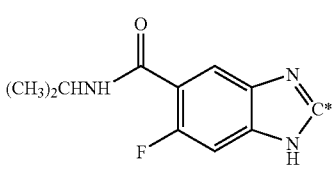
A54 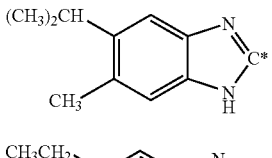
A55 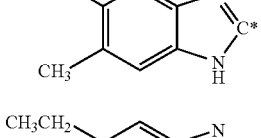
A56 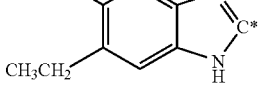

TABLE 1-continued
| | | | | |
|---|---|---|---|---|
| A57 | 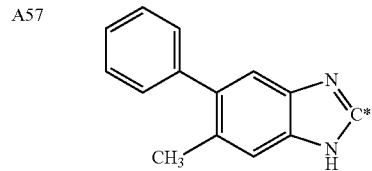 | | A66 | 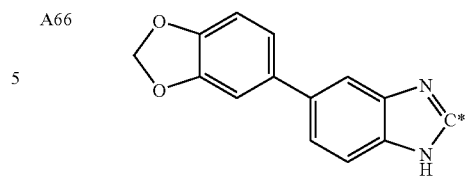 |
| A58 | 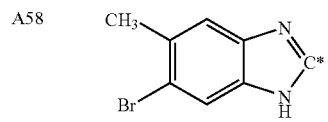 | | A67 | 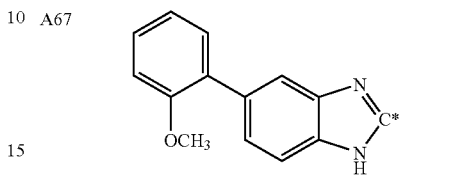 |
| A59 | 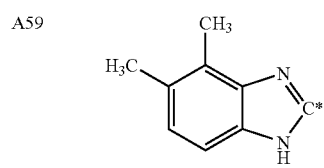 | | A68 | 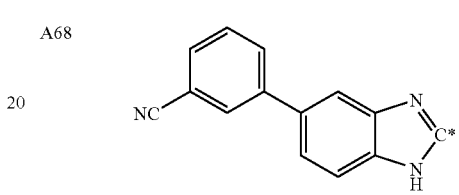 |
| A60 | 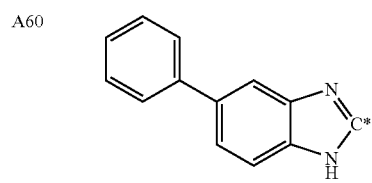 | | A69 |  |
| A61 | 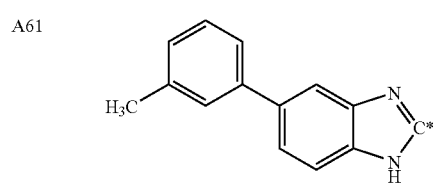 | | A70 | 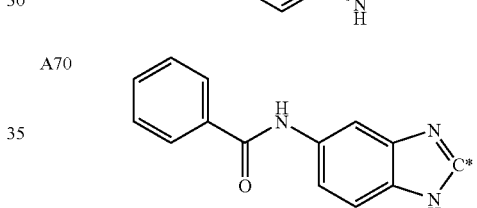 |
| A62 | 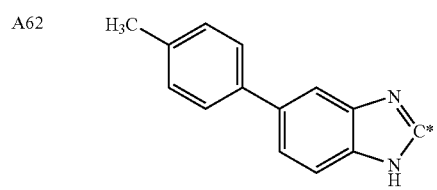 | | A71 | 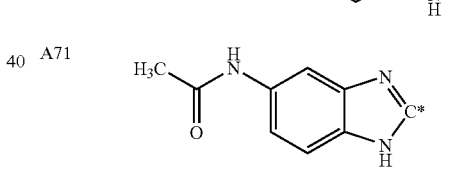 |
| A63 | 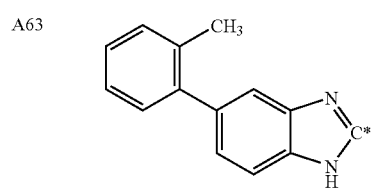 | | A72 | 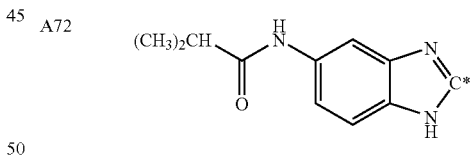 |
| A64 | 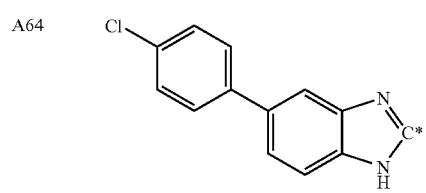 | | A73 | 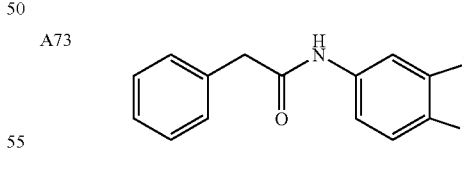 |
| A65 | 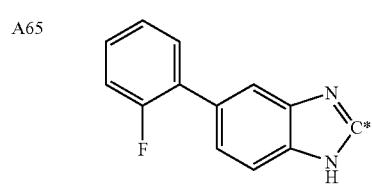 | | A74 | 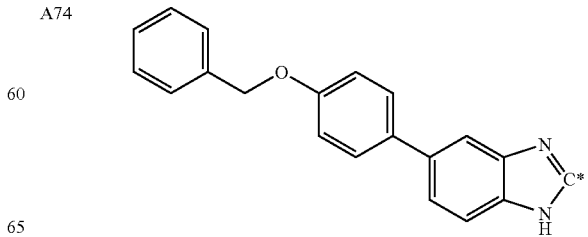 |

TABLE 1-continued
A77 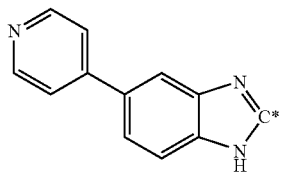
A78 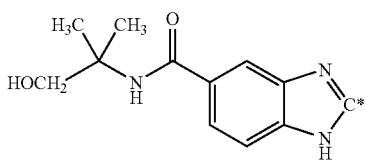
A79 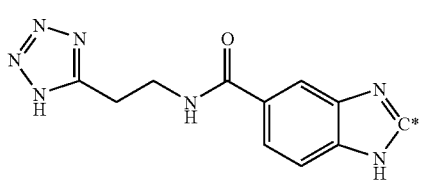
A80 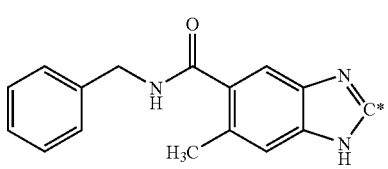
A81 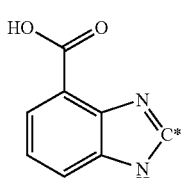
A82 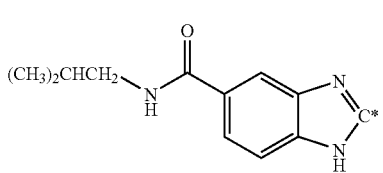
A83 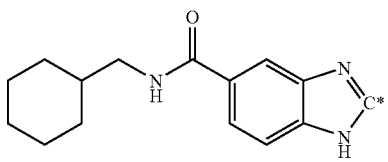
A84 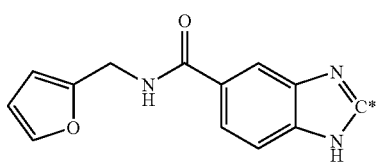
A85 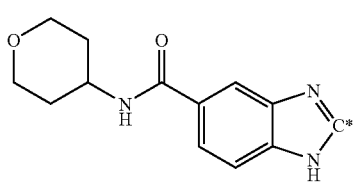
A86 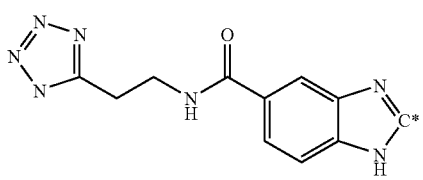
A87 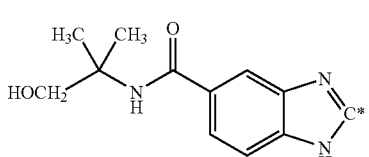
A88 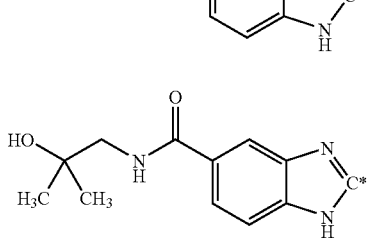
A89 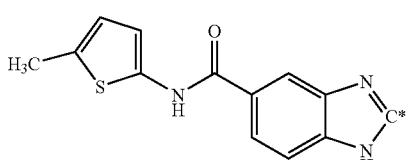
A90 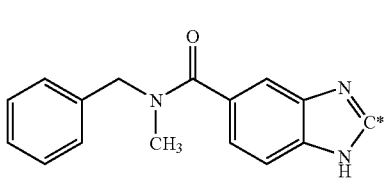
A91 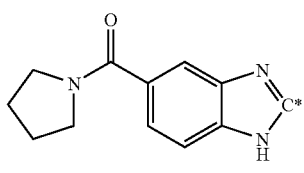
A92 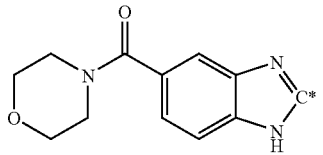
A93 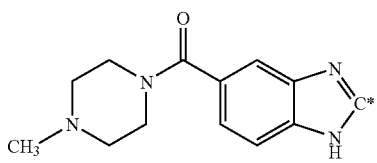
A94 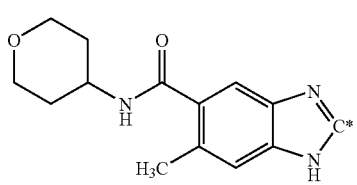

TABLE 1-continued
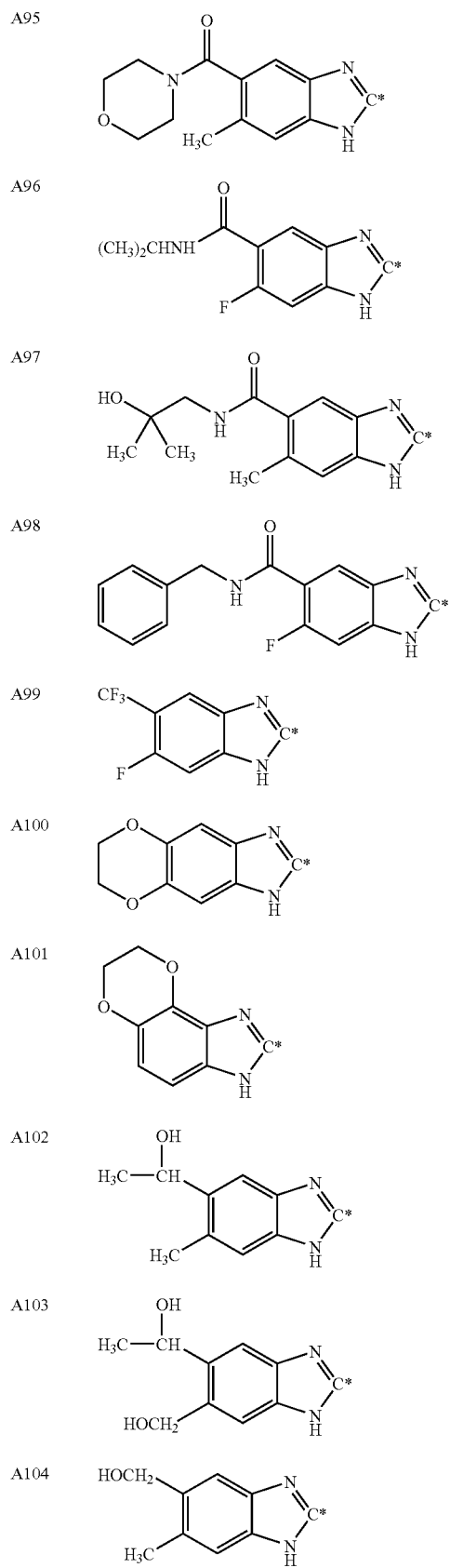
TABLE 1-continued
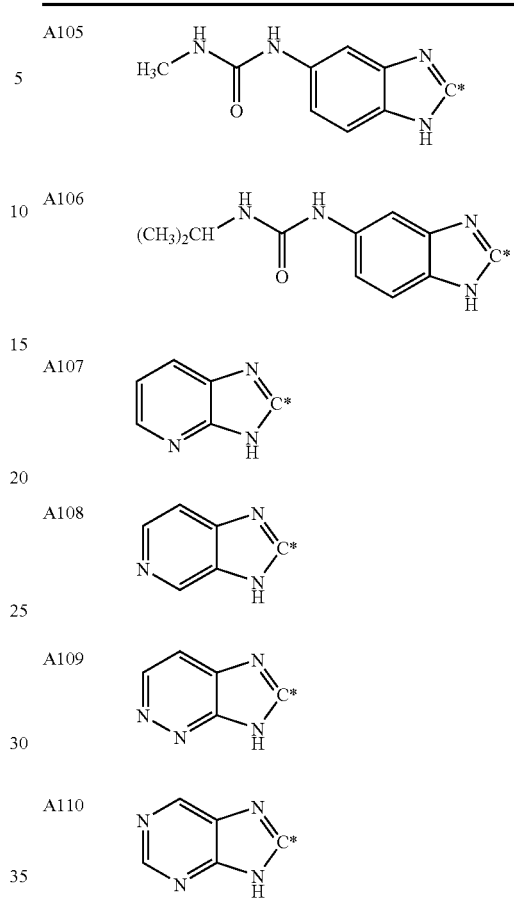
TABLE 2
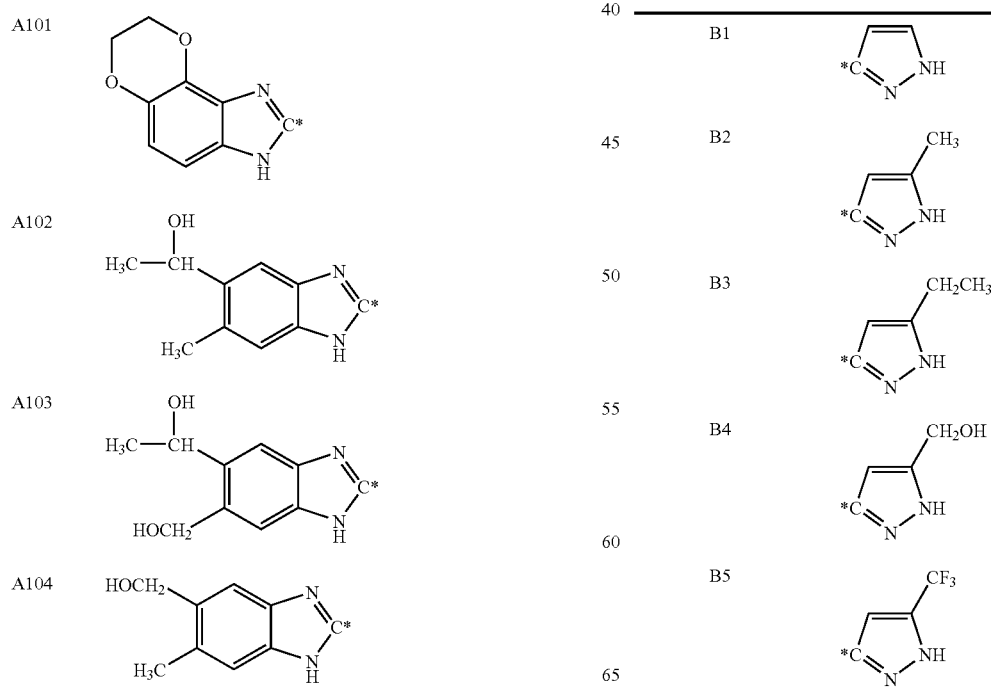

TABLE 2-continued
| | | | | |
|---|---|---|---|---|
| B6 | 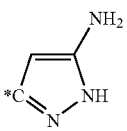 | | B15 | 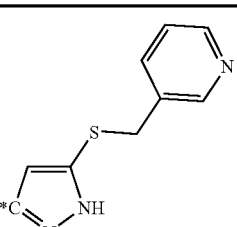 |
| B7 | 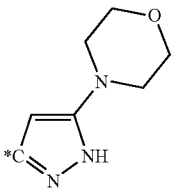 | | B16 | 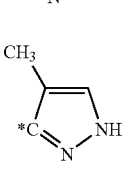 |
| B8 | 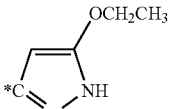 | | B17 | 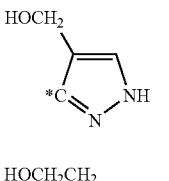 |
| B9 | 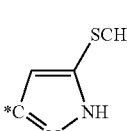 | | B18 | 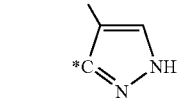 |
| B10 | 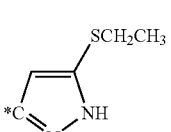 | | B19 | 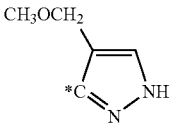 |
| B11 | 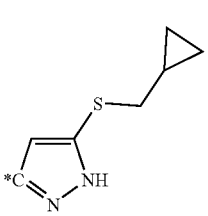 | | B20 | 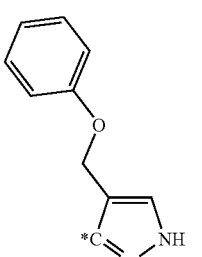 |
| B12 | 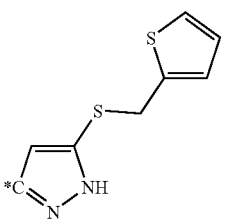 | | B21 | 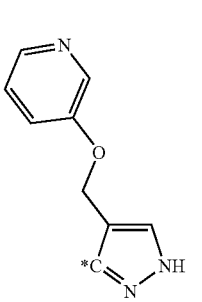 |
| B13 | 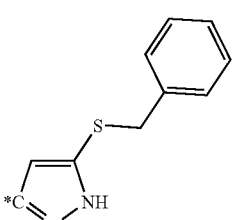 | | B22 | 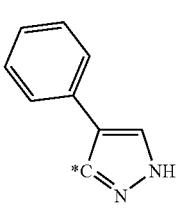 |
| B14 | 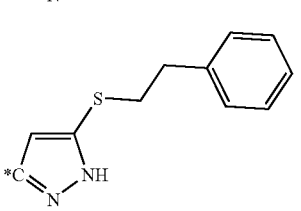 | | | |

TABLE 2-continued
| | | | | |
|---|---|---|---|---|
| B23 | 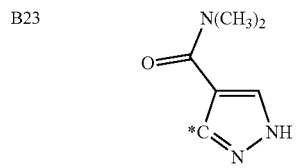 | | B31 | 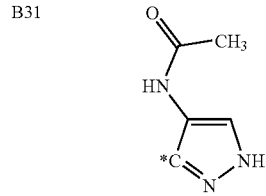 |
| B24 | 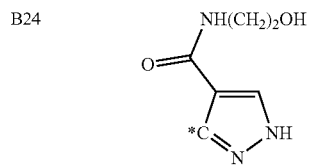 | | B32 | 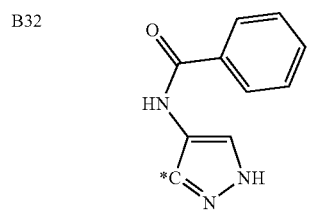 |
| B25 | 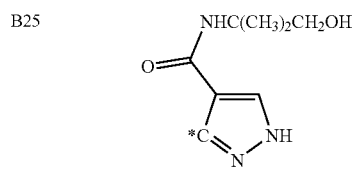 | | B33 |  |
| B26 | 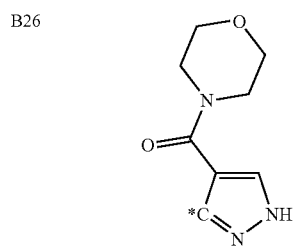 | | B34 | 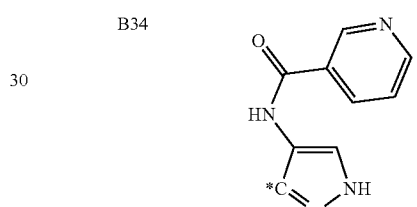 |
| B27 | 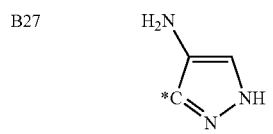 | | B35 | 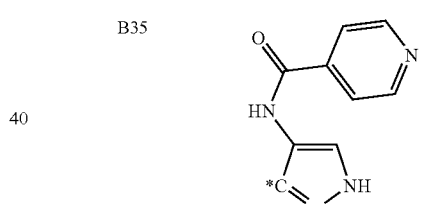 |
| B28 | 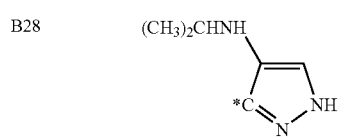 | | B36 | 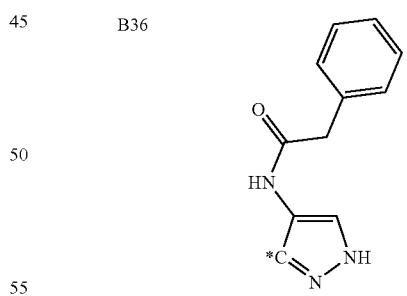 |
| B29 | 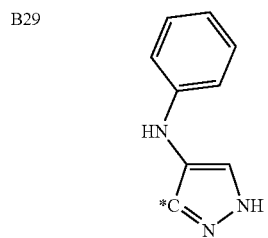 | | B37 | 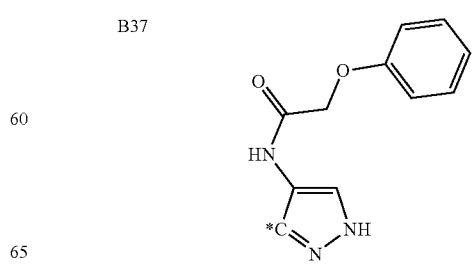 |
| B30 | 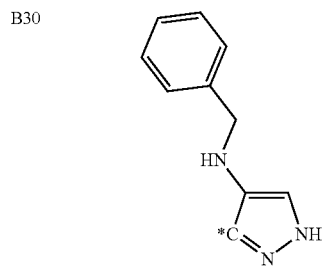 | | | |

TABLE 2-continued
| | |
|---|---|
| B38 | 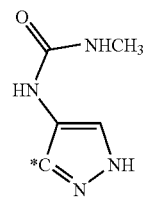 |
| B39 | 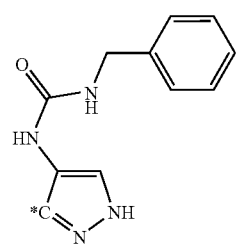 |
| B40 | 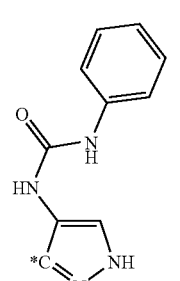 |
| B41 | 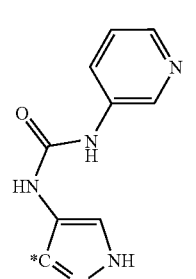 |
| B42 | 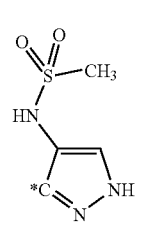 |
| B43 | 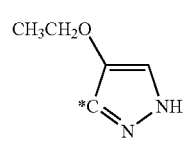 |
| B44 | 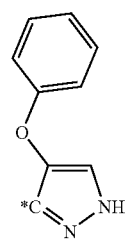 |
TABLE 2-continued
| | |
|---|---|
| B45 | 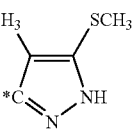 |
| B46 | 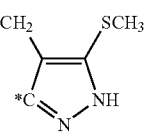 |
| B47 | 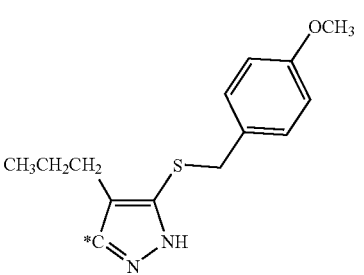 |
| B48 | 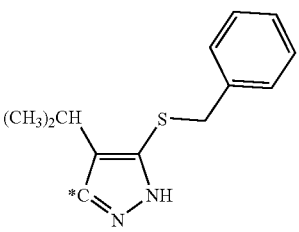 |
| B49 | 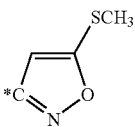 |
| B50 | 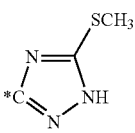 |
| B51 | 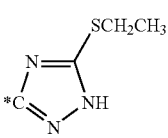 |
| B52 | 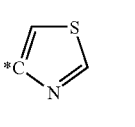 |
| B53 | 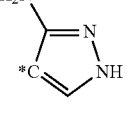 |
| B54 | 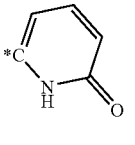 |

TABLE 2-continued
| | | |
|---|---|---|
| B55 | 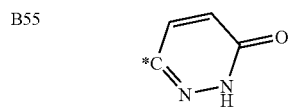 | |
| B56 | 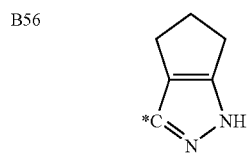 | |
| B57 | 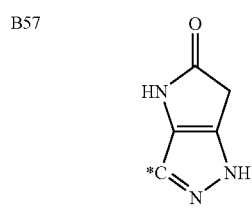 | |
| B58 | 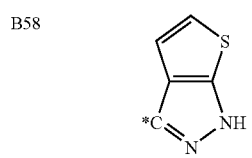 | |
| B59 | 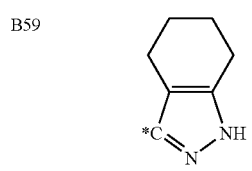 | |
| B60 | 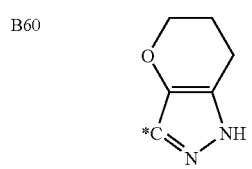 | |
| B61 | 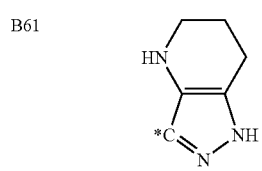 | |
| B62 | 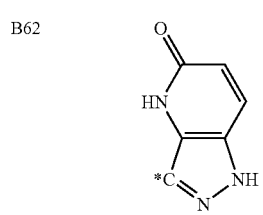 | |
| B63 | 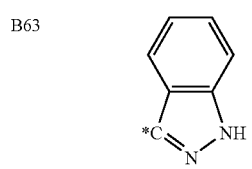 | |
| B64 | 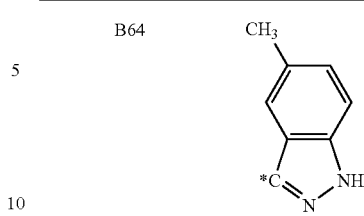 | |
| B65 | 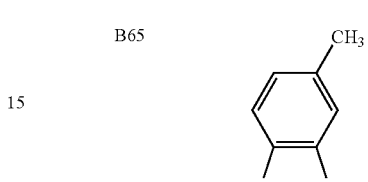 | |
| B66 | 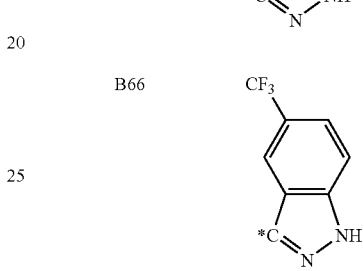 | |
| B67 | 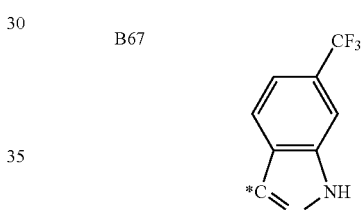 | |
| B68 | 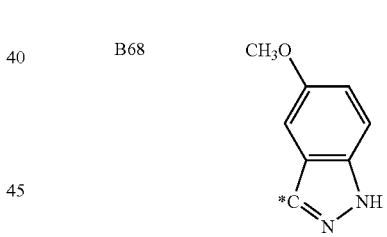 | |
| B69 | 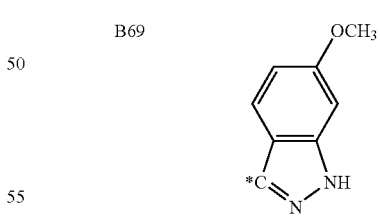 | |
| B70 | 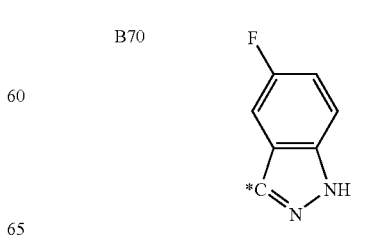 | |

TABLE 2-continued
| | | | | |
|---|---|---|---|---|
| B71 | 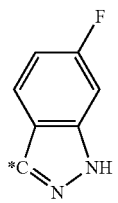 | | B78 | 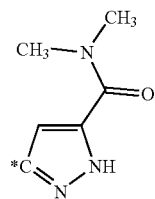 |
| B72 | 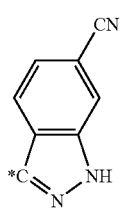 | | B79 | 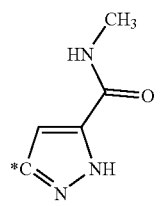 |
| B73 | 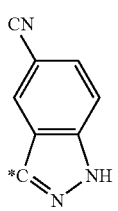 | | B80 | 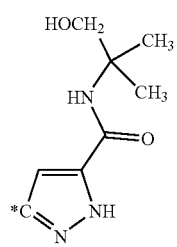 |
| B74 | 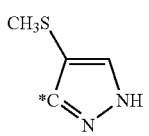 | | B81 | 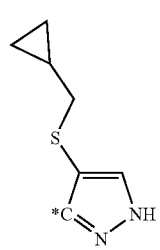 |
| B75 | 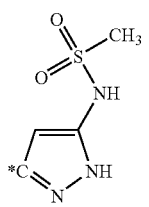 | | B82 | 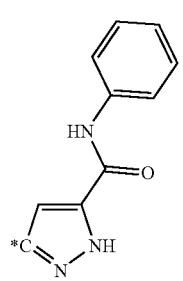 |
| B76 | 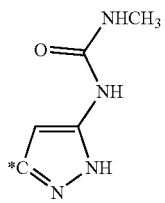 | | B83 | 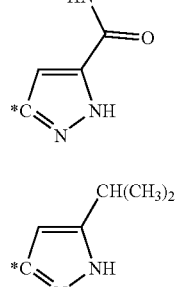 |
| B77 | 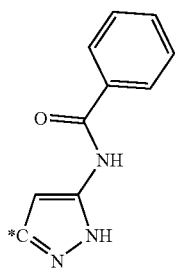 | | B84 | 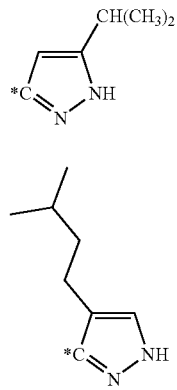 |

TABLE 2-continued
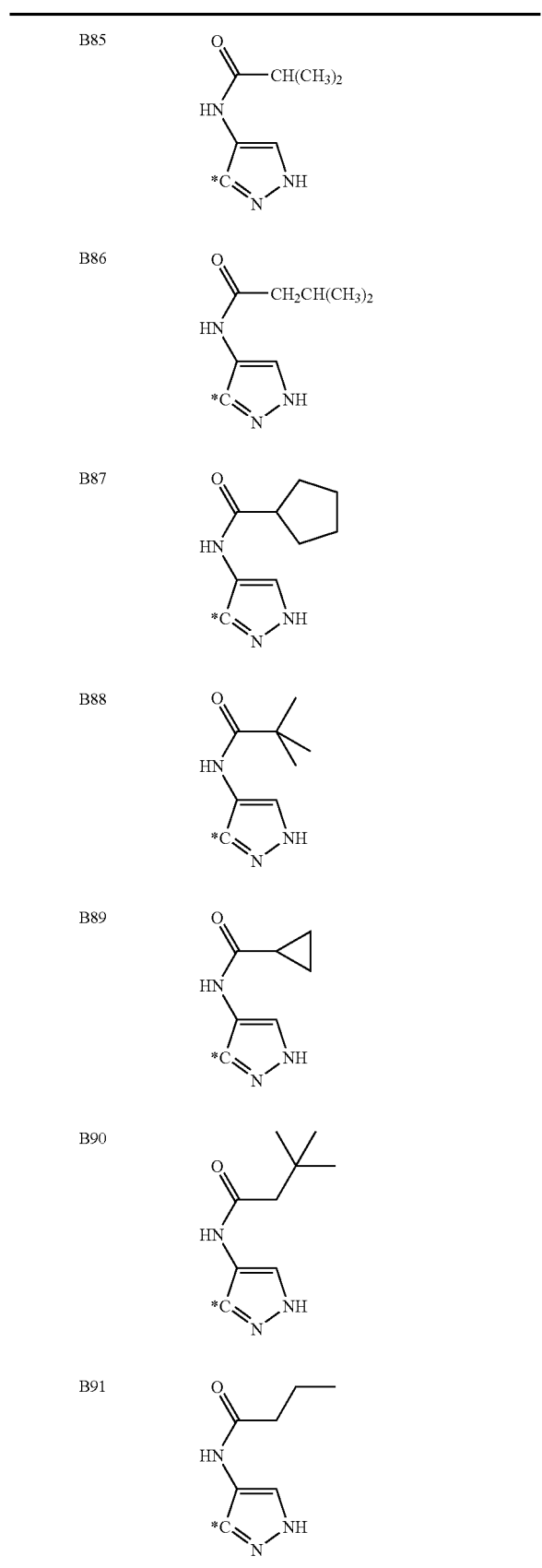
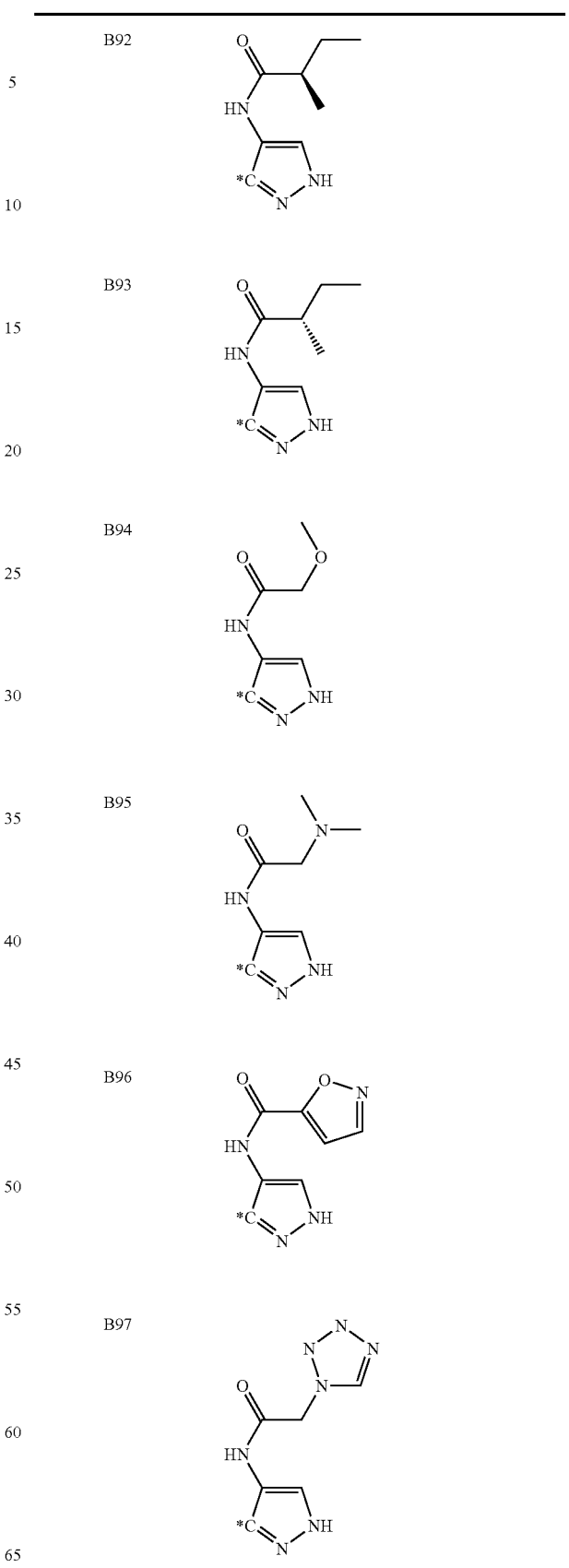

TABLE 2-continued
| B98 | 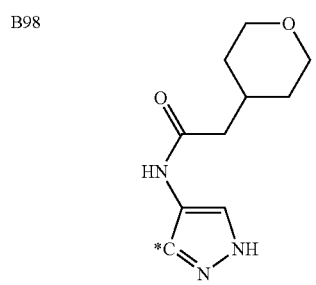 |
| B99 | |
| B100 | 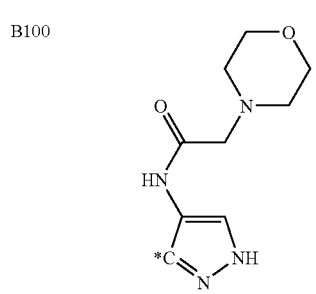 |
| B101 | |
| B102 | |
| B103 | 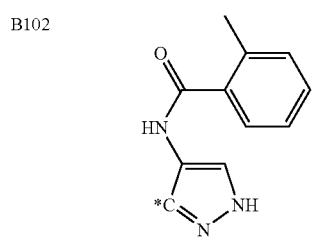 |
TABLE 2-continued
| B104 | 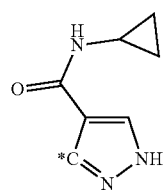 |
| B105 | |
| B106 | |
| B107 | 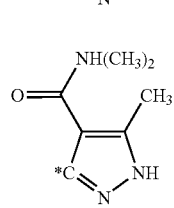 |
| B108 | |
| B109 | 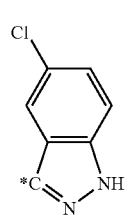 |
| B110 | |
| B111 | |

TABLE 2-continued
| | | |
|---|---|---|
| B112 | 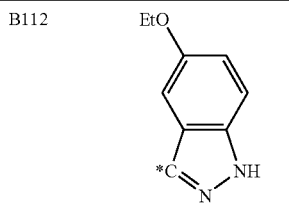 | |
| B113 | 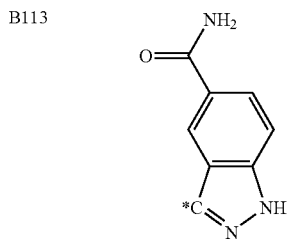 | |
| B114 | 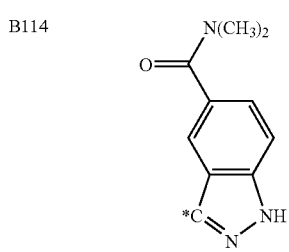 | |
| B115 | 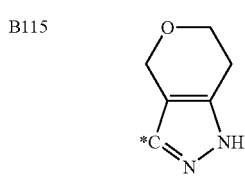 | |
| B116 | 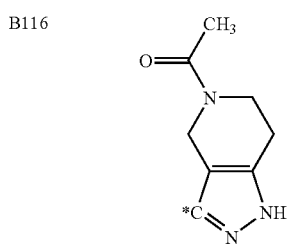 | |
| B117 | 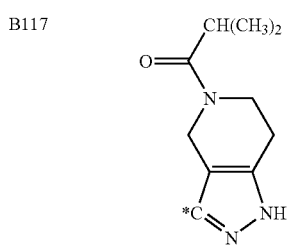 | |
| B118 | 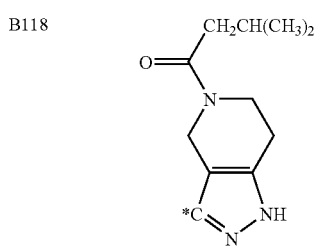 | |
TABLE 2-continued
| | | |
|---|---|---|
| B119 | 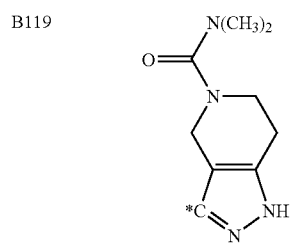 | |
| B120 | 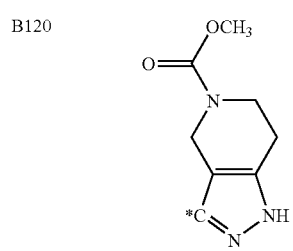 | |
| B121 | 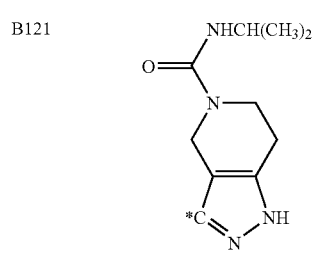 | |
| B122 | 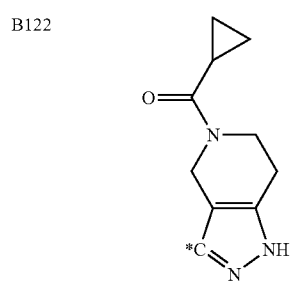 | |
| B123 | 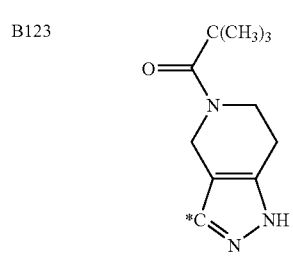 | |
| B124 | 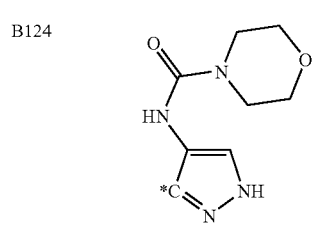 | |

TABLE 2-continued
| | |
|---|---|
| B125 | 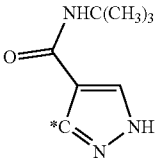 |
| B126 | 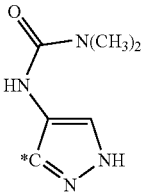 |
| B127 | 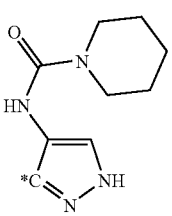 |
| B128 | 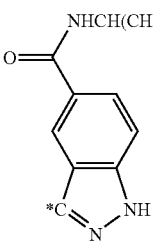 |
| B129 | 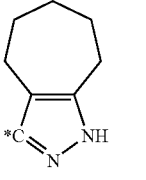 |
| B130 | 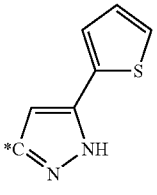 |
| B131 | 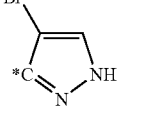 |
| B132 | 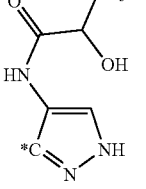 |
TABLE 2-continued
| | |
|---|---|
| B133 | 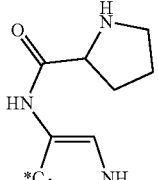 |
| B134 | 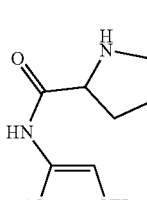 |
| B135 | 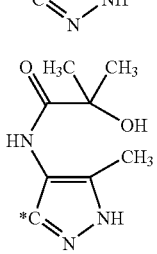 |
| B136 | 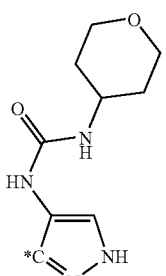 |
| B137 | 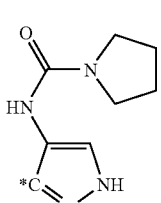 |
| B138 | 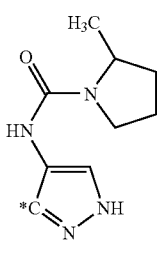 |
| B139 | 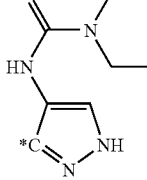 |

TABLE 2-continued
| | |
|---|---|
| B140 | 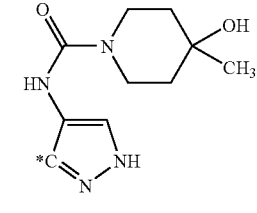 |
| B141 | 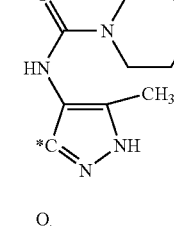 |
| B142 | 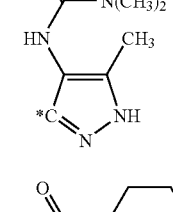 |
| B143 | 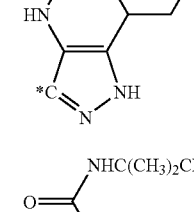 |
| B144 | 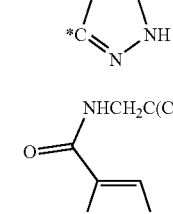 |
| B145 | 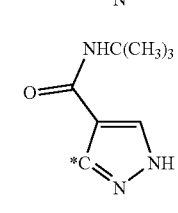 |
| B146 | 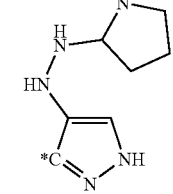 |
| B147 |  |
TABLE 2-continued
| | |
|---|---|
| B148 | |
| B149 | |
| B150 | |
| B151 | |
| B152 | |
| B153 | |

TABLE 2-continued
| | |
|---|---|
| B154 | 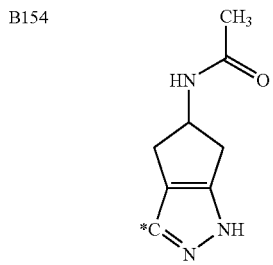 |
| B155 | 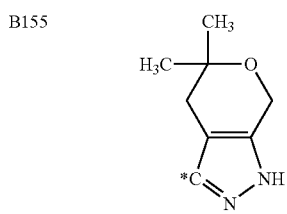 |
| B156 | 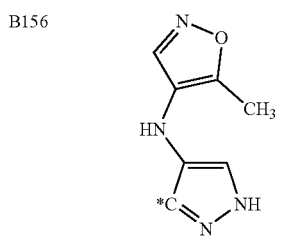 |
| B157 | 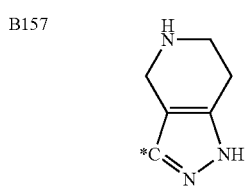 |
| B158 | 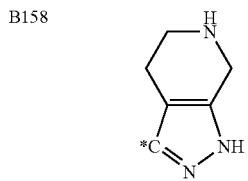 |
| B159 | 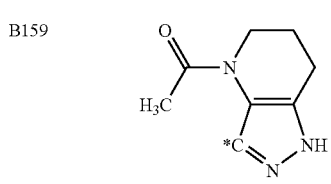 |
| B160 | 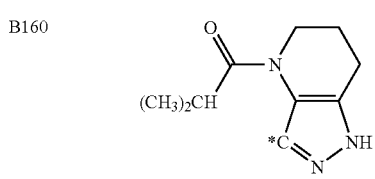 |
TABLE 2-continued
| | |
|---|---|
| B161 | 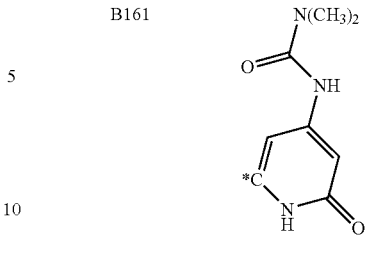 |
| B162 | 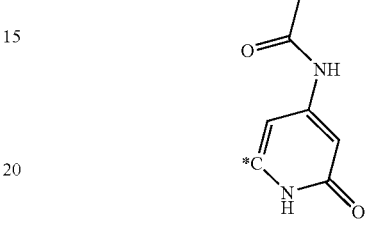 |
| B163 | 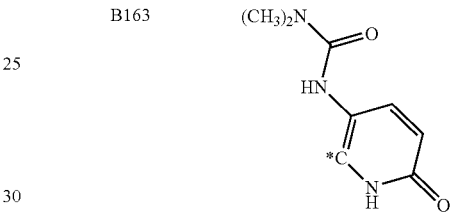 |
| B164 | 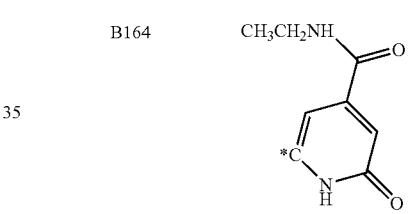 |
| B165 | 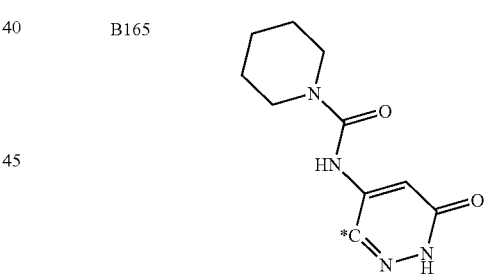 |
| B166 | 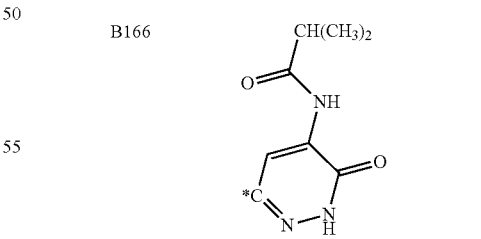 |
| B167 | 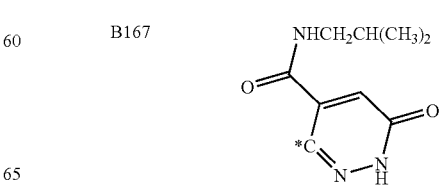 |

| B168 | 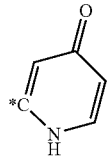 |
|---|---|

| B169 | 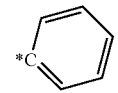 |
|---|---|

Particular compounds of the invention of formula (Ix) denoted as the product of the combination of group A1 to A110 in Table 1 with B1 to B169 in Table 2 are illustrated below:

A1-B1; A1-B2; A1-B3; A1-B4; A1-B5; A1-B6;
A1-B7; A1-B8; A1-B9; A1-B10; A1-B11; A1-B12;
A1-B13; A1-B14; A1-B15; A1-B16; A1-B17; A1-B18;
A1-B19; A1-B20; A1-B21; A1-B22; A1-B23; A1-B24;
A1-B25; A1-B26; A1-B27; A1-B28; A1-B29; A1-B30;
A1-B31; A1-B32; A1-B33; A1-B34; A1-B35; A1-B36;
A1-B37; A1-B38; A1-B39; A1-B40; A1-B41; A1-B42;
A1-B43; A1-B44; A1-B45; A1-B46; A1-B47; A1-B48;
A1-B49; A1-B50; A1-B51; A1-B52; A1-B53; A1-B54;
A1-B55; A1-B56; A1-B57; A1-B58; A1-B59; A1-B60;
A1-B61; A1-B62; A1-B63; A1-B64; A1-B65; A1-B66;
A1-B67; A1-B68; A1-B69; A1-B70; A1-B71; A1-B72;
A1-B73; A1-B74; A1-B75; A1-B76; A1-B77; A1-B78;
A1-B79; A1-B80; A1-B81; A1-B82; A1-B83; A1-B84;
A1-B85; A1-B86; A1-B87; A1-B88; A1-B89; A1-B90;
A1-B91; A1-B92; A1-B93; A1-B94; A1-B95; A1-B96;
A1-B97; A1-B98; A1-B99; A1-B100; A1-B101; A1-B102;
A1-B103; A1-B104; A1-B105; A1-B106; A1-B107; A1-B108;
A1-B109; A1-B110; A1-B111; A1-B112; A1-B113; A1-B114;
A1-B115; A1-B116; A1-B117; A1-B118; A1-B119; A1-B120;
A1-B121; A1-B122; A1-B123; A1-B124; A1-B125; A1-B126;
A1-B127; A1-B128; A1-B129; A1-B130; A1-B131; A1-B132;
A1-B133; A1-B134; A1-B135; A1-B136; A1-B137; A1-B138;
A1-B139; A1-B140; A1-B141; A1-B142; A1-B143; A1-B144;
A1-B145; A1-B146; A1-B147; A1-B148; A1-B149; A1-B150;
A1-B151; A1-B152; A1-B153; A1-B154; A1-B155; A1-B156;
A1-B157; A1-B158; A1-B159; A1-B160; A1-B161; A1-B162;
A1-B163; A1-B164; A1-B165; A1-B166; A1-B167; A1-B168;
A1-B169; A2-B1; A2-B2; A2-B3; A2-B4; A2-B5;
A2-B6; A2-B7; A2-B8; A2-B9; A2-B10; A2-B11;
A2-B12; A2-B13; A2-B14; A2-B15; A2-B16; A2-B17;
A2-B18; A2-B19; A2-B20; A2-B21; A2-B22; A2-B23;
A2-B24; A2-B25; A2-B26; A2-B27; A2-B28; A2-B29;
A2-B30; A2-B31; A2-B32; A2-B33; A2-B34; A2-B35;
A2-B36; A2-B37; A2-B38; A2-B39; A2-B40; A2-B41;
A2-B42; A2-B43; A2-B44; A2-B45; A2-B46; A2-B47;
A2-B48; A2-B49; A2-B50; A2-B51; A2-B52; A2-B53;
A2-B54; A2-B55; A2-B56; A2-B57; A2-B58; A2-B59;
A2-B60; A2-B61; A2-B62; A2-B63; A2-B64; A2-B65;
A2-B66; A2-B67; A2-B68; A2-B69; A2-B70; A2-B71;
A2-B72; A2-B73; A2-B74; A2-B75; A2-B76; A2-B77;
A2-B78; A2-B79; A2-B80; A2-B81; A2-B82; A2-B83;
A2-B84; A2-B85; A2-B86; A2-B87; A2-B88; A2-B89;
A2-B90; A2-B91; A2-B92; A2-B93; A2-B94; A2-B95;
A2-B96; A2-B97; A2-B98; A2-B99; A2-B100; A2-B101;
A2-B102; A2-B103; A2-B104; A2-B105; A2-B106; A2-B107;
A2-B108; A2-B109; A2-B110; A2-B111; A2-B112; A2-B113;
A2-B114; A2-B115; A2-B116; A2-B117; A2-B118; A2-B119;
A2-B120; A2-B121; A2-B122; A2-B123; A2-B124; A2-B125;
A2-B126; A2-B127; A2-B128; A2-B129; A2-B130; A2-B131;
A2-B132; A2-B133; A2-B134; A2-B135; A2-B136; A2-B137;
A2-B138; A2-B139; A2-B140; A2-B141; A2-B142; A2-B143;
A2-B144; A2-B145; A2-B146; A2-B147; A2-B148; A2-B149;
A2-B150; A2-B151; A2-B152; A2-B153; A2-B154; A2-B155;
A2-B156; A2-B157; A2-B158; A2-B159; A2-B160; A2-B161;
A2-B162; A2-B163; A2-B164; A2-B165; A2-B166; A2-B167;
A2-B168; A2-B169; A3-B1; A3-B2; A3-B3; A3-B4;
A3-B5; A3-B6; A3-B7; A3-B8; A3-B9; A3-B10;
A3-B11; A3-B12; A3-B13; A3-B14; A3-B15; A3-B16;
A3-B17; A3-B18; A3-B19; A3-B20; A3-B21; A3-B22;
A3-B23; A3-B24; A3-B25; A3-B26; A3-B27; A3-B28;
A3-B29; A3-B30; A3-B31; A3-B32; A3-B33; A3-B34;
A3-B35; A3-B36; A3-B37; A3-B38; A3-B39; A3-B40;
A3-B41; A3-B42; A3-B43; A3-B44; A3-B45; A3-B46;
A3-B47; A3-B48; A3-B49; A3-B50; A3-B51; A3-B52;
A3-B53; A3-B54; A3-B55; A3-B56; A3-B57; A3-B58;

-continued

| | | | | | |
|---|---|---|---|---|---|
| A3-B59; | A3-B60; | A3-B61; | A3-B62; | A3-B63; | A3-B64; |
| A3-B65; | A3-B66; | A3-B67; | A3-B68; | A3-B69; | A3-B70; |
| A3-B71; | A3-B72; | A3-B73; | A3-B74; | A3-B75; | A3-B76; |
| A3-B77; | A3-B78; | A3-B79; | A3-B80; | A3-B81; | A3-B82; |
| A3-B83; | A3-B84; | A3-B85; | A3-B86; | A3-B87; | A3-B88; |
| A3-B89; | A3-B90; | A3-B91; | A3-B92; | A3-B93; | A3-B94; |
| A3-B95; | A3-B96; | A3-B97; | A3-B98; | A3-B99; | A3-B100; |
| A3-B101; | A3-B102; | A3-B103; | A3-B104; | A3-B105; | A3-B106; |
| A3-B107; | A3-B108; | A3-B109; | A3-B110; | A3-B111; | A3-B112; |
| A3-B113; | A3-B114; | A3-B115; | A3-B116; | A3-B117; | A3-B118; |
| A3-B119; | A3-B120; | A3-B121; | A3-B122; | A3-B123; | A3-B124; |
| A3-B125; | A3-B126; | A3-B127; | A3-B128; | A3-B129; | A3-B130; |
| A3-B131; | A3-B132; | A3-B133; | A3-B134; | A3-B135; | A3-B136; |
| A3-B137; | A3-B138; | A3-B139; | A3-B140; | A3-B141; | A3-B142; |
| A3-B143; | A3-B144; | A3-B145; | A3-B146; | A3-B147; | A3-B148; |
| A3-B149; | A3-B150; | A3-B151; | A3-B152; | A3-B153; | A3-B154; |
| A3-B155; | A3-B156; | A3-B157; | A3-B158; | A3-B159; | A3-B160; |
| A3-B161; | A3-B162; | A3-B163; | A3-B164; | A3-B165; | A3-B166; |
| A3-B167; | A3-B168; | A3-B169; | A4-B1; | A4-B2; | A4-B3; |
| A4-B4; | A4-B5; | A4-B6; | A4-B7; | A4-B8; | A4-B9; |
| A4-B10; | A4-B11; | A4-B12; | A4-B13; | A4-B14; | A4-B15; |
| A4-B16; | A4-B17; | A4-B18; | A4-B19; | A4-B20; | A4-B21; |
| A4-B22; | A4-B23; | A4-B24; | A4-B25; | A4-B26; | A4-B27; |
| A4-B28; | A4-B29; | A4-B30; | A4-B31; | A4-B32; | A4-B33; |
| A4-B34; | A4-B35; | A4-B36; | A4-B37; | A4-B38; | A4-B39; |
| A4-B40; | A4-B41; | A4-B42; | A4-B43; | A4-B44; | A4-B45; |
| A4-B46; | A4-B47; | A4-B48; | A4-B49; | A4-B50; | A4-B51; |
| A4-B52; | A4-B53; | A4-B54; | A4-B55; | A4-B56; | A4-B57; |
| A4-B58; | A4-B59; | A4-B60; | A4-B61; | A4-B62; | A4-B63; |
| A4-B64; | A4-B65; | A4-B66; | A4-B67; | A4-B68; | A4-B69; |
| A4-B70; | A4-B71; | A4-B72; | A4-B73; | A4-B74; | A4-B75; |
| A4-B76; | A4-B77; | A4-B78; | A4-B79; | A4-B80; | A4-B81; |
| A4-B82; | A4-B83; | A4-B84; | A4-B85; | A4-B86; | A4-B87; |
| A4-B88; | A4-B89; | A4-B90; | A4-B91; | A4-B92; | A4-B93; |
| A4-B94; | A4-B95; | A4-B96; | A4-B97; | A4-B98; | A4-B99; |
| A4-B100; | A4-B101; | A4-B102; | A4-B103; | A4-B104; | A4-B105; |
| A4-B106; | A4-B107; | A4-B108; | A4-B109; | A4-B110; | A4-B111; |
| A4-B112; | A4-B113; | A4-B114; | A4-B115; | A4-B116; | A4-B117; |
| A4-B118; | A4-B119; | A4-B120; | A4-B121; | A4-B122; | A4-B123; |
| A4-B124; | A4-B125; | A4-B126; | A4-B127; | A4-B128; | A4-B129; |
| A4-B130; | A4-B131; | A4-B132; | A4-B133; | A4-B134; | A4-B135; |
| A4-B136; | A4-B137; | A4-B138; | A4-B139; | A4-B140; | A4-B141; |
| A4-B142; | A4-B143; | A4-B144; | A4-B145; | A4-B146; | A4-B147; |
| A4-B148; | A4-B149; | A4-B150; | A4-B151; | A4-B152; | A4-B153; |
| A4-B154; | A4-B155; | A4-B156; | A4-B157; | A4-B158; | A4-B159; |
| A4-B160; | A4-B161; | A4-B162; | A4-B163; | A4-B164; | A4-B165; |
| A4-B166; | A4-B167; | A4-B168; | A4-B169; | A5-B1; | A5-B2; |
| A5-B3; | A5-B4; | A5-B5; | A5-B6; | A5-B7; | A5-B8; |
| A5-B9; | A5-B10; | A5-B11; | A5-B12; | A5-B13; | A5-B14; |
| A5-B15; | A5-B16; | A5-B17; | A5-B18; | A5-B19; | A5-B20; |
| A5-B21; | A5-B22; | A5-B23; | A5-B24; | A5-B25; | A5-B26; |
| A5-B27; | A5-B28; | A5-B29; | A5-B30; | A5-B31; | A5-B32; |
| A5-B33; | A5-B34; | A5-B35; | A5-B36; | A5-B37; | A5-B38; |
| A5-B39; | A5-B40; | A5-B41; | A5-B42; | A5-B43; | A5-B44; |
| A5-B45; | A5-B46; | A5-B47; | A5-B48; | A5-B49; | A5-B50; |
| A5-B51; | A5-B52; | A5-B53; | A5-B54; | A5-B55; | A5-B56; |
| A5-B57; | A5-B58; | A5-B59; | A5-B60; | A5-B61; | A5-B62; |
| A5-B63; | A5-B64; | A5-B65; | A5-B66; | A5-B67; | A5-B68; |
| A5-B69; | A5-B70; | A5-B71; | A5-B72; | A5-B73; | A5-B74; |
| A5-B75; | A5-B76; | A5-B77; | A5-B78; | A5-B79; | A5-B80; |
| A5-B81; | A5-B82; | A5-B83; | A5-B84; | A5-B85; | A5-B86; |
| A5-B87; | A5-B88; | A5-B89; | A5-B90; | A5-B91; | A5-B92; |
| A5-B93; | A5-B94; | A5-B95; | A5-B96; | A5-B97; | A5-B98; |
| A5-B99; | A5-B100; | A5-B101; | A5-B102; | A5-B103; | A5-B104; |
| A5-B105; | A5-B106; | A5-B107; | A5-B108; | A5-B109; | A5-B110; |
| A5-B111; | A5-B112; | A5-B113; | A5-B114; | A5-B115; | A5-B116; |
| A5-B117; | A5-B118; | A5-B119; | A5-B120; | A5-B121; | A5-B122; |
| A5-B123; | A5-B124; | A5-B125; | A5-B126; | A5-B127; | A5-B128; |
| A5-B129; | A5-B130; | A5-B131; | A5-B132; | A5-B133; | A5-B134; |
| A5-B135; | A5-B136; | A5-B137; | A5-B138; | A5-B139; | A5-B140; |
| A5-B141; | A5-B142; | A5-B143; | A5-B144; | A5-B145; | A5-B146; |
| A5-B147; | A5-B148; | A5-B149; | A5-B150; | A5-B151; | A5-B152; |
| A5-B153; | A5-B154; | A5-B155; | A5-B156; | A5-B157; | A5-B158; |
| A5-B159; | A5-B160; | A5-B161; | A5-B162; | A5-B163; | A5-B164; |
| A5-B165; | A5-B166; | A5-B167; | A5-B168; | A5-B169; | A6-B1; |
| A6-B2; | A6-B3; | A6-B4; | A6-B5; | A6-B6; | A6-B7; |
| A6-B8; | A6-B9; | A6-B10; | A6-B11; | A6-B12; | A6-B13; |
| A6-B14; | A6-B15; | A6-B16; | A6-B17; | A6-B18; | A6-B19; |
| A6-B20; | A6-B21; | A6-B22; | A6-B23; | A6-B24; | A6-B25; |
| A6-B26; | A6-B27; | A6-B28; | A6-B29; | A6-B30; | A6-B31; |

| | | | | | |
|---|---|---|---|---|---|
| A6-B32; | A6-B33; | A6-B34; | A6-B35; | A6-B36; | A6-B37; |
| A6-B38; | A6-B39; | A6-B40; | A6-B41; | A6-B42; | A6-B43; |
| A6-B44; | A6-B45; | A6-B46; | A6-B47; | A6-B48; | A6-B49; |
| A6-B50; | A6-B51; | A6-B52; | A6-B53; | A6-B54; | A6-B55; |
| A6-B56; | A6-B57; | A6-B58; | A6-B59; | A6-B60; | A6-B61; |
| A6-B62; | A6-B63; | A6-B64; | A6-B65; | A6-B66; | A6-B67; |
| A6-B68; | A6-B69; | A6-B70; | A6-B71; | A6-B72; | A6-B73; |
| A6-B74; | A6-B75; | A6-B76; | A6-B77; | A6-B78; | A6-B79; |
| A6-B80; | A6-B81; | A6-B82; | A6-B83; | A6-B84; | A6-B85; |
| A6-B86; | A6-B87; | A6-B88; | A6-B89; | A6-B90; | A6-B91; |
| A6-B92; | A6-B93; | A6-B94; | A6-B95; | A6-B96; | A6-B97; |
| A6-B98; | A6-B99; | A6-B100; | A6-B101; | A6-B102; | A6-B103; |
| A6-B104; | A6-B105; | A6-B106; | A6-B107; | A6-B108; | A6-B109; |
| A6-B110; | A6-B111; | A6-B112; | A6-B113; | A6-B114; | A6-B115; |
| A6-B116; | A6-B117; | A6-B118; | A6-B119; | A6-B120; | A6-B121; |
| A6-B122; | A6-B123; | A6-B124; | A6-B125; | A6-B126; | A6-B127; |
| A6-B128; | A6-B129; | A6-B130; | A6-B131; | A6-B132; | A6-B133; |
| A6-B134; | A6-B135; | A6-B136; | A6-B137; | A6-B138; | A6-B139; |
| A6-B140; | A6-B141; | A6-B142; | A6-B143; | A6-B144; | A6-B145; |
| A6-B146; | A6-B147; | A6-B148; | A6-B149; | A6-B150; | A6-B151; |
| A6-B152; | A6-B153; | A6-B154; | A6-B155; | A6-B156; | A6-B157; |
| A6-B158; | A6-B159; | A6-B160; | A6-B161; | A6-B162; | A6-B163; |
| A6-B164; | A6-B165; | A6-B166; | A6-B167; | A6-B168; | A6-B169; |
| A7-B1; | A7-B2; | A7-B3; | A7-B4; | A7-B5; | A7-B6; |
| A7-B7; | A7-B8; | A7-B9; | A7-B10; | A7-B11; | A7-B12; |
| A7-B13; | A7-B14; | A7-B15; | A7-B16; | A7-B17; | A7-B18; |
| A7-B19; | A7-B20; | A7-B21; | A7-B22; | A7-B23; | A7-B24; |
| A7-B25; | A7-B26; | A7-B27; | A7-B28; | A7-B29; | A7-B30; |
| A7-B31; | A7-B32; | A7-B33; | A7-B34; | A7-B35; | A7-B36; |
| A7-B37; | A7-B38; | A7-B39; | A7-B40; | A7-B41; | A7-B42; |
| A7-B43; | A7-B44; | A7-B45; | A7-B46; | A7-B47; | A7-B48; |
| A7-B49; | A7-B50; | A7-B51; | A7-B52; | A7-B53; | A7-B54; |
| A7-B55; | A7-B56; | A7-B57; | A7-B58; | A7-B59; | A7-B60; |
| A7-B61; | A7-B62; | A7-B63; | A7-B64; | A7-B65; | A7-B66; |
| A7-B67; | A7-B68; | A7-B69; | A7-B70; | A7-B71; | A7-B72; |
| A7-B73; | A7-B74; | A7-B75; | A7-B76; | A7-B77; | A7-B78; |
| A7-B79; | A7-B80; | A7-B81; | A7-B82; | A7-B83; | A7-B84; |
| A7-B85; | A7-B86; | A7-B87; | A7-B88; | A7-B89; | A7-B90; |
| A7-B91; | A7-B92; | A7-B93; | A7-B94; | A7-B95; | A7-B96; |
| A7-B97; | A7-B98; | A7-B99; | A7-B100; | A7-B101; | A7-B102; |
| A7-B103; | A7-B104; | A7-B105; | A7-B106; | A7-B107; | A7-B108; |
| A7-B109; | A7-B110; | A7-B111; | A7-B112; | A7-B113; | A7-B114; |
| A7-B115; | A7-B116; | A7-B117; | A7-B118; | A7-B119; | A7-B120; |
| A7-B121; | A7-B122; | A7-B123; | A7-B124; | A7-B125; | A7-B126; |
| A7-B127; | A7-B128; | A7-B129; | A7-B130; | A7-B131; | A7-B132; |
| A7-B133; | A7-B134; | A7-B135; | A7-B136; | A7-B137; | A7-B138; |
| A7-B139; | A7-B140; | A7-B141; | A7-B142; | A7-B143; | A7-B144; |
| A7-B145; | A7-B146; | A7-B147; | A7-B148; | A7-B149; | A7-B150; |
| A7-B151; | A7-B152; | A7-B153; | A7-B154; | A7-B155; | A7-B156; |
| A7-B157; | A7-B158; | A7-B159; | A7-B160; | A7-B161; | A7-B162; |
| A7-B163; | A7-B164; | A7-B165; | A7-B166; | A7-B167; | A7-B168; |
| A7-B169; | A8-B1; | A8-B2; | A8-B3; | A8-B4; | A8-B5; |
| A8-B6; | A8-B7; | A8-B8; | A8-B9; | A8-B10; | A8-B11; |
| A8-B12; | A8-B13; | A8-B14; | A8-B15; | A8-B16; | A8-B17; |
| A8-B18; | A8-B19; | A8-B20; | A8-B21; | A8-B22; | A8-B23; |
| A8-B24; | A8-B25; | A8-B26; | A8-B27; | A8-B28; | A8-B29; |
| A8-B30; | A8-B31; | A8-B32; | A8-B33; | A8-B34; | A8-B35; |
| A8-B36; | A8-B37; | A8-B38; | A8-B39; | A8-B40; | A8-B41; |
| A8-B42; | A8-B43; | A8-B44; | A8-B45; | A8-B46; | A8-B47; |
| A8-B48; | A8-B49; | A8-B50; | A8-B51; | A8-B52; | A8-B53; |
| A8-B54; | A8-B55; | A8-B56; | A8-B57; | A8-B58; | A8-B59; |
| A8-B60; | A8-B61; | A8-B62; | A8-B63; | A8-B64; | A8-B65; |
| A8-B66; | A8-B67; | A8-B68; | A8-B69; | A8-B70; | A8-B71; |
| A8-B72; | A8-B73; | A8-B74; | A8-B75; | A8-B76; | A8-B77; |
| A8-B78; | A8-B79; | A8-B80; | A8-B81; | A8-B82; | A8-B83; |
| A8-B84; | A8-B85; | A8-B86; | A8-B87; | A8-B88; | A8-B89; |
| A8-B90; | A8-B91; | A8-B92; | A8-B93; | A8-B94; | A8-B95; |
| A8-B96; | A8-B97; | A8-B98; | A8-B99; | A8-B100; | A8-B101; |
| A8-B102; | A8-B103; | A8-B104; | A8-B105; | A8-B106; | A8-B107; |
| A8-B108; | A8-B109; | A8-B110; | A8-B111; | A8-B112; | A8-B113; |
| A8-B114; | A8-B115; | A8-B116; | A8-B117; | A8-B118; | A8-B119; |
| A8-B120; | A8-B121; | A8-B122; | A8-B123; | A8-B124; | A8-B125; |
| A8-B126; | A8-B127; | A8-B128; | A8-B129; | A8-B130; | A8-B131; |
| A8-B132; | A8-B133; | A8-B134; | A8-B135; | A8-B136; | A8-B137; |
| A8-B138; | A8-B139; | A8-B140; | A8-B141; | A8-B142; | A8-B143; |
| A8-B144; | A8-B145; | A8-B146; | A8-B147; | A8-B148; | A8-B149; |
| A8-B150; | A8-B151; | A8-B152; | A8-B153; | A8-B154; | A8-B155; |
| A8-B156; | A8-B157; | A8-B158; | A8-B159; | A8-B160; | A8-B161; |
| A8-B162; | A8-B163; | A8-B164; | A8-B165; | A8-B166; | A8-B167; |
| A8-B168; | A8-B169; | A9-B1; | A9-B2; | A9-B3; | A9-B4; |

-continued

| | | | | | |
|---|---|---|---|---|---|
| A9-B5; | A9-B6; | A9-B7; | A9-B8; | A9-B9; | A9-B10; |
| A9-B11; | A9-B12; | A9-B13; | A9-B14; | A9-B15; | A9-B16; |
| A9-B17; | A9-B18; | A9-B19; | A9-B20; | A9-B21; | A9-B22; |
| A9-B23; | A9-B24; | A9-B25; | A9-B26; | A9-B27; | A9-B28; |
| A9-B29; | A9-B30; | A9-B31; | A9-B32; | A9-B33; | A9-B34; |
| A9-B35; | A9-B36; | A9-B37; | A9-B38; | A9-B39; | A9-B40; |
| A9-B41; | A9-B42; | A9-B43; | A9-B44; | A9-B45; | A9-B46; |
| A9-B47; | A9-B48; | A9-B49; | A9-B50; | A9-B51; | A9-B52; |
| A9-B53; | A9-B54; | A9-B55; | A9-B56; | A9-B57; | A9-B58; |
| A9-B59; | A9-B60; | A9-B61; | A9-B62; | A9-B63; | A9-B64; |
| A9-B65; | A9-B66; | A9-B67; | A9-B68; | A9-B69; | A9-B70; |
| A9-B71; | A9-B72; | A9-B73; | A9-B74; | A9-B75; | A9-B76; |
| A9-B77; | A9-B78; | A9-B79; | A9-B80; | A9-B81; | A9-B82; |
| A9-B83; | A9-B84; | A9-B85; | A9-B86; | A9-B87; | A9-B88; |
| A9-B89; | A9-B90; | A9-B91; | A9-B92; | A9-B93; | A9-B94; |
| A9-B95; | A9-B96; | A9-B97; | A9-B98; | A9-B99; | A9-B100; |
| A9-B101; | A9-B102; | A9-B103; | A9-B104; | A9-B105; | A9-B106; |
| A9-B107; | A9-B108; | A9-B109; | A9-B110; | A9-B111; | A9-B112; |
| A9-B113; | A9-B114; | A9-B115; | A9-B116; | A9-B117; | A9-B118; |
| A9-B119; | A9-B120; | A9-B121; | A9-B122; | A9-B123; | A9-B124; |
| A9-B125; | A9-B126; | A9-B127; | A9-B128; | A9-B129; | A9-B130; |
| A9-B131; | A9-B132; | A9-B133; | A9-B134; | A9-B135; | A9-B136; |
| A9-B137; | A9-B138; | A9-B139; | A9-B140; | A9-B141; | A9-B142; |
| A9-B143; | A9-B144; | A9-B145; | A9-B146; | A9-B147; | A9-B148; |
| A9-B149; | A9-B150; | A9-B151; | A9-B152; | A9-B153; | A9-B154; |
| A9-B155; | A9-B156; | A9-B157; | A9-B158; | A9-B159; | A9-B160; |
| A9-B161; | A9-B162; | A9-B163; | A9-B164; | A9-B165; | A9-B166; |
| A9-B167; | A9-B168; | A9-B169; | A10-B1; | A10-B2; | A10-B3; |
| A10-B4; | A10-B5; | A10-B6; | A10-B7; | A10-B8; | A10-B9; |
| A10-B10; | A10-B11; | A10-B12; | A10-B13; | A10-B14; | A10-B15; |
| A10-B16; | A10-B17; | A10-B18; | A10-B19; | A10-B20; | A10-B21; |
| A10-B22; | A10-B23; | A10-B24; | A10-B25; | A10-B26; | A10-B27; |
| A10-B28; | A10-B29; | A10-B30; | A10-B31; | A10-B32; | A10-B33; |
| A10-B34; | A10-B35; | A10-B36; | A10-B37; | A10-B38; | A10-B39; |
| A10-B40; | A10-B41; | A10-B42; | A10-B43; | A10-B44; | A10-B45; |
| A10-B46; | A10-B47; | A10-B48; | A10-B49; | A10-B50; | A10-B51; |
| A10-B52; | A10-B53; | A10-B54; | A10-B55; | A10-B56; | A10-B57; |
| A10-B58; | A10-B59; | A10-B60; | A10-B61; | A10-B62; | A10-B63; |
| A10-B64; | A10-B65; | A10-B66; | A10-B67; | A10-B68; | A10-B69; |
| A10-B70; | A10-B71; | A10-B72; | A10-B73; | A10-B74; | A10-B75; |
| A10-B76; | A10-B77; | A10-B78; | A10-B79; | A10-B80; | A10-B81; |
| A10-B82; | A10-B83; | A10-B84; | A10-B85; | A10-B86; | A10-B87; |
| A10-B88; | A10-B89; | A10-B90; | A10-B91; | A10-B92; | A10-B93; |
| A10-B94; | A10-B95; | A10-B96; | A10-B97; | A10-B98; | A10-B99; |
| A10-B100; | A10-B101; | A10-B102; | A10-B103; | A10-B104; | A10-B105; |
| A10-B106; | A10-B107; | A10-B108; | A10-B109; | A10-B110; | A10-B111; |
| A10-B112; | A10-B113; | A10-B114; | A10-B115; | A10-B116; | A10-B117; |
| A10-B118; | A10-B119; | A10-B120; | A10-B121; | A10-B122; | A10-B123; |
| A10-B124; | A10-B125; | A10-B126; | A10-B127; | A10-B128; | A10-B129; |
| A10-B130; | A10-B131; | A10-B132; | A10-B133; | A10-B134; | A10-B135; |
| A10-B136; | A10-B137; | A10-B138; | A10-B139; | A10-B140; | A10-B141; |
| A10-B142; | A10-B143; | A10-B144; | A10-B145; | A10-B146; | A10-B147; |
| A10-B148; | A10-B149; | A10-B150; | A10-B151; | A10-B152; | A10-B153; |
| A10-B154; | A10-B155; | A10-B156; | A10-B157; | A10-B158; | A10-B159; |
| A10-B160; | A10-B161; | A10-B162; | A10-B163; | A10-B164; | A10-B165; |
| A10-B166; | A10-B167; | A10-B168; | A10-B169; | A11-B1; | A11-B2; |
| A11-B3; | A11-B4; | A11-B5; | A11-B6; | A11-B7; | A11-B8; |
| A11-B9; | A11-B10; | A11-B11; | A11-B12; | A11-B13; | A11-B14; |
| A11-B15; | A11-B16; | A11-B17; | A11-B18; | A11-B19; | A11-B20; |
| A11-B21; | A11-B22; | A11-B23; | A11-B24; | A11-B25; | A11-B26; |
| A11-B27; | A11-B28; | A11-B29; | A11-B30; | A11-B31; | A11-B32; |
| A11-B33; | A11-B34; | A11-B35; | A11-B36; | A11-B37; | A11-B38; |
| A11-B39; | A11-B40; | A11-B41; | A11-B42; | A11-B43; | A11-B44; |
| A11-B45; | A11-B46; | A11-B47; | A11-B48; | A11-B49; | A11-B50; |
| A11-B51; | A11-B52; | A11-B53; | A11-B54; | A11-B55; | A11-B56; |
| A11-B57; | A11-B58; | A11-B59; | A11-B60; | A11-B61; | A11-B62; |
| A11-B63; | A11-B64; | A11-B65; | A11-B66; | A11-B67; | A11-B68; |
| A11-B69; | A11-B70; | A11-B71; | A11-B72; | A11-B73; | A11-B74; |
| A11-B75; | A11-B76; | A11-B77; | A11-B78; | A11-B79; | A11-B80; |
| A11-B81; | A11-B82; | A11-B83; | A11-B84; | A11-B85; | A11-B86; |
| A11-B87; | A11-B88; | A11-B89; | A11-B90; | A11-B91; | A11-B92; |
| A11-B93; | A11-B94; | A11-B95; | A11-B96; | A11-B97; | A11-B98; |
| A11-B99; | A11-B100; | A11-B101; | A11-B102; | A11-B103; | A11-B104; |
| A11-B105; | A11-B106; | A11-B107; | A11-B108; | A11-B109; | A11-B110; |
| A11-B111; | A11-B112; | A11-B113; | A11-B114; | A11-B115; | A11-B116; |
| A11-B117; | A11-B118; | A11-B119; | A11-B120; | A11-B121; | A11-B122; |
| A11-B123; | A11-B124; | A11-B125; | A11-B126; | A11-B127; | A11-B128; |
| A11-B129; | A11-B130; | A11-B131; | A11-B132; | A11-B133; | A11-B134; |
| A11-B135; | A11-B136; | A11-B137; | A11-B138; | A11-B139; | A11-B140; |
| A11-B141; | A11-B142; | A11-B143; | A11-B144; | A11-B145; | A11-B146; |

-continued

A11-B147; A11-B148; A11-B149; A11-B150; A11-B151; A11-B152;
A11-B153; A11-B154; A11-B155; A11-B156; A11-B157; A11-B158;
A11-B159; A11-B160; A11-B161; A11-B162; A11-B163; A11-B164;
A11-B165; A11-B166; A11-B167; A11-B168; A11-B169; A12-B1;
A12-B2; A12-B3; A12-B4; A12-B5; A12-B6; A12-B7;
A12-B8; A12-B9; A12-B10; A12-B11; A12-B12; A12-B13;
A12-B14; A12-B15; A12-B16; A12-B17; A12-B18; A12-B19;
A12-B20; A12-B21; A12-B22; A12-B23; A12-B24; A12-B25;
A12-B26; A12-B27; A12-B28; A12-B29; A12-B30; A12-B31;
A12-B32; A12-B33; A12-B34; A12-B35; A12-B36; A12-B37;
A12-B38; A12-B39; A12-B40; A12-B41; A12-B42; A12-B43;
A12-B44; A12-B45; A12-B46; A12-B47; A12-B48; A12-B49;
A12-B50; A12-B51; A12-B52; A12-B53; A12-B54; A12-B55;
A12-B56; A12-B57; A12-B58; A12-B59; A12-B60; A12-B61;
A12-B62; A12-B63; A12-B64; A12-B65; A12-B66; A12-B67;
A12-B68; A12-B69; A12-B70; A12-B71; A12-B72; A12-B73;
A12-B74; A12-B75; A12-B76; A12-B77; A12-B78; A12-B79;
A12-B80; A12-B81; A12-B82; A12-B83; A12-B84; A12-B85;
A12-B86; A12-B87; A12-B88; A12-B89; A12-B90; A12-B91;
A12-B92; A12-B93; A12-B94; A12-B95; A12-B96; A12-B97;
A12-B98; A12-B99; A12-B100; A12-B101; A12-B102; A12-B103;
A12-B104; A12-B105; A12-B106; A12-B107; A12-B108; A12-B109;
A12-B110; A12-B111; A12-B112; A12-B113; A12-B114; A12-B115;
A12-B116; A12-B117; A12-B118; A12-B119; A12-B120; A12-B121;
A12-B122; A12-B123; A12-B124; A12-B125; A12-B126; A12-B127;
A12-B128; A12-B129; A12-B130; A12-B131; A12-B132; A12-B133;
A12-B134; A12-B135; A12-B136; A12-B137; A12-B138; A12-B139;
A12-B140; A12-B141; A12-B142; A12-B143; A12-B144; A12-B145;
A12-B146; A12-B147; A12-B148; A12-B149; A12-B150; A12-B151;
A12-B152; A12-B153; A12-B154; A12-B155; A12-B156; A12-B157;
A12-B158; A12-B159; A12-B160; A12-B161; A12-B162; A12-B163;
A12-B164; A12-B165; A12-B166; A12-B167; A12-B168; A12-B169;
A13-B1; A13-B2; A13-B3; A13-B4; A13-B5; A13-B6;
A13-B7; A13-B8; A13-B9; A13-B10; A13-B11; A13-B12;
A13-B13; A13-B14; A13-B15; A13-B16; A13-B17; A13-B18;
A13-B19; A13-B20; A13-B21; A13-B22; A13-B23; A13-B24;
A13-B25; A13-B26; A13-B27; A13-B28; A13-B29; A13-B30;
A13-B31; A13-B32; A13-B33; A13-B34; A13-B35; A13-B36;
A13-B37; A13-B38; A13-B39; A13-B40; A13-B41; A13-B42;
A13-B43; A13-B44; A13-B45; A13-B46; A13-B47; A13-B48;
A13-B49; A13-B50; A13-B51; A13-B52; A13-B53; A13-B54;
A13-B55; A13-B56; A13-B57; A13-B58; A13-B59; A13-B60;
A13-B61; A13-B62; A13-B63; A13-B64; A13-B65; A13-B66;
A13-B67; A13-B68; A13-B69; A13-B70; A13-B71; A13-B72;
A13-B73; A13-B74; A13-B75; A13-B76; A13-B77; A13-B78;
A13-B79; A13-B80; A13-B81; A13-B82; A13-B83; A13-B84;
A13-B85; A13-B86; A13-B87; A13-B88; A13-B89; A13-B90;
A13-B91; A13-B92; A13-B93; A13-B94; A13-B95; A13-B96;
A13-B97; A13-B98; A13-B99; A13-B100; A13-B101; A13-B102;
A13-B103; A13-B104; A13-B105; A13-B106; A13-B107; A13-B108;
A13-B109; A13-B110; A13-B111; A13-B112; A13-B113; A13-B114;
A13-B115; A13-B116; A13-B117; A13-B118; A13-B119; A13-B120;
A13-B121; A13-B122; A13-B123; A13-B124; A13-B125; A13-B126;
A13-B127; A13-B128; A13-B129; A13-B130; A13-B131; A13-B132;
A13-B133; A13-B134; A13-B135; A13-B136; A13-B137; A13-B138;
A13-B139; A13-B140; A13-B141; A13-B142; A13-B143; A13-B144;
A13-B145; A13-B146; A13-B147; A13-B148; A13-B149; A13-B150;
A13-B151; A13-B152; A13-B153; A13-B154; A13-B155; A13-B156;
A13-B157; A13-B158; A13-B159; A13-B160; A13-B161; A13-B162;
A13-B163; A13-B164; A13-B165; A13-B166; A13-B167; A13-B168;
A13-B169; A14-B1; A14-B2; A14-B3; A14-B4; A14-B5;
A14-B6; A14-B7; A14-B8; A14-B9; A14-B10; A14-B11;
A14-B12; A14-B13; A14-B14; A14-B15; A14-B16; A14-B17;
A14-B18; A14-B19; A14-B20; A14-B21; A14-B22; A14-B23;
A14-B24; A14-B25; A14-B26; A14-B27; A14-B28; A14-B29;
A14-B30; A14-B31; A14-B32; A14-B33; A14-B34; A14-B35;
A14-B36; A14-B37; A14-B38; A14-B39; A14-B40; A14-B41;
A14-B42; A14-B43; A14-B44; A14-B45; A14-B46; A14-B47;
A14-B48; A14-B49; A14-B50; A14-B51; A14-B52; A14-B53;
A14-B54; A14-B55; A14-B56; A14-B57; A14-B58; A14-B59;
A14-B60; A14-B61; A14-B62; A14-B63; A14-B64; A14-B65;
A14-B66; A14-B67; A14-B68; A14-B69; A14-B70; A14-B71;
A14-B72; A14-B73; A14-B74; A14-B75; A14-B76; A14-B77;
A14-B78; A14-B79; A14-B80; A14-B81; A14-B82; A14-B83;
A14-B84; A14-B85; A14-B86; A14-B87; A14-B88; A14-B89;
A14-B90; A14-B91; A14-B92; A14-B93; A14-B94; A14-B95;
A14-B96; A14-B97; A14-B98; A14-B99; A14-B100; A14-B101;
A14-B102; A14-B103; A14-B104; A14-B105; A14-B106; A14-B107;
A14-B108; A14-B109; A14-B110; A14-B111; A14-B112; A14-B113;
A14-B114; A14-B115; A14-B116; A14-B117; A14-B118; A14-B119;

-continued

| | | | | | |
|---|---|---|---|---|---|
| A14-B120; | A14-B121; | A14-B122; | A14-B123; | A14-B124; | A14-B125; |
| A14-B126; | A14-B127; | A14-B128; | A14-B129; | A14-B130; | A14-B131; |
| A14-B132; | A14-B133; | A14-B134; | A14-B135; | A14-B136; | A14-B137; |
| A14-B138; | A14-B139; | A14-B140; | A14-B141; | A14-B142; | A14-B143; |
| A14-B144; | A14-B145; | A14-B146; | A14-B147; | A14-B148; | A14-B149; |
| A14-B150; | A14-B151; | A14-B152; | A14-B153; | A14-B154; | A14-B155; |
| A14-B156; | A14-B157; | A14-B158; | A14-B159; | A14-B160; | A14-B161; |
| A14-B162; | A14-B163; | A14-B164; | A14-B165; | A14-B166; | A14-B167; |
| A14-B168; | A14-B169; | A15-B1; | A15-B2; | A15-B3; | A15-B4; |
| A15-B5; | A15-B6; | A15-B7; | A15-B8; | A15-B9; | A15-B10; |
| A15-B11; | A15-B12; | A15-B13; | A15-B14; | A15-B15; | A15-B16; |
| A15-B17; | A15-B18; | A15-B19; | A15-B20; | A15-B21; | A15-B22; |
| A15-B23; | A15-B24; | A15-B25; | A15-B26; | A15-B27; | A15-B28; |
| A15-B29; | A15-B30; | A15-B31; | A15-B32; | A15-B33; | A15-B34; |
| A15-B35; | A15-B36; | A15-B37; | A15-B38; | A15-B39; | A15-B40; |
| A15-B41; | A15-B42; | A15-B43; | A15-B44; | A15-B45; | A15-B46; |
| A15-B47; | A15-B48; | A15-B49; | A15-B50; | A15-B51; | A15-B52; |
| A15-B53; | A15-B54; | A15-B55; | A15-B56; | A15-B57; | A15-B58; |
| A15-B59; | A15-B60; | A15-B61; | A15-B62; | A15-B63; | A15-B64; |
| A15-B65; | A15-B66; | A15-B67; | A15-B68; | A15-B69; | A15-B70; |
| A15-B71; | A15-B72; | A15-B73; | A15-B74; | A15-B75; | A15-B76; |
| A15-B77; | A15-B78; | A15-B79; | A15-B80; | A15-B81; | A15-B82; |
| A15-B83; | A15-B84; | A15-B85; | A15-B86; | A15-B87; | A15-B88; |
| A15-B89; | A15-B90; | A15-B91; | A15-B92; | A15-B93; | A15-B94; |
| A15-B95; | A15-B96; | A15-B97; | A15-B98; | A15-B99; | A15-B100; |
| A15-B101; | A15-B102; | A15-B103; | A15-B104; | A15-B105; | A15-B106; |
| A15-B107; | A15-B108; | A15-B109; | A15-B110; | A15-B111; | A15-B112; |
| A15-B113; | A15-B114; | A15-B115; | A15-B116; | A15-B117; | A15-B118; |
| A15-B119; | A15-B120; | A15-B121; | A15-B122; | A15-B123; | A15-B124; |
| A15-B125; | A15-B126; | A15-B127; | A15-B128; | A15-B129; | A15-B130; |
| A15-B131; | A15-B132; | A15-B133; | A15-B134; | A15-B135; | A15-B136; |
| A15-B137; | A15-B138; | A15-B139; | A15-B140; | A15-B141; | A15-B142; |
| A15-B143; | A15-B144; | A15-B145; | A15-B146; | A15-B147; | A15-B148; |
| A15-B149; | A15-B150; | A15-B151; | A15-B152; | A15-B153; | A15-B154; |
| A15-B155; | A15-B156; | A15-B157; | A15-B158; | A15-B159; | A15-B160; |
| A15-B161; | A15-B162; | A15-B163; | A15-B164; | A15-B165; | A15-B166; |
| A15-B167; | A15-B168; | A15-B169; | A16-B1; | A16-B2; | A16-B3; |
| A16-B4; | A16-B5; | A16-B6; | A16-B7; | A16-B8; | A16-B9; |
| A16-B10; | A16-B11; | A16-B12; | A16-B13; | A16-B14; | A16-B15; |
| A16-B16; | A16-B17; | A16-B18; | A16-B19; | A16-B20; | A16-B21; |
| A16-B22; | A16-B23; | A16-B24; | A16-B25; | A16-B26; | A16-B27; |
| A16-B28; | A16-B29; | A16-B30; | A16-B31; | A16-B32; | A16-B33; |
| A16-B34; | A16-B35; | A16-B36; | A16-B37; | A16-B38; | A16-B39; |
| A16-B40; | A16-B41; | A16-B42; | A16-B43; | A16-B44; | A16-B45; |
| A16-B46; | A16-B47; | A16-B48; | A16-B49; | A16-B50; | A16-B51; |
| A16-B52; | A16-B53; | A16-B54; | A16-B55; | A16-B56; | A16-B57; |
| A16-B58; | A16-B59; | A16-B60; | A16-B61; | A16-B62; | A16-B63; |
| A16-B64; | A16-B65; | A16-B66; | A16-B67; | A16-B68; | A16-B69; |
| A16-B70; | A16-B71; | A16-B72; | A16-B73; | A16-B74; | A16-B75; |
| A16-B76; | A16-B77; | A16-B78; | A16-B79; | A16-B80; | A16-B81; |
| A16-B82; | A16-B83; | A16-B84; | A16-B85; | A16-B86; | A16-B87; |
| A16-B88; | A16-B89; | A16-B90; | A16-B91; | A16-B92; | A16-B93; |
| A16-B94; | A16-B95; | A16-B96; | A16-B97; | A16-B98; | A16-B99; |
| A16-B100; | A16-B101; | A16-B102; | A16-B103; | A16-B104; | A16-B105; |
| A16-B106; | A16-B107; | A16-B108; | A16-B109; | A16-B110; | A16-B111; |
| A16-B112; | A16-B113; | A16-B114; | A16-B115; | A16-B116; | A16-B117; |
| A16-B118; | A16-B119; | A16-B120; | A16-B121; | A16-B122; | A16-B123; |
| A16-B124; | A16-B125; | A16-B126; | A16-B127; | A16-B128; | A16-B129; |
| A16-B130; | A16-B131; | A16-B132; | A16-B133; | A16-B134; | A16-B135; |
| A16-B136; | A16-B137; | A16-B138; | A16-B139; | A16-B140; | A16-B141; |
| A16-B142; | A16-B143; | A16-B144; | A16-B145; | A16-B146; | A16-B147; |
| A16-B148; | A16-B149; | A16-B150; | A16-B151; | A16-B152; | A16-B153; |
| A16-B154; | A16-B155; | A16-B156; | A16-B157; | A16-B158; | A16-B159; |
| A16-B160; | A16-B161; | A16-B162; | A16-B163; | A16-B164; | A16-B165; |
| A16-B166; | A16-B167; | A16-B168; | A16-B169; | A17-B1; | A17-B2; |
| A17-B3; | A17-B4; | A17-B5; | A17-B6; | A17-B7; | A17-B8; |
| A17-B9; | A17-B10; | A17-B11; | A17-B12; | A17-B13; | A17-B14; |
| A17-B15; | A17-B16; | A17-B17; | A17-B18; | A17-B19; | A17-B20; |
| A17-B21; | A17-B22; | A17-B23; | A17-B24; | A17-B25; | A17-B26; |
| A17-B27; | A17-B28; | A17-B29; | A17-B30; | A17-B31; | A17-B32; |
| A17-B33; | A17-B34; | A17-B35; | A17-B36; | A17-B37; | A17-B38; |
| A17-B39; | A17-B40; | A17-B41; | A17-B42; | A17-B43; | A17-B44; |
| A17-B45; | A17-B46; | A17-B47; | A17-B48; | A17-B49; | A17-B50; |
| A17-B51; | A17-B52; | A17-B53; | A17-B54; | A17-B55; | A17-B56; |
| A17-B57; | A17-B58; | A17-B59; | A17-B60; | A17-B61; | A17-B62; |
| A17-B63; | A17-B64; | A17-B65; | A17-B66; | A17-B67; | A17-B68; |
| A17-B69; | A17-B70; | A17-B71; | A17-B72; | A17-B73; | A17-B74; |
| A17-B75; | A17-B76; | A17-B77; | A17-B78; | A17-B79; | A17-B80; |
| A17-B81; | A17-B82; | A17-B83; | A17-B84; | A17-B85; | A17-B86; |
| A17-B87; | A17-B88; | A17-B89; | A17-B90; | A17-B91; | A17-B92; |

-continued

| | | | | | |
|---|---|---|---|---|---|
| A17-B93; | A17-B94; | A17-B95; | A17-B96; | A17-B97; | A17-B98; |
| A17-B99; | A17-B100; | A17-B101; | A17-B102; | A17-B103; | A17-B104; |
| A17-B105; | A17-B106; | A17-B107; | A17-B108; | A17-B109; | A17-B110; |
| A17-B111; | A17-B112; | A17-B113; | A17-B114; | A17-B115; | A17-B116; |
| A17-B117; | A17-B118; | A17-B119; | A17-B120; | A17-B121; | A17-B122; |
| A17-B123; | A17-B124; | A17-B125; | A17-B126; | A17-B127; | A17-B128; |
| A17-B129; | A17-B130; | A17-B131; | A17-B132; | A17-B133; | A17-B134; |
| A17-B135; | A17-B136; | A17-B137; | A17-B138; | A17-B139; | A17-B140; |
| A17-B141; | A17-B142; | A17-B143; | A17-B144; | A17-B145; | A17-B146; |
| A17-B147; | A17-B148; | A17-B149; | A17-B150; | A17-B151; | A17-B152; |
| A17-B153; | A17-B154; | A17-B155; | A17-B156; | A17-B157; | A17-B158; |
| A17-B159; | A17-B160; | A17-B161; | A17-B162; | A17-B163; | A17-B164; |
| A17-B165; | A17-B166; | A17-B167; | A17-B168; | A17-B169; | A18-B1; |
| A18-B2; | A18-B3; | A18-B4; | A18-B5; | A18-B6; | A18-B7; |
| A18-B8; | A18-B9; | A18-B10; | A18-B11; | A18-B12; | A18-B13; |
| A18-B14; | A18-B15; | A18-B16; | A18-B17; | A18-B18; | A18-B19; |
| A18-B20; | A18-B21; | A18-B22; | A18-B23; | A18-B24; | A18-B25; |
| A18-B26; | A18-B27; | A18-B28; | A18-B29; | A18-B30; | A18-B31; |
| A18-B32; | A18-B33; | A18-B34; | A18-B35; | A18-B36; | A18-B37; |
| A18-B38; | A18-B39; | A18-B40; | A18-B41; | A18-B42; | A18-B43; |
| A18-B44; | A18-B45; | A18-B46; | A18-B47; | A18-B48; | A18-B49; |
| A18-B50; | A18-B51; | A18-B52; | A18-B53; | A18-B54; | A18-B55; |
| A18-B56; | A18-B57; | A18-B58; | A18-B59; | A18-B60; | A18-B61; |
| A18-B62; | A18-B63; | A18-B64; | A18-B65; | A18-B66; | A18-B67; |
| A18-B68; | A18-B69; | A18-B70; | A18-B71; | A18-B72; | A18-B73; |
| A18-B74; | A18-B75; | A18-B76; | A18-B77; | A18-B78; | A18-B79; |
| A18-B80; | A18-B81; | A18-B82; | A18-B83; | A18-B84; | A18-B85; |
| A18-B86; | A18-B87; | A18-B88; | A18-B89; | A18-B90; | A18-B91; |
| A18-B92; | A18-B93; | A18-B94; | A18-B95; | A18-B96; | A18-B97; |
| A18-B98; | A18-B99; | A18-B100; | A18-B101; | A18-B102; | A18-B103; |
| A18-B104; | A18-B105; | A18-B106; | A18-B107; | A18-B108; | A18-B109; |
| A18-B110; | A18-B111; | A18-B112; | A18-B113; | A18-B114; | A18-B115; |
| A18-B116; | A18-B117; | A18-B118; | A18-B119; | A18-B120; | A18-B121; |
| A18-B122; | A18-B123; | A18-B124; | A18-B125; | A18-B126; | A18-B127; |
| A18-B128; | A18-B129; | A18-B130; | A18-B131; | A18-B132; | A18-B133; |
| A18-B134; | A18-B135; | A18-B136; | A18-B137; | A18-B138; | A18-B139; |
| A18-B140; | A18-B141; | A18-B142; | A18-B143; | A18-B144; | A18-B145; |
| A18-B146; | A18-B147; | A18-B148; | A18-B149; | A18-B150; | A18-B151; |
| A18-B152; | A18-B153; | A18-B154; | A18-B155; | A18-B156; | A18-B157; |
| A18-B158; | A18-B159; | A18-B160; | A18-B161; | A18-B162; | A18-B163; |
| A18-B164; | A18-B165; | A18-B166; | A18-B167; | A18-B168; | A18-B169; |
| A19-B1; | A19-B2; | A19-B3; | A19-B4; | A19-B5; | A19-B6; |
| A19-B7; | A19-B8; | A19-B9; | A19-B10; | A19-B11; | A19-B12; |
| A19-B13; | A19-B14; | A19-B15; | A19-B16; | A19-B17; | A19-B18; |
| A19-B19; | A19-B20; | A19-B21; | A19-B22; | A19-B23; | A19-B24; |
| A19-B25; | A19-B26; | A19-B27; | A19-B28; | A19-B29; | A19-B30; |
| A19-B31; | A19-B32; | A19-B33; | A19-B34; | A19-B35; | A19-B36; |
| A19-B37; | A19-B38; | A19-B39; | A19-B40; | A19-B41; | A19-B42; |
| A19-B43; | A19-B44; | A19-B45; | A19-B46; | A19-B47; | A19-B48; |
| A19-B49; | A19-B50; | A19-B51; | A19-B52; | A19-B53; | A19-B54; |
| A19-B55; | A19-B56; | A19-B57; | A19-B58; | A19-B59; | A19-B60; |
| A19-B61; | A19-B62; | A19-B63; | A19-B64; | A19-B65; | A19-B66; |
| A19-B67; | A19-B68; | A19-B69; | A19-B70; | A19-B71; | A19-B72; |
| A19-B73; | A19-B74; | A19-B75; | A19-B76; | A19-B77; | A19-B78; |
| A19-B79; | A19-B80; | A19-B81; | A19-B82; | A19-B83; | A19-B84; |
| A19-B85; | A19-B86; | A19-B87; | A19-B88; | A19-B89; | A19-B90; |
| A19-B91; | A19-B92; | A19-B93; | A19-B94; | A19-B95; | A19-B96; |
| A19-B97; | A19-B98; | A19-B99; | A19-B100; | A19-B101; | A19-B102; |
| A19-B103; | A19-B104; | A19-B105; | A19-B106; | A19-B107; | A19-B108; |
| A19-B109; | A19-B110; | A19-B111; | A19-B112; | A19-B113; | A19-B114; |
| A19-B115; | A19-B116; | A19-B117; | A19-B118; | A19-B119; | A19-B120; |
| A19-B121; | A19-B122; | A19-B123; | A19-B124; | A19-B125; | A19-B126; |
| A19-B127; | A19-B128; | A19-B129; | A19-B130; | A19-B131; | A19-B132; |
| A19-B133; | A19-B134; | A19-B135; | A19-B136; | A19-B137; | A19-B138; |
| A19-B139; | A19-B140; | A19-B141; | A19-B142; | A19-B143; | A19-B144; |
| A19-B145; | A19-B146; | A19-B147; | A19-B148; | A19-B149; | A19-B150; |
| A19-B151; | A19-B152; | A19-B153; | A19-B154; | A19-B155; | A19-B156; |
| A19-B157; | A19-B158; | A19-B159; | A19-B160; | A19-B161; | A19-B162; |
| A19-B163; | A19-B164; | A19-B165; | A19-B166; | A19-B167; | A19-B168; |
| A19-B169; | A20-B1; | A20-B2; | A20-B3; | A20-B4; | A20-B5; |
| A20-B6; | A20-B7; | A20-B8; | A20-B9; | A20-B10; | A20-B11; |
| A20-B12; | A20-B13; | A20-B14; | A20-B15; | A20-B16; | A20-B17; |
| A20-B18; | A20-B19; | A20-B20; | A20-B21; | A20-B22; | A20-B23; |
| A20-B24; | A20-B25; | A20-B26; | A20-B27; | A20-B28; | A20-B29; |
| A20-B30; | A20-B31; | A20-B32; | A20-B33; | A20-B34; | A20-B35; |
| A20-B36; | A20-B37; | A20-B38; | A20-B39; | A20-B40; | A20-B41; |
| A20-B42; | A20-B43; | A20-B44; | A20-B45; | A20-B46; | A20-B47; |
| A20-B48; | A20-B49; | A20-B50; | A20-B51; | A20-B52; | A20-B53; |
| A20-B54; | A20-B55; | A20-B56; | A20-B57; | A20-B58; | A20-B59; |
| A20-B60; | A20-B61; | A20-B62; | A20-B63; | A20-B64; | A20-B65; |

-continued

| | | | | | |
|---|---|---|---|---|---|
| A20-B66; | A20-B67; | A20-B68; | A20-B69; | A20-B70; | A20-B71; |
| A20-B72; | A20-B73; | A20-B74; | A20-B75; | A20-B76; | A20-B77; |
| A20-B78; | A20-B79; | A20-B80; | A20-B81; | A20-B82; | A20-B83; |
| A20-B84; | A20-B85; | A20-B86; | A20-B87; | A20-B88; | A20-B89; |
| A20-B90; | A20-B91; | A20-B92; | A20-B93; | A20-B94; | A20-B95; |
| A20-B96; | A20-B97; | A20-B98; | A20-B99; | A20-B100; | A20-B101; |
| A20-B102; | A20-B103; | A20-B104; | A20-B105; | A20-B106; | A20-B107; |
| A20-B108; | A20-B109; | A20-B110; | A20-B111; | A20-B112; | A20-B113; |
| A20-B114; | A20-B115; | A20-B116; | A20-B117; | A20-B118; | A20-B119; |
| A20-B120; | A20-B121; | A20-B122; | A20-B123; | A20-B124; | A20-B125; |
| A20-B126; | A20-B127; | A20-B128; | A20-B129; | A20-B130; | A20-B131; |
| A20-B132; | A20-B133; | A20-B134; | A20-B135; | A20-B136; | A20-B137; |
| A20-B138; | A20-B139; | A20-B140; | A20-B141; | A20-B142; | A20-B143; |
| A20-B144; | A20-B145; | A20-B146; | A20-B147; | A20-B148; | A20-B149; |
| A20-B150; | A20-B151; | A20-B152; | A20-B153; | A20-B154; | A20-B155; |
| A20-B156; | A20-B157; | A20-B158; | A20-B159; | A20-B160; | A20-B161; |
| A20-B162; | A20-B163; | A20-B164; | A20-B165; | A20-B166; | A20-B167; |
| A20-B168; | A20-B169; | A21-B1; | A21-B2; | A21-B3; | A21-B4; |
| A21-B5; | A21-B6; | A21-B7; | A21-B8; | A21-B9; | A21-B10; |
| A21-B11; | A21-B12; | A21-B13; | A21-B14; | A21-B15; | A21-B16; |
| A21-B17; | A21-B18; | A21-B19; | A21-B20; | A21-B21; | A21-B22; |
| A21-B23; | A21-B24; | A21-B25; | A21-B26; | A21-B27; | A21-B28; |
| A21-B29; | A21-B30; | A21-B31; | A21-B32; | A21-B33; | A21-B34; |
| A21-B35; | A21-B36; | A21-B37; | A21-B38; | A21-B39; | A21-B40; |
| A21-B41; | A21-B42; | A21-B43; | A21-B44; | A21-B45; | A21-B46; |
| A21-B47; | A21-B48; | A21-B49; | A21-B50; | A21-B51; | A21-B52; |
| A21-B53; | A21-B54; | A21-B55; | A21-B56; | A21-B57; | A21-B58; |
| A21-B59; | A21-B60; | A21-B61; | A21-B62; | A21-B63; | A21-B64; |
| A21-B65; | A21-B66; | A21-B67; | A21-B68; | A21-B69; | A21-B70; |
| A21-B71; | A21-B72; | A21-B73; | A21-B74; | A21-B75; | A21-B76; |
| A21-B77; | A21-B78; | A21-B79; | A21-B80; | A21-B81; | A21-B82; |
| A21-B83; | A21-B84; | A21-B85; | A21-B86; | A21-B87; | A21-B88; |
| A21-B89; | A21-B90; | A21-B91; | A21-B92; | A21-B93; | A21-B94; |
| A21-B95; | A21-B96; | A21-B97; | A21-B98; | A21-B99; | A21-B100; |
| A21-B101; | A21-B102; | A21-B103; | A21-B104; | A21-B105; | A21-B106; |
| A21-B107; | A21-B108; | A21-B109; | A21-B110; | A21-B111; | A21-B112; |
| A21-B113; | A21-B114; | A21-B115; | A21-B116; | A21-B117; | A21-B118; |
| A21-B119; | A21-B120; | A21-B121; | A21-B122; | A21-B123; | A21-B124; |
| A21-B125; | A21-B126; | A21-B127; | A21-B128; | A21-B129; | A21-B130; |
| A21-B131; | A21-B132; | A21-B133; | A21-B134; | A21-B135; | A21-B136; |
| A21-B137; | A21-B138; | A21-B139; | A21-B140; | A21-B141; | A21-B142; |
| A21-B143; | A21-B144; | A21-B145; | A21-B146; | A21-B147; | A21-B148; |
| A21-B149; | A21-B150; | A21-B151; | A21-B152; | A21-B153; | A21-B154; |
| A21-B155; | A21-B156; | A21-B157; | A21-B158; | A21-B159; | A21-B160; |
| A21-B161; | A21-B162; | A21-B163; | A21-B164; | A21-B165; | A21-B166; |
| A21-B167; | A21-B168; | A21-B169; | A22-B1; | A22-B2; | A22-B3; |
| A22-B4; | A22-B5; | A22-B6; | A22-B7; | A22-B8; | A22-B9; |
| A22-B10; | A22-B11; | A22-B12; | A22-B13; | A22-B14; | A22-B15; |
| A22-B16; | A22-B17; | A22-B18; | A22-B19; | A22-B20; | A22-B21; |
| A22-B22; | A22-B23; | A22-B24; | A22-B25; | A22-B26; | A22-B27; |
| A22-B28; | A22-B29; | A22-B30; | A22-B31; | A22-B32; | A22-B33; |
| A22-B34; | A22-B35; | A22-B36; | A22-B37; | A22-B38; | A22-B39; |
| A22-B40; | A22-B41; | A22-B42; | A22-B43; | A22-B44; | A22-B45; |
| A22-B46; | A22-B47; | A22-B48; | A22-B49; | A22-B50; | A22-B51; |
| A22-B52; | A22-B53; | A22-B54; | A22-B55; | A22-B56; | A22-B57; |
| A22-B58; | A22-B59; | A22-B60; | A22-B61; | A22-B62; | A22-B63; |
| A22-B64; | A22-B65; | A22-B66; | A22-B67; | A22-B68; | A22-B69; |
| A22-B70; | A22-B71; | A22-B72; | A22-B73; | A22-B74; | A22-B75; |
| A22-B76; | A22-B77; | A22-B78; | A22-B79; | A22-B80; | A22-B81; |
| A22-B82; | A22-B83; | A22-B84; | A22-B85; | A22-B86; | A22-B87; |
| A22-B88; | A22-B89; | A22-B90; | A22-B91; | A22-B92; | A22-B93; |
| A22-B94; | A22-B95; | A22-B96; | A22-B97; | A22-B98; | A22-B99; |
| A22-B100; | A22-B101; | A22-B102; | A22-B103; | A22-B104; | A22-B105; |
| A22-B106; | A22-B107; | A22-B108; | A22-B109; | A22-B110; | A22-B111; |
| A22-B112; | A22-B113; | A22-B114; | A22-B115; | A22-B116; | A22-B117; |
| A22-B118; | A22-B119; | A22-B120; | A22-B121; | A22-B122; | A22-B123; |
| A22-B124; | A22-B125; | A22-B126; | A22-B127; | A22-B128; | A22-B129; |
| A22-B130; | A22-B131; | A22-B132; | A22-B133; | A22-B134; | A22-B135; |
| A22-B136; | A22-B137; | A22-B138; | A22-B139; | A22-B140; | A22-B141; |
| A22-B142; | A22-B143; | A22-B144; | A22-B145; | A22-B146; | A22-B147; |
| A22-B148; | A22-B149; | A22-B150; | A22-B151; | A22-B152; | A22-B153; |
| A22-B154; | A22-B155; | A22-B156; | A22-B157; | A22-B158; | A22-B159; |
| A22-B160; | A22-B161; | A22-B162; | A22-B163; | A22-B164; | A22-B165; |
| A22-B166; | A22-B167; | A22-B168; | A22-B169; | A23-B1; | A23-B2; |
| A23-B3; | A23-B4; | A23-B5; | A23-B6; | A23-B7; | A23-B8; |
| A23-B9; | A23-B10; | A23-B11; | A23-B12; | A23-B13; | A23-B14; |
| A23-B15; | A23-B16; | A23-B17; | A23-B18; | A23-B19; | A23-B20; |
| A23-B21; | A23-B22; | A23-B23; | A23-B24; | A23-B25; | A23-B26; |
| A23-B27; | A23-B28; | A23-B29; | A23-B30; | A23-B31; | A23-B32; |
| A23-B33; | A23-B34; | A23-B35; | A23-B36; | A23-B37; | A23-B38; |

-continued

| | | | | | |
|---|---|---|---|---|---|
| A23-B39; | A23-B40; | A23-B41; | A23-B42; | A23-B43; | A23-B44; |
| A23-B45; | A23-B46; | A23-B47; | A23-B48; | A23-B49; | A23-B50; |
| A23-B51; | A23-B52; | A23-B53; | A23-B54; | A23-B55; | A23-B56; |
| A23-B57; | A23-B58; | A23-B59; | A23-B60; | A23-B61; | A23-B62; |
| A23-B63; | A23-B64; | A23-B65; | A23-B66; | A23-B67; | A23-B68; |
| A23-B69; | A23-B70; | A23-B71; | A23-B72; | A23-B73; | A23-B74; |
| A23-B75; | A23-B76; | A23-B77; | A23-B78; | A23-B79; | A23-B80; |
| A23-B81; | A23-B82; | A23-B83; | A23-B84; | A23-B85; | A23-B86; |
| A23-B87; | A23-B88; | A23-B89; | A23-B90; | A23-B91; | A23-B92; |
| A23-B93; | A23-B94; | A23-B95; | A23-B96; | A23-B97; | A23-B98; |
| A23-B99; | A23-B100; | A23-B101; | A23-B102; | A23-B103; | A23-B104; |
| A23-B105; | A23-B106; | A23-B107; | A23-B108; | A23-B109; | A23-B110; |
| A23-B111; | A23-B112; | A23-B113; | A23-B114; | A23-B115; | A23-B116; |
| A23-B117; | A23-B118; | A23-B119; | A23-B120; | A23-B121; | A23-B122; |
| A23-B123; | A23-B124; | A23-B125; | A23-B126; | A23-B127; | A23-B128; |
| A23-B129; | A23-B130; | A23-B131; | A23-B132; | A23-B133; | A23-B134; |
| A23-B135; | A23-B136; | A23-B137; | A23-B138; | A23-B139; | A23-B140; |
| A23-B141; | A23-B142; | A23-B143; | A23-B144; | A23-B145; | A23-B146; |
| A23-B147; | A23-B148; | A23-B149; | A23-B150; | A23-B151; | A23-B152; |
| A23-B153; | A23-B154; | A23-B155; | A23-B156; | A23-B157; | A23-B158; |
| A23-B159; | A23-B160; | A23-B161; | A23-B162; | A23-B163; | A23-B164; |
| A23-B165; | A23-B166; | A23-B167; | A23-B168; | A23-B169; | A24-B1; |
| A24-B2; | A24-B3; | A24-B4; | A24-B5; | A24-B6; | A24-B7; |
| A24-B8; | A24-B9; | A24-B10; | A24-B11; | A24-B12; | A24-B13; |
| A24-B14; | A24-B15; | A24-B16; | A24-B17; | A24-B18; | A24-B19; |
| A24-B20; | A24-B21; | A24-B22; | A24-B23; | A24-B24; | A24-B25; |
| A24-B26; | A24-B27; | A24-B28; | A24-B29; | A24-B30; | A24-B31; |
| A24-B32; | A24-B33; | A24-B34; | A24-B35; | A24-B36; | A24-B37; |
| A24-B38; | A24-B39; | A24-B40; | A24-B41; | A24-B42; | A24-B43; |
| A24-B44; | A24-B45; | A24-B46; | A24-B47; | A24-B48; | A24-B49; |
| A24-B50; | A24-B51; | A24-B52; | A24-B53; | A24-B54; | A24-B55; |
| A24-B56; | A24-B57; | A24-B58; | A24-B59; | A24-B60; | A24-B61; |
| A24-B62; | A24-B63; | A24-B64; | A24-B65; | A24-B66; | A24-B67; |
| A24-B68; | A24-B69; | A24-B70; | A24-B71; | A24-B72; | A24-B73; |
| A24-B74; | A24-B75; | A24-B76; | A24-B77; | A24-B78; | A24-B79; |
| A24-B80; | A24-B81; | A24-B82; | A24-B83; | A24-B84; | A24-B85; |
| A24-B86; | A24-B87; | A24-B88; | A24-B89; | A24-B90; | A24-B91; |
| A24-B92; | A24-B93; | A24-B94; | A24-B95; | A24-B96; | A24-B97; |
| A24-B98; | A24-B99; | A24-B100; | A24-B101; | A24-B102; | A24-B103; |
| A24-B104; | A24-B105; | A24-B106; | A24-B107; | A24-B108; | A24-B109; |
| A24-B110; | A24-B111; | A24-B112; | A24-B113; | A24-B114; | A24-B115; |
| A24-B116; | A24-B117; | A24-B118; | A24-B119; | A24-B120; | A24-B121; |
| A24-B122; | A24-B123; | A24-B124; | A24-B125; | A24-B126; | A24-B127; |
| A24-B128; | A24-B129; | A24-B130; | A24-B131; | A24-B132; | A24-B133; |
| A24-B134; | A24-B135; | A24-B136; | A24-B137; | A24-B138; | A24-B139; |
| A24-B140; | A24-B141; | A24-B142; | A24-B143; | A24-B144; | A24-B145; |
| A24-B146; | A24-B147; | A24-B148; | A24-B149; | A24-B150; | A24-B151; |
| A24-B152; | A24-B153; | A24-B154; | A24-B155; | A24-B156; | A24-B157; |
| A24-B158; | A24-B159; | A24-B160; | A24-B161; | A24-B162; | A24-B163; |
| A24-B164; | A24-B165; | A24-B166; | A24-B167; | A24-B168; | A24-B169; |
| A25-B1; | A25-B2; | A25-B3; | A25-B4; | A25-B5; | A25-B6; |
| A25-B7; | A25-B8; | A25-B9; | A25-B10; | A25-B11; | A25-B12; |
| A25-B13; | A25-B14; | A25-B15; | A25-B16; | A25-B17; | A25-B18; |
| A25-B19; | A25-B20; | A25-B21; | A25-B22; | A25-B23; | A25-B24; |
| A25-B25; | A25-B26; | A25-B27; | A25-B28; | A25-B29; | A25-B30; |
| A25-B31; | A25-B32; | A25-B33; | A25-B34; | A25-B35; | A25-B36; |
| A25-B37; | A25-B38; | A25-B39; | A25-B40; | A25-B41; | A25-B42; |
| A25-B43; | A25-B44; | A25-B45; | A25-B46; | A25-B47; | A25-B48; |
| A25-B49; | A25-B50; | A25-B51; | A25-B52; | A25-B53; | A25-B54; |
| A25-B55; | A25-B56; | A25-B57; | A25-B58; | A25-B59; | A25-B60; |
| A25-B61; | A25-B62; | A25-B63; | A25-B64; | A25-B65; | A25-B66; |
| A25-B67; | A25-B68; | A25-B69; | A25-B70; | A25-B71; | A25-B72; |
| A25-B73; | A25-B74; | A25-B75; | A25-B76; | A25-B77; | A25-B78; |
| A25-B79; | A25-B80; | A25-B81; | A25-B82; | A25-B83; | A25-B84; |
| A25-B85; | A25-B86; | A25-B87; | A25-B88; | A25-B89; | A25-B90; |
| A25-B91; | A25-B92; | A25-B93; | A25-B94; | A25-B95; | A25-B96; |
| A25-B97; | A25-B98; | A25-B99; | A25-B100; | A25-B101; | A25-B102; |
| A25-B103; | A25-B104; | A25-B105; | A25-B106; | A25-B107; | A25-B108; |
| A25-B109; | A25-B110; | A25-B111; | A25-B112; | A25-B113; | A25-B114; |
| A25-B115; | A25-B116; | A25-B117; | A25-B118; | A25-B119; | A25-B120; |
| A25-B121; | A25-B122; | A25-B123; | A25-B124; | A25-B125; | A25-B126; |
| A25-B127; | A25-B128; | A25-B129; | A25-B130; | A25-B131; | A25-B132; |
| A25-B133; | A25-B134; | A25-B135; | A25-B136; | A25-B137; | A25-B138; |
| A25-B139; | A25-B140; | A25-B141; | A25-B142; | A25-B143; | A25-B144; |
| A25-B145; | A25-B146; | A25-B147; | A25-B148; | A25-B149; | A25-B150; |
| A25-B151; | A25-B152; | A25-B153; | A25-B154; | A25-B155; | A25-B156; |
| A25-B157; | A25-B158; | A25-B159; | A25-B160; | A25-B161; | A25-B162; |
| A25-B163; | A25-B164; | A25-B165; | A25-B166; | A25-B167; | A25-B168; |
| A25-B169; | A26-B1; | A26-B2; | A26-B3; | A26-B4; | A26-B5; |
| A26-B6; | A26-B7; | A26-B8; | A26-B9; | A26-B10; | A26-B11; |

-continued

| | | | | | |
|---|---|---|---|---|---|
| A26-B12; | A26-B13; | A26-B14; | A26-B15; | A26-B16; | A26-B17; |
| A26-B18; | A26-B19; | A26-B20; | A26-B21; | A26-B22; | A26-B23; |
| A26-B24; | A26-B25; | A26-B26; | A26-B27; | A26-B28; | A26-B29; |
| A26-B30; | A26-B31; | A26-B32; | A26-B33; | A26-B34; | A26-B35; |
| A26-B36; | A26-B37; | A26-B38; | A26-B39; | A26-B40; | A26-B41; |
| A26-B42; | A26-B43; | A26-B44; | A26-B45; | A26-B46; | A26-B47; |
| A26-B48; | A26-B49; | A26-B50; | A26-B51; | A26-B52; | A26-B53; |
| A26-B54; | A26-B55; | A26-B56; | A26-B57; | A26-B58; | A26-B59; |
| A26-B60; | A26-B61; | A26-B62; | A26-B63; | A26-B64; | A26-B65; |
| A26-B66; | A26-B67; | A26-B68; | A26-B69; | A26-B70; | A26-B71; |
| A26-B72; | A26-B73; | A26-B74; | A26-B75; | A26-B76; | A26-B77; |
| A26-B78; | A26-B79; | A26-B80; | A26-B81; | A26-B82; | A26-B83; |
| A26-B84; | A26-B85; | A26-B86; | A26-B87; | A26-B88; | A26-B89; |
| A26-B90; | A26-B91; | A26-B92; | A26-B93; | A26-B94; | A26-B95; |
| A26-B96; | A26-B97; | A26-B98; | A26-B99; | A26-B100; | A26-B101; |
| A26-B102; | A26-B103; | A26-B104; | A26-B105; | A26-B106; | A26-B107; |
| A26-B108; | A26-B109; | A26-B110; | A26-B111; | A26-B112; | A26-B113; |
| A26-B114; | A26-B115; | A26-B116; | A26-B117; | A26-B118; | A26-B119; |
| A26-B120; | A26-B121; | A26-B122; | A26-B123; | A26-B124; | A26-B125; |
| A26-B126; | A26-B127; | A26-B128; | A26-B129; | A26-B130; | A26-B131; |
| A26-B132; | A26-B133; | A26-B134; | A26-B135; | A26-B136; | A26-B137; |
| A26-B138; | A26-B139; | A26-B140; | A26-B141; | A26-B142; | A26-B143; |
| A26-B144; | A26-B145; | A26-B146; | A26-B147; | A26-B148; | A26-B149; |
| A26-B150; | A26-B151; | A26-B152; | A26-B153; | A26-B154; | A26-B155; |
| A26-B156; | A26-B157; | A26-B158; | A26-B159; | A26-B160; | A26-B161; |
| A26-B162; | A26-B163; | A26-B164; | A26-B165; | A26-B166; | A26-B167; |
| A26-B168; | A26-B169; | A27-B1; | A27-B2; | A27-B3; | A27-B4; |
| A27-B5; | A27-B6; | A27-B7; | A27-B8; | A27-B9; | A27-B10; |
| A27-B11; | A27-B12; | A27-B13; | A27-B14; | A27-B15; | A27-B16; |
| A27-B17; | A27-B18; | A27-B19; | A27-B20; | A27-B21; | A27-B22; |
| A27-B23; | A27-B24; | A27-B25; | A27-B26; | A27-B27; | A27-B28; |
| A27-B29; | A27-B30; | A27-B31; | A27-B32; | A27-B33; | A27-B34; |
| A27-B35; | A27-B36; | A27-B37; | A27-B38; | A27-B39; | A27-B40; |
| A27-B41; | A27-B42; | A27-B43; | A27-B44; | A27-B45; | A27-B46; |
| A27-B47; | A27-B48; | A27-B49; | A27-B50; | A27-B51; | A27-B52; |
| A27-B53; | A27-B54; | A27-B55; | A27-B56; | A27-B57; | A27-B58; |
| A27-B59; | A27-B60; | A27-B61; | A27-B62; | A27-B63; | A27-B64; |
| A27-B65; | A27-B66; | A27-B67; | A27-B68; | A27-B69; | A27-B70; |
| A27-B71; | A27-B72; | A27-B73; | A27-B74; | A27-B75; | A27-B76; |
| A27-B77; | A27-B78; | A27-B79; | A27-B80; | A27-B81; | A27-B82; |
| A27-B83; | A27-B84; | A27-B85; | A27-B86; | A27-B87; | A27-B88; |
| A27-B89; | A27-B90; | A27-B91; | A27-B92; | A27-B93; | A27-B94; |
| A27-B95; | A27-B96; | A27-B97; | A27-B98; | A27-B99; | A27-B100; |
| A27-B101; | A27-B102; | A27-B103; | A27-B104; | A27-B105; | A27-B106; |
| A27-B107; | A27-B108; | A27-B109; | A27-B110; | A27-B111; | A27-B112; |
| A27-B113; | A27-B114; | A27-B115; | A27-B116; | A27-B117; | A27-B118; |
| A27-B119; | A27-B120; | A27-B121; | A27-B122; | A27-B123; | A27-B124; |
| A27-B125; | A27-B126; | A27-B127; | A27-B128; | A27-B129; | A27-B130; |
| A27-B131; | A27-B132; | A27-B133; | A27-B134; | A27-B135; | A27-B136; |
| A27-B137; | A27-B138; | A27-B139; | A27-B140; | A27-B141; | A27-B142; |
| A27-B143; | A27-B144; | A27-B145; | A27-B146; | A27-B147; | A27-B148; |
| A27-B149; | A27-B150; | A27-B151; | A27-B152; | A27-B153; | A27-B154; |
| A27-B155; | A27-B156; | A27-B157; | A27-B158; | A27-B159; | A27-B160; |
| A27-B161; | A27-B162; | A27-B163; | A27-B164; | A27-B165; | A27-B166; |
| A27-B167; | A27-B168; | A27-B169; | A28-B1; | A28-B2; | A28-B3; |
| A28-B4; | A28-B5; | A28-B6; | A28-B7; | A28-B8; | A28-B9; |
| A28-B10; | A28-B11; | A28-B12; | A28-B13; | A28-B14; | A28-B15; |
| A28-B16; | A28-B17; | A28-B18; | A28-B19; | A28-B20; | A28-B21; |
| A28-B22; | A28-B23; | A28-B24; | A28-B25; | A28-B26; | A28-B27; |
| A28-B28; | A28-B29; | A28-B30; | A28-B31; | A28-B32; | A28-B33; |
| A28-B34; | A28-B35; | A28-B36; | A28-B37; | A28-B38; | A28-B39; |
| A28-B40; | A28-B41; | A28-B42; | A28-B43; | A28-B44; | A28-B45; |
| A28-B46; | A28-B47; | A28-B48; | A28-B49; | A28-B50; | A28-B51; |
| A28-B52; | A28-B53; | A28-B54; | A28-B55; | A28-B56; | A28-B57; |
| A28-B58; | A28-B59; | A28-B60; | A28-B61; | A28-B62; | A28-B63; |
| A28-B64; | A28-B65; | A28-B66; | A28-B67; | A28-B68; | A28-B69; |
| A28-B70; | A28-B71; | A28-B72; | A28-B73; | A28-B74; | A28-B75; |
| A28-B76; | A28-B77; | A28-B78; | A28-B79; | A28-B80; | A28-B81; |
| A28-B82; | A28-B83; | A28-B84; | A28-B85; | A28-B86; | A28-B87; |
| A28-B88; | A28-B89; | A28-B90; | A28-B91; | A28-B92; | A28-B93; |
| A28-B94; | A28-B95; | A28-B96; | A28-B97; | A28-B98; | A28-B99; |
| A28-B100; | A28-B101; | A28-B102; | A28-B103; | A28-B104; | A28-B105; |
| A28-B106; | A28-B107; | A28-B108; | A28-B109; | A28-B110; | A28-B111; |
| A28-B112; | A28-B113; | A28-B114; | A28-B115; | A28-B116; | A28-B117; |
| A28-B118; | A28-B119; | A28-B120; | A28-B121; | A28-B122; | A28-B123; |
| A28-B124; | A28-B125; | A28-B126; | A28-B127; | A28-B128; | A28-B129; |
| A28-B130; | A28-B131; | A28-B132; | A28-B133; | A28-B134; | A28-B135; |
| A28-B136; | A28-B137; | A28-B138; | A28-B139; | A28-B140; | A28-B141; |
| A28-B142; | A28-B143; | A28-B144; | A28-B145; | A28-B146; | A28-B147; |
| A28-B148; | A28-B149; | A28-B150; | A28-B151; | A28-B152; | A28-B153; |

-continued

A28-B154; A28-B155; A28-B156; A28-B157; A28-B158; A28-B159;
A28-B160; A28-B161; A28-B162; A28-B163; A28-B164; A28-B165;
A28-B166; A28-B167; A28-B168; A28-B169; A29-B1; A29-B2;
A29-B3; A29-B4; A29-B5; A29-B6; A29-B7; A29-B8;
A29-B9; A29-B10; A29-B11; A29-B12; A29-B13; A29-B14;
A29-B15; A29-B16; A29-B17; A29-B18; A29-B19; A29-B20;
A29-B21; A29-B22; A29-B23; A29-B24; A29-B25; A29-B26;
A29-B27; A29-B28; A29-B29; A29-B30; A29-B31; A29-B32;
A29-B33; A29-B34; A29-B35; A29-B36; A29-B37; A29-B38;
A29-B39; A29-B40; A29-B41; A29-B42; A29-B43; A29-B44;
A29-B45; A29-B46; A29-B47; A29-B48; A29-B49; A29-B50;
A29-B51; A29-B52; A29-B53; A29-B54; A29-B55; A29-B56;
A29-B57; A29-B58; A29-B59; A29-B60; A29-B61; A29-B62;
A29-B63; A29-B64; A29-B65; A29-B66; A29-B67; A29-B68;
A29-B69; A29-B70; A29-B71; A29-B72; A29-B73; A29-B74;
A29-B75; A29-B76; A29-B77; A29-B78; A29-B79; A29-B80;
A29-B81; A29-B82; A29-B83; A29-B84; A29-B85; A29-B86;
A29-B87; A29-B88; A29-B89; A29-B90; A29-B91; A29-B92;
A29-B93; A29-B94; A29-B95; A29-B96; A29-B97; A29-B98;
A29-B99; A29-B100; A29-B101; A29-B102; A29-B103; A29-B104;
A29-B105; A29-B106; A29-B107; A29-B108; A29-B109; A29-B110;
A29-B111; A29-B112; A29-B113; A29-B114; A29-B115; A29-B116;
A29-B117; A29-B118; A29-B119; A29-B120; A29-B121; A29-B122;
A29-B123; A29-B124; A29-B125; A29-B126; A29-B127; A29-B128;
A29-B129; A29-B130; A29-B131; A29-B132; A29-B133; A29-B134;
A29-B135; A29-B136; A29-B137; A29-B138; A29-B139; A29-B140;
A29-B141; A29-B142; A29-B143; A29-B144; A29-B145; A29-B146;
A29-B147; A29-B148; A29-B149; A29-B150; A29-B151; A29-B152;
A29-B153; A29-B154; A29-B155; A29-B156; A29-B157; A29-B158;
A29-B159; A29-B160; A29-B161; A29-B162; A29-B163; A29-B164;
A29-B165; A29-B166; A29-B167; A29-B168; A29-B169; A30-B1;
A30-B2; A30-B3; A30-B4; A30-B5; A30-B6; A30-B7;
A30-B8; A30-B9; A30-B10; A30-B11; A30-B12; A30-B13;
A30-B14; A30-B15; A30-B16; A30-B17; A30-B18; A30-B19;
A30-B20; A30-B21; A30-B22; A30-B23; A30-B24; A30-B25;
A30-B26; A30-B27; A30-B28; A30-B29; A30-B30; A30-B31;
A30-B32; A30-B33; A30-B34; A30-B35; A30-B36; A30-B37;
A30-B38; A30-B39; A30-B40; A30-B41; A30-B42; A30-B43;
A30-B44; A30-B45; A30-B46; A30-B47; A30-B48; A30-B49;
A30-B50; A30-B51; A30-B52; A30-B53; A30-B54; A30-B55;
A30-B56; A30-B57; A30-B58; A30-B59; A30-B60; A30-B61;
A30-B62; A30-B63; A30-B64; A30-B65; A30-B66; A30-B67;
A30-B68; A30-B69; A30-B70; A30-B71; A30-B72; A30-B73;
A30-B74; A30-B75; A30-B76; A30-B77; A30-B78; A30-B79;
A30-B80; A30-B81; A30-B82; A30-B83; A30-B84; A30-B85;
A30-B86; A30-B87; A30-B88; A30-B89; A30-B90; A30-B91;
A30-B92; A30-B93; A30-B94; A30-B95; A30-B96; A30-B97;
A30-B98; A30-B99; A30-B100; A30-B101; A30-B102; A30-B103;
A30-B104; A30-B105; A30-B106; A30-B107; A30-B108; A30-B109;
A30-B110; A30-B111; A30-B112; A30-B113; A30-B114; A30-B115;
A30-B116; A30-B117; A30-B118; A30-B119; A30-B120; A30-B121;
A30-B122; A30-B123; A30-B124; A30-B125; A30-B126; A30-B127;
A30-B128; A30-B129; A30-B130; A30-B131; A30-B132; A30-B133;
A30-B134; A30-B135; A30-B136; A30-B137; A30-B138; A30-B139;
A30-B140; A30-B141; A30-B142; A30-B143; A30-B144; A30-B145;
A30-B146; A30-B147; A30-B148; A30-B149; A30-B150; A30-B151;
A30-B152; A30-B153; A30-B154; A30-B155; A30-B156; A30-B157;
A30-B158; A30-B159; A30-B160; A30-B161; A30-B162; A30-B163;
A30-B164; A30-B165; A30-B166; A30-B167; A30-B168; A30-B169;
A31-B1; A31-B2; A31-B3; A31-B4; A31-B5; A31-B6;
A31-B7; A31-B8; A31-B9; A31-B10; A31-B11; A31-B12;
A31-B13; A31-B14; A31-B15; A31-B16; A31-B17; A31-B18;
A31-B19; A31-B20; A31-B21; A31-B22; A31-B23; A31-B24;
A31-B25; A31-B26; A31-B27; A31-B28; A31-B29; A31-B30;
A31-B31; A31-B32; A31-B33; A31-B34; A31-B35; A31-B36;
A31-B37; A31-B38; A31-B39; A31-B40; A31-B41; A31-B42;
A31-B43; A31-B44; A31-B45; A31-B46; A31-B47; A31-B48;
A31-B49; A31-B50; A31-B51; A31-B52; A31-B53; A31-B54;
A31-B55; A31-B56; A31-B57; A31-B58; A31-B59; A31-B60;
A31-B61; A31-B62; A31-B63; A31-B64; A31-B65; A31-B66;
A31-B67; A31-B68; A31-B69; A31-B70; A31-B71; A31-B72;
A31-B73; A31-B74; A31-B75; A31-B76; A31-B77; A31-B78;
A31-B79; A31-B80; A31-B81; A31-B82; A31-B83; A31-B84;
A31-B85; A31-B86; A31-B87; A31-B88; A31-B89; A31-B90;
A31-B91; A31-B92; A31-B93; A31-B94; A31-B95; A31-B96;
A31-B97; A31-B98; A31-B99; A31-B100; A31-B101; A31-B102;
A31-B103; A31-B104; A31-B105; A31-B106; A31-B107; A31-B108;
A31-B109; A31-B110; A31-B111; A31-B112; A31-B113; A31-B114;
A31-B115; A31-B116; A31-B117; A31-B118; A31-B119; A31-B120;
A31-B121; A31-B122; A31-B123; A31-B124; A31-B125; A31-B126;

-continued

| | | | | | |
|---|---|---|---|---|---|
| A31-B127; | A31-B128; | A31-B129; | A31-B130; | A31-B131; | A31-B132; |
| A31-B133; | A31-B134; | A31-B135; | A31-B136; | A31-B137; | A31-B138; |
| A31-B139; | A31-B140; | A31-B141; | A31-B142; | A31-B143; | A31-B144; |
| A31-B145; | A31-B146; | A31-B147; | A31-B148; | A31-B149; | A31-B150; |
| A31-B151; | A31-B152; | A31-B153; | A31-B154; | A31-B155; | A31-B156; |
| A31-B157; | A31-B158; | A31-B159; | A31-B160; | A31-B161; | A31-B162; |
| A31-B163; | A31-B164; | A31-B165; | A31-B166; | A31-B167; | A31-B168; |
| A31-B169; | A32-B1; | A32-B2; | A32-B3; | A32-B4; | A32-B5; |
| A32-B6; | A32-B7; | A32-B8; | A32-B9; | A32-B10; | A32-B11; |
| A32-B12; | A32-B13; | A32-B14; | A32-B15; | A32-B16; | A32-B17; |
| A32-B18; | A32-B19; | A32-B20; | A32-B21; | A32-B22; | A32-B23; |
| A32-B24; | A32-B25; | A32-B26; | A32-B27; | A32-B28; | A32-B29; |
| A32-B30; | A32-B31; | A32-B32; | A32-B33; | A32-B34; | A32-B35; |
| A32-B36; | A32-B37; | A32-B38; | A32-B39; | A32-B40; | A32-B41; |
| A32-B42; | A32-B43; | A32-B44; | A32-B45; | A32-B46; | A32-B47; |
| A32-B48; | A32-B49; | A32-B50; | A32-B51; | A32-B52; | A32-B53; |
| A32-B54; | A32-B55; | A32-B56; | A32-B57; | A32-B58; | A32-B59; |
| A32-B60; | A32-B61; | A32-B62; | A32-B63; | A32-B64; | A32-B65; |
| A32-B66; | A32-B67; | A32-B68; | A32-B69; | A32-B70; | A32-B71; |
| A32-B72; | A32-B73; | A32-B74; | A32-B75; | A32-B76; | A32-B77; |
| A32-B78; | A32-B79; | A32-B80; | A32-B81; | A32-B82; | A32-B83; |
| A32-B84; | A32-B85; | A32-B86; | A32-B87; | A32-B88; | A32-B89; |
| A32-B90; | A32-B91; | A32-B92; | A32-B93; | A32-B94; | A32-B95; |
| A32-B96; | A32-B97; | A32-B98; | A32-B99; | A32-B100; | A32-B101; |
| A32-B102; | A32-B103; | A32-B104; | A32-B105; | A32-B106; | A32-B107; |
| A32-B108; | A32-B109; | A32-B110; | A32-B111; | A32-B112; | A32-B113; |
| A32-B114; | A32-B115; | A32-B116; | A32-B117; | A32-B118; | A32-B119; |
| A32-B120; | A32-B121; | A32-B122; | A32-B123; | A32-B124; | A32-B125; |
| A32-B126; | A32-B127; | A32-B128; | A32-B129; | A32-B130; | A32-B131; |
| A32-B132; | A32-B133; | A32-B134; | A32-B135; | A32-B136; | A32-B137; |
| A32-B138; | A32-B139; | A32-B140; | A32-B141; | A32-B142; | A32-B143; |
| A32-B144; | A32-B145; | A32-B146; | A32-B147; | A32-B148; | A32-B149; |
| A32-B150; | A32-B151; | A32-B152; | A32-B153; | A32-B154; | A32-B155; |
| A32-B156; | A32-B157; | A32-B158; | A32-B159; | A32-B160; | A32-B161; |
| A32-B162; | A32-B163; | A32-B164; | A32-B165; | A32-B166; | A32-B167; |
| A32-B168; | A32-B169; | A33-B1; | A33-B2; | A33-B3; | A33-B4; |
| A33-B5; | A33-B6; | A33-B7; | A33-B8; | A33-B9; | A33-B10; |
| A33-B11; | A33-B12; | A33-B13; | A33-B14; | A33-B15; | A33-B16; |
| A33-B17; | A33-B18; | A33-B19; | A33-B20; | A33-B21; | A33-B22; |
| A33-B23; | A33-B24; | A33-B25; | A33-B26; | A33-B27; | A33-B28; |
| A33-B29; | A33-B30; | A33-B31; | A33-B32; | A33-B33; | A33-B34; |
| A33-B35; | A33-B36; | A33-B37; | A33-B38; | A33-B39; | A33-B40; |
| A33-B41; | A33-B42; | A33-B43; | A33-B44; | A33-B45; | A33-B46; |
| A33-B47; | A33-B48; | A33-B49; | A33-B50; | A33-B51; | A33-B52; |
| A33-B53; | A33-B54; | A33-B55; | A33-B56; | A33-B57; | A33-B58; |
| A33-B59; | A33-B60; | A33-B61; | A33-B62; | A33-B63; | A33-B64; |
| A33-B65; | A33-B66; | A33-B67; | A33-B68; | A33-B69; | A33-B70; |
| A33-B71; | A33-B72; | A33-B73; | A33-B74; | A33-B75; | A33-B76; |
| A33-B77; | A33-B78; | A33-B79; | A33-B80; | A33-B81; | A33-B82; |
| A33-B83; | A33-B84; | A33-B85; | A33-B86; | A33-B87; | A33-B88; |
| A33-B89; | A33-B90; | A33-B91; | A33-B92; | A33-B93; | A33-B94; |
| A33-B95; | A33-B96; | A33-B97; | A33-B98; | A33-B99; | A33-B100; |
| A33-B101; | A33-B102; | A33-B103; | A33-B104; | A33-B105; | A33-B106; |
| A33-B107; | A33-B108; | A33-B109; | A33-B110; | A33-B111; | A33-B112; |
| A33-B113; | A33-B114; | A33-B115; | A33-B116; | A33-B117; | A33-B118; |
| A33-B119; | A33-B120; | A33-B121; | A33-B122; | A33-B123; | A33-B124; |
| A33-B125; | A33-B126; | A33-B127; | A33-B128; | A33-B129; | A33-B130; |
| A33-B131; | A33-B132; | A33-B133; | A33-B134; | A33-B135; | A33-B136; |
| A33-B137; | A33-B138; | A33-B139; | A33-B140; | A33-B141; | A33-B142; |
| A33-B143; | A33-B144; | A33-B145; | A33-B146; | A33-B147; | A33-B148; |
| A33-B149; | A33-B150; | A33-B151; | A33-B152; | A33-B153; | A33-B154; |
| A33-B155; | A33-B156; | A33-B157; | A33-B158; | A33-B159; | A33-B160; |
| A33-B161; | A33-B162; | A33-B163; | A33-B164; | A33-B165; | A33-B166; |
| A33-B167; | A33-B168; | A33-B169; | A34-B1; | A34-B2; | A34-B3; |
| A34-B4; | A34-B5; | A34-B6; | A34-B7; | A34-B8; | A34-B9; |
| A34-B10; | A34-B11; | A34-B12; | A34-B13; | A34-B14; | A34-B15; |
| A34-B16; | A34-B17; | A34-B18; | A34-B19; | A34-B20; | A34-B21; |
| A34-B22; | A34-B23; | A34-B24; | A34-B25; | A34-B26; | A34-B27; |
| A34-B28; | A34-B29; | A34-B30; | A34-B31; | A34-B32; | A34-B33; |
| A34-B34; | A34-B35; | A34-B36; | A34-B37; | A34-B38; | A34-B39; |
| A34-B40; | A34-B41; | A34-B42; | A34-B43; | A34-B44; | A34-B45; |
| A34-B46; | A34-B47; | A34-B48; | A34-B49; | A34-B50; | A34-B51; |
| A34-B52; | A34-B53; | A34-B54; | A34-B55; | A34-B56; | A34-B57; |
| A34-B58; | A34-B59; | A34-B60; | A34-B61; | A34-B62; | A34-B63; |
| A34-B64; | A34-B65; | A34-B66; | A34-B67; | A34-B68; | A34-B69; |
| A34-B70; | A34-B71; | A34-B72; | A34-B73; | A34-B74; | A34-B75; |
| A34-B76; | A34-B77; | A34-B78; | A34-B79; | A34-B80; | A34-B81; |
| A34-B82; | A34-B83; | A34-B84; | A34-B85; | A34-B86; | A34-B87; |
| A34-B88; | A34-B89; | A34-B90; | A34-B91; | A34-B92; | A34-B93; |
| A34-B94; | A34-B95; | A34-B96; | A34-B97; | A34-B98; | A34-B99; |

| | | | | | |
|---|---|---|---|---|---|
| A34-B100; | A34-B101; | A34-B102; | A34-B103; | A34-B104; | A34-B105; |
| A34-B106; | A34-B107; | A34-B108; | A34-B109; | A34-B110; | A34-B111; |
| A34-B112; | A34-B113; | A34-B114; | A34-B115; | A34-B116; | A34-B117; |
| A34-B118; | A34-B119; | A34-B120; | A34-B121; | A34-B122; | A34-B123; |
| A34-B124; | A34-B125; | A34-B126; | A34-B127; | A34-B128; | A34-B129; |
| A34-B130; | A34-B131; | A34-B132; | A34-B133; | A34-B134; | A34-B135; |
| A34-B136; | A34-B137; | A34-B138; | A34-B139; | A34-B140; | A34-B141; |
| A34-B142; | A34-B143; | A34-B144; | A34-B145; | A34-B146; | A34-B147; |
| A34-B148; | A34-B149; | A34-B150; | A34-B151; | A34-B152; | A34-B153; |
| A34-B154; | A34-B155; | A34-B156; | A34-B157; | A34-B158; | A34-B159; |
| A34-B160; | A34-B161; | A34-B162; | A34-B163; | A34-B164; | A34-B165; |
| A34-B166; | A34-B167; | A34-B168; | A34-B169; | A35-B1; | A35-B2; |
| A35-B3; | A35-B4; | A35-B5; | A35-B6; | A35-B7; | A35-B8; |
| A35-B9; | A35-B10; | A35-B11; | A35-B12; | A35-B13; | A35-B14; |
| A35-B15; | A35-B16; | A35-B17; | A35-B18; | A35-B19; | A35-B20; |
| A35-B21; | A35-B22; | A35-B23; | A35-B24; | A35-B25; | A35-B26; |
| A35-B27; | A35-B28; | A35-B29; | A35-B30; | A35-B31; | A35-B32; |
| A35-B33; | A35-B34; | A35-B35; | A35-B36; | A35-B37; | A35-B38; |
| A35-B39; | A35-B40; | A35-B41; | A35-B42; | A35-B43; | A35-B44; |
| A35-B45; | A35-B46; | A35-B47; | A35-B48; | A35-B49; | A35-B50; |
| A35-B51; | A35-B52; | A35-B53; | A35-B54; | A35-B55; | A35-B56; |
| A35-B57; | A35-B58; | A35-B59; | A35-B60; | A35-B61; | A35-B62; |
| A35-B63; | A35-B64; | A35-B65; | A35-B66; | A35-B67; | A35-B68; |
| A35-B69; | A35-B70; | A35-B71; | A35-B72; | A35-B73; | A35-B74; |
| A35-B75; | A35-B76; | A35-B77; | A35-B78; | A35-B79; | A35-B80; |
| A35-B81; | A35-B82; | A35-B83; | A35-B84; | A35-B85; | A35-B86; |
| A35-B87; | A35-B88; | A35-B89; | A35-B90; | A35-B91; | A35-B92; |
| A35-B93; | A35-B94; | A35-B95; | A35-B96; | A35-B97; | A35-B98; |
| A35-B99; | A35-B100; | A35-B101; | A35-B102; | A35-B103; | A35-B104; |
| A35-B105; | A35-B106; | A35-B107; | A35-B108; | A35-B109; | A35-B110; |
| A35-B111; | A35-B112; | A35-B113; | A35-B114; | A35-B115; | A35-B116; |
| A35-B117; | A35-B118; | A35-B119; | A35-B120; | A35-B121; | A35-B122; |
| A35-B123; | A35-B124; | A35-B125; | A35-B126; | A35-B127; | A35-B128; |
| A35-B129; | A35-B130; | A35-B131; | A35-B132; | A35-B133; | A35-B134; |
| A35-B135; | A35-B136; | A35-B137; | A35-B138; | A35-B139; | A35-B140; |
| A35-B141; | A35-B142; | A35-B143; | A35-B144; | A35-B145; | A35-B146; |
| A35-B147; | A35-B148; | A35-B149; | A35-B150; | A35-B151; | A35-B152; |
| A35-B153; | A35-B154; | A35-B155; | A35-B156; | A35-B157; | A35-B158; |
| A35-B159; | A35-B160; | A35-B161; | A35-B162; | A35-B163; | A35-B164; |
| A35-B165; | A35-B166; | A35-B167; | A35-B168; | A35-B169; | A36-B1; |
| A36-B2; | A36-B3; | A36-B4; | A36-B5; | A36-B6; | A36-B7; |
| A36-B8; | A36-B9; | A36-B10; | A36-B11; | A36-B12; | A36-B13; |
| A36-B14; | A36-B15; | A36-B16; | A36-B17; | A36-B18; | A36-B19; |
| A36-B20; | A36-B21; | A36-B22; | A36-B23; | A36-B24; | A36-B25; |
| A36-B26; | A36-B27; | A36-B28; | A36-B29; | A36-B30; | A36-B31; |
| A36-B32; | A36-B33; | A36-B34; | A36-B35; | A36-B36; | A36-B37; |
| A36-B38; | A36-B39; | A36-B40; | A36-B41; | A36-B42; | A36-B43; |
| A36-B44; | A36-B45; | A36-B46; | A36-B47; | A36-B48; | A36-B49; |
| A36-B50; | A36-B51; | A36-B52; | A36-B53; | A36-B54; | A36-B55; |
| A36-B56; | A36-B57; | A36-B58; | A36-B59; | A36-B60; | A36-B61; |
| A36-B62; | A36-B63; | A36-B64; | A36-B65; | A36-B66; | A36-B67; |
| A36-B68; | A36-B69; | A36-B70; | A36-B71; | A36-B72; | A36-B73; |
| A36-B74; | A36-B75; | A36-B76; | A36-B77; | A36-B78; | A36-B79; |
| A36-B80; | A36-B81; | A36-B82; | A36-B83; | A36-B84; | A36-B85; |
| A36-B86; | A36-B87; | A36-B88; | A36-B89; | A36-B90; | A36-B91; |
| A36-B92; | A36-B93; | A36-B94; | A36-B95; | A36-B96; | A36-B97; |
| A36-B98; | A36-B99; | A36-B100; | A36-B101; | A36-B102; | A36-B103; |
| A36-B104; | A36-B105; | A36-B106; | A36-B107; | A36-B108; | A36-B109; |
| A36-B110; | A36-B111; | A36-B112; | A36-B113; | A36-B114; | A36-B115; |
| A36-B116; | A36-B117; | A36-B118; | A36-B119; | A36-B120; | A36-B121; |
| A36-B122; | A36-B123; | A36-B124; | A36-B125; | A36-B126; | A36-B127; |
| A36-B128; | A36-B129; | A36-B130; | A36-B131; | A36-B132; | A36-B133; |
| A36-B134; | A36-B135; | A36-B136; | A36-B137; | A36-B138; | A36-B139; |
| A36-B140; | A36-B141; | A36-B142; | A36-B143; | A36-B144; | A36-B145; |
| A36-B146; | A36-B147; | A36-B148; | A36-B149; | A36-B150; | A36-B151; |
| A36-B152; | A36-B153; | A36-B154; | A36-B155; | A36-B156; | A36-B157; |
| A36-B158; | A36-B159; | A36-B160; | A36-B161; | A36-B162; | A36-B163; |
| A36-B164; | A36-B165; | A36-B166; | A36-B167; | A36-B168; | A36-B169; |
| A37-B1; | A37-B2; | A37-B3; | A37-B4; | A37-B5; | A37-B6; |
| A37-B7; | A37-B8; | A37-B9; | A37-B10; | A37-B11; | A37-B12; |
| A37-B13; | A37-B14; | A37-B15; | A37-B16; | A37-B17; | A37-B18; |
| A37-B19; | A37-B20; | A37-B21; | A37-B22; | A37-B23; | A37-B24; |
| A37-B25; | A37-B26; | A37-B27; | A37-B28; | A37-B29; | A37-B30; |
| A37-B31; | A37-B32; | A37-B33; | A37-B34; | A37-B35; | A37-B36; |
| A37-B37; | A37-B38; | A37-B39; | A37-B40; | A37-B41; | A37-B42; |
| A37-B43; | A37-B44; | A37-B45; | A37-B46; | A37-B47; | A37-B48; |
| A37-B49; | A37-B50; | A37-B51; | A37-B52; | A37-B53; | A37-B54; |
| A37-B55; | A37-B56; | A37-B57; | A37-B58; | A37-B59; | A37-B60; |
| A37-B61; | A37-B62; | A37-B63; | A37-B64; | A37-B65; | A37-B66; |
| A37-B67; | A37-B68; | A37-B69; | A37-B70; | A37-B71; | A37-B72; |

| | | | | | |
|---|---|---|---|---|---|
| A37-B73; | A37-B74; | A37-B75; | A37-B76; | A37-B77; | A37-B78; |
| A37-B79; | A37-B80; | A37-B81; | A37-B82; | A37-B83; | A37-B84; |
| A37-B85; | A37-B86; | A37-B87; | A37-B88; | A37-B89; | A37-B90; |
| A37-B91; | A37-B92; | A37-B93; | A37-B94; | A37-B95; | A37-B96; |
| A37-B97; | A37-B98; | A37-B99; | A37-B100; | A37-B101; | A37-B102; |
| A37-B103; | A37-B104; | A37-B105; | A37-B106; | A37-B107; | A37-B108; |
| A37-B109; | A37-B110; | A37-B111; | A37-B112; | A37-B113; | A37-B114; |
| A37-B115; | A37-B116; | A37-B117; | A37-B118; | A37-B119; | A37-B120; |
| A37-B121; | A37-B122; | A37-B123; | A37-B124; | A37-B125; | A37-B126; |
| A37-B127; | A37-B128; | A37-B129; | A37-B130; | A37-B131; | A37-B132; |
| A37-B133; | A37-B134; | A37-B135; | A37-B136; | A37-B137; | A37-B138; |
| A37-B139; | A37-B140; | A37-B141; | A37-B142; | A37-B143; | A37-B144; |
| A37-B145; | A37-B146; | A37-B147; | A37-B148; | A37-B149; | A37-B150; |
| A37-B151; | A37-B152; | A37-B153; | A37-B154; | A37-B155; | A37-B156; |
| A37-B157; | A37-B158; | A37-B159; | A37-B160; | A37-B161; | A37-B162; |
| A37-B163; | A37-B164; | A37-B165; | A37-B166; | A37-B167; | A37-B168; |
| A37-B169; | A38-B1; | A38-B2; | A38-B3; | A38-B4; | A38-B5; |
| A38-B6; | A38-B7; | A38-B8; | A38-B9; | A38-B10; | A38-B11; |
| A38-B12; | A38-B13; | A38-B14; | A38-B15; | A38-B16; | A38-B17; |
| A38-B18; | A38-B19; | A38-B20; | A38-B21; | A38-B22; | A38-B23; |
| A38-B24; | A38-B25; | A38-B26; | A38-B27; | A38-B28; | A38-B29; |
| A38-B30; | A38-B31; | A38-B32; | A38-B33; | A38-B34; | A38-B35; |
| A38-B36; | A38-B37; | A38-B38; | A38-B39; | A38-B40; | A38-B41; |
| A38-B42; | A38-B43; | A38-B44; | A38-B45; | A38-B46; | A38-B47; |
| A38-B48; | A38-B49; | A38-B50; | A38-B51; | A38-B52; | A38-B53; |
| A38-B54; | A38-B55; | A38-B56; | A38-B57; | A38-B58; | A38-B59; |
| A38-B60; | A38-B61; | A38-B62; | A38-B63; | A38-B64; | A38-B65; |
| A38-B66; | A38-B67; | A38-B68; | A38-B69; | A38-B70; | A38-B71; |
| A38-B72; | A38-B73; | A38-B74; | A38-B75; | A38-B76; | A38-B77; |
| A38-B78; | A38-B79; | A38-B80; | A38-B81; | A38-B82; | A38-B83; |
| A38-B84; | A38-B85; | A38-B86; | A38-B87; | A38-B88; | A38-B89; |
| A38-B90; | A38-B91; | A38-B92; | A38-B93; | A38-B94; | A38-B95; |
| A38-B96; | A38-B97; | A38-B98; | A38-B99; | A38-B100; | A38-B101; |
| A38-B102; | A38-B103; | A38-B104; | A38-B105; | A38-B106; | A38-B107; |
| A38-B108; | A38-B109; | A38-B110; | A38-B111; | A38-B112; | A38-B113; |
| A38-B114; | A38-B115; | A38-B116; | A38-B117; | A38-B118; | A38-B119; |
| A38-B120; | A38-B121; | A38-B122; | A38-B123; | A38-B124; | A38-B125; |
| A38-B126; | A38-B127; | A38-B128; | A38-B129; | A38-B130; | A38-B131; |
| A38-B132; | A38-B133; | A38-B134; | A38-B135; | A38-B136; | A38-B137; |
| A38-B138; | A38-B139; | A38-B140; | A38-B141; | A38-B142; | A38-B143; |
| A38-B144; | A38-B145; | A38-B146; | A38-B147; | A38-B148; | A38-B149; |
| A38-B150; | A38-B151; | A38-B152; | A38-B153; | A38-B154; | A38-B155; |
| A38-B156; | A38-B157; | A38-B158; | A38-B159; | A38-B160; | A38-B161; |
| A38-B162; | A38-B163; | A38-B164; | A38-B165; | A38-B166; | A38-B167; |
| A38-B168; | A38-B169; | A39-B1; | A39-B2; | A39-B3; | A39-B4; |
| A39-B5; | A39-B6; | A39-B7; | A39-B8; | A39-B9; | A39-B10; |
| A39-B11; | A39-B12; | A39-B13; | A39-B14; | A39-B15; | A39-B16; |
| A39-B17; | A39-B18; | A39-B19; | A39-B20; | A39-B21; | A39-B22; |
| A39-B23; | A39-B24; | A39-B25; | A39-B26; | A39-B27; | A39-B28; |
| A39-B29; | A39-B30; | A39-B31; | A39-B32; | A39-B33; | A39-B34; |
| A39-B35; | A39-B36; | A39-B37; | A39-B38; | A39-B39; | A39-B40; |
| A39-B41; | A39-B42; | A39-B43; | A39-B44; | A39-B45; | A39-B46; |
| A39-B47; | A39-B48; | A39-B49; | A39-B50; | A39-B51; | A39-B52; |
| A39-B53; | A39-B54; | A39-B55; | A39-B56; | A39-B57; | A39-B58; |
| A39-B59; | A39-B60; | A39-B61; | A39-B62; | A39-B63; | A39-B64; |
| A39-B65; | A39-B66; | A39-B67; | A39-B68; | A39-B69; | A39-B70; |
| A39-B71; | A39-B72; | A39-B73; | A39-B74; | A39-B75; | A39-B76; |
| A39-B77; | A39-B78; | A39-B79; | A39-B80; | A39-B81; | A39-B82; |
| A39-B83; | A39-B84; | A39-B85; | A39-B86; | A39-B87; | A39-B88; |
| A39-B89; | A39-B90; | A39-B91; | A39-B92; | A39-B93; | A39-B94; |
| A39-B95; | A39-B96; | A39-B97; | A39-B98; | A39-B99; | A39-B100; |
| A39-B101; | A39-B102; | A39-B103; | A39-B104; | A39-B105; | A39-B106; |
| A39-B107; | A39-B108; | A39-B109; | A39-B110; | A39-B111; | A39-B112; |
| A39-B113; | A39-B114; | A39-B115; | A39-B116; | A39-B117; | A39-B118; |
| A39-B119; | A39-B120; | A39-B121; | A39-B122; | A39-B123; | A39-B124; |
| A39-B125; | A39-B126; | A39-B127; | A39-B128; | A39-B129; | A39-B130; |
| A39-B131; | A39-B132; | A39-B133; | A39-B134; | A39-B135; | A39-B136; |
| A39-B137; | A39-B138; | A39-B139; | A39-B140; | A39-B141; | A39-B142; |
| A39-B143; | A39-B144; | A39-B145; | A39-B146; | A39-B147; | A39-B148; |
| A39-B149; | A39-B150; | A39-B151; | A39-B152; | A39-B153; | A39-B154; |
| A39-B155; | A39-B156; | A39-B157; | A39-B158; | A39-B159; | A39-B160; |
| A39-B161; | A39-B162; | A39-B163; | A39-B164; | A39-B165; | A39-B166; |
| A39-B167; | A39-B168; | A39-B169; | A40-B1; | A40-B2; | A40-B3; |
| A40-B4; | A40-B5; | A40-B6; | A40-B7; | A40-B8; | A40-B9; |
| A40-B10; | A40-B11; | A40-B12; | A40-B13; | A40-B14; | A40-B15; |
| A40-B16; | A40-B17; | A40-B18; | A40-B19; | A40-B20; | A40-B21; |
| A40-B22; | A40-B23; | A40-B24; | A40-B25; | A40-B26; | A40-B27; |
| A40-B28; | A40-B29; | A40-B30; | A40-B31; | A40-B32; | A40-B33; |
| A40-B34; | A40-B35; | A40-B36; | A40-B37; | A40-B38; | A40-B39; |
| A40-B40; | A40-B41; | A40-B42; | A40-B43; | A40-B44; | A40-B45; |

-continued

| | | | | | |
|---|---|---|---|---|---|
| A40-B46; | A40-B47; | A40-B48; | A40-B49; | A40-B50; | A40-B51; |
| A40-B52; | A40-B53; | A40-B54; | A40-B55; | A40-B56; | A40-B57; |
| A40-B58; | A40-B59; | A40-B60; | A40-B61; | A40-B62; | A40-B63; |
| A40-B64; | A40-B65; | A40-B66; | A40-B67; | A40-B68; | A40-B69; |
| A40-B70; | A40-B71; | A40-B72; | A40-B73; | A40-B74; | A40-B75; |
| A40-B76; | A40-B77; | A40-B78; | A40-B79; | A40-B80; | A40-B81; |
| A40-B82; | A40-B83; | A40-B84; | A40-B85; | A40-B86; | A40-B87; |
| A40-B88; | A40-B89; | A40-B90; | A40-B91; | A40-B92; | A40-B93; |
| A40-B94; | A40-B95; | A40-B96; | A40-B97; | A40-B98; | A40-B99; |
| A40-B100; | A40-B101; | A40-B102; | A40-B103; | A40-B104; | A40-B105; |
| A40-B106; | A40-B107; | A40-B108; | A40-B109; | A40-B110; | A40-B111; |
| A40-B112; | A40-B113; | A40-B114; | A40-B115; | A40-B116; | A40-B117; |
| A40-B118; | A40-B119; | A40-B120; | A40-B121; | A40-B122; | A40-B123; |
| A40-B124; | A40-B125; | A40-B126; | A40-B127; | A40-B128; | A40-B129; |
| A40-B130; | A40-B131; | A40-B132; | A40-B133; | A40-B134; | A40-B135; |
| A40-B136; | A40-B137; | A40-B138; | A40-B139; | A40-B140; | A40-B141; |
| A40-B142; | A40-B143; | A40-B144; | A40-B145; | A40-B146; | A40-B147; |
| A40-B148; | A40-B149; | A40-B150; | A40-B151; | A40-B152; | A40-B153; |
| A40-B154; | A40-B155; | A40-B156; | A40-B157; | A40-B158; | A40-B159; |
| A40-B160; | A40-B161; | A40-B162; | A40-B163; | A40-B164; | A40-B165; |
| A40-B166; | A40-B167; | A40-B168; | A40-B169; | A41-B1; | A41-B2; |
| A41-B3; | A41-B4; | A41-B5; | A41-B6; | A41-B7; | A41-B8; |
| A41-B9; | A41-B10; | A41-B11; | A41-B12; | A41-B13; | A41-B14; |
| A41-B15; | A41-B16; | A41-B17; | A41-B18; | A41-B19; | A41-B20; |
| A41-B21; | A41-B22; | A41-B23; | A41-B24; | A41-B25; | A41-B26; |
| A41-B27; | A41-B28; | A41-B29; | A41-B30; | A41-B31; | A41-B32; |
| A41-B33; | A41-B34; | A41-B35; | A41-B36; | A41-B37; | A41-B38; |
| A41-B39; | A41-B40; | A41-B41; | A41-B42; | A41-B43; | A41-B44; |
| A41-B45; | A41-B46; | A41-B47; | A41-B48; | A41-B49; | A41-B50; |
| A41-B51; | A41-B52; | A41-B53; | A41-B54; | A41-B55; | A41-B56; |
| A41-B57; | A41-B58; | A41-B59; | A41-B60; | A41-B61; | A41-B62; |
| A41-B63; | A41-B64; | A41-B65; | A41-B66; | A41-B67; | A41-B68; |
| A41-B69; | A41-B70; | A41-B71; | A41-B72; | A41-B73; | A41-B74; |
| A41-B75; | A41-B76; | A41-B77; | A41-B78; | A41-B79; | A41-B80; |
| A41-B81; | A41-B82; | A41-B83; | A41-B84; | A41-B85; | A41-B86; |
| A41-B87; | A41-B88; | A41-B89; | A41-B90; | A41-B91; | A41-B92; |
| A41-B93; | A41-B94; | A41-B95; | A41-B96; | A41-B97; | A41-B98; |
| A41-B99; | A41-B100; | A41-B101; | A41-B102; | A41-B103; | A41-B104; |
| A41-B105; | A41-B106; | A41-B107; | A41-B108; | A41-B109; | A41-B110; |
| A41-B111; | A41-B112; | A41-B113; | A41-B114; | A41-B115; | A41-B116; |
| A41-B117; | A41-B118; | A41-B119; | A41-B120; | A41-B121; | A41-B122; |
| A41-B123; | A41-B124; | A41-B125; | A41-B126; | A41-B127; | A41-B128; |
| A41-B129; | A41-B130; | A41-B131; | A41-B132; | A41-B133; | A41-B134; |
| A41-B135; | A41-B136; | A41-B137; | A41-B138; | A41-B139; | A41-B140; |
| A41-B141; | A41-B142; | A41-B143; | A41-B144; | A41-B145; | A41-B146; |
| A41-B147; | A41-B148; | A41-B149; | A41-B150; | A41-B151; | A41-B152; |
| A41-B153; | A41-B154; | A41-B155; | A41-B156; | A41-B157; | A41-B158; |
| A41-B159; | A41-B160; | A41-B161; | A41-B162; | A41-B163; | A41-B164; |
| A41-B165; | A41-B166; | A41-B167; | A41-B168; | A41-B169; | A42-B1; |
| A42-B2; | A42-B3; | A42-B4; | A42-B5; | A42-B6; | A42-B7; |
| A42-B8; | A42-B9; | A42-B10; | A42-B11; | A42-B12; | A42-B13; |
| A42-B14; | A42-B15; | A42-B16; | A42-B17; | A42-B18; | A42-B19; |
| A42-B20; | A42-B21; | A42-B22; | A42-B23; | A42-B24; | A42-B25; |
| A42-B26; | A42-B27; | A42-B28; | A42-B29; | A42-B30; | A42-B31; |
| A42-B32; | A42-B33; | A42-B34; | A42-B35; | A42-B36; | A42-B37; |
| A42-B38; | A42-B39; | A42-B40; | A42-B41; | A42-B42; | A42-B43; |
| A42-B44; | A42-B45; | A42-B46; | A42-B47; | A42-B48; | A42-B49; |
| A42-B50; | A42-B51; | A42-B52; | A42-B53; | A42-B54; | A42-B55; |
| A42-B56; | A42-B57; | A42-B58; | A42-B59; | A42-B60; | A42-B61; |
| A42-B62; | A42-B63; | A42-B64; | A42-B65; | A42-B66; | A42-B67; |
| A42-B68; | A42-B69; | A42-B70; | A42-B71; | A42-B72; | A42-B73; |
| A42-B74; | A42-B75; | A42-B76; | A42-B77; | A42-B78; | A42-B79; |
| A42-B80; | A42-B81; | A42-B82; | A42-B83; | A42-B84; | A42-B85; |
| A42-B86; | A42-B87; | A42-B88; | A42-B89; | A42-B90; | A42-B91; |
| A42-B92; | A42-B93; | A42-B94; | A42-B95; | A42-B96; | A42-B97; |
| A42-B98; | A42-B99; | A42-B100; | A42-B101; | A42-B102; | A42-B103; |
| A42-B104; | A42-B105; | A42-B106; | A42-B107; | A42-B108; | A42-B109; |
| A42-B110; | A42-B111; | A42-B112; | A42-B113; | A42-B114; | A42-B115; |
| A42-B116; | A42-B117; | A42-B118; | A42-B119; | A42-B120; | A42-B121; |
| A42-B122; | A42-B123; | A42-B124; | A42-B125; | A42-B126; | A42-B127; |
| A42-B128; | A42-B129; | A42-B130; | A42-B131; | A42-B132; | A42-B133; |
| A42-B134; | A42-B135; | A42-B136; | A42-B137; | A42-B138; | A42-B139; |
| A42-B140; | A42-B141; | A42-B142; | A42-B143; | A42-B144; | A42-B145; |
| A42-B146; | A42-B147; | A42-B148; | A42-B149; | A42-B150; | A42-B151; |
| A42-B152; | A42-B153; | A42-B154; | A42-B155; | A42-B156; | A42-B157; |
| A42-B158; | A42-B159; | A42-B160; | A42-B161; | A42-B162; | A42-B163; |
| A42-B164; | A42-B165; | A42-B166; | A42-B167; | A42-B168; | A42-B169; |
| A43-B1; | A43-B2; | A43-B3; | A43-B4; | A43-B5; | A43-B6; |
| A43-B7; | A43-B8; | A43-B9; | A43-B10; | A43-B11; | A43-B12; |
| A43-B13; | A43-B14; | A43-B15; | A43-B16; | A43-B17; | A43-B18; |

-continued

| | | | | | |
|---|---|---|---|---|---|
| A43-B19; | A43-B20; | A43-B21; | A43-B22; | A43-B23; | A43-B24; |
| A43-B25; | A43-B26; | A43-B27; | A43-B28; | A43-B29; | A43-B30; |
| A43-B31; | A43-B32; | A43-B33; | A43-B34; | A43-B35; | A43-B36; |
| A43-B37; | A43-B38; | A43-B39; | A43-B40; | A43-B41; | A43-B42; |
| A43-B43; | A43-B44; | A43-B45; | A43-B46; | A43-B47; | A43-B48; |
| A43-B49; | A43-B50; | A43-B51; | A43-B52; | A43-B53; | A43-B54; |
| A43-B55; | A43-B56; | A43-B57; | A43-B58; | A43-B59; | A43-B60; |
| A43-B61; | A43-B62; | A43-B63; | A43-B64; | A43-B65; | A43-B66; |
| A43-B67; | A43-B68; | A43-B69; | A43-B70; | A43-B71; | A43-B72; |
| A43-B73; | A43-B74; | A43-B75; | A43-B76; | A43-B77; | A43-B78; |
| A43-B79; | A43-B80; | A43-B81; | A43-B82; | A43-B83; | A43-B84; |
| A43-B85; | A43-B86; | A43-B87; | A43-B88; | A43-B89; | A43-B90; |
| A43-B91; | A43-B92; | A43-B93; | A43-B94; | A43-B95; | A43-B96; |
| A43-B97; | A43-B98; | A43-B99; | A43-B100; | A43-B101; | A43-B102; |
| A43-B103; | A43-B104; | A43-B105; | A43-B106; | A43-B107; | A43-B108; |
| A43-B109; | A43-B110; | A43-B111; | A43-B112; | A43-B113; | A43-B114; |
| A43-B115; | A43-B116; | A43-B117; | A43-B118; | A43-B119; | A43-B120; |
| A43-B121; | A43-B122; | A43-B123; | A43-B124; | A43-B125; | A43-B126; |
| A43-B127; | A43-B128; | A43-B129; | A43-B130; | A43-B131; | A43-B132; |
| A43-B133; | A43-B134; | A43-B135; | A43-B136; | A43-B137; | A43-B138; |
| A43-B139; | A43-B140; | A43-B141; | A43-B142; | A43-B143; | A43-B144; |
| A43-B145; | A43-B146; | A43-B147; | A43-B148; | A43-B149; | A43-B150; |
| A43-B151; | A43-B152; | A43-B153; | A43-B154; | A43-B155; | A43-B156; |
| A43-B157; | A43-B158; | A43-B159; | A43-B160; | A43-B161; | A43-B162; |
| A43-B163; | A43-B164; | A43-B165; | A43-B166; | A43-B167; | A43-B168; |
| A43-B169; | A44-B1; | A44-B2; | A44-B3; | A44-B4; | A44-B5; |
| A44-B6; | A44-B7; | A44-B8; | A44-B9; | A44-B10; | A44-B11; |
| A44-B12; | A44-B13; | A44-B14; | A44-B15; | A44-B16; | A44-B17; |
| A44-B18; | A44-B19; | A44-B20; | A44-B21; | A44-B22; | A44-B23; |
| A44-B24; | A44-B25; | A44-B26; | A44-B27; | A44-B28; | A44-B29; |
| A44-B30; | A44-B31; | A44-B32; | A44-B33; | A44-B34; | A44-B35; |
| A44-B36; | A44-B37; | A44-B38; | A44-B39; | A44-B40; | A44-B41; |
| A44-B42; | A44-B43; | A44-B44; | A44-B45; | A44-B46; | A44-B47; |
| A44-B48; | A44-B49; | A44-B50; | A44-B51; | A44-B52; | A44-B53; |
| A44-B54; | A44-B55; | A44-B56; | A44-B57; | A44-B58; | A44-B59; |
| A44-B60; | A44-B61; | A44-B62; | A44-B63; | A44-B64; | A44-B65; |
| A44-B66; | A44-B67; | A44-B68; | A44-B69; | A44-B70; | A44-B71; |
| A44-B72; | A44-B73; | A44-B74; | A44-B75; | A44-B76; | A44-B77; |
| A44-B78; | A44-B79; | A44-B80; | A44-B81; | A44-B82; | A44-B83; |
| A44-B84; | A44-B85; | A44-B86; | A44-B87; | A44-B88; | A44-B89; |
| A44-B90; | A44-B91; | A44-B92; | A44-B93; | A44-B94; | A44-B95; |
| A44-B96; | A44-B97; | A44-B98; | A44-B99; | A44-B100; | A44-B101; |
| A44-B102; | A44-B103; | A44-B104; | A44-B105; | A44-B106; | A44-B107; |
| A44-B108; | A44-B109; | A44-B110; | A44-B111; | A44-B112; | A44-B113; |
| A44-B114; | A44-B115; | A44-B116; | A44-B117; | A44-B118; | A44-B119; |
| A44-B120; | A44-B121; | A44-B122; | A44-B123; | A44-B124; | A44-B125; |
| A44-B126; | A44-B127; | A44-B128; | A44-B129; | A44-B130; | A44-B131; |
| A44-B132; | A44-B133; | A44-B134; | A44-B135; | A44-B136; | A44-B137; |
| A44-B138; | A44-B139; | A44-B140; | A44-B141; | A44-B142; | A44-B143; |
| A44-B144; | A44-B145; | A44-B146; | A44-B147; | A44-B148; | A44-B149; |
| A44-B150; | A44-B151; | A44-B152; | A44-B153; | A44-B154; | A44-B155; |
| A44-B156; | A44-B157; | A44-B158; | A44-B159; | A44-B160; | A44-B161; |
| A44-B162; | A44-B163; | A44-B164; | A44-B165; | A44-B166; | A44-B167; |
| A44-B168; | A44-B169; | A45-B1; | A45-B2; | A45-B3; | A45-B4; |
| A45-B5; | A45-B6; | A45-B7; | A45-B8; | A45-B9; | A45-B10; |
| A45-B11; | A45-B12; | A45-B13; | A45-B14; | A45-B15; | A45-B16; |
| A45-B17; | A45-B18; | A45-B19; | A45-B20; | A45-B21; | A45-B22; |
| A45-B23; | A45-B24; | A45-B25; | A45-B26; | A45-B27; | A45-B28; |
| A45-B29; | A45-B30; | A45-B31; | A45-B32; | A45-B33; | A45-B34; |
| A45-B35; | A45-B36; | A45-B37; | A45-B38; | A45-B39; | A45-B40; |
| A45-B41; | A45-B42; | A45-B43; | A45-B44; | A45-B45; | A45-B46; |
| A45-B47; | A45-B48; | A45-B49; | A45-B50; | A45-B51; | A45-B52; |
| A45-B53; | A45-B54; | A45-B55; | A45-B56; | A45-B57; | A45-B58; |
| A45-B59; | A45-B60; | A45-B61; | A45-B62; | A45-B63; | A45-B64; |
| A45-B65; | A45-B66; | A45-B67; | A45-B68; | A45-B69; | A45-B70; |
| A45-B71; | A45-B72; | A45-B73; | A45-B74; | A45-B75; | A45-B76; |
| A45-B77; | A45-B78; | A45-B79; | A45-B80; | A45-B81; | A45-B82; |
| A45-B83; | A45-B84; | A45-B85; | A45-B86; | A45-B87; | A45-B88; |
| A45-B89; | A45-B90; | A45-B91; | A45-B92; | A45-B93; | A45-B94; |
| A45-B95; | A45-B96; | A45-B97; | A45-B98; | A45-B99; | A45-B100; |
| A45-B101; | A45-B102; | A45-B103; | A45-B104; | A45-B105; | A45-B106; |
| A45-B107; | A45-B108; | A45-B109; | A45-B110; | A45-B111; | A45-B112; |
| A45-B113; | A45-B114; | A45-B115; | A45-B116; | A45-B117; | A45-B118; |
| A45-B119; | A45-B120; | A45-B121; | A45-B122; | A45-B123; | A45-B124; |
| A45-B125; | A45-B126; | A45-B127; | A45-B128; | A45-B129; | A45-B130; |
| A45-B131; | A45-B132; | A45-B133; | A45-B134; | A45-B135; | A45-B136; |
| A45-B137; | A45-B138; | A45-B139; | A45-B140; | A45-B141; | A45-B142; |
| A45-B143; | A45-B144; | A45-B145; | A45-B146; | A45-B147; | A45-B148; |
| A45-B149; | A45-B150; | A45-B151; | A45-B152; | A45-B153; | A45-B154; |
| A45-B155; | A45-B156; | A45-B157; | A45-B158; | A45-B159; | A45-B160; |

-continued

| | | | | | |
|---|---|---|---|---|---|
| A45-B161; | A45-B162; | A45-B163; | A45-B164; | A45-B165; | A45-B166; |
| A45-B167; | A45-B168; | A45-B169; | A46-B1; | A46-B2; | A46-B3; |
| A46-B4; | A46-B5; | A46-B6; | A46-B7; | A46-B8; | A46-B9; |
| A46-B10; | A46-B11; | A46-B12; | A46-B13; | A46-B14; | A46-B15; |
| A46-B16; | A46-B17; | A46-B18; | A46-B19; | A46-B20; | A46-B21; |
| A46-B22; | A46-B23; | A46-B24; | A46-B25; | A46-B26; | A46-B27; |
| A46-B28; | A46-B29; | A46-B30; | A46-B31; | A46-B32; | A46-B33; |
| A46-B34; | A46-B35; | A46-B36; | A46-B37; | A46-B38; | A46-B39; |
| A46-B40; | A46-B41; | A46-B42; | A46-B43; | A46-B44; | A46-B45; |
| A46-B46; | A46-B47; | A46-B48; | A46-B49; | A46-B50; | A46-B51; |
| A46-B52; | A46-B53; | A46-B54; | A46-B55; | A46-B56; | A46-B57; |
| A46-B58; | A46-B59; | A46-B60; | A46-B61; | A46-B62; | A46-B63; |
| A46-B64; | A46-B65; | A46-B66; | A46-B67; | A46-B68; | A46-B69; |
| A46-B70; | A46-B71; | A46-B72; | A46-B73; | A46-B74; | A46-B75; |
| A46-B76; | A46-B77; | A46-B78; | A46-B79; | A46-B80; | A46-B81; |
| A46-B82; | A46-B83; | A46-B84; | A46-B85; | A46-B86; | A46-B87; |
| A46-B88; | A46-B89; | A46-B90; | A46-B91; | A46-B92; | A46-B93; |
| A46-B94; | A46-B95; | A46-B96; | A46-B97; | A46-B98; | A46-B99; |
| A46-B100; | A46-B101; | A46-B102; | A46-B103; | A46-B104; | A46-B105; |
| A46-B106; | A46-B107; | A46-B108; | A46-B109; | A46-B110; | A46-B111; |
| A46-B112; | A46-B113; | A46-B114; | A46-B115; | A46-B116; | A46-B117; |
| A46-B118; | A46-B119; | A46-B120; | A46-B121; | A46-B122; | A46-B123; |
| A46-B124; | A46-B125; | A46-B126; | A46-B127; | A46-B128; | A46-B129; |
| A46-B130; | A46-B131; | A46-B132; | A46-B133; | A46-B134; | A46-B135; |
| A46-B136; | A46-B137; | A46-B138; | A46-B139; | A46-B140; | A46-B141; |
| A46-B142; | A46-B143; | A46-B144; | A46-B145; | A46-B146; | A46-B147; |
| A46-B148; | A46-B149; | A46-B150; | A46-B151; | A46-B152; | A46-B153; |
| A46-B154; | A46-B155; | A46-B156; | A46-B157; | A46-B158; | A46-B159; |
| A46-B160; | A46-B161; | A46-B162; | A46-B163; | A46-B164; | A46-B165; |
| A46-B166; | A46-B167; | A46-B168; | A46-B169; | A47-B1; | A47-B2; |
| A47-B3; | A47-B4; | A47-B5; | A47-B6; | A47-B7; | A47-B8; |
| A47-B9; | A47-B10; | A47-B11; | A47-B12; | A47-B13; | A47-B14; |
| A47-B15; | A47-B16; | A47-B17; | A47-B18; | A47-B19; | A47-B20; |
| A47-B21; | A47-B22; | A47-B23; | A47-B24; | A47-B25; | A47-B26; |
| A47-B27; | A47-B28; | A47-B29; | A47-B30; | A47-B31; | A47-B32; |
| A47-B33; | A47-B34; | A47-B35; | A47-B36; | A47-B37; | A47-B38; |
| A47-B39; | A47-B40; | A47-B41; | A47-B42; | A47-B43; | A47-B44; |
| A47-B45; | A47-B46; | A47-B47; | A47-B48; | A47-B49; | A47-B50; |
| A47-B51; | A47-B52; | A47-B53; | A47-B54; | A47-B55; | A47-B56; |
| A47-B57; | A47-B58; | A47-B59; | A47-B60; | A47-B61; | A47-B62; |
| A47-B63; | A47-B64; | A47-B65; | A47-B66; | A47-B67; | A47-B68; |
| A47-B69; | A47-B70; | A47-B71; | A47-B72; | A47-B73; | A47-B74; |
| A47-B75; | A47-B76; | A47-B77; | A47-B78; | A47-B79; | A47-B80; |
| A47-B81; | A47-B82; | A47-B83; | A47-B84; | A47-B85; | A47-B86; |
| A47-B87; | A47-B88; | A47-B89; | A47-B90; | A47-B91; | A47-B92; |
| A47-B93; | A47-B94; | A47-B95; | A47-B96; | A47-B97; | A47-B98; |
| A47-B99; | A47-B100; | A47-B101; | A47-B102; | A47-B103; | A47-B104; |
| A47-B105; | A47-B106; | A47-B107; | A47-B108; | A47-B109; | A47-B110; |
| A47-B111; | A47-B112; | A47-B113; | A47-B114; | A47-B115; | A47-B116; |
| A47-B117; | A47-B118; | A47-B119; | A47-B120; | A47-B121; | A47-B122; |
| A47-B123; | A47-B124; | A47-B125; | A47-B126; | A47-B127; | A47-B128; |
| A47-B129; | A47-B130; | A47-B131; | A47-B132; | A47-B133; | A47-B134; |
| A47-B135; | A47-B136; | A47-B137; | A47-B138; | A47-B139; | A47-B140; |
| A47-B141; | A47-B142; | A47-B143; | A47-B144; | A47-B145; | A47-B146; |
| A47-B147; | A47-B148; | A47-B149; | A47-B150; | A47-B151; | A47-B152; |
| A47-B153; | A47-B154; | A47-B155; | A47-B156; | A47-B157; | A47-B158; |
| A47-B159; | A47-B160; | A47-B161; | A47-B162; | A47-B163; | A47-B164; |
| A47-B165; | A47-B166; | A47-B167; | A47-B168; | A47-B169; | A48-B1; |
| A48-B2; | A48-B3; | A48-B4; | A48-B5; | A48-B6; | A48-B7; |
| A48-B8; | A48-B9; | A48-B10; | A48-B11; | A48-B12; | A48-B13; |
| A48-B14; | A48-B15; | A48-B16; | A48-B17; | A48-B18; | A48-B19; |
| A48-B20; | A48-B21; | A48-B22; | A48-B23; | A48-B24; | A48-B25; |
| A48-B26; | A48-B27; | A48-B28; | A48-B29; | A48-B30; | A48-B31; |
| A48-B32; | A48-B33; | A48-B34; | A48-B35; | A48-B36; | A48-B37; |
| A48-B38; | A48-B39; | A48-B40; | A48-B41; | A48-B42; | A48-B43; |
| A48-B44; | A48-B45; | A48-B46; | A48-B47; | A48-B48; | A48-B49; |
| A48-B50; | A48-B51; | A48-B52; | A48-B53; | A48-B54; | A48-B55; |
| A48-B56; | A48-B57; | A48-B58; | A48-B59; | A48-B60; | A48-B61; |
| A48-B62; | A48-B63; | A48-B64; | A48-B65; | A48-B66; | A48-B67; |
| A48-B68; | A48-B69; | A48-B70; | A48-B71; | A48-B72; | A48-B73; |
| A48-B74; | A48-B75; | A48-B76; | A48-B77; | A48-B78; | A48-B79; |
| A48-B80; | A48-B81; | A48-B82; | A48-B83; | A48-B84; | A48-B85; |
| A48-B86; | A48-B87; | A48-B88; | A48-B89; | A48-B90; | A48-B91; |
| A48-B92; | A48-B93; | A48-B94; | A48-B95; | A48-B96; | A48-B97; |
| A48-B98; | A48-B99; | A48-B100; | A48-B101; | A48-B102; | A48-B103; |
| A48-B104; | A48-B105; | A48-B106; | A48-B107; | A48-B108; | A48-B109; |
| A48-B110; | A48-B111; | A48-B112; | A48-B113; | A48-B114; | A48-B115; |
| A48-B116; | A48-B117; | A48-B118; | A48-B119; | A48-B120; | A48-B121; |
| A48-B122; | A48-B123; | A48-B124; | A48-B125; | A48-B126; | A48-B127; |
| A48-B128; | A48-B129; | A48-B130; | A48-B131; | A48-B132; | A48-B133; |

-continued

A48-B134; A48-B135; A48-B136; A48-B137; A48-B138; A48-B139;
A48-B140; A48-B141; A48-B142; A48-B143; A48-B144; A48-B145;
A48-B146; A48-B147; A48-B148; A48-B149; A48-B150; A48-B151;
A48-B152; A48-B153; A48-B154; A48-B155; A48-B156; A48-B157;
A48-B158; A48-B159; A48-B160; A48-B161; A48-B162; A48-B163;
A48-B164; A48-B165; A48-B166; A48-B167; A48-B168; A48-B169;
A49-B1; A49-B2; A49-B3; A49-B4; A49-B5; A49-B6;
A49-B7; A49-B8; A49-B9; A49-B10; A49-B11; A49-B12;
A49-B13; A49-B14; A49-B15; A49-B16; A49-B17; A49-B18;
A49-B19; A49-B20; A49-B21; A49-B22; A49-B23; A49-B24;
A49-B25; A49-B26; A49-B27; A49-B28; A49-B29; A49-B30;
A49-B31; A49-B32; A49-B33; A49-B34; A49-B35; A49-B36;
A49-B37; A49-B38; A49-B39; A49-B40; A49-B41; A49-B42;
A49-B43; A49-B44; A49-B45; A49-B46; A49-B47; A49-B48;
A49-B49; A49-B50; A49-B51; A49-B52; A49-B53; A49-B54;
A49-B55; A49-B56; A49-B57; A49-B58; A49-B59; A49-B60;
A49-B61; A49-B62; A49-B63; A49-B64; A49-B65; A49-B66;
A49-B67; A49-B68; A49-B69; A49-B70; A49-B71; A49-B72;
A49-B73; A49-B74; A49-B75; A49-B76; A49-B77; A49-B78;
A49-B79; A49-B80; A49-B81; A49-B82; A49-B83; A49-B84;
A49-B85; A49-B86; A49-B87; A49-B88; A49-B89; A49-B90;
A49-B91; A49-B92; A49-B93; A49-B94; A49-B95; A49-B96;
A49-B97; A49-B98; A49-B99; A49-B100; A49-B101; A49-B102;
A49-B103; A49-B104; A49-B105; A49-B106; A49-B107; A49-B108;
A49-B109; A49-B110; A49-B111; A49-B112; A49-B113; A49-B114;
A49-B115; A49-B116; A49-B117; A49-B118; A49-B119; A49-B120;
A49-B121; A49-B122; A49-B123; A49-B124; A49-B125; A49-B126;
A49-B127; A49-B128; A49-B129; A49-B130; A49-B131; A49-B132;
A49-B133; A49-B134; A49-B135; A49-B136; A49-B137; A49-B138;
A49-B139; A49-B140; A49-B141; A49-B142; A49-B143; A49-B144;
A49-B145; A49-B146; A49-B147; A49-B148; A49-B149; A49-B150;
A49-B151; A49-B152; A49-B153; A49-B154; A49-B155; A49-B156;
A49-B157; A49-B158; A49-B159; A49-B160; A49-B161; A49-B162;
A49-B163; A49-B164; A49-B165; A49-B166; A49-B167; A49-B168;
A49-B169; A50-B1; A50-B2; A50-B3; A50-B4; A50-B5;
A50-B6; A50-B7; A50-B8; A50-B9; A50-B10; A50-B11;
A50-B12; A50-B13; A50-B14; A50-B15; A50-B16; A50-B17;
A50-B18; A50-B19; A50-B20; A50-B21; A50-B22; A50-B23;
A50-B24; A50-B25; A50-B26; A50-B27; A50-B28; A50-B29;
A50-B30; A50-B31; A50-B32; A50-B33; A50-B34; A50-B35;
A50-B36; A50-B37; A50-B38; A50-B39; A50-B40; A50-B41;
A50-B42; A50-B43; A50-B44; A50-B45; A50-B46; A50-B47;
A50-B48; A50-B49; A50-B50; A50-B51; A50-B52; A50-B53;
A50-B54; A50-B55; A50-B56; A50-B57; A50-B58; A50-B59;
A50-B60; A50-B61; A50-B62; A50-B63; A50-B64; A50-B65;
A50-B66; A50-B67; A50-B68; A50-B69; A50-B70; A50-B71;
A50-B72; A50-B73; A50-B74; A50-B75; A50-B76; A50-B77;
A50-B78; A50-B79; A50-B80; A50-B81; A50-B82; A50-B83;
A50-B84; A50-B85; A50-B86; A50-B87; A50-B88; A50-B89;
A50-B90; A50-B91; A50-B92; A50-B93; A50-B94; A50-B95;
A50-B96; A50-B97; A50-B98; A50-B99; A50-B100; A50-B101;
A50-B102; A50-B103; A50-B104; A50-B105; A50-B106; A50-B107;
A50-B108; A50-B109; A50-B110; A50-B111; A50-B112; A50-B113;
A50-B114; A50-B115; A50-B116; A50-B117; A50-B118; A50-B119;
A50-B120; A50-B121; A50-B122; A50-B123; A50-B124; A50-B125;
A50-B126; A50-B127; A50-B128; A50-B129; A50-B130; A50-B131;
A50-B132; A50-B133; A50-B134; A50-B135; A50-B136; A50-B137;
A50-B138; A50-B139; A50-B140; A50-B141; A50-B142; A50-B143;
A50-B144; A50-B145; A50-B146; A50-B147; A50-B148; A50-B149;
A50-B150; A50-B151; A50-B152; A50-B153; A50-B154; A50-B155;
A50-B156; A50-B157; A50-B158; A50-B159; A50-B160; A50-B161;
A50-B162; A50-B163; A50-B164; A50-B165; A50-B166; A50-B167;
A50-B168; A50-B169; A51-B1; A51-B2; A51-B3; A51-B4;
A51-B5; A51-B6; A51-B7; A51-B8; A51-B9; A51-B10;
A51-B11; A51-B12; A51-B13; A51-B14; A51-B15; A51-B16;
A51-B17; A51-B18; A51-B19; A51-B20; A51-B21; A51-B22;
A51-B23; A51-B24; A51-B25; A51-B26; A51-B27; A51-B28;
A51-B29; A51-B30; A51-B31; A51-B32; A51-B33; A51-B34;
A51-B35; A51-B36; A51-B37; A51-B38; A51-B39; A51-B40;
A51-B41; A51-B42; A51-B43; A51-B44; A51-B45; A51-B46;
A51-B47; A51-B48; A51-B49; A51-B50; A51-B51; A51-B52;
A51-B53; A51-B54; A51-B55; A51-B56; A51-B57; A51-B58;
A51-B59; A51-B60; A51-B61; A51-B62; A51-B63; A51-B64;
A51-B65; A51-B66; A51-B67; A51-B68; A51-B69; A51-B70;
A51-B71; A51-B72; A51-B73; A51-B74; A51-B75; A51-B76;
A51-B77; A51-B78; A51-B79; A51-B80; A51-B81; A51-B82;
A51-B83; A51-B84; A51-B85; A51-B86; A51-B87; A51-B88;
A51-B89; A51-B90; A51-B91; A51-B92; A51-B93; A51-B94;
A51-B95; A51-B96; A51-B97; A51-B98; A51-B99; A51-B100;
A51-B101; A51-B102; A51-B103; A51-B104; A51-B105; A51-B106;

-continued

| | | | | | |
|---|---|---|---|---|---|
| A51-B107; | A51-B108; | A51-B109; | A51-B110; | A51-B111; | A51-B112; |
| A51-B113; | A51-B114; | A51-B115; | A51-B116; | A51-B117; | A51-B118; |
| A51-B119; | A51-B120; | A51-B121; | A51-B122; | A51-B123; | A51-B124; |
| A51-B125; | A51-B126; | A51-B127; | A51-B128; | A51-B129; | A51-B130; |
| A51-B131; | A51-B132; | A51-B133; | A51-B134; | A51-B135; | A51-B136; |
| A51-B137; | A51-B138; | A51-B139; | A51-B140; | A51-B141; | A51-B142; |
| A51-B143; | A51-B144; | A51-B145; | A51-B146; | A51-B147; | A51-B148; |
| A51-B149; | A51-B150; | A51-B151; | A51-B152; | A51-B153; | A51-B154; |
| A51-B155; | A51-B156; | A51-B157; | A51-B158; | A51-B159; | A51-B160; |
| A51-B161; | A51-B162; | A51-B163; | A51-B164; | A51-B165; | A51-B166; |
| A51-B167; | A51-B168; | A51-B169; | A52-B1; | A52-B2; | A52-B3; |
| A52-B4; | A52-B5; | A52-B6; | A52-B7; | A52-B8; | A52-B9; |
| A52-B10; | A52-B11; | A52-B12; | A52-B13; | A52-B14; | A52-B15; |
| A52-B16; | A52-B17; | A52-B18; | A52-B19; | A52-B20; | A52-B21; |
| A52-B22; | A52-B23; | A52-B24; | A52-B25; | A52-B26; | A52-B27; |
| A52-B28; | A52-B29; | A52-B30; | A52-B31; | A52-B32; | A52-B33; |
| A52-B34; | A52-B35; | A52-B36; | A52-B37; | A52-B38; | A52-B39; |
| A52-B40; | A52-B41; | A52-B42; | A52-B43; | A52-B44; | A52-B45; |
| A52-B46; | A52-B47; | A52-B48; | A52-B49; | A52-B50; | A52-B51; |
| A52-B52; | A52-B53; | A52-B54; | A52-B55; | A52-B56; | A52-B57; |
| A52-B58; | A52-B59; | A52-B60; | A52-B61; | A52-B62; | A52-B63; |
| A52-B64; | A52-B65; | A52-B66; | A52-B67; | A52-B68; | A52-B69; |
| A52-B70; | A52-B71; | A52-B72; | A52-B73; | A52-B74; | A52-B75; |
| A52-B76; | A52-B77; | A52-B78; | A52-B79; | A52-B80; | A52-B81; |
| A52-B82; | A52-B83; | A52-B84; | A52-B85; | A52-B86; | A52-B87; |
| A52-B88; | A52-B89; | A52-B90; | A52-B91; | A52-B92; | A52-B93; |
| A52-B94; | A52-B95; | A52-B96; | A52-B97; | A52-B98; | A52-B99; |
| A52-B100; | A52-B101; | A52-B102; | A52-B103; | A52-B104; | A52-B105; |
| A52-B106; | A52-B107; | A52-B108; | A52-B109; | A52-B110; | A52-B111; |
| A52-B112; | A52-B113; | A52-B114; | A52-B115; | A52-B116; | A52-B117; |
| A52-B118; | A52-B119; | A52-B120; | A52-B121; | A52-B122; | A52-B123; |
| A52-B124; | A52-B125; | A52-B126; | A52-B127; | A52-B128; | A52-B129; |
| A52-B130; | A52-B131; | A52-B132; | A52-B133; | A52-B134; | A52-B135; |
| A52-B136; | A52-B137; | A52-B138; | A52-B139; | A52-B140; | A52-B141; |
| A52-B142; | A52-B143; | A52-B144; | A52-B145; | A52-B146; | A52-B147; |
| A52-B148; | A52-B149; | A52-B150; | A52-B151; | A52-B152; | A52-B153; |
| A52-B154; | A52-B155; | A52-B156; | A52-B157; | A52-B158; | A52-B159; |
| A52-B160; | A52-B161; | A52-B162; | A52-B163; | A52-B164; | A52-B165; |
| A52-B166; | A52-B167; | A52-B168; | A52-B169; | A53-B1; | A53-B2; |
| A53-B3; | A53-B4; | A53-B5; | A53-B6; | A53-B7; | A53-B8; |
| A53-B9; | A53-B10; | A53-B11; | A53-B12; | A53-B13; | A53-B14; |
| A53-B15; | A53-B16; | A53-B17; | A53-B18; | A53-B19; | A53-B20; |
| A53-B21; | A53-B22; | A53-B23; | A53-B24; | A53-B25; | A53-B26; |
| A53-B27; | A53-B28; | A53-B29; | A53-B30; | A53-B31; | A53-B32; |
| A53-B33; | A53-B34; | A53-B35; | A53-B36; | A53-B37; | A53-B38; |
| A53-B39; | A53-B40; | A53-B41; | A53-B42; | A53-B43; | A53-B44; |
| A53-B45; | A53-B46; | A53-B47; | A53-B48; | A53-B49; | A53-B50; |
| A53-B51; | A53-B52; | A53-B53; | A53-B54; | A53-B55; | A53-B56; |
| A53-B57; | A53-B58; | A53-B59; | A53-B60; | A53-B61; | A53-B62; |
| A53-B63; | A53-B64; | A53-B65; | A53-B66; | A53-B67; | A53-B68; |
| A53-B69; | A53-B70; | A53-B71; | A53-B72; | A53-B73; | A53-B74; |
| A53-B75; | A53-B76; | A53-B77; | A53-B78; | A53-B79; | A53-B80; |
| A53-B81; | A53-B82; | A53-B83; | A53-B84; | A53-B85; | A53-B86; |
| A53-B87; | A53-B88; | A53-B89; | A53-B90; | A53-B91; | A53-B92; |
| A53-B93; | A53-B94; | A53-B95; | A53-B96; | A53-B97; | A53-B98; |
| A53-B99; | A53-B100; | A53-B101; | A53-B102; | A53-B103; | A53-B104; |
| A53-B105; | A53-B106; | A53-B107; | A53-B108; | A53-B109; | A53-B110; |
| A53-B111; | A53-B112; | A53-B113; | A53-B114; | A53-B115; | A53-B116; |
| A53-B117; | A53-B118; | A53-B119; | A53-B120; | A53-B121; | A53-B122; |
| A53-B123; | A53-B124; | A53-B125; | A53-B126; | A53-B127; | A53-B128; |
| A53-B129; | A53-B130; | A53-B131; | A53-B132; | A53-B133; | A53-B134; |
| A53-B135; | A53-B136; | A53-B137; | A53-B138; | A53-B139; | A53-B140; |
| A53-B141; | A53-B142; | A53-B143; | A53-B144; | A53-B145; | A53-B146; |
| A53-B147; | A53-B148; | A53-B149; | A53-B150; | A53-B151; | A53-B152; |
| A53-B153; | A53-B154; | A53-B155; | A53-B156; | A53-B157; | A53-B158; |
| A53-B159; | A53-B160; | A53-B161; | A53-B162; | A53-B163; | A53-B164; |
| A53-B165; | A53-B166; | A53-B167; | A53-B168; | A53-B169; | A54-B1; |
| A54-B2; | A54-B3; | A54-B4; | A54-B5; | A54-B6; | A54-B7; |
| A54-B8; | A54-B9; | A54-B10; | A54-B11; | A54-B12; | A54-B13; |
| A54-B14; | A54-B15; | A54-B16; | A54-B17; | A54-B18; | A54-B19; |
| A54-B20; | A54-B21; | A54-B22; | A54-B23; | A54-B24; | A54-B25; |
| A54-B26; | A54-B27; | A54-B28; | A54-B29; | A54-B30; | A54-B31; |
| A54-B32; | A54-B33; | A54-B34; | A54-B35; | A54-B36; | A54-B37; |
| A54-B38; | A54-B39; | A54-B40; | A54-B41; | A54-B42; | A54-B43; |
| A54-B44; | A54-B45; | A54-B46; | A54-B47; | A54-B48; | A54-B49; |
| A54-B50; | A54-B51; | A54-B52; | A54-B53; | A54-B54; | A54-B55; |
| A54-B56; | A54-B57; | A54-B58; | A54-B59; | A54-B60; | A54-B61; |
| A54-B62; | A54-B63; | A54-B64; | A54-B65; | A54-B66; | A54-B67; |
| A54-B68; | A54-B69; | A54-B70; | A54-B71; | A54-B72; | A54-B73; |
| A54-B74; | A54-B75; | A54-B76; | A54-B77; | A54-B78; | A54-B79; |

| | | | | | |
|---|---|---|---|---|---|
| A54-B80; | A54-B81; | A54-B82; | A54-B83; | A54-B84; | A54-B85; |
| A54-B86; | A54-B87; | A54-B88; | A54-B89; | A54-B90; | A54-B91; |
| A54-B92; | A54-B93; | A54-B94; | A54-B95; | A54-B96; | A54-B97; |
| A54-B98; | A54-B99; | A54-B100; | A54-B101; | A54-B102; | A54-B103; |
| A54-B104; | A54-B105; | A54-B106; | A54-B107; | A54-B108; | A54-B109; |
| A54-B110; | A54-B111; | A54-B112; | A54-B113; | A54-B114; | A54-B115; |
| A54-B116; | A54-B117; | A54-B118; | A54-B119; | A54-B120; | A54-B121; |
| A54-B122; | A54-B123; | A54-B124; | A54-B125; | A54-B126; | A54-B127; |
| A54-B128; | A54-B129; | A54-B130; | A54-B131; | A54-B132; | A54-B133; |
| A54-B134; | A54-B135; | A54-B136; | A54-B137; | A54-B138; | A54-B139; |
| A54-B140; | A54-B141; | A54-B142; | A54-B143; | A54-B144; | A54-B145; |
| A54-B146; | A54-B147; | A54-B148; | A54-B149; | A54-B150; | A54-B151; |
| A54-B152; | A54-B153; | A54-B154; | A54-B155; | A54-B156; | A54-B157; |
| A54-B158; | A54-B159; | A54-B160; | A54-B161; | A54-B162; | A54-B163; |
| A54-B164; | A54-B165; | A54-B166; | A54-B167; | A54-B168; | A54-B169; |
| A55-B1; | A55-B2; | A55-B3; | A55-B4; | A55-B5; | A55-B6; |
| A55-B7; | A55-B8; | A55-B9; | A55-B10; | A55-B11; | A55-B12; |
| A55-B13; | A55-B14; | A55-B15; | A55-B16; | A55-B17; | A55-B18; |
| A55-B19; | A55-B20; | A55-B21; | A55-B22; | A55-B23; | A55-B24; |
| A55-B25; | A55-B26; | A55-B27; | A55-B28; | A55-B29; | A55-B30; |
| A55-B31; | A55-B32; | A55-B33; | A55-B34; | A55-B35; | A55-B36; |
| A55-B37; | A55-B38; | A55-B39; | A55-B40; | A55-B41; | A55-B42; |
| A55-B43; | A55-B44; | A55-B45; | A55-B46; | A55-B47; | A55-B48; |
| A55-B49; | A55-B50; | A55-B51; | A55-B52; | A55-B53; | A55-B54; |
| A55-B55; | A55-B56; | A55-B57; | A55-B58; | A55-B59; | A55-B60; |
| A55-B61; | A55-B62; | A55-B63; | A55-B64; | A55-B65; | A55-B66; |
| A55-B67; | A55-B68; | A55-B69; | A55-B70; | A55-B71; | A55-B72; |
| A55-B73; | A55-B74; | A55-B75; | A55-B76; | A55-B77; | A55-B78; |
| A55-B79; | A55-B80; | A55-B81; | A55-B82; | A55-B83; | A55-B84; |
| A55-B85; | A55-B86; | A55-B87; | A55-B88; | A55-B89; | A55-B90; |
| A55-B91; | A55-B92; | A55-B93; | A55-B94; | A55-B95; | A55-B96; |
| A55-B97; | A55-B98; | A55-B99; | A55-B100; | A55-B101; | A55-B102; |
| A55-B103; | A55-B104; | A55-B105; | A55-B106; | A55-B107; | A55-B108; |
| A55-B109; | A55-B110; | A55-B111; | A55-B112; | A55-B113; | A55-B114; |
| A55-B115; | A55-B116; | A55-B117; | A55-B118; | A55-B119; | A55-B120; |
| A55-B121; | A55-B122; | A55-B123; | A55-B124; | A55-B125; | A55-B126; |
| A55-B127; | A55-B128; | A55-B129; | A55-B130; | A55-B131; | A55-B132; |
| A55-B133; | A55-B134; | A55-B135; | A55-B136; | A55-B137; | A55-B138; |
| A55-B139; | A55-B140; | A55-B141; | A55-B142; | A55-B143; | A55-B144; |
| A55-B145; | A55-B146; | A55-B147; | A55-B148; | A55-B149; | A55-B150; |
| A55-B151; | A55-B152; | A55-B153; | A55-B154; | A55-B155; | A55-B156; |
| A55-B157; | A55-B158; | A55-B159; | A55-B160; | A55-B161; | A55-B162; |
| A55-B163; | A55-B164; | A55-B165; | A55-B166; | A55-B167; | A55-B168; |
| A55-B169; | A56-B1; | A56-B2; | A56-B3; | A56-B4; | A56-B5; |
| A56-B6; | A56-B7; | A56-B8; | A56-B9; | A56-B10; | A56-B11; |
| A56-B12; | A56-B13; | A56-B14; | A56-B15; | A56-B16; | A56-B17; |
| A56-B18; | A56-B19; | A56-B20; | A56-B21; | A56-B22; | A56-B23; |
| A56-B24; | A56-B25; | A56-B26; | A56-B27; | A56-B28; | A56-B29; |
| A56-B30; | A56-B31; | A56-B32; | A56-B33; | A56-B34; | A56-B35; |
| A56-B36; | A56-B37; | A56-B38; | A56-B39; | A56-B40; | A56-B41; |
| A56-B42; | A56-B43; | A56-B44; | A56-B45; | A56-B46; | A56-B47; |
| A56-B48; | A56-B49; | A56-B50; | A56-B51; | A56-B52; | A56-B53; |
| A56-B54; | A56-B55; | A56-B56; | A56-B57; | A56-B58; | A56-B59; |
| A56-B60; | A56-B61; | A56-B62; | A56-B63; | A56-B64; | A56-B65; |
| A56-B66; | A56-B67; | A56-B68; | A56-B69; | A56-B70; | A56-B71; |
| A56-B72; | A56-B73; | A56-B74; | A56-B75; | A56-B76; | A56-B77; |
| A56-B78; | A56-B79; | A56-B80; | A56-B81; | A56-B82; | A56-B83; |
| A56-B84; | A56-B85; | A56-B86; | A56-B87; | A56-B88; | A56-B89; |
| A56-B90; | A56-B91; | A56-B92; | A56-B93; | A56-B94; | A56-B95; |
| A56-B96; | A56-B97; | A56-B98; | A56-B99; | A56-B100; | A56-B101; |
| A56-B102; | A56-B103; | A56-B104; | A56-B105; | A56-B106; | A56-B107; |
| A56-B108; | A56-B109; | A56-B110; | A56-B111; | A56-B112; | A56-B113; |
| A56-B114; | A56-B115; | A56-B116; | A56-B117; | A56-B118; | A56-B119; |
| A56-B120; | A56-B121; | A56-B122; | A56-B123; | A56-B124; | A56-B125; |
| A56-B126; | A56-B127; | A56-B128; | A56-B129; | A56-B130; | A56-B131; |
| A56-B132; | A56-B133; | A56-B134; | A56-B135; | A56-B136; | A56-B137; |
| A56-B138; | A56-B139; | A56-B140; | A56-B141; | A56-B142; | A56-B143; |
| A56-B144; | A56-B145; | A56-B146; | A56-B147; | A56-B148; | A56-B149; |
| A56-B150; | A56-B151; | A56-B152; | A56-B153; | A56-B154; | A56-B155; |
| A56-B156; | A56-B157; | A56-B158; | A56-B159; | A56-B160; | A56-B161; |
| A56-B162; | A56-B163; | A56-B164; | A56-B165; | A56-B166; | A56-B167; |
| A56-B168; | A56-B169; | A57-B1; | A57-B2; | A57-B3; | A57-B4; |
| A57-B5; | A57-B6; | A57-B7; | A57-B8; | A57-B9; | A57-B10; |
| A57-B11; | A57-B12; | A57-B13; | A57-B14; | A57-B15; | A57-B16; |
| A57-B17; | A57-B18; | A57-B19; | A57-B20; | A57-B21; | A57-B22; |
| A57-B23; | A57-B24; | A57-B25; | A57-B26; | A57-B27; | A57-B28; |
| A57-B29; | A57-B30; | A57-B31; | A57-B32; | A57-B33; | A57-B34; |
| A57-B35; | A57-B36; | A57-B37; | A57-B38; | A57-B39; | A57-B40; |
| A57-B41; | A57-B42; | A57-B43; | A57-B44; | A57-B45; | A57-B46; |
| A57-B47; | A57-B48; | A57-B49; | A57-B50; | A57-B51; | A57-B52; |

-continued

A57-B53; A57-B54; A57-B55; A57-B56; A57-B57; A57-B58;
A57-B59; A57-B60; A57-B61; A57-B62; A57-B63; A57-B64;
A57-B65; A57-B66; A57-B67; A57-B68; A57-B69; A57-B70;
A57-B71; A57-B72; A57-B73; A57-B74; A57-B75; A57-B76;
A57-B77; A57-B78; A57-B79; A57-B80; A57-B81; A57-B82;
A57-B83; A57-B84; A57-B85; A57-B86; A57-B87; A57-B88;
A57-B89; A57-B90; A57-B91; A57-B92; A57-B93; A57-B94;
A57-B95; A57-B96; A57-B97; A57-B98; A57-B99; A57-B100;
A57-B101; A57-B102; A57-B103; A57-B104; A57-B105; A57-B106;
A57-B107; A57-B108; A57-B109; A57-B110; A57-B111; A57-B112;
A57-B113; A57-B114; A57-B115; A57-B116; A57-B117; A57-B118;
A57-B119; A57-B120; A57-B121; A57-B122; A57-B123; A57-B124;
A57-B125; A57-B126; A57-B127; A57-B128; A57-B129; A57-B130;
A57-B131; A57-B132; A57-B133; A57-B134; A57-B135; A57-B136;
A57-B137; A57-B138; A57-B139; A57-B140; A57-B141; A57-B142;
A57-B143; A57-B144; A57-B145; A57-B146; A57-B147; A57-B148;
A57-B149; A57-B150; A57-B151; A57-B152; A57-B153; A57-B154;
A57-B155; A57-B156; A57-B157; A57-B158; A57-B159; A57-B160;
A57-B161; A57-B162; A57-B163; A57-B164; A57-B165; A57-B166;
A57-B167; A57-B168; A57-B169; A58-B1; A58-B2; A58-B3;
A58-B4; A58-B5; A58-B6; A58-B7; A58-B8; A58-B9;
A58-B10; A58-B11; A58-B12; A58-B13; A58-B14; A58-B15;
A58-B16; A58-B17; A58-B18; A58-B19; A58-B20; A58-B21;
A58-B22; A58-B23; A58-B24; A58-B25; A58-B26; A58-B27;
A58-B28; A58-B29; A58-B30; A58-B31; A58-B32; A58-B33;
A58-B34; A58-B35; A58-B36; A58-B37; A58-B38; A58-B39;
A58-B40; A58-B41; A58-B42; A58-B43; A58-B44; A58-B45;
A58-B46; A58-B47; A58-B48; A58-B49; A58-B50; A58-B51;
A58-B52; A58-B53; A58-B54; A58-B55; A58-B56; A58-B57;
A58-B58; A58-B59; A58-B60; A58-B61; A58-B62; A58-B63;
A58-B64; A58-B65; A58-B66; A58-B67; A58-B68; A58-B69;
A58-B70; A58-B71; A58-B72; A58-B73; A58-B74; A58-B75;
A58-B76; A58-B77; A58-B78; A58-B79; A58-B80; A58-B81;
A58-B82; A58-B83; A58-B84; A58-B85; A58-B86; A58-B87;
A58-B88; A58-B89; A58-B90; A58-B91; A58-B92; A58-B93;
A58-B94; A58-B95; A58-B96; A58-B97; A58-B98; A58-B99;
A58-B100; A58-B101; A58-B102; A58-B103; A58-B104; A58-B105;
A58-B106; A58-B107; A58-B108; A58-B109; A58-B110; A58-B111;
A58-B112; A58-B113; A58-B114; A58-B115; A58-B116; A58-B117;
A58-B118; A58-B119; A58-B120; A58-B121; A58-B122; A58-B123;
A58-B124; A58-B125; A58-B126; A58-B127; A58-B128; A58-B129;
A58-B130; A58-B131; A58-B132; A58-B133; A58-B134; A58-B135;
A58-B136; A58-B137; A58-B138; A58-B139; A58-B140; A58-B141;
A58-B142; A58-B143; A58-B144; A58-B145; A58-B146; A58-B147;
A58-B148; A58-B149; A58-B150; A58-B151; A58-B152; A58-B153;
A58-B154; A58-B155; A58-B156; A58-B157; A58-B158; A58-B159;
A58-B160; A58-B161; A58-B162; A58-B163; A58-B164; A58-B165;
A58-B166; A58-B167; A58-B168; A58-B169; A59-B1; A59-B2;
A59-B3; A59-B4; A59-B5; A59-B6; A59-B7; A59-B8;
A59-B9; A59-B10; A59-B11; A59-B12; A59-B13; A59-B14;
A59-B15; A59-B16; A59-B17; A59-B18; A59-B19; A59-B20;
A59-B21; A59-B22; A59-B23; A59-B24; A59-B25; A59-B26;
A59-B27; A59-B28; A59-B29; A59-B30; A59-B31; A59-B32;
A59-B33; A59-B34; A59-B35; A59-B36; A59-B37; A59-B38;
A59-B39; A59-B40; A59-B41; A59-B42; A59-B43; A59-B44;
A59-B45; A59-B46; A59-B47; A59-B48; A59-B49; A59-B50;
A59-B51; A59-B52; A59-B53; A59-B54; A59-B55; A59-B56;
A59-B57; A59-B58; A59-B59; A59-B60; A59-B61; A59-B62;
A59-B63; A59-B64; A59-B65; A59-B66; A59-B67; A59-B68;
A59-B69; A59-B70; A59-B71; A59-B72; A59-B73; A59-B74;
A59-B75; A59-B76; A59-B77; A59-B78; A59-B79; A59-B80;
A59-B81; A59-B82; A59-B83; A59-B84; A59-B85; A59-B86;
A59-B87; A59-B88; A59-B89; A59-B90; A59-B91; A59-B92;
A59-B93; A59-B94; A59-B95; A59-B96; A59-B97; A59-B98;
A59-B99; A59-B100; A59-B101; A59-B102; A59-B103; A59-B104;
A59-B105; A59-B106; A59-B107; A59-B108; A59-B109; A59-B110;
A59-B111; A59-B112; A59-B113; A59-B114; A59-B115; A59-B116;
A59-B117; A59-B118; A59-B119; A59-B120; A59-B121; A59-B122;
A59-B123; A59-B124; A59-B125; A59-B126; A59-B127; A59-B128;
A59-B129; A59-B130; A59-B131; A59-B132; A59-B133; A59-B134;
A59-B135; A59-B136; A59-B137; A59-B138; A59-B139; A59-B140;
A59-B141; A59-B142; A59-B143; A59-B144; A59-B145; A59-B146;
A59-B147; A59-B148; A59-B149; A59-B150; A59-B151; A59-B152;
A59-B153; A59-B154; A59-B155; A59-B156; A59-B157; A59-B158;
A59-B159; A59-B160; A59-B161; A59-B162; A59-B163; A59-B164;
A59-B165; A59-B166; A59-B167; A59-B168; A59-B169; A60-B1;
A60-B2; A60-B3; A60-B4; A60-B5; A60-B6; A60-B7;
A60-B8; A60-B9; A60-B10; A60-B11; A60-B12; A60-B13;
A60-B14; A60-B15; A60-B16; A60-B17; A60-B18; A60-B19;
A60-B20; A60-B21; A60-B22; A60-B23; A60-B24; A60-B25;

-continued

| | | | | | |
|---|---|---|---|---|---|
| A60-B26; | A60-B27; | A60-B28; | A60-B29; | A60-B30; | A60-B31; |
| A60-B32; | A60-B33; | A60-B34; | A60-B35; | A60-B36; | A60-B37; |
| A60-B38; | A60-B39; | A60-B40; | A60-B41; | A60-B42; | A60-B43; |
| A60-B44; | A60-B45; | A60-B46; | A60-B47; | A60-B48; | A60-B49; |
| A60-B50; | A60-B51; | A60-B52; | A60-B53; | A60-B54; | A60-B55; |
| A60-B56; | A60-B57; | A60-B58; | A60-B59; | A60-B60; | A60-B61; |
| A60-B62; | A60-B63; | A60-B64; | A60-B65; | A60-B66; | A60-B67; |
| A60-B68; | A60-B69; | A60-B70; | A60-B71; | A60-B72; | A60-B73; |
| A60-B74; | A60-B75; | A60-B76; | A60-B77; | A60-B78; | A60-B79; |
| A60-B80; | A60-B81; | A60-B82; | A60-B83; | A60-B84; | A60-B85; |
| A60-B86; | A60-B87; | A60-B88; | A60-B89; | A60-B90; | A60-B91; |
| A60-B92; | A60-B93; | A60-B94; | A60-B95; | A60-B96; | A60-B97; |
| A60-B98; | A60-B99; | A60-B100; | A60-B101; | A60-B102; | A60-B103; |
| A60-B104; | A60-B105; | A60-B106; | A60-B107; | A60-B108; | A60-B109; |
| A60-B110; | A60-B111; | A60-B112; | A60-B113; | A60-B114; | A60-B115; |
| A60-B116; | A60-B117; | A60-B118; | A60-B119; | A60-B120; | A60-B121; |
| A60-B122; | A60-B123; | A60-B124; | A60-B125; | A60-B126; | A60-B127; |
| A60-B128; | A60-B129; | A60-B130; | A60-B131; | A60-B132; | A60-B133; |
| A60-B134; | A60-B135; | A60-B136; | A60-B137; | A60-B138; | A60-B139; |
| A60-B140; | A60-B141; | A60-B142; | A60-B143; | A60-B144; | A60-B145; |
| A60-B146; | A60-B147; | A60-B148; | A60-B149; | A60-B150; | A60-B151; |
| A60-B152; | A60-B153; | A60-B154; | A60-B155; | A60-B156; | A60-B157; |
| A60-B158; | A60-B159; | A60-B160; | A60-B161; | A60-B162; | A60-B163; |
| A60-B164; | A60-B165; | A60-B166; | A60-B167; | A60-B168; | A60-B169; |
| A61-B1; | A61-B2; | A61-B3; | A61-B4; | A61-B5; | A61-B6; |
| A61-B7; | A61-B8; | A61-B9; | A61-B10; | A61-B11; | A61-B12; |
| A61-B13; | A61-B14; | A61-B15; | A61-B16; | A61-B17; | A61-B18; |
| A61-B19; | A61-B20; | A61-B21; | A61-B22; | A61-B23; | A61-B24; |
| A61-B25; | A61-B26; | A61-B27; | A61-B28; | A61-B29; | A61-B30; |
| A61-B31; | A61-B32; | A61-B33; | A61-B34; | A61-B35; | A61-B36; |
| A61-B37; | A61-B38; | A61-B39; | A61-B40; | A61-B41; | A61-B42; |
| A61-B43; | A61-B44; | A61-B45; | A61-B46; | A61-B47; | A61-B48; |
| A61-B49; | A61-B50; | A61-B51; | A61-B52; | A61-B53; | A61-B54; |
| A61-B55; | A61-B56; | A61-B57; | A61-B58; | A61-B59; | A61-B60; |
| A61-B61; | A61-B62; | A61-B63; | A61-B64; | A61-B65; | A61-B66; |
| A61-B67; | A61-B68; | A61-B69; | A61-B70; | A61-B71; | A61-B72; |
| A61-B73; | A61-B74; | A61-B75; | A61-B76; | A61-B77; | A61-B78; |
| A61-B79; | A61-B80; | A61-B81; | A61-B82; | A61-B83; | A61-B84; |
| A61-B85; | A61-B86; | A61-B87; | A61-B88; | A61-B89; | A61-B90; |
| A61-B91; | A61-B92; | A61-B93; | A61-B94; | A61-B95; | A61-B96; |
| A61-B97; | A61-B98; | A61-B99; | A61-B100; | A61-B101; | A61-B102; |
| A61-B103; | A61-B104; | A61-B105; | A61-B106; | A61-B107; | A61-B108; |
| A61-B109; | A61-B110; | A61-B111; | A61-B112; | A61-B113; | A61-B114; |
| A61-B115; | A61-B116; | A61-B117; | A61-B118; | A61-B119; | A61-B120; |
| A61-B121; | A61-B122; | A61-B123; | A61-B124; | A61-B125; | A61-B126; |
| A61-B127; | A61-B128; | A61-B129; | A61-B130; | A61-B131; | A61-B132; |
| A61-B133; | A61-B134; | A61-B135; | A61-B136; | A61-B137; | A61-B138; |
| A61-B139; | A61-B140; | A61-B141; | A61-B142; | A61-B143; | A61-B144; |
| A61-B145; | A61-B146; | A61-B147; | A61-B148; | A61-B149; | A61-B150; |
| A61-B151; | A61-B152; | A61-B153; | A61-B154; | A61-B155; | A61-B156; |
| A61-B157; | A61-B158; | A61-B159; | A61-B160; | A61-B161; | A61-B162; |
| A61-B163; | A61-B164; | A61-B165; | A61-B166; | A61-B167; | A61-B168; |
| A61-B169; | A62-B1; | A62-B2; | A62-B3; | A62-B4; | A62-B5; |
| A62-B6; | A62-B7; | A62-B8; | A62-B9; | A62-B10; | A62-B11; |
| A62-B12; | A62-B13; | A62-B14; | A62-B15; | A62-B16; | A62-B17; |
| A62-B18; | A62-B19; | A62-B20; | A62-B21; | A62-B22; | A62-B23; |
| A62-B24; | A62-B25; | A62-B26; | A62-B27; | A62-B28; | A62-B29; |
| A62-B30; | A62-B31; | A62-B32; | A62-B33; | A62-B34; | A62-B35; |
| A62-B36; | A62-B37; | A62-B38; | A62-B39; | A62-B40; | A62-B41; |
| A62-B42; | A62-B43; | A62-B44; | A62-B45; | A62-B46; | A62-B47; |
| A62-B48; | A62-B49; | A62-B50; | A62-B51; | A62-B52; | A62-B53; |
| A62-B54; | A62-B55; | A62-B56; | A62-B57; | A62-B58; | A62-B59; |
| A62-B60; | A62-B61; | A62-B62; | A62-B63; | A62-B64; | A62-B65; |
| A62-B66; | A62-B67; | A62-B68; | A62-B69; | A62-B70; | A62-B71; |
| A62-B72; | A62-B73; | A62-B74; | A62-B75; | A62-B76; | A62-B77; |
| A62-B78; | A62-B79; | A62-B80; | A62-B81; | A62-B82; | A62-B83; |
| A62-B84; | A62-B85; | A62-B86; | A62-B87; | A62-B88; | A62-B89; |
| A62-B90; | A62-B91; | A62-B92; | A62-B93; | A62-B94; | A62-B95; |
| A62-B96; | A62-B97; | A62-B98; | A62-B99; | A62-B100; | A62-B101; |
| A62-B102; | A62-B103; | A62-B104; | A62-B105; | A62-B106; | A62-B107; |
| A62-B108; | A62-B109; | A62-B110; | A62-B111; | A62-B112; | A62-B113; |
| A62-B114; | A62-B115; | A62-B116; | A62-B117; | A62-B118; | A62-B119; |
| A62-B120; | A62-B121; | A62-B122; | A62-B123; | A62-B124; | A62-B125; |
| A62-B126; | A62-B127; | A62-B128; | A62-B129; | A62-B130; | A62-B131; |
| A62-B132; | A62-B133; | A62-B134; | A62-B135; | A62-B136; | A62-B137; |
| A62-B138; | A62-B139; | A62-B140; | A62-B141; | A62-B142; | A62-B143; |
| A62-B144; | A62-B145; | A62-B146; | A62-B147; | A62-B148; | A62-B149; |
| A62-B150; | A62-B151; | A62-B152; | A62-B153; | A62-B154; | A62-B155; |
| A62-B156; | A62-B157; | A62-B158; | A62-B159; | A62-B160; | A62-B161; |
| A62-B162; | A62-B163; | A62-B164; | A62-B165; | A62-B166; | A62-B167; |

-continued

A62-B168; A62-B169; A63-B1; A63-B2; A63-B3; A63-B4;
A63-B5; A63-B6; A63-B7; A63-B8; A63-B9; A63-B10;
A63-B11; A63-B12; A63-B13; A63-B14; A63-B15; A63-B16;
A63-B17; A63-B18; A63-B19; A63-B20; A63-B21; A63-B22;
A63-B23; A63-B24; A63-B25; A63-B26; A63-B27; A63-B28;
A63-B29; A63-B30; A63-B31; A63-B32; A63-B33; A63-B34;
A63-B35; A63-B36; A63-B37; A63-B38; A63-B39; A63-B40;
A63-B41; A63-B42; A63-B43; A63-B44; A63-B45; A63-B46;
A63-B47; A63-B48; A63-B49; A63-B50; A63-B51; A63-B52;
A63-B53; A63-B54; A63-B55; A63-B56; A63-B57; A63-B58;
A63-B59; A63-B60; A63-B61; A63-B62; A63-B63; A63-B64;
A63-B65; A63-B66; A63-B67; A63-B68; A63-B69; A63-B70;
A63-B71; A63-B72; A63-B73; A63-B74; A63-B75; A63-B76;
A63-B77; A63-B78; A63-B79; A63-B80; A63-B81; A63-B82;
A63-B83; A63-B84; A63-B85; A63-B86; A63-B87; A63-B88;
A63-B89; A63-B90; A63-B91; A63-B92; A63-B93; A63-B94;
A63-B95; A63-B96; A63-B97; A63-B98; A63-B99; A63-B100;
A63-B101; A63-B102; A63-B103; A63-B104; A63-B105; A63-B106;
A63-B107; A63-B108; A63-B109; A63-B110; A63-B111; A63-B112;
A63-B113; A63-B114; A63-B115; A63-B116; A63-B117; A63-B118;
A63-B119; A63-B120; A63-B121; A63-B122; A63-B123; A63-B124;
A63-B125; A63-B126; A63-B127; A63-B128; A63-B129; A63-B130;
A63-B131; A63-B132; A63-B133; A63-B134; A63-B135; A63-B136;
A63-B137; A63-B138; A63-B139; A63-B140; A63-B141; A63-B142;
A63-B143; A63-B144; A63-B145; A63-B146; A63-B147; A63-B148;
A63-B149; A63-B150; A63-B151; A63-B152; A63-B153; A63-B154;
A63-B155; A63-B156; A63-B157; A63-B158; A63-B159; A63-B160;
A63-B161; A63-B162; A63-B163; A63-B164; A63-B165; A63-B166;
A63-B167; A63-B168; A63-B169; A64-B1; A64-B2; A64-B3;
A64-B4; A64-B5; A64-B6; A64-B7; A64-B8; A64-B9;
A64-B10; A64-B11; A64-B12; A64-B13; A64-B14; A64-B15;
A64-B16; A64-B17; A64-B18; A64-B19; A64-B20; A64-B21;
A64-B22; A64-B23; A64-B24; A64-B25; A64-B26; A64-B27;
A64-B28; A64-B29; A64-B30; A64-B31; A64-B32; A64-B33;
A64-B34; A64-B35; A64-B36; A64-B37; A64-B38; A64-B39;
A64-B40; A64-B41; A64-B42; A64-B43; A64-B44; A64-B45;
A64-B46; A64-B47; A64-B48; A64-B49; A64-B50; A64-B51;
A64-B52; A64-B53; A64-B54; A64-B55; A64-B56; A64-B57;
A64-B58; A64-B59; A64-B60; A64-B61; A64-B62; A64-B63;
A64-B64; A64-B65; A64-B66; A64-B67; A64-B68; A64-B69;
A64-B70; A64-B71; A64-B72; A64-B73; A64-B74; A64-B75;
A64-B76; A64-B77; A64-B78; A64-B79; A64-B80; A64-B81;
A64-B82; A64-B83; A64-B84; A64-B85; A64-B86; A64-B87;
A64-B88; A64-B89; A64-B90; A64-B91; A64-B92; A64-B93;
A64-B94; A64-B95; A64-B96; A64-B97; A64-B98; A64-B99;
A64-B100; A64-B101; A64-B102; A64-B103; A64-B104; A64-B105;
A64-B106; A64-B107; A64-B108; A64-B109; A64-B110; A64-B111;
A64-B112; A64-B113; A64-B114; A64-B115; A64-B116; A64-B117;
A64-B118; A64-B119; A64-B120; A64-B121; A64-B122; A64-B123;
A64-B124; A64-B125; A64-B126; A64-B127; A64-B128; A64-B129;
A64-B130; A64-B131; A64-B132; A64-B133; A64-B134; A64-B135;
A64-B136; A64-B137; A64-B138; A64-B139; A64-B140; A64-B141;
A64-B142; A64-B143; A64-B144; A64-B145; A64-B146; A64-B147;
A64-B148; A64-B149; A64-B150; A64-B151; A64-B152; A64-B153;
A64-B154; A64-B155; A64-B156; A64-B157; A64-B158; A64-B159;
A64-B160; A64-B161; A64-B162; A64-B163; A64-B164; A64-B165;
A64-B166; A64-B167; A64-B168; A64-B169; A65-B1; A65-B2;
A65-B3; A65-B4; A65-B5; A65-B6; A65-B7; A65-B8;
A65-B9; A65-B10; A65-B11; A65-B12; A65-B13; A65-B14;
A65-B15; A65-B16; A65-B17; A65-B18; A65-B19; A65-B20;
A65-B21; A65-B22; A65-B23; A65-B24; A65-B25; A65-B26;
A65-B27; A65-B28; A65-B29; A65-B30; A65-B31; A65-B32;
A65-B33; A65-B34; A65-B35; A65-B36; A65-B37; A65-B38;
A65-B39; A65-B40; A65-B41; A65-B42; A65-B43; A65-B44;
A65-B45; A65-B46; A65-B47; A65-B48; A65-B49; A65-B50;
A65-B51; A65-B52; A65-B53; A65-B54; A65-B55; A65-B56;
A65-B57; A65-B58; A65-B59; A65-B60; A65-B61; A65-B62;
A65-B63; A65-B64; A65-B65; A65-B66; A65-B67; A65-B68;
A65-B69; A65-B70; A65-B71; A65-B72; A65-B73; A65-B74;
A65-B75; A65-B76; A65-B77; A65-B78; A65-B79; A65-B80;
A65-B81; A65-B82; A65-B83; A65-B84; A65-B85; A65-B86;
A65-B87; A65-B88; A65-B89; A65-B90; A65-B91; A65-B92;
A65-B93; A65-B94; A65-B95; A65-B96; A65-B97; A65-B98;
A65-B99; A65-B100; A65-B101; A65-B102; A65-B103; A65-B104;
A65-B105; A65-B106; A65-B107; A65-B108; A65-B109; A65-B110;
A65-B111; A65-B112; A65-B113; A65-B114; A65-B115; A65-B116;
A65-B117; A65-B118; A65-B119; A65-B120; A65-B121; A65-B122;
A65-B123; A65-B124; A65-B125; A65-B126; A65-B127; A65-B128;
A65-B129; A65-B130; A65-B131; A65-B132; A65-B133; A65-B134;
A65-B135; A65-B136; A65-B137; A65-B138; A65-B139; A65-B140;

-continued

A65-B141; A65-B142; A65-B143; A65-B144; A65-B145; A65-B146;
A65-B147; A65-B148; A65-B149; A65-B150; A65-B151; A65-B152;
A65-B153; A65-B154; A65-B155; A65-B156; A65-B157; A65-B158;
A65-B159; A65-B160; A65-B161; A65-B162; A65-B163; A65-B164;
A65-B165; A65-B166; A65-B167; A65-B168; A65-B169; A66-B1;
A66-B2; A66-B3; A66-B4; A66-B5; A66-B6; A66-B7;
A66-B8; A66-B9; A66-B10; A66-B11; A66-B12; A66-B13;
A66-B14; A66-B15; A66-B16; A66-B17; A66-B18; A66-B19;
A66-B20; A66-B21; A66-B22; A66-B23; A66-B24; A66-B25;
A66-B26; A66-B27; A66-B28; A66-B29; A66-B30; A66-B31;
A66-B32; A66-B33; A66-B34; A66-B35; A66-B36; A66-B37;
A66-B38; A66-B39; A66-B40; A66-B41; A66-B42; A66-B43;
A66-B44; A66-B45; A66-B46; A66-B47; A66-B48; A66-B49;
A66-B50; A66-B51; A66-B52; A66-B53; A66-B54; A66-B55;
A66-B56; A66-B57; A66-B58; A66-B59; A66-B60; A66-B61;
A66-B62; A66-B63; A66-B64; A66-B65; A66-B66; A66-B67;
A66-B68; A66-B69; A66-B70; A66-B71; A66-B72; A66-B73;
A66-B74; A66-B75; A66-B76; A66-B77; A66-B78; A66-B79;
A66-B80; A66-B81; A66-B82; A66-B83; A66-B84; A66-B85;
A66-B86; A66-B87; A66-B88; A66-B89; A66-B90; A66-B91;
A66-B92; A66-B93; A66-B94; A66-B95; A66-B96; A66-B97;
A66-B98; A66-B99; A66-B100; A66-B101; A66-B102; A66-B103;
A66-B104; A66-B105; A66-B106; A66-B107; A66-B108; A66-B109;
A66-B110; A66-B111; A66-B112; A66-B113; A66-B114; A66-B115;
A66-B116; A66-B117; A66-B118; A66-B119; A66-B120; A66-B121;
A66-B122; A66-B123; A66-B124; A66-B125; A66-B126; A66-B127;
A66-B128; A66-B129; A66-B130; A66-B131; A66-B132; A66-B133;
A66-B134; A66-B135; A66-B136; A66-B137; A66-B138; A66-B139;
A66-B140; A66-B141; A66-B142; A66-B143; A66-B144; A66-B145;
A66-B146; A66-B147; A66-B148; A66-B149; A66-B150; A66-B151;
A66-B152; A66-B153; A66-B154; A66-B155; A66-B156; A66-B157;
A66-B158; A66-B159; A66-B160; A66-B161; A66-B162; A66-B163;
A66-B164; A66-B165; A66-B166; A66-B167; A66-B168; A66-B169;
A67-B1; A67-B2; A67-B3; A67-B4; A67-B5; A67-B6;
A67-B7; A67-B8; A67-B9; A67-B10; A67-B11; A67-B12;
A67-B13; A67-B14; A67-B15; A67-B16; A67-B17; A67-B18;
A67-B19; A67-B20; A67-B21; A67-B22; A67-B23; A67-B24;
A67-B25; A67-B26; A67-B27; A67-B28; A67-B29; A67-B30;
A67-B31; A67-B32; A67-B33; A67-B34; A67-B35; A67-B36;
A67-B37; A67-B38; A67-B39; A67-B40; A67-B41; A67-B42;
A67-B43; A67-B44; A67-B45; A67-B46; A67-B47; A67-B48;
A67-B49; A67-B50; A67-B51; A67-B52; A67-B53; A67-B54;
A67-B55; A67-B56; A67-B57; A67-B58; A67-B59; A67-B60;
A67-B61; A67-B62; A67-B63; A67-B64; A67-B65; A67-B66;
A67-B67; A67-B68; A67-B69; A67-B70; A67-B71; A67-B72;
A67-B73; A67-B74; A67-B75; A67-B76; A67-B77; A67-B78;
A67-B79; A67-B80; A67-B81; A67-B82; A67-B83; A67-B84;
A67-B85; A67-B86; A67-B87; A67-B88; A67-B89; A67-B90;
A67-B91; A67-B92; A67-B93; A67-B94; A67-B95; A67-B96;
A67-B97; A67-B98; A67-B99; A67-B100; A67-B101; A67-B102;
A67-B103; A67-B104; A67-B105; A67-B106; A67-B107; A67-B108;
A67-B109; A67-B110; A67-B111; A67-B112; A67-B113; A67-B114;
A67-B115; A67-B116; A67-B117; A67-B118; A67-B119; A67-B120;
A67-B121; A67-B122; A67-B123; A67-B124; A67-B125; A67-B126;
A67-B127; A67-B128; A67-B129; A67-B130; A67-B131; A67-B132;
A67-B133; A67-B134; A67-B135; A67-B136; A67-B137; A67-B138;
A67-B139; A67-B140; A67-B141; A67-B142; A67-B143; A67-B144;
A67-B145; A67-B146; A67-B147; A67-B148; A67-B149; A67-B150;
A67-B151; A67-B152; A67-B153; A67-B154; A67-B155; A67-B156;
A67-B157; A67-B158; A67-B159; A67-B160; A67-B161; A67-B162;
A67-B163; A67-B164; A67-B165; A67-B166; A67-B167; A67-B168;
A67-B169; A68-B1; A68-B2; A68-B3; A68-B4; A68-B5;
A68-B6; A68-B7; A68-B8; A68-B9; A68-B10; A68-B11;
A68-B12; A68-B13; A68-B14; A68-B15; A68-B16; A68-B17;
A68-B18; A68-B19; A68-B20; A68-B21; A68-B22; A68-B23;
A68-B24; A68-B25; A68-B26; A68-B27; A68-B28; A68-B29;
A68-B30; A68-B31; A68-B32; A68-B33; A68-B34; A68-B35;
A68-B36; A68-B37; A68-B38; A68-B39; A68-B40; A68-B41;
A68-B42; A68-B43; A68-B44; A68-B45; A68-B46; A68-B47;
A68-B48; A68-B49; A68-B50; A68-B51; A68-B52; A68-B53;
A68-B54; A68-B55; A68-B56; A68-B57; A68-B58; A68-B59;
A68-B60; A68-B61; A68-B62; A68-B63; A68-B64; A68-B65;
A68-B66; A68-B67; A68-B68; A68-B69; A68-B70; A68-B71;
A68-B72; A68-B73; A68-B74; A68-B75; A68-B76; A68-B77;
A68-B78; A68-B79; A68-B80; A68-B81; A68-B82; A68-B83;
A68-B84; A68-B85; A68-B86; A68-B87; A68-B88; A68-B89;
A68-B90; A68-B91; A68-B92; A68-B93; A68-B94; A68-B95;
A68-B96; A68-B97; A68-B98; A68-B99; A68-B100; A68-B101;
A68-B102; A68-B103; A68-B104; A68-B105; A68-B106; A68-B107;
A68-B108; A68-B109; A68-B110; A68-B111; A68-B112; A68-B113;

-continued

A68-B114; A68-B115; A68-B116; A68-B117; A68-B118; A68-B119;
A68-B120; A68-B121; A68-B122; A68-B123; A68-B124; A68-B125;
A68-B126; A68-B127; A68-B128; A68-B129; A68-B130; A68-B131;
A68-B132; A68-B133; A68-B134; A68-B135; A68-B136; A68-B137;
A68-B138; A68-B139; A68-B140; A68-B141; A68-B142; A68-B143;
A68-B144; A68-B145; A68-B146; A68-B147; A68-B148; A68-B149;
A68-B150; A68-B151; A68-B152; A68-B153; A68-B154; A68-B155;
A68-B156; A68-B157; A68-B158; A68-B159; A68-B160; A68-B161;
A68-B162; A68-B163; A68-B164; A68-B165; A68-B166; A68-B167;
A68-B168; A68-B169; A69-B1; A69-B2; A69-B3; A69-B4;
A69-B5; A69-B6; A69-B7; A69-B8; A69-B9; A69-B10;
A69-B11; A69-B12; A69-B13; A69-B14; A69-B15; A69-B16;
A69-B17; A69-B18; A69-B19; A69-B20; A69-B21; A69-B22;
A69-B23; A69-B24; A69-B25; A69-B26; A69-B27; A69-B28;
A69-B29; A69-B30; A69-B31; A69-B32; A69-B33; A69-B34;
A69-B35; A69-B36; A69-B37; A69-B38; A69-B39; A69-B40;
A69-B41; A69-B42; A69-B43; A69-B44; A69-B45; A69-B46;
A69-B47; A69-B48; A69-B49; A69-B50; A69-B51; A69-B52;
A69-B53; A69-B54; A69-B55; A69-B56; A69-B57; A69-B58;
A69-B59; A69-B60; A69-B61; A69-B62; A69-B63; A69-B64;
A69-B65; A69-B66; A69-B67; A69-B68; A69-B69; A69-B70;
A69-B71; A69-B72; A69-B73; A69-B74; A69-B75; A69-B76;
A69-B77; A69-B78; A69-B79; A69-B80; A69-B81; A69-B82;
A69-B83; A69-B84; A69-B85; A69-B86; A69-B87; A69-B88;
A69-B89; A69-B90; A69-B91; A69-B92; A69-B93; A69-B94;
A69-B95; A69-B96; A69-B97; A69-B98; A69-B99; A69-B100;
A69-B101; A69-B102; A69-B103; A69-B104; A69-B105; A69-B106;
A69-B107; A69-B108; A69-B109; A69-B110; A69-B111; A69-B112;
A69-B113; A69-B114; A69-B115; A69-B116; A69-B117; A69-B118;
A69-B119; A69-B120; A69-B121; A69-B122; A69-B123; A69-B124;
A69-B125; A69-B126; A69-B127; A69-B128; A69-B129; A69-B130;
A69-B131; A69-B132; A69-B133; A69-B134; A69-B135; A69-B136;
A69-B137; A69-B138; A69-B139; A69-B140; A69-B141; A69-B142;
A69-B143; A69-B144; A69-B145; A69-B146; A69-B147; A69-B148;
A69-B149; A69-B150; A69-B151; A69-B152; A69-B153; A69-B154;
A69-B155; A69-B156; A69-B157; A69-B158; A69-B159; A69-B160;
A69-B161; A69-B162; A69-B163; A69-B164; A69-B165; A69-B166;
A69-B167; A69-B168; A69-B169; A70-B1; A70-B2; A70-B3;
A70-B4; A70-B5; A70-B6; A70-B7; A70-B8; A70-B9;
A70-B10; A70-B11; A70-B12; A70-B13; A70-B14; A70-B15;
A70-B16; A70-B17; A70-B18; A70-B19; A70-B20; A70-B21;
A70-B22; A70-B23; A70-B24; A70-B25; A70-B26; A70-B27;
A70-B28; A70-B29; A70-B30; A70-B31; A70-B32; A70-B33;
A70-B34; A70-B35; A70-B36; A70-B37; A70-B38; A70-B39;
A70-B40; A70-B41; A70-B42; A70-B43; A70-B44; A70-B45;
A70-B46; A70-B47; A70-B48; A70-B49; A70-B50; A70-B51;
A70-B52; A70-B53; A70-B54; A70-B55; A70-B56; A70-B57;
A70-B58; A70-B59; A70-B60; A70-B61; A70-B62; A70-B63;
A70-B64; A70-B65; A70-B66; A70-B67; A70-B68; A70-B69;
A70-B70; A70-B71; A70-B72; A70-B73; A70-B74; A70-B75;
A70-B76; A70-B77; A70-B78; A70-B79; A70-B80; A70-B81;
A70-B82; A70-B83; A70-B84; A70-B85; A70-B86; A70-B87;
A70-B88; A70-B89; A70-B90; A70-B91; A70-B92; A70-B93;
A70-B94; A70-B95; A70-B96; A70-B97; A70-B98; A70-B99;
A70-B100; A70-B101; A70-B102; A70-B103; A70-B104; A70-B105;
A70-B106; A70-B107; A70-B108; A70-B109; A70-B110; A70-B111;
A70-B112; A70-B113; A70-B114; A70-B115; A70-B116; A70-B117;
A70-B118; A70-B119; A70-B120; A70-B121; A70-B122; A70-B123;
A70-B124; A70-B125; A70-B126; A70-B127; A70-B128; A70-B129;
A70-B130; A70-B131; A70-B132; A70-B133; A70-B134; A70-B135;
A70-B136; A70-B137; A70-B138; A70-B139; A70-B140; A70-B141;
A70-B142; A70-B143; A70-B144; A70-B145; A70-B146; A70-B147;
A70-B148; A70-B149; A70-B150; A70-B151; A70-B152; A70-B153;
A70-B154; A70-B155; A70-B156; A70-B157; A70-B158; A70-B159;
A70-B160; A70-B161; A70-B162; A70-B163; A70-B164; A70-B165;
A70-B166; A70-B167; A70-B168; A70-B169; A71-B1; A71-B2;
A71-B3; A71-B4; A71-B5; A71-B6; A71-B7; A71-B8;
A71-B9; A71-B10; A71-B11; A71-B12; A71-B13; A71-B14;
A71-B15; A71-B16; A71-B17; A71-B18; A71-B19; A71-B20;
A71-B21; A71-B22; A71-B23; A71-B24; A71-B25; A71-B26;
A71-B27; A71-B28; A71-B29; A71-B30; A71-B31; A71-B32;
A71-B33; A71-B34; A71-B35; A71-B36; A71-B37; A71-B38;
A71-B39; A71-B40; A71-B41; A71-B42; A71-B43; A71-B44;
A71-B45; A71-B46; A71-B47; A71-B48; A71-B49; A71-B50;
A71-B51; A71-B52; A71-B53; A71-B54; A71-B55; A71-B56;
A71-B57; A71-B58; A71-B59; A71-B60; A71-B61; A71-B62;
A71-B63; A71-B64; A71-B65; A71-B66; A71-B67; A71-B68;
A71-B69; A71-B70; A71-B71; A71-B72; A71-B73; A71-B74;
A71-B75; A71-B76; A71-B77; A71-B78; A71-B79; A71-B80;
A71-B81; A71-B82; A71-B83; A71-B84; A71-B85; A71-B86;

-continued

| | | | | | |
|---|---|---|---|---|---|
| A71-B87; | A71-B88; | A71-B89; | A71-B90; | A71-B91; | A71-B92; |
| A71-B93; | A71-B94; | A71-B95; | A71-B96; | A71-B97; | A71-B98; |
| A71-B99; | A71-B100; | A71-B101; | A71-B102; | A71-B103; | A71-B104; |
| A71-B105; | A71-B106; | A71-B107; | A71-B108; | A71-B109; | A71-B110; |
| A71-B111; | A71-B112; | A71-B113; | A71-B114; | A71-B115; | A71-B116; |
| A71-B117; | A71-B118; | A71-B119; | A71-B120; | A71-B121; | A71-B122; |
| A71-B123; | A71-B124; | A71-B125; | A71-B126; | A71-B127; | A71-B128; |
| A71-B129; | A71-B130; | A71-B131; | A71-B132; | A71-B133; | A71-B134; |
| A71-B135; | A71-B136; | A71-B137; | A71-B138; | A71-B139; | A71-B140; |
| A71-B141; | A71-B142; | A71-B143; | A71-B144; | A71-B145; | A71-B146; |
| A71-B147; | A71-B148; | A71-B149; | A71-B150; | A71-B151; | A71-B152; |
| A71-B153; | A71-B154; | A71-B155; | A71-B156; | A71-B157; | A71-B158; |
| A71-B159; | A71-B160; | A71-B161; | A71-B162; | A71-B163; | A71-B164; |
| A71-B165; | A71-B166; | A71-B167; | A71-B168; | A71-B169; | A72-B1; |
| A72-B2; | A72-B3; | A72-B4; | A72-B5; | A72-B6; | A72-B7; |
| A72-B8; | A72-B9; | A72-B10; | A72-B11; | A72-B12; | A72-B13; |
| A72-B14; | A72-B15; | A72-B16; | A72-B17; | A72-B18; | A72-B19; |
| A72-B20; | A72-B21; | A72-B22; | A72-B23; | A72-B24; | A72-B25; |
| A72-B26; | A72-B27; | A72-B28; | A72-B29; | A72-B30; | A72-B31; |
| A72-B32; | A72-B33; | A72-B34; | A72-B35; | A72-B36; | A72-B37; |
| A72-B38; | A72-B39; | A72-B40; | A72-B41; | A72-B42; | A72-B43; |
| A72-B44; | A72-B45; | A72-B46; | A72-B47; | A72-B48; | A72-B49; |
| A72-B50; | A72-B51; | A72-B52; | A72-B53; | A72-B54; | A72-B55; |
| A72-B56; | A72-B57; | A72-B58; | A72-B59; | A72-B60; | A72-B61; |
| A72-B62; | A72-B63; | A72-B64; | A72-B65; | A72-B66; | A72-B67; |
| A72-B68; | A72-B69; | A72-B70; | A72-B71; | A72-B72; | A72-B73; |
| A72-B74; | A72-B75; | A72-B76; | A72-B77; | A72-B78; | A72-B79; |
| A72-B80; | A72-B81; | A72-B82; | A72-B83; | A72-B84; | A72-B85; |
| A72-B86; | A72-B87; | A72-B88; | A72-B89; | A72-B90; | A72-B91; |
| A72-B92; | A72-B93; | A72-B94; | A72-B95; | A72-B96; | A72-B97; |
| A72-B98; | A72-B99; | A72-B100; | A72-B101; | A72-B102; | A72-B103; |
| A72-B104; | A72-B105; | A72-B106; | A72-B107; | A72-B108; | A72-B109; |
| A72-B110; | A72-B111; | A72-B112; | A72-B113; | A72-B114; | A72-B115; |
| A72-B116; | A72-B117; | A72-B118; | A72-B119; | A72-B120; | A72-B121; |
| A72-B122; | A72-B123; | A72-B124; | A72-B125; | A72-B126; | A72-B127; |
| A72-B128; | A72-B129; | A72-B130; | A72-B131; | A72-B132; | A72-B133; |
| A72-B134; | A72-B135; | A72-B136; | A72-B137; | A72-B138; | A72-B139; |
| A72-B140; | A72-B141; | A72-B142; | A72-B143; | A72-B144; | A72-B145; |
| A72-B146; | A72-B147; | A72-B148; | A72-B149; | A72-B150; | A72-B151; |
| A72-B152; | A72-B153; | A72-B154; | A72-B155; | A72-B156; | A72-B157; |
| A72-B158; | A72-B159; | A72-B160; | A72-B161; | A72-B162; | A72-B163; |
| A72-B164; | A72-B165; | A72-B166; | A72-B167; | A72-B168; | A72-B169; |
| A73-B1; | A73-B2; | A73-B3; | A73-B4; | A73-B5; | A73-B6; |
| A73-B7; | A73-B8; | A73-B9; | A73-B10; | A73-B11; | A73-B12; |
| A73-B13; | A73-B14; | A73-B15; | A73-B16; | A73-B17; | A73-B18; |
| A73-B19; | A73-B20; | A73-B21; | A73-B22; | A73-B23; | A73-B24; |
| A73-B25; | A73-B26; | A73-B27; | A73-B28; | A73-B29; | A73-B30; |
| A73-B31; | A73-B32; | A73-B33; | A73-B34; | A73-B35; | A73-B36; |
| A73-B37; | A73-B38; | A73-B39; | A73-B40; | A73-B41; | A73-B42; |
| A73-B43; | A73-B44; | A73-B45; | A73-B46; | A73-B47; | A73-B48; |
| A73-B49; | A73-B50; | A73-B51; | A73-B52; | A73-B53; | A73-B54; |
| A73-B55; | A73-B56; | A73-B57; | A73-B58; | A73-B59; | A73-B60; |
| A73-B61; | A73-B62; | A73-B63; | A73-B64; | A73-B65; | A73-B66; |
| A73-B67; | A73-B68; | A73-B69; | A73-B70; | A73-B71; | A73-B72; |
| A73-B73; | A73-B74; | A73-B75; | A73-B76; | A73-B77; | A73-B78; |
| A73-B79; | A73-B80; | A73-B81; | A73-B82; | A73-B83; | A73-B84; |
| A73-B85; | A73-B86; | A73-B87; | A73-B88; | A73-B89; | A73-B90; |
| A73-B91; | A73-B92; | A73-B93; | A73-B94; | A73-B95; | A73-B96; |
| A73-B97; | A73-B98; | A73-B99; | A73-B100; | A73-B101; | A73-B102; |
| A73-B103; | A73-B104; | A73-B105; | A73-B106; | A73-B107; | A73-B108; |
| A73-B109; | A73-B110; | A73-B111; | A73-B112; | A73-B113; | A73-B114; |
| A73-B115; | A73-B116; | A73-B117; | A73-B118; | A73-B119; | A73-B120; |
| A73-B121; | A73-B122; | A73-B123; | A73-B124; | A73-B125; | A73-B126; |
| A73-B127; | A73-B128; | A73-B129; | A73-B130; | A73-B131; | A73-B132; |
| A73-B133; | A73-B134; | A73-B135; | A73-B136; | A73-B137; | A73-B138; |
| A73-B139; | A73-B140; | A73-B141; | A73-B142; | A73-B143; | A73-B144; |
| A73-B145; | A73-B146; | A73-B147; | A73-B148; | A73-B149; | A73-B150; |
| A73-B151; | A73-B152; | A73-B153; | A73-B154; | A73-B155; | A73-B156; |
| A73-B157; | A73-B158; | A73-B159; | A73-B160; | A73-B161; | A73-B162; |
| A73-B163; | A73-B164; | A73-B165; | A73-B166; | A73-B167; | A73-B168; |
| A73-B169; | A74-B1; | A74-B2; | A74-B3; | A74-B4; | A74-B5; |
| A74-B6; | A74-B7; | A74-B8; | A74-B9; | A74-B10; | A74-B11; |
| A74-B12; | A74-B13; | A74-B14; | A74-B15; | A74-B16; | A74-B17; |
| A74-B18; | A74-B19; | A74-B20; | A74-B21; | A74-B22; | A74-B23; |
| A74-B24; | A74-B25; | A74-B26; | A74-B27; | A74-B28; | A74-B29; |
| A74-B30; | A74-B31; | A74-B32; | A74-B33; | A74-B34; | A74-B35; |
| A74-B36; | A74-B37; | A74-B38; | A74-B39; | A74-B40; | A74-B41; |
| A74-B42; | A74-B43; | A74-B44; | A74-B45; | A74-B46; | A74-B47; |
| A74-B48; | A74-B49; | A74-B50; | A74-B51; | A74-B52; | A74-B53; |
| A74-B54; | A74-B55; | A74-B56; | A74-B57; | A74-B58; | A74-B59; |

-continued

A74-B60; A74-B61; A74-B62; A74-B63; A74-B64; A74-B65;
A74-B66; A74-B67; A74-B68; A74-B69; A74-B70; A74-B71;
A74-B72; A74-B73; A74-B74; A74-B75; A74-B76; A74-B77;
A74-B78; A74-B79; A74-B80; A74-B81; A74-B82; A74-B83;
A74-B84; A74-B85; A74-B86; A74-B87; A74-B88; A74-B89;
A74-B90; A74-B91; A74-B92; A74-B93; A74-B94; A74-B95;
A74-B96; A74-B97; A74-B98; A74-B99; A74-B100; A74-B101;
A74-B102; A74-B103; A74-B104; A74-B105; A74-B106; A74-B107;
A74-B108; A74-B109; A74-B110; A74-B111; A74-B112; A74-B113;
A74-B114; A74-B115; A74-B116; A74-B117; A74-B118; A74-B119;
A74-B120; A74-B121; A74-B122; A74-B123; A74-B124; A74-B125;
A74-B126; A74-B127; A74-B128; A74-B129; A74-B130; A74-B131;
A74-B132; A74-B133; A74-B134; A74-B135; A74-B136; A74-B137;
A74-B138; A74-B139; A74-B140; A74-B141; A74-B142; A74-B143;
A74-B144; A74-B145; A74-B146; A74-B147; A74-B148; A74-B149;
A74-B150; A74-B151; A74-B152; A74-B153; A74-B154; A74-B155;
A74-B156; A74-B157; A74-B158; A74-B159; A74-B160; A74-B161;
A74-B162; A74-B163; A74-B164; A74-B165; A74-B166; A74-B167;
A74-B168; A74-B169; A75-B1; A75-B2; A75-B3; A75-B4;
A75-B5; A75-B6; A75-B7; A75-B8; A75-B9; A75-B10;
A75-B11; A75-B12; A75-B13; A75-B14; A75-B15; A75-B16;
A75-B17; A75-B18; A75-B19; A75-B20; A75-B21; A75-B22;
A75-B23; A75-B24; A75-B25; A75-B26; A75-B27; A75-B28;
A75-B29; A75-B30; A75-B31; A75-B32; A75-B33; A75-B34;
A75-B35; A75-B36; A75-B37; A75-B38; A75-B39; A75-B40;
A75-B41; A75-B42; A75-B43; A75-B44; A75-B45; A75-B46;
A75-B47; A75-B48; A75-B49; A75-B50; A75-B51; A75-B52;
A75-B53; A75-B54; A75-B55; A75-B56; A75-B57; A75-B58;
A75-B59; A75-B60; A75-B61; A75-B62; A75-B63; A75-B64;
A75-B65; A75-B66; A75-B67; A75-B68; A75-B69; A75-B70;
A75-B71; A75-B72; A75-B73; A75-B74; A75-B75; A75-B76;
A75-B77; A75-B78; A75-B79; A75-B80; A75-B81; A75-B82;
A75-B83; A75-B84; A75-B85; A75-B86; A75-B87; A75-B88;
A75-B89; A75-B90; A75-B91; A75-B92; A75-B93; A75-B94;
A75-B95; A75-B96; A75-B97; A75-B98; A75-B99; A75-B100;
A75-B101; A75-B102; A75-B103; A75-B104; A75-B105; A75-B106;
A75-B107; A75-B108; A75-B109; A75-B110; A75-B111; A75-B112;
A75-B113; A75-B114; A75-B115; A75-B116; A75-B117; A75-B118;
A75-B119; A75-B120; A75-B121; A75-B122; A75-B123; A75-B124;
A75-B125; A75-B126; A75-B127; A75-B128; A75-B129; A75-B130;
A75-B131; A75-B132; A75-B133; A75-B134; A75-B135; A75-B136;
A75-B137; A75-B138; A75-B139; A75-B140; A75-B141; A75-B142;
A75-B143; A75-B144; A75-B145; A75-B146; A75-B147; A75-B148;
A75-B149; A75-B150; A75-B151; A75-B152; A75-B153; A75-B154;
A75-B155; A75-B156; A75-B157; A75-B158; A75-B159; A75-B160;
A75-B161; A75-B162; A75-B163; A75-B164; A75-B165; A75-B166;
A75-B167; A75-B168; A75-B169; A76-B1; A76-B2; A76-B3;
A76-B4; A76-B5; A76-B6; A76-B7; A76-B8; A76-B9;
A76-B10; A76-B11; A76-B12; A76-B13; A76-B14; A76-B15;
A76-B16; A76-B17; A76-B18; A76-B19; A76-B20; A76-B21;
A76-B22; A76-B23; A76-B24; A76-B25; A76-B26; A76-B27;
A76-B28; A76-B29; A76-B30; A76-B31; A76-B32; A76-B33;
A76-B34; A76-B35; A76-B36; A76-B37; A76-B38; A76-B39;
A76-B40; A76-B41; A76-B42; A76-B43; A76-B44; A76-B45;
A76-B46; A76-B47; A76-B48; A76-B49; A76-B50; A76-B51;
A76-B52; A76-B53; A76-B54; A76-B55; A76-B56; A76-B57;
A76-B58; A76-B59; A76-B60; A76-B61; A76-B62; A76-B63;
A76-B64; A76-B65; A76-B66; A76-B67; A76-B68; A76-B69;
A76-B70; A76-B71; A76-B72; A76-B73; A76-B74; A76-B75;
A76-B76; A76-B77; A76-B78; A76-B79; A76-B80; A76-B81;
A76-B82; A76-B83; A76-B84; A76-B85; A76-B86; A76-B87;
A76-B88; A76-B89; A76-B90; A76-B91; A76-B92; A76-B93;
A76-B94; A76-B95; A76-B96; A76-B97; A76-B98; A76-B99;
A76-B100; A76-B101; A76-B102; A76-B103; A76-B104; A76-B105;
A76-B106; A76-B107; A76-B108; A76-B109; A76-B110; A76-B111;
A76-B112; A76-B113; A76-B114; A76-B115; A76-B116; A76-B117;
A76-B118; A76-B119; A76-B120; A76-B121; A76-B122; A76-B123;
A76-B124; A76-B125; A76-B126; A76-B127; A76-B128; A76-B129;
A76-B130; A76-B131; A76-B132; A76-B133; A76-B134; A76-B135;
A76-B136; A76-B137; A76-B138; A76-B139; A76-B140; A76-B141;
A76-B142; A76-B143; A76-B144; A76-B145; A76-B146; A76-B147;
A76-B148; A76-B149; A76-B150; A76-B151; A76-B152; A76-B153;
A76-B154; A76-B155; A76-B156; A76-B157; A76-B158; A76-B159;
A76-B160; A76-B161; A76-B162; A76-B163; A76-B164; A76-B165;
A76-B166; A76-B167; A76-B168; A76-B169; A77-B1; A77-B2;
A77-B3; A77-B4; A77-B5; A77-B6; A77-B7; A77-B8;
A77-B9; A77-B10; A77-B11; A77-B12; A77-B13; A77-B14;
A77-B15; A77-B16; A77-B17; A77-B18; A77-B19; A77-B20;
A77-B21; A77-B22; A77-B23; A77-B24; A77-B25; A77-B26;
A77-B27; A77-B28; A77-B29; A77-B30; A77-B31; A77-B32;

-continued

| | | | | | |
|---|---|---|---|---|---|
| A77-B33; | A77-B34; | A77-B35; | A77-B36; | A77-B37; | A77-B38; |
| A77-B39; | A77-B40; | A77-B41; | A77-B42; | A77-B43; | A77-B44; |
| A77-B45; | A77-B46; | A77-B47; | A77-B48; | A77-B49; | A77-B50; |
| A77-B51; | A77-B52; | A77-B53; | A77-B54; | A77-B55; | A77-B56; |
| A77-B57; | A77-B58; | A77-B59; | A77-B60; | A77-B61; | A77-B62; |
| A77-B63; | A77-B64; | A77-B65; | A77-B66; | A77-B67; | A77-B68; |
| A77-B69; | A77-B70; | A77-B71; | A77-B72; | A77-B73; | A77-B74; |
| A77-B75; | A77-B76; | A77-B77; | A77-B78; | A77-B79; | A77-B80; |
| A77-B81; | A77-B82; | A77-B83; | A77-B84; | A77-B85; | A77-B86; |
| A77-B87; | A77-B88; | A77-B89; | A77-B90; | A77-B91; | A77-B92; |
| A77-B93; | A77-B94; | A77-B95; | A77-B96; | A77-B97; | A77-B98; |
| A77-B99; | A77-B100; | A77-B101; | A77-B102; | A77-B103; | A77-B104; |
| A77-B105; | A77-B106; | A77-B107; | A77-B108; | A77-B109; | A77-B110; |
| A77-B111; | A77-B112; | A77-B113; | A77-B114; | A77-B115; | A77-B116; |
| A77-B117; | A77-B118; | A77-B119; | A77-B120; | A77-B121; | A77-B122; |
| A77-B123; | A77-B124; | A77-B125; | A77-B126; | A77-B127; | A77-B128; |
| A77-B129; | A77-B130; | A77-B131; | A77-B132; | A77-B133; | A77-B134; |
| A77-B135; | A77-B136; | A77-B137; | A77-B138; | A77-B139; | A77-B140; |
| A77-B141; | A77-B142; | A77-B143; | A77-B144; | A77-B145; | A77-B146; |
| A77-B147; | A77-B148; | A77-B149; | A77-B150; | A77-B151; | A77-B152; |
| A77-B153; | A77-B154; | A77-B155; | A77-B156; | A77-B157; | A77-B158; |
| A77-B159; | A77-B160; | A77-B161; | A77-B162; | A77-B163; | A77-B164; |
| A77-B165; | A77-B166; | A77-B167; | A77-B168; | A77-B169; | A78-B1; |
| A78-B2; | A78-B3; | A78-B4; | A78-B5; | A78-B6; | A78-B7; |
| A78-B8; | A78-B9; | A78-B10; | A78-B11; | A78-B12; | A78-B13; |
| A78-B14; | A78-B15; | A78-B16; | A78-B17; | A78-B18; | A78-B19; |
| A78-B20; | A78-B21; | A78-B22; | A78-B23; | A78-B24; | A78-B25; |
| A78-B26; | A78-B27; | A78-B28; | A78-B29; | A78-B30; | A78-B31; |
| A78-B32; | A78-B33; | A78-B34; | A78-B35; | A78-B36; | A78-B37; |
| A78-B38; | A78-B39; | A78-B40; | A78-B41; | A78-B42; | A78-B43; |
| A78-B44; | A78-B45; | A78-B46; | A78-B47; | A78-B48; | A78-B49; |
| A78-B50; | A78-B51; | A78-B52; | A78-B53; | A78-B54; | A78-B55; |
| A78-B56; | A78-B57; | A78-B58; | A78-B59; | A78-B60; | A78-B61; |
| A78-B62; | A78-B63; | A78-B64; | A78-B65; | A78-B66; | A78-B67; |
| A78-B68; | A78-B69; | A78-B70; | A78-B71; | A78-B72; | A78-B73; |
| A78-B74; | A78-B75; | A78-B76; | A78-B77; | A78-B78; | A78-B79; |
| A78-B80; | A78-B81; | A78-B82; | A78-B83; | A78-B84; | A78-B85; |
| A78-B86; | A78-B87; | A78-B88; | A78-B89; | A78-B90; | A78-B91; |
| A78-B92; | A78-B93; | A78-B94; | A78-B95; | A78-B96; | A78-B97; |
| A78-B98; | A78-B99; | A78-B100; | A78-B101; | A78-B102; | A78-B103; |
| A78-B104; | A78-B105; | A78-B106; | A78-B107; | A78-B108; | A78-B109; |
| A78-B110; | A78-B111; | A78-B112; | A78-B113; | A78-B114; | A78-B115; |
| A78-B116; | A78-B117; | A78-B118; | A78-B119; | A78-B120; | A78-B121; |
| A78-B122; | A78-B123; | A78-B124; | A78-B125; | A78-B126; | A78-B127; |
| A78-B128; | A78-B129; | A78-B130; | A78-B131; | A78-B132; | A78-B133; |
| A78-B134; | A78-B135; | A78-B136; | A78-B137; | A78-B138; | A78-B139; |
| A78-B140; | A78-B141; | A78-B142; | A78-B143; | A78-B144; | A78-B145; |
| A78-B146; | A78-B147; | A78-B148; | A78-B149; | A78-B150; | A78-B151; |
| A78-B152; | A78-B153; | A78-B154; | A78-B155; | A78-B156; | A78-B157; |
| A78-B158; | A78-B159; | A78-B160; | A78-B161; | A78-B162; | A78-B163; |
| A78-B164; | A78-B165; | A78-B166; | A78-B167; | A78-B168; | A78-B169; |
| A79-B1; | A79-B2; | A79-B3; | A79-B4; | A79-B5; | A79-B6; |
| A79-B7; | A79-B8; | A79-B9; | A79-B10; | A79-B11; | A79-B12; |
| A79-B13; | A79-B14; | A79-B15; | A79-B16; | A79-B17; | A79-B18; |
| A79-B19; | A79-B20; | A79-B21; | A79-B22; | A79-B23; | A79-B24; |
| A79-B25; | A79-B26; | A79-B27; | A79-B28; | A79-B29; | A79-B30; |
| A79-B31; | A79-B32; | A79-B33; | A79-B34; | A79-B35; | A79-B36; |
| A79-B37; | A79-B38; | A79-B39; | A79-B40; | A79-B41; | A79-B42; |
| A79-B43; | A79-B44; | A79-B45; | A79-B46; | A79-B47; | A79-B48; |
| A79-B49; | A79-B50; | A79-B51; | A79-B52; | A79-B53; | A79-B54; |
| A79-B55; | A79-B56; | A79-B57; | A79-B58; | A79-B59; | A79-B60; |
| A79-B61; | A79-B62; | A79-B63; | A79-B64; | A79-B65; | A79-B66; |
| A79-B67; | A79-B68; | A79-B69; | A79-B70; | A79-B71; | A79-B72; |
| A79-B73; | A79-B74; | A79-B75; | A79-B76; | A79-B77; | A79-B78; |
| A79-B79; | A79-B80; | A79-B81; | A79-B82; | A79-B83; | A79-B84; |
| A79-B85; | A79-B86; | A79-B87; | A79-B88; | A79-B89; | A79-B90; |
| A79-B91; | A79-B92; | A79-B93; | A79-B94; | A79-B95; | A79-B96; |
| A79-B97; | A79-B98; | A79-B99; | A79-B100; | A79-B101; | A79-B102; |
| A79-B103; | A79-B104; | A79-B105; | A79-B106; | A79-B107; | A79-B108; |
| A79-B109; | A79-B110; | A79-B111; | A79-B112; | A79-B113; | A79-B114; |
| A79-B115; | A79-B116; | A79-B117; | A79-B118; | A79-B119; | A79-B120; |
| A79-B121; | A79-B122; | A79-B123; | A79-B124; | A79-B125; | A79-B126; |
| A79-B127; | A79-B128; | A79-B129; | A79-B130; | A79-B131; | A79-B132; |
| A79-B133; | A79-B134; | A79-B135; | A79-B136; | A79-B137; | A79-B138; |
| A79-B139; | A79-B140; | A79-B141; | A79-B142; | A79-B143; | A79-B144; |
| A79-B145; | A79-B146; | A79-B147; | A79-B148; | A79-B149; | A79-B150; |
| A79-B151; | A79-B152; | A79-B153; | A79-B154; | A79-B155; | A79-B156; |
| A79-B157; | A79-B158; | A79-B159; | A79-B160; | A79-B161; | A79-B162; |
| A79-B163; | A79-B164; | A79-B165; | A79-B166; | A79-B167; | A79-B168; |
| A79-B169; | A80-B1; | A80-B2; | A80-B3; | A80-B4; | A80-B5; |

-continued

| | | | | | |
|---|---|---|---|---|---|
| A80-B6; | A80-B7; | A80-B8; | A80-B9; | A80-B10; | A80-B11; |
| A80-B12; | A80-B13; | A80-B14; | A80-B15; | A80-B16; | A80-B17; |
| A80-B18; | A80-B19; | A80-B20; | A80-B21; | A80-B22; | A80-B23; |
| A80-B24; | A80-B25; | A80-B26; | A80-B27; | A80-B28; | A80-B29; |
| A80-B30; | A80-B31; | A80-B32; | A80-B33; | A80-B34; | A80-B35; |
| A80-B36; | A80-B37; | A80-B38; | A80-B39; | A80-B40; | A80-B41; |
| A80-B42; | A80-B43; | A80-B44; | A80-B45; | A80-B46; | A80-B47; |
| A80-B48; | A80-B49; | A80-B50; | A80-B51; | A80-B52; | A80-B53; |
| A80-B54; | A80-B55; | A80-B56; | A80-B57; | A80-B58; | A80-B59; |
| A80-B60; | A80-B61; | A80-B62; | A80-B63; | A80-B64; | A80-B65; |
| A80-B66; | A80-B67; | A80-B68; | A80-B69; | A80-B70; | A80-B71; |
| A80-B72; | A80-B73; | A80-B74; | A80-B75; | A80-B76; | A80-B77; |
| A80-B78; | A80-B79; | A80-B80; | A80-B81; | A80-B82; | A80-B83; |
| A80-B84; | A80-B85; | A80-B86; | A80-B87; | A80-B88; | A80-B89; |
| A80-B90; | A80-B91; | A80-B92; | A80-B93; | A80-B94; | A80-B95; |
| A80-B96; | A80-B97; | A80-B98; | A80-B99; | A80-B100; | A80-B101; |
| A80-B102; | A80-B103; | A80-B104; | A80-B105; | A80-B106; | A80-B107; |
| A80-B108; | A80-B109; | A80-B110; | A80-B111; | A80-B112; | A80-B113; |
| A80-B114; | A80-B115; | A80-B116; | A80-B117; | A80-B118; | A80-B119; |
| A80-B120; | A80-B121; | A80-B122; | A80-B123; | A80-B124; | A80-B125; |
| A80-B126; | A80-B127; | A80-B128; | A80-B129; | A80-B130; | A80-B131; |
| A80-B132; | A80-B133; | A80-B134; | A80-B135; | A80-B136; | A80-B137; |
| A80-B138; | A80-B139; | A80-B140; | A80-B141; | A80-B142; | A80-B143; |
| A80-B144; | A80-B145; | A80-B146; | A80-B147; | A80-B148; | A80-B149; |
| A80-B150; | A80-B151; | A80-B152; | A80-B153; | A80-B154; | A80-B155; |
| A80-B156; | A80-B157; | A80-B158; | A80-B159; | A80-B160; | A80-B161; |
| A80-B162; | A80-B163; | A80-B164; | A80-B165; | A80-B166; | A80-B167; |
| A80-B168; | A80-B169; | A81-B1; | A81-B2; | A81-B3; | A81-B4; |
| A81-B5; | A81-B6; | A81-B7; | A81-B8; | A81-B9; | A81-B10; |
| A81-B11; | A81-B12; | A81-B13; | A81-B14; | A81-B15; | A81-B16; |
| A81-B17; | A81-B18; | A81-B19; | A81-B20; | A81-B21; | A81-B22; |
| A81-B23; | A81-B24; | A81-B25; | A81-B26; | A81-B27; | A81-B28; |
| A81-B29; | A81-B30; | A81-B31; | A81-B32; | A81-B33; | A81-B34; |
| A81-B35; | A81-B36; | A81-B37; | A81-B38; | A81-B39; | A81-B40; |
| A81-B41; | A81-B42; | A81-B43; | A81-B44; | A81-B45; | A81-B46; |
| A81-B47; | A81-B48; | A81-B49; | A81-B50; | A81-B51; | A81-B52; |
| A81-B53; | A81-B54; | A81-B55; | A81-B56; | A81-B57; | A81-B58; |
| A81-B59; | A81-B60; | A81-B61; | A81-B62; | A81-B63; | A81-B64; |
| A81-B65; | A81-B66; | A81-B67; | A81-B68; | A81-B69; | A81-B70; |
| A81-B71; | A81-B72; | A81-B73; | A81-B74; | A81-B75; | A81-B76; |
| A81-B77; | A81-B78; | A81-B79; | A81-B80; | A81-B81; | A81-B82; |
| A81-B83; | A81-B84; | A81-B85; | A81-B86; | A81-B87; | A81-B88; |
| A81-B89; | A81-B90; | A81-B91; | A81-B92; | A81-B93; | A81-B94; |
| A81-B95; | A81-B96; | A81-B97; | A81-B98; | A81-B99; | A81-B100; |
| A81-B101; | A81-B102; | A81-B103; | A81-B104; | A81-B105; | A81-B106; |
| A81-B107; | A81-B108; | A81-B109; | A81-B110; | A81-B111; | A81-B112; |
| A81-B113; | A81-B114; | A81-B115; | A81-B116; | A81-B117; | A81-B118; |
| A81-B119; | A81-B120; | A81-B121; | A81-B122; | A81-B123; | A81-B124; |
| A81-B125; | A81-B126; | A81-B127; | A81-B128; | A81-B129; | A81-B130; |
| A81-B131; | A81-B132; | A81-B133; | A81-B134; | A81-B135; | A81-B136; |
| A81-B137; | A81-B138; | A81-B139; | A81-B140; | A81-B141; | A81-B142; |
| A81-B143; | A81-B144; | A81-B145; | A81-B146; | A81-B147; | A81-B148; |
| A81-B149; | A81-B150; | A81-B151; | A81-B152; | A81-B153; | A81-B154; |
| A81-B155; | A81-B156; | A81-B157; | A81-B158; | A81-B159; | A81-B160; |
| A81-B161; | A81-B162; | A81-B163; | A81-B164; | A81-B165; | A81-B166; |
| A81-B167; | A81-B168; | A81-B169; | A82-B1; | A82-B2; | A82-B3; |
| A82-B4; | A82-B5; | A82-B6; | A82-B7; | A82-B8; | A82-B9; |
| A82-B10; | A82-B11; | A82-B12; | A82-B13; | A82-B14; | A82-B15; |
| A82-B16; | A82-B17; | A82-B18; | A82-B19; | A82-B20; | A82-B21; |
| A82-B22; | A82-B23; | A82-B24; | A82-B25; | A82-B26; | A82-B27; |
| A82-B28; | A82-B29; | A82-B30; | A82-B31; | A82-B32; | A82-B33; |
| A82-B34; | A82-B35; | A82-B36; | A82-B37; | A82-B38; | A82-B39; |
| A82-B40; | A82-B41; | A82-B42; | A82-B43; | A82-B44; | A82-B45; |
| A82-B46; | A82-B47; | A82-B48; | A82-B49; | A82-B50; | A82-B51; |
| A82-B52; | A82-B53; | A82-B54; | A82-B55; | A82-B56; | A82-B57; |
| A82-B58; | A82-B59; | A82-B60; | A82-B61; | A82-B62; | A82-B63; |
| A82-B64; | A82-B65; | A82-B66; | A82-B67; | A82-B68; | A82-B69; |
| A82-B70; | A82-B71; | A82-B72; | A82-B73; | A82-B74; | A82-B75; |
| A82-B76; | A82-B77; | A82-B78; | A82-B79; | A82-B80; | A82-B81; |
| A82-B82; | A82-B83; | A82-B84; | A82-B85; | A82-B86; | A82-B87; |
| A82-B88; | A82-B89; | A82-B90; | A82-B91; | A82-B92; | A82-B93; |
| A82-B94; | A82-B95; | A82-B96; | A82-B97; | A82-B98; | A82-B99; |
| A82-B100; | A82-B101; | A82-B102; | A82-B103; | A82-B104; | A82-B105; |
| A82-B106; | A82-B107; | A82-B108; | A82-B109; | A82-B110; | A82-B111; |
| A82-B112; | A82-B113; | A82-B114; | A82-B115; | A82-B116; | A82-B117; |
| A82-B118; | A82-B119; | A82-B120; | A82-B121; | A82-B122; | A82-B123; |
| A82-B124; | A82-B125; | A82-B126; | A82-B127; | A82-B128; | A82-B129; |
| A82-B130; | A82-B131; | A82-B132; | A82-B133; | A82-B134; | A82-B135; |
| A82-B136; | A82-B137; | A82-B138; | A82-B139; | A82-B140; | A82-B141; |
| A82-B142; | A82-B143; | A82-B144; | A82-B145; | A82-B146; | A82-B147; |

-continued

A82-B148; A82-B149; A82-B150; A82-B151; A82-B152; A82-B153;
A82-B154; A82-B155; A82-B156; A82-B157; A82-B158; A82-B159;
A82-B160; A82-B161; A82-B162; A82-B163; A82-B164; A82-B165;
A82-B166; A82-B167; A82-B168; A82-B169; A83-B1; A83-B2;
A83-B3; A83-B4; A83-B5; A83-B6; A83-B7; A83-B8;
A83-B9; A83-B10; A83-B11; A83-B12; A83-B13; A83-B14;
A83-B15; A83-B16; A83-B17; A83-B18; A83-B19; A83-B20;
A83-B21; A83-B22; A83-B23; A83-B24; A83-B25; A83-B26;
A83-B27; A83-B28; A83-B29; A83-B30; A83-B31; A83-B32;
A83-B33; A83-B34; A83-B35; A83-B36; A83-B37; A83-B38;
A83-B39; A83-B40; A83-B41; A83-B42; A83-B43; A83-B44;
A83-B45; A83-B46; A83-B47; A83-B48; A83-B49; A83-B50;
A83-B51; A83-B52; A83-B53; A83-B54; A83-B55; A83-B56;
A83-B57; A83-B58; A83-B59; A83-B60; A83-B61; A83-B62;
A83-B63; A83-B64; A83-B65; A83-B66; A83-B67; A83-B68;
A83-B69; A83-B70; A83-B71; A83-B72; A83-B73; A83-B74;
A83-B75; A83-B76; A83-B77; A83-B78; A83-B79; A83-B80;
A83-B81; A83-B82; A83-B83; A83-B84; A83-B85; A83-B86;
A83-B87; A83-B88; A83-B89; A83-B90; A83-B91; A83-B92;
A83-B93; A83-B94; A83-B95; A83-B96; A83-B97; A83-B98;
A83-B99; A83-B100; A83-B101; A83-B102; A83-B103; A83-B104;
A83-B105; A83-B106; A83-B107; A83-B108; A83-B109; A83-B110;
A83-B111; A83-B112; A83-B113; A83-B114; A83-B115; A83-B116;
A83-B117; A83-B118; A83-B119; A83-B120; A83-B121; A83-B122;
A83-B123; A83-B124; A83-B125; A83-B126; A83-B127; A83-B128;
A83-B129; A83-B130; A83-B131; A83-B132; A83-B133; A83-B134;
A83-B135; A83-B136; A83-B137; A83-B138; A83-B139; A83-B140;
A83-B141; A83-B142; A83-B143; A83-B144; A83-B145; A83-B146;
A83-B147; A83-B148; A83-B149; A83-B150; A83-B151; A83-B152;
A83-B153; A83-B154; A83-B155; A83-B156; A83-B157; A83-B158;
A83-B159; A83-B160; A83-B161; A83-B162; A83-B163; A83-B164;
A83-B165; A83-B166; A83-B167; A83-B168; A83-B169; A84-B1;
A84-B2; A84-B3; A84-B4; A84-B5; A84-B6; A84-B7;
A84-B8; A84-B9; A84-B10; A84-B11; A84-B12; A84-B13;
A84-B14; A84-B15; A84-B16; A84-B17; A84-B18; A84-B19;
A84-B20; A84-B21; A84-B22; A84-B23; A84-B24; A84-B25;
A84-B26; A84-B27; A84-B28; A84-B29; A84-B30; A84-B31;
A84-B32; A84-B33; A84-B34; A84-B35; A84-B36; A84-B37;
A84-B38; A84-B39; A84-B40; A84-B41; A84-B42; A84-B43;
A84-B44; A84-B45; A84-B46; A84-B47; A84-B48; A84-B49;
A84-B50; A84-B51; A84-B52; A84-B53; A84-B54; A84-B55;
A84-B56; A84-B57; A84-B58; A84-B59; A84-B60; A84-B61;
A84-B62; A84-B63; A84-B64; A84-B65; A84-B66; A84-B67;
A84-B68; A84-B69; A84-B70; A84-B71; A84-B72; A84-B73;
A84-B74; A84-B75; A84-B76; A84-B77; A84-B78; A84-B79;
A84-B80; A84-B81; A84-B82; A84-B83; A84-B84; A84-B85;
A84-B86; A84-B87; A84-B88; A84-B89; A84-B90; A84-B91;
A84-B92; A84-B93; A84-B94; A84-B95; A84-B96; A84-B97;
A84-B98; A84-B99; A84-B100; A84-B101; A84-B102; A84-B103;
A84-B104; A84-B105; A84-B106; A84-B107; A84-B108; A84-B109;
A84-B110; A84-B111; A84-B112; A84-B113; A84-B114; A84-B115;
A84-B116; A84-B117; A84-B118; A84-B119; A84-B120; A84-B121;
A84-B122; A84-B123; A84-B124; A84-B125; A84-B126; A84-B127;
A84-B128; A84-B129; A84-B130; A84-B131; A84-B132; A84-B133;
A84-B134; A84-B135; A84-B136; A84-B137; A84-B138; A84-B139;
A84-B140; A84-B141; A84-B142; A84-B143; A84-B144; A84-B145;
A84-B146; A84-B147; A84-B148; A84-B149; A84-B150; A84-B151;
A84-B152; A84-B153; A84-B154; A84-B155; A84-B156; A84-B157;
A84-B158; A84-B159; A84-B160; A84-B161; A84-B162; A84-B163;
A84-B164; A84-B165; A84-B166; A84-B167; A84-B168; A84-B169;
A85-B1; A85-B2; A85-B3; A85-B4; A85-B5; A85-B6;
A85-B7; A85-B8; A85-B9; A85-B10; A85-B11; A85-B12;
A85-B13; A85-B14; A85-B15; A85-B16; A85-B17; A85-B18;
A85-B19; A85-B20; A85-B21; A85-B22; A85-B23; A85-B24;
A85-B25; A85-B26; A85-B27; A85-B28; A85-B29; A85-B30;
A85-B31; A85-B32; A85-B33; A85-B34; A85-B35; A85-B36;
A85-B37; A85-B38; A85-B39; A85-B40; A85-B41; A85-B42;
A85-B43; A85-B44; A85-B45; A85-B46; A85-B47; A85-B48;
A85-B49; A85-B50; A85-B51; A85-B52; A85-B53; A85-B54;
A85-B55; A85-B56; A85-B57; A85-B58; A85-B59; A85-B60;
A85-B61; A85-B62; A85-B63; A85-B64; A85-B65; A85-B66;
A85-B67; A85-B68; A85-B69; A85-B70; A85-B71; A85-B72;
A85-B73; A85-B74; A85-B75; A85-B76; A85-B77; A85-B78;
A85-B79; A85-B80; A85-B81; A85-B82; A85-B83; A85-B84;
A85-B85; A85-B86; A85-B87; A85-B88; A85-B89; A85-B90;
A85-B91; A85-B92; A85-B93; A85-B94; A85-B95; A85-B96;
A85-B97; A85-B98; A85-B99; A85-B100; A85-B101; A85-B102;
A85-B103; A85-B104; A85-B105; A85-B106; A85-B107; A85-B108;
A85-B109; A85-B110; A85-B111; A85-B112; A85-B113; A85-B114;
A85-B115; A85-B116; A85-B117; A85-B118; A85-B119; A85-B120;

-continued

A85-B121; A85-B122; A85-B123; A85-B124; A85-B125; A85-B126;
A85-B127; A85-B128; A85-B129; A85-B130; A85-B131; A85-B132;
A85-B133; A85-B134; A85-B135; A85-B136; A85-B137; A85-B138;
A85-B139; A85-B140; A85-B141; A85-B142; A85-B143; A85-B144;
A85-B145; A85-B146; A85-B147; A85-B148; A85-B149; A85-B150;
A85-B151; A85-B152; A85-B153; A85-B154; A85-B155; A85-B156;
A85-B157; A85-B158; A85-B159; A85-B160; A85-B161; A85-B162;
A85-B163; A85-B164; A85-B165; A85-B166; A85-B167; A85-B168;
A85-B169; A86-B1; A86-B2; A86-B3; A86-B4; A86-B5;
A86-B6; A86-B7; A86-B8; A86-B9; A86-B10; A86-B11;
A86-B12; A86-B13; A86-B14; A86-B15; A86-B16; A86-B17;
A86-B18; A86-B19; A86-B20; A86-B21; A86-B22; A86-B23;
A86-B24; A86-B25; A86-B26; A86-B27; A86-B28; A86-B29;
A86-B30; A86-B31; A86-B32; A86-B33; A86-B34; A86-B35;
A86-B36; A86-B37; A86-B38; A86-B39; A86-B40; A86-B41;
A86-B42; A86-B43; A86-B44; A86-B45; A86-B46; A86-B47;
A86-B48; A86-B49; A86-B50; A86-B51; A86-B52; A86-B53;
A86-B54; A86-B55; A86-B56; A86-B57; A86-B58; A86-B59;
A86-B60; A86-B61; A86-B62; A86-B63; A86-B64; A86-B65;
A86-B66; A86-B67; A86-B68; A86-B69; A86-B70; A86-B71;
A86-B72; A86-B73; A86-B74; A86-B75; A86-B76; A86-B77;
A86-B78; A86-B79; A86-B80; A86-B81; A86-B82; A86-B83;
A86-B84; A86-B85; A86-B86; A86-B87; A86-B88; A86-B89;
A86-B90; A86-B91; A86-B92; A86-B93; A86-B94; A86-B95;
A86-B96; A86-B97; A86-B98; A86-B99; A86-B100; A86-B101;
A86-B102; A86-B103; A86-B104; A86-B105; A86-B106; A86-B107;
A86-B108; A86-B109; A86-B110; A86-B111; A86-B112; A86-B113;
A86-B114; A86-B115; A86-B116; A86-B117; A86-B118; A86-B119;
A86-B120; A86-B121; A86-B122; A86-B123; A86-B124; A86-B125;
A86-B126; A86-B127; A86-B128; A86-B129; A86-B130; A86-B131;
A86-B132; A86-B133; A86-B134; A86-B135; A86-B136; A86-B137;
A86-B138; A86-B139; A86-B140; A86-B141; A86-B142; A86-B143;
A86-B144; A86-B145; A86-B146; A86-B147; A86-B148; A86-B149;
A86-B150; A86-B151; A86-B152; A86-B153; A86-B154; A86-B155;
A86-B156; A86-B157; A86-B158; A86-B159; A86-B160; A86-B161;
A86-B162; A86-B163; A86-B164; A86-B165; A86-B166; A86-B167;
A86-B168; A86-B169; A87-B1; A87-B2; A87-B3; A87-B4;
A87-B5; A87-B6; A87-B7; A87-B8; A87-B9; A87-B10;
A87-B11; A87-B12; A87-B13; A87-B14; A87-B15; A87-B16;
A87-B17; A87-B18; A87-B19; A87-B20; A87-B21; A87-B22;
A87-B23; A87-B24; A87-B25; A87-B26; A87-B27; A87-B28;
A87-B29; A87-B30; A87-B31; A87-B32; A87-B33; A87-B34;
A87-B35; A87-B36; A87-B37; A87-B38; A87-B39; A87-B40;
A87-B41; A87-B42; A87-B43; A87-B44; A87-B45; A87-B46;
A87-B47; A87-B48; A87-B49; A87-B50; A87-B51; A87-B52;
A87-B53; A87-B54; A87-B55; A87-B56; A87-B57; A87-B58;
A87-B59; A87-B60; A87-B61; A87-B62; A87-B63; A87-B64;
A87-B65; A87-B66; A87-B67; A87-B68; A87-B69; A87-B70;
A87-B71; A87-B72; A87-B73; A87-B74; A87-B75; A87-B76;
A87-B77; A87-B78; A87-B79; A87-B80; A87-B81; A87-B82;
A87-B83; A87-B84; A87-B85; A87-B86; A87-B87; A87-B88;
A87-B89; A87-B90; A87-B91; A87-B92; A87-B93; A87-B94;
A87-B95; A87-B96; A87-B97; A87-B98; A87-B99; A87-B100;
A87-B101; A87-B102; A87-B103; A87-B104; A87-B105; A87-B106;
A87-B107; A87-B108; A87-B109; A87-B110; A87-B111; A87-B112;
A87-B113; A87-B114; A87-B115; A87-B116; A87-B117; A87-B118;
A87-B119; A87-B120; A87-B121; A87-B122; A87-B123; A87-B124;
A87-B125; A87-B126; A87-B127; A87-B128; A87-B129; A87-B130;
A87-B131; A87-B132; A87-B133; A87-B134; A87-B135; A87-B136;
A87-B137; A87-B138; A87-B139; A87-B140; A87-B141; A87-B142;
A87-B143; A87-B144; A87-B145; A87-B146; A87-B147; A87-B148;
A87-B149; A87-B150; A87-B151; A87-B152; A87-B153; A87-B154;
A87-B155; A87-B156; A87-B157; A87-B158; A87-B159; A87-B160;
A87-B161; A87-B162; A87-B163; A87-B164; A87-B165; A87-B166;
A87-B167; A87-B168; A87-B169; A88-B1; A88-B2; A88-B3;
A88-B4; A88-B5; A88-B6; A88-B7; A88-B8; A88-B9;
A88-B10; A88-B11; A88-B12; A88-B13; A88-B14; A88-B15;
A88-B16; A88-B17; A88-B18; A88-B19; A88-B20; A88-B21;
A88-B22; A88-B23; A88-B24; A88-B25; A88-B26; A88-B27;
A88-B28; A88-B29; A88-B30; A88-B31; A88-B32; A88-B33;
A88-B34; A88-B35; A88-B36; A88-B37; A88-B38; A88-B39;
A88-B40; A88-B41; A88-B42; A88-B43; A88-B44; A88-B45;
A88-B46; A88-B47; A88-B48; A88-B49; A88-B50; A88-B51;
A88-B52; A88-B53; A88-B54; A88-B55; A88-B56; A88-B57;
A88-B58; A88-B59; A88-B60; A88-B61; A88-B62; A88-B63;
A88-B64; A88-B65; A88-B66; A88-B67; A88-B68; A88-B69;
A88-B70; A88-B71; A88-B72; A88-B73; A88-B74; A88-B75;
A88-B76; A88-B77; A88-B78; A88-B79; A88-B80; A88-B81;
A88-B82; A88-B83; A88-B84; A88-B85; A88-B86; A88-B87;
A88-B88; A88-B89; A88-B90; A88-B91; A88-B92; A88-B93;

-continued

| | | | | | |
|---|---|---|---|---|---|
| A88-B94; | A88-B95; | A88-B96; | A88-B97; | A88-B98; | A88-B99; |
| A88-B100; | A88-B101; | A88-B102; | A88-B103; | A88-B104; | A88-B105; |
| A88-B106; | A88-B107; | A88-B108; | A88-B109; | A88-B110; | A88-B111; |
| A88-B112; | A88-B113; | A88-B114; | A88-B115; | A88-B116; | A88-B117; |
| A88-B118; | A88-B119; | A88-B120; | A88-B121; | A88-B122; | A88-B123; |
| A88-B124; | A88-B125; | A88-B126; | A88-B127; | A88-B128; | A88-B129; |
| A88-B130; | A88-B131; | A88-B132; | A88-B133; | A88-B134; | A88-B135; |
| A88-B136; | A88-B137; | A88-B138; | A88-B139; | A88-B140; | A88-B141; |
| A88-B142; | A88-B143; | A88-B144; | A88-B145; | A88-B146; | A88-B147; |
| A88-B148; | A88-B149; | A88-B150; | A88-B151; | A88-B152; | A88-B153; |
| A88-B154; | A88-B155; | A88-B156; | A88-B157; | A88-B158; | A88-B159; |
| A88-B160; | A88-B161; | A88-B162; | A88-B163; | A88-B164; | A88-B165; |
| A88-B166; | A88-B167; | A88-B168; | A88-B169; | A89-B1; | A89-B2; |
| A89-B3; | A89-B4; | A89-B5; | A89-B6; | A89-B7; | A89-B8; |
| A89-B9; | A89-B10; | A89-B11; | A89-B12; | A89-B13; | A89-B14; |
| A89-B15; | A89-B16; | A89-B17; | A89-B18; | A89-B19; | A89-B20; |
| A89-B21; | A89-B22; | A89-B23; | A89-B24; | A89-B25; | A89-B26; |
| A89-B27; | A89-B28; | A89-B29; | A89-B30; | A89-B31; | A89-B32; |
| A89-B33; | A89-B34; | A89-B35; | A89-B36; | A89-B37; | A89-B38; |
| A89-B39; | A89-B40; | A89-B41; | A89-B42; | A89-B43; | A89-B44; |
| A89-B45; | A89-B46; | A89-B47; | A89-B48; | A89-B49; | A89-B50; |
| A89-B51; | A89-B52; | A89-B53; | A89-B54; | A89-B55; | A89-B56; |
| A89-B57; | A89-B58; | A89-B59; | A89-B60; | A89-B61; | A89-B62; |
| A89-B63; | A89-B64; | A89-B65; | A89-B66; | A89-B67; | A89-B68; |
| A89-B69; | A89-B70; | A89-B71; | A89-B72; | A89-B73; | A89-B74; |
| A89-B75; | A89-B76; | A89-B77; | A89-B78; | A89-B79; | A89-B80; |
| A89-B81; | A89-B82; | A89-B83; | A89-B84; | A89-B85; | A89-B86; |
| A89-B87; | A89-B88; | A89-B89; | A89-B90; | A89-B91; | A89-B92; |
| A89-B93; | A89-B94; | A89-B95; | A89-B96; | A89-B97; | A89-B98; |
| A89-B99; | A89-B100; | A89-B101; | A89-B102; | A89-B103; | A89-B104; |
| A89-B105; | A89-B106; | A89-B107; | A89-B108; | A89-B109; | A89-B110; |
| A89-B111; | A89-B112; | A89-B113; | A89-B114; | A89-B115; | A89-B116; |
| A89-B117; | A89-B118; | A89-B119; | A89-B120; | A89-B121; | A89-B122; |
| A89-B123; | A89-B124; | A89-B125; | A89-B126; | A89-B127; | A89-B128; |
| A89-B129; | A89-B130; | A89-B131; | A89-B132; | A89-B133; | A89-B134; |
| A89-B135; | A89-B136; | A89-B137; | A89-B138; | A89-B139; | A89-B140; |
| A89-B141; | A89-B142; | A89-B143; | A89-B144; | A89-B145; | A89-B146; |
| A89-B147; | A89-B148; | A89-B149; | A89-B150; | A89-B151; | A89-B152; |
| A89-B153; | A89-B154; | A89-B155; | A89-B156; | A89-B157; | A89-B158; |
| A89-B159; | A89-B160; | A89-B161; | A89-B162; | A89-B163; | A89-B164; |
| A89-B165; | A89-B166; | A89-B167; | A89-B168; | A89-B169; | A90-B1; |
| A90-B2; | A90-B3; | A90-B4; | A90-B5; | A90-B6; | A90-B7; |
| A90-B8; | A90-B9; | A90-B10; | A90-B11; | A90-B12; | A90-B13; |
| A90-B14; | A90-B15; | A90-B16; | A90-B17; | A90-B18; | A90-B19; |
| A90-B20; | A90-B21; | A90-B22; | A90-B23; | A90-B24; | A90-B25; |
| A90-B26; | A90-B27; | A90-B28; | A90-B29; | A90-B30; | A90-B31; |
| A90-B32; | A90-B33; | A90-B34; | A90-B35; | A90-B36; | A90-B37; |
| A90-B38; | A90-B39; | A90-B40; | A90-B41; | A90-B42; | A90-B43; |
| A90-B44; | A90-B45; | A90-B46; | A90-B47; | A90-B48; | A90-B49; |
| A90-B50; | A90-B51; | A90-B52; | A90-B53; | A90-B54; | A90-B55; |
| A90-B56; | A90-B57; | A90-B58; | A90-B59; | A90-B60; | A90-B61; |
| A90-B62; | A90-B63; | A90-B64; | A90-B65; | A90-B66; | A90-B67; |
| A90-B68; | A90-B69; | A90-B70; | A90-B71; | A90-B72; | A90-B73; |
| A90-B74; | A90-B75; | A90-B76; | A90-B77; | A90-B78; | A90-B79; |
| A90-B80; | A90-B81; | A90-B82; | A90-B83; | A90-B84; | A90-B85; |
| A90-B86; | A90-B87; | A90-B88; | A90-B89; | A90-B90; | A90-B91; |
| A90-B92; | A90-B93; | A90-B94; | A90-B95; | A90-B96; | A90-B97; |
| A90-B98; | A90-B99; | A90-B100; | A90-B101; | A90-B102; | A90-B103; |
| A90-B104; | A90-B105; | A90-B106; | A90-B107; | A90-B108; | A90-B109; |
| A90-B110; | A90-B111; | A90-B112; | A90-B113; | A90-B114; | A90-B115; |
| A90-B116; | A90-B117; | A90-B118; | A90-B119; | A90-B120; | A90-B121; |
| A90-B122; | A90-B123; | A90-B124; | A90-B125; | A90-B126; | A90-B127; |
| A90-B128; | A90-B129; | A90-B130; | A90-B131; | A90-B132; | A90-B133; |
| A90-B134; | A90-B135; | A90-B136; | A90-B137; | A90-B138; | A90-B139; |
| A90-B140; | A90-B141; | A90-B142; | A90-B143; | A90-B144; | A90-B145; |
| A90-B146; | A90-B147; | A90-B148; | A90-B149; | A90-B150; | A90-B151; |
| A90-B152; | A90-B153; | A90-B154; | A90-B155; | A90-B156; | A90-B157; |
| A90-B158; | A90-B159; | A90-B160; | A90-B161; | A90-B162; | A90-B163; |
| A90-B164; | A90-B165; | A90-B166; | A90-B167; | A90-B168; | A90-B169; |
| A91-B1; | A91-B2; | A91-B3; | A91-B4; | A91-B5; | A91-B6; |
| A91-B7; | A91-B8; | A91-B9; | A91-B10; | A91-B11; | A91-B12; |
| A91-B13; | A91-B14; | A91-B15; | A91-B16; | A91-B17; | A91-B18; |
| A91-B19; | A91-B20; | A91-B21; | A91-B22; | A91-B23; | A91-B24; |
| A91-B25; | A91-B26; | A91-B27; | A91-B28; | A91-B29; | A91-B30; |
| A91-B31; | A91-B32; | A91-B33; | A91-B34; | A91-B35; | A91-B36; |
| A91-B37; | A91-B38; | A91-B39; | A91-B40; | A91-B41; | A91-B42; |
| A91-B43; | A91-B44; | A91-B45; | A91-B46; | A91-B47; | A91-B48; |
| A91-B49; | A91-B50; | A91-B51; | A91-B52; | A91-B53; | A91-B54; |
| A91-B55; | A91-B56; | A91-B57; | A91-B58; | A91-B59; | A91-B60; |
| A91-B61; | A91-B62; | A91-B63; | A91-B64; | A91-B65; | A91-B66; |

-continued

A91-B67; A91-B68; A91-B69; A91-B70; A91-B71; A91-B72;
A91-B73; A91-B74; A91-B75; A91-B76; A91-B77; A91-B78;
A91-B79; A91-B80; A91-B81; A91-B82; A91-B83; A91-B84;
A91-B85; A91-B86; A91-B87; A91-B88; A91-B89; A91-B90;
A91-B91; A91-B92; A91-B93; A91-B94; A91-B95; A91-B96;
A91-B97; A91-B98; A91-B99; A91-B100; A91-B101; A91-B102;
A91-B103; A91-B104; A91-B105; A91-B106; A91-B107; A91-B108;
A91-B109; A91-B110; A91-B111; A91-B112; A91-B113; A91-B114;
A91-B115; A91-B116; A91-B117; A91-B118; A91-B119; A91-B120;
A91-B121; A91-B122; A91-B123; A91-B124; A91-B125; A91-B126;
A91-B127; A91-B128; A91-B129; A91-B130; A91-B131; A91-B132;
A91-B133; A91-B134; A91-B135; A91-B136; A91-B137; A91-B138;
A91-B139; A91-B140; A91-B141; A91-B142; A91-B143; A91-B144;
A91-B145; A91-B146; A91-B147; A91-B148; A91-B149; A91-B150;
A91-B151; A91-B152; A91-B153; A91-B154; A91-B155; A91-B156;
A91-B157; A91-B158; A91-B159; A91-B160; A91-B161; A91-B162;
A91-B163; A91-B164; A91-B165; A91-B166; A91-B167; A91-B168;
A91-B169; A92-B1; A92-B2; A92-B3; A92-B4; A92-B5;
A92-B6; A92-B7; A92-B8; A92-B9; A92-B10; A92-B11;
A92-B12; A92-B13; A92-B14; A92-B15; A92-B16; A92-B17;
A92-B18; A92-B19; A92-B20; A92-B21; A92-B22; A92-B23;
A92-B24; A92-B25; A92-B26; A92-B27; A92-B28; A92-B29;
A92-B30; A92-B31; A92-B32; A92-B33; A92-B34; A92-B35;
A92-B36; A92-B37; A92-B38; A92-B39; A92-B40; A92-B41;
A92-B42; A92-B43; A92-B44; A92-B45; A92-B46; A92-B47;
A92-B48; A92-B49; A92-B50; A92-B51; A92-B52; A92-B53;
A92-B54; A92-B55; A92-B56; A92-B57; A92-B58; A92-B59;
A92-B60; A92-B61; A92-B62; A92-B63; A92-B64; A92-B65;
A92-B66; A92-B67; A92-B68; A92-B69; A92-B70; A92-B71;
A92-B72; A92-B73; A92-B74; A92-B75; A92-B76; A92-B77;
A92-B78; A92-B79; A92-B80; A92-B81; A92-B82; A92-B83;
A92-B84; A92-B85; A92-B86; A92-B87; A92-B88; A92-B89;
A92-B90; A92-B91; A92-B92; A92-B93; A92-B94; A92-B95;
A92-B96; A92-B97; A92-B98; A92-B99; A92-B100; A92-B101;
A92-B102; A92-B103; A92-B104; A92-B105; A92-B106; A92-B107;
A92-B108; A92-B109; A92-B110; A92-B111; A92-B112; A92-B113;
A92-B114; A92-B115; A92-B116; A92-B117; A92-B118; A92-B119;
A92-B120; A92-B121; A92-B122; A92-B123; A92-B124; A92-B125;
A92-B126; A92-B127; A92-B128; A92-B129; A92-B130; A92-B131;
A92-B132; A92-B133; A92-B134; A92-B135; A92-B136; A92-B137;
A92-B138; A92-B139; A92-B140; A92-B141; A92-B142; A92-B143;
A92-B144; A92-B145; A92-B146; A92-B147; A92-B148; A92-B149;
A92-B150; A92-B151; A92-B152; A92-B153; A92-B154; A92-B155;
A92-B156; A92-B157; A92-B158; A92-B159; A92-B160; A92-B161;
A92-B162; A92-B163; A92-B164; A92-B165; A92-B166; A92-B167;
A92-B168; A92-B169; A93-B1; A93-B2; A93-B3; A93-B4;
A93-B5; A93-B6; A93-B7; A93-B8; A93-B9; A93-B10;
A93-B11; A93-B12; A93-B13; A93-B14; A93-B15; A93-B16;
A93-B17; A93-B18; A93-B19; A93-B20; A93-B21; A93-B22;
A93-B23; A93-B24; A93-B25; A93-B26; A93-B27; A93-B28;
A93-B29; A93-B30; A93-B31; A93-B32; A93-B33; A93-B34;
A93-B35; A93-B36; A93-B37; A93-B38; A93-B39; A93-B40;
A93-B41; A93-B42; A93-B43; A93-B44; A93-B45; A93-B46;
A93-B47; A93-B48; A93-B49; A93-B50; A93-B51; A93-B52;
A93-B53; A93-B54; A93-B55; A93-B56; A93-B57; A93-B58;
A93-B59; A93-B60; A93-B61; A93-B62; A93-B63; A93-B64;
A93-B65; A93-B66; A93-B67; A93-B68; A93-B69; A93-B70;
A93-B71; A93-B72; A93-B73; A93-B74; A93-B75; A93-B76;
A93-B77; A93-B78; A93-B79; A93-B80; A93-B81; A93-B82;
A93-B83; A93-B84; A93-B85; A93-B86; A93-B87; A93-B88;
A93-B89; A93-B90; A93-B91; A93-B92; A93-B93; A93-B94;
A93-B95; A93-B96; A93-B97; A93-B98; A93-B99; A93-B100;
A93-B101; A93-B102; A93-B103; A93-B104; A93-B105; A93-B106;
A93-B107; A93-B108; A93-B109; A93-B110; A93-B111; A93-B112;
A93-B113; A93-B114; A93-B115; A93-B116; A93-B117; A93-B118;
A93-B119; A93-B120; A93-B121; A93-B122; A93-B123; A93-B124;
A93-B125; A93-B126; A93-B127; A93-B128; A93-B129; A93-B130;
A93-B131; A93-B132; A93-B133; A93-B134; A93-B135; A93-B136;
A93-B137; A93-B138; A93-B139; A93-B140; A93-B141; A93-B142;
A93-B143; A93-B144; A93-B145; A93-B146; A93-B147; A93-B148;
A93-B149; A93-B150; A93-B151; A93-B152; A93-B153; A93-B154;
A93-B155; A93-B156; A93-B157; A93-B158; A93-B159; A93-B160;
A93-B161; A93-B162; A93-B163; A93-B164; A93-B165; A93-B166;
A93-B167; A93-B168; A93-B169; A94-B1; A94-B2; A94-B3;
A94-B4; A94-B5; A94-B6; A94-B7; A94-B8; A94-B9;
A94-B10; A94-B11; A94-B12; A94-B13; A94-B14; A94-B15;
A94-B16; A94-B17; A94-B18; A94-B19; A94-B20; A94-B21;
A94-B22; A94-B23; A94-B24; A94-B25; A94-B26; A94-B27;
A94-B28; A94-B29; A94-B30; A94-B31; A94-B32; A94-B33;
A94-B34; A94-B35; A94-B36; A94-B37; A94-B38; A94-B39;

-continued

| | | | | | |
|---|---|---|---|---|---|
| A94-B40; | A94-B41; | A94-B42; | A94-B43; | A94-B44; | A94-B45; |
| A94-B46; | A94-B47; | A94-B48; | A94-B49; | A94-B50; | A94-B51; |
| A94-B52; | A94-B53; | A94-B54; | A94-B55; | A94-B56; | A94-B57; |
| A94-B58; | A94-B59; | A94-B60; | A94-B61; | A94-B62; | A94-B63; |
| A94-B64; | A94-B65; | A94-B66; | A94-B67; | A94-B68; | A94-B69; |
| A94-B70; | A94-B71; | A94-B72; | A94-B73; | A94-B74; | A94-B75; |
| A94-B76; | A94-B77; | A94-B78; | A94-B79; | A94-B80; | A94-B81; |
| A94-B82; | A94-B83; | A94-B84; | A94-B85; | A94-B86; | A94-B87; |
| A94-B88; | A94-B89; | A94-B90; | A94-B91; | A94-B92; | A94-B93; |
| A94-B94; | A94-B95; | A94-B96; | A94-B97; | A94-B98; | A94-B99; |
| A94-B100; | A94-B101; | A94-B102; | A94-B103; | A94-B104; | A94-B105; |
| A94-B106; | A94-B107; | A94-B108; | A94-B109; | A94-B110; | A94-B111; |
| A94-B112; | A94-B113; | A94-B114; | A94-B115; | A94-B116; | A94-B117; |
| A94-B118; | A94-B119; | A94-B120; | A94-B121; | A94-B122; | A94-B123; |
| A94-B124; | A94-B125; | A94-B126; | A94-B127; | A94-B128; | A94-B129; |
| A94-B130; | A94-B131; | A94-B132; | A94-B133; | A94-B134; | A94-B135; |
| A94-B136; | A94-B137; | A94-B138; | A94-B139; | A94-B140; | A94-B141; |
| A94-B142; | A94-B143; | A94-B144; | A94-B145; | A94-B146; | A94-B147; |
| A94-B148; | A94-B149; | A94-B150; | A94-B151; | A94-B152; | A94-B153; |
| A94-B154; | A94-B155; | A94-B156; | A94-B157; | A94-B158; | A94-B159; |
| A94-B160; | A94-B161; | A94-B162; | A94-B163; | A94-B164; | A94-B165; |
| A94-B166; | A94-B167; | A94-B168; | A94-B169; | A95-B1; | A95-B2; |
| A95-B3; | A95-B4; | A95-B5; | A95-B6; | A95-B7; | A95-B8; |
| A95-B9; | A95-B10; | A95-B11; | A95-B12; | A95-B13; | A95-B14; |
| A95-B15; | A95-B16; | A95-B17; | A95-B18; | A95-B19; | A95-B20; |
| A95-B21; | A95-B22; | A95-B23; | A95-B24; | A95-B25; | A95-B26; |
| A95-B27; | A95-B28; | A95-B29; | A95-B30; | A95-B31; | A95-B32; |
| A95-B33; | A95-B34; | A95-B35; | A95-B36; | A95-B37; | A95-B38; |
| A95-B39; | A95-B40; | A95-B41; | A95-B42; | A95-B43; | A95-B44; |
| A95-B45; | A95-B46; | A95-B47; | A95-B48; | A95-B49; | A95-B50; |
| A95-B51; | A95-B52; | A95-B53; | A95-B54; | A95-B55; | A95-B56; |
| A95-B57; | A95-B58; | A95-B59; | A95-B60; | A95-B61; | A95-B62; |
| A95-B63; | A95-B64; | A95-B65; | A95-B66; | A95-B67; | A95-B68; |
| A95-B69; | A95-B70; | A95-B71; | A95-B72; | A95-B73; | A95-B74; |
| A95-B75; | A95-B76; | A95-B77; | A95-B78; | A95-B79; | A95-B80; |
| A95-B81; | A95-B82; | A95-B83; | A95-B84; | A95-B85; | A95-B86; |
| A95-B87; | A95-B88; | A95-B89; | A95-B90; | A95-B91; | A95-B92; |
| A95-B93; | A95-B94; | A95-B95; | A95-B96; | A95-B97; | A95-B98; |
| A95-B99; | A95-B100; | A95-B101; | A95-B102; | A95-B103; | A95-B104; |
| A95-B105; | A95-B106; | A95-B107; | A95-B108; | A95-B109; | A95-B110; |
| A95-B111; | A95-B112; | A95-B113; | A95-B114; | A95-B115; | A95-B116; |
| A95-B117; | A95-B118; | A95-B119; | A95-B120; | A95-B121; | A95-B122; |
| A95-B123; | A95-B124; | A95-B125; | A95-B126; | A95-B127; | A95-B128; |
| A95-B129; | A95-B130; | A95-B131; | A95-B132; | A95-B133; | A95-B134; |
| A95-B135; | A95-B136; | A95-B137; | A95-B138; | A95-B139; | A95-B140; |
| A95-B141; | A95-B142; | A95-B143; | A95-B144; | A95-B145; | A95-B146; |
| A95-B147; | A95-B148; | A95-B149; | A95-B150; | A95-B151; | A95-B152; |
| A95-B153; | A95-B154; | A95-B155; | A95-B156; | A95-B157; | A95-B158; |
| A95-B159; | A95-B160; | A95-B161; | A95-B162; | A95-B163; | A95-B164; |
| A95-B165; | A95-B166; | A95-B167; | A95-B168; | A95-B169; | A96-B1; |
| A96-B2; | A96-B3; | A96-B4; | A96-B5; | A96-B6; | A96-B7; |
| A96-B8; | A96-B9; | A96-B10; | A96-B11; | A96-B12; | A96-B13; |
| A96-B14; | A96-B15; | A96-B16; | A96-B17; | A96-B18; | A96-B19; |
| A96-B20; | A96-B21; | A96-B22; | A96-B23; | A96-B24; | A96-B25; |
| A96-B26; | A96-B27; | A96-B28; | A96-B29; | A96-B30; | A96-B31; |
| A96-B32; | A96-B33; | A96-B34; | A96-B35; | A96-B36; | A96-B37; |
| A96-B38; | A96-B39; | A96-B40; | A96-B41; | A96-B42; | A96-B43; |
| A96-B44; | A96-B45; | A96-B46; | A96-B47; | A96-B48; | A96-B49; |
| A96-B50; | A96-B51; | A96-B52; | A96-B53; | A96-B54; | A96-B55; |
| A96-B56; | A96-B57; | A96-B58; | A96-B59; | A96-B60; | A96-B61; |
| A96-B62; | A96-B63; | A96-B64; | A96-B65; | A96-B66; | A96-B67; |
| A96-B68; | A96-B69; | A96-B70; | A96-B71; | A96-B72; | A96-B73; |
| A96-B74; | A96-B75; | A96-B76; | A96-B77; | A96-B78; | A96-B79; |
| A96-B80; | A96-B81; | A96-B82; | A96-B83; | A96-B84; | A96-B85; |
| A96-B86; | A96-B87; | A96-B88; | A96-B89; | A96-B90; | A96-B91; |
| A96-B92; | A96-B93; | A96-B94; | A96-B95; | A96-B96; | A96-B97; |
| A96-B98; | A96-B99; | A96-B100; | A96-B101; | A96-B102; | A96-B103; |
| A96-B104; | A96-B105; | A96-B106; | A96-B107; | A96-B108; | A96-B109; |
| A96-B110; | A96-B111; | A96-B112; | A96-B113; | A96-B114; | A96-B115; |
| A96-B116; | A96-B117; | A96-B118; | A96-B119; | A96-B120; | A96-B121; |
| A96-B122; | A96-B123; | A96-B124; | A96-B125; | A96-B126; | A96-B127; |
| A96-B128; | A96-B129; | A96-B130; | A96-B131; | A96-B132; | A96-B133; |
| A96-B134; | A96-B135; | A96-B136; | A96-B137; | A96-B138; | A96-B139; |
| A96-B140; | A96-B141; | A96-B142; | A96-B143; | A96-B144; | A96-B145; |
| A96-B146; | A96-B147; | A96-B148; | A96-B149; | A96-B150; | A96-B151; |
| A96-B152; | A96-B153; | A96-B154; | A96-B155; | A96-B156; | A96-B157; |
| A96-B158; | A96-B159; | A96-B160; | A96-B161; | A96-B162; | A96-B163; |
| A96-B164; | A96-B165; | A96-B166; | A96-B167; | A96-B168; | A96-B169; |
| A97-B1; | A97-B2; | A97-B3; | A97-B4; | A97-B5; | A97-B6; |
| A97-B7; | A97-B8; | A97-B9; | A97-B10; | A97-B11; | A97-B12; |

-continued

| | | | | | |
|---|---|---|---|---|---|
| A97-B13; | A97-B14; | A97-B15; | A97-B16; | A97-B17; | A97-B18; |
| A97-B19; | A97-B20; | A97-B21; | A97-B22; | A97-B23; | A97-B24; |
| A97-B25; | A97-B26; | A97-B27; | A97-B28; | A97-B29; | A97-B30; |
| A97-B31; | A97-B32; | A97-B33; | A97-B34; | A97-B35; | A97-B36; |
| A97-B37; | A97-B38; | A97-B39; | A97-B40; | A97-B41; | A97-B42; |
| A97-B43; | A97-B44; | A97-B45; | A97-B46; | A97-B47; | A97-B48; |
| A97-B49; | A97-B50; | A97-B51; | A97-B52; | A97-B53; | A97-B54; |
| A97-B55; | A97-B56; | A97-B57; | A97-B58; | A97-B59; | A97-B60; |
| A97-B61; | A97-B62; | A97-B63; | A97-B64; | A97-B65; | A97-B66; |
| A97-B67; | A97-B68; | A97-B69; | A97-B70; | A97-B71; | A97-B72; |
| A97-B73; | A97-B74; | A97-B75; | A97-B76; | A97-B77; | A97-B78; |
| A97-B79; | A97-B80; | A97-B81; | A97-B82; | A97-B83; | A97-B84; |
| A97-B85; | A97-B86; | A97-B87; | A97-B88; | A97-B89; | A97-B90; |
| A97-B91; | A97-B92; | A97-B93; | A97-B94; | A97-B95; | A97-B96; |
| A97-B97; | A97-B98; | A97-B99; | A97-B100; | A97-B101; | A97-B102; |
| A97-B103; | A97-B104; | A97-B105; | A97-B106; | A97-B107; | A97-B108; |
| A97-B109; | A97-B110; | A97-B111; | A97-B112; | A97-B113; | A97-B114; |
| A97-B115; | A97-B116; | A97-B117; | A97-B118; | A97-B119; | A97-B120; |
| A97-B121; | A97-B122; | A97-B123; | A97-B124; | A97-B125; | A97-B126; |
| A97-B127; | A97-B128; | A97-B129; | A97-B130; | A97-B131; | A97-B132; |
| A97-B133; | A97-B134; | A97-B135; | A97-B136; | A97-B137; | A97-B138; |
| A97-B139; | A97-B140; | A97-B141; | A97-B142; | A97-B143; | A97-B144; |
| A97-B145; | A97-B146; | A97-B147; | A97-B148; | A97-B149; | A97-B150; |
| A97-B151; | A97-B152; | A97-B153; | A97-B154; | A97-B155; | A97-B156; |
| A97-B157; | A97-B158; | A97-B159; | A97-B160; | A97-B161; | A97-B162; |
| A97-B163; | A97-B164; | A97-B165; | A97-B166; | A97-B167; | A97-B168; |
| A97-B169; | A98-B1; | A98-B2; | A98-B3; | A98-B4; | A98-B5; |
| A98-B6; | A98-B7; | A98-B8; | A98-B9; | A98-B10; | A98-B11; |
| A98-B12; | A98-B13; | A98-B14; | A98-B15; | A98-B16; | A98-B17; |
| A98-B18; | A98-B19; | A98-B20; | A98-B21; | A98-B22; | A98-B23; |
| A98-B24; | A98-B25; | A98-B26; | A98-B27; | A98-B28; | A98-B29; |
| A98-B30; | A98-B31; | A98-B32; | A98-B33; | A98-B34; | A98-B35; |
| A98-B36; | A98-B37; | A98-B38; | A98-B39; | A98-B40; | A98-B41; |
| A98-B42; | A98-B43; | A98-B44; | A98-B45; | A98-B46; | A98-B47; |
| A98-B48; | A98-B49; | A98-B50; | A98-B51; | A98-B52; | A98-B53; |
| A98-B54; | A98-B55; | A98-B56; | A98-B57; | A98-B58; | A98-B59; |
| A98-B60; | A98-B61; | A98-B62; | A98-B63; | A98-B64; | A98-B65; |
| A98-B66; | A98-B67; | A98-B68; | A98-B69; | A98-B70; | A98-B71; |
| A98-B72; | A98-B73; | A98-B74; | A98-B75; | A98-B76; | A98-B77; |
| A98-B78; | A98-B79; | A98-B80; | A98-B81; | A98-B82; | A98-B83; |
| A98-B84; | A98-B85; | A98-B86; | A98-B87; | A98-B88; | A98-B89; |
| A98-B90; | A98-B91; | A98-B92; | A98-B93; | A98-B94; | A98-B95; |
| A98-B96; | A98-B97; | A98-B98; | A98-B99; | A98-B100; | A98-B101; |
| A98-B102; | A98-B103; | A98-B104; | A98-B105; | A98-B106; | A98-B107; |
| A98-B108; | A98-B109; | A98-B110; | A98-B111; | A98-B112; | A98-B113; |
| A98-B114; | A98-B115; | A98-B116; | A98-B117; | A98-B118; | A98-B119; |
| A98-B120; | A98-B121; | A98-B122; | A98-B123; | A98-B124; | A98-B125; |
| A98-B126; | A98-B127; | A98-B128; | A98-B129; | A98-B130; | A98-B131; |
| A98-B132; | A98-B133; | A98-B134; | A98-B135; | A98-B136; | A98-B137; |
| A98-B138; | A98-B139; | A98-B140; | A98-B141; | A98-B142; | A98-B143; |
| A98-B144; | A98-B145; | A98-B146; | A98-B147; | A98-B148; | A98-B149; |
| A98-B150; | A98-B151; | A98-B152; | A98-B153; | A98-B154; | A98-B155; |
| A98-B156; | A98-B157; | A98-B158; | A98-B159; | A98-B160; | A98-B161; |
| A98-B162; | A98-B163; | A98-B164; | A98-B165; | A98-B166; | A98-B167; |
| A98-B168; | A98-B169; | A99-B1; | A99-B2; | A99-B3; | A99-B4; |
| A99-B5; | A99-B6; | A99-B7; | A99-B8; | A99-B9; | A99-B10; |
| A99-B11; | A99-B12; | A99-B13; | A99-B14; | A99-B15; | A99-B16; |
| A99-B17; | A99-B18; | A99-B19; | A99-B20; | A99-B21; | A99-B22; |
| A99-B23; | A99-B24; | A99-B25; | A99-B26; | A99-B27; | A99-B28; |
| A99-B29; | A99-B30; | A99-B31; | A99-B32; | A99-B33; | A99-B34; |
| A99-B35; | A99-B36; | A99-B37; | A99-B38; | A99-B39; | A99-B40; |
| A99-B41; | A99-B42; | A99-B43; | A99-B44; | A99-B45; | A99-B46; |
| A99-B47; | A99-B48; | A99-B49; | A99-B50; | A99-B51; | A99-B52; |
| A99-B53; | A99-B54; | A99-B55; | A99-B56; | A99-B57; | A99-B58; |
| A99-B59; | A99-B60; | A99-B61; | A99-B62; | A99-B63; | A99-B64; |
| A99-B65; | A99-B66; | A99-B67; | A99-B68; | A99-B69; | A99-B70; |
| A99-B71; | A99-B72; | A99-B73; | A99-B74; | A99-B75; | A99-B76; |
| A99-B77; | A99-B78; | A99-B79; | A99-B80; | A99-B81; | A99-B82; |
| A99-B83; | A99-B84; | A99-B85; | A99-B86; | A99-B87; | A99-B88; |
| A99-B89; | A99-B90; | A99-B91; | A99-B92; | A99-B93; | A99-B94; |
| A99-B95; | A99-B96; | A99-B97; | A99-B98; | A99-B99; | A99-B100; |
| A99-B101; | A99-B102; | A99-B103; | A99-B104; | A99-B105; | A99-B106; |
| A99-B107; | A99-B108; | A99-B109; | A99-B110; | A99-B111; | A99-B112; |
| A99-B113; | A99-B114; | A99-B115; | A99-B116; | A99-B117; | A99-B118; |
| A99-B119; | A99-B120; | A99-B121; | A99-B122; | A99-B123; | A99-B124; |
| A99-B125; | A99-B126; | A99-B127; | A99-B128; | A99-B129; | A99-B130; |
| A99-B131; | A99-B132; | A99-B133; | A99-B134; | A99-B135; | A99-B136; |
| A99-B137; | A99-B138; | A99-B139; | A99-B140; | A99-B141; | A99-B142; |
| A99-B143; | A99-B144; | A99-B145; | A99-B146; | A99-B147; | A99-B148; |
| A99-B149; | A99-B150; | A99-B151; | A99-B152; | A99-B153; | A99-B154; |

-continued

A99-B155; A99-B156; A99-B157; A99-B158; A99-B159; A99-B160;
A99-B161; A99-B162; A99-B163; A99-B164; A99-B165; A99-B166;
A99-B167; A99-B168; A99-B169; A100-B1; A100-B2; A100-B3;
A100-B4; A100-B5; A100-B6; A100-B7; A100-B8; A100-B9;
A100-B10; A100-B11; A100-B12; A100-B13; A100-B14; A100-B15;
A100-B16; A100-B17; A100-B18; A100-B19; A100-B20; A100-B21;
A100-B22; A100-B23; A100-B24; A100-B25; A100-B26; A100-B27;
A100-B28; A100-B29; A100-B30; A100-B31; A100-B32; A100-B33;
A100-B34; A100-B35; A100-B36; A100-B37; A100-B38; A100-B39;
A100-B40; A100-B41; A100-B42; A100-B43; A100-B44; A100-B45;
A100-B46; A100-B47; A100-B48; A100-B49; A100-B50; A100-B51;
A100-B52; A100-B53; A100-B54; A100-B55; A100-B56; A100-B57;
A100-B58; A100-B59; A100-B60; A100-B61; A100-B62; A100-B63;
A100-B64; A100-B65; A100-B66; A100-B67; A100-B68; A100-B69;
A100-B70; A100-B71; A100-B72; A100-B73; A100-B74; A100-B75;
A100-B76; A100-B77; A100-B78; A100-B79; A100-B80; A100-B81;
A100-B82; A100-B83; A100-B84; A100-B85; A100-B86; A100-B87;
A100-B88; A100-B89; A100-B90; A100-B91; A100-B92; A100-B93;
A100-B94; A100-B95; A100-B96; A100-B97; A100-B98; A100-B99;
A100-B100; A100-B101; A100-B102; A100-B103; A100-B104; A100-B105;
A100-B106; A100-B107; A100-B108; A100-B109; A100-B110; A100-B111;
A100-B112; A100-B113; A100-B114; A100-B115; A100-B116; A100-B117;
A100-B118; A100-B119; A100-B120; A100-B121; A100-B122; A100-B123;
A100-B124; A100-B125; A100-B126; A100-B127; A100-B128; A100-B129;
A100-B130; A100-B131; A100-B132; A100-B133; A100-B134; A100-B135;
A100-B136; A100-B137; A100-B138; A100-B139; A100-B140; A100-B141;
A100-B142; A100-B143; A100-B144; A100-B145; A100-B146; A100-B147;
A100-B148; A100-B149; A100-B150; A100-B151; A100-B152; A100-B153;
A100-B154; A100-B155; A100-B156; A100-B157; A100-B158; A100-B159;
A100-B160; A100-B161; A100-B162; A100-B163; A100-B164; A100-B165;
A100-B166; A100-B167; A100-B168; A100-B169; A101-B1; A101-B2;
A101-B3; A101-B4; A101-B5; A101-B6; A101-B7; A101-B8;
A101-B9; A101-B10; A101-B11; A101-B12; A101-B13; A101-B14;
A101-B15; A101-B16; A101-B17; A101-B18; A101-B19; A101-B20;
A101-B21; A101-B22; A101-B23; A101-B24; A101-B25; A101-B26;
A101-B27; A101-B28; A101-B29; A101-B30; A101-B31; A101-B32;
A101-B33; A101-B34; A101-B35; A101-B36; A101-B37; A101-B38;
A101-B39; A101-B40; A101-B41; A101-B42; A101-B43; A101-B44;
A101-B45; A101-B46; A101-B47; A101-B48; A101-B49; A101-B50;
A101-B51; A101-B52; A101-B53; A101-B54; A101-B55; A101-B56;
A101-B57; A101-B58; A101-B59; A101-B60; A101-B61; A101-B62;
A101-B63; A101-B64; A101-B65; A101-B66; A101-B67; A101-B68;
A101-B69; A101-B70; A101-B71; A101-B72; A101-B73; A101-B74;
A101-B75; A101-B76; A101-B77; A101-B78; A101-B79; A101-B80;
A101-B81; A101-B82; A101-B83; A101-B84; A101-B85; A101-B86;
A101-B87; A101-B88; A101-B89; A101-B90; A101-B91; A101-B92;
A101-B93; A101-B94; A101-B95; A101-B96; A101-B97; A101-B98;
A101-B99; A101-B100; A101-B101; A101-B102; A101-B103; A101-B104;
A101-B105; A101-B106; A101-B107; A101-B108; A101-B109; A101-B110;
A101-B111; A101-B112; A101-B113; A101-B114; A101-B115; A101-B116;
A101-B117; A101-B118; A101-B119; A101-B120; A101-B121; A101-B122;
A101-B123; A101-B124; A101-B125; A101-B126; A101-B127; A101-B128;
A101-B129; A101-B130; A101-B131; A101-B132; A101-B133; A101-B134;
A101-B135; A101-B136; A101-B137; A101-B138; A101-B139; A101-B140;
A101-B141; A101-B142; A101-B143; A101-B144; A101-B145; A101-B146;
A101-B147; A101-B148; A101-B149; A101-B150; A101-B151; A101-B152;
A101-B153; A101-B154; A101-B155; A101-B156; A101-B157; A101-B158;
A101-B159; A101-B160; A101-B161; A101-B162; A101-B163; A101-B164;
A101-B165; A101-B166; A101-B167; A101-B168; A101-B169; A102-B1;
A102-B2; A102-B3; A102-B4; A102-B5; A102-B6; A102-B7;
A102-B8; A102-B9; A102-B10; A102-B11; A102-B12; A102-B13;
A102-B14; A102-B15; A102-B16; A102-B17; A102-B18; A102-B19;
A102-B20; A102-B21; A102-B22; A102-B23; A102-B24; A102-B25;
A102-B26; A102-B27; A102-B28; A102-B29; A102-B30; A102-B31;
A102-B32; A102-B33; A102-B34; A102-B35; A102-B36; A102-B37;
A102-B38; A102-B39; A102-B40; A102-B41; A102-B42; A102-B43;
A102-B44; A102-B45; A102-B46; A102-B47; A102-B48; A102-B49;
A102-B50; A102-B51; A102-B52; A102-B53; A102-B54; A102-B55;
A102-B56; A102-B57; A102-B58; A102-B59; A102-B60; A102-B61;
A102-B62; A102-B63; A102-B64; A102-B65; A102-B66; A102-B67;
A102-B68; A102-B69; A102-B70; A102-B71; A102-B72; A102-B73;
A102-B74; A102-B75; A102-B76; A102-B77; A102-B78; A102-B79;
A102-B80; A102-B81; A102-B82; A102-B83; A102-B84; A102-B85;
A102-B86; A102-B87; A102-B88; A102-B89; A102-B90; A102-B91;
A102-B92; A102-B93; A102-B94; A102-B95; A102-B96; A102-B97;
A102-B98; A102-B99; A102-B100; A102-B101; A102-B102; A102-B103;
A102-B104; A102-B105; A102-B106; A102-B107; A102-B108; A102-B109;
A102-B110; A102-B111; A102-B112; A102-B113; A102-B114; A102-B115;
A102-B116; A102-B117; A102-B118; A102-B119; A102-B120; A102-B121;
A102-B122; A102-B123; A102-B124; A102-B125; A102-B126; A102-B127;

-continued

A102-B128; A102-B129; A102-B130; A102-B131; A102-B132; A102-B133;
A102-B134; A102-B135; A102-B136; A102-B137; A102-B138; A102-B139;
A102-B140; A102-B141; A102-B142; A102-B143; A102-B144; A102-B145;
A102-B146; A102-B147; A102-B148; A102-B149; A102-B150; A102-B151;
A102-B152; A102-B153; A102-B154; A102-B155; A102-B156; A102-B157;
A102-B158; A102-B159; A102-B160; A102-B161; A102-B162; A102-B163;
A102-B164; A102-B165; A102-B166; A102-B167; A102-B168; A102-B169;
A103-B1; A103-B2; A103-B3; A103-B4; A103-B5; A103-B6;
A103-B7; A103-B8; A103-B9; A103-B10; A103-B11; A103-B12;
A103-B13; A103-B14; A103-B15; A103-B16; A103-B17; A103-B18;
A103-B19; A103-B20; A103-B21; A103-B22; A103-B23; A103-B24;
A103-B25; A103-B26; A103-B27; A103-B28; A103-B29; A103-B30;
A103-B31; A103-B32; A103-B33; A103-B34; A103-B35; A103-B36;
A103-B37; A103-B38; A103-B39; A103-B40; A103-B41; A103-B42;
A103-B43; A103-B44; A103-B45; A103-B46; A103-B47; A103-B48;
A103-B49; A103-B50; A103-B51; A103-B52; A103-B53; A103-B54;
A103-B55; A103-B56; A103-B57; A103-B58; A103-B59; A103-B60;
A103-B61; A103-B62; A103-B63; A103-B64; A103-B65; A103-B66;
A103-B67; A103-B68; A103-B69; A103-B70; A103-B71; A103-B72;
A103-B73; A103-B74; A103-B75; A103-B76; A103-B77; A103-B78;
A103-B79; A103-B80; A103-B81; A103-B82; A103-B83; A103-B84;
A103-B85; A103-B86; A103-B87; A103-B88; A103-B89; A103-B90;
A103-B91; A103-B92; A103-B93; A103-B94; A103-B95; A103-B96;
A103-B97; A103-B98; A103-B99; A103-B100; A103-B101; A103-B102;
A103-B103; A103-B104; A103-B105; A103-B106; A103-B107; A103-B108;
A103-B109; A103-B110; A103-B111; A103-B112; A103-B113; A103-B114;
A103-B115; A103-B116; A103-B117; A103-B118; A103-B119; A103-B120;
A103-B121; A103-B122; A103-B123; A103-B124; A103-B125; A103-B126;
A103-B127; A103-B128; A103-B129; A103-B130; A103-B131; A103-B132;
A103-B133; A103-B134; A103-B135; A103-B136; A103-B137; A103-B138;
A103-B139; A103-B140; A103-B141; A103-B142; A103-B143; A103-B144;
A103-B145; A103-B146; A103-B147; A103-B148; A103-B149; A103-B150;
A103-B151; A103-B152; A103-B153; A103-B154; A103-B155; A103-B156;
A103-B157; A103-B158; A103-B159; A103-B160; A103-B161; A103-B162;
A103-B163; A103-B164; A103-B165; A103-B166; A103-B167; A103-B168;
A103-B169; A104-B1; A104-B2; A104-B3; A104-B4; A104-B5;
A104-B6; A104-B7; A104-B8; A104-B9; A104-B10; A104-B11;
A104-B12; A104-B13; A104-B14; A104-B15; A104-B16; A104-B17;
A104-B18; A104-B19; A104-B20; A104-B21; A104-B22; A104-B23;
A104-B24; A104-B25; A104-B26; A104-B27; A104-B28; A104-B29;
A104-B30; A104-B31; A104-B32; A104-B33; A104-B34; A104-B35;
A104-B36; A104-B37; A104-B38; A104-B39; A104-B40; A104-B41;
A104-B42; A104-B43; A104-B44; A104-B45; A104-B46; A104-B47;
A104-B48; A104-B49; A104-B50; A104-B51; A104-B52; A104-B53;
A104-B54; A104-B55; A104-B56; A104-B57; A104-B58; A104-B59;
A104-B60; A104-B61; A104-B62; A104-B63; A104-B64; A104-B65;
A104-B66; A104-B67; A104-B68; A104-B69; A104-B70; A104-B71;
A104-B72; A104-B73; A104-B74; A104-B75; A104-B76; A104-B77;
A104-B78; A104-B79; A104-B80; A104-B81; A104-B82; A104-B83;
A104-B84; A104-B85; A104-B86; A104-B87; A104-B88; A104-B89;
A104-B90; A104-B91; A104-B92; A104-B93; A104-B94; A104-B95;
A104-B96; A104-B97; A104-B98; A104-B99; A104-B100; A104-B101;
A104-B102; A104-B103; A104-B104; A104-B105; A104-B106; A104-B107;
A104-B108; A104-B109; A104-B110; A104-B111; A104-B112; A104-B113;
A104-B114; A104-B115; A104-B116; A104-B117; A104-B118; A104-B119;
A104-B120; A104-B121; A104-B122; A104-B123; A104-B124; A104-B125;
A104-B126; A104-B127; A104-B128; A104-B129; A104-B130; A104-B131;
A104-B132; A104-B133; A104-B134; A104-B135; A104-B136; A104-B137;
A104-B138; A104-B139; A104-B140; A104-B141; A104-B142; A104-B143;
A104-B144; A104-B145; A104-B146; A104-B147; A104-B148; A104-B149;
A104-B150; A104-B151; A104-B152; A104-B153; A104-B154; A104-B155;
A104-B156; A104-B157; A104-B158; A104-B159; A104-B160; A104-B161;
A104-B162; A104-B163; A104-B164; A104-B165; A104-B166; A104-B167;
A104-B168; A104-B169; A105-B1; A105-B2; A105-B3; A105-B4;
A105-B5; A105-B6; A105-B7; A105-B8; A105-B9; A105-B10;
A105-B11; A105-B12; A105-B13; A105-B14; A105-B15; A105-B16;
A105-B17; A105-B18; A105-B19; A105-B20; A105-B21; A105-B22;
A105-B23; A105-B24; A105-B25; A105-B26; A105-B27; A105-B28;
A105-B29; A105-B30; A105-B31; A105-B32; A105-B33; A105-B34;
A105-B35; A105-B36; A105-B37; A105-B38; A105-B39; A105-B40;
A105-B41; A105-B42; A105-B43; A105-B44; A105-B45; A105-B46;
A105-B47; A105-B48; A105-B49; A105-B50; A105-B51; A105-B52;
A105-B53; A105-B54; A105-B55; A105-B56; A105-B57; A105-B58;
A105-B59; A105-B60; A105-B61; A105-B62; A105-B63; A105-B64;
A105-B65; A105-B66; A105-B67; A105-B68; A105-B69; A105-B70;
A105-B71; A105-B72; A105-B73; A105-B74; A105-B75; A105-B76;
A105-B77; A105-B78; A105-B79; A105-B80; A105-B81; A105-B82;
A105-B83; A105-B84; A105-B85; A105-B86; A105-B87; A105-B88;
A105-B89; A105-B90; A105-B91; A105-B92; A105-B93; A105-B94;
A105-B95; A105-B96; A105-B97; A105-B98; A105-B99; A105-B100;

-continued

A105-B101; A105-B102; A105-B103; A105-B104; A105-B105; A105-B106;
A105-B107; A105-B108; A105-B109; A105-B110; A105-B111; A105-B112;
A105-B113; A105-B114; A105-B115; A105-B116; A105-B117; A105-B118;
A105-B119; A105-B120; A105-B121; A105-B122; A105-B123; A105-B124;
A105-B125; A105-B126; A105-B127; A105-B128; A105-B129; A105-B130;
A105-B131; A105-B132; A105-B133; A105-B134; A105-B135; A105-B136;
A105-B137; A105-B138; A105-B139; A105-B140; A105-B141; A105-B142;
A105-B143; A105-B144; A105-B145; A105-B146; A105-B147; A105-B148;
A105-B149; A105-B150; A105-B151; A105-B152; A105-B153; A105-B154;
A105-B155; A105-B156; A105-B157; A105-B158; A105-B159; A105-B160;
A105-B161; A105-B162; A105-B163; A105-B164; A105-B165; A105-B166;
A105-B167; A105-B168; A105-B169; A106-B1; A106-B2; A106-B3;
A106-B4; A106-B5; A106-B6; A106-B7; A106-B8; A106-B9;
A106-B10; A106-B11; A106-B12; A106-B13; A106-B14; A106-B15;
A106-B16; A106-B17; A106-B18; A106-B19; A106-B20; A106-B21;
A106-B22; A106-B23; A106-B24; A106-B25; A106-B26; A106-B27;
A106-B28; A106-B29; A106-B30; A106-B31; A106-B32; A106-B33;
A106-B34; A106-B35; A106-B36; A106-B37; A106-B38; A106-B39;
A106-B40; A106-B41; A106-B42; A106-B43; A106-B44; A106-B45;
A106-B46; A106-B47; A106-B48; A106-B49; A106-B50; A106-B51;
A106-B52; A106-B53; A106-B54; A106-B55; A106-B56; A106-B57;
A106-B58; A106-B59; A106-B60; A106-B61; A106-B62; A106-B63;
A106-B64; A106-B65; A106-B66; A106-B67; A106-B68; A106-B69;
A106-B70; A106-B71; A106-B72; A106-B73; A106-B74; A106-B75;
A106-B76; A106-B77; A106-B78; A106-B79; A106-B80; A106-B81;
A106-B82; A106-B83; A106-B84; A106-B85; A106-B86; A106-B87;
A106-B88; A106-B89; A106-B90; A106-B91; A106-B92; A106-B93;
A106-B94; A106-B95; A106-B96; A106-B97; A106-B98; A106-B99;
A106-B100; A106-B101; A106-B102; A106-B103; A106-B104; A106-B105;
A106-B106; A106-B107; A106-B108; A106-B109; A106-B110; A106-B111;
A106-B112; A106-B113; A106-B114; A106-B115; A106-B116; A106-B117;
A106-B118; A106-B119; A106-B120; A106-B121; A106-B122; A106-B123;
A106-B124; A106-B125; A106-B126; A106-B127; A106-B128; A106-B129;
A106-B130; A106-B131; A106-B132; A106-B133; A106-B134; A106-B135;
A106-B136; A106-B137; A106-B138; A106-B139; A106-B140; A106-B141;
A106-B142; A106-B143; A106-B144; A106-B145; A106-B146; A106-B147;
A106-B148; A106-B149; A106-B150; A106-B151; A106-B152; A106-B153;
A106-B154; A106-B155; A106-B156; A106-B157; A106-B158; A106-B159;
A106-B160; A106-B161; A106-B162; A106-B163; A106-B164; A106-B165;
A106-B166; A106-B167; A106-B168; A106-B169; A107-B1; A107-B2;
A107-B3; A107-B4; A107-B5; A107-B6; A107-B7; A107-B8;
A107-B9; A107-B10; A107-B11; A107-B12; A107-B13; A107-B14;
A107-B15; A107-B16; A107-B17; A107-B18; A107-B19; A107-B20;
A107-B21; A107-B22; A107-B23; A107-B24; A107-B25; A107-B26;
A107-B27; A107-B28; A107-B29; A107-B30; A107-B31; A107-B32;
A107-B33; A107-B34; A107-B35; A107-B36; A107-B37; A107-B38;
A107-B39; A107-B40; A107-B41; A107-B42; A107-B43; A107-B44;
A107-B45; A107-B46; A107-B47; A107-B48; A107-B49; A107-B50;
A107-B51; A107-B52; A107-B53; A107-B54; A107-B55; A107-B56;
A107-B57; A107-B58; A107-B59; A107-B60; A107-B61; A107-B62;
A107-B63; A107-B64; A107-B65; A107-B66; A107-B67; A107-B68;
A107-B69; A107-B70; A107-B71; A107-B72; A107-B73; A107-B74;
A107-B75; A107-B76; A107-B77; A107-B78; A107-B79; A107-B80;
A107-B81; A107-B82; A107-B83; A107-B84; A107-B85; A107-B86;
A107-B87; A107-B88; A107-B89; A107-B90; A107-B91; A107-B92;
A107-B93; A107-B94; A107-B95; A107-B96; A107-B97; A107-B98;
A107-B99; A107-B100; A107-B101; A107-B102; A107-B103; A107-B104;
A107-B105; A107-B106; A107-B107; A107-B108; A107-B109; A107-B110;
A107-B111; A107-B112; A107-B113; A107-B114; A107-B115; A107-B116;
A107-B117; A107-B118; A107-B119; A107-B120; A107-B121; A107-B122;
A107-B123; A107-B124; A107-B125; A107-B126; A107-B127; A107-B128;
A107-B129; A107-B130; A107-B131; A107-B132; A107-B133; A107-B134;
A107-B135; A107-B136; A107-B137; A107-B138; A107-B139; A107-B140;
A107-B141; A107-B142; A107-B143; A107-B144; A107-B145; A107-B146;
A107-B147; A107-B148; A107-B149; A107-B150; A107-B151; A107-B152;
A107-B153; A107-B154; A107-B155; A107-B156; A107-B157; A107-B158;
A107-B159; A107-B160; A107-B161; A107-B162; A107-B163; A107-B164;
A107-B165; A107-B166; A107-B167; A107-B168; A107-B169; A108-B1;
A108-B2; A108-B3; A108-B4; A108-B5; A108-B6; A108-B7;
A108-B8; A108-B9; A108-B10; A108-B11; A108-B12; A108-B13;
A108-B14; A108-B15; A108-B16; A108-B17; A108-B18; A108-B19;
A108-B20; A108-B21; A108-B22; A108-B23; A108-B24; A108-B25;
A108-B26; A108-B27; A108-B28; A108-B29; A108-B30; A108-B31;
A108-B32; A108-B33; A108-B34; A108-B35; A108-B36; A108-B37;
A108-B38; A108-B39; A108-B40; A108-B41; A108-B42; A108-B43;
A108-B44; A108-B45; A108-B46; A108-B47; A108-B48; A108-B49;
A108-B50; A108-B51; A108-B52; A108-B53; A108-B54; A108-B55;
A108-B56; A108-B57; A108-B58; A108-B59; A108-B60; A108-B61;
A108-B62; A108-B63; A108-B64; A108-B65; A108-B66; A108-B67;
A108-B68; A108-B69; A108-B70; A108-B71; A108-B72; A108-B73;

-continued

A108-B74; A108-B75; A108-B76; A108-B77; A108-B78; A108-B79;
A108-B80; A108-B81; A108-B82; A108-B83; A108-B84; A108-B85;
A108-B86; A108-B87; A108-B88; A108-B89; A108-B90; A108-B91;
A108-B92; A108-B93; A108-B94; A108-B95; A108-B96; A108-B97;
A108-B98; A108-B99; A108-B100; A108-B101; A108-B102; A108-B103;
A108-B104; A108-B105; A108-B106; A108-B107; A108-B108; A108-B109;
A108-B110; A108-B111; A108-B112; A108-B113; A108-B114; A108-B115;
A108-B116; A108-B117; A108-B118; A108-B119; A108-B120; A108-B121;
A108-B122; A108-B123; A108-B124; A108-B125; A108-B126; A108-B127;
A108-B128; A108-B129; A108-B130; A108-B131; A108-B132; A108-B133;
A108-B134; A108-B135; A108-B136; A108-B137; A108-B138; A108-B139;
A108-B140; A108-B141; A108-B142; A108-B143; A108-B144; A108-B145;
A108-B146; A108-B147; A108-B148; A108-B149; A108-B150; A108-B151;
A108-B152; A108-B153; A108-B154; A108-B155; A108-B156; A108-B157;
A108-B158; A108-B159; A108-B160; A108-B161; A108-B162; A108-B163;
A108-B164; A108-B165; A108-B166; A108-B167; A108-B168; A108-B169;
A109-B1; A109-B2; A109-B3; A109-B4; A109-B5; A109-B6;
A109-B7; A109-B8; A109-B9; A109-B10; A109-B11; A109-B12;
A109-B13; A109-B14; A109-B15; A109-B16; A109-B17; A109-B18;
A109-B19; A109-B20; A109-B21; A109-B22; A109-B23; A109-B24;
A109-B25; A109-B26; A109-B27; A109-B28; A109-B29; A109-B30;
A109-B31; A109-B32; A109-B33; A109-B34; A109-B35; A109-B36;
A109-B37; A109-B38; A109-B39; A109-B40; A109-B41; A109-B42;
A109-B43; A109-B44; A109-B45; A109-B46; A109-B47; A109-B48;
A109-B49; A109-B50; A109-B51; A109-B52; A109-B53; A109-B54;
A109-B55; A109-B56; A109-B57; A109-B58; A109-B59; A109-B60;
A109-B61; A109-B62; A109-B63; A109-B64; A109-B65; A109-B66;
A109-B67; A109-B68; A109-B69; A109-B70; A109-B71; A109-B72;
A109-B73; A109-B74; A109-B75; A109-B76; A109-B77; A109-B78;
A109-B79; A109-B80; A109-B81; A109-B82; A109-B83; A109-B84;
A109-B85; A109-B86; A109-B87; A109-B88; A109-B89; A109-B90;
A109-B91; A109-B92; A109-B93; A109-B94; A109-B95; A109-B96;
A109-B97; A109-B98; A109-B99; A109-B100; A109-B101; A109-B102;
A109-B103; A109-B104; A109-B105; A109-B106; A109-B107; A109-B108;
A109-B109; A109-B110; A109-B111; A109-B112; A109-B113; A109-B114;
A109-B115; A109-B116; A109-B117; A109-B118; A109-B119; A109-B120;
A109-B121; A109-B122; A109-B123; A109-B124; A109-B125; A109-B126;
A109-B127; A109-B128; A109-B129; A109-B130; A109-B131; A109-B132;
A109-B133; A109-B134; A109-B135; A109-B136; A109-B137; A109-B138;
A109-B139; A109-B140; A109-B141; A109-B142; A109-B143; A109-B144;
A109-B145; A109-B146; A109-B147; A109-B148; A109-B149; A109-B150;
A109-B151; A109-B152; A109-B153; A109-B154; A109-B155; A109-B156;
A109-B157; A109-B158; A109-B159; A109-B160; A109-B161; A109-B162;
A109-B163; A109-B164; A109-B165; A109-B166; A109-B167; A109-B168;
A109-B169; A110-B1; A110-B2; A110-B3; A110-B4; A110-B5;
A110-B6; A110-B7; A110-B8; A110-B9; A110-B10; A110-B11;
A110-B12; A110-B13; A110-B14; A110-B15; A110-B16; A110-B17;
A110-B18; A110-B19; A110-B20; A110-B21; A110-B22; A110-B23;
A110-B24; A110-B25; A110-B26; A110-B27; A110-B28; A110-B29;
A110-B30; A110-B31; A110-B32; A110-B33; A110-B34; A110-B35;
A110-B36; A110-B37; A110-B38; A110-B39; A110-B40; A110-B41;
A110-B42; A110-B43; A110-B44; A110-B45; A110-B46; A110-B47;
A110-B48; A110-B49; A110-B50; A110-B51; A110-B52; A110-B53;
A110-B54; A110-B55; A110-B56; A110-B57; A110-B58; A110-B59;
A110-B60; A110-B61; A110-B62; A110-B63; A110-B64; A110-B65;
A110-B66; A110-B67; A110-B68; A110-B69; A110-B70; A110-B71;
A110-B72; A110-B73; A110-B74; A110-B75; A110-B76; A110-B77;
A110-B78; A110-B79; A110-B80; A110-B81; A110-B82; A110-B83;
A110-B84; A110-B85; A110-B86; A110-B87; A110-B88; A110-B89;
A110-B90; A110-B91; A110-B92; A110-B93; A110-B94; A110-B95;
A110-B96; A110-B97; A110-B98; A110-B99; A110-B100; A110-B101;
A110-B102; A110-B103; A110-B104; A110-B105; A110-B106; A110-B107;
A110-B108; A110-B109; A110-B110; A110-B111; A110-B112; A110-B113;
A110-B114; A110-B115; A110-B116; A110-B117; A110-B118; A110-B119;
A110-B120; A110-B121; A110-B122; A110-B123; A110-B124; A110-B125;
A110-B126; A110-B127; A110-B128; A110-B129; A110-B130; A110-B131;
A110-B132; A110-B133; A110-B134; A110-B135; A110-B136; A110-B137;
A110-B138; A110-B139; A110-B140; A110-B141; A110-B142; A110-B143;
A110-B144; A110-B145; A110-B146; A110-B147; A110-B148; A110-B149;
A110-B150; A110-B151; A110-B152; A110-B153; A110-B154; A110-B155;
A110-B156; A110-B157; A110-B158; A110-B159; A110-B160; A110-B161;
A110-B162; A110-B163; A110-B164; A110-B165; A110-B166; A110-B167;
A110-B168; A110-B169.

Thus, for example, in the above list the compound denoted as A9-B9 is the product of the combination of group A9 in Table 1 and B9 in Table 2, namely

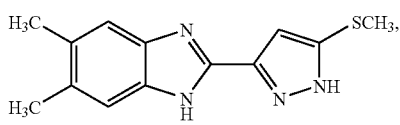

Example 230(a) hereinafter described.
Particular compounds of the invention of formula (Ix) for the inhibition of SYK are:
2-(1H-indazol-3-yl)-1H-benzimidazole-5-carboxylic acid benzylamide;
2-(1H-indazol-3-yl)-1H-benzimidazole-5-carboxylic acid N-methylamide;
2-(1H-indazol-3-yl)-1H-benzimidazole-5-carboxylic acid N-ethylamide;
2-(1H-indazol-3-yl)-1H-benzimidazole-5-carboxylic acid N-isopropylamide;
2-(1H-indazol-3-yl)-1H-benzimidazole-5-carboxylic acid N-phenylamide;
2-(1H-indazol-3-yl)-1H-benzimidazole-5-carboxylic acid N-phenethylamide;
5,6-dimethyl-2-(5-methylsulfanyl-1H-pyrazol-3-yl)-1H-benzoimidazole;
6-chloro-5-methyl-2-(5-methylsulfanyl-1H-pyrazol-3-yl)-1H-benzoimidazole;
6-chloro-2-(5-ethylsulfanyl-1H-pyrazol-3-yl)-5-methyl-1H-benzoimidazole;
2-(5-methylsulfanyl-1H-pyrazol-3-yl)-5-trifluoromethyl-1H-benzoimidazole;
2-(5-cyclopropylmethylsulfanyl-1H-pyrazol-3-yl)-5,6-dimethyl-1H-benzoimidazole;
2-(5-ethylsulfanyl-1H-pyrazol-3-yl)-5,6-dimethyl-1H-benzoimidazole;
5,6-dimethyl-2-[5-(pyridin-3-ylmethylsulfanyl)-1H-pyrazol-3-yl]-1H-benzoimidazole;
5-fluoro-2-[5-methylsulfanyl)-1H-pyrazol-3-yl]-1H-benzoimidazole;
5,6-dimethyl-2-(5-phenethylsulfanyl-1H-pyrazol-3-yl)-1H-benzoimidazole;
4-methyl-2-(5-methylsulfanyl-1H-pyrazol-3-yl)-1H-benzoimidazole;
5,6-dimethyl-2-(5-benzylsulfanyl-1H-pyrazol-3-yl)-1H-benzoimidazole;
6-chloro-5-methyl-2-(5-morpholin-4-yl-1H-pyrazol-3-yl)-1H-benzoimidazole;
5,6-dimethyl-2-[5-(thiophen-2-ylmethylsulfanyl)-1H-pyrazol-3-yl]-1H-benzoimidazole;
2-(5-ethylsulfanyl-1H-pyrazol-3-yl)-5-methoxy-1H-benzoimidazole hydrochloride;
5-methyl-2-(5-methylsulfanyl-4-propyl-1H-pyrazol-3-yl)-1H-benzoimidazole;
2-(5-(4-methoxy-benzylsulfanyl)₄-propyl-1H-pyrazol-3-yl)-5-methyl-1H-benzoimidazole;
2-(5-benzylsulfanyl-4-isopropyl-1H-pyrazol-3-yl)-5-methyl-1H-benzoimidazole;
2-(5-methylsulfanyl-4-methyl-1H-pyrazol-3-yl)-5-methoxy-1H-benzoimidazole;
2-(5-methylsulfanyl-4-methyl-1H-pyrazol-3-yl)-5-methyl-1H-benzoimidazole;
3-(5-chloro-1H-benzoimidazol-2-yl)-1H-pyrazol-4-ylamine;
3-(5,6-dichloro-1H-benzoimidazol-2-yl)-1H-pyrazol-4-ylamine;
3-(5,6-dimethyl-1H-benzoimidazol-2-yl)-1H-pyrazol-4-ylamine;
3-(5-ethyl-6-methyl-1H-benzoimidazol-2-yl)-1H-pyrazol-4-ylamine;
3-(6-chloro-5-methoxy-1H-benzoimidazol-2-yl)-1H-pyrazol-4-ylamine;
3-(5-methoxy-1H-benzoimidazol-2-yl)-1H-pyrazol-4-ylamine;
3-(5-ethoxy-1H-benzoimidazol-2-yl)-1H-pyrazol-4-ylamine;
3-(5-fluoro-6-methyl-1H-benzoimidazol-2-yl)-1H-pyrazol-4-ylamine;
3-(5-trifluoromethoxy-1H-benzoimidazol-2-yl)-1H-pyrazol-4-ylamine;
3-(5-trifluoromethyl-1H-benzoimidazol-2-yl)-1H-pyrazol-4-ylamine;
2-(4-amino-1H-pyrazol-3-yl)-1H-benzoimidazole-5-carboxylic acid methyl ester;
3-(1H-benzoimidazol-2-yl)-1H-indazole;
3-(5-methoxy-1H-benzoimidazol-2-yl)-1H-indazole;
[2-(indazol-3-yl)-1H-benzoimidazol-5-yl]-phenyl-methanone;
2-(1H-indazol-3-yl)-3H-benzoimidazol-4-ol;
2-phenyl-1H-imidazol[4,5-b]pyrazine;
3-(5,6-dimethyl-1H-benzoimidazol-2-yl)-1H-indazole;
2-(1H-indazol-3-yl)-3H-imidazo[4,5-c]pyridine;
2-(1H-indazole-3-yl)-3H-imidazo[4,5-b]pyridine;
2-(1H-pyrazol-3-yl)-1H-benzoimidazole;
3-(5,6-dimethyl-1H-benzoimidazol-2-yl)-5-methoxy-1H-indazole;
3-(5-ethyl-6-methyl-1H-benzoimidazol-2-yl)-5-methoxy-1H-indazole;
3-(5,6-dimethyl-1H-benzoimidazol-2-yl)-5-fluoro-1H-indazole;
3-(5,6-dimethyl-1H-benzoimidazol-2-yl)-6-fluoro-1H-indazole;
3-(5,6-dimethyl-1H-benzoimidazol-2-yl)-5-methyl-1H-indazole;
3-(5,6-dimethyl-1H-benzoimidazol-2-yl)-6-methoxy-1H-indazole;
5,6-dimethyl-2-(4-phenyl-1H-pyrazol-3-yl)-1H-benzoimidazole;
3-(5-ethyl-1H-benzoimidazol-2-yl)-1H-indazole;
3-(5-ethyl-6-methyl-1H-benzoimidazol-2-yl)-1H-indazole;
3-(5-isopropyl-6-methyl-1H-benzoimidazol-2-yl)-1H-indazole;
3-(5-bromo-6-methyl-1H-benzoimidazol-2-yl)-1H-indazole;
3-(5-bromo-1H-benzoimidazol-2-yl)-1H-indazole;
3-(5-(3-cyano)phenyl-1H-benzoimidazol-2-yl)-1H-indazole;
3-(5-pyrid-3-yl)-1H-benzoimidazol-2-yl)-1H-indazole;
3-(6-methyl-5-phenyl-1H-benzoimidazol-2-yl)-1H-indazole;
3-(5-phenyl-1H-benzoimidazol-2-yl)-1H-indazole;
3-(5-(2-fluoro)phenyl-1H-benzoimidazol-2-yl)-1H-indazole;
3-(5-(5,6-methylenedioxy)phenyl-1H-benzoimidazol-2-yl)-1H-indazole;
3-(5-(2-methoxy)phenyl-1H-benzoimidazol-2-yl)-1H-indazole;
3-(5-(4-chloro)phenyl-1H-benzoimidazol-2-yl)-1H-indazole;
3-(5-(4-methyl)phenyl-1H-benzoimidazol-2-yl)-1H-indazole;
3-(5-benzyloxy-1H-benzoimidazol-2-yl)-1H-indazole;
3-(5,6-methylenedioxy-1H-benzoimidazol-2-yl)-1H-indazole;
3-(5,6-dimethoxy-1H-benzoimidazol-2-yl)-1H-indazole;

3-(5,6-diethyl-1H-benzoimidazol-2-yl)-1H-indazole;
3-(4,5-dimethyl-1H-benzoimidazol-2-yl)-1H-indazole;
2-(1H-indazol-3-yl)-1H-benzoimidazole-5-carbonitrile;
3-(5-methoxycarbonyl-1H-benzoimidazol-2-yl)-1H-indazole;
3-(5,6-dimethyl-1H-benzoimidazol-2-yl)-5-ethoxy-1H-indazole;
3-(5,6-dimethyl-1H-benzoimidazol-2-yl)-pyrazole-4-carboxylic acid ethyl ester;
2-(4-isopropylcarbamoyl-1H-pyrazol-3-yl)-1H-benzoimidazole-5-carboxylic acid methyl ester;
3-(5,6-dimethyl-1H-benzoimidazol-2-yl)-5-methyl-pyrazole-4-carboxylic acid ethyl ester;
3-(1,5,6,7-tetrahydro-1,3-diaza-s-indacen-2-yl)-1H-pyrazole-4-carboxylic acid cyclopropylamide;
3-(5-methoxy-6-methyl-1H-benzoimidazol-2-yl)-1H-pyrazole-4-carboxylic acid isopropylamide;
3-[5-(2-morpholin-4-yl-ethoxy)-1H-benzoimidazol-2-yl]-1H-indazole;
3-(5,6-dimethyl-1H-benzoimidazol-2-yl)-1H-pyrazole-4-carboxylic acid (2-methoxy-ethyl)-amide;
3-(5,6-dimethyl-1H-benzoimidazol-2-yl)-1H-pyrazole-4-carboxylic acid propylamide;
3-(5,6-dimethyl-1H-benzoimidazol-2-yl)-1H-pyrazole-4-carboxylic acid (tetrahydro-pyran-4-yl)-amide;
3-(5-ethyl-6-methyl-1H-benzoimidazol-2-yl)-1H-indazole-5-carbonitrile;
3-(5-difluoromethoxy-1H-benzoimidazol-2-yl)-1H-pyrazole-4-carboxylic acid isopropylamide;
3-(5-difluoromethoxy-1H-benzoimidazol-2-yl)-1H-pyrazole-4-carboxylic acid cyclopropylamide;
3-(6-ethyl-5-methoxy-1H-benzoimidazol-2-yl)-1H-pyrazole-4-carboxylic acid isopropylamide;
3-(5,6-dimethyl-1H-benzoimidazol-2-yl)-1H-indazole-5-carbonitrile;
2-(5-methyl-1H-pyrazol-3-yl)-1H-benzoimidazole;
2-(5-ethoxy-1H-pyrazol-3-yl)-1H-benzoimidazole;
2-(5-methylsulfanyl-isoxazol-3-yl)-1H-benzoimidazole;
5-chloro-2-(4-nitro-1H-pyrazol-3-yl)-1H-benzoimidazole;
5,6-dichloro-2-(4-nitro-1H-pyrazol-3-yl)-1H-benzoimidazole;
(benzoimidazol-2-yl)-5-methylthio-3-pyrazole;
3-(5,6-dimethyl-1H-benzoimidazol-2-yl)-4,5,6,7-tetrahydro-1H-indazole;
2-(5-isopropyl-1H-pyrazol-3-yl)-5,6-dimethyl-1H-benzoimidazole;
2-(5-ethyl-1H-pyrazol-3-yl)-5,6-dimethyl-1H-benzoimidazole;
5,6-dimethyl-2-(1,4,5,6-tetrahydro-cyclopentapyrazol-3-yl)-1H-benzoimidazole;
3-(5,6-dimethyl-1H-benzoimidazol-2-yl)-4-fluoro-1H-indazole;
4-chloro-3-(5,6-dimethyl-1H-benzoimidazol-2-yl)-1H-indazole;
3-(5,6-dimethyl-1H-benzoimidazol-2-yl)-5-chloro-1H-indazole;
3-(5,6-dimethyl-1H-benzoimidazol-2-yl)-1H-indazol-5-ol;
3-(5-n-propyl-1H-benzoimidazol-2-yl)-1H-indazole;
2-(1H-indazol-3-yl)-1H-benzoimidazole-5-sulfonic acid benzylamide;
3-(5-methanesulfonyl-1H-benzoimidazol-2-yl)-1H-indazole;
[2-(indazol-3-yl)-1H-benzoimidazol-5-yl]-phenyl-methanol;
[2-(indazol-3-yl)-1H-benzoimidazol-5-yl]-carboxylic acid;
[2-(indazol-3-yl)-1H-benzoimidazol-5-yl]-carboxylic acid, methylamide;
[2-indazol-3-yl)-1H-benzoimidazol-5-yl]-carboxylic acid, dimethylamide;
[2-(indazol-3-yl)-1H-benzoimidazol-5-yl]-carboxylic acid, isopropylamide;
1H-benzoimidazol-5-yl]-carboxylic acid, benzylamide;
[2-(indazol-3-yl)-1H-benzoimidazol-5-yl]-carboxylic acid, benzamide;
3-(5,6-dimethyl-1H-benzoimidazol-2-yl)-1H-pyrazole-4-carboxylic acid isopropylamide;
3-(5,6-dimethyl-1H-benzoimidazol-2-yl)-1H-pyrazole-4-carboxylic acid (2-hydroxy-1,1-dimethylethyl)-amide;
2-(4-isopropylcarbamoyl-1H-pyrazol-3-yl)-1H-benzoimidazole-5-carboxylic acid (pyridin-3-ylmethyl)-amide;
3-(5,6-dimethyl-1H-benzoimidazol-2-yl)-5-methyl-1H-pyrazole-4-carboxylic acid cyclopropylamide;
2-(4-isopropylcarbamoyl-1H-pyrazol-3-yl)-1H-benzoimidazole-5-carboxylic acid phenylmethyl-amide;
2-(4-isopropylcarbamoyl-1H-pyrazol-3-yl)-1H-benzoimidazole-5-carboxylic acid (pyridin-2-ylmethyl)-amide;
2-(1H-indazol-3-yl)-1H-benzoimidazole-5-carboxylic acid (pyridin-3-ylmethyl)-amide;
2-(1H-indazol-3-yl)-1H-benzoimidazole-5-carboxylic acid 3-methyl-benzylamide;
2-(1H-indazol-3-yl)-1H-benzoimidazole-5-carboxylic acid 4-methyl-benzylamide;
2-(1H-indazol-3-yl)-1H-benzoimidazole-5-carboxylic acid [3-(2-oxo-pyrrolidin-1-yl)-propyl]-amide;
2-(1H-indazol-3-yl)-1H-benzoimidazole-5-carboxylic acid (2-morpholin-4-yl-ethyl)-amide;
2-(1H-indazol-3-yl)-1H-benzoimidazole-5-carboxylic acid (2-methoxy-ethyl)-amide;
2-(1H-indazol-3-yl)-1H-benzoimidazole-5-carboxylic acid (2-cyano-ethyl)-amide;
2-(1H-indazol-3-yl)-1H-benzoimidazole-5-carboxylic acid (2-hydroxy-1,1-dimethyl-ethyl)-amide;
2-(1H-Indazol-3-yl)-1H-benzoimidazole-5-carboxylic acid (3-imidazol-1-yl-propyl)-amide;
3-(5,6-dimethyl-1H-benzoimidazol-2-yl)-1H-pyrazole-4-carboxylic acid isobutyl-amide;
3-(5,6-dimethyl-1H-benzoimidazol-2-yl)-1H-pyrazole-4-carboxylic acid isopropylamide;
3-(5,6-dimethyl-1H-benzoimidazol-2-yl-1H-pyrazole-4-carboxylic acid cyclopropylmethyl-amide;
3-(5,6-dimethyl-1H-benzoimidazol-2-yl)-5-methyl-1H-pyrazole-4-carboxylic acid tert-butylamide;
3-(5,6-dimethyl-1H-benzoimidazol-2-yl)-1H-indazole-5-carboxylic acid dimethylamide;
2-(4-isobutyrylamino-1H-pyrazol-3-yl)-1H-benzoimidazole-5-carboxylic acid benzylamide;
[2-(indazol-3-yl)-1H-benzoimidazol-5-yl]-carboxylic acid;
3-(5,6-dimethyl-1H-benzoimidazol-2-yl)-pyrazole-4-carboxylic acid;
2-(4-isopropylcarbamoyl-1H-pyrazol-3-yl)-1H-benzoimidazole-5-carboxylic acid;
3-(5,6-dimethyl-1H-benzoimidazol-2-yl)-5-methyl-pyrazole-4-carboxylic acid;
N-[3-(5,6-dimethyl-1H-benzoimidazol-2-yl)-1H-pyrazol-4-yl]-isobutyramide;
N-[3-(5,6-dimethyl-1H-benzoimidazol-2-yl)-1H-pyrazol-4-yl]-3-methyl-butyramide;
N-[3-(5,6-dimethyl-1H-benzoimidazol-2-yl)-1H-pyrazol-4-yl]-2-phenyl-acetamide;
cyclopropanecarboxylic acid [3-(5,6-dimethyl-1H-benzoimidazol-2-yl)-1H-pyrazol-4-yl]-amide;
methoxyacetic acid [3-(5,6-dimethyl-1H-benzoimidazol-2-yl)-1H-pyrazol-4-yl]-amide;

cyclopentanecarboxylic acid [3-(5,6-dimethyl-1H-benzoimidazol-2-yl)-1H-pyrazol-4-yl]-amide;
trimethylacetic acid [3-(5,6-dimethyl-1H-benzoimidazol-2-yl)-1H-pyrazol-4-yl]-amide;
tert-butylacetic acid [3-(5,6-dimethyl-1H-benzoimidazol-2-yl)-1H-pyrazol-4-yl]-amide;
butanoic acid [3-(5,6-dimethyl-1H-benzoimidazol-2-yl)-1H-pyrazol-4-yl]-amide;
isoxazole-5-carboxylic acid [3-(5,6-dimethyl-1H-benzoimidazol-2-yl)-1H-pyrazol-4-yl]-amide;
S(+)-2-methylbutanoic acid [3-(5,6-dimethyl-1H-benzoimidazol-2-yl)-1H-pyrazol-4-yl]-amide;
cyclopropanecarboxylic acid [3-(5-ethyl-6-methyl-1H-benzoimidazol-2-yl)-1H-pyrazol-4-yl]-amide;
piperidine-1-carboxylic acid[3-(6-chloro-5-methoxy-1H-benzoimidazol-2-yl)-1H-pyrazol-4-yl]-amide;
3-[3-(6-chloro-5-methoxy-1H-benzoimidazol-2-yl)-1H-pyrazol-4-yl]-1,1-dimethylurea;
cyclopropanecarboxylic acid [3-(5-methoxy-1H-benzoimidazol-2-yl)-1H-pyrazol-4-yl]-amide;
cyclopropanecarboxylic acid [3-(5-ethoxy-1H-benzoimidazol-2-yl)-1H-pyrazol-4-yl]-amide;
cyclopropanecarboxylic acid [3-(5-fluoro-6-methyl-1H-benzoimidazol-2-yl)-1H-pyrazol-4-yl]-amide;
cyclopropanecarboxylic acid [3-(5-trifluoromethoxy-1H-benzoimidazol-2-yl)-1H-pyrazol-4-yl]-amide;
cyclopropanecarboxylic acid [3-(5-trifluoromethyl-1H-benzoimidazol-2-yl)-1H-pyrazol-4-yl]-amide;
N-[3-(5-trifluoromethyl-1H-benzoimidazol-2-yl)-1H-pyrazol-4-yl]-isobutyramide;
cyclopropanecarboxylic acid [3-(5-chloro-6-methyl-1H-benzoimidazol-2-yl)-1H-pyrazol-4-yl]-amide;
3,5-dimethyl-isoxazole-4-carboxylic acid [3-(5,6-dimethyl-1H-benzoimidazol-2-yl)-1H-pyrazol-4-yl]-amide;
N-[3-(5,6-dimethyl-1H-benzoimidazol-2-yl)-1H-pyrazol-4-yl]-acetamide;
furan-3-carboxylic acid [3-(5-chloro-6-methyl-1H-benzoimidazol-2-yl)-1H-pyrazol-4-yl]-amide;
N-[3-(5,6-dimethyl-1H-benzoimidazol-2-yl)-1H-pyrazol-4-yl]4-methyl-benzamide;
5,6-dimethyl-2-(4-nitro-1H-pyrazol-3-yl)-1H-benzoimidazole;
5-ethyl-6-methyl-2-(4-nitro-1H-pyrazol-3-yl)-1H-benzoimidazole;
6-chloro-5-methoxy-2-(4-nitro-1H-pyrazol-3-yl)-1H-benzoimidazole;
5-fluoro-6-methyl-2-(4-nitro-1H-pyrazol-3-yl)-1H-benzoimidazole;
2-(4-nitro-1H-pyrazol-3-yl)-5-trifluoromethoxy-1H-benzoimidazole;
2-(4-nitro-1H-pyrazol-3-yl)-5-trifluoromethyl-1H-benzoimidazole;
5-chloro-6-methyl-2-(4-nitro-1H-pyrazol-3-yl)-1H-benzoimidazole;
2-(4-nitro-1H-pyrazol-3-yl)-1H-benzoimidazole-5-carboxylic acid methyl ester;
3-(5,6-dimethyl-1H-benzoimidazol-2-yl)-1,4,6,7-tetrahydro-pyrazolo[4,3-c]pyridine-5-carboxylic acid isopropylamide;
cyclopropyl-[3-(5,6-dimethyl-1H-benzoimidazol-2-yl)-1,4,6,7-tetrahydro-pyrazolo[4,3-c]pyridin-5-yl]-methanone;
isopropyl-[3-(5,6-dimethyl-1H-benzoimidazol-2-yl)-1,4,6,7-tetrahydro-pyrazolo[4,3-c]pyridin-5-yl]-methanone;
1-[3-(5,6-dimethyl-1H-benzoimidazol-2-yl)-1,4,6,7-tetrahydro-pyrazolo[4,3-c]pyridin-5-yl]-2,2-dimethyl-propan-1-one;
3-(5,6-dimethyl-1H-benzoimidazol-2-yl)-1,4,6,7-tetrahydro-pyrazolo[4,3-c]pyridine-5-carboxylic acid methyl ester;
3-(5,6-dimethyl-1H-benzoimidazol-2-yl)-4,5,6,7-tetrahydro-1H-pyrazolo[4,3-c]pyridine;
3-(5-chloro-6-methyl-1H-benzoimidazol-2-yl)-4,5,6,7-tetrahydro-1H-pyrazolo[4,3-c]pyridine;
3-[5-(2-morpholin-4-yl-ethoxy)-1H-benzoimidazol-2-yl]-4,5,6,7-tetrahydro-1H-pyrazolo[4,3-c]pyridine;
3-(5-trifluoromethyl-1H-benzoimidazol-2-yl)-4,5,6,7-tetrahydro-1H-pyrazolo[4,3-c]pyridine;
3-(5,6-dimethyl-1H-benzoimidazol-2-yl)-1,4,6,7-tetrahydro-pyrazolo[4,3-c]pyridine-5-carboxylic acid tert-butyl ester;
5-methoxy-2-(4-nitro-1H-pyrazol-3-yl)-1H-benzoimidazole;
5-ethoxy-2-(4-nitro-1H-pyrazol-3-yl)-1H-benzoimidazole;
3-(5-chloro-6-methyl-1H-benzoimidazol-2-yl)-1,4,6,7-tetrahydro-pyrazolo[4,3-c]pyridine-5-carboxylic acid tert-butyl ester;
3-[5-(2-morpholin-4-yl-ethoxy)-1H-benzoimidazol-2-yl]-1,4,6,7-tetrahydro-pyrazolo[4,3-c]pyridine-5-carboxylic acid tert-butyl ester;
3-(5,6-dimethyl-1H-benzoimidazol-2-yl)-1,4,6,7-tetrahydro-pyrano[4,3-c]pyrazole;
3-(5-trifluoromethyl-1H-benzoimidazol-2-yl)-1,4,6,7-tetrahydro-pyrazolo[4,3-c]pyridine-5-carboxylic acid tert-butyl ester;
N-[3-(5,6-dimethyl-1H-benzoimidazol-2-yl)-1H-pyrazol-4-yl]-2-morpholin-4-yl-acetamide;
2-dimethylamino-N-[3-(5,6-dimethyl-1H-benzoimidazol-2-yl)-1H-pyrazol-4-yl]-acetamide;
N-[3-(5,6-dimethyl-1H-benzoimidazol-2-yl)-1H-pyrazol-4-yl]-2-(1H-1,2,3,4-tetraazol-1-yl)-acetamide;
N-[3-(5,6-dimethyl-1H-benzoimidazol-2-yl)-1H-pyrazol-4-yl]-isonicotinamide;
2-cyclopropyl-N-[3-(5,6-dimethyl-1H-benzoimidazol-2-yl)-1H-pyrazol-4-yl]-acetamide;
1-[3-(5,6-dimethyl-1H-benzoimidazol-2-yl)-1H-pyrazol-4-yl]-3-methyl-urea;
1-[3-(5,6-dimethyl-1H-benzoimidazol-2-yl)-1H-pyrazol-4-yl]-3-isopropyl-urea;
1-[3-(5,6-dimethyl-1H-benzoimidazol-2-yl)-1H-pyrazol-4-yl]-3-phenyl-urea;
1-benzyl-3-[3-(5,6-dimethyl-1H-benzoimidazol-2-yl)-1H-pyrazol-4-yl]-urea;
3-(5,6-dimethyl-1H-benzoimidazol-2-yl)-1,4,6,7-tetrahydro-pyrazolo[4,3-c]pyridine-5-carboxylic acid isopropylamide;
cyclopropanecarboxylic acid[3-(5-ethoxy-6-ethyl-1H-benzoimidazol-2-yl)-1H-pyrazol-4-yl]amide;
3-(1,5,6,7-tetrahydro-1,3-diaza-s-indacen-2-yl)-1H-pyrazol-4-ylamine;
4-methylpiperazine-1-carboxylic acid [3-(1,5,6,7-tetrahydro-1,3-diaza-s-indacen-2-yl)-1H-pyrazol-4-yl]amide;
1,1-dimethyl-3-[3-(1,5,6,7-tetrahydro-s-indacen-2-yl)-1H-pyrazol-4-yl]urea;
cyclopropanecarboxylic acid [3-(6-ethoxy-5-fluoro-1H-benzimidazol-2-yl)-1H-pyrazol-4-yl]amide;
tetrahydropyran-4-carboxylic acid [3-(6-ethoxy-5-fluoro-1H-benzimidazol-2-yl)-1H-pyrazole-4-yl]amide;
morpholine-4-carboxylic acid[3-(6-ethoxy-5-fluoro-1H-benzimidazol-2-yl)-1H-pyrazol-4-yl]amide;
piperidine-4-carboxylic acid[3-(6-ethoxy-5-fluoro-1H-benzimidazol-2-yl)-1H-pyrazol-4-yl]amide;
3-[6-ethoxy-5-fluoro-1H-benzimidazol-2-yl)-1H-pyrazol-4-yl]-1,1-diethylurea;

5-methoxy-2-(4-nitro-1H-pyrazol-3-yl)-1H-benzoimidazole;

morpholine-4-carboxylic acid [3-(5,6-dimethyl-1H-benzoimidazol-2-yl)-1H-pyrazol-4-ylmethyl]-amide;

3-[3-(5-difluoromethoxy-1H-benzoimidazol-2-yl)-1H-pyrazol-4-yl]-1,1-diethyl-urea;

piperidine-1-carboxylic acid [3-(5-difluoromethoxy-1H-benzoimidazol-2-yl)-1H-pyrazol-4-yl]-amide;

cyclopropanecarboxylic acid [3-(6-chloro-5-methoxy-1H-benzoimidazol-2-yl)-1H-pyrazol-4-yl]-amide;

cyclopropanecarboxylic acid [3-(1,5,6,7-tetrahydro-1,3-diaza-s-indacen-2-yl)-1H-pyrazol-4-yl]amide;

morpholine-4-carboxylic acid[3-(1,5,6,7-tetrahydro-1,3-diaza-s-indacen-2-yl)-1H-pyrazol-4-yl]-amide;

piperidine-1-carboxylic acid [3-(5-methoxy-1H-benzoimidazol-2-yl)-1H-pyrazol-4-yl]-amide;

3-[3-(5-methoxy-1H-benzoimidazol-2-yl)-1H-pyrazol-4-yl]-1,1-dimethyl-urea;

piperidine-1-carboxylic acid [3-(5-ethyl-6-methyl-1H-benzoimidazol-2-yl)-1H-pyrazol-4-yl]-amide;

3-[3-(5-fluoro-6-methyl-1H-benzoimidazol-2-yl)-1H-pyrazol-4-yl]-1,1-dimethyl-urea;

morpholine-4-carboxylic acid [3-(5-trifluoromethyl-1H-benzoimidazol-2-yl)-1H-pyrazol-4-yl]-amide;

3-(5,6-dimethyl-1H-benzoimidazol-2-yl)-1,4,6,7-tetrahydro-pyrazolo[4,3-c]pyridine-5-carboxylic acid diethylamide;

[3-(5,6-dimethyl-1H-benzoimidazol-2-yl)-1,4,6,7-tetrahydro-pyrazolo[4,3-c]pyridin-5-yl]-pyrrolidin-1-yl-methanone;

[3-(5,6-dimethyl-1H-benzoimidazol-2-yl)-1,4,6,7-tetrahydro-pyrazolo[4,3-c]pyridin-5-yl]-piperidin-1-yl-methanone;

[3-(5,6-dimethyl-1H-benzoimidazol-2-yl)-1,4,6,7-tetrahydro-pyrazolo[4,3-c]pyridin-5-yl]-morpholin-4-yl-methanone;

3-(5-chloro-6-methyl-1H-benzoimidazol-2-yl)-1,4,6,7-tetrahydro-pyrazolo[4,3-c]pyridine-5-carboxylic acid diethylamide;

morpholine-4-carboxylic acid [3-(5,6-dimethyl-1H-benzoimidazol-2-yl)-1H-pyrazol-4-yl]-amide;

piperidine-1-carboxylic acid [3-(5,6-dimethyl-1H-benzoimidazol-2-yl)-1H-pyrazol-4-yl]-amide;

3-[5-(2-morpholin-4-yl-ethoxy)-1H-benzoimidazol-2-yl]-1,4,6,7-tetrahydro-pyrazolo[4,3-c]pyridine-5-carboxylic acid diethylamide;

3-(5-trifluoromethyl-1H-benzoimidazol-2-yl)-1,4,6,7-tetrahydro-pyrazolo[4,3-c]pyridine-5-carboxylic acid diethylamide;

2-(1H-indazol-3-yl)-1H-benzoimidazole-5-carboxylic acid [2-(2H-tetrazol-5-yl)ethyl]-amide;

1-cyclopropyl-3-[3-(5-ethyl-6-methyl-1H-benzoimidazol-2-yl)-1H-pyrazol-4-yl]-urea;

1-[3-(5-ethyl-6-methyl-1H-benzoimidazol-2-yl)-1H-pyrazol-4-yl]-3-methyl-urea;

4-methyl-piperazine-1-carboxylic acid [3-(5-ethyl-6-methyl-1H-benzoimidazol-2-yl)-1H-pyrazol-4-yl]-amide;

piperidine-1-carboxylic acid [3-(5-fluoro-6-methyl-1H-benzoimidazol-2-yl)-1H-pyrazol-4-yl]-amide;

1-[3-(5-fluoro-6-methyl-1H-benzoimidazol-2-yl)-1H-pyrazol-4-yl]-3-methyl-urea;

morpholine-4-carboxylic acid [3-(5-fluoro-6-methyl-1H-benzoimidazol-2-yl)-1H-pyrazol-4-yl]-amide;

4-methyl-piperazine-1-carboxylic acid [3-(5-fluoro-6-methyl-1H-benzoimidazol-2-yl)-1H-pyrazol-4-yl]-amide;

1-methyl-3-[3-(5-trifluoromethyl-1H-benzoimidazol-2-yl)-1H-pyrazol-4-yl]-urea;

1-[3-(5-chloro-6-methyl-1H-benzoimidazol-2-yl)-1H-pyrazol-4-yl]-3-methyl-urea;

4-methyl-piperazine-1-carboxylic acid [3-(5-chloro-6-methyl-1H-benzoimidazol-2-yl)-1H-pyrazol-4-yl]-amide;

1-tert-butyl-3-[3-(5,6-dimethyl-1H-benzoimidazol-2-yl)-1H-pyrazol-4-yl]-urea;

1-[3-(5,6-dimethyl-1H-benzoimidazol-2-yl)-1H-pyrazol-4-yl]-3-ethyl-urea;

4-methyl-piperazine-1-carboxylic acid [3-(5,6-dimethyl-1H-benzoimidazol-2-yl)-1H-pyrazol-4-yl]-amide;

1-cyclopropyl-3-[3-(5,6-dimethyl-1H-benzoimidazol-2-yl)-1H-pyrazol-4-yl]-urea;

3-[3-(5,6-dimethyl-1H-benzoimidazol-2-yl)-1H-pyrazol-4-yl]-1,1-diethyl-urea;

1-[3-(5,6-dimethyl-1H-benzoimidazol-2-yl)-1H-pyrazol-4-yl]-3-isobutyl-urea;

1-cyclopropylmethyl-3-[3-(5,6-dimethyl-1H-benzoimidazol-2-yl)-1H-pyrazol-4-yl]-urea;

3-(5-chloro-6-methyl-1H-benzoimidazol-2-yl)-1H-pyrazol-4-ylamine;

3-(5-ethyl-6-methyl-1H-benzoimidazol-2-yl)-1H-indazole-5-carboxylic acid amide dihydrochloride;

3-(5,6-dimethyl-1H-benzoimidazol-2-yl)-1H-indazole-5-carboxylic acid;

2-(4-isobutyrylamino-1H-pyrazol-3-yl)-1H-benzoimidazole-5-carboxylic acid;

3-[3-(5,6-dimethyl-1H-benzoimidazol-2-yl)-1H-pyrazol-4-yl]-1,1-dimethyl-urea;

3-(5-nitro-1H-benzoimidazol-2-yl)-1H-indazole;

2-(1H-Indazol-3-yl)-1H-benzoimidazole-5-carboxylic acid (2-piperidin-1-yl-ethyl)-amide;

2-(1H-Indazol-3-yl)-1H-benzoimidazole-5-carboxylic acid (pyridin-2-ylmethyl)-amide;

2-(1H-Indazol-3-yl)-1H-benzoimidazole-5-carboxylic acid [3-(4-methyl-piperazin-1-yl)-propyl]-amide;

N-[2-(1H-Indazol-3-yl)-1H-benzoimidazol-5-yl]-isobutyramide;

N-[3-(5,6-Dimethyl-1H-benzoimidazol-2-yl)-1H-pyrazol-4-yl]-2-piperidin-1-yl-acetamide;

2-(1H-indazol-3-yl)-3H-benzoimidazol-5-amine;

piperidine-1-carboxylic acid [3-(5,6-dimethyl-1H-benzoimidazol-2-yl)-1H-pyrazol-4-yl]-amide;

and the corresponding N-oxides, and their prodrugs; and pharmaceutically acceptable salts and solvates (e.g. hydrates) of such compounds and their N-oxides and prodrugs.

Preferred compounds of formula (Ixa) of the invention for the inhibition of SYK are:—

2-(1H-indazol-3-yl)-1H-benzimidazole-5-carboxylic acid benzylamide;

2-(1H-indazol-3-yl)-1H-benzimidazole-5-carboxylic acid N-methylamide;

2-(1H-indazol-3-yl)-1H-benzimidazole-5-carboxylic acid N-ethylamide;

2-(1H-indazol-3-yl)-1H-benzimidazole-5-carboxylic acid N-isopropylamide;

2-(1H-indazol-3-yl)-1H-benzimidazole-5-carboxylic acid N-phenylamide;

2-(1H-indazol-3-yl)-1H-benzimidazole-5-carboxylic acid N-phenethylamide;

5,6-dimethyl-2-(5-methylsulfanyl-1H-pyrazol-3-yl)-1H-benzoimidazole;

6-chloro-5-methyl-2-(5-methylsulfanyl-1H-pyrazol-3-yl)-1H-benzoimidazole;

6-chloro-2-(5-ethylsulfanyl-1H-pyrazol-3-yl)-5-methyl-1H-benzoimidazole;

2-(5-methylsulfanyl-1H-pyrazol-3-yl)-5-trifluoromethyl-1H-benzoimidazole;
2-(5-cyclopropylmethylsulfanyl-1H-pyrazol-3-yl)-5,6-dimethyl-1H-benzoimidazole;
2-(5-ethylsulfanyl-1H-pyrazol-3-yl)-5,6-dimethyl-1H-benzoimidazole;
5,6-dimethyl-2-[5-(pyridin-3-ylmethylsulfanyl)-1H-pyrazol-3-yl]-1H-benzoimidazole;
5-fluoro-2-[5-methylsulfanyl)-1H-pyrazol-3-yl]-1H-benzoimidazole;
5,6-dimethyl-2-(5-phenethylsulfanyl-1H-pyrazol-3-yl)-1H-benzoimidazole;
4-methyl-2-(5-methylsulfanyl-1H-pyrazol-3-yl)-1H-benzoimidazole;
5,6-dimethyl-2-(5-benzylsulfanyl-1H-pyrazol-3-yl)-1H-benzoimidazole;
5,6-dimethyl-2-[5-(thiophen-2-ylmethylsulfanyl)-1H-pyrazol-3-yl]-1H-benzoimidazole;
2-(5-ethylsulfanyl-1H-pyrazol-3-yl)-5-methoxy-1H-benzoimidazole hydrochloride;
5-methyl-2-(5-methylsulfanyl-4-propyl-1H-pyrazol-3-yl)-1H-benzoimidazole;
2-(5-(4-methoxy-benzylsulfanyl)-4-propyl-1H-pyrazol-3-yl)-5-methyl-1H-benzoimidazole;
2-(5-benzylsulfanyl-4-isopropyl-1H-pyrazol-3-yl)-5-methyl-1H-benzoimidazole;
2-(5-methylsulfanyl-4-methyl-1H-pyrazol-3-yl)-5-methoxy-1H-benzoimidazole;
2-(5-methylsulfanyl-4-methyl-1H-pyrazol-3-yl)-5-methyl-1H-benzoimidazole;
3-(5-chloro-1H-benzoimidazol-2-yl)-1H-pyrazol-4-ylamine;
3-(5,6-dichloro-1H-benzoimidazol-2-yl)-1H-pyrazol-4-ylamine;
5,6-dimethyl-2-(4-phenyl-1H-pyrazol-3-yl)-1H-benzoimidazole;
3-(1,5,6,7-tetrahydro-1,3-diaza-s-indacen-2-yl)-1H-pyrazole-4-carboxylic acid cyclopropylamide;
3-(5-methoxy-6-methyl-1H-benzoimidazol-2-yl)-1H-pyrazole-4-carboxylic acid isopropylamide;
3-(5,6-dimethyl-1H-benzoimidazol-2-yl)-1H-pyrazole-4-carboxylic acid (2-methoxy-ethyl)-amide;
3-(5,6-dimethyl-1H-benzoimidazol-2-yl)-1H-pyrazole-4-carboxylic acid propylamide;
3-(5,6-dimethyl-1H-benzoimidazol-2-yl)-1H-pyrazole-4-carboxylic acid (tetrahydro-pyran-4-yl)-amide;
3-(5-difluoromethoxy-1H-benzoimidazol-2-yl)-1H-pyrazole-4-carboxylic acid isopropylamide;
3-(5-difluoromethoxy-1H-benzoimidazol-2-yl)-1H-pyrazole-4-carboxylic acid cyclopropylamide;
3-(6-ethyl-5-methoxy-1H-benzoimidazol-2-yl)-1H-pyrazole-4-carboxylic acid isopropylamide;
2-(5-ethoxy-1H-pyrazol-3-yl)-1H-benzoimidazole;
(benzoimidazol-2-yl)-5-methylthio-3-pyrazole;
2-(5-isopropyl-1H-pyrazol-3-yl)-5,6-dimethyl-1H-benzoimidazole;
2-(5-ethyl-1H-pyrazol-3-yl)-5,6-dimethyl-1H-benzoimidazole;
3-(5,6-dimethyl-1H-benzoimidazol-2-yl)-1H-pyrazole-4-carboxylic acid isopropylamide;
3-(5,6-dimethyl-1H-benzoimidazol-2-yl)-1H-pyrazole-4-carboxylic acid (2-hydroxy-1,1-dimethylethyl)-amide;
2-(4-isopropylcarbamoyl-1H-pyrazol-3-yl)-1H-benzoimidazole-5-carboxylic acid (pyridin-3-ylmethyl)-amide;
3-(5,6-dimethyl-1H-benzoimidazol-2-yl)-5-methyl-1H-pyrazole-4-carboxylic acid cyclopropylamide;
2-(4-isopropylcarbamoyl-1H-pyrazol-3-yl)-1H-benzoimidazole-5-carboxylic acid phenylmethyl-amide;
3-(5,6-dimethyl-1H-benzoimidazol-2-yl)-1H-pyrazole-4-carboxylic acid isobutyl-amide;
3-(5,6-dimethyl-1H-benzoimidazol-2-yl)-1H-pyrazole-4-carboxylic acid isopropylamide;
3-(5,6-dimethyl-1H-benzoimidazol-2-yl)-1H-pyrazole-4-carboxylic acid cyclopropylmethyl-amide;
3-(5,6-dimethyl-1H-benzoimidazol-2-yl)-5-methyl-1H-pyrazole-4-carboxylic acid tert-butylamide;
2-(4-isobutyrylamino-1H-pyrazol-3-yl)-1H-benzoimidazole-5-carboxylic acid benzylamide;
N-[3-(5,6-dimethyl-1H-benzoimidazol-2-yl)-1H-pyrazol-4-yl]-isobutyramide;
N-[3-(5,6-dimethyl-1H-benzoimidazol-2-yl)-1H-pyrazol-4-yl]-3-methyl-butyramide;
N-[3-(5,6-dimethyl-1H-benzoimidazol-2-yl)-1H-pyrazol-4-yl]-2-phenyl-acetamide;
cyclopropanecarboxylic acid [3-(5,6-dimethyl-1H-benzoimidazol-2-yl)-1H-pyrazol-4-yl]-amide;
methoxyacetic acid [3-(5,6-dimethyl-1H-benzoimidazol-2-yl)-1H-pyrazol-4-yl]-amide;
cyclopentanecarboxylic acid [3-(5,6-dimethyl-1H-benzoimidazol-2-yl)-1H-pyrazol-4-yl]-amide;
trimethylacetic acid [3-(5,6-dimethyl-1H-benzoimidazol-2-yl)-1H-pyrazol-4-yl]-amide;
tert-butylacetic acid [3-(5,6-dimethyl-1H-benzoimidazol-2-yl)-1H-pyrazol-4-yl]-amide;
butanoic acid [3-(5,6-dimethyl-1H-benzoimidazol-2-yl)-1H-pyrazol-4-yl]-amide;
isoxazole-5-carboxylic acid [3-(5,6-dimethyl-1H-benzoimidazol-2-yl)-1H-pyrazol-4-yl]-amide;
S(+)-2-methylbutanoic acid [3-(5,6-dimethyl-1H-benzoimidazol-2-yl)-1H-pyrazol-4-yl]-amide;
cyclopropanecarboxylic acid [3-(5-ethyl-6-methyl-1H-benzoimidazol-2-yl)-1H-pyrazol-4-yl]-amide;
piperidine-1-carboxylic acid[3-(6-chloro-5-methoxy-1H-benzoimidazol-2-yl)-1H-pyrazol-4-yl]-amide;
3-[3-(6-chloro-5-methoxy-1H-benzoimidazol-2-yl)-1H-pyrazol-4-yl]-1,1-dimethylurea;
cyclopropanecarboxylic acid [3-(5-methoxy-1H-benzoimidazol-2-yl)-1H-pyrazol-4-yl]-amide;
cyclopropanecarboxylic acid [3-(5-ethoxy-1H-benzoimidazol-2-yl)-1H-pyrazol-4-yl]-amide;
cyclopropanecarboxylic acid [3-(5-fluoro-6-methyl-1H-benzoimidazol-2-yl)-1H-pyrazol-4-yl]-amide;
cyclopropanecarboxylic acid [3-(5-trifluoromethoxy-1H-benzoimidazol-2-yl)-1H-pyrazol-4-yl]-amide;
cyclopropanecarboxylic acid [3-(5-trifluoromethyl-1H-benzoimidazol-2-yl)-1H-pyrazol-4-yl]-amide;
N-[3-(5-trifluoromethyl-1H-benzoimidazol-2-yl)-1H-pyrazol-4-yl]-isobutyramide;
cyclopropanecarboxylic acid [3-(5-chloro-6-methyl-1H-benzoimidazol-2-yl)-1H-pyrazol-4-yl]-amide;
3,5-dimethyl-isoxazole-4-carboxylic acid [3-(5,6-dimethyl-1H-benzoimidazol-2-yl)-1H-pyrazol-4-yl]-amide;
N-[3-(5,6-dimethyl-1H-benzoimidazol-2-yl)-1H-pyrazol-4-yl]-acetamide;
furan-3-carboxylic acid [3-(5-chloro-6-methyl-1H-benzoimidazol-2-yl)-1H-pyrazol-4-yl]-amide;
N-[3-(5,6-dimethyl-1H-benzoimidazol-2-yl)-1H-pyrazol-4-yl]4-methyl-benzamide;
N-[3-(5,6-dimethyl-1H-benzoimidazol-2-yl)-1H-pyrazol-4-yl]-2-morpholin-4-yl-acetamide;
2-dimethylamino-N-[3-(5,6-dimethyl-1H-benzoimidazol-2-yl)-1H-pyrazol-4-yl]-acetamide;

N-[3-(5,6-dimethyl-1H-benzoimidazol-2-yl)-1H-pyrazol-4-yl]-2-(1H-1,2,3,4-tetraazol-1-yl)-acetamide;
N-[3-(5,6-dimethyl-1H-benzoimidazol-2-yl)-1H-pyrazol-4-yl]-isonicotinamide;
2-cyclopropyl-N-[3-(5,6-dimethyl-1H-benzoimidazol-2-yl)-1H-pyrazol-4-yl]-acetamide;
1-[3-(5,6-dimethyl-1H-benzoimidazol-2-yl)-1H-pyrazol-4-yl]-3-methyl-urea;
1-[3-(5,6-dimethyl-1H-benzoimidazol-2-yl)-1H-pyrazol-4-yl]-3-isopropyl-urea;
1-[3-(5,6-dimethyl-1H-benzoimidazol-2-yl)-1H-pyrazol-4-yl]-3-phenyl-urea;
1-benzyl-3-[3-(5,6-dimethyl-1H-benzoimidazol-2-yl)-1H-pyrazol-4-yl]-urea;
cyclopropanecarboxylic acid[3-(5-ethoxy-6-ethyl-1H-benzoimidazol-2-yl)-1H-pyrazol-4-yl]amide;
4-methylpiperazine-1-carboxylic acid [3-(1,5,6,7-tetrahydro-1,3-diaza-s-indacen-2-yl)-1H-pyrazol-4-yl]amide;
1,1-dimethyl-3-[3-(1,5,6,7-tetrahydro-s-indacen-2-yl)-1H-pyrazol-4-yl]urea;
cyclopropanecarboxylic acid [3-(6-ethoxy-5-fluoro-1H-benzimidazol-2-yl)-1H-pyrazol-4-yl]amide;
tetrahydropyran-4-carboxylic acid [3-(6-ethoxy-5-fluoro-1H-benzimidazol-2-yl)-1H-pyrazole-4-yl]amide;
morpholine-4-carboxylic acid[3-(6-ethoxy-5-fluoro-1H-benzimidazol-2-yl)-1H-pyrazol-4-yl]amide;
piperidine-4-carboxylic acid[3-(6-ethoxy-5-fluoro-1H-benzimidazol-2-yl)-1H-pyrazol-4-yl]amide;
3-[6-ethoxy-5-fluoro-1H-benzimidazol-2-yl)-1H-pyrazol-4-yl]-1,1-diethylurea;
morpholine-4-carboxylic acid [3-(5,6-dimethyl-1H-benzoimidazol-2-yl)-1H-pyrazol-4-ylmethyl]-amide;
3-[3-(5-difluoromethoxy-1H-benzoimidazol-2-yl)-1H-pyrazol-4-yl]-1,1-diethyl-urea;
piperidine-1-carboxylic acid [3-(5-difluoromethoxy-1H-benzoimidazol-2-yl)-1H-pyrazol-4-yl]-amide;
cyclopropanecarboxylic acid [3-(6-chloro-5-methoxy-1H-benzoimidazol-2-yl)-1H-pyrazol-4-yl]-amide;
cyclopropanecarboxylic acid [3-(1,5,6,7-tetrahydro-1,3-diaza-s-indacen-2-yl)-1H-pyrazol-4-yl]amide;
morpholine-4-carboxylic acid[3-(1,5,6,7-tetrahydro-1,3-diaza-s-indacen-2-yl)-1H-pyrazol-4-yl]-amide;
piperidine-1-carboxylic acid [3-(5-methoxy-1H-benzoimidazol-2-yl)-1H-pyrazol-4-yl]-amide;
3-[3-(5-methoxy-1H-benzoimidazol-2-yl)-1H-pyrazol-4-yl]-1,1-dimethyl-urea;
piperidine-1-carboxylic acid [3-(5-ethyl-6-methyl-1H-benzoimidazol-2-yl)-1H-pyrazol-4-yl]-amide;
3-[3-(5-fluoro-6-methyl-1H-benzoimidazol-2-yl)-1H-pyrazol-4-yl]-1,1-dimethyl-urea;
morpholine-4-carboxylic acid [3-(5-trifluoromethyl-1H-benzoimidazol-2-yl)-1H-pyrazol-4-yl]-amide;
morpholine-4-carboxylic acid [3-(5,6-dimethyl-1H-benzoimidazol-2-yl)-1H-pyrazol-4-yl]-amide;
piperidine-1-carboxylic acid [3-(5,6-dimethyl-1H-benzoimidazol-2-yl)-1H-pyrazol-4-yl]-amide;
1-cyclopropyl-3-[3-(5-ethyl-6-methyl-1H-benzoimidazol-2-yl)-1H-pyrazol-4-yl]-urea;
1-[3-(5-ethyl-6-methyl-1H-benzoimidazol-2-yl)-1H-pyrazol-4-yl]-3-methyl-urea;
4-methyl-piperazine-1-carboxylic acid [3-(5-ethyl-6-methyl-1H-benzoimidazol-2-yl)-1H-pyrazol-4-yl]-amide;
piperidine-1-carboxylic acid [3-(5-fluoro-6-methyl-1H-benzoimidazol-2-yl)-1H-pyrazol-4-yl]-amide;
1-[3-(5-fluoro-6-methyl-1H-benzoimidazol-2-yl)-1H-pyrazol-4-yl]-3-methyl-urea;
morpholine-4-carboxylic acid [3-(5-fluoro-6-methyl-1H-benzoimidazol-2-yl)-1H-pyrazol-4-yl]-amide;
4-methyl-piperazine-1-carboxylic acid [3-(5-fluoro-6-methyl-1H-benzoimidazol-2-yl)-1H-pyrazol-4-yl]-amide;
1-methyl-3-[3-(5-trifluoromethyl-1H-benzoimidazol-2-yl)-1H-pyrazol-4-yl]-urea;
1-[3-(5-chloro-6-methyl-1H-benzoimidazol-2-yl)-1H-pyrazol-4-yl]-3-methyl-urea;
4-methyl-piperazine-1-carboxylic acid [3-(5-chloro-6-methyl-1H-benzoimidazol-2-yl)-1H-pyrazol-4-yl]-amide;
1-tert-butyl-3-[3-(5,6-dimethyl-1H-benzoimidazol-2-yl)-1H-pyrazol-4-yl]-urea;
1-[3-(5,6-dimethyl-1H-benzoimidazol-2-yl)-1H-pyrazol-4-yl]-3-ethyl-urea;
4-methyl-piperazine-1-carboxylic acid [3-(5,6-dimethyl-1H-benzoimidazol-2-yl)-1H-pyrazol-4-yl]-amide;
1-cyclopropyl-3-[3-(5,6-dimethyl-1H-benzoimidazol-2-yl)-1H-pyrazol-4-yl]-urea;
3-[3-(5,6-dimethyl-1H-benzoimidazol-2-yl)-1H-pyrazol-4-yl]-1,1-diethyl-urea;
1-[3-(5,6-dimethyl-1H-benzoimidazol-2-yl-1H-pyrazol-4-yl]-3-isobutyl-urea;
1-cyclopropylmethyl-3-[3-(5,6-dimethyl-1H-benzoimidazol-2-yl)-1H-pyrazol-4-yl]-urea;
3-[3-(5,6-dimethyl-1H-benzoimidazol-2-yl)-1H-pyrazol-4-yl]-1,1-dimethyl-urea;
2-(1H-indazol-3-yl)-1H-benzoimidazole-5-carboxylic acid (2-piperidin-1-yl-ethyl)-amide;
2-(1H-indazol-3-yl)-1H-benzoimidazole-5-carboxylic acid (pyridin-2-ylmethyl)-amide;
N-[2-(1H-indazol-3-yl)-1H-benzoimidazol-5-yl]-isobutyramide;
N-[3-(5,6-dimethyl-1H-benzoimidazol-2-yl)-1H-pyrazol-4-yl]-2-piperidin-1-yl-acetamide;
2-(1H-indazol-3-yl)-1H-benzimidazole-5-carboxylic acid N-morpholinoamide;
2-(1H-indazol-3-yl)-1H-benzimidazole-5-carboxylic acid N—(N'-methylpiperazino)amide;
2-(1H-indazol-3-yl)-1H-benzimidazole-5-carboxylic acid N-pyrrolidinoamide;
2-(1H-indazol-3-yl)-1H-benzimidazole-5-carboxylic acid N-(isobutyl)amide;
2-(1H-indazol-3-yl)-1H-benzimidazole-5-carboxylic acid N-(cyclohexylmethyl)amide;
2-(1H-indazol-3-yl)-1H-benzimidazole-5-carboxylic acid N-(2-furfuryl)amide;
2-(1H-indazol-3-yl)-1H-benzimidazole-5-carboxylic acid N-benzyl-N-methylamide;
methyl 2-(1H-indazol-3-yl)-3H-benzimidazole-5-carboxylate;
5,6-dimethyl-2-(1H-indazol-3-yl)-1H-benzimidazole;
2-(1H-indazol-3-yl)-3H-benzimidazole-4-carboxylic acid;
2-(5-ethoxy-2H-pyrazol-3-yl)-1H-benzimidazole-4-carboxylic acid;
5,6-dimethyl-2-(5-methyl-2H-pyrazol-3-yl)-1H-benzimidazole;
5,6-dimethyl-2-(5-thiophen-2-yl-2H-pyrazol-3-yl)-1H-benzimidazole;
2-(4-bromo-2H-pyrazol-3-yl)-5,6-dimethyl-1H-benzimidazole;
2-(5-ethyl-2H-pyrazol-3-yl)-5,6-dimethyl-1H-benzimidazole;
2-(5-ethyl-2H-pyrazol-3-yl)-4,5-ethylenedioxy-1H-benzimidazole;
2-(5-ethyl-2H-pyrazol-3-yl)-5-methoxy-1H-benzimidazole;
2-(5-ethyl-2H-pyrazol-3-yl)-4-hydroxy-1H-benzimidazole
2-(5-ethyl-2H-pyrazol-3-yl)-5-bromo-1H-benzimidazole;

and the corresponding N-oxides, and their prodrugs; and pharmaceutically acceptable salts and solvates (e.g. hydrates) of such compounds and their N-oxides and prodrugs.

Particularly preferred compounds of formula (Ixa) of the invention for the inhibition of SYK are:—

2-(1H-indazol-3-yl)-1H-benzimidazole-5-carboxylic acid benzylamide, Example 1;
2-(1H-indazol-3-yl)-1H-benzimidazole-5-carboxylic acid N-methylamide, Example 2;
2-(1H-indazol-3-yl)-1H-benzimidazole-5-carboxylic acid N-ethylamide, Example 3;
2-(1H-indazol-3-yl)-1H-benzimidazole-5-carboxylic acid N-isopropylamide, Example 4;
2-(1H-indazol-3-yl)-1H-benzimidazole-5-carboxylic acid N-phenylamide, Example 5;
2-(1H-indazol-3-yl)-1H-benzimidazole-5-carboxylic acid N-phenethylamide, Example 6
5,6-dimethyl-2-(5-methylsulfanyl-1H-pyrazol-3-yl)-1H-benzoimidazole, (compound denoted as A9-B9), Example 230(a);
6-chloro-2-(5-methylsulfanyl-1H-pyrazol-3-yl)-5-methyl-1H-benzoimidazole, (compound denoted as A12-B9), Example 230(b);
6-chloro-2-(5-ethylsulfanyl-1H-pyrazol-3-yl)-5-methyl-1H-benzoimidazole, (compound denoted as A12-B10), Example 230(c);
2-(5-methylsulfanyl-1H-pyrazol-3-yl)-5-trifluoromethyl-1H-benzoimidazole, (compound denoted as A4-B9), Example 230(d);
2-(5-cyclopropylmethylsulfanyl-1H-pyrazol-3-yl)-5,6-dimethyl-1H-benzoimidazole, (compound denoted as A9-B11), Example 230(e);
2-(5-ethylsulfanyl-1H-pyrazol-3-yl)-5,6-dimethyl-1H-benzoimidazole, (compound denoted as A9-B10), Example 230(f);
3-(1,5,6,7-tetrahydro-1,3-diaza-s-indacen-2-yl)-1H-pyrazole-4-carboxylic acid cyclopropylamide, Example 235 (ah);
3-(5-methoxy-6-methyl-1H-benzoimidazol-2-yl)-1H-pyrazole-4-carboxylic acid isopropylamide, Example 235(ai);
3-(5,6-dimethyl-1H-benzoimidazol-2-yl)-1H-pyrazole-4-carboxylic acid (2-methoxy-ethyl)-amide, Example 235 (ak);
3-(5,6-dimethyl-1H-benzoimidazol-2-yl)-1H-pyrazole-4-carboxylic acid propylamide, Example 235(al);
3-(5,6-dimethyl-1H-benzoimidazol-2-yl)-1H-pyrazole-4-carboxylic acid (tetrahydro-pyran-4-yl)-amide, Example 235(am);
3-(5-difluoromethoxy-1H-benzoimidazol-2-yl)-1H-pyrazole-4-carboxylic acid isopropylamide, Example 235(ao);
3-(5-difluoromethoxy-1H-benzoimidazol-2-yl)-1H-pyrazole-4-carboxylic acid cyclopropylamide, Example 235 (ap);
3-(6-ethyl-5-methoxy-1H-benzoimidazol-2-yl)-1H-pyrazole-4-carboxylic acid isopropylamide, Example 235(aq);
2-(5-isopropyl-1H-pyrazol-3-yl)-5,6-dimethyl-1H-benzoimidazole, (compound denoted as A9-B83), Example 241 (b);
3-(5,6-dimethyl-1H-benzoimidazol-2-yl)-1H-pyrazole-4-carboxylic acid isopropylamide, (compound denoted as A9-B106), Example 246(g);
3-(5,6-dimethyl-1H-benzoimidazol-2-yl)-1H-pyrazole-4-carboxylic acid (2-hydroxy-1,1-dimethylethyl)-amide, (compound denoted as A9-B25), Example 246(h);
2-(4-isopropylcarbamoyl-1H-pyrazol-3-yl)-1H-benzoimidazole-5-carboxylic acid (pyridin-3-ylmethyl)-amide, (compound denoted as A40-B106), Example 246(i);
3-(5,6-dimethyl-1H-benzoimidazol-2-yl)-5-methyl-1H-pyrazole-4-carboxylic acid cyclopropylamide, (compound denoted as A9-B105), Example 246(j);
2-(4-isopropylcarbamoyl-1H-pyrazol-3-yl)-1H-benzoimidazole-5-carboxylic acid phenylmethyl-amide, (compound denoted as A17-B106), Example 246(k);
3-(5,6-dimethyl-1H-benzoimidazol-2-yl)-1H-pyrazole-4-carboxylic acid isobutyl-amide, Example 246(v);
3-(5,6-dimethyl-1H-benzoimidazol-2-yl)-1H-pyrazole-4-carboxylic acid isopropylamide, Example 246(w);
3-(5,6-dimethyl-1H-benzoimidazol-2-yl)-1H-pyrazole-4-carboxylic acid cyclopropylmethyl-amide, Example 246 (x);
3-(5,6-dimethyl-1H-benzoimidazol-2-yl)-5-methyl-1H-pyrazole-4-carboxylic acid tert-butylamide, Example 246 (y);
2-(4-isobutyrylamino-1H-pyrazol-3-yl)-1H-benzoimidazole-5-carboxylic acid benzylamide, Example 246(aa);
N-[3-(5,6-dimethyl-1H-benzoimidazol-2-yl)-1H-pyrazol-4-yl]-isobutyramide, (compound denoted as A9-B85), Example 248(a);
N-[3-(5,6-dimethyl-1H-benzoimidazol-2-yl)-1H-pyrazol-4-yl]-3-methyl-butyramide, (compound denoted as A9-B86), Example 248(b);
N-[3-(5,6-dimethyl-1H-benzoimidazol-2-yl)-1H-pyrazol-4-yl]-2-phenyl-acetamide, (compound denoted as A9-B36), Example 248(c);
cyclopropanecarboxylic acid [3-(5,6-dimethyl-1H-benzoimidazol-2-yl)-1H-pyrazol-4-yl]-amide, (compound denoted as A9-B89), Example 248(d);
methoxyacetic acid [3-(5,6-dimethyl-1H-benzoimidazol-2-yl)-1H-pyrazol-4-yl]-amide, (compound denoted as A9-B94), Example 248(e);
cyclopentanecarboxylic acid [3-(5,6-dimethyl-1H-benzoimidazol-2-yl)-1H-pyrazol-4-yl]-amide, (compound denoted as A9-B87), Example 248(f);
trimethylacetic acid [3-(5,6-dimethyl-1H-benzoimidazol-2-yl)-1H-pyrazol-4-yl]-amide, (compound denoted as A9-B88), Example 248(g);
tert-butylacetic acid [3-(5,6-dimethyl-1H-benzoimidazol-2-yl)-1H-pyrazol-4-yl]-amide, (compound denoted as A9-B90), Example 248(h);
butanoic acid [3-(5,6-dimethyl-1H-benzoimidazol-2-yl)-1H-pyrazol-4-yl]-amide, (compound denoted as A9-B91), Example 248(i);
isoxazole-5-carboxylic acid [3-(5,6-dimethyl-1H-benzoimidazol-2-yl)-1H-pyrazol-4-yl]-amide, (compound denoted as A9-B96), Example 248(j);
S(+)-2-methylbutanoic acid [3-(5,6-dimethyl-1H-benzoimidazol-2-yl)-1H-pyrazol-4-yl]-amide, (compound denoted as A9-B93), Example 248(k);
cyclopropanecarboxylic acid [3-(5-ethyl-6-methyl-1H-benzoimidazol-2-yl)-1H-pyrazol-4-yl]-amide, (compound denoted as A55-B89), Example 248(l);
piperidine-1-carboxylic acid[3-(6-chloro-5-methoxy-1H-benzoimidazol-2-yl)-1H-pyrazol-4-yl]-amide, Example 248(m);
3-[3-(6-chloro-5-methoxy-1H-benzoimidazol-2-yl)-1H-pyrazol-4-yl]-1,1-dimethylurea, Example 248(n);
cyclopropanecarboxylic acid [3-(5-methoxy-1H-benzoimidazol-2-yl)-1H-pyrazol-4-yl]-amide, Example 248(o);
cyclopropanecarboxylic acid [3-(5-ethoxy-1H-benzoimidazol-2-yl)-1H-pyrazol-4-yl]-amide, Example 248(p);

cyclopropanecarboxylic acid [3-(5-fluoro-6-methyl-1H-benzoimidazol-2-yl)-1H-pyrazol-4-yl]-amide, Example 248(q);
cyclopropanecarboxylic acid [3-(5-trifluoromethoxy-1H-benzoimidazol-2-yl)-1H-pyrazol-4-yl]-amide, Example 248(r);
cyclopropanecarboxylic acid [3-(5-trifluoromethyl-1H-benzoimidazol-2-yl)-1H-pyrazol-4-yl]-amide, Example 248(s);
N-[3-(5-trifluoromethyl-1H-benzoimidazol-2-yl)-1H-pyrazol-4-yl]-isobutyramide, Example 248(t);
cyclopropanecarboxylic acid [3-(5-chloro-6-methyl-1H-benzoimidazol-2-yl)-1H-pyrazol-4-yl]-amide, Example 248(u);
3,5-dimethyl-isoxazole-4-carboxylic acid [3-(5,6-dimethyl-1H-benzoimidazol-2-yl)-1H-pyrazol-4-yl]-amide, Example 248(v);
N-[3-(5,6-dimethyl-1H-benzoimidazol-2-yl)-1H-pyrazol-4-yl]-acetamide, Example 248(w);
furan-3-carboxylic acid [3-(5-chloro-6-methyl-1H-benzoimidazol-2-yl)-1H-pyrazol-4-yl]-amide, Example 248(x);
N-[3-(5,6-dimethyl-1H-benzoimidazol-2-yl)-1H-pyrazol-4-yl]-4-methyl-benzamide, Example 248(y);
N-[3-(5,6-dimethyl-1H-benzoimidazol-2-yl)-1H-pyrazol-4-yl]-2-morpholin-4-yl-acetamide, (compound denoted as A9-B99), Example 253;
N-[3-(5,6-dimethyl-1H-benzoimidazol-2-yl)-1H-pyrazol-4-yl]-2-(1H-1,2,3,4-tetraazol-1-yl)-acetamide, (compound denoted as A9-B97), Example 254(a);
N-[3-(5,6-dimethyl-1H-benzoimidazol-2-yl)-1H-pyrazol-4-yl]-isonicotinamide; Example 254(b);
2-cyclopropyl-N-[3-(5,6-dimethyl-1H-benzoimidazol-2-yl)-1H-pyrazol-4-yl]-acetamide; Example 254(c);
1-[3-(5,6-dimethyl-1H-benzoimidazol-2-yl)-1H-pyrazol-4-yl]-3-methyl-urea, (compound denoted as A9-B38), Example 255(a);
1-[3-(5,6-dimethyl-1H-benzoimidazol-2-yl)-1H-pyrazol-4-yl]-3-isopropyl-urea, (compound denoted as A9-B103), Example 255(b);
1-[3-(5,6-dimethyl-1H-benzoimidazol-2-yl)-1H-pyrazol-4-yl]-3-phenyl-urea, (compound denoted as A9-B40), Example 255(c);
1-benzyl-3-[3-(5,6-dimethyl-1H-benzoimidazol-2-yl)-1H-pyrazol-4-yl]-urea, (compound denoted as A9-B39), Example 255(d);
cyclopropanecarboxylic acid[3-(5-ethoxy-6-ethyl-1H-benzoimidazol-2-yl)-1H-pyrazol-4-yl]amide, Example 256(a);
4-methylpiperazine-1-carboxylic acid [3-(1,5,6,7-tetrahydro-1,3-diaza-s-indacen-2-yl)-1H-pyrazol-4-yl]amide, Example 256(c);
1,1-dimethyl-3-[3-(1,5,6,7-tetrahydro-s-indacen-2-yl)-1H-pyrazol-4-yl]urea, Example 256(d);
cyclopropanecarboxylic acid [3-(6-ethoxy-5-fluoro-1H-benzimidazol-2-yl)-1H-pyrazol-4-yl]amide, Example 257(a);
tetrahydropyran-4-carboxylic acid [3-(6-ethoxy-5-fluoro-1H-benzimidazol-2-yl)-1H-pyrazole-4-yl]amide, Example 257(b);
morpholine-4-arboxylic acid[3-(6-ethoxy-5-fluoro-1H-benzimidazol-2-yl)-1H-pyrazol-4-yl]amide, Example 257(c);
piperidine-4-carboxylic acid[3-(6-ethoxy-5-fluoro-1H-benzimidazol-2-yl)-1H-pyrazol-4-yl]amide, Example 257(d);
3-[6-ethoxy-5-fluoro-1H-benzimidazol-2-yl)-1H-pyrazol-4-yl]-1,1-diethylurea, Example 257(e);
morpholine-4-carboxylic acid [3-(5,6-dimethyl-1H-benzoimidazol-2-yl)-1H-pyrazol-4-ylmethyl]-amide, Example 257(g);
3-[3-(5-difluoromethoxy-1H-benzoimidazol-2-yl)-1H-pyrazol-4-yl]-1,1-diethyl-urea, Example 257(h);
piperidine-1-carboxylic acid [3-(5-difluoromethoxy-1H-benzoimidazol-2-yl)-1H-pyrazol-4-yl]-amide, Example 257(i);
cyclopropanecarboxylic acid [3-(6-chloro-5-methoxy-1H-benzoimidazol-2-yl)-1H-pyrazol-4-yl]-amide, Example 258(a);
cyclopropanecarboxylic acid [3-(1,5,6,7-tetrahydro-1,3-diaza-s-indacen-2-yl)-1H-pyrazol-4-yl]amide, Example 258(b);
morpholine-4-carboxylic acid[3-(1,5,6,7-tetrahydro-1,3-diaza-s-indacen-2-yl)-1H-pyrazol-4-yl]-amide, Example 258(c);
piperidine-1-carboxylic acid [3-(5-methoxy-1H-benzoimidazol-2-yl)-1H-pyrazol-4-yl]-amide, Example 258(d);
3-[3-(5-methoxy-1H-benzoimidazol-2-yl)-1H-pyrazol-4-yl]-1,1-dimethyl-urea, Example 258(e);
piperidine-1-carboxylic acid [3-(5-ethyl-6-methyl-1H-benzoimidazol-2-yl)-1H-pyrazol-4-yl]-amide, Example 258(f);
3-[3-(5-fluoro-6-methyl-1H-benzoimidazol-2-yl)-1H-pyrazol-4-yl]-1,1-dimethyl-urea, Example 258(g);
morpholine-4-carboxylic acid [3-(5-trifluoromethyl-1H-benzoimidazol-2-yl)-1H-pyrazol-4-yl]-amide, Example 258(h);
morpholine-4-carboxylic acid [3-(5,6-dimethyl-1H-benzoimidazol-2-yl)-1H-pyrazol-4-yl]-amide, Example 258(n);
piperidine-1-carboxylic acid [3-(5,6-dimethyl-1H-benzoimidazol-2-yl)-1H-pyrazol-4-yl]-amide, Example 258(o);
1-cyclopropyl-3-[3-(5-ethyl-6-methyl-1H-benzoimidazol-2-yl)-1H-pyrazol-4-yl]-urea, Example 260(a);
1-[3-(5-ethyl-6-methyl-1H-benzoimidazol-2-yl)-1H-pyrazol-4-yl]-3-methyl-urea, Example 260(b);
4-methyl-piperazine-1-carboxylic acid [3-(5-ethyl-6-methyl-1H-benzoimidazol-2-yl)-1H-pyrazol-4-yl]-amide, Example 260(c);
piperidine-1-carboxylic acid [3-(5-fluoro-6-methyl-1H-benzoimidazol-2-yl)-1H-pyrazol-4-yl]-amide, Example 260(d);
1-[3-(5-fluoro-6-methyl-1H-benzoimidazol-2-yl)-1H-pyrazol-4-yl]-3-methyl-urea, Example 260(e);
morpholine-4-carboxylic acid [3-(5-fluoro-6-methyl-1H-benzoimidazol-2-yl)-1H-pyrazol-4-yl]-amide, Example 260(f);
4-methyl-piperazine-1-carboxylic acid [3-(5-fluoro-6-methyl-1H-benzoimidazol-2-yl)-1H-pyrazol-4-yl]-amide, Example 260(g);
1-methyl-3-[3-(5-trifluoromethyl-1H-benzoimidazol-2-yl)-1H-pyrazol-4-yl]-urea, Example 260(h);
1-[3-(5-chloro-6-methyl-1H-benzoimidazol-2-yl)-1H-pyrazol-4-yl]-3-methyl-urea, Example 260(i);
4-methyl-piperazine-1-carboxylic acid [3-(5-chloro-6-methyl-1H-benzoimidazol-2-yl)-1H-pyrazol-4-yl]-amide, Example 260(j);
1-tert-butyl-3-[3-(5,6-dimethyl-1H-benzoimidazol-2-yl)-1H-pyrazol-4-yl]-urea, Example 260(k);
1-[3-(5,6-dimethyl-1H-benzoimidazol-2-yl)-1H-pyrazol-4-yl]-3-ethyl-urea, Example 260(l);
4-methyl-piperazine-1-carboxylic acid [3-(5,6-dimethyl-1H-benzoimidazol-2-yl)-1H-pyrazol-4-yl]-amide, Example 260(m);

1-cyclopropyl-3-[3-(5,6-dimethyl-1H-benzoimidazol-2-yl)-1H-pyrazol-4-yl]-urea, Example 260(n);
3-[3-(5,6-dimethyl-1H-benzoimidazol-2-yl)-1H-pyrazol-4-yl]-1,1-diethyl-urea, Example 260(o);
1-[3-(5,6-dimethyl-1H-benzoimidazol-2-yl)-1H-pyrazol-4-yl]-3-isobutyl-urea, Example 260(p);
1-cyclopropylmethyl-3-[3-(5,6-dimethyl-1H-benzoimidazol-2-yl)-1H-pyrazol-4-yl]-urea, Example 260(q);
3-[3-(5,6-dimethyl-1H-benzoimidazol-2-yl)-1H-pyrazol-4-yl]-1,1-dimethyl-urea, Example 258(r);
2-(1H-Indazol-3-yl)-1H-benzoimidazole-5-carboxylic acid (2-piperidin-1-yl-ethyl)-amide, Example 246(ab);
2-(1H-Indazol-3-yl)-1H-benzoimidazole-5-carboxylic acid (pyridin-2-ylmethyl)-amide, Example 246(ac);
N-[3-(5,6-Dimethyl-1H-benzoimidazol-2-yl)-1H-pyrazol-4-yl]-2-piperidin-1-yl-acetamide, Example 253(c);
and the corresponding N-oxides, and their prodrugs; and pharmaceutically acceptable salts and solvates (e.g. hydrates) of such compounds and their N-oxides and prodrugs.

Especially preferred compounds of formula (Ixa), denoted as the product of the combination of group A1 in Table 1 and B1 in Table 2, of the invention for the inhibition of SYK are:—
3-(1,5,6,7-tetrahydro-1,3-diaza-s-indacen-2-yl)-1H-pyrazole-4-carboxylic acid cyclopropylamide, Example 235 (ah);
3-(5-methoxy-6-methyl-1H-benzoimidazol-2-yl)-1H-pyrazole-4-carboxylic acid isopropylamide, Example 235(ai);
3-(5,6-dimethyl-1H-benzoimidazol-2-yl)-1H-pyrazole-4-carboxylic acid (2-methoxy-ethyl)-amide, Example 235 (ak);
3-(5,6-dimethyl-1H-benzoimidazol-2-yl)-1H-pyrazole-4-carboxylic acid propylamide, Example 235(al);
3-(5,6-dimethyl-1H-benzoimidazol-2-yl)-1H-pyrazole-4-carboxylic acid (tetrahydro-pyran-4-yl)-amide, Example 235(am);
3-(5-difluoromethoxy-1H-benzoimidazol-2-yl)-1H-pyrazole-4-carboxylic acid isopropylamide, Example 235(ao);
3-(5-difluoromethoxy-1H-benzoimidazol-2-yl)-1H-pyrazole-4-carboxylic acid cyclopropylamide, Example 235 (ap);
3-(6-ethyl-5-methoxy-1H-benzoimidazol-2-yl)-1H-pyrazole-4-carboxylic acid isopropylamide, Example 235(aq);
3-(5,6-dimethyl-1H-benzoimidazol-2-yl)-1H-pyrazole-4-carboxylic acid isopropylamide, (compound denoted as A9-B106), Example 246(g);
3-(5,6-dimethyl-1H-benzoimidazol-2-yl)-1H-pyrazole-4-carboxylic acid (2-hydroxy-1,1-dimethyl-ethyl)-amide, (compound denoted as A9-B25), Example 246(h);
2-(4-isopropylcarbamoyl-1H-pyrazol-3-yl)-1H-benzoimidazole-5-carboxylic acid (pyridin-3-ylmethyl)-amide, (compound denoted as A40-B106), Example 246(i);
3-(5,6-dimethyl-1H-benzoimidazol-2-yl)-5-methyl-1H-pyrazole-4-carboxylic acid cyclopropylamide, (compound denoted as A9-B105), Example 246(j);
2-(4-isopropylcarbamoyl-1H-pyrazol-3-yl)-1H-benzoimidazole-5-carboxylic acid phenylmethyl-amide, (compound denoted as A17-B106), Example 246(k);
3-(5,6-dimethyl-1H-benzoimidazol-2-yl)-1H-pyrazole-4-carboxylic acid isobutyl-amide, Example 246(v);
3-(5,6-dimethyl-1H-benzoimidazol-2-yl)-1H-pyrazole-4-carboxylic acid isopropylamide, Example 246(w);
3-(5,6-dimethyl-1H-benzoimidazol-2-yl)-1H-pyrazole-4-carboxylic acid cyclopropylmethyl-amide, Example 246 (x);
3-(5,6-dimethyl-1H-benzoimidazol-2-yl)-5-methyl-1H-pyrazole-4-carboxylic acid tert-butylamide, Example 246 (y);
2-(4-isobutyrylamino-1H-pyrazol-3-yl)-1H-benzoimidazole-5-carboxylic acid benzylamide, Example 246(aa);
N-[3-(5,6-dimethyl-1H-benzoimidazol-2-yl)-1H-pyrazol-4-yl]-isobutyramide, (compound denoted as A9-B85), Example 248(a);
N-[3-(5,6-dimethyl-1H-benzoimidazol-2-yl)-1H-pyrazol-4-yl]-3-methyl-butyramide, (compound denoted as A9-B86), Example 248(b);
cyclopropanecarboxylic acid [3-(5,6-dimethyl-1H-benzoimidazol-2-yl)-1H-pyrazol-4-yl]-amide, (compound denoted as A9-B89), Example 248(d);
methoxyacetic acid [3-(5,6-dimethyl-1H-benzoimidazol-2-yl)-1H-pyrazol-4-yl]-amide, (compound denoted as A9-B94), Example 248(e);
cyclopentanecarboxylic acid [3-(5,6-dimethyl-1H-benzoimidazol-2-yl)-1H-pyrazol-4-yl]-amide, (compound denoted as A9-B87), Example 248(f);
trimethylacetic acid [3-(5,6-dimethyl-1H-benzoimidazol-2-yl)-1H-pyrazol-4-yl]-amide, (compound denoted as A9-B88), Example 248(g);
tert-butylacetic acid [3-(5,6-dimethyl-1H-benzoimidazol-2-yl)-1H-pyrazol-4-yl]-amide, (compound denoted as A9-B90), Example 248(h);
butanoic acid [3-(5,6-dimethyl-1H-benzoimidazol-2-yl)-1H-pyrazol-4-yl]-amide, (compound denoted as A9-B91), Example 248(i);
isoxazole-5-carboxylic acid [3-(5,6-dimethyl-1H-benzoimidazol-2-yl)-1H-pyrazol-4-yl]-amide, (compound denoted as A9-B96), Example 248(j);
S(+)-2-methylbutanoic acid [3-(5,6-dimethyl-1H-benzoimidazol-2-yl)-1H-pyrazol-4-yl]-amide, (compound denoted as A9-B93), Example 248(k);
cyclopropanecarboxylic acid [3-(5-ethyl-6-methyl-1H-benzoimidazol-2-yl)-1H-pyrazol-4-yl]-amide, (compound denoted as A55-B89), Example 248(l);
piperidine-1-carboxylic acid[3-(6-chloro-5-methoxy-1H-benzoimidazol-2-yl)-1H-pyrazol-4-yl]-amide, Example 248(m);
3-[3-(6-chloro-5-methoxy-1H-benzoimidazol-2-yl)-1H-pyrazol-4-yl]-1,1-dimethylurea, Example 248(n);
cyclopropanecarboxylic acid [3-(5-methoxy-1H-benzoimidazol-2-yl)-1H-pyrazol-4-yl]-amide, Example 248(o);
cyclopropanecarboxylic acid [3-(5-ethoxy-1H-benzoimidazol-2-yl)-1H-pyrazol-4-yl]-amide, Example 248(p);
cyclopropanecarboxylic acid [3-(5-fluoro-6-methyl-1H-benzoimidazol-2-yl)-1H-pyrazol-4-yl]-amide, Example 248(q);
cyclopropanecarboxylic acid [3-(5-trifluoromethyl-1H-benzoimidazol-2-yl)-1H-pyrazol-4-yl]-amide, Example 248(s);
N-[3-(5-trifluoromethyl-1H-benzoimidazol-2-yl)-1H-pyrazol-4-yl]-isobutyramide, Example 248(t);
cyclopropanecarboxylic acid [3-(5-chloro-6-methyl-1H-benzoimidazol-2-yl)-1H-pyrazol-4-yl]-amide, Example 248(u);
3,5-dimethyl-isoxazole-4-carboxylic acid [3-(5,6-dimethyl-1H-benzoimidazol-2-yl)-1H-pyrazol-4-yl]-amide, Example 248(v);
furan-3-carboxylic acid [3-(5-chloro-6-methyl-1H-benzoimidazol-2-yl)-1H-pyrazol-4-yl]-amide, Example 248(x);
N-[3-(5,6-dimethyl-1H-benzoimidazol-2-yl)-1H-pyrazol-4-yl]-2-morpholin-4-yl-acetamide, (compound denoted as A9-B99), Example 253;

N-[3-(5,6-dimethyl-1H-benzoimidazol-2-yl)-1H-pyrazol-4-yl]-2-(1H-1,2,3,4-tetraazol-1-yl)-acetamide, (compound denoted as A9-B97), Example 254(a);

N-[3-(5,6-dimethyl-1H-benzoimidazol-2-yl)-1H-pyrazol-4-yl]-isonicotinamide; Example 254(b);

2-cyclopropyl-N-[3-(5,6-dimethyl-1H-benzoimidazol-2-yl)-1H-pyrazol-4-yl]-acetamide; Example 254(c);

1-[3-(5,6-dimethyl-1H-benzoimidazol-2-yl)-1H-pyrazol-4-yl]-3-methyl-urea, (compound denoted as A9-B38), Example 255(a);

1-[3-(5,6-dimethyl-1H-benzoimidazol-2-yl)-1H-pyrazol-4-yl]-3-isopropyl-urea, (compound denoted as A9-B103), Example 255(b);

1-[3-(5,6-dimethyl-1H-benzoimidazol-2-yl)-1H-pyrazol-4-yl]-3-phenyl-urea, (compound denoted as A9-B40), Example 255(c);

1-benzyl-3-[3-(5,6-dimethyl-1H-benzoimidazol-2-yl)-1H-pyrazol-4-yl]-urea, (compound denoted as A9-B39), Example 255(d);

cyclopropanecarboxylic acid[3-(5-ethoxy-6-ethyl-1H-benzoimidazol-2-yl)-1H-pyrazol-4-yl]amide, Example 256(a);

4-methylpiperazine-1-carboxylic acid [3-(1,5,6,7-tetrahydro-1,3-diaza-s-indacen-2-yl)-1H-pyrazol-4-yl]amide, Example 256(c);

1,1-dimethyl-3-[3-(1,5,6,7-tetrahydro-s-indacen-2-yl)-1H-pyrazol-4-yl]urea, Example 256(d);

cyclopropanecarboxylic acid [3-(6-ethoxy-5-fluoro-1H-benzimidazol-2-yl)-1H-pyrazol-4-yl]amide, Example 257(a);

tetrahydropyran-4-carboxylic acid [3-(6-ethoxy-5-fluoro-1H-benzimidazol-2-yl)-1H-pyrazole-4-yl]amide, Example 257(b);

morpholine-4-carboxylic acid[3-(6-ethoxy-5-fluoro-1H-benzimidazol-2-yl)-1H-pyrazol-4-yl]amide, Example 257 (c);

piperidine-4-carboxylic acid[3-(6-ethoxy-5-fluoro-1H-benzimidazol-2-yl)-1H-pyrazol-4-yl]amide, Example 257(d);

3-[6-ethoxy-5-fluoro-1H-benzimidazol-2-yl)-1H-pyrazol-4-yl]-1,1-diethylurea, Example 257(e);

3-[3-(5-difluoromethoxy-1H-benzoimidazol-2-yl)-1H-pyrazol-4-yl]-1,1-diethyl-urea, Example 257(h);

piperidine-1-carboxylic acid [3-(5-difluoromethoxy-1H-benzoimidazol-2-yl)-1H-pyrazol-4-yl]-amide, Example 257(i);

cyclopropanecarboxylic acid [3-(6-chloro-5-methoxy-1H-benzoimidazol-2-yl)-1H-pyrazol-4-yl]-amide, Example 258(a);

cyclopropanecarboxylic acid [3-(1,5,6,7-tetrahydro-1,3-diaza-s-indacen-2-yl)-1H-pyrazol-4-yl]amide, Example 258(b);

morpholine-4-carboxylic acid[3-(1,5,6,7-tetrahydro-1,3-diaza-s-indacen-2-yl)-1H-pyrazol-4-yl]-amide, Example 258(c);

piperidine-1-carboxylic acid [3-(5-methoxy-1H-benzoimidazol-2-yl)-1H-pyrazol-4-yl]-amide, Example 258(d);

3-[3-(5-methoxy-1H-benzoimidazol-2-yl)-1H-pyrazol-4-yl]-1,1-dimethyl-urea, Example 258(e);

piperidine-1-carboxylic acid [3-(5-ethyl-6-methyl-1H-benzoimidazol-2-yl)-1H-pyrazol-4-yl]-amide, Example 258(f);

3-[3-(5-fluoro-6-methyl-1H-benzoimidazol-2-yl)-1H-pyrazol-4-yl]-1,1-dimethyl-urea, Example 258(g);

morpholine-4-carboxylic acid [3-(5-trifluoromethyl-1H-benzoimidazol-2-yl)-1H-pyrazol-4-yl]-amide, Example 258(h);

morpholine-4-carboxylic acid [3-(5,6-dimethyl-1H-benzoimidazol-2-yl)-1H-pyrazol-4-yl]-amide, Example 258(n);

piperidine-1-carboxylic acid [3-(5,6-dimethyl-1H-benzoimidazol-2-yl)-1H-pyrazol-4-yl]-amide, Example 258(o);

1-cyclopropyl-3-[3-(5-ethyl-6-methyl-1H-benzoimidazol-2-yl)-1H-pyrazol-4-yl]-urea, Example 260(a);

1-[3-(5-ethyl-6-methyl-1H-benzoimidazol-2-yl)-1H-pyrazol-4-yl]-3-methyl-urea, Example 260(b);

4-methyl-piperazine-1-carboxylic acid [3-(5-ethyl-6-methyl-1H-benzoimidazol-2-yl)-1H-pyrazol-4-yl]-amide, Example 260(c);

piperidine-1-carboxylic acid [3-(5-fluoro-6-methyl-1H-benzoimidazol-2-yl)-1H-pyrazol-4-yl]-amide, Example 260(d);

1-[3-(5-fluoro-6-methyl-1H-benzoimidazol-2-yl)-1H-pyrazol-4-yl]-3-methyl-urea, Example 260(e);

morpholine-4-carboxylic acid [3-(5-fluoro-6-methyl-1H-benzoimidazol-2-yl)-1H-pyrazol-4-yl]-amide, Example 260(f);

1-methyl-3-[3-(5-trifluoromethyl-1H-benzoimidazol-2-yl)-1H-pyrazol-4-yl]-urea, Example 260(h);

1-[3-(5-chloro-6-methyl-1H-benzoimidazol-2-yl)-1H-pyrazol-4-yl]-3-methyl-urea, Example 260(i);

4-methyl-piperazine-1-carboxylic acid [3-(5-chloro-6-methyl-1H-benzoimidazol-2-yl)-1H-pyrazol-4-yl]-amide, Example 260(j);

1-tert-butyl-3-[3-(5,6-dimethyl-1H-benzoimidazol-2-yl)-1H-pyrazol-4-yl]-urea, Example 260(k);

1-[3-(5,6-dimethyl-1H-benzoimidazol-2-yl)-1H-pyrazol-4-yl]-3-ethyl-urea, Example 260(l);

4-methyl-piperazine-1-carboxylic acid [3-(5,6-dimethyl-1H-benzoimidazol-2-yl)-1H-pyrazol-4-yl]-amide, Example 260(m);

1-cyclopropyl-3-[3-(5,6-dimethyl-1H-benzoimidazol-2-yl)-1H-pyrazol-4-yl]-urea, Example 260(n);

3-[3-(5,6-dimethyl-1H-benzoimidazol-2-yl)-1H-pyrazol-4-yl]-1,1-diethyl-urea, Example 260(o);

1-[3-(5,6-dimethyl-1H-benzoimidazol-2-yl)-1H-pyrazol-4-yl]-3-isobutyl-urea, Example 260(p);

1-cyclopropylmethyl-3-[3-(5,6-dimethyl-1H-benzoimidazol-2-yl)-1H-pyrazol-4-yl]-urea, Example 260(q);

3-[3-(5,6-dimethyl-1H-benzoimidazol-2-yl)-1H-pyrazol-4-yl]-1,1-dimethyl-urea, (compound denoted as A9-B142), Example 258(r);

and the corresponding N-oxides, and their prodrugs; and pharmaceutically acceptable salts and solvates (e.g. hydrates) of such compounds and their N-oxides and prodrugs.

More especially preferred compounds of formula (Ixa) of the invention for the inhibition of SYK are:—

3-(5-methoxy-6-methyl-1H-benzoimidazol-2-yl)-1H-pyrazole-4-carboxylic acid isopropylamide, Example 235(ai);

3-(1,5,6,7-tetrahydro-1,3-diaza-s-indacen-2-yl)-1H-pyrazole-4-carboxylic acid cyclopropylamide, Example 235 (ah);

3-(5,6-dimethyl-1H-benzoimidazol-2-yl)-1H-pyrazole-4-carboxylic acid (tetrahydro-pyran-4-yl)-amide, Example 235(am);

3-(5,6-dimethyl-1H-benzoimidazol-2-yl)-1H-pyrazole-4-carboxylic acid isobutyl-amide, Example 246(v);

cyclopropanecarboxylic acid[3-(5-ethoxy-6-ethyl-1H-benzoimidazol-2-yl)-1H-pyrazol-4-yl]amide, Example 256(a);

1,1-dimethyl-3-[3-(1,5,6,7-tetrahydro-s-indacen-2-yl)-1H-pyrazol-4-yl]urea, Example 256(d);

piperidine-4-carboxylic acid[3-(6-ethoxy-5-fluoro-1H-benzimidazol-2-yl)-1H-pyrazol-4-yl]amide, Example 257(d);
3-[6-ethoxy-5-fluoro-1H-benzimidazol-2-yl)-1H-pyrazol-4-yl]-1,1-diethylurea, Example 257(e);
3-[3-(5-difluoromethoxy-1H-benzoimidazol-2-yl)-1H-pyrazol-4-yl]-1,1-diethyl-urea, Example 257(h);
piperidine-1-carboxylic acid [3-(5-difluoromethoxy-1H-benzoimidazol-2-yl)-1H-pyrazol-4-yl]-amide, Example 257(i);
cyclopropanecarboxylic acid [3-(1,5,6,7-tetrahydro-1,3-diaza-s-indacen-2-yl)-1H-pyrazol-4-yl]amide, Example 258(b);
piperidine-1-carboxylic acid [3-(5-methoxy-1H-benzoimidazol-2-yl)-1H-pyrazol-4-yl]-amide, Example 258(d);
piperidine-1-carboxylic acid [3-(5-ethyl-6-methyl-1H-benzoimidazol-2-yl)-1H-pyrazol-4-yl]-amide, Example 258(f);
piperidine-1-carboxylic acid [3-(5,6-dimethyl-1H-benzoimidazol-2-yl)-1H-pyrazol-4-yl]-amide, Example 258(o);
1-cyclopropyl-3-[3-(5-ethyl-6-methyl-1H-benzoimidazol-2-yl)-1H-pyrazol-4-yl]-urea, Example 260(a);
piperidine-1-carboxylic acid [3-(5-fluoro-6-methyl-1H-benzoimidazol-2-yl)-1H-pyrazol-4-yl]-amide, Example 260(d);
1-tert-butyl-3-[3-(5,6-dimethyl-1H-benzoimidazol-2-yl)-1H-pyrazol-4-yl]-urea, Example 260(k);
1-cyclopropyl-3-[3-(5,6-dimethyl-1H-benzoimidazol-2-yl)-1H-pyrazol-4-yl]-urea, Example 260(n);
3-[3-(5,6-dimethyl-1H-benzoimidazol-2-yl)-1H-pyrazol-4-yl]-1,1-diethyl-urea, Example 260(o);
1-cyclopropylmethyl-3-[3-(5,6-dimethyl-1H-benzoimidazol-2-yl)-1H-pyrazol-4-yl]-urea, Example 260(q);
3-[3-(5,6-dimethyl-1H-benzoimidazol-2-yl)-1H-pyrazol-4-yl]-1,1-dimethyl-urea, Example 258(r);
and the corresponding N-oxides, and their prodrugs; and pharmaceutically acceptable salts and solvates (e.g. hydrates) of such compounds and their N-oxides and prodrugs.

Preferred compounds of formula (Ixb) of the invention for the inhibition of SYK are:—
3-(1H-benzoimidazol-2-yl)-1H-indazole;
3-(5-methoxy-1H-benzoimidazol-2-yl)-1H-indazole;
[2-(indazol-3-yl)-1H-benzoimidazol-5-yl]-phenyl-methanone;
2-(1H-indazol-3-yl)-3H-benzoimidazol-4-ol;
3-(5,6-dimethyl-1H-benzoimidazol-2-yl)-1H-indazole;
2-(1H-indazol-3-yl)-3H-imidazo[4,5-c]pyridine;
2-(1H-indazole-3-yl)-3H-imidazo[4,5-b]pyridine;
3-(5,6-dimethyl-1H-benzoimidazol-2-yl)-5-methoxy-1H-indazole;
3-(5,6-dimethyl-1H-benzoimidazol-2-yl)-5-fluoro-1H-indazole;
3-(5,6-dimethyl-1H-benzoimidazol-2-yl)-6-fluoro-1H-indazole;
3-(5,6-dimethyl-1H-benzoimidazol-2-yl)-5-methyl-1H-indazole;
3-(5,6-dimethyl-1H-benzoimidazol-2-yl)-6-methoxy-1H-indazole;
3-(5-ethyl-1H-benzoimidazol-2-yl)-1H-indazole;
3-(5-ethyl-6-methyl-1H-benzoimidazol-2-yl)-1H-indazole;
3-(5-isopropyl-6-methyl-1H-benzoimidazol-2-yl)-1H-indazole;
3-(5-bromo-6-methyl-1H-benzoimidazol-2-yl)-1H-indazole;
3-(5-bromo-1H-benzoimidazol-2-yl 1H-indazole;
3-(5-(3-cyano)phenyl-1H-benzoimidazol-2-yl)-1H-indazole;
3-(5-(pyrid-3-yl)-1H-benzoimidazol-2-yl)-1H-indazole;
3-(6-methyl-5-phenyl-1H-benzoimidazol-2-yl)-1H-indazole;
3-(5-phenyl-1H-benzoimidazol-2-yl)-1H-indazole;
3-(5-(2-fluoro)phenyl-1H-benzoimidazol-2-yl)-1H-indazole;
3-(5-(5,6-methylenedioxy)phenyl-1H-benzoimidazol-2-yl)-1H-indazole;
3-(5-(2-methoxy)phenyl-1H-benzoimidazol-2-yl)-1H-indazole;
3-(5-(4-chloro)phenyl-1H-benzoimidazol-2-yl)-1H-indazole;
3-(5-(4-methyl)phenyl-1H-benzoimidazol-2-yl)-1H-indazole;
3-(5-benzyloxy-1H-benzoimidazol-2-yl)-1H-indazole;
3-(5,6-methylenedioxy-1H-benzoimidazol-2-yl)-1H-indazole;
3-(5,6-dimethoxy-1H-benzoimidazol-2-yl)-1H-indazole;
3-(5,6-diethyl-1H-benzoimidazol-2-yl)-1H-indazole;
2-(1H-indazol-3-yl)-1H-benzoimidazole-5-carbonitrile;
3-(5-methoxycarbonyl-1H-benzoimidazol-2-yl)-1H-indazole;
3-(5,6-dimethyl-1H-benzoimidazol-2-yl)-5-ethoxy-1H-indazole;
3-[5-(2-morpholin-4-yl-ethoxy)-1H-benzoimidazol-2-yl]-1H-indazole;
3-(5-ethyl-6-methyl-1H-benzoimidazol-2-yl)-1H-indazole-5-carbonitrile;
3-(5,6-dimethyl-1H-benzoimidazol-2-yl)-1H-indazole-5-carbonitrile;
3-(5,6-dimethyl-1H-benzoimidazol-2-yl)-4-fluoro-1H-indazole;
3-(5,6-dimethyl-1H-benzoimidazol-2-yl)-5-chloro-1H-indazole;
3-(5-n-propyl-1H-benzoimidazol-2-yl)-1H-indazole;
2-(1H-indazol-3-yl)-1H-benzoimidazole-5-sulfonic acid benzylamide;
3-(5-methanesulfonyl-1H-benzoimidazol-2-yl)-1H-indazole;
[2-(indazol-3-yl)-1H-benzoimidazol-5-yl]-phenyl-methanol;
[2-(indazol-3-yl)-1H-benzoimidazol-5-yl]-carboxylic acid;
[2-(indazol-3-yl)-1H-benzoimidazol-5-yl]-carboxylic acid, methylamide;
[2-(indazol-3-yl)-1H-benzoimidazol-5-yl]-carboxylic acid, dimethylamide;
[2-(indazol-3-yl)-1H-benzoimidazol-5-yl]-carboxylic acid, isopropylamide;
[2-(indazol-3-yl)-1H-benzoimidazol-5-yl]-carboxylic acid, benzylamide;
[2-(indazol-3-yl)-1H-benzoimidazol-5-yl]-carboxylic acid, benzamide;
2-(1H-indazol-3-yl)-1H-benzoimidazole-5-carboxylic acid (pyridin-3-ylmethyl)-amide;
2-(1H-indazol-3-yl)-1H-benzoimidazole-5-carboxylic acid 3-methyl-benzylamide;
2-(1H-indazol-3-yl)-1H-benzoimidazole-5-carboxylic acid 4-methyl-benzylamide;
2-(1H-indazol-3-yl)-1H-benzoimidazole-5-carboxylic acid [3-(2-oxo-pyrrolidin-1-yl)-propyl]-amide;
2-(1H-indazol-3-yl)-1H-benzoimidazole-5-carboxylic acid (2-morpholin-4-yl-ethyl)-amide;
2-(1H-indazol-3-yl)-1H-benzoimidazole-5-carboxylic acid (2-methoxy-ethyl)-amide;
2-(1H-indazol-3-yl)-1H-benzoimidazole-5-carboxylic acid (2-cyano-ethyl)-amide;

2-(1H-indazol-3-yl)-1H-benzoimidazole-5-carboxylic acid (2-hydroxy-1,1-dimethyl-ethyl)-amide;
2-(1H-Indazol-3-yl)-1H-benzoimidazole-5-carboxylic acid (3-imidazol-1-yl-propyl)-amide;
3-(5,6-dimethyl-1H-benzoimidazol-2-yl)-1H-indazole-5-carboxylic acid dimethylamide;
[2-(indazol-3-yl)-1H-benzoimidazol-5-yl]-carboxylic acid;
3-(5-ethyl-6-methyl-1H-benzoimidazol-2-yl)-1H-indazole-5-carboxylic acid amide dihydrochloride;
and the corresponding N-oxides, and their prodrugs; and pharmaceutically acceptable salts and solvates (e.g. hydrates) of such compounds and their N-oxides and prodrugs.

Particularly preferred compounds of formula (Ixb), denoted as the product of the combination of group A1 in Table 1 and B1 in Table 2, of the invention for the inhibition of SYK are:—

3-(1H-benzoimidazol-2-yl)-1H-indazole, (compound denoted as A1-B63), Example 234(a);
3-(5-methoxy-1H-benzoimidazol-2-yl)-1H-indazole, (compound denoted as A6-B63), Example 234(b);
3-(5,6-dimethyl-1H-benzoimidazol-2-yl)-1H-indazole, (compound denoted as A9-B63), Example 234(f);
3-(5,6-dimethyl-1H-benzoimidazol-2-yl)-5-methoxy-1H-indazole, (compound denoted as A9-B68), Example 235(b);
3-(5,6-dimethyl-1H-benzoimidazol-2-yl)-5-fluoro-1H-indazole, (compound denoted as A9-B70), Example 235(d);
3-(5,6-dimethyl-1H-benzoimidazol-2-yl)-6-fluoro-1H-indazole, (compound denoted as A9-B71), Example 235(e);
3-(5,6-dimethyl-1H-benzoimidazol-2-yl)-5-methyl-1H-indazole, (compound denoted as A9-B64), Example 235(f);
3-(5,6-dimethyl-1H-benzoimidazol-2-yl)-6-methoxy-1H-indazole, (compound denoted as A9-B69), Example 235(g);
3-(5-ethyl-1H-benzoimidazol-2-yl)-1H-indazole, (compound denoted as A27-B63), Example 235(i);
3-(5-ethyl-6-methyl-1H-benzoimidazol-2-yl)-1H-indazole, (compound denoted as A55-B63), Example 235(j);
3-(5-isopropyl-6-methyl-1H-benzoimidazol-2-yl)-1H-indazole, (compound denoted as A54-B63), Example 235(k);
3-(5-bromo-6-methyl-1H-benzoimidazol-2-yl)-1H-indazole, (compound denoted as A58-B63), Example 235(l);
3-(5-bromo-1H-benzoimidazol-2-yl)-1H-indazole, (compound denoted as A32-B63), Example 235(m);
3-(5-(3-cyano)phenyl-1H-benzoimidazol-2-yl)-1H-indazole, (compound denoted as A68-B63), Example 235(n);
3-(5-(pyrid-3-yl)-1H-benzoimidazol-2-yl)-1H-indazole, (compound denoted as A69-B63), Example 235(o);
3-(6-methyl-5-phenyl-1H-benzoimidazol-2-yl)-1H-indazole, (compound denoted as A57-B63), Example 235(p);
3-(5-phenyl-1H-benzoimidazol-2-yl)-1H-indazole, (compound denoted as A60-B63), Example 235(q);
3-(5-(2-fluoro)phenyl-1H-benzoimidazol-2-yl)-1H-indazole, (compound denoted as A65-B63), Example 235(r);
3-(5-(3,4-methylenedioxy)phenyl-1H-benzoimidazol-2-yl)-1H-indazole, (compound denoted as A66-B63), Example 235(s);
3-(5-benzyloxy-1H-benzoimidazol-2-yl)-1H-indazole, (compound denoted as A74-B63), Example 235(w);
3-(5,6-methylenedioxy-1H-benzoimidazol-2-yl)-1H-indazole, (compound denoted as A22-B63), Example 235(x);
3-(5,6-dimethoxy-1H-benzoimidazol-2-yl)-1H-indazole, (compound denoted as A23-B63), Example 235(y);
3-(5,6-diethyl-1H-benzoimidazol-2-yl)-1H-indazole, (compound denoted as A56-B63), Example 235(z);
2-(1H-indazol-3-yl)-1H-benzoimidazole-5-carbonitrile, (compound denoted as A33-B63), Example 235(ab);
3-(5-methoxycarbonyl-1H-benzoimidazol-2-yl)-1H-indazole, (compound denoted as A35-B63), Example 235(ac);
3-(5,6-dimethyl-1H-benzoimidazol-2-yl)-5-ethoxy-1H-indazole, (compound denoted as A9-B63), (compound denoted as A9-B112), Example 235(ad);
3-[5-(2-morpholin-4-yl-ethoxy)-1H-benzoimidazol-2-yl]-1H-indazole, Example 235(aj);
3-(5-ethyl-6-methyl-1H-benzoimidazol-2-yl)-1H-indazole-5-carbonitrile, Example 235(an);
3-(5,6-dimethyl-1H-benzoimidazol-2-yl)-1H-indazole-5-carbonitrile, Example 235(ar);
3-(5,6-dimethyl-1H-benzoimidazol-2-yl)₄-fluoro-1H-indazole, (compound denoted as A9-B110), Example 242(a);
3-(5,6-dimethyl-1H-benzoimidazol-2-yl)-5-chloro-1H-indazole, (compound denoted as A9-B109), Example 242(c);
3-(5-n-propyl-1H-benzoimidazol-2-yl)-1H-indazole, (compound denoted as A28-B63), Example 244(a);
2-(1H-indazol-3-yl)-1H-benzoimidazole-5-sulfonic acid benzylamide, Example 244(b);
3-(5-methanesulfonyl-1H-benzoimidazol-2-yl)-1H-indazole; Example 244(c)
[2-(indazol-3-yl)-1H-benzoimidazol-5-yl]-phenyl-methanol, (compound denoted as A34-B63), Example 245;
[2-(indazol-3-yl)-1H-benzoimidazol-5-yl]-carboxylic acid, ethylamide, (compound denoted as A36-B63), Example 246(a);
[2-(indazol-3-yl)-1H-benzoimidazol-5-yl]-carboxylic acid, methylamide, (compound denoted as A15-B63), Example 246(b);
[2-(indazol-3-yl)-1H-benzoimidazol-5-yl]-carboxylic acid, isopropylamide, (compound denoted as A16-B63), Example 246(d);
[2-(indazol-3-yl)-1H-benzoimidazol-5-yl]-carboxylic acid, benzylamide, (compound denoted as A17-B63), Example 246(e);
[2-(indazol-3-yl)-1H-benzoimidazol-5-yl]-carboxylic acid, benzamide, (compound denoted as A52-B63), Example 246(f);
2-(1H-indazol-3-yl)-1H-benzoimidazole-5-carboxylic acid (pyridin-3-ylmethyl)-amide, Example 246(m);
2-(1H-indazol-3-yl)-1H-benzoimidazole-5-carboxylic acid 3-methyl-benzylamide, Example 246(n);
2-(1H-indazol-3-yl)-1H-benzoimidazole-5-carboxylic acid 4-methyl-benzylamide, Example 246(o);
2-(1H-indazol-3-yl)-1H-benzoimidazole-5-carboxylic acid [3-(2-oxo-pyrrolidin-1-yl)-propyl]-amide, Example 246(p);
2-(1H-indazol-3-yl)-1H-benzoimidazole-5-carboxylic acid (2-morpholin-4-yl-ethyl)-amide, Example 246(q);
2-(1H-indazol-3-yl)-1H-benzoimidazole-5-carboxylic acid (2-methoxy-ethyl)-amide, Example 246(r);
2-(1H-indazol-3-yl)-1H-benzoimidazole-5-carboxylic acid (2-cyano-ethyl)-amide, Example 246(s);
2-(1H-indazol-3-yl)-1H-benzoimidazole-5-carboxylic acid (2-hydroxy-1,1-dimethyl-ethyl)-amide, Example 246(t);
2-(1H-Indazol-3-yl)-1H-benzoimidazole-5-carboxylic acid (3-imidazol-1-yl-propyl)-amide, Example 246(u),
3-(5,6-dimethyl-1H-benzoimidazol-2-yl)-1H-indazole-5-carboxylic acid dimethylamide, Example 246(x);
[2-(indazol-3-yl)-1H-benzoimidazol-5-yl]-carboxylic acid, (compound denoted as A14-B63), Example 247(a);
3-(5-ethyl-6-methyl-1H-benzoimidazol-2-yl)-1H-indazole-5-carboxylic acid amide dihydrochloride, Example 262;

and the corresponding N-oxides, and their prodrugs; and pharmaceutically acceptable salts and solvates (e.g. hydrates) of such compounds and their N-oxides and prodrugs.

Especially preferred compounds of formula (Ixb) of the invention for the inhibition of SYK are:—
3-(5,6-dimethyl-1H-benzoimidazol-2-yl)-5-methoxy-1H-indazole, (compound denoted as A9-B68), Example 235 (b);
3-(5-ethyl-6-methyl-1H-benzoimidazol-2-yl)-1H-indazole, (compound denoted as A55-B63), Example 235(j);
3-(5,6-diethyl-1H-benzoimidazol-2-yl)-1H-indazole, (compound denoted as A56-B63), Example 235(z);
3-(5,6-dimethyl-1H-benzoimidazol-2-yl)-1H-indazole-5-carboxylic acid dimethylamide, Example 246(x);
and the corresponding N-oxides, and their prodrugs; and pharmaceutically acceptable salts and solvates (e.g. hydrates) of such compounds and their N-oxides and prodrugs.

Preferred compounds of formula (Ixc) of the invention for the inhibition of SYK are:—
3-(5,6-dimethyl-1H-benzoimidazol-2-yl)-4,5,6,7-tetrahydro-1H-indazole; 5,6-dimethyl-2-(1,4,5,6-tetrahydro-cyclopentapyrazol-3-yl)-1H-benzoimidazole;
3-(5,6-dimethyl-1H-benzoimidazol-2-yl)-1,4,5,6,7,8-hexahydro-cycloheptapyrazole;
and the corresponding N-oxides, and their prodrugs; and pharmaceutically acceptable salts and solvates (e.g. hydrates) of such compounds and their N-oxides and prodrugs.

Particularly preferred compounds of formula (Ixc), denoted as the product of the combination of group A1 in Table 1 and B1 in Table 2, of the invention for the inhibition of SYK are:—
3-(5,6-dimethyl-1H-benzoimidazol-2-yl)-4,5,6,7-tetrahydro-1H-indazole, (compound denoted as A9-B59), Example 241(a);
5,6-dimethyl-2-(1,4,5,6-tetrahydro-cyclopentapyrazol-3-yl)-1H-benzoimidazole, (compound denoted as A9-B56), Example 241(d);
and the corresponding N-oxides, and their prodrugs; and pharmaceutically acceptable salts and solvates (e.g. hydrates) of such compounds and their N-oxides and prodrugs.

Preferred compounds of formula (Ixd) of the invention for the inhibition of SYK are:—
3-(5,6-dimethyl-1H-benzoimidazol-2-yl)-1,4,6,7-tetrahydro-pyrazolo[4,3-c]pyridine-5-carboxylic acid isopropylamide;
cyclopropyl-[3-(5,6-dimethyl-1H-benzoimidazol-2-yl)-1,4,6,7-tetrahydro-pyrazolo[4,3-c]pyridin-5-yl]-methanone;
isopropyl-[3-(5,6-dimethyl-1H-benzoimidazol-2-yl)-1,4,6,7-tetrahydro-pyrazolo[4,3-c]pyridin-5-yl]-methanone;
1-[3-(5,6-dimethyl-1H-benzoimidazol-2-yl)-1,4,6,7-tetrahydro-pyrazolo[4,3-c]pyridin-5-yl]-ethanone;
1-[3-(5,6-dimethyl-1H-benzoimidazol-2-yl)-1,4,6,7-tetrahydro-pyrazolo[4,3-c]pyridin-5-yl]-2-methyl-propan-1-one;
3-(5,6-dimethyl-1H-benzoimidazol-2-yl)-1,4,6,7-tetrahydro-pyrazolo[4,3-c]pyridine-5-carboxylic acid methyl ester;
3-(5,6-dimethyl-1H-benzoimidazol-2-yl)-1,4,6,7-tetrahydro-pyrazolo[4,3-c]pyridine-5-carboxylic acid dimethylamide;
1-[3-(5,6-dimethyl-1H-benzoimidazol-2-yl)-1,4,6,7-tetrahydro-pyrazolo[4,3-c]pyridin-5-yl]-3-methyl-butan-1-one;
1-[3-(5,6-dimethyl-1H-benzoimidazol-2-yl)-1,4,6,7-tetrahydro-pyrazolo[4,3-c]pyridin-5-yl]-2,2-dimethyl-propan-1-one;
3-(5,6-dimethyl-1H-benzoimidazol-2-yl)-1,4,6,7-tetrahydro-pyrazolo[4,3-c]pyridine-5-carboxylic acid methyl ester;
3-(5,6-dimethyl-1H-benzoimidazol-2-yl)-1,4,6,7-tetrahydro-pyrazolo[4,3-c]pyridine-5-carboxylic acid isopropylamide;
3-(5,6-dimethyl-1H-benzoimidazol-2-yl)-1,4,6,7-tetrahydro-pyrazolo[4,3-c]pyridine-5-carboxylic acid diethylamide;
[3-(5,6-dimethyl-1H-benzoimidazol-2-yl)-1,4,6,7-tetrahydro-pyrazolo[4,3-c]pyridin-5-yl]-pyrrolidin-1-yl-methanone;
[3-(5,6-dimethyl-1H-benzoimidazol-2-yl)-1,4,6,7-tetrahydro-pyrazolo[4,3-c]pyridin-5-yl]-piperidin-1-yl-methanone;
[3-(5,6-dimethyl-1H-benzoimidazol-2-yl)-1,4,6,7-tetrahydro-pyrazolo[4,3-c]pyridin-5-yl]-morpholin-4-yl-methanone;
3-(5-chloro-6-methyl-1H-benzoimidazol-2-yl)-1,4,6,7-tetrahydro-pyrazolo[4,3-c]pyridine-5-carboxylic acid diethylamide;
3-[5-(2-morpholin-4-yl-ethoxy)-1H-benzoimidazol-2-yl]-1,4,6,7-tetrahydro-pyrazolo[4,3-c]pyridine-5-carboxylic acid diethylamide;
3-(5-trifluoromethyl-1H-benzoimidazol-2-yl)-1,4,6,7-tetrahydro-pyrazolo[4,3-c]pyridine-5-carboxylic acid diethylamide;
1-[3-(5,6-dimethyl-1H-benzoimidazol-2-yl)-1,4,6,7-tetrahydro-pyrazolo[4,3-c]pyridin-5-yl]-2,2-dimethyl-propan-1-one;
3-(5,6-dimethyl-1H-benzoimidazol-2-yl)-5-(propane-2-sulfonyl)-4,5,6,7-tetrahydro-1H-pyrazolo[4,3-c]pyridine;
3-(5,6-dimethyl-1H-benzoimidazol-2-yl)-1,4,6,7-tetrahydro-pyrano[4,3-c]pyrazole;
and the corresponding N-oxides, and their prodrugs; and pharmaceutically acceptable salts and solvates (e.g. hydrates) of such compounds and their N-oxides and prodrugs.

Particularly preferred compounds of formula (Ixd), denoted as the product of the combination of group A1 in Table 1 and B1 in Table 2, of the invention for the inhibition of SYK are:—
3-(5,6-dimethyl-1H-benzoimidazol-2-yl)-1,4,6,7-tetrahydro-pyrazolo[4,3-c]pyridine-5-carboxylic acid isopropylamide, (compound denoted as A9-B121), Example 250 (a);
cyclopropyl-[3-(5,6-dimethyl-1H-benzoimidazol-2-yl)-1,4,6,7-tetrahydro-pyrazolo[4,3-c]pyridin-5-yl]-methanone, (compound denoted as A9-B122);
isopropyl-[3-(5,6-dimethyl-1H-benzoimidazol-2-yl)-1,4,6,7-tetrahydro-pyrazolo[4,3-c]pyridin-5-yl]-methanone;
1-[3-(5,6-dimethyl-1H-benzoimidazol-2-yl)-1,4,6,7-tetrahydro-pyrazolo[4,3-c]pyridin-5-yl]-2,2-dimethyl-propan-1-one;
3-(5,6-dimethyl-1H-benzoimidazol-2-yl)-1,4,6,7-tetrahydro-pyrazolo[4,3-c]pyridine-5-carboxylic acid methyl ester;
3-(5,6-dimethyl-1H-benzoimidazol-2-yl)-1,4,6,7-tetrahydro-pyrazolo[4,3-c]pyridine-5-carboxylic acid isopropylamide; 26(e)
prepared 3-(5,6-dimethyl-1H-benzoimidazol-2-yl)-1,4,6,7-tetrahydro-pyrazolo[4,3-c]pyridine-5-carboxylic acid diethylamide;

[3-(5,6-dimethyl-1H-benzoimidazol-2-yl)-1,4,6,7-tetrahydro-pyrazolo[4,3-c]pyridin-5-yl]-pyrrolidin-1-yl-methanone;

[3-(5,6-dimethyl-1H-benzoimidazol-2-yl)-1,4,6,7-tetrahydro-pyrazolo[4,3-c]pyridin-5-yl]-piperidin-1-yl-methanone;

[3-(5,6-dimethyl-1H-benzoimidazol-2-yl)-1,4,6,7-tetrahydro-pyrazolo[4,3-c]pyridin-5-yl]-morpholin-4-yl-methanone;

3-(5-chloro-6-methyl-1H-benzoimidazol-2-yl)-1,4,6,7-tetrahydro-pyrazolo[4,3-c]pyridine-5-carboxylic acid diethylamide;

3-[5-(2-morpholin-4-yl-ethoxy)-1H-benzoimidazol-2-yl]-1,4,6,7-tetrahydro-pyrazolo[4,3-c]pyridine-5-carboxylic acid diethylamide;

3-(5-trifluoromethyl-1H-benzoimidazol-2-yl)-1,4,6,7-tetrahydro-pyrazolo[4,3-c]pyridine-5-carboxylic acid diethylamide;

3-(5,6-dimethyl-1H-benzoimidazol-2-yl)-1,4,6,7-tetrahydro-pyrazolo[4,3-c]pyridine-5-carboxylic acid dimethylamide, (compound denoted as A9-B119);

1-[3-(5,6-dimethyl-1H-benzoimidazol-2-yl)-1,4,6,7-tetrahydro-pyrazolo[4,3-c]pyridin-5-yl]-2-methyl-propan-1-one, (compound denoted as A9-B117);

3-(5,6-dimethyl-1H-benzoimidazol-2-yl-1,4,6,7-tetrahydro-pyrazolo[4,3-c]pyridine-5-carboxylic acid methyl ester, (compound denoted as A9-B120);

1-[3-(5,6-dimethyl-1H-benzoimidazol-2-yl)-1,4,6,7-tetrahydro-pyrazolo[4,3-c]pyridin-5-yl]-3-methyl-butan-1-one, (compound denoted as A9-B118);

1-[3-(5,6-dimethyl-1H-benzoimidazol-2-yl)-1,4,6,7-tetrahydro-pyrazolo[4,3-c]pyridin-5-yl]-2,2-dimethyl-propan-1-one, (compound denoted as A9-B123);

and the corresponding N-oxides, and their prodrugs; and pharmaceutically acceptable salts and solvates (e.g. hydrates) of such compounds and their N-oxides and prodrugs.

Especially preferred compounds of formula (Ixd), denoted as the product of the combination of group A1 in Table 1 and B1 in Table 2, of the invention for the inhibition of SYK are:—

3-(5,6-dimethyl-1H-benzoimidazol-2-yl)-1,4,6,7-tetrahydro-pyrazolo[4,3-c]pyridine-5-carboxylic acid isopropylamide, (compound denoted as A9-B121), Example 250(a);

cyclopropyl-[3-(5,6-dimethyl-1H-benzoimidazol-2-yl)-1,4,6,7-tetrahydro-pyrazolo[4,3-c]pyridin-5-yl]-methanone, (compound denoted as A9-B122); Example 250(b);

3-(5,6-dimethyl-1H-benzoimidazol-2-yl)-1,4,6,7-tetrahydro-pyrazolo[4,3-c]pyridine-5-carboxylic acid isopropylamide, Example 255(e);

prepared 3-(5,6-dimethyl-1H-benzoimidazol-2-yl)-1,4,6,7-tetrahydro-pyrazolo[4,3-c]pyridine-5-carboxylic acid diethylamide, Example 258(i);

[3-(5,6-dimethyl-1H-benzoimidazol-2-yl)-1,4,6,7-tetrahydro-pyrazolo[4,3-c]pyridin-5-yl]-pyrrolidin-1-yl-methanone, Example 258(j);

[3-(5,6-dimethyl-1H-benzoimidazol-2-yl)-1,4,6,7-tetrahydro-pyrazolo[4,3-c]pyridin-5-yl]-piperidin-1-yl-methanone, Example 258(k);

3-(5-chloro-6-methyl-1H-benzoimidazol-2-yl)-1,4,6,7-tetrahydro-pyrazolo[4,3-e]pyridine-5-carboxylic acid diethylamide, Example 258(m);

3-(5,6-dimethyl-1H-benzoimidazol-2-yl)-1,4,6,7-tetrahydro-pyrazolo[4,3-c]pyridine-5-carboxylic acid dimethylamide, (compound denoted as A9-B119);

and the corresponding N-oxides, and their prodrugs; and pharmaceutically acceptable salts and solvates (e.g. hydrates) of such compounds and their N-oxides and prodrugs.

Particular compounds of formula (Lx) of the invention for the inhibition of KDR are:—

2-(1H-indazol-3-yl)-1H-benzimidazole-5-carboxylic acid benzylamide;

2-(1H-indazol-3-yl)-1H-benzimidazole-5-carboxylic acid N-methylamide;

2-(1H-indazol-3-yl)-1H-benzimidazole-5-carboxylic acid N-ethylamide;

2-(1H-indazol-3-yl)-1H-benzimidazole-5-carboxylic acid N-isopropylamide;

2-(1H-indazol-3-yl)-1H-benzimidazole-5-carboxylic acid N-phenylamide;

2-(1H-indazol-3-yl)-1H-benzimidazole-5-carboxylic acid N-phenethylamide;

2-(1H-indazol-3-yl)-1H-benzimidazole-5-carboxylic acid N-morpholinoamide;

2-(1H-indazol-3-yl)-1H-benzimidazole-5-carboxylic acid N—(N'-methylpiperazino)amide;

2-(1H-indazol-3-yl)-1H-benzimidazole-5-carboxylic acid N-pyrrolidinoamide;

2-(1H-indazol-3-yl)-1H-benzimidazole-5-carboxylic acid N-(isobutyl)amide;

2-(1H-indazol-3-yl)-1H-benzimidazole-5-carboxylic acid N-(cyclohexylmethyl)amide;

2-(1H-indazol-3-yl)-1H-benzimidazole-5-carboxylic acid N-(2-furfuryl)amide;

2-(1H-indazol-3-yl)-1H-benzimidazole-5-carboxylic acid N-benzyl-N-methylamide;

methyl 2-(1H-indazol-3-yl)-3H-benzimidazole-5-carboxylate;

5,6-dimethyl-2-(1H-indazol-3-yl)-1H-benzimidazole;

5-methoxy-2-(1H-indazol-3-yl)-1H-benzimidazole;

2-(1H-indazol-3-yl)-3H-benzimidazole-4-carboxylic acid;

5-bromo 2-(1H-indazol-3-yl)-3H-benzimidazole;

2-(5-ethoxy-2H-pyrazol-3-yl)-1H-benzimidazole-4-carboxylic acid;

5,6-dimethyl-2-(5-methyl-2H-pyrazol-3-yl)-1H-benzimidazole;

5,6-dimethyl-2-(5-thiophen-2-yl-2H-pyrazol-3-yl)-1H-benzimidazole;

2-(4-bromo-2H-pyrazol-3-yl)-5,6-dimethyl-1H-benzimidazole;

2-(5-ethyl-2H-pyrazol-3-yl)-5,6-dimethyl-1H-benzimidazole;

2-(5-ethyl-2H-pyrazol-3-yl)-4,5-ethylenedioxy-1H-benzimidazole;

2-(5-ethyl-2H-pyrazol-3-yl)-5-methoxy-1H-benzimidazole;

2-(5-ethyl-2H-pyrazol-3-yl)-4-hydroxy-1H-benzimidazole.

2-(5-ethyl-2H-pyrazol-3-yl)-5-bromo-1H-benzimidazole;

2-(1H-indazol-3-yl)-1H-benzoimidazole-5-carboxylic acid 2,4-dichloro-benzylamide;

2-(1H-indazol-3-yl)-1H-benzoimidazole-5-carboxylic acid (3-ethoxy-propyl)-amide;

2-(1H-indazol-3-yl)-1H-benzoimidazole-5-carboxylic acid 4-bromo-benzylamide;

2-(1H-indazol-3-yl)-1H-benzoimidazole-5-carboxylic acid 4-methanesulfonyl-benzylamide;

2-(1H-indazol-3-yl)-1H-benzoimidazole-5-carboxylic acid (naphthalen-1-ylmethyl)-amide;

2-(1H-indazol-3-yl)-1H-benzoimidazole-5-carboxylic acid 4-trifluoromethyl-benzylamide;

2-(1H-indazol-3-yl)-1H-benzoimidazole-5-carboxylic acid (thiophen-2-ylmethyl)-amide;

2-(1H-indazol-3-yl)-1H-benzoimidazole-5-carboxylic acid 4-dimethylamino-benzylamide;
4-({[2-(1H-indazol-3-yl)-1H-benzoimidazole-5-carbonyl]-amino}-methyl)-piperidine-1-carboxylic acid tert-butyl ester;
2-(1H-indazol-3-yl)-1H-benzoimidazole-5-carboxylic acid 4-nitro-benzylamide;
2-(1H-indazol-3-yl)-1H-benzoimidazole-5-carboxylic acid (pyridin-3-ylmethyl)-amide;
2-(1H-indazol-3-yl)-1H-benzoimidazole-5-carboxylic acid 3-bromo-benzylamide;
2-(1H-indazol-3-yl)-1H-benzoimidazole-5-carboxylic acid 3-methoxy-benzylamide;
2-(1H-indazol-3-yl)-1H-benzoimidazole-5-carboxylic acid (benzo[1,3]dioxol-5-ylmethyl)amide;
2-(1H-indazol-3-yl)-1H-benzoimidazole-5-carboxylic acid (benzo[b]thiophen-3-ylmethyl)-amide;
2-(1H-indazol-3-yl)-1H-benzoimidazole-5-carboxylic acid (1,3-dimethyl-1H-pyrazol-4-ylmethyl)-amide;
2-(1H-indazol-3-yl)-1H-benzoimidazole-5-carboxylic acid 2-trifluoromethoxy-benzylamide;
2-(1H-indazol-3-yl)-1H-benzoimidazole-5-carboxylic acid 2-methyl-benzylamide;
2-(1H-indazol-3-yl)-1H-benzoimidazole-5-carboxylic acid (3-methyl-thiophen-2-ylmethyl)-amide;
2-(1H-indazol-3-yl)-1H-benzoimidazole-5-carboxylic acid 2-trifluoromethyl-benzylamide;
2-(1H-indazol-3-yl)-1H-benzoimidazole-5-carboxylic acid 4-phenoxy-benzylamide;
2-(1H-indazol-3-yl)-1H-benzoimidazole-5-carboxylic acid 3-trifluoromethoxy-benzylamide;
2-(1H-indazol-3-yl)-1H-benzoimidazole-5-carboxylic acid (3-isopropoxy-propyl)-amide;
2-(1H-indazol-3-yl)-1H-benzoimidazole-5-carboxylic acid (1-methyl-1H-pyrazol-4-ylmethyl)-amide;
2-(1H-indazol-3-yl)-1H-benzoimidazole-5-carboxylic acid 4-isopropyl-benzylamide;
2-(1H-indazol-3-yl)-1H-benzoimidazole-5-carboxylic acid (2,5-dimethyl-furan-3-ylmethyl)-amide;
2-(1H-indazol-3-yl)-1H-benzoimidazole-5-carboxylic acid (benzo[b]thiophen-2-ylmethyl)-amide;
2-(1H-indazol-3-yl)-1H-benzoimidazole-5-carboxylic acid [3-(3-acetylamino-phenoxy)-propyl]-amide;
2-(1H-indazol-3-yl)-1H-benzoimidazole-5-carboxylic acid (6-chloro-pyridin-3-ylmethyl)-amide;
2-(1H-indazol-3-yl)-1H-benzoimidazole-5-carboxylic acid ([2,2']bithiophenyl-5-ylmethyl)-amide;
2-(1H-indazol-3-yl)-1H-benzoimidazole-5-carboxylic acid (2,3-dihydro-benzofuran-5-ylmethyl)-amide;
2-(1H-indazol-3-yl)-1H-benzoimidazole-5-carboxylic acid 4-cyano-benzylamide;
2-(1H-indazol-3-yl)-1H-benzoimidazole-5-carboxylic acid (5-chloro-benzo[b]thiophen-3-ylmethyl)-amide;
2-(1H-indazol-3-yl)-1H-benzoimidazole-5-carboxylic acid 3-trifluoromethyl-benzylamide;
2-(1H-indazol-3-yl)-1H-benzoimidazole-5-carboxylic acid 2-methylsulfanyl-benzylamide;
2-(1H-indazol-3-yl)-1H-benzoimidazole-5-carboxylic acid (benzo[b]thiophen-3-ylmethyl)-amide;
2-(1H-indazol-3-yl)-1H-benzoimidazole-5-carboxylic acid (tetrahydro-pyran-4-ylmethyl)-amide;
2-(1H-indazol-3-yl)-1H-benzoimidazole-5-carboxylic acid (2,3-dihydro-benzo[1,4]dioxin-2-ylmethyl)-amide;
2-(1H-indazol-3-yl)-1H-benzoimidazole-5-carboxylic acid (furan-3-ylmethyl)-amide;
2-(1H-indazol-3-yl)-1H-benzoimidazole-5-carboxylic acid 2-nitro-benzylamide;
2-(1H-indazol-3-yl)-1H-benzoimidazole-5-carboxylic acid (thiophen-3-ylmethyl)-amide;
2-(1H-indazol-3-yl)-1H-benzoimidazole-5-carboxylic acid 3,5-dimethyl-benzylamide;
2-(1H-indazol-3-yl)-1H-benzoimidazole-5-carboxylic acid (1-methyl-1H-benzoimidazol-2-ylmethyl)-amide;
2-(1H-indazol-3-yl)-1H-benzoimidazole-5-carboxylic acid 3-methyl-benzylamide;
2-(1H-indazol-3-yl)-1H-benzoimidazole-5-carboxylic acid 3-chloro-benzylamide;
2-(1H-indazol-3-yl)3H-benzoimidazole-4-carboxylic acid 4-sulfamoyl-benzylamide;
2-(1H-indazol-3-yl)-3H-benzoimidazole-4-carboxylic acid (3-ethoxy-propyl)-amide;
2-(1H-indazol-3-yl)-3H-benzoimidazole-4-carboxylic acid 4-bromo-benzylamide;
2-(1H-indazol-3-yl)-3H-benzoimidazole-4-carboxylic acid (naphthalen-1-ylmethyl)-amide;
2-(1H-indazol-3-yl)-3H-benzoimidazole-4-carboxylic acid (thiophen-2-ylmethyl)-amide;
2-(1H-indazol-3-yl)-3H-benzoimidazole-4-carboxylic acid 4-dimethylamino-benzylamide;
2-(1H-indazol-3-yl)-3H-benzoimidazole-4-carboxylic acid 4-nitro-benzylamide;
2-(1H-indazol-3-yl)-3H-benzoimidazole-4-carboxylic acid (pyridin-3-ylmethyl)-amide;
2-(1H-indazol-3-yl)-3H-benzoimidazole-4-carboxylic acid 3-bromo-benzylamide;
2-(1H-indazol-3-yl)-3H-benzoimidazole-4-carboxylic acid 3-methoxy-benzylamide;
2-(1H-indazol-3-yl)-3H-benzoimidazole-4-carboxylic acid (benzo[b]thiophen-3-ylmethyl)-amide;
2-(1H-indazol-3-yl)-3H-benzoimidazole-4-carboxylic acid 4-phenoxy-benzylamide;
2-(1H-indazol-3-yl)-3H-benzoimidazole-4-carboxylic acid 3-trifluoromethoxy-benzylamide;
2-(1H-indazol-3-yl)-3H-benzoimidazole-4-carboxylic acid (6-chloro-pyridin-3-ylmethyl)-amide;
2-(1H-indazol-3-yl)-3H-benzoimidazole-4-carboxylic acid (2,3-dihydro-benzofuran-5-ylmethyl)-amide;
2-(1H-indazol-3-yl)-3H-benzoimidazole-4-carboxylic acid 3-trifluoromethyl-benzylamide;
2-(1H-indazol-3-yl)-3H-benzoimidazole-4-carboxylic acid 2-methylsulfanyl-benzylamide;
2-(1H-indazol-3-yl)-3H-benzoimidazole-4-carboxylic acid (furan-3-ylmethyl)-amide;
2-(1H-indazol-3-yl)-3H-benzoimidazole-4-carboxylic acid 2-nitro-benzylamide;
2-(1H-indazol-3-yl)-3H-benzoimidazole-4-carboxylic acid 3,5-dimethyl-benzylamide;
2-(1H-indazol-3-yl)-3H-benzoimidazole-4-carboxylic acid 3-chloro-benzylamide;
2-(1H-indazol-3-yl)-3H-benzoimidazole-4-carboxylic acid phenylamide;
2-(1H-indazol-3-yl)-3H-benzoimidazole-4-carboxylic acid benzylamide;
2-(1H-indazol-3-yl)-3H-benzoimidazole-4-carboxylic acid phenethyl-amide;
3-(6-phenyl-1H-benzoimidazol-2-yl)-2H-indazole;
3-[6-(2,4-dichloro-phenyl)-1H-benzoimidazol-2-yl]-2H-indazole;
3-(6-naphthalen-1-yl-1H-benzoimidazol-2-yl)-2H-indazole;
3-[6-(4-fluoro-phenyl)-1H-benzoimidazol-2-yl]-2H-indazole;
3-[6-(4-chloro-phenyl)-1H-benzoimidazol-2-yl]-2H-indazole;

3-[6-(4-methoxy-phenyl)-1H-benzoimidazol-2-yl]-2H-indazole;
3-[6-(3-chloro-4-fluoro-phenyl)-1H-benzoimidazol-2-yl]-2H-indazole;
3-[6-(3,5-dichloro-phenyl)-1H-benzoimidazol-2-yl]-2H-indazole;
3-(6-thianthren-1-yl-1H-benzoimidazol-2-yl)-2H-indazole;
3-(6-biphenyl-4-yl-1H-benzoimidazol-2-yl)-2H-indazole;
3-(6-p-tolyl-1H-benzoimidazol-2-yl)-2H-indazole;
3-(6-m-tolyl-1H-benzoimidazol-2-yl)-2H-indazole;
3-(6-o-tolyl-1H-benzoimidazol-2-yl)-2H-indazole;
3-(6-thiophen-3-yl-1H-benzoimidazol-2-yl)-2H-indazole;
3-[6-(3-trifluoromethyl-phenyl)-1H-benzoimidazol-2-yl]-2H-indazole;
3-[6-(4-trifluoromethyl-phenyl)-1H-benzoimidazol-2-yl]-2H-indazole;
3-[6-(3-chloro-phenyl)-1H-benzoimidazol-2-yl]-2H-indazole;
3-[6-(3-methoxy-phenyl)-1H-benzoimidazol-2-yl]-2H-indazole;
3-[6-(3,5-dimethyl-phenyl)-1H-benzoimidazol-2-yl]-2H-indazole;
3-[6-(3,4-dimethyl-phenyl)-1H-benzoimidazol-2-yl]-2H-indazole;
3-(6-benzo[1,3]dioxol-5-yl-1H-benzoimidazol-2-yl)-2H-indazole;
3-[6-(4-tert-butyl-phenyl)-1H-benzoimidazol-2-yl]-2H-indazole;
3-(6-hex-1-enyl-1H-benzoimidazol-2-yl)-2H-indazole;
3-[6-(3,4-dimethoxy-phenyl)-1H-benzoimidazol-2-yl]-2H-indazole;
3-[2-(2H-indazol-3-yl)-3H-benzoimidazol-5-yl]-phenol;
4-[2-(2H-indazol-3-yl)-3H-benzoimidazol-5-yl]-phenol;
3-[6-(3,4-dichloro-phenyl)-1H-benzoimidazol-2-yl]-2H-indazole;
3-[6-(4-trifluoromethoxy-phenyl)-1H-benzoimidazol-2-yl]-2H-indazole;
1-{4-[2-(2H-indazol-3-yl)-3H-benzoimidazol-5-yl]-phenyl}-ethanone;
3-(6-benzo[b]thiophen-2-yl-1H-benzoimidazol-2-yl)-2H-indazole;
3-[6-(3,4,5-trimethoxy-phenyl)-1H-benzoimidazol-2-yl]-2H-indazole;
1-{5-[2-(2H-indazol-3-yl)-3H-benzoimidazol-5-yl]-thiophen-2-yl}-ethanone;
1-{3-[2-(2H-indazol-3-yl)-3H-benzoimidazol-5-yl]-phenyl}-ethanone;
3-[6-(4-benzyloxy-phenyl)-1H-benzoimidazol-2-yl]-2H-indazole;
3-[6-(2-fluoro-biphenyl-4-yl)-1H-benzoimidazol-2-yl]-2H-indazole;
3-(6-benzo[b]thiophen-3-yl-1H-benzoimidazol-2-yl)-2H-indazole;
{3-[2-(2H-indazol-3-yl)-3H-benzoimidazol-5-yl]-phenyl}-methanol;
3-[6-(4-ethylsulfanyl-phenyl)-1H-benzoimidazol-2-yl]-2H-indazole;
3-[6-(2,4-difluoro-phenyl)-1H-benzoimidazol-2-yl]-2H-indazole;
3-[6-(3-trifluoromethoxy-phenyl)-1H-benzoimidazol-2-yl]-2H-indazole;
3-[6-(4-fluoro-2-methyl-phenyl)-1H-benzoimidazol-2-yl]-2H-indazole;
3-{6-[2-(4-fluoro-phenyl)-vinyl]-1H-benzoimidazol-2-yl}-2H-indazole;
3-{6-[2-(4-chloro-phenyl)-vinyl]-1H-benzoimidazol-2-yl}-2H-indazole;
3-{4-[2-(2H-indazol-3-yl)-3H-benzoimidazol-5-yl]-phenyl}-propionic acid;
{4-[2-(2H-indazol-3-yl)-3H-benzoimidazol-5-yl]-phenyl}-methanol;
3-(6-furan-2-yl-1H-benzoimidazol-2-yl)-2H-indazole;
3-[6-(3-benzyloxy-phenyl)-1H-benzoimidazol-2-yl]-2H-indazole;
3-[6-(4-isopropyl-phenyl)-1H-benzoimidazol-2-yl]-2H-indazole;
3-[6-(4-methanesulfonyl-phenyl)-1H-benzoimidazol-2-yl]-2H-indazole;
2-(1H-indazol-3-yl)-1H-benzoimidazole-5-carboxylic acid (tetrahydro-pyran-4-ylmethyl)-amide;
2-(1H-indazol-3-yl)-1H-benzoimidazole-5-carboxylic acid 4-acetylamino-benzylamide;
2-(1H-indazol-3-yl)-1H-benzoimidazole-5-carboxylic acid methylamide;
2-(1H-indazol-3-yl)-1H-benzoimidazole-5-carboxylic acid isopropylamide;
[2-(1H-indazol-3-yl)-1H-benzoimidazol-5-yl]-morpholin-4-yl-methanone;
[2-(1H-indazol-3-yl)-1H-benzoimidazol-5-yl]-(4-methyl-piperazin-1-yl)-methanone;
2-(1H-indazol-3-yl)-1H-benzoimidazole-5-carboxylic acid benzyl-methyl-amide;
2-(1H-indazol-3-yl)-1H-benzoimidazole-5-carboxylic acid 3-nitro-benzylamide;
2-(1H-indazol-3-yl)-1H-benzoimidazole-5-carboxylic acid 2-fluoro-benzylamide;
2-(1H-indazol-3-yl)-1H-benzoimidazole-5-carboxylic acid 2,4-difluoro-benzylamide;
2-(1H-indazol-3-yl)-1H-benzoimidazole-5-carboxylic acid 2,6-difluoro-benzylamide;
2-(1H-indazol-3-yl)-1H-benzoimidazole-5-carboxylic acid 4-bromo-2-fluoro-benzylamide;
2-(1H-indazol-3-yl)-1H-benzoimidazole-5-carboxylic acid 4-chloro-2-fluoro-benzylamide;
2-(1H-indazol-3-yl)-1H-benzoimidazole-5-carboxylic acid 4-bromo-2-fluoro-benzylamide;
2-(1H-indazol-3-yl)-1H-benzoimidazole-5-carboxylic acid 3,4-difluoro-benzylamide;
2-(1H-indazol-3-yl)-1H-benzoimidazole-5-carboxylic acid 3,4,5-trifluoro-benzylamide;
2-(1H-indazol-3-yl)-1H-benzoimidazole-5-carboxylic acid (4'-chloro-biphenyl-4-ylmethyl)-amide;
2-(1H-indazol-3-yl)-1H-benzoimidazole-5-carboxylic acid (3',5'-dichloro-biphenyl-4-ylmethyl)-amide;
2-(1H-indazol-3-yl)-1H-benzoimidazole-5-carboxylic acid (4'-fluoro-biphenyl-4-ylmethyl)-amide;
2-(1H-indazol-3-yl)-1H-benzoimidazole-5-carboxylic acid 2-fluoro-benzylamide;
2-(1H-indazol-3-yl)-1H-benzoimidazole-5-carboxylic acid 2,6-difluoro-3-methyl-benzylamide;
2-(1H-indazol-3-yl)-1H-benzoimidazole-5-carboxylic acid 2,4-dichloro-benzylamide;
2-(1H-indazol-3-yl)-1H-benzoimidazole-5-carboxylic acid 4-chloro-benzylamide;
2-(1H-indazol-3-yl)-1H-benzoimidazole-5-carboxylic acid 4-chloro-2-methyl-benzylamide;
2-(1H-indazol-3-yl)-1H-benzoimidazole-5-carboxylic acid 4-fluoro-benzylamide;
2-(1H-indazol-3-yl)-1H-benzoimidazole-5-carboxylic acid (2'-chloro-biphenyl-4-ylmethyl)-amide;
2-(1H-indazol-3-yl)-1H-benzoimidazole-5-carboxylic acid (6-trifluoromethyl-pyridin-3-ylmethyl)-amide;
2-(1H-indazol-3-yl)-1H-benzoimidazole-5-carboxylic acid (5-pyridin-2-yl-thiophen-2-ylmethyl)-amide;

2-(1H-indazol-3-yl)-1H-benzoimidazole-5-carboxylic acid (3-imidazol-1-yl-propyl)-amide;
4-[2-(1H-indazol-3-yl)-1H-benzoimidazole-5-carbonyl]-piperazine-1-carboxylic acid tert-butyl ester;
2-(1H-indazol-3-yl)-1H-benzoimidazole-5-carboxylic acid (2,6-difluoro-4-chloro-benzyl)amide;
2-(1H-indazol-3-yl)-1H-benzoimidazole-5-carboxylic acid (2,4-dichloro-6-fluoro-benzyl)amide;
2-(1H-indazol-3-yl)-1H-benzoimidazole-5-carboxylic acid (3-fluoro-4-chloro-benzyl)amide;
2-(1H-indazol-3-yl)-1H-benzoimidazole-5-carboxylic acid (2-fluoro-4-chloro-6-methyl-benzyl)amide;
2-(1H-indazol-3-yl)-1H-benzoimidazole-5-carboxylic acid (6-methoxy-pyridin-3-ylmethyl)-amide;
2-[5-(benzyloxy)-2H-pyrazol-3-yl]-1H-benzoimidazole;
2-[5-(3-phenyl-allyloxy)-2H-pyrazol-3-yl]-1H-benzoimidazole;
2-[5-(2-methyl-allyloxy)-2H-pyrazol-3-yl]-1H-benzoimidazole;
2-[5-(3,7-dimethyl-octa-2,6-dienyloxy)-2H-pyrazol-3-yl]-1H-benzoimidazole;
2-[5-(3-bromo-benzyloxy)-2H-pyrazol-3-yl]-1H-benzoimidazole;
3-[5-(1H-benzoimidazol-2-yl)-1H-pyrazol-3-yloxymethyl]-benzonitrile;
2-[5-(4-trifluoromethyl-benzyloxy)-2H-pyrazol-3-yl]-1H-benzoimidazole;
2-[5-(3,4-dichloro-benzyloxy)-2H-pyrazol-3-yl]-1H-benzoimidazole;
2-[5-pentafluorophenylmethoxy)-2H-pyrazol-3-yl]-1H-benzoimidazole;
2-[5-(4-tert-butyl-benzyloxy)-2H-pyrazol-3-yl]-1H-benzoimidazole;
2-[5-(2-benzenesulfonylmethyl-benzyloxy)-2H-pyrazol-3-yl]-1H-benzoimidazole;
4-[5-(1H-benzoimidazol-2-yl)-1H-pyrazol-3-yloxymethyl]-benzonitrile;
2-[5-(biphenyl-4-ylmethoxy)-2H-pyrazol-3-yl]-1H-benzoimidazole;
2,3-dichloro-benzenesulfonic acid 5-(1H-benzoimidazol-2-yl)-1H-pyrazol-3-yl ester;
2-[5-(2-morpholin-4-yl-ethoxy)-2H-pyrazol-3-yl]-1H-benzoimidazole;
2-[5-(2-piperidin-1-yl-ethoxy)-2H-pyrazol-3-yl]-1H-benzoimidazole;
2-[5-(3-methoxy-benzyloxy)-2H-pyrazol-3-yl]-1H-benzoimidazole;
2-[5-(1H-benzoimidazol-2-yl)-1H-pyrazol-3-yloxy]-1-p-tolyl-ethanone;
1-[5-(1H-benzoimidazol-2-yl)-1H-pyrazol-3-yloxy]-3,3,4,4,4-pentafluoro-butan-2-one;
2-[5-(1H-benzoimidazol-2-yl)-1H-pyrazol-3-yloxy]-1-biphenyl-4-yl-ethanone;
1-[5-(1H-benzoimidazol-2-yl)-1H-pyrazol-3-yloxy]-butan-2-one;
2-[5-(1H-benzoimidazol-2-yl)-1H-pyrazol-3-yloxy]-1-(4-dimethylamino-phenyl)-ethanone;
2-[5-(1H-benzoimidazol-2-yl)-1H-pyrazol-3-yloxy]-1-(3-phenyl-isoxazol-5-yl)-ethanone;
2-[5-(1H-benzoimidazol-2-yl)-1H-pyrazol-3-yloxy]-N-phenyl-acetamide;
1-[5-(1H-benzoimidazol-2-yl)-1H-pyrazol-3-yloxy]-3,3-dimethyl-butan-2-one;
1-adamantan-1-yl-2-[5-(1H-benzoimidazol-2-yl 1H-pyrazol-3-yloxy]-ethanone;
2-[5-(1H-benzoimidazol-2-yl)-1H-pyrazol-3-yloxy]-1-naphthalen-2-yl-ethanone;
4-{2-[5-(1H-benzoimidazol-2-yl)-1H-pyrazol-3-yloxy]-acetyl}-benzonitrile;
6-{2-[5-(1H-benzoimidazol-2-yl)-1H-pyrazol-3-yloxy]-acetyl}-3,4-dihydro 1H-quinolin-2-one;
2-[5-(1H-benzoimidazol-2-yl)-1H-pyrazol-3-yloxy]-1-(4-trifluoromethoxy-phenyl)-ethanone;
5-{2-[5-(1H-benzoimidazol-2-yl)-1H-pyrazol-3-yloxy]-acetyl}-2-chloro-benzenesulfonamide;
2-[5-(1H-benzoimidazol-2-yl)-1H-pyrazol-3-yloxy]-1-(4-methoxy-phenyl)-ethanone;
2-[5 (1H-benzoimidazol-2-yl)-1H-pyrazol-3-yloxy]-1-cyclopropyl-ethanone;
isonicotinic acid 5-(1H-benzoimidazol-2-yl)-1H-pyrazol-3-yl ester;
2,2-dimethyl-propionic acid 5-(1H-benzoimidazol-2-yl)-1H-pyrazol-3-yl ester;
benzyloxy-acetic acid 5-(1H-benzoimidazol-2-yl)-1H-pyrazol-3-yl ester,
benzoic acid 5-(1H-benzoimidazol-2-yl)-1H-pyrazol-3-yl ester;
4-methoxy-benzoic acid 5-(1H-benzoimidazol-2-yl)-1H-pyrazol-3-yl ester,
phenyl-acetic acid 5-(1H-benzoimidazol-2-yl)-1H-pyrazol-3-yl ester;
2,3,4,5,6-Pentafluoro-benzoic acid 5-(1H-benzoimidazol-2-yl)-1H-pyrazol-3-yl ester;
cyclopropanecarboxylic acid 5-(1H-benzoimidazol-2-yl 1H-pyrazol-3-yl ester;
2,2,3,3,4,4,4-heptafluoro-butyric acid 5-(1H-benzoimidazol-2-yl)-1H-pyrazol-3-yl ester;
cyclopentanecarboxylic acid 5-(1H-benzoimidazol-2-yl)-1H-pyrazol-3-yl ester;
3-phenyl-propionic acid 5-(1H-benzoimidazol-2-yl)-1H-pyrazol-3-yl ester,
biphenyl-4-carboxylic acid 5-(1H-benzoimidazol-2-yl)-1H-pyrazol-3-yl ester;
3,5-bis-trifluoromethyl-benzoic acid 5-(H-benzoimidazol-2-yl)-1H-pyrazol-3-yl ester;
4-trifluoromethyl-benzoic acid 5-(1H-benzoimidazol-2-yl)-1H-pyrazol-3-yl ester;
thiophene-2-carboxylic acid 5-(1H-benzoimidazol-2-yl)-1H-pyrazol-3-yl ester;
and the corresponding N-oxides, and their prodrugs; and pharmaceutically acceptable salts and solvates (e.g. hydrates) of such compounds and their N-oxides and prodrugs.

Preferred compounds of formula (Ixa), denoted as the product of the combination of group A1 in Table 1 and B1 in Table 2, of the invention for the inhibition of KDR are:—
2-(5-ethyl-2H-pyrazol-3-yl)-5,6-dimethyl-1H-benzimidazole, (compound denoted as A9-B3);
2-(5-methyl-2H-pyrazol-3-yl)-5,6-dimethyl-1H-benzimidazole (compound denoted as A9-B2);
and the corresponding N-oxides, and their prodrugs; and pharmaceutically acceptable salts and solvates (e.g. hydrates) of such compounds and their N-oxides and prodrugs.

Preferred compounds of formula (Ixb), denoted as the product of the combination of group A1 in Table 1 and B1 in Table 2, of the invention for the inhibition of KDR are:—
2-(1H-indazol-3-yl)-1H-benzimidazole-5-carboxylic acid benzylamide, (compound denoted as A17-B63);
2-(1H-indazol-3-yl)-1H-benzimidazole-5-carboxylic acid N-methylamide, (compound denoted as A15-B63);
2-(1H-indazol-3-yl)-1H-benzimidazole-5-carboxylic acid N-ethylamide, (compound denoted as A36-B63);

2-(1H-indazol-3-yl)-1H-benzimidazole-5-carboxylic acid N-isopropylamide, (compound denoted as A37-B63);
2-(1H-indazol-3-yl)-1H-benzimidazole-5-carboxylic acid N-phenylamide, (compound denoted as A52-B63);
2-(1H-indazol-3-yl)-1H-benzimidazole-5-carboxylic acid N-phenethylamide, (compound denoted as A51-B63);
2-(1H-indazol-3-yl)-1H-benzimidazole-5-carboxylic acid N-morpholinoamide, (compound denoted as A92-B63);
2-(1H-indazol-3-yl)-1H-benzimidazole-5-carboxylic acid N—(N'-methylpiperazino)amide, (compound denoted as A93-B63);
2-(1H-indazol-3-yl)-1H-benzimidazole-5-carboxylic acid N-pyrrolidinoamide, (compound denoted as A91-B63);
2-(1H-indazol-3-yl)-1H-benzimidazole-5-carboxylic acid N-(isobutyl)amide, (compound denoted as A82-B63);
2-(1H-indazol-3-yl)-1H-benzimidazole-5-carboxylic acid N-(cyclohexylmethyl)amide, (compound denoted as A83-B63);
2-(1H-indazol-3-yl)-1H-benzimidazole-5-carboxylic acid N-(2-furfuryl)amide, (compound denoted as A84-B63);
2-(1H-indazol-3-yl)-1H-benzimidazole-5-carboxylic acid N-benzyl-N-methylamide, (compound denoted as A90-B63);
2-(1H-indazol-3-yl)-1H-benzoimidazole-5-carboxylic acid 2,4-dichloro-benzylamide;
2-(1H-indazol-3-yl)-1H-benzoimidazole-5-carboxylic acid (3-ethoxy-propyl)-amide;
2-(1H-indazol-3-yl)-1H-benzoimidazole-5-carboxylic acid 4-bromo-benzylamide;
2-(1H-indazol-3-yl)-1H-benzoimidazole-5-carboxylic acid 4-methanesulfonyl-benzylamide;
2-(1H-indazol-3-yl)-1H-benzoimidazole-5-carboxylic acid (naphthalen-1-ylmethyl)-amide;
2-(1H-indazol-3-yl)-1H-benzoimidazole-5-carboxylic acid 4-trifluoromethyl-benzylamide;
2-(1H-indazol-3-yl)-1H-benzoimidazole-5-carboxylic acid (thiophen-2-ylmethyl)-amide;
2-(1H-indazol-3-yl)-1H-benzoimidazole-5-carboxylic acid 4-dimethylamino-benzylamide;
4-({[2-(1H-indazol-3-yl)-1H-benzoimidazole-5-carbonyl]-amino}-methyl)-piperidine-1-carboxylic acid tert-butyl ester;
2-(1H-indazol-3-yl)-1H-benzoimidazole-5-carboxylic acid 4-nitro-benzylamide;
2-(1H-indazol-3-yl)-1H-benzoimidazole-5-carboxylic acid (pyridin-3-ylmethyl)-amide;
2-(1H-indazol-3-yl)-1H-benzoimidazole-5-carboxylic acid 3-bromo-benzylamide;
2-(1H-indazol-3-yl)-1H-benzoimidazole-5-carboxylic acid 3-methoxy-benzylamide;
2-(1H-indazol-3-yl)-1H-benzoimidazole-5-carboxylic acid (benzo[1,3]dioxol-5-ylmethyl)-amide;
2-(1H-indazol-3-yl)-1H-benzoimidazole-5-carboxylic acid (benzo[b]thiophen-3-ylmethyl)-amide;
2-(1H-indazol-3-yl)-1H-benzoimidazole-5-carboxylic acid (1,3-dimethyl-1H-pyrazol-4-ylmethyl)-amide;
2-(1H-indazol-3-yl)-1H-benzoimidazole-5-carboxylic acid 2-trifluoromethoxy-benzylamide;
2-(1H-indazol-3-yl)-1H-benzoimidazole-5-carboxylic acid 2-methyl-benzylamide;
2-(1H-indazol-3-yl)-1H-benzoimidazole-5-carboxylic acid (3-methyl-thiophen-2-ylmethyl)-amide;
2-(1H-indazol-3-yl)-1H-benzoimidazole-5-carboxylic acid 2-trifluoromethyl-benzylamide;
2-(1H-indazol-3-yl)-1H-benzoimidazole-5-carboxylic acid 4-phenoxy-benzylamide;
2-(1H-indazol-3-yl)-1H-benzoimidazole-5-carboxylic acid 3-trifluoromethoxy-benzylamide;
2-(1H-indazol-3-yl)-1H-benzoimidazole-5-carboxylic acid (3-isopropoxy-propyl)-amide;
2-(1H-indazol-3-yl)-1H-benzoimidazole-5-carboxylic acid (1-methyl-1H-pyrazol-4-ylmethyl)-amide;
2-(1H-indazol-3-yl)-1H-benzoimidazole-5-carboxylic acid 4-isopropyl-benzylamide;
2-(1H-indazol-3-yl)-1H-benzoimidazole-5-carboxylic acid (2,5-dimethyl-furan-3-ylmethyl)-amide;
2-(1H-indazol-3-yl)-1H-benzoimidazole-5-carboxylic acid (benzo[b]thiophen-2-ylmethyl)-amide;
2-(1H-indazol-3-yl)-1H-benzoimidazole-5-carboxylic acid [3-(3-acetylamino-phenoxy)-propyl]-amide;
2-(1H-indazol-3-yl)-1H-benzoimidazole-5-carboxylic acid (6-chloro-pyridin-3-ylmethyl)-amide;
2-(1H-indazol-3-yl)-1H-benzoimidazole-5-carboxylic acid ([2,2']bithiophenyl-5-ylmethyl)-amide;
2-(1H-indazol-3-yl)-1H-benzoimidazole-5-carboxylic acid (2,3-dihydro-benzofuran-5-ylmethyl)-amide;
2-(1H-indazol-3-yl)-1H-benzoimidazole-5-carboxylic acid 4-cyano-benzylamide;
2-(1H-indazol-3-yl)-1H-benzoimidazole-5-carboxylic acid 2-methylsulfanyl-benzylamide;
2-(1H-indazol-3-yl)-1H-benzoimidazole-5-carboxylic acid (benzo[b]thiophen-3-ylmethyl)-amide;
2-(1H-indazol-3-yl)-1H-benzoimidazole-5-carboxylic acid (tetrahydro-pyran-4-ylmethyl)-amide;
2-(1H-indazol-3-yl)-1H-benzoimidazole-5-carboxylic acid (2,3-dihydro-benzo[1,4]dioxin-2-ylmethyl)-amide;
2-(1H-indazol-3-yl)-1H-benzoimidazole-5-carboxylic acid (furan-3-ylmethyl)-amide;
2-(1H-indazol-3-yl)-1H-benzoimidazole-5-carboxylic acid 2-nitro-benzylamide;
2-(1H-indazol-3-yl)-1H-benzoimidazole-5-carboxylic acid (thiophen-3-ylmethyl)-amide;
2-(1H-indazol-3-yl)-1H-benzoimidazole-5-carboxylic acid 3,5-dimethyl-benzylamide;
2-(1H-indazol-3-yl)-1H-benzoimidazole-5-carboxylic acid (1-methyl-1H-benzoimidazol-2-ylmethyl)-amide;
2-(1H-indazol-3-yl)-1H-benzoimidazole-5-carboxylic acid 3-methyl-benzylamide;
2-(1H-indazol-3-yl)-1H-benzoimidazole-5-carboxylic acid 3-chloro-benzylamide;
2-(1H-indazol-3-yl)-3H-benzoimidazole-4-carboxylic acid 4-sulfamoyl-benzylamide;
2-(1H-indazol-3-yl)-3H-benzoimidazole-4-carboxylic acid (pyridin-3-ylmethyl)-amide;
2-(1H-indazol-3-yl)-3H-benzoimidazole-4-carboxylic acid 3-methoxy-benzylamide;
2-(1H-indazol-3-yl)-3H-benzoimidazole-4-carboxylic acid 2-methylsulfanyl-benzylamide;
2-(1H-indazol-3-yl)-3H-benzoimidazole-4-carboxylic acid (furan-3-ylmethyl)-amide;
2-(1H-indazol-3-yl)-3H-benzoimidazole-4-carboxylic acid 2-nitro-benzylamide;
2-(1H-indazol-3-yl)-3H-benzoimidazole-4-carboxylic acid 3,5-dimethyl-benzylamide;
2-(1H-indazol-3-yl)-3H-benzoimidazole-4-carboxylic acid phenylamide;
3-[6-(4-fluoro-phenyl)-1H-benzoimidazol-2-yl]-2H-indazole;
3-[6-(4-methoxy-phenyl)-1H-benzoimidazol-2-yl]-2H-indazole;
3-[6-(3-chloro-4-fluoro-phenyl)-1H-benzoimidazol-2-yl]-2H-indazole;
3-(6-m-tolyl-1H-benzoimidazol-2-yl)-2H-indazole;

3-(6-o-tolyl-1H-benzoimidazol-2-yl)-2H-indazole;
3-(6-thiophen-3-yl-1H-benzoimidazol-2-yl)-2H-indazole;
3-[6-(3-chloro-phenyl)-1H-benzoimidazol-2-yl]-2H-indazole;
3-[6-(3-methoxy-phenyl)-1H-benzoimidazol-2-yl]-2H-indazole;
3-[6-(3,5-dimethyl-phenyl)-1H-benzoimidazol-2-yl]-2H-indazole;
3-(6-benzo[1,3]dioxol-5-yl-1H-benzoimidazol-2-yl)-2H-indazole;
3-(6-hex-1-enyl-1H-benzoimidazol-2-yl)-2H-indazole;
3-[6-(3,4-dimethoxy-phenyl)-1H-benzoimidazol-2-yl]-2H-indazole;
3-[2-(2H-indazol-3-yl)-3H-benzoimidazol-5-yl]-phenol;
4-[2-(2H-indazol-3-yl)-3H-benzoimidazol-5-yl]-phenol;
3-[6-(3,4,5-trimethoxy-phenyl)-1H-benzoimidazol-2-yl]-2H-indazole;
1-{5-[2-(2H-indazol-3-yl)-3H-benzoimidazol-5-yl]-thiophen-2-yl}-ethanone;
{3-[2-(2H-indazol-3-yl)-3H-benzoimidazol-5-yl]-phenyl}-methanol;
3-[6-(2,4-difluoro-phenyl)-1H-benzoimidazol-2-yl]-2H-indazole;
3-[6-(4-fluoro-2-methyl-phenyl)-1H-benzoimidazol-2-yl]-2H-indazole;
{4-[2-(2H-indazol-3-yl)-3H-benzoimidazol-5-yl]-phenyl}-methanol;
3-(6-furan-2-yl-1H-benzoimidazol-2-yl)-2H-indazole;
3-[6-(4-isopropyl-phenyl)-1H-benzoimidazol-2-yl]-2H-indazole;
2-(1H-indazol-3-yl)-1H-benzoimidazole-5-carboxylic acid (tetrahydro-pyran-4-ylmethyl)-amide;
2-(1H-indazol-3-yl)-1H-benzoimidazole-5-carboxylic acid 4-acetylamino-benzylamide;
2-(1H-indazol-3-yl)-1H-benzoimidazole-5-carboxylic acid methylamide;
2-(1H-indazol-3-yl)-1H-benzoimidazole-5-carboxylic acid isopropylamide;
[2-(1H-indazol-3-yl)-1H-benzoimidazol-5-yl]-morpholin-4-yl-methanone;
[2-(1H-indazol-3-yl)-1H-benzoimidazol-5-yl]-(4-methyl-piperazin-1-yl)-methanone;
2-(1H-indazol-3-yl)-1H-benzoimidazole-5-carboxylic acid benzyl-methyl-amide;
2-(1H-indazol-3-yl)-1H-benzoimidazole-5-carboxylic acid 3-nitro-benzylamide;
2-(1H-indazol-3-yl)-1H-benzoimidazole-5-carboxylic acid 2-fluoro-benzylamide;
2-(1H-indazol-3-yl)-1H-benzoimidazole-5-carboxylic acid 2,4-difluoro-benzylamide;
2-(1H-indazol-3-yl)-1H-benzoimidazole-5-carboxylic acid 2,6-difluoro-benzylamide;
2-(1H-indazol-3-yl)-1H-benzoimidazole-5-carboxylic acid 4-bromo-2-fluoro-benzylamide;
2-(1H-indazol-3-yl)-1H-benzoimidazole-5-carboxylic acid 4-chloro-2-fluoro-benzylamide;
2-(1H-indazol-3-yl)-1H-benzoimidazole-5-carboxylic acid 4-bromo-2-fluoro-benzylamide;
2-(1H-indazol-3-yl)-1H-benzoimidazole-5-carboxylic acid 3,4-difluoro-benzylamide;
2-(1H-indazol-3-yl)-1H-benzoimidazole-5-carboxylic acid 3,4,5-trifluoro-benzylamide;
2-(1H-indazol-3-yl)-1H-benzoimidazole-5-carboxylic acid 2,6-difluoro-3-methyl-benzylamide;
2-(1H-indazol-3-yl)-1H-benzoimidazole-5-carboxylic acid 2,4-dichloro-benzylamide;
2-(1H-indazol-3-yl)-1H-benzoimidazole-5-carboxylic acid 4-chloro-benzylamide;
2-(1H-indazol-3-yl)-1H-benzoimidazole-5-carboxylic acid 4-chloro-2-methyl-benzylamide;
2-(1H-indazol-3-yl)-1H-benzoimidazole-5-carboxylic acid 4-fluoro-benzylamide;
2-(1H-indazol-3-yl)-1H-benzoimidazole-5-carboxylic acid (2'-chloro-biphenyl-4-ylmethyl)-amide;
2-(1H-indazol-3-yl)-1H-benzoimidazole-5-carboxylic acid (6-trifluoromethyl-pyridin-3-ylmethyl)-amide;
2-(1H-indazol-3-yl)-1H-benzoimidazole-5-carboxylic acid (5-pyridin-2-yl-thiophen-2-ylmethyl)-amide;
2-(1H-indazol-3-yl)-1H-benzoimidazole-5-carboxylic acid (3-imidazol-1-yl-propyl)-amide;
4-[2-(1H-indazol-3-yl)-1H-benzoimidazole-5-carbonyl]-piperazine-1-carboxylic acid tert-butyl ester;
2-(1H-indazol-3-yl)-1H-benzoimidazole-5-carboxylic acid (2,6-difluoro-4-chloro-benzyl)amide;
2-(1H-indazol-3-yl)-1H-benzoimidazole-5-carboxylic acid (2,4-dichloro-6-fluoro-benzyl)amide;
2-(1H-indazol-3-yl)-1H-benzoimidazole-5-carboxylic acid (3-fluoro-4-chloro-benzyl)amide;
2-(1H-indazol-3-yl)-1H-benzoimidazole-5-carboxylic acid (2-fluoro-4-chloro-6-methyl-benzyl)amide;
2-(1H-indazol-3-yl)-1H-benzoimidazole-5-carboxylic acid (6-methoxy-pyridin-3-ylmethyl)-amide;
2-[5-(benzyloxy)-2H-pyrazol-3-yl]-1H-benzoimidazole;
2-[5-(3-phenyl-allyloxy)-2H-pyrazol-3-yl]-1H-benzoimidazole;
2-[5-(3,7-dimethyl-octa-2,6-dienyloxy)-2H-pyrazol-3-yl]-1H-benzoimidazole;
2-[5-(3-bromo-benzyloxy)-2H-pyrazol-3-yl]-1H-benzoimidazole;
2-[5-(3,4-dichloro-benzyloxy)-2H-pyrazol-3-yl]-1H-benzoimidazole;
2-[5-(2-benzenesulfonylmethyl-benzyloxy)-2H-pyrazol-3-yl]-1H-benzoimidazole;
2-[5-(biphenyl-4-ylmethoxy)-2H-pyrazol-3-yl]-1H-benzoimidazole;
2-[5-(3-methoxy-benzyloxy)-2H-pyrazol-3-yl]-1H-benzoimidazole;
isonicotinic acid 5-(1H-benzoimidazol-2-yl)-1H-pyrazol-3-yl ester;
benzoic acid 5-(1H-benzoimidazol-2-yl)-1H-pyrazol-3-yl ester;
3-phenyl-propionic acid 5-(1H-benzoimidazol-2-yl)-1H-pyrazol-3-yl ester,
methyl 2-(1H-indazol-3-yl)-3H-benzimidazole-5-carboxylate;
5-methoxy-2-(1H-indazol-3-yl)-1H-benzimidazole;
5-bromo 2-(1H-indazol-3-yl)-3H-benzimidazole, (compound denoted as A32-B63);
and the corresponding N-oxides, and their prodrugs; and pharmaceutically acceptable salts and solvates (e.g. hydrates) of such compounds and their N-oxides and prodrugs.

Particularly preferred compounds of formula (Ixb) of the invention for the inhibition of KDR are:—
2-(1H-indazol-3-yl)-1H-benzimidazole-5-carboxylic acid N-cyclohexylmethyl)amide;
2-(1H-indazol-3-yl)-1H-benzimidazole-5-carboxylic acid N-(2-furfuryl)amide;
2-(1H-indazol-3-yl)-1H-benzimidazole-5-carboxylic acid 2,4-dichloro-benzylamide;
2-(1H-indazol-3-yl)-1H-benzimidazole-5-carboxylic acid 4-bromo-benzylamide;

2-(1H-indazol-3-yl)-1H-benzoimidazole-5-carboxylic acid 4-methanesulfonyl-benzylamide;
2-(1H-indazol-3-yl)-1H-benzoimidazole-5-carboxylic acid 4-nitro-benzylamide;
2-(1H-indazol-3-yl)-1H-benzoimidazole-5-carboxylic acid 2-methyl-benzylamide;
2-(1H-indazol-3-yl)-1H-benzoimidazole-5-carboxylic acid (6-chloro-pyridin-3-ylmethyl)-amide;
2-(1H-indazol-3-yl)-1H-benzoimidazole-5-carboxylic acid (2,3-dihydro-benzofuran-5-ylmethyl)-amide;
2-(1H-Indazol-3-yl)-1H-benzoimidazole-5-carboxylic acid 2-methylsulfanyl-benzylamide;
2-(1H-indazol-3-yl)-1H-benzoimidazole-5-carboxylic acid (benzo[b]thiophen-3-ylmethyl)-amide; 2-(1H-indazol-3-yl)-1H-benzoimidazole-5-carboxylic acid 3-methyl-benzylamide;
2-(1H-indazol-3-yl)-1H-benzoimidazole-5-carboxylic acid 3-chloro-benzylamide;
2-(1H-indazol-3-yl)-3H-benzoimidazole-4-carboxylic acid 2-methylsulfanyl-benzylamide;
2-(1H-indazol-3-yl)-1H-benzoimidazole-5-carboxylic acid 4-bromo-2-fluoro-benzylamide;
2-(1H-indazol-3-yl)-1H-benzoimidazole-5-carboxylic acid 2,4-dichloro-benzylamide;
2-(1H-indazol-3-yl)-1H-benzoimidazole-5-carboxylic acid 4-chloro-benzylamide;
2-(1H-indazol-3-yl)-1H-benzoimidazole-5-carboxylic acid 4-chloro-2-methyl-benzylamide;
2-(1H-indazol-3-yl)-1H-benzoimidazole-5-carboxylic acid (2,6-difluoro-4-chloro-benzyl)amide;
2-(1H-indazol-3-yl)-1H-benzoimidazole-5-carboxylic acid (2,4-dichloro-6-fluoro-benzyl)amide;
2-(1H-indazol-3-yl)-1H-benzoimidazole-5-carboxylic acid (3-fluoro-4-chloro-benzyl)amide;
2-(1H-indazol-3-yl)-1H-benzoimidazole-5-carboxylic acid (2-fluoro-4-chloro-6-methyl-benzyl)amide;
2-(1H-indazol-3-yl)-1H-benzoimidazole-5-carboxylic acid (6-methoxy-pyridin-3-ylmethyl)-amide;
and the corresponding N-oxides, and their prodrugs; and pharmaceutically acceptable salts and solvates (e.g. hydrates) of such compounds and their N-oxides and prodrugs.

Particular compounds of formula (Ix) of the invention for the inhibition of ITK are:—

2-(1H-Indazol-3-yl)-1H-benzoimidazole-5-carboxylic acid (2-piperidin-1-yl-ethyl)-amide, Example 246(ab);
2-(1H-Indazol-3-yl)-1H-benzoimidazole-5-carboxylic acid (pyridin-2-ylmethyl)-amide, Example 246(ac);
2-(1H-Indazol-3-yl)-1H-benzoimidazole-5-carboxylic acid [3-(4-methyl-piperazin-1-yl)-propyl]-amide, Example 246(ad);
N-[2-(1H-Indazol-3-yl)-1H-benzoimidazol-5-yl]-isobutyramide, Example 246(ae)
N-[3-(5,6-Dimethyl-1H-benzoimidazol-2-yl)-1H-pyrazol-4-yl]-2-piperidin-1-yl-acetamide, Example 253(c)
and the corresponding N-oxides, and their prodrugs; and pharmaceutically acceptable salts and solvates (e.g. hydrates) of such compounds and their N-oxides and prodrugs.

The compounds of formula (Ix) of the invention exhibit useful pharmacological activity and accordingly are incorporated into pharmaceutical compositions and used in the treatment of patients suffering from certain medical disorders. The present invention thus provides, according to a further aspect, compounds of formula (Ix) of the invention and compositions containing compounds of formula (Ix) of the invention for use in therapy.

Compounds of formula (Ix) within the scope of the present invention block kinase catalytic activity according to tests described in the literature and in vitro procedures described hereinafter, and which tests results are believed to correlate to pharmacological activity in humans and other mammals. Thus, in a further embodiment, the present invention provides compounds of formula (Ix) of the invention and compositions containing compounds of formula (Ix) of the invention for use in the treatment of a patient suffering from, or subject to, conditions which can be ameliorated by the administration of protein kinase inhibitors (e.g. Syk, KDR, tie2 or ITK). For example, compounds of formula (Ix) of the present invention are useful in the treatment of inflammatory diseases, for example asthma: atopic dermatitis, inflammatory dermatoses (e.g. psoriasis, dematitis herpetiformis, eczema, necrotizing and cutaneous vasculitis, bullous disease, acute and chronic urticaria,); allergic rhinitis and allergic conjunctivitis; joint inflammation, including arthritis, rheumatoid arthritis and other arthritic conditions such as rheumatoid spondylitis, gouty arthritis, traumatic arthritis, rubella arthritis, psoriatic arthritis and osteoarthritis. The compounds of formula (Ix) are also useful in the treatment of Chronic Obstructive Pulmonary Disease (COPD), adult respiratory distress syndrome, silicosis, pulmonary sarcoidosis, acute synovitis, autoimmune diabetes, autoimmune encephalomyelitis, collitis, atherosclerosis, peripheral vascular disease, cardiovascular disease, cutaneous and systemic anaphylaxis, endotoxemia, sepsis, septic shock, endotoxic shock, gram negative sepsis, diabetes, multiple sclerosis, restenosis, myocarditis, B cell lymphomas, systemic lupus erythematosus, viral infections, bacterial infections, parasitic infections, graft v host disease and other transplant associated rejection events, reperfusion injury, Crohn's disease and ulcerative colitis, cancers and tumours (such as colorectal, prostate, breast, thyroid, colon and lung cancers), atherosclerosis, degenerative muscle diseases, obesity, conjestive heart failure, Parkinson's, depression, schizophrenia, stroke, head trauma, spinal cord injury, Alzheimer's, neuropathic pain syndrome, amyotrophic lateral sclerosis, cachexia, osteoporosis, fibrotic diseases of the viscera, and inflammatory bowel disease.

The products of the present patent application as SYK inhibitors may be used for the treatment of diseases chosen from the following: asthma, allergic rhinitis, atopic dermatitis, allergic conjunctivitis, chronic obstructive pulmonary disease, adult respiratory distress syndrome, silicosis, pulmonary sarcoidosis, rheumatoid arthritis, osteoarthritis, rheumatoid spondylitis, gouty arthritis, traumatic arthritis, rubella arthritis, psoriatic arthritis, acute and chronic urticaria, cutaneous and systemic anaphylaxis, endotoxemia, sepsis, septic shock, endotoxic shock, gram negative sepsis, diabetes, multiple sclerosis, systemic lupus erythromatosis, viral infections, bacterial infections, parasitic infections, graft vs. host disease, organ transplant rejection, reperfusion injury, Crohn's disease and ulcerative colitis.

The products of the present patent application as KDR inhibitors may be used especially for the treatment or prevention of diseases chosen from the following group: cancers, especially breast, colon, lung and prostate cancer, atherosclerosis, degenerative muscle diseases, obesity, conjestive heart failure, Parkinson's, depression, schizophrenia, stroke, head trauma, spinal cord injury, Alzheimer's, neuropathic pain syndrome, amyotrophic lateral sclerosis, cachexia, osteoporosis and fibrotic diseases of the viscera.

A special embodiment of the therapeutic methods of the present invention is the treating of asthma.

Another special embodiment of the therapeutic methods of the present invention is the treating of psoriasis.

Another special embodiment of the therapeutic methods of the present invention is the treating of joint inflammation.

Another special embodiment of the therapeutic methods of the present invention is the treating of inflammatory bowel disease.

Another special embodiment of the therapeutic methods of the present invention is the treating of cancers and tumours.

According to a further feature of the invention there is provided a method for the treatment of a human or animal patient suffering from, or subject to, conditions which can be ameliorated by the administration of a protein kinase inhibitor (e.g. Syk, KDR, tie2 or ITK) for example conditions as hereinbefore described, which comprises the administration to the patient of an effective amount of compound of the invention or a composition containing a compound of the invention. "Effective amount" is meant to describe an amount of compound of the present invention effective in inhibiting the catalytic activity a protein kinase, such as. Syk, KDR, tie2 or ITK, and thus producing the desired therapeutic effect.

References herein to treatment should be understood to include prophylactic therapy as well as treatment of established conditions.

The present invention also includes within its scope pharmaceutical compositions comprising at least one of the compounds of formula (Ix) of the invention, as defined above, or a pharmaceutically acceptable salt or a prodrug, in association, where appropriate, with a pharmaceutically acceptable carrier or excipient.

Pharmaceutical compositions of the present invention for the treatment of KDR or tie2 associated disease states can also, where appropriate, contain active principles of other antimitotic medicinal products such as, in particular, those based on taxol, cis-platin, DNA-intercalating agents and the like.

Compounds of formula (Ix) of the invention may be administered by any suitable means. In practice compounds of formula (Ix) of the present invention may generally be administered parenterally, locally by topical application to the skin and mucous membranes, rectally, orally, by inhalation, or by intravenous or intramuscular injection, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of formula (Ix) of the invention may be used. Compounds of formula (Ix) of the invention may also be incorporated in a gel or matrix base for application in a patch, which would allow a controlled release of compound through the transdermal barrier.

For administration by inhalation compounds of formula (Ix) of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds of formula (Ix) according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of formula (Ix) of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (Ix) wherein W, X, Y, Z and $R^1$ are as hereinbefore defined for compounds of formula (Ix) and $A_5$ is H, may be prepared by reaction of compounds of formula (IIx):—

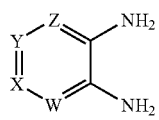
(IIx)

in which W, X, Y and Z are as hereinbefore defined for compounds of formula (Ix), with acids of formula (IIIx):—

$R^1$—$CO_2H$ (IIIx)

in which $R^1$ is as hereinbefore defined for compounds of formula (Ix), at a temperature at about 160° C. Alternatively the reaction may (i) be carried in the presence of hydrochloric acid at about reflux temperature, or polyphosphoric acid at a temperature at about 160° C. or (ii) be carried out in a microwave oven.

Compounds of formula (Ix) wherein W, X, Y, Z and $R^1$ are as hereinbefore defined and $A_5$ is H, may be prepared by reaction of compounds of formula (IIx) in which W, X, Y and Z are as hereinbefore defined for compounds of formula (Ix), with aldehydes of formula (IVx):—

$R^1CHO$ (IVx)

in which $R^1$ is as hereinbefore defined for compounds of formula (Ix), in the presence of in inert solvent, such as dimethylformamide or nitrobenzene, and at a temperature up to about 145° C. Alternatively the reaction may (i) be carried in the presence of sodium bisulfite at a temperature at about reflux temperature or (ii) be carried out in a microwave oven at a temperature up to about 200° C.

Compounds of formula (Ix) wherein W, X, Y, Z and $R^1$ are as hereinbefore defined for compounds of formula (Ix) and $A_5$ is H, may be prepared by cyclisation of compounds of formula (Vx):—

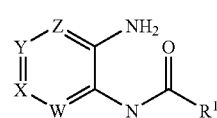
(Vx)

wherein W, X, Y, Z and $R^1$ are as hereinbefore defined for compounds of formula (Ix). The cyclisation may be carried out by heating in the presence of an acid catalyst, such as acetic acid, and at a temperature up to about 120° C.

Compounds of formula (Ixa) wherein W, X, Y and Z are as hereinbefore defined for compounds of formula (Ix) and $R^1$ is

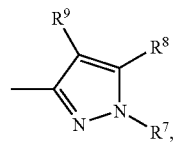

in which $R^9$ is as hereinbefore defined for compounds of formula (Ix), $R^7$ is hydrogen and $R^8$ is $SR^4$, i.e. compounds of formula (Ixaa), may be prepared as shown in scheme 1.

Scheme 1

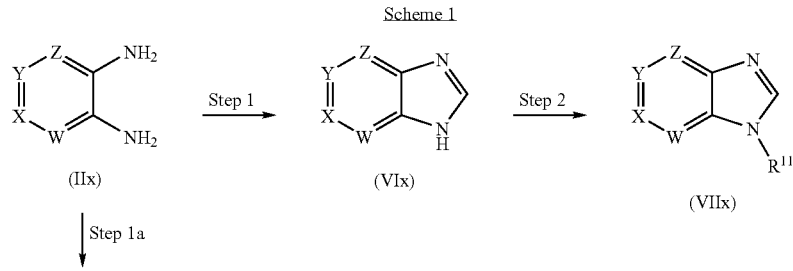

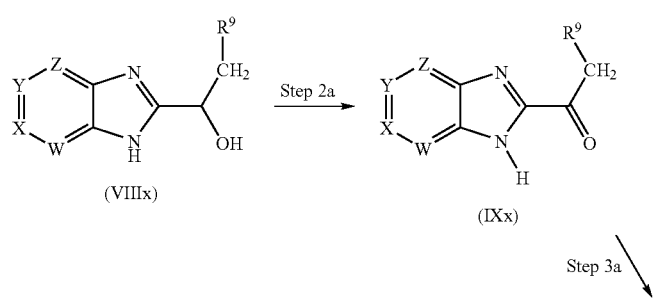

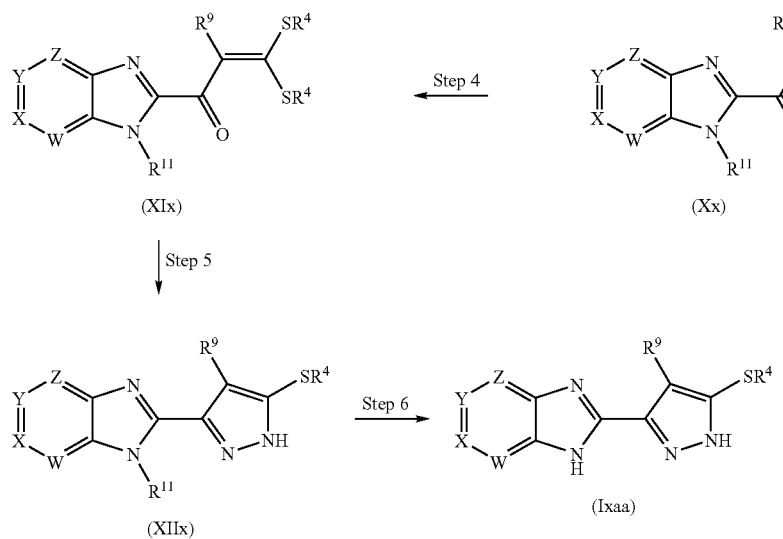

For example diamines of formula (IIx), wherein W, X, Y and Z are as hereinbefore defined for compounds of formula (Ix), may be treated, in Step 1, with formic acid in the presence of hydrochloric acid at a temperature at about 50° C. The imino group of the resulting compounds of formula (VIx) wherein W, X, Y and Z are as hereinbefore defined for compounds of formula (Ix), may then be protected, in Step 2, with a suitable protecting group, for example when this is a 2-(trimethylsilanyl)ethoxymethyl group the protection is conveniently carried out by (i) reaction with sodium hydride in dimethylformamide then (ii) reaction with 2-(trimethylsilanyl)ethoxymethyl chloride. The resulting compounds of formula (VIIx), wherein W, X, Y and Z are as hereinbefore defined for compounds of formula (Ix) and $R^{11}$ is a suitable protecting group, such as a 2-(trimethylsilanyl)ethoxymethyl group, may then be treated, in Step 3, with (i) lithium diisopropylamide, in an inert solvent, such as tetrahydrofuran, and at a temperature at about −78° C., then (ii) acetamides of formula $R^9$—C(=O)—N(CH$_3$)$_2$ [in which $R^9$ is as hereinbefore defined for compounds of formula (Ix)]. The resulting compounds of formula (Xx), wherein W, X, Y, Z, $R^9$ and $R^{11}$ are as hereinbefore defined for compounds of formula (Ix), [alternatively prepared by (i) reaction of diamines of formula (IIx) with β-hydroxy-acids of formula $R^9CH_2CH(OH)CO_2H$ [in which $R^9$ is as hereinbefore defined for compounds of formula (Ix)], in Step 1a, at a temperature at about 70° C., (ii) oxidation, in Step 2a, of the resulting compounds of formula (VIIIx) with manganese dioxide in an inert solvent, such as chloroform, and at a temperature at about 60° C. and (iii) protection of the imino group, in Step 3a, as described in Step 2 above] may then be treated, in Step 4, with (i) sodium tertiary butoxide, in an inert solvent, such as benzene or tetrahydrofuran, at −5° C., then (ii) carbon disulfide and then (iii) compounds of formula $R^4$—$X^1$ [in which $R^4$ is as hereinbefore defined for compounds of formula (Ix)] and $X^1$ is halo. The resulting compounds of formula (XIx), wherein W, X, Y, Z, $R^4$, $R^9$ and $R^{11}$ are as hereinbefore defined for compounds of formula (Ix), may then be treated, in Step 5, with hydrazine, in an inert solvent, such as ethanol, and at a temperature from about room temperature to about reflux temperature. The resulting compounds of formula (XIIx), wherein W, X, Y, Z, $R^4$, $R^9$ and $R^{11}$ are as hereinbefore defined for compounds of formula (Ix), may then be deprotected {for example when $R^{11}$ is a 2-(trimethylsilanyl)ethoxymethyl group by treatment with hydrochloric acid in an inert solvent, such as ethanol, and at a temperature from about room temperature to about reflux temperature}, in Step 6, to liberate the pyrazoles of general formula (Ixaa), wherein W, X, Y, Z, $R^4$ and $R^9$ are as hereinbefore defined for compounds of formula (Ix). Compounds of formula (XIx) in which $R^{11}$ is a tetrahydropyran-2-yl protecting group may be deprotected by treatment with an acid, such as p-toluenesulfonic acid, in water at reflux temperature and subsequently treated with hydrazine, in an inert solvent, such as ethanol, and at a temperature from about room temperature to about reflux temperature to give pyrazoles of general formula (Ixaa), wherein W, X, Y, Z, $R^4$ and $R^9$ are as hereinbefore defined for compounds of formula (Ix).

Compounds of formula (Ix) wherein W, X, Y and Z are as hereinbefore defined for compounds of formula (Ix) and $A_5$ is H, and $R^1$ is

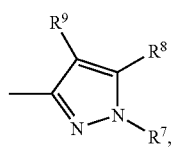

in which $R^9$ is as hereinbefore defined for compounds of formula (Ix), $R^7$ is hydrogen and $R^8$ is $OR^4$, i.e. compounds of formula (Ixab), may be prepared as shown in scheme 2.

Scheme 2

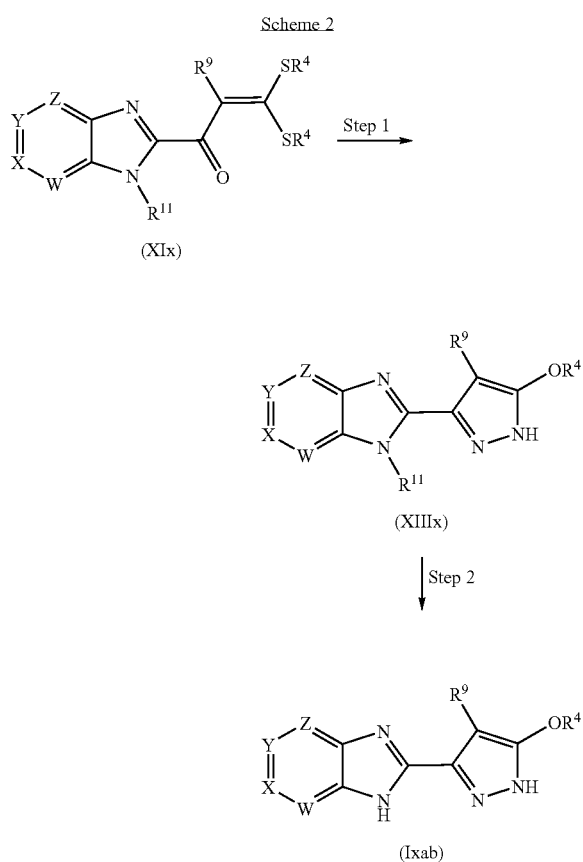

For example compounds of formula (XIx), wherein W, X, Y, Z, $R^9$, $R^{11}$ are as hereinbefore defined for compounds of formula (Ix), and $R^4$ is lower alkyl, may be treated, in Step 1, with the sodium salt of an alcohol of formula $R^4$—OH (in which $R^4$ is lower alkyl), such as sodium ethoxide, followed by treatment with hydrazine as described hereinabove for scheme 1. The resulting compounds of formula (XIIIx), wherein W, X, Y, Z, $R^4$, $R^9$ and $R^{11}$ are as hereinbefore defined for compounds of formula (Ix), may then be deprotected [for example when $R^{11}$ is a 2-(trimethylsilanyl)ethoxymethyl group by treatment with trifluoroacetic acid at about 50° C.], in Step 2, to liberate the pyrazoles of general formula (Ixab).

Compounds of formula (Ix) wherein W, X, Y and Z are as hereinbefore defined for compounds of formula (Ix) and $A_5$ is H, and $R^1$ is

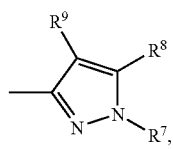

in which $R^9$ is as hereinbefore defined for compounds of formula (Ix), $R^7$ is hydrogen and $R^8$ is —$NY^1Y^2$, i.e. compounds of formula (Ixac), may be prepared as shown in scheme 3.

Scheme 3

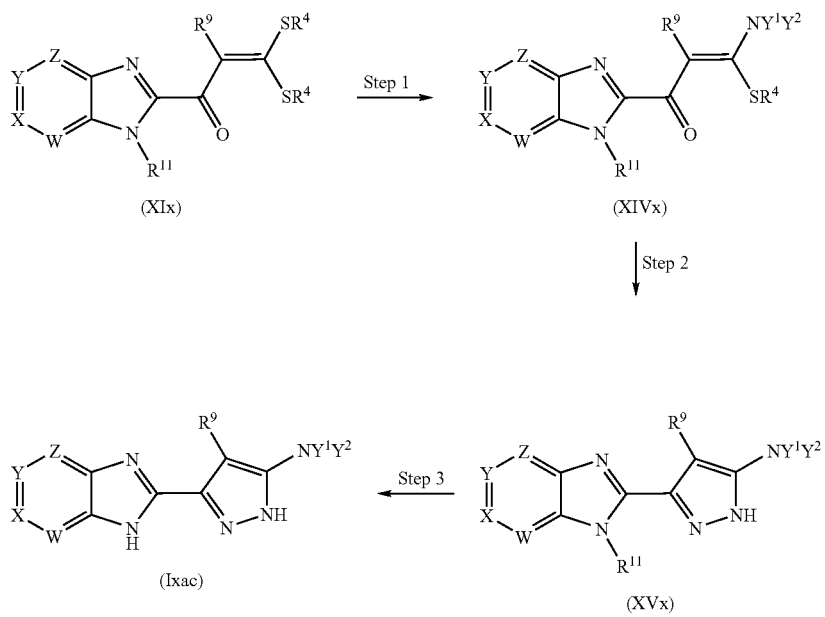

For example compounds of formula (XIx), wherein W, X, Y, Z, $R^9$ and $R^{11}$ are as hereinbefore defined for compounds of formula (Ix), and $R^4$ is lower alkyl, may be treated, in Step 3, with an amine of formula $HNY^1Y^2$ [in which $Y^1$ and $Y^2$ are as hereinbefore defined for compounds of formula (Ix)], e.g. morpholine. The resulting compounds of formula (XIVx), wherein W, X, Y. Z. $R^9$, $R^{11}$, $Y^1$ and $Y^2$ are as hereinbefore defined for compounds of formula (Ix), and $R^4$ is lower allyl, may then be treated, in step 2, with hydrazine as described hereinabove for scheme 1. The resulting compounds of formula (XVx), wherein W, X, Y, Z, $R^9$, $R^{11}$, $Y^1$ and $Y^2$ are as hereinbefore defined for compounds of formula (Ix), may then be deprotected as described hereinabove, in Step 3, to liberate the pyrazoles of general formula (Ixac).

Compounds of formula (Ix) wherein W, X, Y and Z are as hereinbefore defined for compounds of formula (Ix) and $A_5$ is H, and $R^1$ is

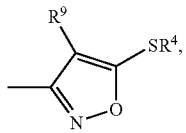

i.e. compounds of formula (Ixad), may be prepared as shown in scheme 4.

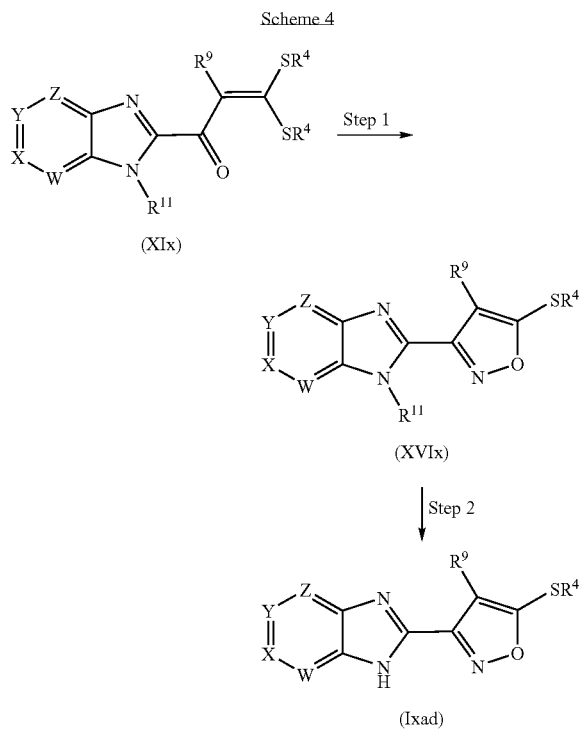

Scheme 4

For example compounds of formula (XIx), wherein W, X, Y, Z, $R^9$ and $R^{11}$ are as hereinbefore defined for compounds of formula (Ix), and $R^4$ is lower alkyl, may be treated, in Step 1, with hydroxylamine in the presence of sodium methoxide and in methanol at reflux temperature. The resulting compounds of formula (XVIx), wherein W, X, Y, Z, $R^4$, $R^9$ and $R^{11}$ are as hereinbefore defined for compounds of formula (Ix), may then be deprotected as described hereinabove, in Step 2, to liberate the isoxazoles of general formula (Ixad).

Compounds of the invention of formula (Ix) may also be prepared by interconversion of other compounds of the invention.

Thus, for example, compounds of formula (Ix) containing a carboxy group may be prepared by hydrolysis of the corresponding esters. The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (Ix) containing a carboxy group may be prepared by acid catalysed removal of the tert-butyl group of the corresponding tert-butyl esters using standard reaction conditions, for example reaction with trifluoroacetic acid at a temperature at about room temperature.

As another example compounds of formula (Ix) containing a carboxy group may be prepared by hydrogenation of the corresponding benzyl esters. The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

As another example compounds of formula (Ix) containing a carboxy group may be prepared by treatment of compounds of formula I(x) containing a cyano group with hydrochloric acid in acetic acid at a temperature at about 100° C.

As another example of the interconversion process, compounds of formula (Ix) containing a —C(═O)—$NY^1Y^2$ group may be prepared by reaction of compounds of formula (Ix) containing a carboxy group with an amine of formula $HNY^1Y^2$ to give an amide bond using standard peptide coupling procedures, for example coupling in the presence of 1-(3-dimethylaminopropyl)-3-ethylcarbodiimide, hydroxybenzotriazole and di-isopropylethylamine in an inert solvent, such as dimethylformamide and a temperature up to about 80° C. The reaction may alternatively be carried out in the presence of O-(7-azabenzotriazol-1-yl)-1,1,3,3-tetramethyluronium hexafluorophosphate and triethylamine (or diisopropylethylamine) in tetrahydrofuran (or dimethylformamide) at room temperature.

As another example of the interconversion process, compounds of formula (Ix) containing a —NH—C(═O)—$R^4$ group may be prepared by: (i) coupling compounds of formula (Ix) containing an amino group with acids of formula $R^4$—$CO_2H$ using standard coupling conditions as described above; or (ii) by reaction of compounds of formula (Ix) containing an amino group with acid chlorides of formula $R^4$—C(═)O—Cl in the presence of a tertiary base, such as di-isopropylethylamine, in an inert solvent, such a dichloromethane, and at a temperature at about room temperature. In some instances a bis-acylated derivative is obtained by reaction of compounds of formula (Ix) containing an amino group and in which $A_5$ is H, with acid chlorides of formula $R^4$—C(═)O—Cl. These bis-acylated derivatives may be converted to compounds of formula (Ix) containing a —NH—C(=O)—R⁴ group and in which A₅ is H, by treatment with potassium hydroxide in aqueous methanol at a temperature at about 60° C.

As another example of the interconversion process, compounds of formula (Ix) wherein R¹ is a pyrazolyl moiety

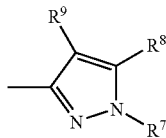

in which R⁸ and R⁹ together with the carbon atoms to which they are attached form a 5 or 6 membered heterocyclic ring containing a NY⁵ group (where Y⁵ is —C(=O)R⁴) may be prepared by reaction of compounds of formula (Ix) wherein R¹ is a pyrazolyl moiety

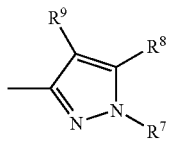

in which R⁸ and R⁹ together with the carbon atoms to which they are attached form a 5 or 6 membered heterocyclic ring containing a NY⁵ group (where Y⁵ is hydrogen) with acid chlorides of formula R⁴—C(=O)—Cl in the presence of a tertiary base, such as di-isopropylethylamine, in an inert solvent, such a dichloromethane, and at a temperature at about room temperature.

As another example of the interconversion process, compounds of formula (Ix) wherein R¹ is a pyrazolyl moiety

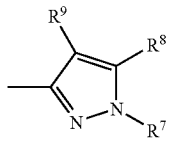

in which R⁸ and R⁹ together with the carbon atoms to which they are attached form a 5 or 6 membered heterocyclic ring containing a NY⁵ group (where Y⁵ is —C(=O)NY¹Y²) may be prepared by reaction of compounds of formula (Ix) wherein R¹ is a pyrazolyl moiety

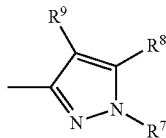

in which R⁸ and R⁹ together with the carbon atoms to which they are attached form a 5 or 6 membered heterocyclic ring containing a NY⁵ group (where Y⁵ is hydrogen) with carbamoyl chlorides of formula Y¹Y²N—C(=O)—Cl in the presence of a tertiary base, such as diisopropylethylamine, in an inert solvent, such a dichloromethane, and at a temperature at about room temperature.

As another example of the interconversion process, compounds of formula (Ix) wherein R¹ is a pyrazolyl moiety

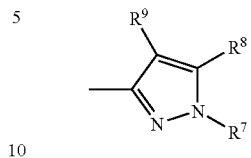

in which R⁸ and R⁹ together with the carbon atoms to which they are attached form a 5 or 6 membered heterocyclic ring containing a NY⁵ group (where Y⁵ is —C(=O)OR⁴) may be prepared by reaction of compounds of formula (Ix) wherein R¹ is a pyrazolyl moiety

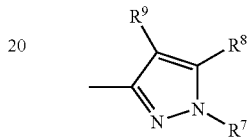

in which R⁸ and R⁹ together with the carbon atoms to which they are attached form a 5 or 6 membered heterocyclic ring containing a NY⁵ group (where Y⁵ is hydrogen) with chloroformates of formula R⁴O—C(=O)—Cl in the presence of a tertiary base, such as diisopropylethylamine, in an inert solvent, such a dichloromethane, and at a temperature at about room temperature.

As another example of the interconversion process, compounds of formula (Ix) wherein R¹ is a pyrazolyl moiety

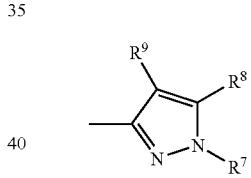

in which R⁸ and R⁹ together with the carbon atoms to which they are attached form a 5 or 6 membered heterocyclic ring containing a NY⁵ group (where Y⁵ is —SO₂R⁴) may be prepared by reaction of compounds of formula (Ix) wherein R¹ is a pyrazolyl moiety

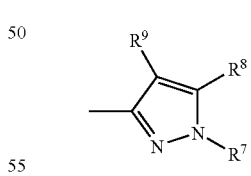

in which R⁸ and R⁹ together with the carbon atoms to which they are attached form a 5 or 6 membered heterocyclic ring containing a NY⁵ group (where Y⁵ is hydrogen) with sulfonyl chlorides of formula R⁴SO₂—Cl in the presence of a tertiary base, such as diisopropylethylamine, in an inert solvent, such a dichloromethane, and at a temperature at about room temperature.

As another example of the interconversion process, compounds of formula (Ix) containing a —NH—C(=O)—R⁴ group, in which R⁴ is alkyl substituted by NY¹Y², may be prepared by (i) coupling compounds of formula (Ix) containing an amino group with the appropriate chloroalkyl acid chloride, in the presence of a tertiary base, such as di-isopropylethylamine, in an inert solvent, such a dichloromethane, and at a temperature at about room temperature, followed by (ii) reaction with an amine of formula $HNY^1Y^2$.

As another example of the interconversion process, compounds of formula (Ix) containing a —$N(R^6)C(=O)NY^1Y^2$ group [in which $R^6$ is hydrogen, $Y^1$ is hydrogen and $Y^2$ is alkenyl, aryl, cycloalkyl, heteroaryl, or optionally substituted alkyl] may be prepared by reaction of compounds of formula (Ix) containing an amino group with isocyanates of formula $Y^2N=C=O$ [in which $Y^2$ is alkenyl, aryl, cycloalkyl, heteroaryl, or optionally substituted alkyl], in an inert solvent, such as tetrahydrofuran, and at a temperature at about room temperature.

As another example of the interconversion process, compounds of formula (Ix) containing a —$N(R^6)C(=O)NY^1Y^2$ group [in which $R^6$ is hydrogen] may be prepared by reaction of compounds of formula (Ix) containing an amino group with 1,1-carbonyldiimidazole in an inert solvent such as tetrahydrofuran and at a temperature at about 60° C. followed by reaction with an amine of formula $HNY^1Y^2$.

As another example of the interconversion process, compounds of formula (Ix) containing an amino group may be prepared by reduction of the corresponding compounds of formula (Ix) containing a nitro group. For example, the reduction may conveniently be carried out by hydrogenation in the presence of a suitable metal catalyst, e.g. platinum or palladium optionally supported on an inert carrier such as carbon, preferably in a solvent such as methanol or ethanol. The reduction may also conveniently be carried out by means of reaction with tin chloride, in an inert solvent, such as methanol or ethanol, and at a temperature at about reflux temperature. Alternatively the reaction with tin chloride may be carried out in a microwave oven at a temperature at about 140° C.

As another example of the interconversion process, compounds of formula (Ix) containing a —$CH_2OH$ group may be prepared by the reduction of corresponding compounds of formula (Ix) containing a —CHO or —$CO_2$ lower alkyl group. For example, the reduction may conveniently be carried out by means of reaction with lithium aluminium hydride, in an inert solvent, such as tetrahydrofuran, and at a temperature from about room temperature to about reflux temperature.

As another example of the interconversion process, compounds of formula (Ix) containing a —$CH(OH)R^4$ group may be prepared by treating compounds of formula (Ix) containing a —$C(=O)R^4$ group with diisobutylaluminium hydride, in an inert solvent, such as tetrahydrofuran, and at a temperature from about −78° C. to about room temperature.

As another example of the interconversion process, compounds of formula (Ix) in which $R^1$ is aryl or heteroaryl substituted by hydroxy may be prepared by reaction of the corresponding compounds of formula (Ix) in which $R^1$ is aryl or heteroaryl substituted by methoxy with a Lewis acid, such as boron tribromide, in an inert solvent, such as dichloromethane, and at a temperature from about 0° C. to about room temperature.

As another example of the interconversion process, compounds of formula (Ix) containing sulfoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulfate in a medium such as aqueous methanol, buffered to about pH 5, at temperatures between about 0° C. and room temperature. This latter method is preferred for compounds containing an acid-labile group.

As another example of the interconversion process, compounds of formula (Ix) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (Ix) containing a cyano group may be prepared by reaction of the corresponding compounds of formula (Ix) containing a —$C(=O)$—$NH_2$ group with phosphorus pentachloride in the presence of triethylamine. The reaction may conveniently be carried out in an inert solvent, such as tetrahydrofuran, and at a temperature at about reflux temperature.

As another example of the interconversion process, compounds of formula (Ix) containing a —$C(=O)NH_2$ group may be prepared by reaction of the corresponding compounds of formula (Ix) containing a cyano group with hydrogen peroxide in the presence of sodium hydroxide. The reaction may conveniently be carried out in methanol at a temperature at about room temperature. Alternatively compounds of formula (Ix) containing a —$C(=O)$—$NH_2$ group may be prepared by reaction of the corresponding compounds of formula (Ix) containing a cyano group with hydrochloric acid in acetic acid at a temperature from about 80° C. to about 100° C.

As another example of the interconversion process, compounds of formula (Ix) containing a tetrazolyl group may be prepared by reaction of the corresponding compounds of formula (Ix) containing a cyano group with azidotributyltin. The reaction may conveniently be carried out in an inert solvent, such as toluene, and at a temperature at about reflux temperature.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

Compounds of this invention can be regenerated from their acid addition salts by the application or adaptation of known methods. For example, parent compounds of the invention can be regenerated from their acid addition salts by treatment with an alkali, e.g. aqueous sodium bicarbonate solution or aqueous ammonia solution.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

The starting materials and intermediates may be prepared by the application or adaptation of known methods, for example methods as described in the Reference Examples or their obvious chemical equivalents.

Intermediates of formula (IIx), wherein W, X, Y and Z are as hereinbefore defined for compounds of formula (Ix), may be prepared by reduction of the corresponding nitro compounds of formula (1):

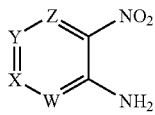

(1)

wherein W, X, Y and Z are as hereinbefore defined for compounds of formula (Ix). For example, the reduction may conveniently be carried out by means of reaction with tin chloride, in an inert solvent, such as methanol or ethanol, and at a temperature at about reflux temperature. Alternatively the reaction may be carried out in a microwave oven at a temperature at about 140° C.

Intermediates of formula (IIx), wherein W, X, Y and Z are as hereinbefore defined for compounds of formula (Ix), may also be prepared by reduction of the corresponding dinitro compounds of formula (2):

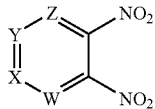

(2)

wherein W, X, Y and Z are as hereinbefore defined for compounds of formula (Ix), with tin chloride as above.

Nitro compounds of formula (1), wherein W is CH, X is C—R², Y is C—R³ and Z is CH [in which R³ is as hereinbefore defined for compounds of formula (Ix)], may be prepared from the corresponding anilines of formula (3)

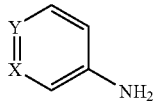

(3)

wherein X is C—R² and Y is C—R³ [in which R³ is as hereinbefore defined for compounds of formula (Ix)], by (i) reaction with acetic anhydride in the presence of triethylamine, in an inert solvent, such as dichloromethane, and at a temperature from about 0° C. to about room temperature, (ii) reaction with nitric acid in the presence of acetic acid and acetic anhydride at a temperature at about −5° C. and (iii) reaction with an alkali metal alkoxide, such as sodium methoxide, in methanol and at room temperature.

Nitro compounds of formula (1), wherein W is CH, X is C—R² (in which R² is alkyl), Y is C—R³ (in which R³ is an aryl or heteroaryl group) and Z is CH may be prepared by reaction of compounds of formula (4):

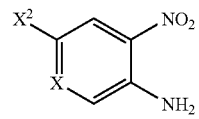

(4)

wherein X is C—R² (in which R² is alkyl) and X² is bromo or iodo, with an aryl (or heteroaryl) boronic acid in the presence of a suitable catalyst, such as tetrakis(triphenylphosphine) palladium, in an inert solvent, such as tetrahydrofuran, and at a temperature at about 85° C.

Intermediates of formula (IIIx), wherein R¹ is

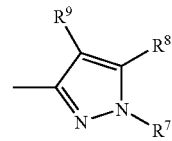

in which R⁷ is hydrogen, R⁸ is alkyl and R⁹ is hydrogen or alkyl may be prepared by reaction of compounds of formula (5):

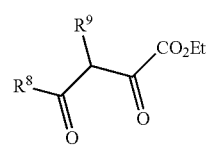

(5)

wherein R⁸ is alkyl and R⁹ is hydrogen, with hydrazine in the presence of acetic acid at reflux temperature, followed by hydrolysis.

Intermediates of formula (IIIx), wherein R¹ is

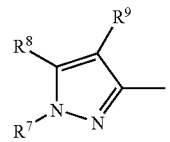

in which R⁷ is hydrogen and R⁸ and R⁹ together with the carbon atoms to which they are attached form a 5, 6 or 7 membered carbocyclic ring may be similarly prepared by reaction of compounds of formula (5) wherein R⁸ and R⁹ together with the carbon atoms to which they are attached form a 5, 6 or 7 membered carbocyclic ring, with hydrazine, followed by hydrolysis.

Intermediates of formula (IIIx), wherein $R^1$ is

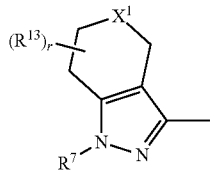

in which $R^7$ is hydrogen, $R^{13}$ is alkyl and $X^1$ is O, S, SO$_2$, or NY$^5$ (where Y$^5$ is $R^4$, —C(=O)R$^4$, —C(=O)NY$^1$Y$^2$, —C(=O)OR$^4$ or —SO$_2$R$^4$) may be similarly prepared by reaction of compounds of formula (6):

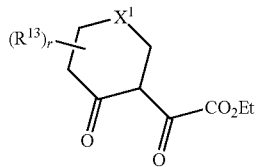

(6)

wherein $R^{13}$ is alkyl and $X^1$ is O, S, SO$_2$, or NY$^5$ (where Y$^5$ is $R^4$, —C(=O)R$^4$, —C(=O)NY$^1$Y$^2$, —C(=O)OR$^4$ or —SO$_2$R$^4$), with hydrazine, followed by hydrolysis.

Compounds of formula (5), wherein $R^8$ is alkyl and $R^9$ is hydrogen, may be prepared by reaction of compounds of formula (7):

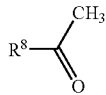

(7)

wherein $R^8$ is alkyl, with diethyl oxalate, in the presence of an alkali metal alkoxide, such as sodium ethoxide, in an inert solvent, such as ethanol, and at a temperature at about 60° C.

Compounds of formula (5), wherein $R^8$ and $R^9$ together with the carbon atoms to which they are attached form a 5, 6 or 7 membered carbocyclic ring may be similarly prepared by reaction of cyclopentanone, or cyclohexanone, with diethyl oxalate.

Compounds of formula (6), wherein $R^{13}$ is alkyl and $X^1$ is O, S, SO$_2$, or NY$^5$ (where Y$^5$ is $R^4$, —C(=O)R$^4$, —C(=O)NY$^1$Y$^2$, —C(=O)OR$^4$ or —SO$_2$R$^4$) may be similarly prepared by reaction of compounds of formula (8):

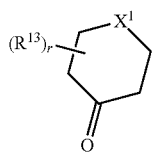

(8)

wherein $R^{13}$ is alkyl and $X^1$ is O, S, SO$_2$, or NY$^5$ (where Y$^5$ is $R^4$, —C(=O)R$^4$, —C(=O)NY$^1$Y$^2$, —C(=O)OR$^4$ or —SO$_2$R$^4$), with diethyl oxalate.

Intermediates of formula (IVx), wherein $R^1$ is as hereinbefore defined for compounds of formula (Ix), may be prepared by oxidation of compounds of formula (9):

$$R^1-CH_2OH \qquad (9)$$

wherein $R^1$ is as hereinbefore defined for compounds of formula (Ix). The oxidation may conveniently be carried out with manganese dioxide, or pyridinium chlorochromate, in an inert solvent, such as chloroform, or dichloromethane, and at a temperature at about 60° C. This procedure is particularly suitable for intermediates of formula (IVx) wherein $R^1$ is

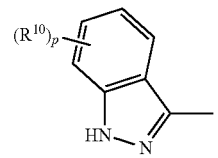

(in which $R^{10}$ and p are as hereinbefore defined).

Compounds of formula (9), wherein $R^1$ is as hereinbefore defined for compounds of formula (Ix), may be prepared by reduction of acids of formula (10):

$$R^1-CO_2H \qquad (10)$$

wherein $R^1$ is as hereinbefore defined for compounds of formula (Ix). The reduction may conveniently be carried out with lithium aluminium hydride, in an inert solvent, such as tetrahydrofuran, and at a temperature at about room temperature.

Compounds of formula (9), wherein $R^1$ is as hereinbefore defined for compounds of formula (Ix), may be prepared by reduction of alkyl esters of formula (10a):

$$R^1-CO_2alkyl \qquad (10a)$$

wherein $R^1$ is as hereinbefore defined for compounds of formula (Ix). The reduction may conveniently be carried out with lithium aluminium hydride, in an inert solvent, such as tetrahydrofuran, and at a temperature at about room temperature.

Acids of formula (10), wherein $R^1$ is

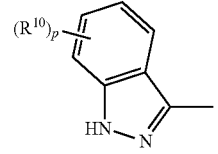

(in which $R^{10}$ and p are as hereinbefore defined), may be prepared by reaction of indole-diones of formula (11):

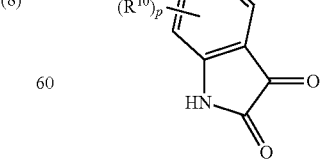

(11)

wherein $R^{10}$ and p are as hereinbefore defined, with (i) sodium hydroxide at 50° C., (ii) sodium nitrite then sulfuric acid at 5° C. and (iii) tin (II) chloride.

Indole-diones of formula (11), wherein $R^{10}$ is as hereinbefore defined and p is one, may be prepared by reaction of compounds of formula (12):

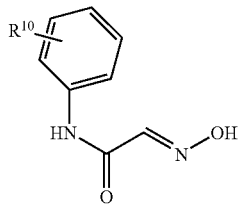

(12)

wherein $R^{10}$ is as hereinbefore defined, with polyphosphoric acid at a temperature at about 80° C.

Compounds of formula (12), wherein $R^{10}$ is as hereinbefore defined, may be prepared by reaction of anilines of formula (13):

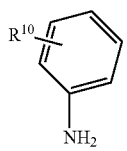

(13)

wherein $R^{10}$ is as hereinbefore defined, with chloral hydrate and hydroxylamine in the presence of hydrochloric acid at a temperature at about 80° C.

Intermediates of formula (Vx), wherein W, X, Y, Z and $R^1$ are as hereinbefore defined for compounds of formula (Ix), may be prepared by reaction of compounds of formula (1) with acid chlorides of formula $R^1$—C(=O)—Cl, optionally in the presence of a tertiary base, such as pyridine, and in an inert solvent, such as dichloromethane, at a temperature at about room temperature.

The following references are also cited, which may be used for the preparation of benzimidazoles, pyrazoles or indazoles in the context of the present invention:

G. R. Newkome, W. W. Paudler, Comtemporary Heterocyclic Chemistry, Syntheses, Reactions and Applications, J. Wiley, 1982

Preston, Heterocyclic Compounds, Benzimidazoles and congeneric tricyclic compounds, J. Wiley, 1981

Behr, Fusco, Jarboe, Heterocyclic Compounds, Pyrazoles, Pyrazolines, Pyrazolidines, indazoles and condensed rings, J. Wiley, 1967.

The following schemes, schemes 5 to 13, illustrate the synthesis of specific examples within the specification using the processes hereinbefore described with the use of appropriate protecting groups where necessary.

Scheme 5

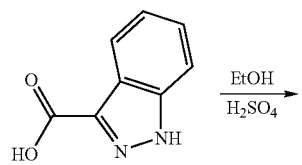

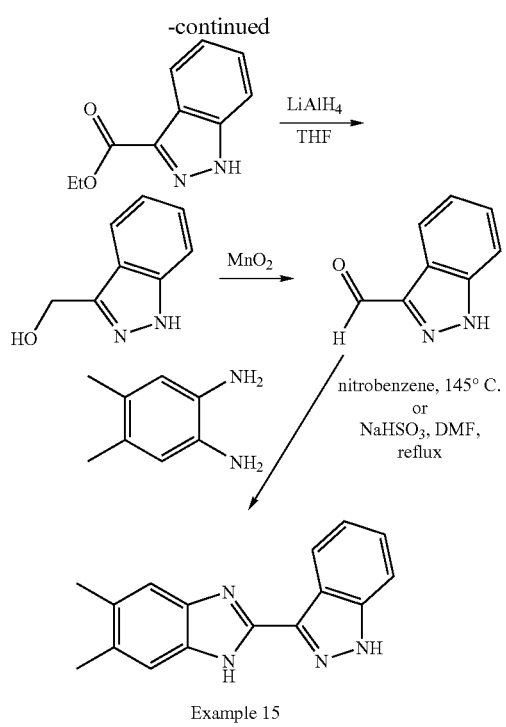

Example 15

Scheme 6

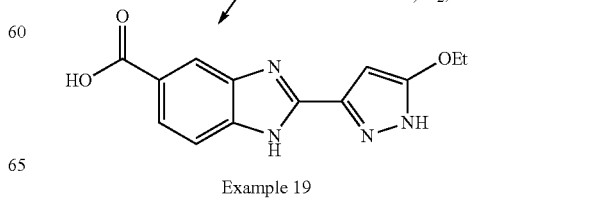

Example 19

Scheme 7
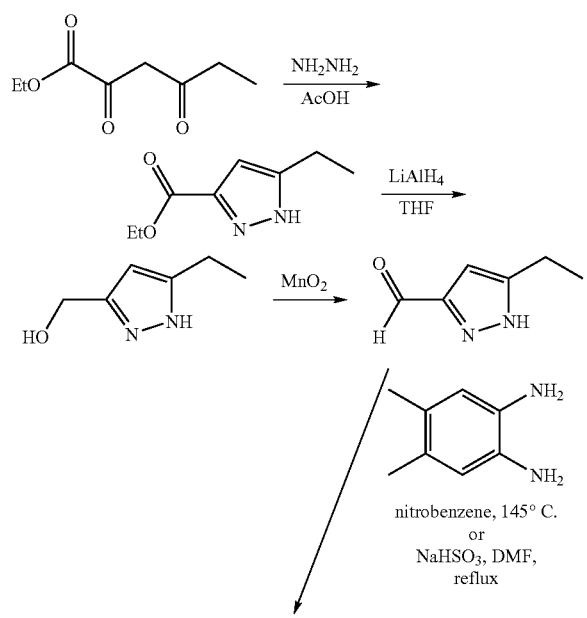
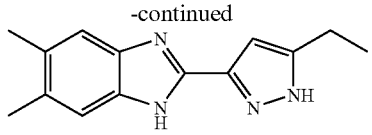
Example 23
Scheme 8
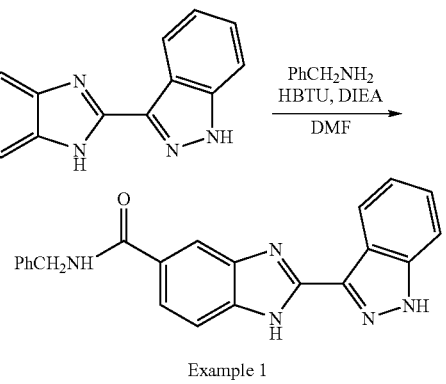
Example 1
Scheme 9
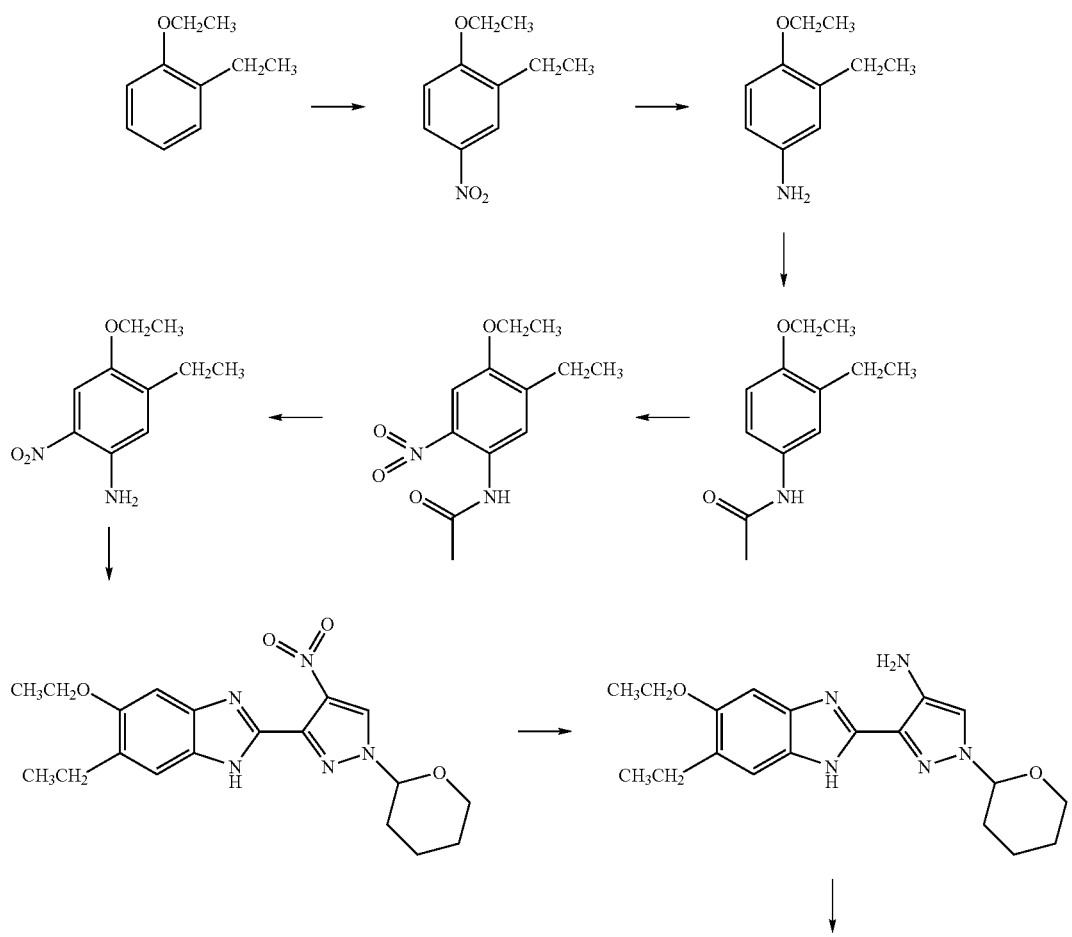

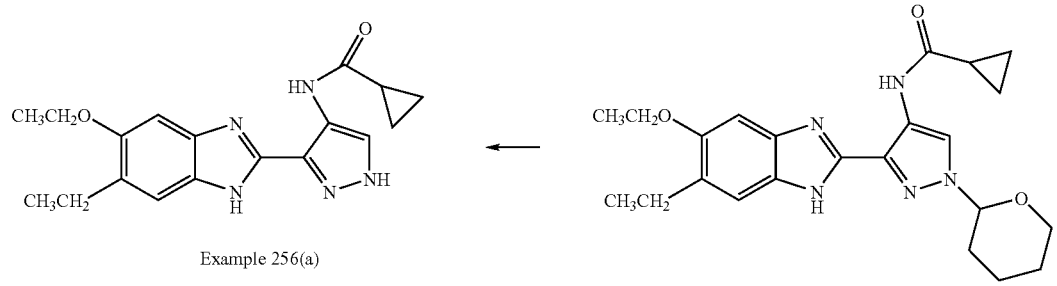
Example 256(a)
Scheme 10
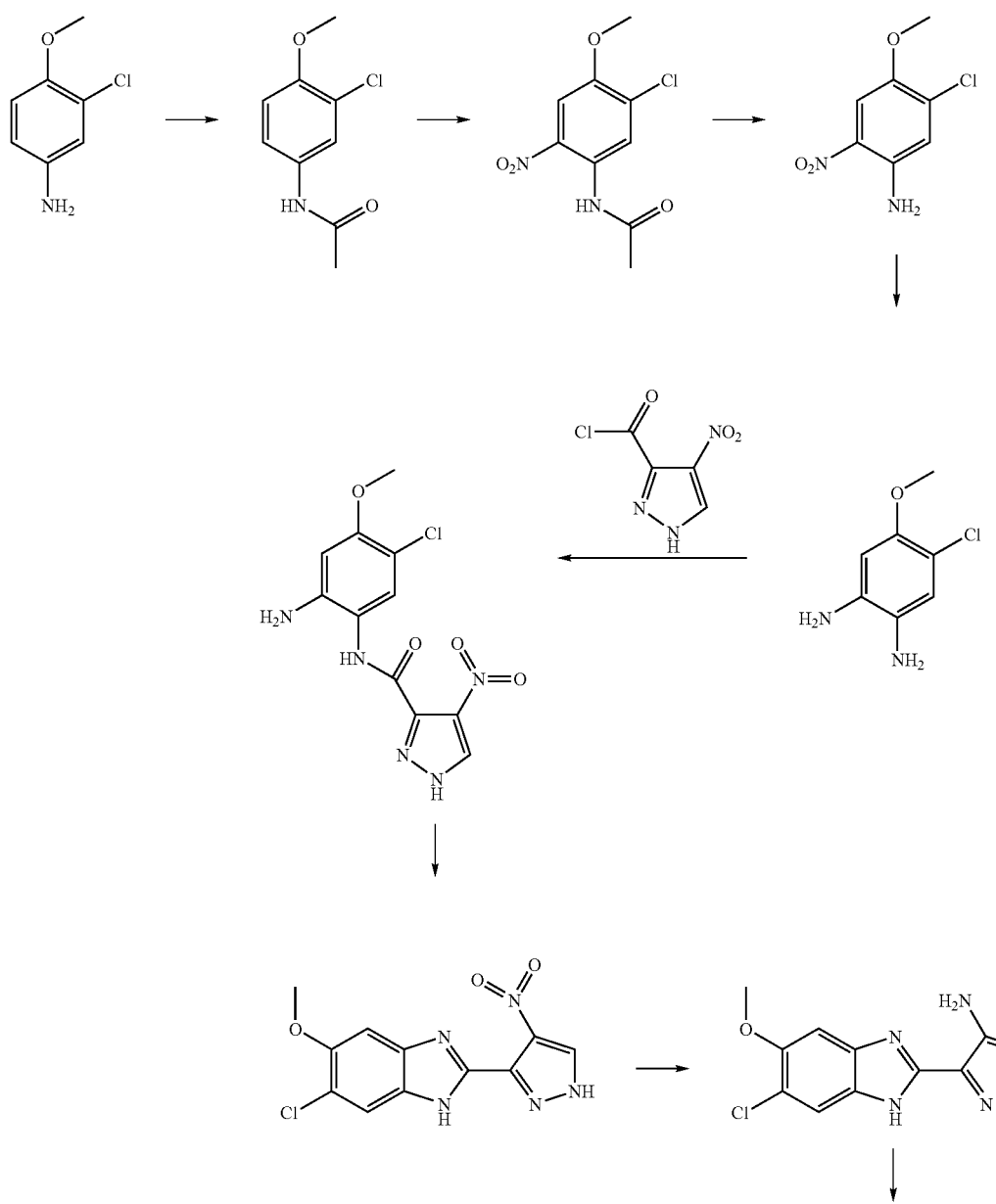

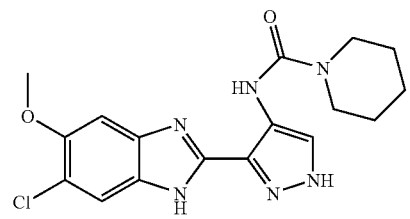
Example 248(m)
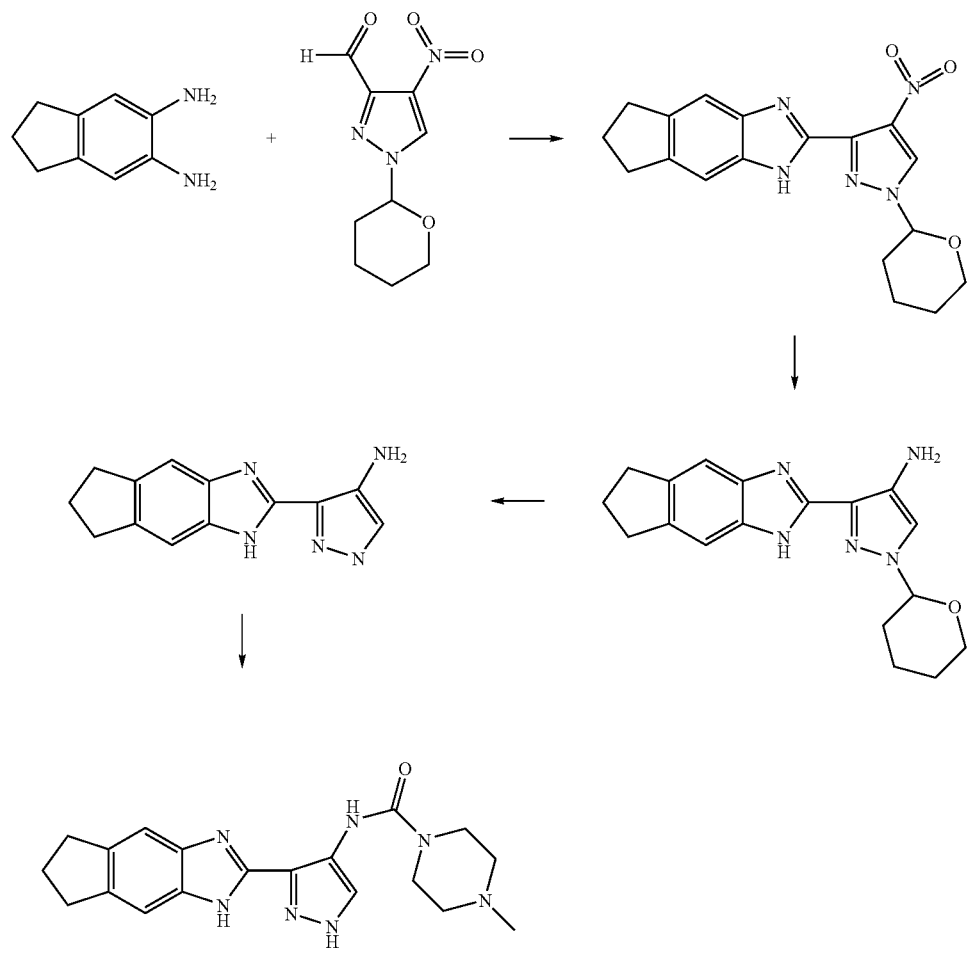
Example 256(c)
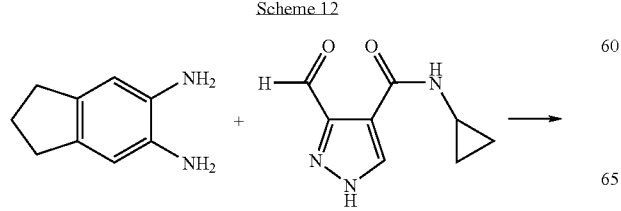
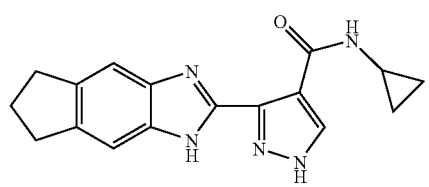

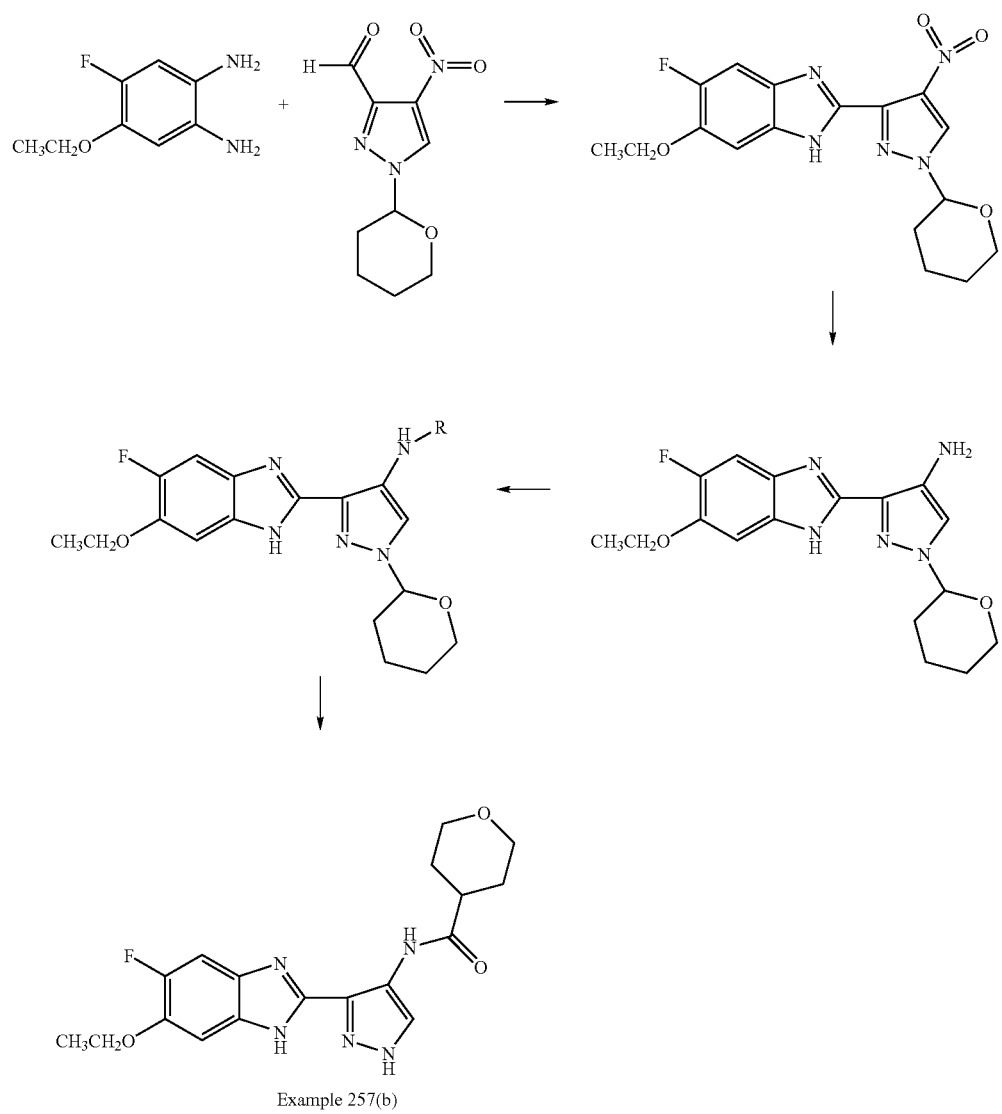
Example 257(b)
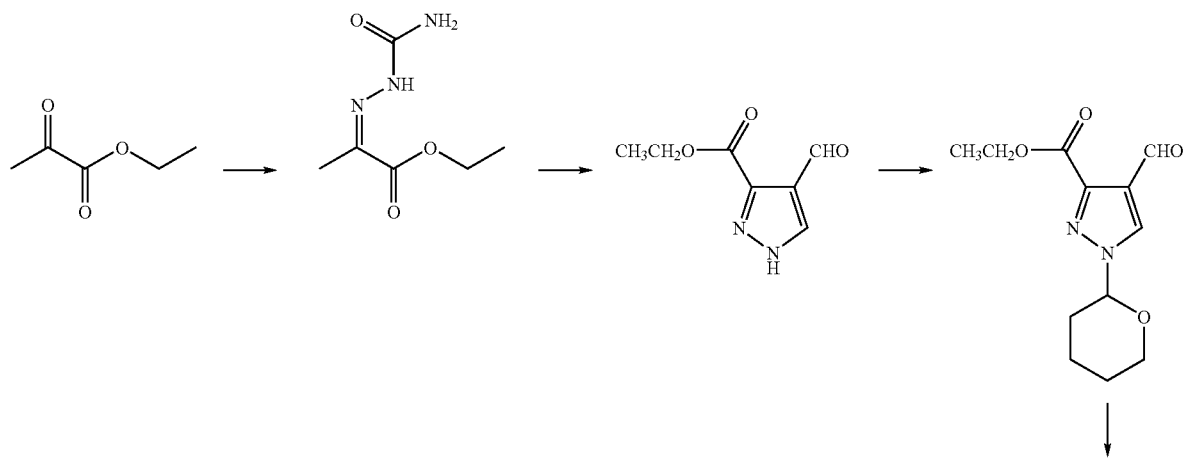

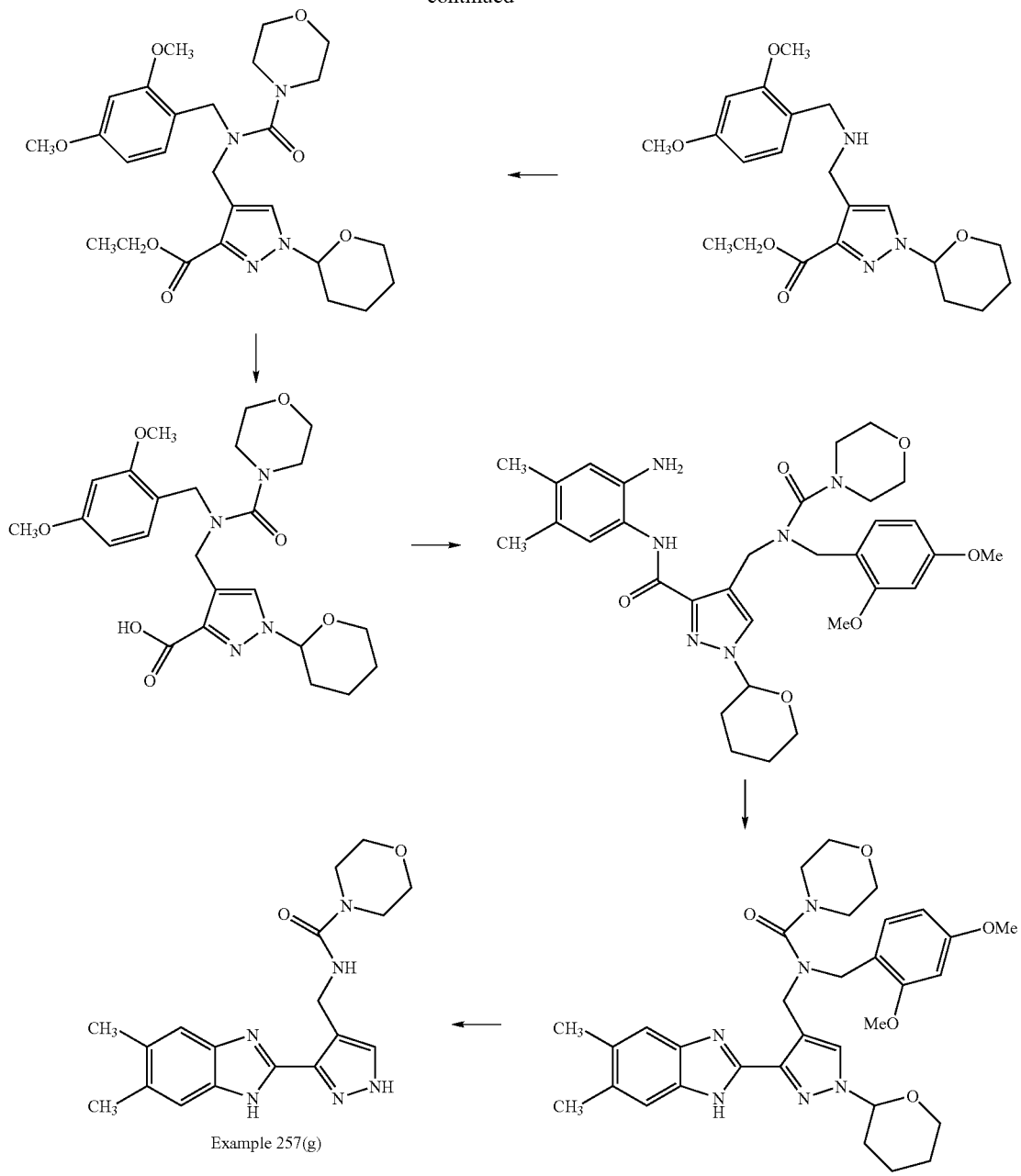

Example 257(g)

The present invention is further exemplified but not limited by the following illustrative Examples and Reference Examples.

400M Hz $^1$H nuclear magnetic resonance spectra (NMR) were recorded on a Varian Unity INOVA machine. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd=doublet of doublets; ddd=doublet of double doublets.

The thin layer chromatography (TLC) $R_F$ values were determined using Merck silica plates.

High Pressure Liquid Chromatography-Mass Spectrometry (LC-MS) conditions for determination of retention times ($R_T$) and associated mass ions were as follows:—

Method A:

Mass Spectrometer (MS)—LCT Time-of-Flight (Micromass UK Ltd) Serial No. KA014 [Ionization Mode: Electrospray (Positive Ion); Scan: Tof MS (Full Scan m/z 100-1200, sum for 0.4 s @ 50 us/scan) Centroid Mode]. Liquid Chromatograph (LC): Hewlett Packard HP1100 Series Binary Pump (Serial # US80301343)& Degasser (serial # JP73008973). Hypersil BDS C-18, 3μ (4.6 mm×50 mm), Reverse Phase Column operated under gradient elution conditions using (A) water containing 0.05% trifluoroacetic acid and (B) acetonitrile containing 0.05% trifluoroacetic acid as the mobile phase (gradient: 0.00 minutes, 100% A; linear gradient to 100% B at 2 minutes; then hold until 1.5 minutes); flow rate 1 ml/minute to column & to UV detector, flow split after UV detector such that 0.75 ml/minute to ELS detector and 0.25 ml/minute to mass spectrometer; injection volume 10 μl; Auxiliary Detectors: (i) Hewlett Packard Model BP1100 Series UV detector (serial # JP73704703) wavelength=220 nm; (ii) Sedere (France) Model SEDEX 75 Evaporative Light Scattering (ELS) detector (serial #9970002A); temperature=46° C., Nitrogen pressure=4 bar; Autosampler/Injector: Gilson Model 215 Liquid Handler with Model 819 injection valve (serial #259E8280).

Method B:
Waters Symmetry C8 3.5 μm HPLC column operated under gradient conditions with mixtures of (A) water containing 0.1% formic and (B) acetonitrile containing 0.1% formic acid as the mobile phase (gradient: 0.00 minutes, 95% A:5% B; 0.75 minutes, 95% A:5% B; 3.00 minutes 100% B; 4.00 minutes 100% B; 4.25 minutes 95% A:5% B); flow rate 1.5 ml/minute with approximately 200 μl/minute split to the Mass Spectrometer; injection volume 20 μl; in line Diode Array (210-300 nm), in line Evaporative light scattering (ELS) detection ELS—temperature 40° C., Gain 7-1.5 m/minute; Source temperature 150° C.

Method C:
Waters Symmetry C8 3.5 μm HPLC column operated under gradient conditions with mixtures of (A) water containing 10 mM ammonium acetate and (B) methanol containing 10 mM ammonium acetate as the mobile phase (gradient: 0.00 minutes, 95% A:5% B; 0.75 minutes, 95% A:5% B; 3.00 minutes 100% B; 4.00 minutes 100% B; 4.25 minutes 95% A:5% B); flow rate 1.5 mL/minute with approximately 200 μl/minute split to the Mass Spectrometer; injection volume 20 μl; in line Diode Array (210-300 nm), in line Evaporative light scattering (ELS) detection ELS—temperature 40° C., Gain 7-1.5 ml/minute; Source temperature 150° C.

Method D:
C8 Phenomenex Luna 5 μm (250×4.6 mm) HPLC column operated under gradient conditions with mixtures of (A) methanol containing 10 mM ammonium acetate and (B) water containing 10 mM ammonium acetate as the mobile phase (gradient: 0 to 2 minutes 10% A:90% B; 2 to 23 minutes ramp up to 100% A; 23 to 30 minutes 100% A; 30 to 37 minutes 10% A:90% B); flow rate 1 ml/minute.

Method E:
Mass Spectrometer (MS)—LCT Time-of-Flight (Micromass UK Ltd) Serial No. KA014 [Ionization Mode: Electrospray (Positive Ion); Scan: Tof MS (Full Scan m/z 100-1200, sum for 0.4 s @ 50 us/scan) Centroid Mode]. Liquid Chromatograph (LC): Hewlett Packard HP1100 Series Binary Pump (Serial # US80301343)& Degasser (serial # JP73008973). Synergi 2U Hydro reverse phase 20×4 mm column. solvent A 0.1% trifluoroacetic acid in water, Solvent B 0.1% trifluoroacetic acid in acetonitrile. Gradient 5% B at time 0 to 90% B at time 2 minutes to 100% B at 5 minutes; flow rate 1 ml/minute to column & to UV detector, flow split after UV detector such that 0.75 m/minute to ELS detector and 0.25 ml/minute to mass spectrometer; injection volume 10 μl; Auxiliary Detectors: (i) Hewlett Packard Model HP1100 Series UV detector (serial # JP73704703) wavelength=220 nm; (ii) Sedere (France) Model SEDEX 75 Evaporative Light Scattering (ELS) detector (serial #9970002A); temperature=46° C., Nitrogen pressure=4 bar; Autosampler/Injector: Gilson Model 215 Liquid Handler with Model 819 injection valve (serial #259E8280).

Method F:
Agilent 1100 Series HPLC with a YMC CombiScreen Pro C18 5.5 μm 4.6 mm by 33 mm reverse phase column using gradient elution with a mixture of (A) acetonitrile/ 0.1% trifluoroacetic acid and (B) water/0.1% trifluoroacetic acid (5% A:95% B to 95% A:5% B over 5.1 minutes) with a 1.2 mL/minute flow rate; Agilent 1100 Series wellplate autosampler with 2 μL injection; Agilent 1100 Series diode array detector with 215, 254 and 300 nM wavelength detection; Hewlett Packard 1100 Series mass spectrometer with electrospray and positive ionisation.

Method G:
Rainin HPXL dual pump HPLC system with a Rainin Dynamax UV-D II detector for 254 nM wavelength, C18 Metachem Monochrom 10 μM (100×4.6 mm) column using gradient elution with a mixture of (A) water with 0.1% trifluoroacetic acid and (B) acetonitrile as the mobile phase (90% A:10% B to 0% A in 12 minutes) with a flow rate of 1.0 ml/minute
C18 Phenomenex Luna 5 μM (150×4.6 mm) column using gradient elution with a mixture of (A) methanol and (B) water with 10 mM ammonium acetate as the mobile phase (0-2 minutes 10% A:90% B; 2-25 minutes ramp up to 100% A; 25-32 minutes 100% A; 32-33 minutes 10% A:90% B) with a flow rate of 1.0 ml/minute.

Method H:
Waters Symmetry C8 3.5 μM Column (50×4.6 mm) using gradient elution with a mixture of (A) water/0.1% formic acid and (B) acetonitrile/0.1% formic acid (5% B:95% A to 100% B in 3.5 min, 100% B for 1 min, 100% B to 5% B:95% A in 0.1 min, Equilibrate 5% B:95% A 0.49 minutes, Total run time 5 min) with a flow rate of 1.5 mL/minute; Detection 210-300 nM, 2 nM range interval; Column Temp 30° C.; Mass Spec Quadrupole, Electrospray, cone voltage 25V, +/−ion switching, centroid data, 140 to 850 Da, 0.6 sec scan, 0.4 sec inter scan delay.

Method J:
Waters Symmetry C8 3.5 μM Column (50×4.6 mm) using gradient elution with a mixture of (A) 0.1% formic acid in water and (B) 0.1% formic acid in acetonitrile (5% B:95% A 0.75 minutes to 100% B in 4 minutes, 100% B for 0.5 minutes, 100% B to 5% B:95% A in 1 minute, Total run time 5 minutes with a flow rate of 1.5 mL/minute; Detection 210-300 nM, 2 nM range interval; Column Temp 30° C.; Mass Spec Quadrupole, Electrospray, cone voltage 25V, +/−ion switching, centroid data, 140 to 850 Da, 0.6 sec scan, 0.4 sec inter scan delay.

Method K:
Waters Symmetry C8 3.5μ Column (50×4.6 mm) using gradient elution with a mixture of (A) 10 mM ammonium acetate in water and (B) 10 mM ammonium acetate in methanol (5% B:95% A 0.75 minutes to 100% B in 4 minutes, 100% B for 0.5 minutes, 100% B to 5% B:95% A in 1 minute, Total run time 5 min) with a flow rate of 1.5 mL/minute; Detection 210-300 nM, 2 nm range interval; Column Temp 30° C.; Mass Spec Quadrupole, Electrospray, cone voltage 25V, +/−ion switching, centroid data, 140 to 850 Da, 0.6 sec scan, 0.4 sec inter scan delay.

Method L:
Phenomenex Luna C18(2) 3 μM Column (150×4.6 mm) using gradient elution with a mixture of (A) 0.1% formic acid in water and (B) 0.1% formic acid in acetonitrile (20% B:80% A to 100% B in 10 minutes, 100% B for 2 minutes, 100% B to 20% B:80% A in 0.5 minutes, 20% B:80% A for 3.5 minutes, Total run time 16 minutes with a flow rate of 1.0 mL/minute; 210-300 nM, 220 and 254 nM extracted and ELSD; Column Temp 30° C.; Mass Spec Quadrupole, Electrospray, cone voltage 25V, +/−ion switching, centroid data, 100 to 900 Da, 0.6 sec scan, 0.4 sec inter scan delay.

Method M:
Phenomenex Luna C18(2) 3 μM Column (150×4.6 mm) using gradient elution with a mixture of (A) 0.1% formic acid in water and (B) 0.1% formic acid in acetonitrile (5% B:95% A to 60% B:40% A in 10 minutes, 60% B:40% A for 2 minutes, 60% B:40% A to 5% B:95% A in 0.5 minutes, 5% B:95% A for 3.5 minutes, Total run time 16 minutes with a flow rate of 1.0 mL/minute; 210-300 nM, 220 and 254 nM extracted and ELSD; Column Temp 30° C.; Mass Spec Quadrupole, Electrospray, cone voltage 25V, +/−ion switching, centroid data, 100 to 900 Da, 0.6 sec scan, 0.4 sec inter scan delay.

Method N:
Waters Symmetry C8 3.5 μM Column (50×4.6 mm) using gradient elution with a mixture of (A) 10 mM ammonium acetate in water and (B) 10 mM ammonium acetate in methanol (5% B:95% A to 100% B in 3.5 minutes, 100% B for 1 minute, 100% B to 5% B:95% A in 0.1 minute, Equilibrate 5% B:95% A 0.49 minutes, Total run time 5 minutes) with a flow rate of 1.5 mL/minute; Detection 210-300 nM, 2 nM range interval; Column Temp 30° C.; Mass Spec Quadrupole, Electrospray, cone voltage 25V, +/−ion switching, centroid data, 140 to 850 Da, 0.6 sec scan, 0.4 sec inter scan delay.

Method P:
Phenomenex Luna C18(2) 3 μM Column (150×4.6 mm) using gradient elution with a mixture of (A) 10 mm ammonium acetate in water and (B) 10 mm ammonium acetate in methanol (5% B:95% A to 60% B:40% A in 10 minutes, 60% B:40% A for 2 minutes, 60% B:40% A to 5% B:95% A in 0.5 minutes, 5% B:95% A for 3.5 minutes, Total run time 16 minutes with a flow rate of 1.0 mL/minute; 210-300 nM, 220 and 254 nM extracted and ELSD; Column Temp 30° C.; Mass Spec Quadrupole, Electrospray, cone voltage 25V, +/−ion switching, centroid data, 100 to 900 Da, 0.6 sec scan, 0.4 sec inter scan delay.

Method Q:
Phenomenex Luna C18(2) 3 μM Column (150×4.6 mm) using gradient elution with a mixture of (A) 10 mm ammonium acetate in water and (B) 10 mm ammonium acetate in methanol (20% B:80% A to 100% B in 10 minutes, 100% B for 2 minutes, 100% B to 20% B:80% A in 0.5 minutes, 20% B:80% A for 3.5 minutes, Total run time 16 minutes with a flow rate of 1.0 mL/minute; 210-300 nM, 220 and 254 nM extracted and ELSD; Column Temp 30° C.; Mass Spec Quadrupole, Electrospray, cone voltage 25V, +/−ion switching, centroid data, 100 to 900 Da, 0.6 sec scan, 0.4 sec inter scan delay.

Method R:
Phenomenex Luna C18(2) 5 μM Column (150×4.6 mm) using gradient elution with a mixture of (A) 10 mm ammonium acetate in water and (B) 10 mm ammonium acetate in methanol (40% B:60% A to 100% B in 10 minutes, 100% B for 2 minutes, 100% B to 40% B:60% A in 0.5 minutes, 40% B:60% A for 3.5 minutes, Total run time 16 minutes with a flow rate of 1.0 mL/minute; 210-300 nM, 220 and 254 nM extracted and ELSD; Column Temp 30° C.; Mass Spec Quadrupole, Electrospray, cone voltage 25V, +/−ion switching, centroid data, 100 to 900 Da, 0.6 sec scan, 0.4 sec inter scan delay.

High Pressure Liquid Chromatography conditions for determination of retention times ($R_T$) were as follows:—

Method A1:
YMC ODS-AQ (2×50 mm) column using gradient elution conditions with mixtures of acetonitrile, water and formic acid as the mobile phase [95/5/0.1% to 5/95/0.1%] and a flow rate of 0.4 mL/minute.

Method B1:
C18 Phenomenex Luna 5 μM (150×4.6 mm) column using gradient elution with a mixtures of (A) acetonitrile containing 0.1% formic acid and (B) water containing 0.1% formic acid as the mobile phase (gradient: 0-2 minutes 10% A:90% B; 2-25 minutes ramp up to 100% A; 25-32 minutes 100% A; 32-33 minutes 10% A:90% B) with a flow rate of 1.0 ml/minute.

Method C1:
C18 Phenomenex Luna 5 μM (150×4.6 mm) column using gradient elution with a mixture of (A) methanol and (B) water with 10 mM ammonium acetate as the mobile phase (0-2 minutes 10% A:90% B; 2-25 minutes ramp up to 100% A; 25-32 minutes 100% A; 32-33 minutes 10% A:90% B) with a flow rate of 1.0 ml/minute.

Method D1:
C18 Phenomenex Luna 3 μM (150×4.6 mm) column using gradient elution with a mixture of (A) acetonitrile containing 0.1% formic acid and (B) water containing 0.1% formic acid with a flow rate of 1.0 ml/minute Method E1:
C18 Phenomenex Luna 3 μM (150×4.6 mm) column using gradient elution with a mixture of (A) methanol and (B) water with 10 mM ammonium acetate as the mobile phase (20% A:80% B to 100% A in 10 minutes; 100% A for 2 minutes; 100% A to 20% A:80% B in 0.5 minutes; 20% A:80% B for 3.5 minutes) with a flow rate of 1.0 ml/minute.

Method F1:
C18 Phenomenex Luna 3 μM (150×4.6 mm) column using gradient elution with a mixture of acetonitrile and water with 0.1% formic acid.

Method G1:
C18 Phenomenex Luna 3 μM (150×4.6 mm) column using gradient elution with a mixture of (A) methanol and (B) water with 10 mM ammonium acetate as the mobile phase (5% A; 95% B to 60% A:40% B in 10 minutes; 60% A:40% B for 2 minutes; 60% A:40% B to 5% A:95% B in 0.5 minutes; 5% A:95% B for 3.5 minutes) with a flow rate of 1.5 ml/minute.

Gas Chromatography-Mass Spectrometry (GC-MS) conditions for determination of retention times ($R_T$) and associated mass ions were as follows:
Varian 3800 Gas Chromatograph with Chrompack 0.25 mm diameter fused silica 30 m column using a 20 minute elution with 25° C./minute gradient from 50 to 300° C. from time 1 to 11 minute; helium mobile phase with 1.2 mL/minute flow rate; 3-8 μL injection volume with 50:50 injection split ratio; Varian 2000R mass spectrometer with electron impact detection for ions 40 to 650 m/z.

General method of LC-MS purification of examples 1 to 229: a Waters Fraction Lynx system is used, and the separations were carried out on a Waters Symmetry column (C18, 5 μM, 19×50 mm, catalogue number 186000210), eluting with a linear gradient of acetonitrile containing 0.07% trifluoroacetic acid (v/v) in water containing 0.07% trifluoroacetic acid (v/v), gradient rising from 5% to 95% (v/v) of acetonitrile/trifluoroacetic acid over 8 minutes, and then 2 minutes at 95% acetonitrile/trifluoroacetic acid at a flow rate of 10 ml/minute. The products are injected in solution in dimethylsulfoxide, and collected according to the detection of their molecular weight.

Compound names were generated using an auto-nom plug in for ISIS2.3 or ISIS2.4.

EXAMPLE 1

2-(1H-indazol-3-yl)-1H-benzimidazole-5-carboxylic acid benzylamide

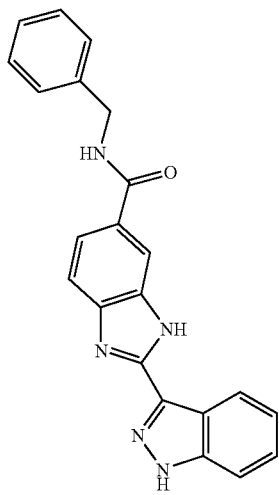

2-(1H-Indazol-3-yl)-1H-benzimidazole-5-carboxylic acid benzylamide may be prepared in the following manner.

A solution of 27.3 mg of HBTU in 0.2 ml of dimethylformamide is added, at a temperature in the region of 20° C., to a solution of 20 mg of 2-(1H-indazol-3-yl)-1H-benzimidazole-5-carboxylic acid in 0.42 ml of anhydrous dimethylformamide. After stirring at a temperature in the region of 20° C. for one hour, 15.7 ml of benzylamine are added, followed by addition of 12.4 ml of N,N-diisopropylethylamine dissolved in 0.32 ml of dimethylformamide. After 20 hours, at a temperature in the region of 20° C., the reaction medium is concentrated under reduced pressure, at a temperature in the region of 40° C. The crude residue obtained is dissolved in DMSO and purified by preparative LC-MS. The fractions containing the desired product are combined and concentrated under reduced pressure at a temperature in the region of 40° C. 20 mg of 21H-indazol-3-yl)-1H-benzimidazole-5-carboxylic acid benzylamide are thus obtained in the form of a cream-coloured powder, the characteristics of which are as follows:

LC-MS retention time=2.86 minutes 2-(1H-Indazol-3-yl)-1H-benzimidazole-5-carboxylic acid may be prepared in the following manner: 1.3 g of sodium metabisulphite and 1.04 g of 3,4-diaminobenzoic acid are added, at a temperature in the region of 20° C., to a solution of 1 g of 1H-indazole-3-carboxaldehyde in 10 ml of dimethylformamide. The reaction mixture is refluxed for one hour and then cooled to a temperature in the region of 20° C. and diluted with dichloromethane, and the mixture is filtered. The collected filtrate is concentrated under reduced pressure. The brown lacquer obtained (340 mg) is purified by preparative LC-MS. 138.8 mg of 2-(1H-indazol-3-yl)-1H-benzimidazole-5-carboxylic acid are thus obtained in the form of a beige-coloured powder.

1H-Indazole-3-carboxaldehyde may be prepared in the following manner:

A solution of 2.27 g of (1H-indazol-3-yl)methanol in 220 ml of 1,2-dimethoxyethane is added to 13.32 g of manganese dioxide. After one hour at a temperature in the region of 20° C., the reaction mixture is refluxed for 15 minutes. After cooling to a temperature in the region of 20° C., the reaction medium is filtered through a sinter funnel packed with Celite. The collected filtrate is concentrated under reduced pressure at a temperature in the region of 40° C. 2.02 g of 1H-indazole-3-carboxaldehyde are thus obtained in the form of a yellow powder, the characteristics of which are as follows:

$^1$H NMR (DMSO d6, 400 MHz): 7.40 ppm (triplet, 1H); 7.55 ppm (triplet, 1H); 7.75 ppm (doublet, 1H); 8.18 ppm (doublet, 1H); 10.23 ppm (singlet, 1H); 14.2 ppm (multiplet, 1H).

(1H-Indazol-3-yl)methanol may be prepared in the following manner:

3.2 g of lithium aluminium hydride are added portionwise to a solution of 7.08 g of methyl 3-indazolecarboxylate in 80 ml of tetrahydrofuran, cooled to a temperature in the region of 0° C. by an ice bath. After 4 hours at a temperature in the region of 0° C., 1.6 g of lithium aluminium hydride are added. After 2 hours at a temperature in the region of 0° C., the reaction medium is treated successively with 6 ml of water and then 6 ml of aqueous 1N sodium hydroxide solution and finally 18 ml of water. The reaction mixture is filtered through paper and the aqueous filtrate is then extracted with dichloromethane. The collected organic fractions are combined, dried over magnesium sulphate and concentrated under reduced pressure at a temperature in the region of 40° C. 3.15 g of (1H-indazol-3-yl)methanol are obtained in the form of an off-white powder, the characteristics of which are as follows:

$^1$H NMR (DMSO d6, 400 MHz): 4.80 ppm (doublet, 21); 5.25 ppm (triplet, 1H); 7.15 ppm (triplet, 1H); 7.35 ppm (triplet, 1H); 7.51 ppm (doublet, 1H); 7.87 ppm (doublet, 1H); 12.81 ppm (multiplet, 1H).

Methyl 3-indazolecarboxylate may be prepared in the following manner:

0.5 ml of concentrated sulphuric acid (95%) is added dropwise, at a temperature in the region of 20° C., to a solution of 9.13 g of 3-indazolecarboxylic acid in 100 ml of methanol. After refluxing for 20 hours, the reaction medium is concentrated under reduced pressure at a temperature in the region of 40° C. The aqueous residue obtained is extracted with dichloromethane. The organic phases are combined, washed with water until neutral, dried over magnesium sulphate and then concentrated under reduced pressure at a temperature in the region of 40° C. The yellow powder obtained is washed with ethyl ether. A white powder is obtained. The filtrate is concentrated under reduced pressure until a yellow powder is obtained. This yellow powder is washed again with ethyl ether until a white powder is obtained. The yellow filtrate is concentrated a third time under reduced pressure and the yellow powder collected is itself also washed with ethyl ether. All the fractions of white powder are combined. 7.08 g of methyl 3-indazolecarboxylate are thus obtained in the form of a white powder.

EXAMPLE 2

2-(1H-indazol-3-yl)-1H-benzimidazole-5-carboxylic acid N-methylamide

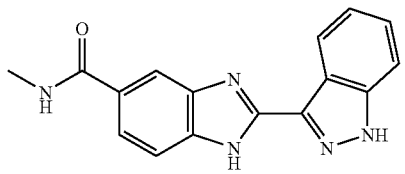

2-(1H-Indazol-3-yl)-1H-benzimidazole-5-carboxylic acid N-methylamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 71.8 µl of a methylamine solution (2M in tetrahydrofuran), 14.8 mg of expected product are obtained.

EXAMPLE 3

2-(1H-Indazol-3-yl)-1H-benzimidazole-5-carboxylic acid N-ethylamide

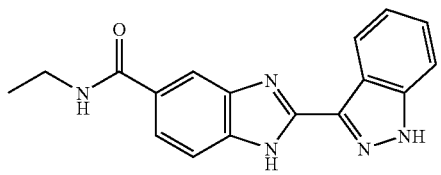

2-(1H-Indazol-3-yl)-1H-benzimidazole-5-carboxylic acid N-ethylamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 19.4 ml of an ethylamine solution (33% in water) 14.8 mg of 2-(1H-indazol-3-yl)-1H-benzimidazole-5-carboxylic acid N-ethylamide are obtained.

EXAMPLE 4

2-(1H-Indazol-3-yl)-1H-benzimidazole-5-carboxylic acid N-isopropylamide

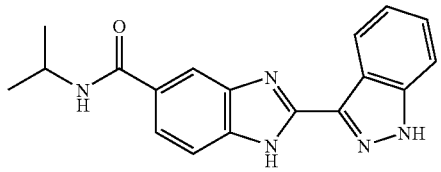

2-(1H-Indazol-3-yl)-1H-benzimidazole-5-carboxylic acid N-isopropylamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 12.3 ml of isopropylamine, 16.5 mg of 2-(1H-indazol-3-yl)-1H-benzimidazole-5-carboxylic acid N-isopropylamide are obtained.

EXAMPLE 5

2-(1H-Indazol-3-yl)-1H-benzimidazole-5-carboxylic acid N-phenylamide

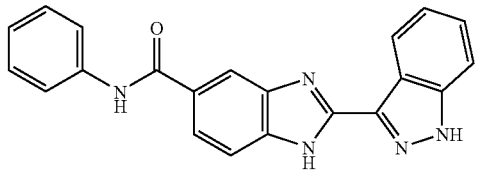

2-(1H-Indazol-3-yl)-1H-benzimidazole-5-carboxylic acid N-phenylamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 13.1 ml of aniline, 14.1 mg of 2-(1H-indazol-3-yl)-1H-benzimidazole-5-carboxylic acid N-phenylamide are obtained in the form of a white powder.

EXAMPLE 6

2-(1H-Indazol-3-yl)-1H-benzimidazole-5-carboxylic acid N-phenethylamide

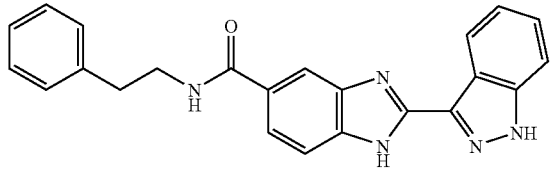

2-(1H-Indazol-3-yl)-1H-benzimidazole-5-carboxylic acid N-phenethylamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 18 ml of phenethylamine, 17.7 mg of 2-(1H-indazol-3-yl)-1H-benzimidazole-5-carboxylic acid N-phenethylamide are obtained in the form of a white powder.

EXAMPLE 7

2-(1H-Indazol-3-yl)-1H-benzimidazole-5-carboxylic acid N-morpholinoamide

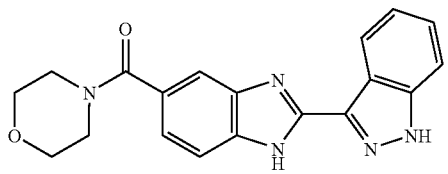

2-(1H-Indazol-3-yl)-1H-benzimidazole-5-carboxylic acid N-morpholinoamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 12.5 ml of morpholine, 18.6 mg of 2-(1H-indazol-3-yl)-1H-benzimidazole-5-carboxylic acid N-morpholinoamide are obtained in the form of a pale yellow powder.

EXAMPLE 8

2-(1H-Indazol-3-yl)-1H-benzimidazole-5-carboxylic acid N—(N'-methyl-piperazino)amide

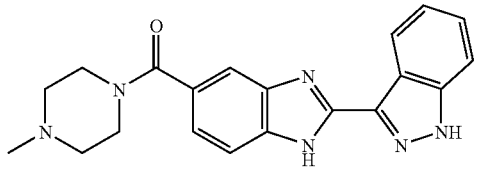

2-(1H-Indazol-3-yl)-1H-benzimidazole-5-carboxylic acid N—(N'-methyl-piperazino)amide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 15.9 ml of N-methylpiperazine, 16.1 mg of 2-(1H-indazol-3-yl)-1H-benzimidazole-5-carboxylic acid N—(N'-methyl-piperazino)amide are obtained in the form of a yellow oil.

EXAMPLE 9

2-(1H-Indazol-3-yl)-1H-benzimidazole-5-carboxylic acid N-pyrrolidinoamide

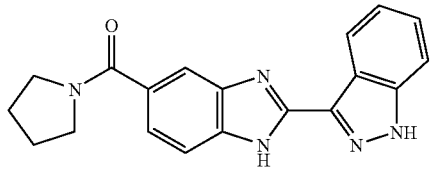

2-(1H-Indazol-3-yl)-1H-benzimidazole-5-carboxylic acid N-pyrrolidinoamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 12 ml of pyrrolidine, 17.7 mg of 2-(1H-indazol-3-yl)-1H-benzimidazole-5-carboxylic acid N-pyrrolidinoamide are obtained in the form of a pale yellow powder.

EXAMPLE 10

2-(1H-Indazol-3-yl)-1H-benzimidazole-5-carboxylic acid N-(isobutyl)amide

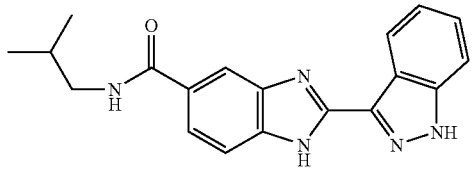

2-(1H-Indazol-3-yl)-1H-benzimidazole-5-carboxylic acid N-(isobutyl)amide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 14.6 ml of isobutylamine, 7.6 mg of 2-(1H-indazol-3-yl)-1H-benzimidazole-5-carboxylic acid N-(isobutyl)amide are obtained in the form of a pale yellow powder.

EXAMPLE 11

2-(1H-Indazol-3-yl)-1H-benzimidazole-5-carboxylic acid N-(cyclohexylmethyl)amide

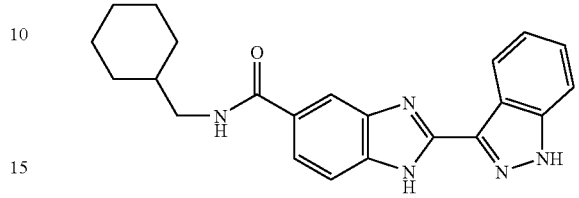

2-(1H-Indazol-3-yl)-1H-benzimidazole-5-carboxylic acid N-(cyclohexylmethyl)amide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 18.7 ml of cyclohexylmethylamine, 16.1 mg of 2-(1H-indazol-3-yl)-1H-benzimidazole-5-carboxylic acid N-cyclohexylmethyl)amide are obtained in the form of a white powder.

EXAMPLE 12

2-(1H-Indazol-3-yl)-1H-benzimidazole-5-carboxylic acid N-(2-furfuryl)amide

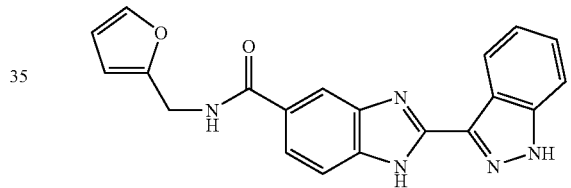

2-(1H-Indazol-3-yl)-1H-benzimidazole-5-carboxylic acid N-(2-furfuryl)amide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 13.3 ml of 2-furfurylamine, 14.8 mg of 2-(1H-indazol-3-yl)-1H-benzimidazole-5-carboxylic acid N-(2-furfuryl)amide are obtained in the form of a white powder.

EXAMPLE 13

2-(1H-Indazol-3-yl)-1H-benzimidazole-5-carboxylic acid N-benzyl-N-methylamide

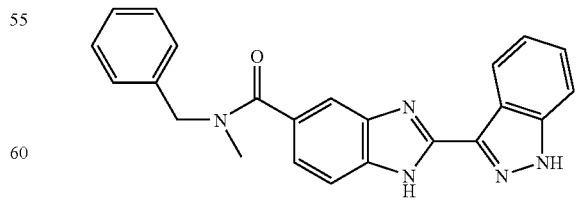

2-(1H-Indazol-3-yl)-1H-benzimidazole-5-carboxylic acid N-benzyl-N-methylamide may be prepared by following the procedure for the preparation of 2-(1H-indazol-3-yl)-1H-benzimidazole-5-carboxylic acid N-benzylamide (Example 1):

Starting with 20 mg of 2-(1H-indazol-3-yl)-1H-benzimidazole-5-carboxylic acid and 18.6 ml of N-methylbenzylamine, 7.3 mg of 2-(1H-indazol-3-yl)-1H-benzimidazole-5-carboxylic acid N-benzyl-N-methylamide are obtained in the form of a pale yellow powder.

EXAMPLE 14

Methyl 2-(1H-indazol-3-yl)-3H-benzimidazole-5-carboxylate

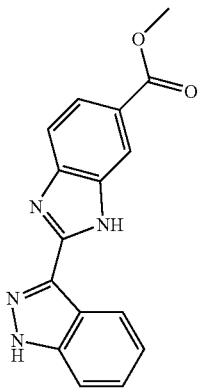

Methyl 2-(1H-indazol-3-yl)-3H-benzimidazole-5-carboxylate may be prepared in the following manner:

A mixture of 0.1 g of 1H-indazole-3-carboxaldehyde and 113.7 mg of methyl 3,4-diaminobenzoate in 10 ml of nitrobenzene is maintained at a temperature in the region of 145° C. for 3 hours and 45 minutes. After cooling to a temperature in the region of 20° C., the reaction mixture is purified on SPE (5 g of SCX phase, processing and washing with methanol, extraction with a 2N ammoniacal methanol solution). The ammoniacal solution collected during the detachment is then concentrated under reduced pressure at a temperature in the region of 40° C. 198.3 mg of an orange lacquer are obtained and are purified by preparative LC-MS. 42.7 mg of methyl 2-(1H-indazol-3-yl)-3H-benzimidazole-5-carboxylate are thus obtained in the form of a beige-coloured powder, the characteristics of which are as follows:

$^1$H NMR (DMSO d6, 400 MHz): 3.95 ppm (singlet, 3H); 7.40 ppm (triplet, 1H); 7.55 ppm (triplet, 1H); 7.75 ppm (doublet, 1H); 7.77 ppm (doublet, 1H); 7.95 ppm (doublet, 1H); 8.57 ppm (doublet, 1H); 13.85 ppm (multiplet, 1H).

EXAMPLE 15

5,6-dimethyl-2-(1H-indazol-3-yl)-1H-benzimidazole

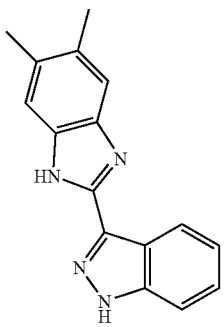

5,6-Dimethyl-2-(1H-indazol-3-yl)-1H-benzimidazole may be prepared by following the procedure for the preparation of methyl 2-(1H-indazol-3-yl)-3H-benzimidazole-5-carboxylate (Example 14):

Starting with 200 mg of 1H-indazole-3-carboxaldehyde and 177 mg of 4,5-dimethyl-1,2-phenylenediamine in 10 ml of nitrobenzene, 15.9 mg of 5,6-dimethyl-2-(1H-indazol-3-yl)-1H-benzimidazole are obtained in the form of a dark red powder, the characteristics of which are as follows:

$^1$H NMR (DMSO d6, 400 MHz): 2.60 ppm (singlet, 6H); 7.42 ppm (triplet, 1H); 7.53 ppm (singlet, 2H); 7.58 ppm (triplet, 1H); 7.78 ppm (doublet, 1H); 8.52 ppm (doublet, 1H); 14.05 ppm (multiplet, 1H).

5,6-Dimethyl-2-(1H-indazol-3-yl)-1H-benzimidazole may also be prepared according to the following procedure:

389 mg of sodium metabisulphite are added, at a temperature in the region of 20° C., to a solution of 300 mg of 1H-indazole-3-carboxaldehyde and 279 mg of 4,5-dimethyl-1,2-phenylenediamine in 3 ml of dimethylformamide. The reaction mixture is refluxed for 4 hours and then cooled to a temperature in the region of 20° C. and filtered through paper. The collected filtrate is concentrated under reduced pressure. The brown lacquer obtained (340 mg) is purified by preparative LC-MS. 138.8 mg of 5,6-dimethyl-2-(1H-indazol-3-yl)-1H-benzimidazole are thus obtained in the form of a beige-coloured powder.

EXAMPLE 16

5-methoxy-2-(1H-indazol-3-yl)-1H-benzimidazole

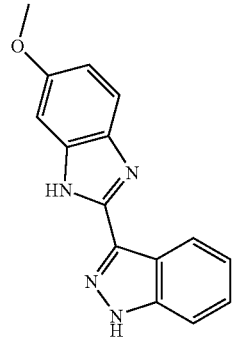

5-Methoxy-2-(1H-indazol-3-yl)-1H-benzimidazole may be prepared by following the procedure for the preparation of methyl 2-(1H-indazol-3-yl)-3H-benzimidazole-5-carboxylate (Example 14):

Starting with 200 mg of 1H-indazole-3-carboxaldehyde and 274.4 mg of 4-methoxy-1,2-phenylenediamine dihydrochloride in 10 ml of nitrobenzene, 45.6 mg of 5-methoxy-2-(1H-indazol-3-yl)-1H-benzimidazole are obtained in the form of a light brown powder, the characteristics of which are as follows:

$^1$H NMR (DMSO d6, 400 MHz): 3.90 ppm (singlet, 3H); 7.00 ppm (doublet, 1H); 7.18 ppm (doublet, 1H); 7.40 ppm (triplet, 1H); 7.55 ppm (triplet, 1H); 7.64 ppm (doublet, 1H); 7.73 ppm (doublet, 1H); 8.52 ppm (doublet, 1H); 13.91 ppm (multiplet, 1H).

EXAMPLE 17

2-(1H-Indazol-3-yl)-3H-benzimidazole-4-carboxylic acid

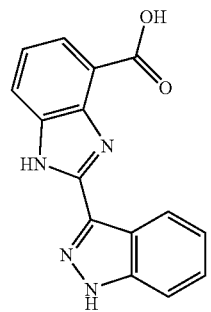

2-(1H-Indazol-3-yl)-3H-benzimidazole-4-carboxylic acid may be prepared by following the procedure for the preparation of methyl 2-(1H-indazol-3-yl)-3H-benzimidazole-5-carboxylate (Example 14):

Starting with 237 mg of 1H-indazole-3-carboxaldehyde and 305.5 mg of 2,3-diaminobenzoic acid hydrochloride in 10 ml of nitrobenzene, 20.5 mg of 2-(1H-indazol-3-yl)-3H-benzimidazole-4-carboxylic acid are obtained in the form of a beige-coloured powder, the characteristics of which are as follows:

1H NMR, DMSO d6, 400 MHz: 7.40 ppm (triplet, 1H); 7.42 ppm (triplet, 1H); 7.55 ppm (triplet, 1H); 7.72 ppm (doublet, 1H); 7.90 ppm (doublet, 1H); 8.02 ppm (doublet, 1H); 8.52 ppm (doublet, 1H); 13.68 ppm (multiplet, 1H).

EXAMPLE 18

5-bromo-2-(1H-indazol-3-yl)-3H-benzimidazole

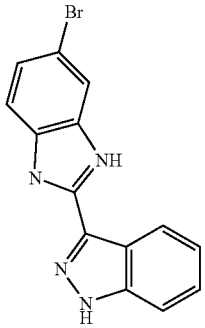

5-Bromo-2 (1H-indazol-3-yl)-3H-benzimidazole may be prepared by following the procedure for the preparation of 5,6-dimethyl-2-(1H-indazol-3-yl)-1H-benzimidazole (Example 15):

Starting with 643 mg of 1H-indazole-3-carboxaldehyde, 816 mg of 4-bromo-1,2-phenylenediamine, and 836.5 mg of sodium metabisulphite in 15 ml of dimethylformamide, and after purification by SPE (SCX phase, washing with methanol, extraction with 2N ammoniacal methanol) followed by a chromatography under pressure on silica, 939 mg of 5-bromo-2-(1H-indazol-3-yl)-3H-benzimidazole are obtained in the form of a brick-red powder.

EXAMPLE 19

2-(5-Ethoxy-2H-pyrazol-3-yl)-1H-benzimidazole-4-carboxylic acid

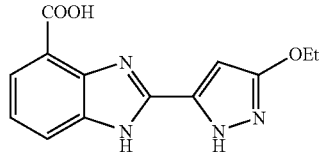

2-(5-Ethoxy-2H-pyrazol-3-yl)-1H-benzimidazole-4-carboxylic acid may be obtained from 2-(2-benzyl-5-ethoxy-2H-pyrazol-3-yl)-1H-benzimidazole-4-carboxylic acid by deprotection of the benzyl group in the presence of hydrogen and a catalyst such as palladium.

2-(2-Benzyl-5-ethoxy-2H-pyrazol-3-yl)-1H-benzimidazole-4-carboxylic acid may be prepared by following the procedure for the preparation of 5,6-dimethyl-2-(1H-indazol-3-yl)-1H-benzimidazole (Example 15):

Starting with 21.6 mg of 2-benzyl-5-ethoxy-2H-pyrazole-3-carboxaldehyde, and 17.7 mg of 3,4-diaminobenzoic acid hydrochloride in 1 ml of nitrobenzene, and after purification by SPE (SCX phase, washing with methanol, extraction with 2N ammoniacal methanol), 50.9 mg of 2-(2-benzyl-5-ethoxy-2H-pyrazol-3-yl)-1H-benzimidazole-4-carboxylic acid are obtained in the form of a yellow lacquer.

2-Benzyl-5-ethoxy-2H-pyrazole-3-carboxaldehyde may be prepared in the following manner:

4 Å molecular sieves are added to a solution of 45.7 mg of (2-benzyl-5-ethoxy-2H-pyrazol-3-yl)methanol in 0.5 ml of dichloromethane, followed by addition of 43.1 mg of pyridinium chlorochromate. After 20 hours at a temperature in the region of 20° C., the reaction mixture is filtered through Celite. The insoluble material formed is rinsed with ethyl acetate and then with dichloromethane. The filtrate is washed with water. After separation of the phases by settling, the aqueous phase is re-extracted with dichloromethane. The organic phases are combined, dried over magnesium sulphate, filtered and then concentrated under reduced pressure. 21.6 mg of 2-benzyl-5-ethoxy-2H-pyrazole-3-carboxaldehyde are thus obtained in the form of a brown lacquer, the characteristics of which are as follows:

$^1$H NMR (DMSO d6, 400 MHz): 1.35 ppm (triplet, 3H); 4.25 ppm (quartet, 2H); 5.30 ppm (singlet, 2H); 6.30 ppm (singlet, 1H); 7.25-7.40 ppm (multiplet, 5H); 9.72 ppm (singlet, 1H).

(2-Benzyl-5-ethoxy-2H-pyrazol-3-yl)methanol may be prepared in the following manner:

11.1 mg of lithium aluminium hydride are added to a solution of 76 mg of methyl 2-benzyl-5-ethoxy-2H-pyrazole-3-carboxylate in 0.75 ml of tetrahydrofuran, cooled to a temperature in the region of 0° C. by an ice bath. After 3 hours at a temperature in the region of 0° C., 22.2 mg of lithium aluminium hydride are added and the reaction medium is allowed to warm to a temperature in the region of 20° C. After 30 minutes at a temperature in the region of 20° C., 10 ml of ice-cold water are added and the reaction mixture is then filtered through Celite. After separation of the phases by settling, the aqueous phase is extracted with ethyl acetate. The organic phases are combined, dried over magnesium sulphate and concentrated under reduced pressure. 45.7 mg of (2-benzyl-5-ethoxy-2H-pyrazol-3-yl)methanol are thus obtained in the form of a brown lacquer, the characteristics of which are as follows:

$^1$HNMR (DMSO d6, 400 MHz): 1.35 ppm (triplet, 3H); 4.15 ppm (quartet, 2H); 4.30 ppm (doublet, 2H); 5.00 ppm (triplet, 1H); 5.08 ppm (singlet, 2H); 5.70 ppm (singlet, 1H); 7.20-7.40 ppm (multiplet, 5H).

Methyl 2-benzyl-5-ethoxy-2H-pyrazole-3-carboxylate may be prepared in the following manner:

5 mg of sodium iodide, 36 µl of bromoethane and 70 mg of potassium carbonate are added, at a temperature in the region of 20° C., to a solution of 100 mg of methyl 2-benzyl-5-hydroxy-2H-pyrazole-3-carboxylate in 1 ml of acetone. The reaction mixture is refluxed for 9 hours, cooled to a temperature in the region of 20° C. and filtered. The filtrate is concentrated under reduced pressure. 76 mg of methyl 2-benzyl-5-ethoxy-2H-pyrazole-3-carboxylate are thus obtained in the form of a solid, the characteristics of which are as follows:

$^1$H NMR (DMSO d6, 400 MHz): 1.35 ppm (triplet, 3H); 3.50 ppm (singlet, 3H); 4.22 ppm (quartet, 2H); 5.22 ppm (singlet, 2H); 6.28 ppm (singlet, 1H); 7.20-7.40 ppm (multiplet, 5H).

Methyl 2-benzyl-5-hydroxy-2H-pyrazole-3-carboxylate may be prepared in the following manner:

1.72 ml of dimethylacetylene dicarboxylate are added, at a temperature in the region of 20° C., to a solution of 2.73 g of benzylhydrazine dihydrochloride in 45 ml of glacial acetic acid. The reaction mixture is refluxed for 3 hours, cooled to a temperature in the region of 20° C. and then concentrated under reduced pressure. After filtering off the insoluble material formed, 252 mg of methyl 2-benzyl-5-hydroxy-2H-pyrazole-3-carboxylate are collected in the form of a white powder, the characteristics of which are as follows:

$^1$H NMR (DMSO d6, 400 MHz): 3.76 ppm (singlet, 3H); 5.19 ppm (singlet, 2H); 5.85 ppm (singlet, 1H); 7.25-7.45 ppm (multiplet, 5H); 11.69 ppm (multiplet, 1H).

The filtrate may be purified by flash chromatography on 400 g of 20-45 μm silica (applied in a 25/75 ethyl acetate/cyclohexane mixture; eluant: 25/75 and then 40/60 ethyl acetate/cyclohexane) to give an additional batch of methyl 2-benzyl-5-hydroxy-2H-pyrazole-3-carboxylate in the form of a white powder.

EXAMPLE 20

5,6-dimethyl-2-(5-methyl-2H-pyrazol-3-yl)-1H-benzimidazole

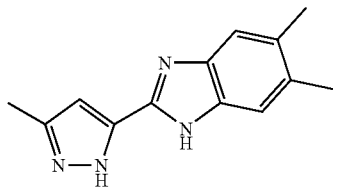

5,6-Dimethyl-2-(5-methyl-2H-pyrazol-3-yl)-1H-benzimidazole may be prepared by following the procedure described for the preparation of 5,6-dimethyl-2-(1H-indazol-3-yl)-1H-benzimidazole (Example 15):

Starting with 53.3 mg of 5-methyl-2H-pyrazole-3-carboxaldehyde, 65.9 mg of 4,5-dimethyl-1,2-phenylenediamine, and 92 mg of sodium metabisulphite, in 0.5 ml of ethanol and 1.5 ml of dimethylformamide, and after purification by SPE (SCX phase, washing with methanol, extraction with 2N ammoniacal methanol) followed by a chromatography under pressure on silica, 20.8 mg of 5,6-dimethyl-2-(5-methyl-2H-pyrazol-3-yl)-1H-benzimidazole are obtained in the form of a white powder.

5-Methyl-2H-pyrazole-3-carboxaldehyde may be prepared from commercial ethyl 5-methyl-2H-pyrazole-3-carboxylate by following the procedure described for the preparation of 1H-indazole-3-carboxaldehyde, starting with methyl 3-indazolecarboxylate.

EXAMPLE 21

5,6-dimethyl-2-(5-thiophen-2-yl-2H-pyrazol-3-yl)-1H-benzimidazole

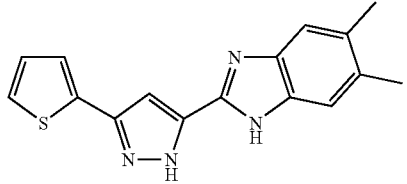

5,6-Dimethyl-2-(5-thiophen-2-yl-2H-pyrazol-3-yl)-1H-benzimidazole may be prepared by following the procedure described for the preparation of 5,6-dimethyl-2-(1H-indazol-3-yl)-1H-benzimidazole (Example 15):

Starting with 16.2 mg of 5-thiophen-2-yl-2H-pyrazole-3-carboxaldehyde, 12.4 mg of 4,5-dimethyl-1,2-phenylenediamine, and 17.3 mg of sodium metabisulphite, in 0.2 ml of ethanol and 0.6 ml of dimethylformamide, and after purification by SPE (SCX phase, washing with methanol, extraction with 2N ammoniacal methanol) followed by a chromatography under pressure on silica and a purification by LC-MS, 5,6-dimethyl-2-(5-thiophen-2-yl-2H-pyrazol-3-yl)-1H-benzimidazole is obtained in the form of a white powder.

5-Thiophen-2-yl-2H-pyrazole-3-carboxaldehyde may be prepared from commercial ethyl 5-thiophen-2-yl-2H-pyrazole-3-carboxylate by following the procedure described for the preparation of 1H-indazole-3-carboxaldehyde starting with methyl 3-indazolecarboxylate.

EXAMPLE 22

2-(4-bromo-2H-pyrazol-3-yl)-5,6-dimethyl-1H-benzimidazole

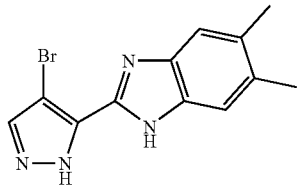

2-(4-Bromo-2H-pyrazol-3-yl)-5,6-dimethyl-1H-benzimidazole may be prepared by following the procedure described for the preparation of 5,6-dimethyl-2-(1H-indazol-3-yl)-1H-benzimidazole (Example 15):

Starting with 100 mg of commercial 4-bromo-2H-pyrazole-3-carboxaldehyde, 77.8 mg of 4,5-dimethyl-1,2-phenylenediamine, and 108.6 mg of sodium metabisulphite, in 1 ml of ethanol and 2 ml of dimethylformamide, and after purification by SPE (SCX phase, washing with methanol, extraction with 2N ammoniacal methanol) followed by a chromatography under pressure on silica, 143.2 mg of 2-(4-bromo-2H-pyrazol-3-yl)-5,6-dimethyl-1H-benzimidazole are obtained in the form of a yellow foam.

EXAMPLE 23

2-(5-ethyl-2H-pyrazol-3-yl)-5,6-dimethyl-1H-benzimidazole

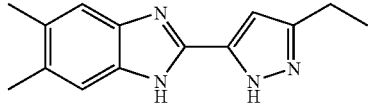

2-(5-Ethyl-2H-pyrazol-3-yl)-5,6-dimethyl-1H-benzimidazole may be prepared by following the procedure described for the preparation of 5,6-dimethyl-2-(1H-indazol-3-yl)-1H-benzimidazole (Example 15):

Starting with 100 mg of 5-ethyl-2H-pyrazole-3-carboxaldehyde, 110 mg of 4,5-dimethyl-1,2-phenylenediamine, and 153 mg of sodium metabisulphite, in 1 ml of ethanol and 3 ml of dimethylformamide, and after purification by SPE (SCX phase, washing with methanol, extraction with 2N ammoniacal methanol) followed by a reverse-phase HPLC (5 mm C18 phase, dimensions 100×25 mm, flow rate 20 m/min, elution gradient acetonitrile/0.07% TFA—water/0.07% TFA from 5-95 to 95-5 (v/v)), and desalification by SPE (SCX phase, washing with methanol, extraction with 2N ammoniacal methanol), 82 mg of 2-(5-ethyl-2H-pyrazol-3-yl)-5,6-dimethyl-1H-benzimidazole are obtained in the form of a beige-coloured powder, the characteristics of which are as follows:

¹H NMR (DMSO d6, 300 MHz): 1.26 (t, J=7 Hz: 3H); 2.31 (s: 6H); 2.70 (broad q, J=7 Hz: 2H); 6.60 (broad s: 1H); 7.22 (mult: 1H); 7.36 (mult: 1H); 12.37 (mult: 1H); 12.92 (mult: 1H).

5-Ethyl-2H-pyrazole-3-carboxaldehyde may be prepared from ethyl 5-ethyl-2H-pyrazole-3-carboxylate by following the procedure described for the preparation of 1H-indazole-3-carboxaldehyde starting with methyl 3-indazolecarboxylate.

Ethyl 5-ethyl-2H-pyrazole-3-carboxylate may be prepared according to the general procedure in the following reference: Kunio Seki et al., Chem. Pharm. Bull., 32(4), 1568-1577 (1984).

EXAMPLE 24

2-(5-ethyl-2H-pyrazol-3-yl)-4,5-ethylenedioxy-1H-benzimidazole

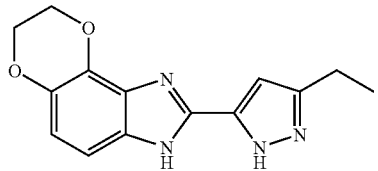

2-(5-Ethyl-2H-pyrazol-3-yl)-4,5-ethylenedioxy-1H-benzimidazole may be prepared by following the procedure described for the preparation of 5,6-dimethyl-2-(1H-indazol-3-yl)-1H-benzimidazole (Example 15):

Starting with 100 mg of 5-ethyl-2H-pyrazole-3-carboxaldehyde, 134 mg of 3,4-ethylenedioxy-1,2-phenylenediamine, and 153 mg of sodium metabisulphite, in 1 ml of ethanol and 3 ml of dimethylformamide, and after purification by SPE (SCX phase, washing with methanol, extraction with 2N ammoniacal methanol) followed by a reverse-phase HPLC (5 mm, C18 phase, dimensions 100×25 mm, flow rate 20 m/min, elution gradient acetonitrile/0.07% TFA-water/0.07% TFA from 5-95 to 95-5 (v/v)), and desalification by SPE (SCX phase, washing with methanol, extraction with 2N ammoniacal methanol), 60 mg of 2-(5-ethyl-2H-pyrazol-3-yl)-4,5-ethylenedioxy-1H-benzimidazole are obtained in the form of a brown lacquer, the characteristics of which are as follows:

¹H NMR (DMSO d6, 300 MHz): 1.27 (t, J=7 Hz: 3H); 2.70 (broad q, J=7 Hz: 2H); from 4.20 to 4.45 (mt: 4H); 6.61 (broad s: 1H); 6.72 (d, J=8 Hz: 1H); 6.88 (broad d, J=8 Hz: 1H); 12.50 (mult: 1H); 12.94 (mult: 1H).

EXAMPLE 25

2-(5-ethyl-2H-pyrazol-3-yl)-5-methoxy-1H-benzimidazole

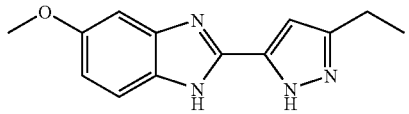

2-(5-Ethyl-2H-pyrazol-3-yl)-5-methoxy-1H-benzimidazole may be prepared by following the procedure described for the preparation of 5,6-dimethyl-2-(1H-indazol-3-yl)-1H-benzimidazole (Example 15):

Starting with 100 mg of 5-ethyl-2H-pyrazole-3-carboxaldehyde, 138 mg of 4-methoxy-1,2-phenylenediamine, and 153 mg of sodium metabisulphite, in 1 ml of ethanol and 3 ml of dimethylformamide, and after purification by SPE (SCX phase, washing with methanol, extraction with 2N ammoniacal methanol) followed by a reverse-phase HPLC (5 mm C18 phase, dimensions 100×25 mm, flow rate 20 ml/min, elution gradient: acetonitrile/0.07% TFA—water/0.07% TFA from 5-95 to 95-5 (v/v)), and desalification by SPE (SCX phase, washing with methanol, extraction with 2N ammoniacal methanol), 61 mg of 2-(5-ethyl-2H-pyrazol-3-yl)-5-methoxy-1H-benzimidazole are obtained in the form of a brown lacquer, the characteristics of which are as follows:

¹H NMR (DMSO d6 with addition of a few drops of CD₃COOD, 300 MHz): 1.26 (t, J=7 Hz: 31); 2.70 (q, J=7 Hz: 2H); 3.79 (s: 3H); 6.61 (s: 1H); 6.81 (dd, J=8.5 and 2.5 Hz: 1H); 7.03 (broad s: 1H); 7.42 (d, J=8.5 Hz: 1H).

EXAMPLE 26

2-(5-ethyl-2H-pyrazol-3-yl)-4-hydroxy-1H-benzimidazole

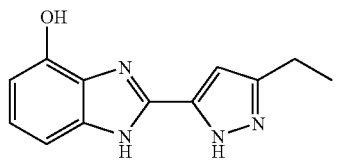

2-(5-Ethyl-2H-pyrazol-3-yl)-4-hydroxy-1H-benzimidazole may be prepared by following the procedure described for the preparation of 5,6-dimethyl-2-(1H-indazol-3-yl)-1H-benzimidazole (Example 15): Starting with 100 mg of 5-ethyl-2H-pyrazole-3-carboxaldehyde, 100 mg of 2,3-diaminophenol, and 153 mg of sodium metabisulphite, in 1 ml of ethanol and 3 ml of dimethylformamide, and after purification by SPE (SCX phase, washing with methanol, extraction with 2N ammoniacal methanol) followed by a reverse-phase HPLC (5 mm, C18 phase, dimensions: 100×25 mm, flow rate 20 ml/min, elution gradient: acetonitrile/0.07% TFA—water/0.07% TFA from 5-95 to 95-5 (v/v)), and desalification by SPE (SCX phase, washing with methanol, extraction with 2N ammoniacal methanol), 16 mg of 2-(5-ethyl-2H-pyrazol-3-yl)-4-hydroxy-1H-benzimidazole are obtained in the form of a brown lacquer, the characteristics of which are as follows:

¹H NMR (DMSO d6 with addition of a few drops of CD₃COOD, 300 MHz): 1.26 (t, J=7 Hz: 3H); 2.70 (q, J=7 Hz: 2H); 6.55 (t, J=4.5 Hz: 1H); 6.66 (s: 1H); 6.96 (broad d, J=4.5 Hz: 2H).

EXAMPLE 27

2-(5-ethyl-2H-pyrazol-3-yl)-5-bromo-1H-benzimidazole

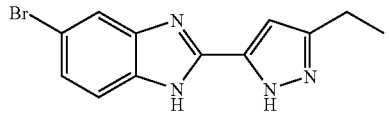

2-(5-Ethyl-2H-pyrazol-3-yl)-5-bromo-1H-benzimidazole may be prepared by following the procedure described for the preparation of 5,6-dimethyl-2-(1H-indazol-3-yl)-1H-benzimidazole (Example 15):

Starting with 20 mg of 5-ethyl-2H-pyrazole-3-carboxaldehyde, 30 mg of 4-bromo-1,2-phenylenediamine and 30 mg of sodium metabisulphite, in 1 ml of ethanol and 2 ml of dimethylformamide, and after purification by SPE (SCX phase, washing with methanol, extraction with 2N ammoniacal methanol) followed by a reverse-phase HPLC (5 mm C18 phase, dimensions: 100×25 mm, flow rate 20 ml/min, elution gradient: acetonitrile/0.07% TFA-water/0.07% TFA from 5-95 to 95-5 (v/v)), and desalification by SPE (SCX phase, washing with methanol, extraction with 2N ammoniacal methanol), 21 mg of 2-(5-ethyl-2H-pyrazol-3-yl)-5-bromo-1H-benzimidazole are obtained in the form of a yellow powder, the characteristics of which are as follows:

$^1$H NMR (DMSO d6, 300 MHz): 1.28 (t, J=7 Hz: 3H); 2.71 (q, J=7 Hz: 2H); 6.67 (s: 1H); 7.30 (dd, J=8.5 and 2.5 Hz: 1H); 7.49 (mt: 1H); 7.712 (broad s: 1H); from 12.5 to 13.5 (broad mult: 2H).

The products of formula (I) of the present application can also be prepared according to the following process:

dried over magnesium sulphate and then concentrated to dryness under reduced pressure. 18 g of a brown oil are thus obtained, which oil is taken up in 100 ml of a 20% solution of hydrochloric acid in ethanol. The mixture is brought to reflux for 4 hours and then concentrated to dryness, the brown oil obtained is taken up in 20 ml of water, and an aqueous ammonia solution is run in until a pH of the mixture of about 8-9 is obtained. The aqueous phase is then extracted 3 times with 30 ml of ethyl acetate and the organic phases are combined, dried over magnesium sulphate and concentrated to dryness under reduced pressure. After purification by chromatography under pressure on silica (eluent water/acetonitrile), 5 g of 3-(6-bromo-1H-benzimidazol-2-yl)-2H-indazole are thus obtained.

IR spectrum (KBr): characteristic bands at 1621, 1570, 1441, 1344, 1324, 1273, 1239, 1135, 1042, 914, 804, 774 and 746 cm$^{-1}$

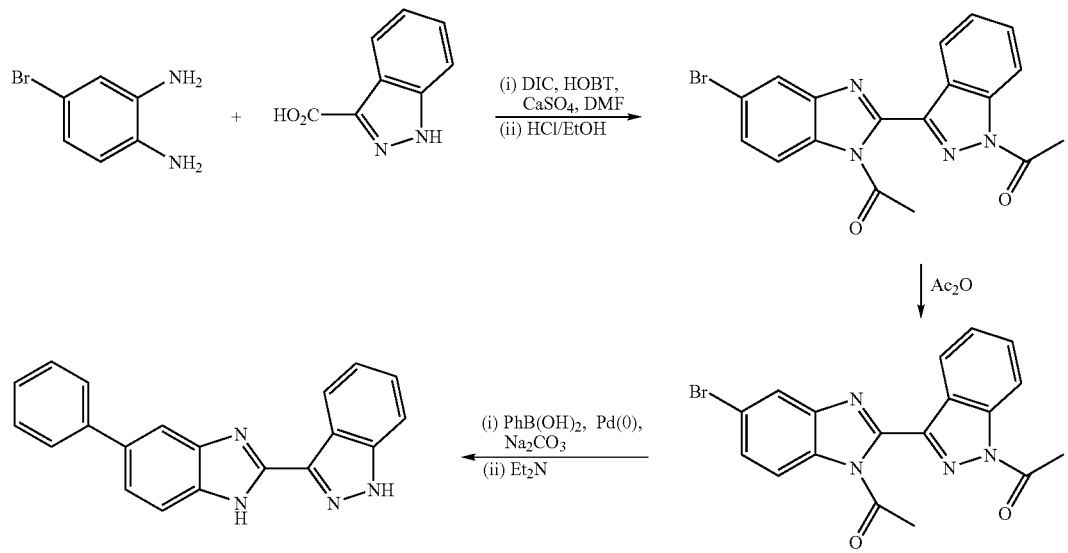

The products of Examples 97 to 145 of the present application represented in the TABLE 3 below can be prepared according to the schemes indicated above and in particular according to the procedures indicated below.

EXAMPLE 97

3-(6-phenyl-1H-benzimidazol-2-yl)-2H-indazole

Step 1: Synthesis of 3-(6-bromo-1H-benzimidazol-2-yl)-2H-indazole (other preparation of example 18)

4.25 g of 1-hydroxybenzotriazole and 4.3 g of calcium sulphate are added at ambient temperature to a solution of 4.6 g of indazole-3-carboxylic acid in 50 ml of dimethylformamide. The reaction mixture is cooled to approximately 0° C. and then 4.9 ml of N,N-diisopropylcarbodiimide are slowly added. After stirring for 2 hours at ambient temperature, 5.9 g of 4-bromo-o-phenylenediamine are added. After stirring for 60 hours at ambient temperature, the reaction mixture is concentrated to dryness under reduced pressure. The brown oil obtained is taken up in 50 ml of water and extracted 3 times with 50 ml of ethyl acetate. The organic phases are combined, Step 2: Synthesis of 1-[2-(1-acetyl-1H-indazol-3-yl)-5-bromobenzimidazol-1-yl]ethanone 5 g of 3-(6-bromo-1H-benzimidazol-2-yl)-2H-indazole are charged to a solution of 40 ml of acetic anhydride and 40 ml of pyridine. The mixture is brought to reflux for 4 hours and then concentrated to dryness after returning to ambient temperature. The brown solid obtained is taken up in 50 ml of ethyl acetate and washed with 50 ml of a saturated sodium hydrogencarbonate solution until a pH of 7-8 is obtained. The organic phase is dried over magnesium sulphate, filtered and then concentrated to dryness under reduced pressure. The light brown solid obtained is triturated in 20 ml of ethyl acetate and then filtered off on a sintered glass funnel. 1.5 g of the compound 1-[2-(1-acetyl-1H-indazol-3-yl)-5-bromobenzimidazol-1-yl]ethanone are thus obtained. A second crop is obtained by chromatographing the filtrate obtained above under pressure on silica (eluent cyclohexane/ethyl acetate), i.e. 1.3 g of the same compound.

Characteristics of the Compound:
$^1$H NMR spectrum (300 MHz, (CD$_3$)$_2$SO d6, δ in ppm).
The mixture of the two positional isomers in the proportions 50/50 is observed.

2.61 and 2.62 (2 s, 3H in all); 2.80 (s, 3H); 7.62 (broad t, J=7.5 Hz, 1H); 7.68 and 7.71 (2 dd, J=9 and 2 Hz, 1H in all); 7.80 (ddd, J=8.5, 7.5 and 0.5 Hz, 1H); 7.91 and 8.01 (2 d, J=9 Hz, 1H); 8.18 and 8.20 (2 d, J=2 Hz, 1H in all); 8.27 and 8.30 (2 d, J=7.5 Hz, 1H in all); 8.46 (d, J=8.5 Hz, 1H)

IR spectrum (KBr): characteristic bands at 1727, 1610, 1450, 1405, 1374, 1326, 1290, 1198, 1176, 964 and 760 cm$^{-1}$ Step 3: Synthesis of 3-(6-phenyl-1H-benzimidazol-2-yl)-2H-indazole 40 mg of sodium carbonate, 7 mg of dihydrogendichlorobis(di-tert-butylphosphonite-κP)palladate(2-) (POPd[0]) and 46 mg of phenylboronic acid are added under an argon atmosphere to a solution of 50 mg of 1-[2-(1-acetyl-1H-indazol-3-yl)-5-bromobenzimidazol-1-yl]ethanone in 800 μl of anhydrous tetrahydrofuran. The reaction mixture is brought to reflux for 3 hours and then cooled to ambient temperature. The mixture is then diluted with 3 ml of ethyl acetate and then washed with 2 times 2 ml of water. The organic phase is dried over magnesium sulphate and then concentrated to dryness under reduced pressure. 48 mg of a brown solid are obtained, which solid is dissolved in 500 μl of tetrahydrofuran, to which 500 μl of diethylamine are added. The reaction mixture is heated at 60° C. for 4 hours and then allowed to return to ambient temperature. The mixture is then concentrated to dryness and then the brown solid obtained is purified by LC-MS to produce 12.5 mg of 3-(6-phenyl-1H-benzimidazol-2-yl)-2H-indazole (6); analytical retention time 3.10, MS 311 [M+H]$^+$.

The products of formula (I) of the present application and in particular examples 98 to 145 can be prepared according to the following process:

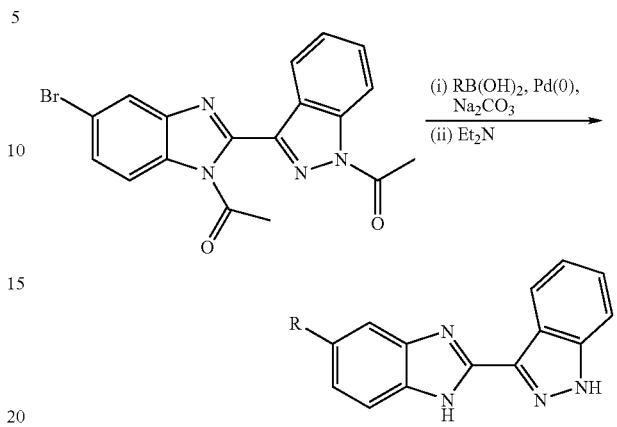

The synthesis of examples 98 to 145 is carried out in a similar way to the synthesis of 3-(6-phenyl-1H-benzimidazol-2-yl)-2H-indazole (example 97) but replacing phenylboronic acid with boronic acids of formula RB(OH)$_2$.

Products of formula (I) of the present application which constitute Examples 28 to 96 and 146 to 180 of the present application are represented in Table 3: these products can be prepared according to the schemes indicated above and in particular as indicated above for the product of Example 1.

TABLE 3

| Example number | STRUCTURE | RNH₂ or RB(OH)₂ | Molecular Formula | MW | MS Characteristic Method | | time (minutes) | Nomenclature |
|---|---|---|---|---|---|---|---|---|
| 28 | 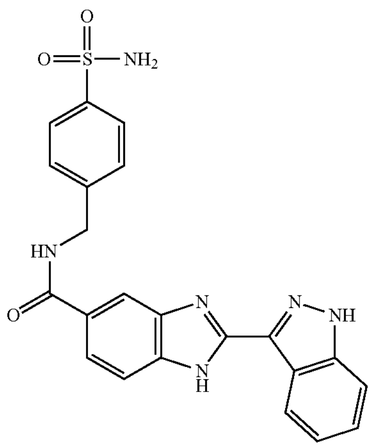 | HCl · H₂N-CH₂-C₆H₄-SO₂NH₂ (MFCD00013005) | C22H18N6O3S | 446.49 | 447 | [M + H]⁺ | 2.77 | 2-(1H-Indazol-3-yl)-1H-benzoimidazole-5-carboxylic acid 2,4-dichloro-benzylamide |
| 29 | 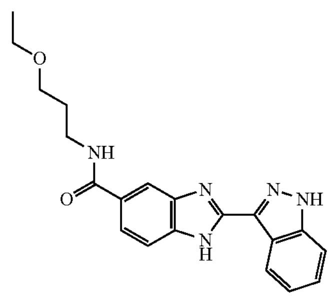 | H₂N-(CH₂)₃-O-CH₂CH₃ (MFCD00008221) | C20H21N5O2 | 363.42 | 364 | [M + H]⁺ | 2.8 | 2-(1H-Indazol-3-yl)-1H-benzoimidazole-5-carboxylic acid (3-ethoxy-propyl)-amide chemistry |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 30 | [structure] | [4-bromobenzylamine] MFCD00047931 | C22H16BrN5O | 446.31 | 447 | [M + H]⁺ | 3.35 | 2-(1H-Indazol-3-yl)-1H-benzoimidazole-5-carboxylic acid 4-bromo-benzylamide |
| 31 chemistry 3 | [structure] | [4-(methanesulfonyl)benzylamine·HCl] MFCD00216491 | C23H19N5O3S | 445.50 | 446 | [M + H]⁺ | 2.81 | 2-(1H-Indazol-3-yl)-1H-benzoimidazole-5-carboxylic acid 4-methanesulfonyl-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 32 | 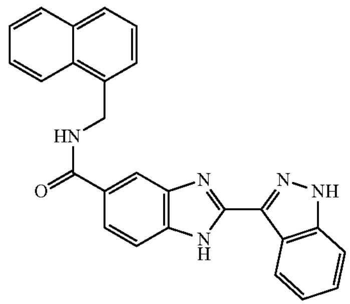 | MFCD00004048 | C26H19N5O | 417.47 | 418 | [M + H]⁺ | 3.38 | 2-(1H-Indazol-3-yl)-1H-benzoimidazole-5-carboxylic acid (naphthalen-1-ylmethyl)-amide |
| 33 | chemistry 6 | MFCD00010220 | C23H16F3N5O | 435.41 | 436 | [M + H]⁺ | 3.41 | 2-(1H-Indazol-3-yl)-1H-benzoimidazole-5-carboxylic acid 4-trifluoromethyl-benzylamide |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 34 | 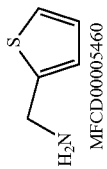 chemistry 7 | 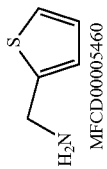 MFCD00005460 | C20H15N5OS | 373.44 | 374 | [M + H]⁺ | 3.01 | 2-(1H-Indazol-3-yl)-1H-benzoimidazole-5-carboxylic acid (thiophen-2-ylmethyl)-amide |
| 35 | 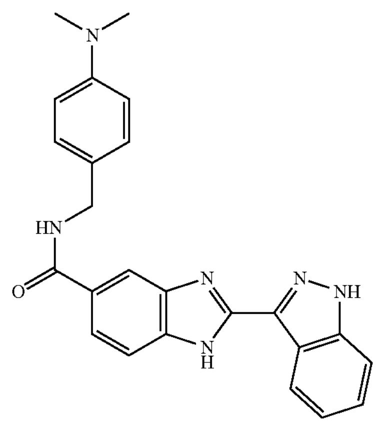 | HCl HCl 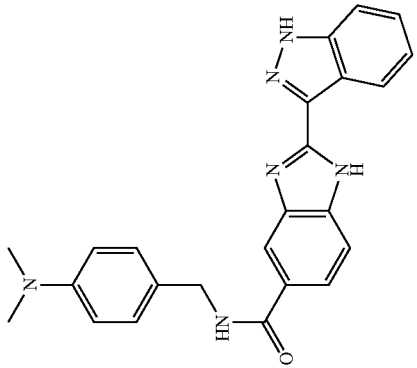 MFCD00012862 | C24H22N6O | 410.48 | 411 | [M + H]⁺ | 2.49 | 2-(1H-Indazol-3-yl)-1H-benzoimidazole-5-carboxylic acid 4-dimethylamino-benzylamide |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 36 | 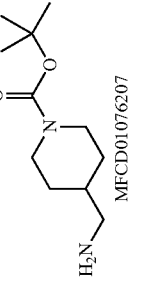 | 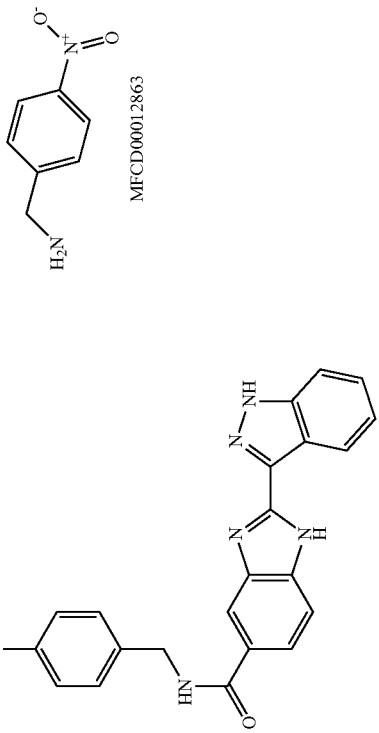 MFCD01076207 | C26H30N6O3 | 474.56 | 475 | [M + H]⁺ | 3.31 | 4-({[2-(1H-Indazol-3-yl)-1H-benzoimidazole-5-carbonyl]-amino}-methyl)-piperidine-1-carboxylic acid tert-butyl ester |
| 37 | 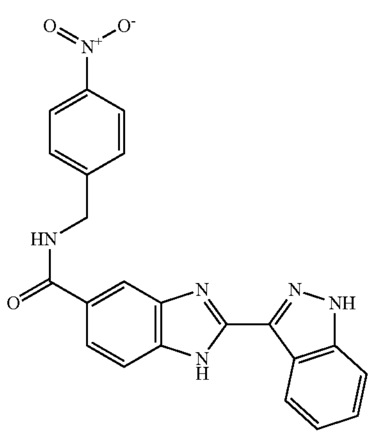 |  HCl MFCD00012863 | C22H16N6O3 | 412.41 | 413 | [M + H]⁺ | 3.14 | 2-(1H-Indazol-3-yl)-1H-benzoimidazole-5-carboxylic acid 4-nitro-benzylamide |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 38 | 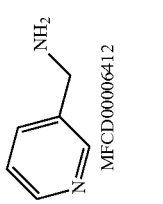 | 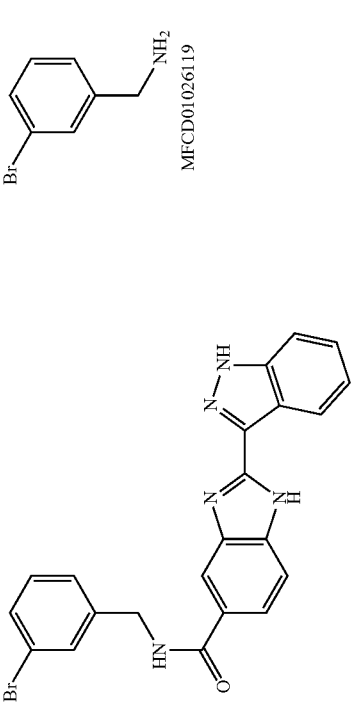MFCD00006412 | C21H16N6O | 368.40 | 369 | [M + H]⁺ | 2.39 | 2-(1H-Indazol-3-yl)-1H-benzoimidazole-5-carboxylic acid (pyridin-3-ylmethyl)-amide |
| 39 | chemistry 12 | MFCD01026119 | C22H16BrN5O | 446.31 | 447 | [M + H]⁺ | 3.36 | 2-(1H-Indazol-3-yl)-1H-benzoimidazole-5-carboxylic acid 3-bromo-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 40 | chemistry 16 | MFCD00008115 | C23H19N5O2 | 397.44 | 398 | [M + H]⁺ | 3.1 | 2-(1H-Indazol-3-yl)-1H-benzoimidazole-5-carboxylic acid 3-methoxy-benzylamide |
| 41 | chemistry 18 | MFCD00005840 | C23H17N5O3 | 411.42 | 412 | [M + H]⁺ | 3.07 | 2-(1H-Indazol-3-yl)-1H-benzoimidazole-5-carboxylic acid (benzo[1,3]dioxol-5-ylmethyl)-amide |

TABLE 3-continued
| Example number | STRUCTURE | RNH₂ or RB(OH)₂ | Molecular Formula | MW | MS Characteristic Method | time (minutes) | Nomenclature |
|---|---|---|---|---|---|---|---|
| 42 |  chemistry 19 | 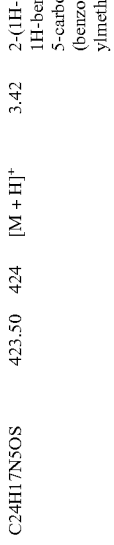 MFCD00176440 | C24H17N5OS | 423.50 | 424 [M + H]⁺ | 3.42 | 2-(1H-Indazol-3-yl)-1H-benzoimidazole-5-carboxylic acid (benzo[b]thiophen-3-ylmethyl)-amide |
| 43 |  chemistry 20 |  MFCD02055709 | C21H19N7O | 385.43 | 386 [M + H]⁺ | 2.59 | 2-(1H-Indazol-3-yl)-1H-benzoimidazole-5-carboxylic acid (1,3-dimethyl-1H-pyrazol-4-ylmethyl)-amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 44 | 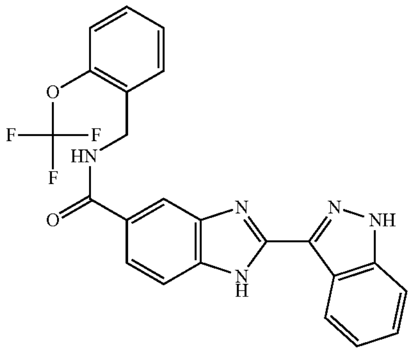 | MFCD00085176 | C23H16F3N5O2 | 451.41 | 452 [M + H]⁺ | 3.44 | 2-(1H-Indazol-3-yl)-1H-benzoimidazole-5-carobyxlic acid 2-trifluoromethoxy-benzylamide |
| 45 | chemistry 54 | MFCD00008112 | C23H19N5O | 381.44 | 382 [M + H]⁺ | 3.21 | 2-(1H-Indazol-3-yl)-1H-benzoimidazole-5-carboxylic acid 2-methyl-benzylamide |

| Example number | STRUCTURE | RNH₂ or RB(OH)₂ | Molecular Formula | MW | MS Characteristic Method | time (minutes) | Nomenclature |
|---|---|---|---|---|---|---|---|
| 46 | 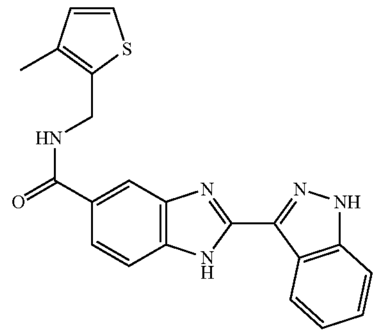 | MFCD02093988 | C21H17N5OS | 387.46 | 388 [M + H]⁺ | 3.16 | 2-(1H-Indazol-3-yl)-1H-benzoimidazole-5-carboxylic acid (3-methyl-thiophen-2-ylmethyl)-amide |
| 47 | 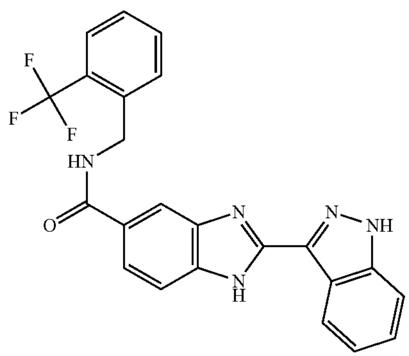 | MFCD00010297 | C23H16F3N5O | 435.41 | 436 [M + H]⁺ | 3.38 | 2-(1H-Indazol-3-yl)-1H-benzoimidazole-5-carboxylic acid 2-trifluoromethyl-benzylamide |

TABLE 3-continued

| Example number | STRUCTURE | RNH$_2$ or RB(OH)$_2$ | Molecular Formula | MW | MS Characteristic | Method | time (minutes) | Nomenclature |
|---|---|---|---|---|---|---|---|---|
| 48 | 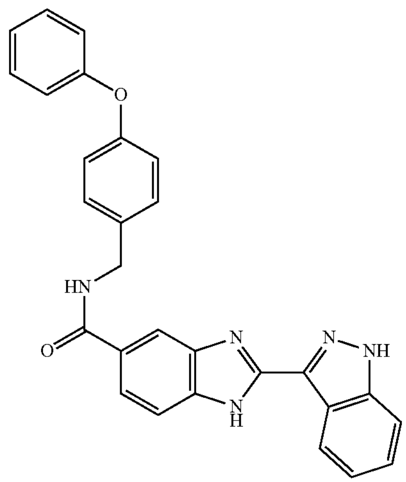 | MFCD01310836 | C28H21N5O2 | 459.51 | 460 | [M + H]$^+$ | 3.56 | 2-(1H-Indazol-3-yl)-1H-benzoimidazole-5-carboxylic acid 4-phenoxy-benzylamide |
| 49 | 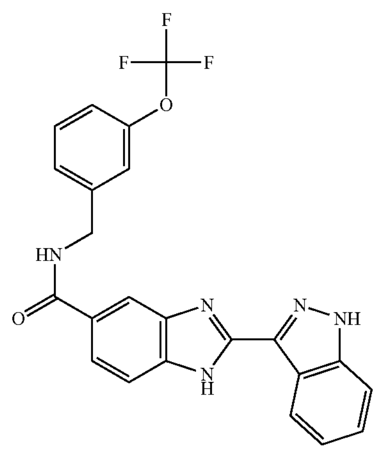 | MFCD00061267 | C23H16F3N5O2 | 451.41 | 452 | [M + H]$^+$ | 3.46 | 2-(1H-Indazol-3-yl)-1H-benzoimidazole-5-carboxylic acid 3-trifluoromethoxy-benzylamide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 50 | 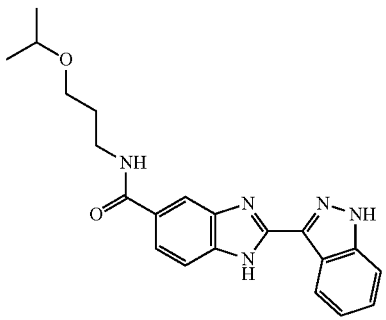 | MFCD00008220 | C21H23N5O2 | 377.45 | 378 [M + H]⁺ | 2.94 | 2-(1H-Indazol-3-yl)-1H-benzoimidazole-5-carboxylic acid (3-isopropoxy-propyl)-amide |
| 51 | chemistry 29 | MFCD02090924 | C20H17N7O | 371.40 | 372 [M + H]⁺ | 2.56 | 2-(1H-Indazol-3-yl)-1H-benzoimidazole-5-carboxylic aicd (1-methyl-1H-pyrazol-4-ylmethyl)-amide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 52 | 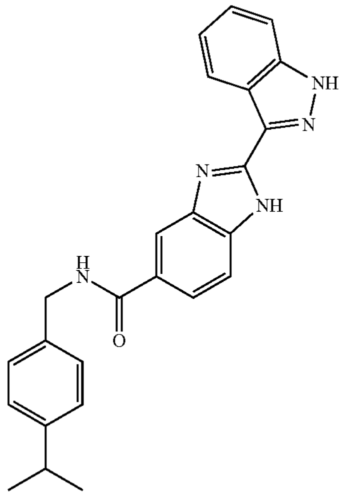 | MFCD00025580 | C25H23N5O | 409.49 | 410 | [M + H]⁺ | 3.51 | 2-(1H-Indazol-3-yl)-1H-benzoimidazole-5-carboxylic acid 4-isopropyl-benzylamide |
| 53 | 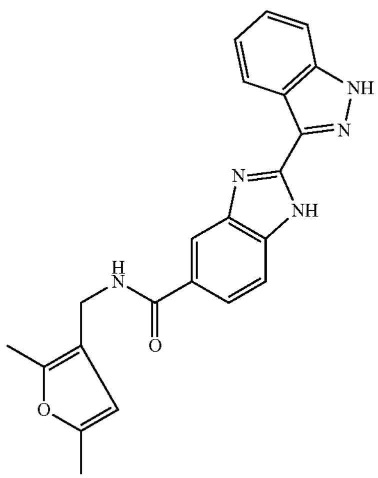 | MFCD02677701 | C22H19N5O2 | 385.43 | 386 | [M + H]⁺ | 3.19 | 2-(1H-Indazol-3-yl)-1H-benzoimidazole-5-carboxylic acid (2,5-dimethyl-furan-3-ylmethyl)-amide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 54 | 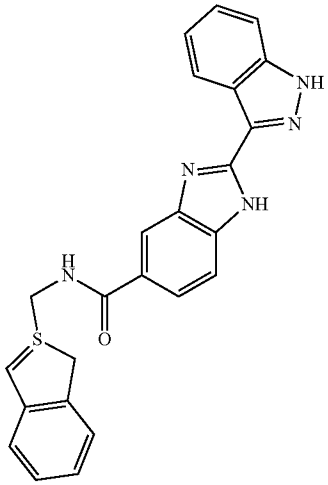 | MFCD00965305 | C24H17N5OS | 423.50 | 424 | [M + H]⁺ | 3.38 | 2-(1H-Indazol-3-yl)-1H-benzoimidazole-5-carboxylic acid (benzo[b]thiophen-2-ylmethyl)-amide |
| 55 | 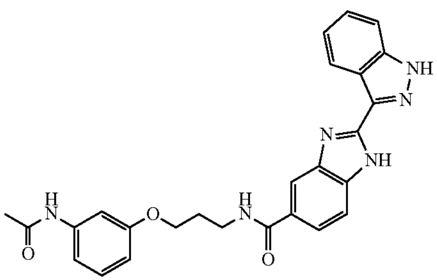 | MFCD00277760 | C26H24N6O3 | 468.52 | 469 | [M + H]⁺ | 2.92 | 2-(1H-Indazol-3-yl)-1H-benzoimidazole-5-carboxylic acid [3-(3-acetylamino-phenoxy)-propyl]-amide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 56 | 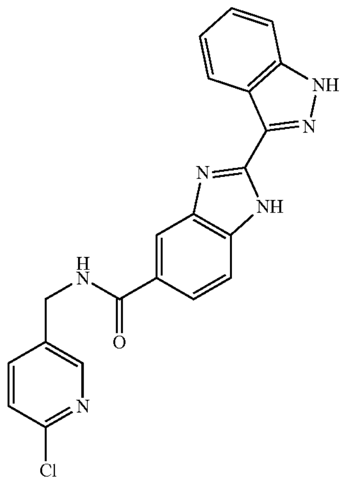 | MFCD00673153 | C21H15ClN6O | 402.84 | 403 | [M + H]⁺ | 2.92 | 2-(1H-Indazol-3-yl)-1H-benzoimidazole-5-carboxylic acid (6-chloro-pyridin-3-ylmethyl)-amide |
| 57 | 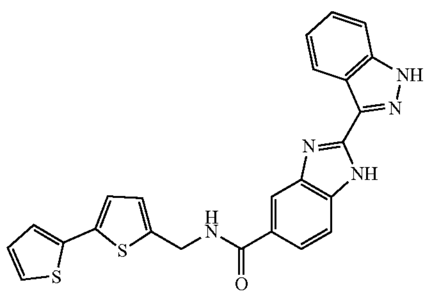 | MFCD00110111 | C24H17N5OS2 | 455.56 | 456 | [M + H]⁺ | 3.47 | 2-(1H-Indazol-3-yl)-1H-benzoimidazole-5-carboxylic acid ([2,2']bithiophenyl-5-ylmethyl)-amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 58 | chemistry 40 | MFCD00728869 | C24H19N5O2 | 409.45 | 410 [M + H]⁺ | 3.07 | 2-(1H-Indazol-3-yl)-1H-benzoimidazole-5-carboxylic acid (2,3-dihydro-benzofuran-5-ylmethyl)-amide |
| 59 | chemistry 41 | MFCD01861472 | C23H16N6O | 392.42 | 393 [M + H]⁺ | 3.03 | 2-(1H-Indazol-3-yl)-1H-benzoimidazole-5-carboxylic acid 4-cyano-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 60 | chemistry 42 | MFCD02677713 | C24H16ClN5OS | 457.94 | 458 | [M + H]⁺ | 3.55 | 2-(1H-Indazol-3-yl)-1H-benzoimidazole-5-carboxylic acid (5-chloro-benzo[b]thiophen-3-ylmethyl)-amide |
| 61 | 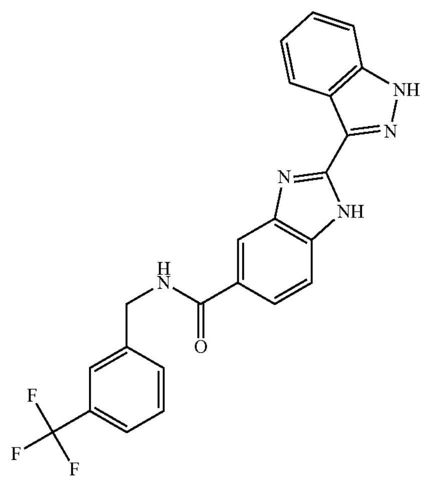 | MFCD00008117 | C23H16F3N5O | 435.41 | 436 | [M + H]⁺ | 3.41 | 2-(1H-Indazol-3-yl)-1H-benzoimidazole-5-carboxylic acid 3-trifluoromethyl-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 62 | 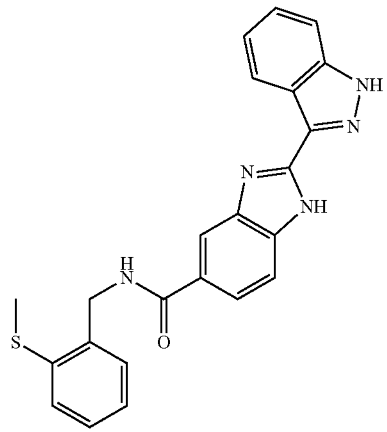 | MFCD00831039 | C23H19N5OS | 413.50 | 414 | [M + H]⁺ | 3.26 | 2-(1H-Indazol-3-yl)-1H-benzoimidazole-5-carboxylic acid 2-methylsulfanyl-benzylamide |
| 63 | chemistry 46 | MFCD00176440 | C24H17N5OS | 423.50 | 424 | [M + H]⁺ | 3.38 | 2-(1H-Indazol-3-yl)-1H-benzoimidazole-5-carboxylic acid (benzo[b]thiophen-3-ylmethyl)-amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 64 | 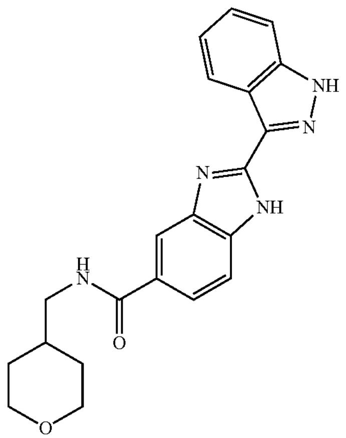 | MFCD02179435 | C21H21N5O2 | 375.43 | 376 [M + H]⁺ | 2.65 | 2-(1H-Indazol-3-yl)-1H-benzoimidazole-5-carboxylic acid (tetrahydro-pyran-4-ylmethyl)-amide |
| 65 | | MFCD00203985 | C24H19N5O3 | 425.45 | 426 [M + H]⁺ | 3.28 | 2-(1H-Indazol-3-yl)-1H-benzoimidazole-5-carboxylic acid (2,3-dihydro-benzo[1,4]dioxin-2-ylmethyl)-amide | chemistry 48

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 66 | chemistry 49 | MFCD02681983 | C20H15N5O2 | 357.37 | 358 [M + H]⁺ | 2.92 | 2-(1H-Indazol-3-yl)-1H-benzoimidazole-5-carboxylic acid (furan-3-ylmethyl)-amide |
| 67 | chemistry 50 | MFCD00136280 | C22H16N6O3 | 412.41 | 413 [M + H]⁺ | 3.14 | 2-(1H-Indazol-3-yl)-1H-benzoimidazole-5-carboxylic acid 2-nitro-benzylamide |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 68 | 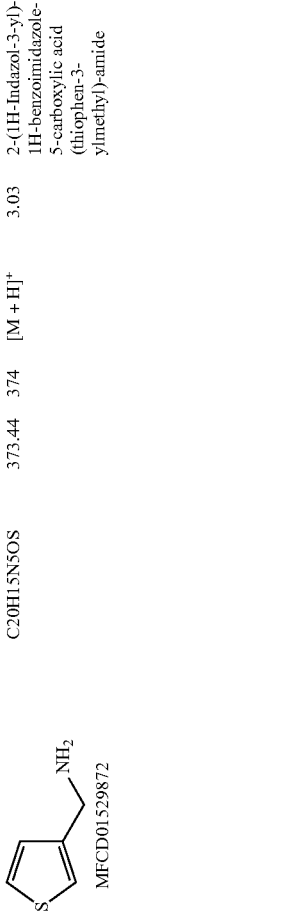 chemistry 51 | 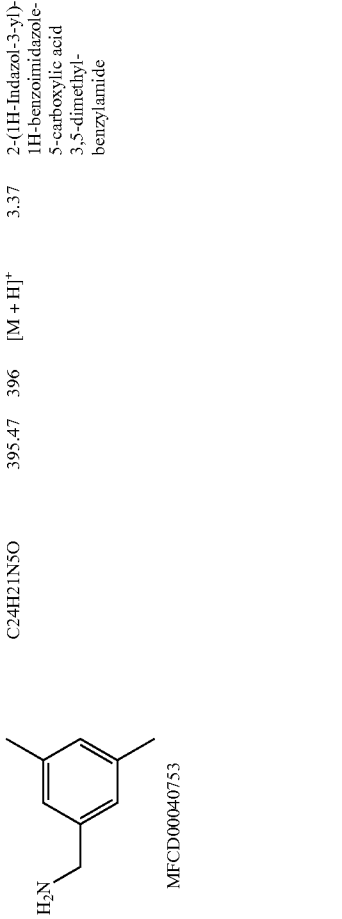 MFCD01529872 | C20H15N5OS | 373.44 | 374 | [M + H]⁺ | 3.03 | 2-(1H-Indazol-3-yl)-1H-benzoimidazole-5-carboxylic acid (thiophen-3-ylmethyl)-amide |
| 69 | 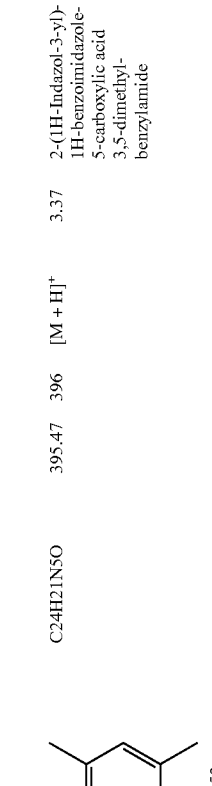 chemistry 52 | 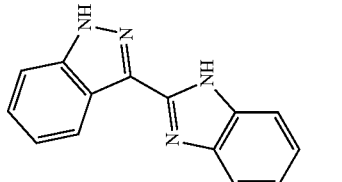 MFCD00040753 | C24H21N5O | 395.47 | 396 | [M + H]⁺ | 3.37 | 2-(1H-Indazol-3-yl)-1H-benzoimidazole-5-carboxylic acid 3,5-dimethyl-benzylamide |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 70 | 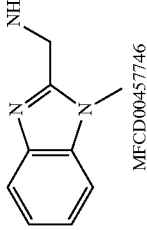 chemistry 53 | MFCD00457746 | C24H19N7O | 421.46 | 422 | [M + H]⁺ | 2.61 | 2-(1H-Indazol-3-yl)-1H-benzoimidazole-5-carboxylic acid (1-methyl-1H-benzoimidazol-2-ylmethyl)-amide |
| 71 | 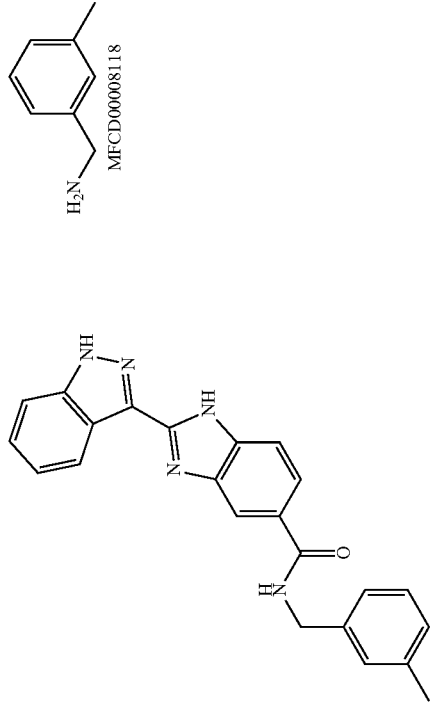 chemistry 54 | MFCD00008118 | C23H19N5O | 381.44 | 382 | [M + H]⁺ | 3.24 | 2-(1H-Indazol-3-yl)-1H-benzoimidazole-5-carboxylic acid 3-methyl-benzylamide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 72 | chemistry 55 | MFCD00040752 | C22H16ClN5O | 401.86 | 402 [M + H]⁺ | 3.29 | 2-(1H-Indazol-3-yl)-1H-benzoimidazole-5-carboxylic acid 3-chloro-benzylamide |
| 73 | 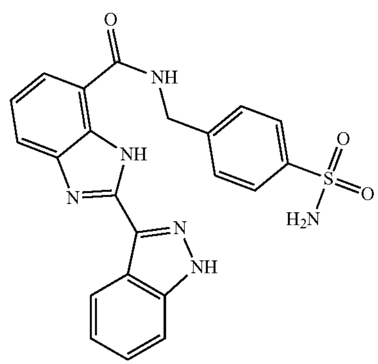 | HCl MFCD00013005 | C22H18N6O3S | 446.49 | 447 [M + H]⁺ | 3.07 | 2-(1H-Indazol-3-yl)-3H-benzoimidazole-4-carboxylic acid 4-sulfamoyl-benzylamide |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 74 | chemistry 57 | MFCD00008221 | C20H21N5O2 | 363.42 | 364 | [M + H]⁺ | 3.45 | 2-(1H-Indazol-3-yl)-3H-benzoimidazole-4-carboxylic acid (3-ethoxy-propyl)-amide |
| 75 | chemistry 58 | 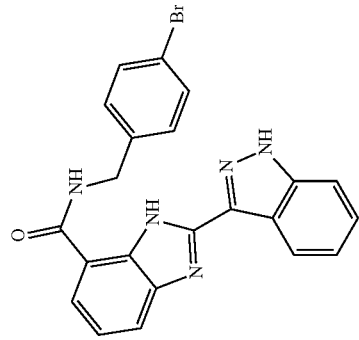 MFCD00047931 | C22H16BrN5O | 446.31 | 447 | [M + H]⁺ | 4.38 | 2-(1H-Indazol-3-yl)-3H-benzoimidazole-4-carboxylic acid 4-bromo-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 76 | 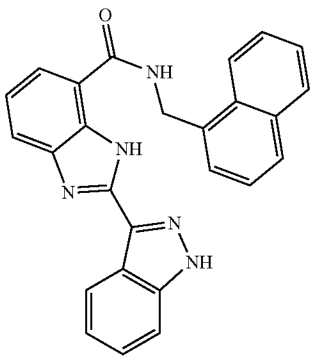 | MFCD00004048 | C26H19N5O | 417.47 | 418 | [M + H]⁺ | 4.4 | 2-(1H-Indazol-3-yl)-3H-benzoimidazole-4-carboxylic acid (naphthalen-1-ylmethyl)-amide |
| 77 | 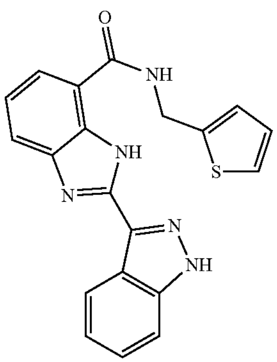 | MFCD00005460 | C20H15N5OS | 373.44 | 374 | [M + H]⁺ | 3.93 | 2-(1H-Indazol-3-yl)-3H-benzoimidazole-4-carboxylic acid (thiophen-2-ylmethyl)-amide |

TABLE 3-continued

| Example number | STRUCTURE | RNH₂ or RB(OH)₂ | Molecular Formula | MW | MS Characteristic Method | | time (minutes) | Nomenclature |
|---|---|---|---|---|---|---|---|---|
| 78 | 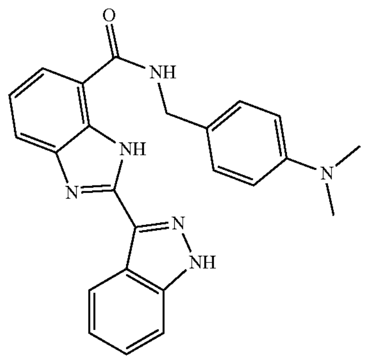 | HCl / MFCD00012862 | C24H22N6O | 410.48 | 411 | [M + H]⁺ | 2.93 | 2-(1H-Indazol-3-yl)-3H-benzoimidazole-4-carboxylic acid 4-dimethylamino-benzylamide |
| 79 | 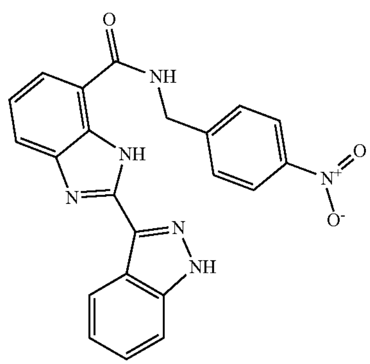 | HCl / MFCD00012863 | C22H16N6O3 | 412.41 | 413 | [M + H]⁺ | 3.87 | 2-(1H-Indazol-3-yl)-3H-benzoimidazole-4-carboxylic acid 4-nitro-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 80 | 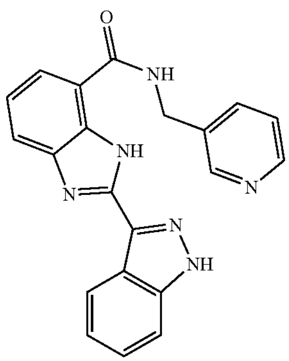 | MFCD00006412 | C21H16N6O | 368.40 | 369 | [M + H]⁺ | 2.4 | 2-(1H-Indazol-3-yl)-3H-benzoimidazole-4-carboxylic acid (pyridin-3-ylmethyl)-amide |
| 81 | chemistry 65 | MFCD01026119 | C22H16BrN5O | 446.31 | 447 | [M + H]⁺ | 4.18 | 2-(1H-Indazol-3-yl)-3H-benzoimidazole-4-carboxylic acid 3-bromo-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 82 | 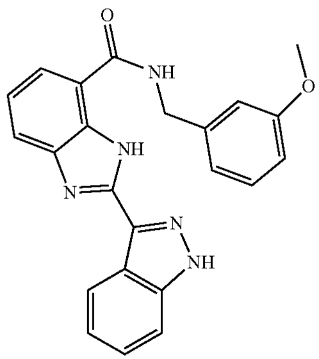 | MFCD00008115 | C23H19N5O2 | 397.44 | 398 | [M + H]⁺ | 3.95 | 2-(1H-Indazol-3-yl)-3H-benzoimidazole-4-carboxylic acid 3-methoxy-benzylamide |
| 83 | 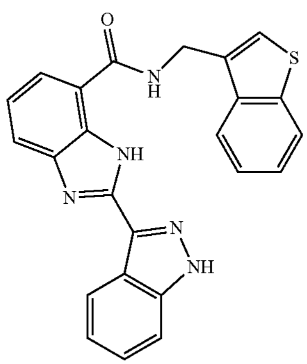 | MFCD00176440 | C24H17N5OS | 423.50 | 424 | [M + H]⁺ | 4.68 | 2-(1H-Indazol-3-yl)-3H-benzoimidazole-4-carboxylic acid (benzo[b]thiophen-3-ylmethyl)-amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 84 | 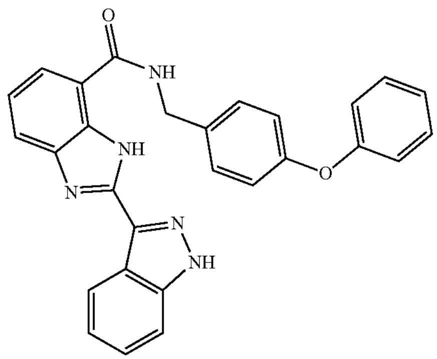 | MFCD01310836 | C28H21N5O2 | 459.51 | 460 [M + H]⁺ | 4.55 | 2-(1H-Indazol-3-yl)-3H-benzoimidazole-4-carboxylic acid 4-phenoxy-benzylamide |
| 85 | 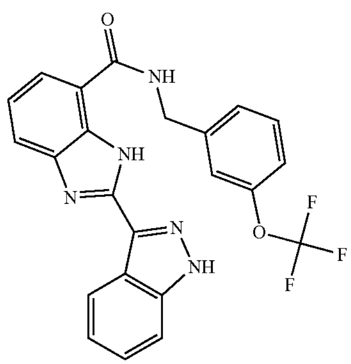 | MFCD00061267 | C23H16F3N5O2 | 451.41 | 452 [M + H]⁺ | 4.43 | 2-(1H-Indazol-3-yl)-3H-benzoimidazole-4-carboxylic acid 3-trifluoromethoxy-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 86 | 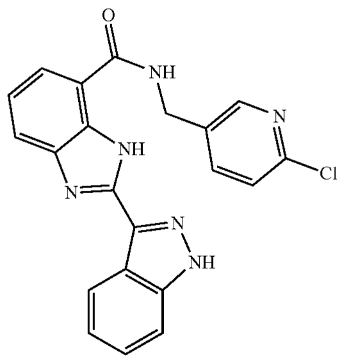 | MFCD00673153 | C21H15ClN6O | 402.84 | 403 | [M + H]⁺ | 3.9 | 2-(1H-Indazol-3-yl)-3H-benzoimidazole-4-carboxylic acid (6-chloro-pyridin-3-ylmethyl)-amide |
| 87 | 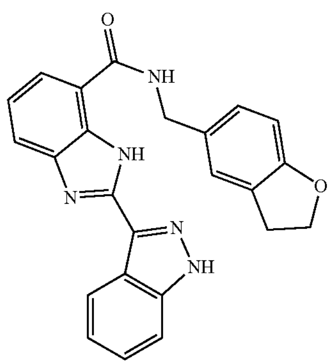 | MFCD00728869 | C24H19N5O2 | 409.45 | 410 | [M + H]⁺ | 3.9 | 2-(1H-Indazol-3-yl)-3H-benzoimidazole-4-carboxylic acid (2,3-dihydro-benzofuran-5-ylmethyl)-amide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 88 | 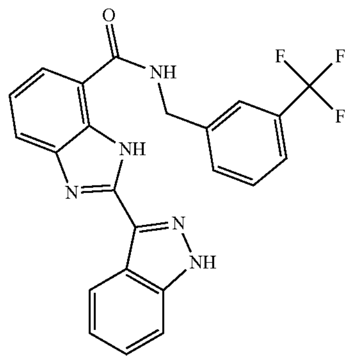 | MFCD00008117 | C23H16F3N5O | 435.41 | 436 | [M + H]⁺ | 4.3 | 2-(1H-Indazol-3-yl)-3H-benzoimidazole-4-carboxylic acid 3-trifluoromethyl-benzylamide |
| 89 chemistry 73 | | MFCD00831039 | C23H19N5OS | 413.50 | 414 | [M + H]⁺ | 3.98 | 2-(1H-Indazol-3-yl)-3H-benzoimidazole-4-carboxylic acid 2-methylsulfanyl-benzylamide |

TABLE 3-continued

| Example number | STRUCTURE | RNH$_2$ or RB(OH)$_2$ | Molecular Formula | MW | MS Characteristic | Method | time (minutes) | Nomenclature |
|---|---|---|---|---|---|---|---|---|
| 90 | 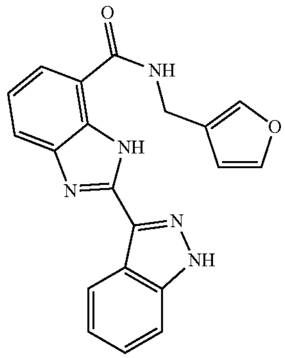 | MFCD02681983 | C20H15N5O2 | 357.37 | 358 | [M + H]$^+$ | 3.68 | 2-(1H-Indazol-3-yl)-3H-benzoimidazole-4-carboxylic acid (furan-3-ylmethyl)-amide |
| 91 | chemistry 75 | MFCD00136280 | C22H16N6O3 | 412.41 | 413 | [M + H]$^+$ | 3.95 | 2-(1H-Indazol-3-yl)-3H-benzoimidazole-4-carboxylic acid 2-nitro-benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 92 | 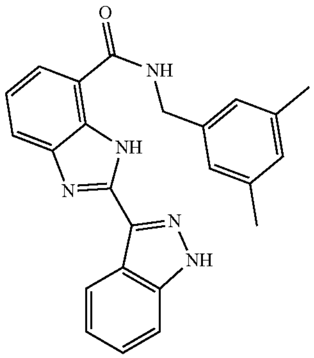 | MFCD00040753 (3,5-dimethylbenzylamine) | C24H21N5O | 395.47 | 396 | [M + H]⁺ | 4.45 | 2-(1H-Indazol-3-yl)-3H-benzoimidazole-4-carboxylic acid 3,5-dimethyl-benzylamide |
| 93 | 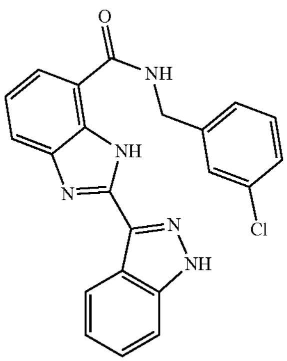 | MFCD00040752 (3-chlorobenzylamine) | C22H16ClN5O | 401.86 | 402 | [M + H]⁺ | 5.03 | 2-(1H-Indazol-3-yl)-3H-benzoimidazole-4-carboxylic acid 3-chloro-benzylamide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 94 | 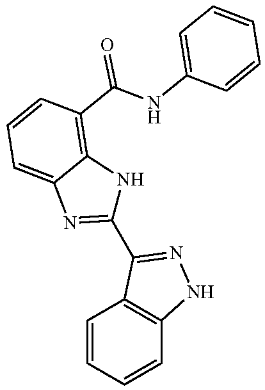 | MFCD00007629 | C21H15N5O | 353.38 | 354 [M + H]⁺ | 4.27 | 2-(1H-Indazol-3-yl)-3H-benzoimidazole-4-carboxylic acid phenylamide |
| 95 | 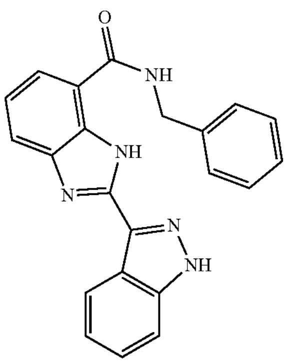 | MFCD00008106 | C22H17N5O | 367.41 | 368 [M + H]⁺ | 3.94 | 2-(1H-Indazol-3-yl)-3H-benzoimidazole-4-carboxylic acid benzylamide |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 96 | chemistry 54 | MFCD00008184 | C23H19N5O | 381.44 | 382 | [M + H]+ | 4.01 | 2-(1H-Indazol-3-yl)-3H-benzoimidazole-4-carboxylic acid phenethyl-amide |
| 97 | chemistry 121 | MFCD00002103 | C20H14N4 | 310.36 | 311 | [M + H]+ | 3.14 | 3-(6-Phenyl-1H-benzoimidazol-2-yl)-2H-indazole |

TABLE 3-continued
| Example number | STRUCTURE | RNH$_2$ or RB(OH)$_2$ | Molecular Formula | MW | MS Characteristic | Method | time (minutes) | Nomenclature |
|---|---|---|---|---|---|---|---|---|
| 98 | 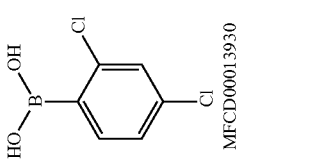 chemistry 124 | MFCD00013930 | C20H12Cl2N4 | 379.25 | 379 | [M + H]+ | 3.63 | 3-[6-(2,4-Dichloro-phenyl)-1H-benzoimidazol-2-yl]-2H-indazole |
| 99 | 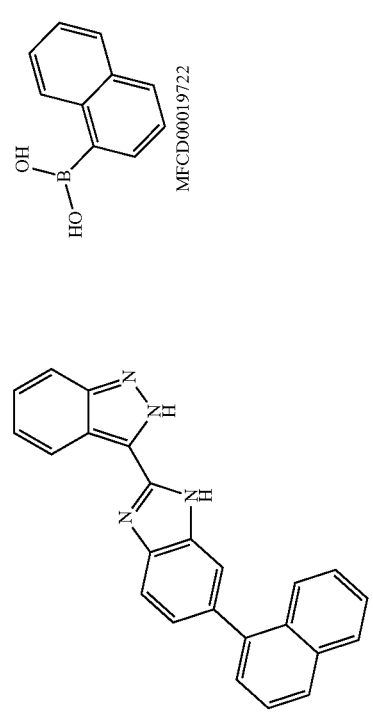 chemistry 125 | MFCD00019722 | C24H16N4 | 360.42 | 361 | [M + H]+ | 3.51 | 3-(6-Naphthalen-1-yl-1H-benzoimidazol-2-yl)-2H-indazole |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 100 | 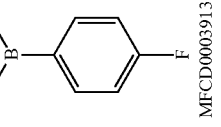 chemistry 126 | 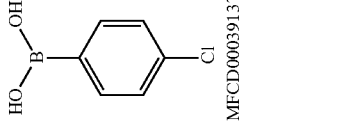 MFCD00039136 | C20H13FN4 | 328.35 | 329 | [M + H]+ | 3.21 | 3-[6-(4-Fluoro-phenyl)-1H-benzoimidazol-2-yl]-2H-indazole |
| 101 | chemistry 127 | MFCD00039137 | C20H13ClN4 | 344.805 | 345 | [M + H+ | 3.44 | 3-[6-(4-Chloro-phenyl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 102 | chemistry 128 | MFCD00039139 | C21H16N4O | 340.386 | 341 | [M + H]+ | 3.14 | 3-[6-(4-Methoxy-phenyl)-1H-benzoimidazol-2-yl]-2H-indazole |
| 103 | chemistry 129 | MFCD00051800 | C20H12ClFN4 | 362.795 | 362 | [M + H]+ | 3.51 | 3-[6-(3-Chloro-4-fluoro-phenyl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 104 | chemistry 130 | MFCD00051935 | C20H12Cl2N4 | 379.25 | [378-380] | [M + H]+ | 3.81 | 3-[6-(3,5-Dichlorophenyl)-1H-benzoimidazol-2-yl]-2H-indazole |
| 105 | chemistry 132 | MFCD00093039 | C26H16N4S2 | 448.57 | 449 | [M + H]+ | 3.91 | 3-(6-Thianthren-1-yl-1H-benzoimidazol-2-yl)-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 106 | chemistry 133 | MFCD00093311 | C26H18N4 | 386.458 | 387 | [M + H]+ | 3.78 | 3-(6-Biphenyl-4-yl-1H-benzoimidazol-2-yl)-2H-indazole |
| 107 | chemistry 137 | MFCD00039138 | C21H16N4 | 324.387 | 324 | [M] | 3.38 | 3-(6-p-Tolyl-1H-benzoimidazol-2-yl)-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 108 | chemistry 138 | MFCD00040198 | C21H16N4 | 324.387 | 324 | [M + H]+ | 3.41 | 3-(6-m-Tolyl-1H-benzoimidazol-2-yl)-2H-indazole |
| 109 | chemistry 139 | MFCD00093526 | C21H16N4 | 324.387 | 325 | [M + H]+ | 3.41 | 3-(6-o-Tolyl-1H-benzoimidazol-2-yl)-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 110 | chemistry 140 | MFCD0015851 | C18H12N4S | 316.386 | 317 | [M + H]+ | 3.13 | 3-(6-Thiophen-3-yl-1H-benzoimidazol-2-yl)-2H-indazole |
| 111 | chemistry 141 | MFCD0015854 | C21H13F3N4 | 378.357 | 379 | [M + H]+ | 3.65 | 3-[6-(3-Trifluoromethyl-phenyl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 112 | chemistry 142 | MFCD00151855 | C21H13F3N4 | 378.357 | 379 | [M + H]+ | 3.68 | 3-[6-(4-Trifluoromethyl-phenyl)-1H-benzoimidazol-2-yl]-2H-indazole |
| 113 | chemistry 143 | MFCD00161354 | C20H13ClN4 | 344.805 | 345 | [M + H]+ | 3.55 | 3-[6-(3-Chloro-phenyl)-1H-benzoimidazol-2-yl]-2H-indazole |

TABLE 3-continued
| Example number | STRUCTURE | RNH₂ or RB(OH)₂ | Molecular Formula | MW | MS Characteristic | Method | time (minutes) | Nomenclature |
|---|---|---|---|---|---|---|---|---|
| 114 | 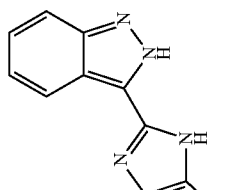 chemistry 144 | 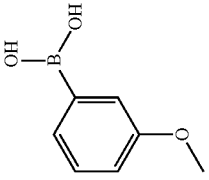 MFCD00161359 | C21H16N4O | 340.386 | 341 | [M + H]+ | 3.41 | 3-[6-(3-Methoxy-phenyl)-1H-benzoimidazol-2-yl]-2H-indazole |
| 115 |  chemistry 145 | 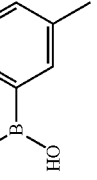 MFCD00185689 | C22H18N4 | 338.414 | 339 | [M + H]+ | 3.39 | 3-[6-(3,5-Dimethyl-phenyl)-1H-benzoimidazol-2-yl]-2H-indazole |

TABLE 3-continued
| Example number | STRUCTURE | RNH₂ or RB(OH)₂ | Molecular Formula | MW | MS Characteristic Method | time (minutes) | Nomenclature |
|---|---|---|---|---|---|---|---|
| 116 |  chemistry 146 | MFCD01009694 | C22H18N4 | 338.414 | 339 [M + H]+ | 3.55 | 3-[6-(3,4-Dimethyl-phenyl)-1H-benzoimidazol-2-yl]-2H-indazole |
| 117 |  chemistry 147 | MFCD01009695 | C21H14N4O2 | 354.369 | 354 [M] | 3.18 | 3-(6-Benzo[1,3]dioxol-5-yl-1H-benzoimidazol-2-yl)-2H-indazole |

TABLE 3-continued
| Example number | STRUCTURE | RNH$_2$ or RB(OH)$_2$ | Molecular Formula | MW | MS Characteristic Method | time (minutes) | Nomenclature |
|---|---|---|---|---|---|---|---|
| 118 |  chemistry 148 | MFCD01009697 | C24H22N4 | 366.468 | 367 [M + H]+ | 3.95 | 3-[6-(4-tert-Butyl-phenyl)-1H-benzoimidazol-2-yl]-2H-indazole |
| 119 | 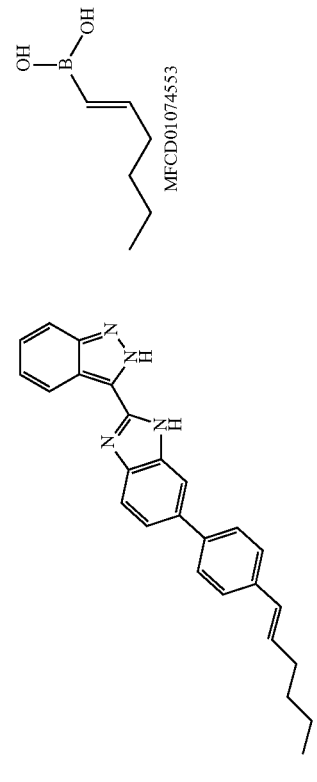 chemistry 149 | MFCD01074553 | C20H20N4 | 316.408 | 317 [M + H]+ | 3.72 | 3-(6-Hex-1-enyl-1H-benzoimidazol-2-yl)-2H-indazole |

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 120 | chemistry 150 | MFCD01074574 | C22H18N4O2 | 370.412 | 371 | [M + H]+ | 3.00 | 3-[6-(3,4-Dimethoxy-phenyl)-1H-benzoimidazol-2-yl]-2H-indazole |
| 121 | chemistry 152 | MFCD01074603 | C20H14N4O | 326.359 | 327 | [M + H]+ | 2.92 | 3-[2-(2H-Indazol-3-yl)-3H-benzoimidazol-5-yl]-phenol |

TABLE 3-continued
| Example number | STRUCTURE | RNH$_2$ or RB(OH)$_2$ | Molecular Formula | MW | MS Characteristic | Method | time (minutes) | Nomenclature |
|---|---|---|---|---|---|---|---|---|
| 122 | 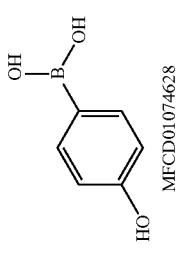 chemistry 153 | 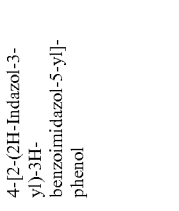 MFCD01074628 | C20H14N4O | 326.359 | 327 | [M + H]+ | 2.84 | 4-[2-(2H-Indazol-3-yl)-3H-benzoimidazol-5-yl]-phenol |
| 123 | 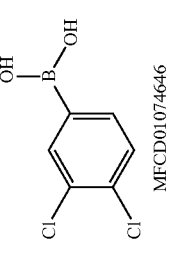 chemistry 154 | 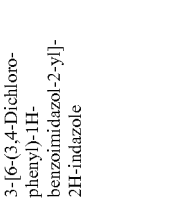 MFCD01074646 | C20H12Cl2N4 | 379.25 | 378 | [M + H]+ | 3.82 | 3-[6-(3,4-Dichloro-phenyl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 124 | chemistry 157 | MFCD01074648 | C21H13F3N4O | 394.356 | 395 | [M + H]+ | 3.72 | 3-[6-(4-Trifluoromethoxy-phenyl)-1H-benzoimidazol-2-yl]-2H-indazole |
| 125 | chemistry 159 | MFCD01074667 | C22H16N4O | 352.397 | 353 | [M + H]+ | 3.08 | 1-{4-[2-(2H-Indazol-3-yl)-3H-benzoimidazol-5-yl]-phenyl}-ethanone |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 126 | chemistry 160 | MFCD01075674 | C22H14N4S | 366.446 | 367 | [M + H]+ | 3.82 | 3-(6-Benzo[b]thiophen-2-yl-1H-benzoimidazol-2-yl)-2H-indazole |
| 127 | chemistry 161 | MFCD01075676 | C23H20N4O3 | 400.438 | 401 | [M + H]+ | 3.02 | 3-[6-(3,4,5-Trimethoxy-phenyl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 128 | chemistry 162 | MFCD01075681 | C20H14N4OS | 358.423 | 359 | [M + H]+ | 3.09 | 1-{5-[2-(2H-Indazol-3-yl)-3H-benzoimidazol-5-yl]-thiophen-2-yl}-ethanone |
| 129 | chemistry 163 | MFCD01074678 | C22H16N4O | 352.397 | 353 | [M + H]+ | 3.05 | 1-{3-[2-(2H-Indazol-3-yl)-3H-benzoimidazol-5-yl]-phenyl}-ethanone |

TABLE 3-continued

| Example number | STRUCTURE | RNH$_2$ or RB(OH)$_2$ | Molecular Formula | MW | MS Characteristic | Method | time (minutes) | Nomenclature |
|---|---|---|---|---|---|---|---|---|
| 130 | 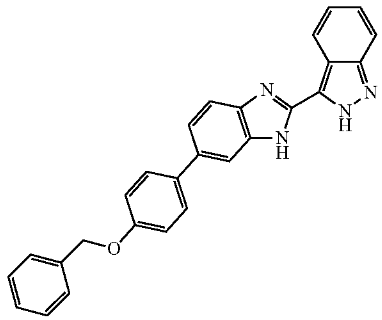 | MFCD01075705 | C27H20N4O | 416.484 | 417 | [M + H]+ | 3.75 | 3-[6-(4-Benzyloxy-phenyl)-1H-benzoimidazol-2-yl]-2H-indazole |
| 131 | chemistry 165 | MFCD01075707 | C26H17FN4 | 404.448 | 405 | [M + H]+ | 4.02 | 3-[6-(2-Fluoro-biphenyl-4-yl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 132 | chemistry 167 | MFCD01114669 | C22H14N4S | 366.446 | 367 | [M + H]+ | 3.55 | 3-(6-Benzo[b]thiophen-3-yl-1H-benzoimidazol-2-yl)-2H-indazole |
| 133 | chemistry 168 | MFCD01317846 | C21H16N4O | 340.386 | 341 | [M + H]+ | 2.79 | {3-[2-(2H-Indazol-3-yl)-3H-benzoimidazol-5-yl]-phenyl}-methanol |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 134 | chemistry 171 | MFCD01318146 | C22H18N4S | 370.478 | 371 [M + H]+ | 3.62 | 3-[6-(4-Ethylsulfanyl-phenyl)-1H-benzoimidazol-2-yl]-2H-indazole |
| 135 | chemistry 176 | MFCD01318998 | C20H12F2N4 | 346.34 | 347 [M + H]+ | 3.29 | 3-[6-(2,4-Difluoro-phenyl)-1H-benzoimidazol-2-yl]-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 136 | chemistry 178 | MFCD01320697 | C21H13F3N4O | 394.356 | 395 | [M + H]+ | 3.66 | 3-[6-(3-Trifluoromethoxy-phenyl)-1H-benzoimidazol-2-yl]-2H-indazole |
| 137 | chemistry 183 | MFCD02093072 | C21H15FN4 | 342.377 | 343 | [M + H]+ | 3.36 | 3-[6-(4-Fluoro-2-methyl-phenyl)-1H-benzoimidazol-2-yl]-2H-indazole |
| 138 | chemistry 184 | MFCD02093725 | C22H15FN4 | 354.388 | 355 | [M + H]+ | 3.49 | 3-{6-[2-(4-Fluoro-phenyl)-vinyl]-1H-benzoimidazol-2-yl}-2H-indazole |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 139 | chemistry 185 | MFCD02093767 | C22H15ClN4 | 370.843 | 371 | [M + H]+ | 3.76 | 3-{6-[2-(4-Chloro-phenyl)-vinyl]-1H-benzoimidazol-2-yl]-2H-indazole |
| 140 | chemistry 188 | MFCD01318119 | C23H18N4O2 | 382.423 | 383 | [M + H]+ | 3.03 | 3-{4-[2-(2H-Indazol-3-yl)-3H-benzoimidazol-5-yl]-phenyl}-propionic acid |

TABLE 3-continued

| Example number | STRUCTURE | RNH₂ or RB(OH)₂ | Molecular Formula | MW | MS Characteristic | Method | time (minutes) | Nomenclature |
|---|---|---|---|---|---|---|---|---|
| 141 | chemistry 190 | MFCD00792672 | C21H16N4O | 340.386 | 341 | [M + H]+ | 2.72 | {4-[2-(2H-Indazol-3-yl)-3H-benzoimidazol-5-yl]-phenyl}-methanol |
| 142 | chemistry 191 | MFCD00799544 | C18H12N4O | 300.321 | 301 | [M + H]+ | 3.02 | 3-(6-Furan-2-yl-1H-benzoimidazol-2-yl)-2H-indazole |
| 143 | 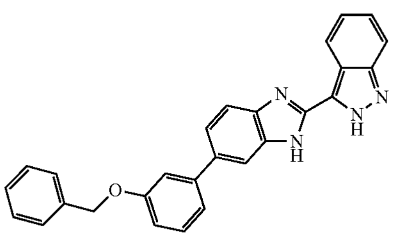 | MFCD02093063 | C27H20N4O | 416.484 | 417 | [M + H]+ | 3.93 | 3-(6-(3-Benzyloxy-phenyl)-1H-benzoimidazol-2-yl]-2H-indazole |

TABLE 3-continued

| Example number | STRUCTURE | RNH$_2$ or RB(OH)$_2$ | Molecular Formula | MW | MS Characteristic Method | time (minutes) | Nomenclature |
|---|---|---|---|---|---|---|---|
| 144 | chemistry 194 | MFCD01074614 | C23H20N4 | 352.441 | 353 [M + H]+ | 3.88 | 3-[6-(4-Isopropyl-phenyl)-1H-benzoimidazol-2-yl]-2H-indazole |
| 145 | chemistry 195 | MFCD01630820 | C21H16N4O2S | 388.449 | 389 [M + H]+ | 3.03 | 3-[6-(4-Methanesulfonyl-phenyl)-1H-benzoimidazol-2-yl]-2H-indazole |
| 146 | chemistry 84 | 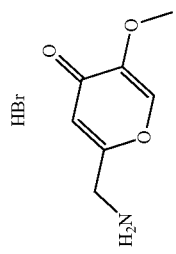 HBr 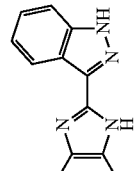 MFCD00223987 | C22H17N5O4 | 415.409 | 415 ,[M] | 2.31 | 2-(1H-Indazol-3-yl)-1H-benzoimidazole-5-carboxylic acid (tetrahydro-pyran-4-ylmethyl)-amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 147 | chemistry 85 | MFCD01861391 | C24H20N6O2 | 424.464 | 424 ,[M] | 2.58 | 2-(1H-Indazol-3-yl)-1H-benzoimidazole-5-carboxylic acid 4-acetylamino-benzylamide |
| 148 | chemistry 88 | MFCD00008104 | C16H13N5O | 291.314 | 291 ,[M] | 2.22 | 2-(1H-Indazol-3-yl)-1H-benzoimidazole-5-carboxylic acid methylamide |
| 149 | chemistry 89 | MFCD00008082 | C18H17N5O | 319.368 | 319 ,[M] | 2.63 | 2-(1H-Indazol-3-yl)-1H-benzoimidazole-5-carboxylic acid isopropylamide |
| 150 | chemistry 90 | MFCD00005972 | C19H17N5O2 | 347.378 | 347 ,[M] | 2.23 | [2-(1H-Indazol-3-yl)-1H-benzoimidazol-5-yl]-morpholin-4-yl-methanone |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 151 | 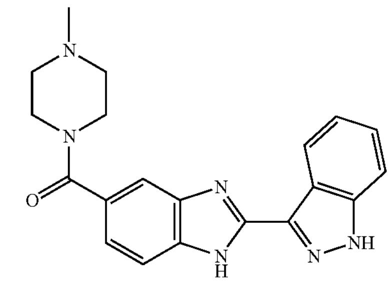 | MFCD00005966 | C20H20N6O | 360.421 | 361 [M + H]⁺ | 1.94 | [2-(1H-Indazol-3-yl)-1H-benzoimidazol-5-yl]-(4-methyl-piperazin-1-yl)-methanone |
| 152 | chemistry 96 | MFCD00008289 | C23H19N5O | 381.439 | 381 ,[M] | 3.45 | 2-(1H-Indazol-3-yl)-1H-benzoimidazole-5-carboxylic acid benzyl-methyl-amide |
| 153 | chemistry 97 | HCl MFCD00012858 | C22H16N6O3 | 412.409 | 412 ,[M] | 3.32 | 2-(1H-Indazol-3-yl)-1H-benzoimidazole-5-carboxylic acid 3-nitro-benzylamide |
| 154 | chemistry 98 | MFCD00008107 | C22H16FN5O | 385.402 | 385 ,[M] | 2.96 | 2-(1H-Indazol-3-yl)-1H-benzoimidazole-5-carboxylic acid 2-fluoro-benzylamide |
| 155 | chemistry 99 | MFCD00010142 | C22H15F2N5O | 403.392 | 403 ,[M] | 3.26 | 2-(1H-Indazol-3-yl)-1H-benzoimidazole-5-carboxylic acid 2,4-difluoro-benzylamide |

TABLE 3-continued

| Example number | STRUCTURE | RNH$_2$ or RB(OH)$_2$ | Molecular Formula | MW | MS Characteristic Method | time (minutes) | Nomenclature |
|---|---|---|---|---|---|---|---|
| 156 | chemistry 100 | MFCD00010144 | C22H15F2N5O | 403.392 | 403 ,[M] | 2.93 | 2-(1H-Indazol-3-yl)-1H-benzoimidazole-5-carboxylic acid 2,6-difluoro-benzylamide |
| 157 | chemistry 101 | HCl MFCD00143266 | C22H15BrFN5O | 464.303 | 464 ,[M] | 3.34 | 2-(1H-Indazol-3-yl)-1H-benzoimidazole-5-carboxylic acid 4-bromo-2-fluoro-benzylamide |
| 158 | chemistry 102 | HCl MFCD00143286 | C22H15ClFN5O | 419.847 | 419 ,[M] | 3.21 | 2-(1H-Indazol-3-yl)-1H-benzoimidazole-5-carboxylic acid 4-chloro-2-fluoro-benzylamide |
| 159 | chemistry 103 | MFCD00153076 | C22H15BrFN5O | 464.303 | 464 ,[M] | 3.31 | 2-(1H-Indazol-3-yl)-1H-benzoimidazole-5-carboxylic acid 4-bromo-2-fluoro-benzylamide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 160 | chemistry 104 | MFCD00010145 | C22H15F2N5O | 403.392 | 403 ,[M] | 3.64 | 2-(1H-Indazol-3-yl)-1H-benzoimidazole-5-carboxylic acid 3,4-difluoro-benzylamide |
| 161 | chemistry 105 | MFCD00236318 | C22H14F3N5O | 421.382 | 421 ,[M] | 3.35 | 2-(1H-Indazol-3-yl)-1H-benzoimidazole-5-carboxylic acid 3,4,5-trifluoro-benzylamide |
| 162 | chemistry 107 | MFCD02089424 | C28H20ClN5O | 477.955 | 477 ,[M] | 3.89 | 2-(1H-Indazol-3-yl)-1H-benzoimidazole-5-carboxylic acid (4'-chloro-biphenyl-4-ylmethyl)-amide |
| 163 | chemistry 108 | MFCD02089425 | C28H19Cl2N5O | 512.4 | 512 ,[M] | 4.36 | 2-(1H-Indazol-3-yl)-1H-benzoimidazole-5-carboxylic acid (3',5'-dichloro-biphenyl-4-ylmethyl)-amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 164 | chemistry 109 | MFCD02089427 | C28H20FN5O | 461.5 | 461 ,[M] | 3.6 | 2-(1H-Indazol-3-yl)-1H-benzoimidazole-5-carboxylic acid (4'-fluoro-biphenyl-4-ylmethyl)-amide |
| 165 | chemistry 110 | HCl MFCD01566531 | C22H16FN5O | 385.402 | 385 ,[M] | 2.94 | 2-(1H-Indazol-3-yl)-1H-benzoimidazole-5-carboxylic acid 2-fluoro-benzylamide |
| 166 | chemistry 111 | MFCD01631410 | C23H17F2N5O | 417.419 | 417 ,[M] | 3.14 | 2-(1H-Indazol-3-yl)-1H-benzoimidazole-5-carboxylic acid 2,6-difluor-3-methyl-benzylamide |
| 167 | chemistry 112 | MFCD00008109 | C22H15Cl2N5O | 436.302 | 436 ,[M] | 3.48 | 2-(1H-Indazol-3-yl)-1H-benzoimidazole-5-carboxylic acid 2,4-dichloro-benzylamide |
| 168 | chemistry 113 | MFCD00008121 | C22H16ClN5O | 401.857 | 401 ,[M] | 3.73 | 2-(1H-Indazol-3-yl)-1H-benzoimidazole-5-carboxylic acid 4-chloro-benzylamide |

TABLE 3-continued

| Example number | STRUCTURE | RNH2 or RB(OH)2 | Molecular Formula | MW | MS Characteristic Method | time (minutes) | Nomenclature |
|---|---|---|---|---|---|---|---|
| 169 | chemistry 114 | MFCD00047932 | C23H18ClN5O | 415.884 | 385 ,[M] | 3.52 | 2-(1H-Indazol-3-yl)-1H-benzoimidazole-5-carboxylic acid 4-chloro-2-methyl-benzylamide |
| 170 | chemistry 115 | MFCD00008120 | C22H16FN5O | 385.402 | 385 ,[M] | 3.09 | 2-(1H-Indazol-3-yl)-1H-benzoimidazole-5-carboxylic acid 4-fluoro-benzylamide |
| 171 | chemistry 116 | MFCD02089431 | C28H20ClN5O | 477.955 | 477 ,[M] | 3.9 | 2-(1H-Indazol-3-yl)-1H-benzoimidazole-5-carboxylic acid (2'-chloro-biphenyl-4-ylmethyl)-amide |

TABLE 3-continued

| Example number | STRUCTURE | RNH$_2$ or RB(OH)$_2$ | Molecular Formula | MW | MS Characteristic Method | time (minutes) | Nomenclature |
|---|---|---|---|---|---|---|---|
| 172 | chemistry 117 | MFCD01862649 | C22H15F3N6O | 436.397 | 436 [M] | 2.93 | 2-(1H-Indazol-3-yl)-1H-benzoimidazole-5-carboxylic acid (6-trifluoromethyl-pyridin-3-ylmethyl)-amide |
| 173 | chemistry 118 | MFCD02681984 | C25H18N6OS | 450.524 | 450 [M] | 2.67 | 2-(1H-Indazol-3-yl)-1H-benzoimidazole-5-carboxylic acid (5-pyridin-2-yl-thiophen-2-ylmethyl)-amide |
| 174 | chemistry 119 | MFCD00009819 | C21H19N7O | 385.431 | 385 [M] | 2.11 | 2-(1H-Indazol-3-yl)-1H-benzoimidazole-5-carboxylic acid (3-imidazol-1-yl-propyl)-amide |

TABLE 3-continued

| Example number | STRUCTURE | RNH₂ or RB(OH)₂ | Molecular Formula | MW | MS Characteristic Method | | time (minutes) | Nomenclature |
|---|---|---|---|---|---|---|---|---|
| 175 | 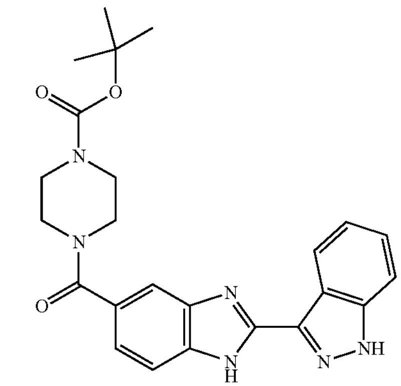 | MFCD00075265 | C24H26N6O3 | 446.511 | 447 | [M + H]⁺ | 3.11 | 4-[2-(1H-Indazol-3-yl)-1H-benzoimidazole-5-carbonyl]-piperazine-1-carboxylic acid tert-butyl ester |
| 176 | chemistry 121 | | | | 438 | [M + H]⁺ | | 2-(1H-Indazol-3-yl)-1H-benzoimidazole-5-carboxylic acid (2,6-difluoro-4-chloro-benzyl)amide |
| 177 | chemistry 122 | | | | 437 | [M + H]⁺ | | 2-(1H-Indazol-3-yl)-1H-benzoimidazole-5-carboxylic acid (2,4-dichloro-6-fluoro-benzyl)amide |
| 178 | chemistry | | | | 420 | [M + H]⁺ | | 2-(1H-Indazol-3-yl)-1H-benzoimidazole-5-carboxylic acid (3-fluoro-4-chloro-benzyl)amide |

TABLE 3-continued

| Example number | STRUCTURE | RNH₂ or RB(OH)₂ | Molecular Formula | MW | MS Characteristic Method | time (minutes) | Nomenclature |
|---|---|---|---|---|---|---|---|
| 179 | chemistry 124 | | | | 434 [M + H]⁺ | | 2-(1H-Indazol-3-yl)-1H-benzoimidazole-5-carboxylic acid (2-fluoro-4-chloro-6-methyl-benzyl)amide |
| 180 | chemistry 125 | | | | 399 [M + H]⁺ | | 2-(1H-Indazol-3-yl)-1H-benzoimidazole-5-carboxylic acid (6-methoxy-pyridin-3-ylmethyl)-amide |

The products of formula (I) of the present application can also be prepared according to the following process:

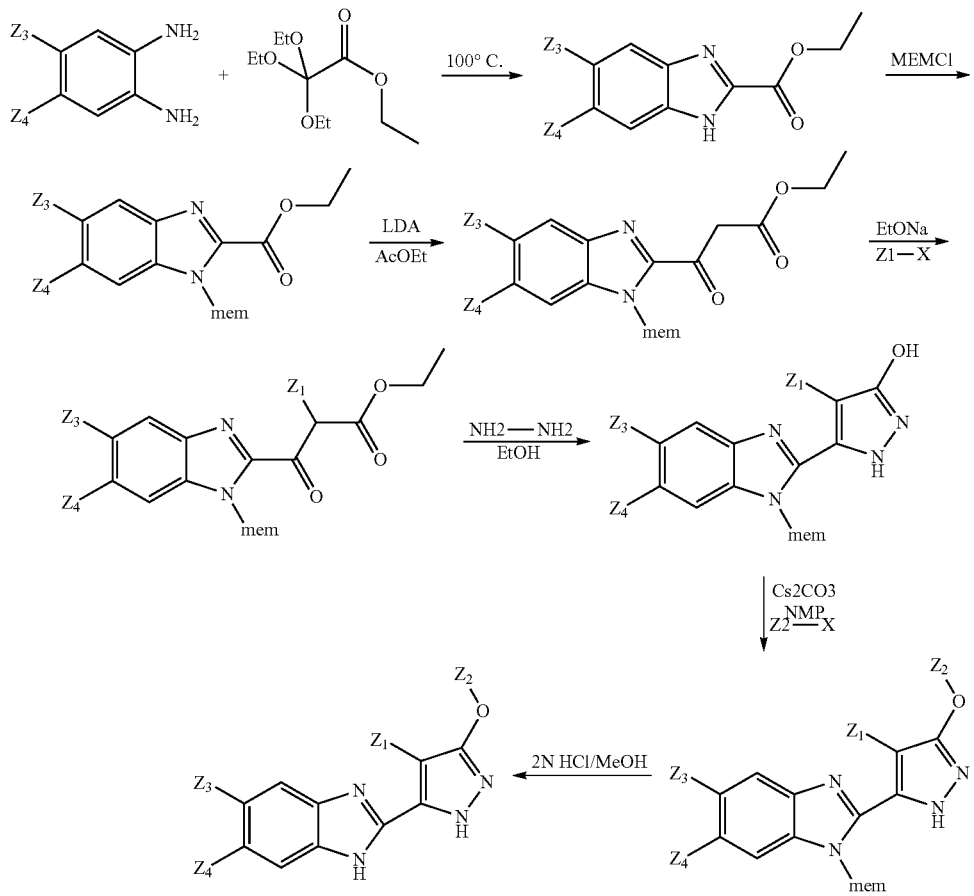

In the above scheme, the values of Z3 and Z4 are chosen from the values of R2 and R3 as defined above and the values of Z1 and —OZ2 are chosen from the values of X1, X2 or X3 with R1 representing a pyrazole radical, When Z1, Z3 and Z4 represent a hydrogen atom, it is possible in particular to prepare products of formula (I) of the present application according to the following synthesis scheme:

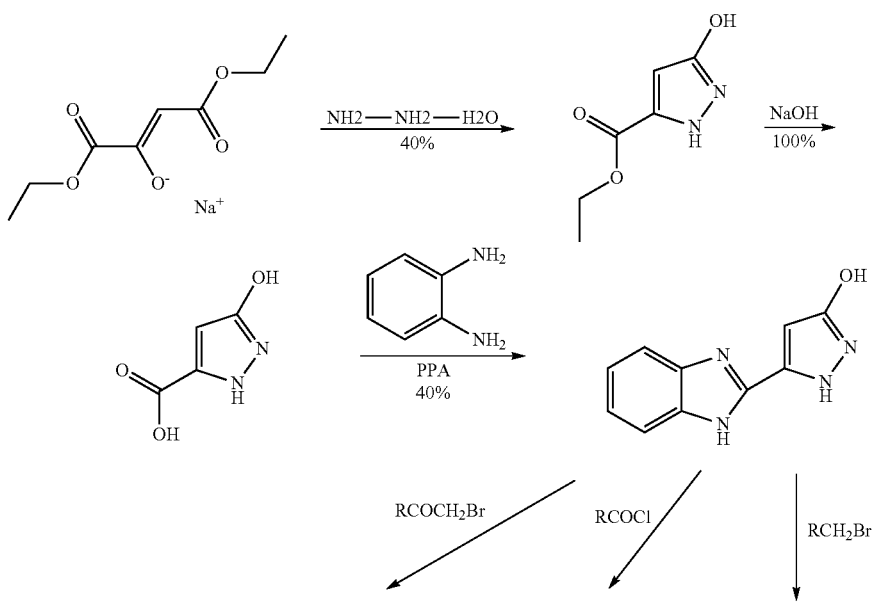

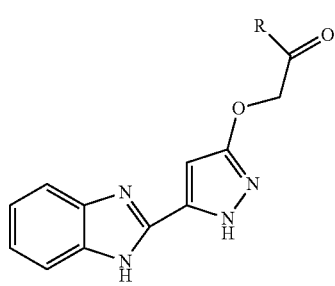
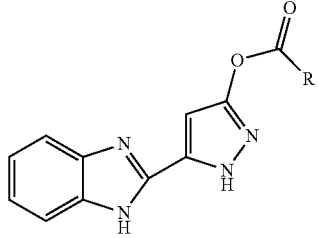
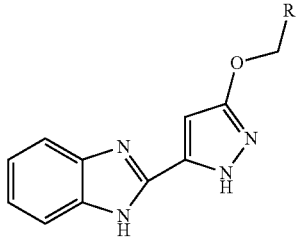

Products of formula (I) of the present application which constitute Examples 181 to 228 of the present application are represented in the table 4 hereinbelow: these products can be prepared according to the schemes indicated above and in particular the product of Example 181 can be prepared according to the procedure indicated below. The products of Examples 182 to 228 can be prepared like the product of Example 181.

EXAMPLE 181

2-[5-(benzyloxy)-2H-pyrazol-3-yl]-1H-benzoimidazole

Step 1: the cyclization is performed as in: Chem. Pharm. Bull., 31(4), 1228-1234 (1983); J. Org. Chem., 47(2), 214-221 (1982).

Step 2: To the crude ester 1.015 g in 50 ml of MeOH, was added 5.5 ml of 6N NaOH and the mixture is heated to reflux during 2 h. After evaporation of most of the methanol, the medium is cooled and conc. HCl is carefully added until pH=2. After further evaporation to dryness, the solid is triturated three times with 30 ml of MeOH/AcOEt 1/1 and the filtrate evaporated to give 0.875 g of light brown solid after desiccation.

LC-MS: [gradient acetonitrile/water 0.1% HCOOH; Xterra RP18 2.1×50 mm] retention time 0.53 minutes, MH+=129, 95% pure Step 3: To 3.5 g of PPA (polyphosphoric acid) were added 0.701 g of 1,2-phenylenediamine and 0.87 g of the step 2 acid. The mixture is heated to 150° C. during 1.5 h. After cooling, conc NH4OH was added until pH=3. The green precipitate is filtered, washed with water and then with acetone. After one night drying under vacuum at 50° C., 2.1 g of solid remains containing around 50% of mineral salts.

MS: EI M+=200.

Step 4: Ex. 181: To 80 mg of the step 3 solid in 4 ml of NMP were added caesium carbonate 137 mg and benzyl bromide 72 mg. After 2 h the mixture is hydrolysed with saturated KH2PO4 and extracted with AcOEt. After evaporation, the crude mixture was submitted to preparative LC-MS to give 8 mg of pure compound:

LC-MS: [gradient acetonitrile/water 0.1% HCOOH; Xterra RP18 2.1×50 mm] retention time 3.17 minutes, MH+=291.97% pure In the same way, the step 4 is carried out with 15 benzyl or allyl bromides, 15 α-bromocarbonyl compounds and 15 acid chlorides in either DMF or NMP to give the expected compounds of TABLE 4. Examples 181 to 228 of the present application are represented in TABLE 4.

TABLE 4

| CHEMISTRY | |
|---|---|
| 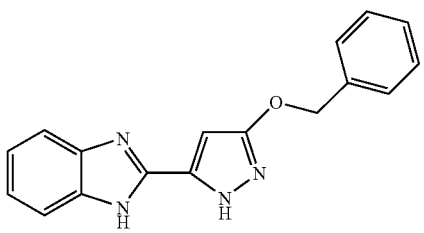 | 181 2-[5-(benzyloxy)-2H-pyrazol-3-yl]-1H-benzoimidazole |
| 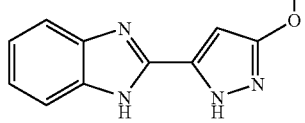 | 182 2-[5-(3-Phenyl-allyloxy)-2H-pyrazol-3-yl]-1H-benzoimidazole |

TABLE 4-continued

| CHEMISTRY | |
|---|---|
| | 183  2-[5-(2-Methyl-allyloxy)-2H-pyrazol-3-yl]-1H-benzoimidazole |
| | 184  2-[5-(3,7-Dimethyl-octa-2,6-dienyloxy)-2H-pyrazol-3-yl]-1H-benzoimidazole |
| | 185  2-[5-(3-Bromo-benzyloxy)-2H-pyrazol-3-yl]-1H-benzoimidazole |
| | 186  3-[5-(1H-Benzoimidazol-2-yl)-1H-pyrazol-3-yloxymethyl]-benzonitrile- |
| | 187  2-[5-(4-Trifluoromethyl-benzyloxy)-2H-pyrazol-3-yl]-1H-benzoimidazole |

TABLE 4-continued
| CHEMISTRY | | |
|---|---|---|
| 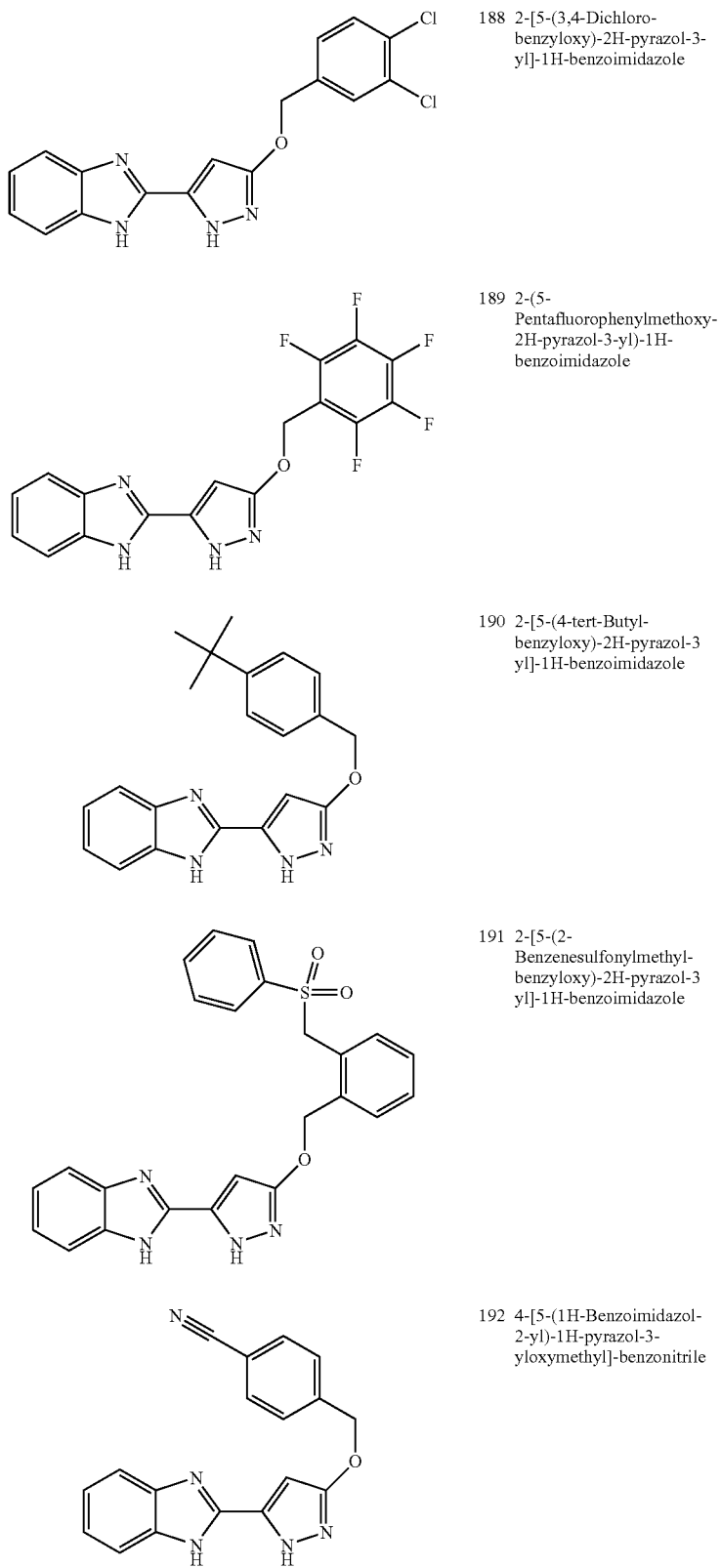 | 188 | 2-[5-(3,4-Dichloro-benzyloxy)-2H-pyrazol-3-yl]-1H-benzoimidazole |
| | 189 | 2-(5-Pentafluorophenylmethoxy-2H-pyrazol-3-yl)-1H-benzoimidazole |
| | 190 | 2-[5-(4-tert-Butyl-benzyloxy)-2H-pyrazol-3-yl]-1H-benzoimidazole |
| | 191 | 2-[5-(2-Benzenesulfonylmethyl-benzyloxy)-2H-pyrazol-3-yl]-1H-benzoimidazole |
| | 192 | 4-[5-(1H-Benzoimidazol-2-yl)-1H-pyrazol-3-yloxymethyl]-benzonitrile |

TABLE 4-continued
| CHEMISTRY | | |
|---|---|---|
| 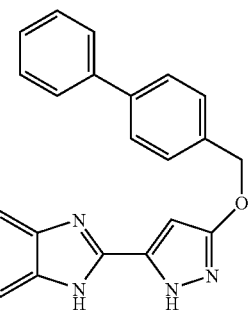 | 193 | 2-[5-(Biphenyl-4-ylmethoxy)-2H-pyrazol-3-yl]-1H-benzoimidazole |
| 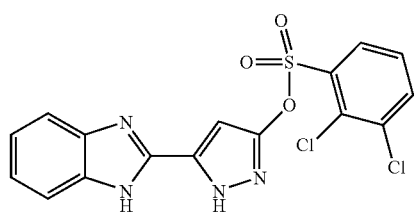 | 194 | 2,3-Dichloro-benzenesulfonic acid 5-(1H-benzoimidazol-2-yl)-1H-pyrazol-3-yl ester |
| 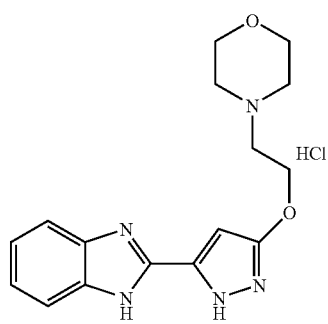 | 195 | 2-[5-(2-Morpholin-4-yl-ethoxy)-2H-pyrazol-3-yl]-1H-benzoimidazole |
| 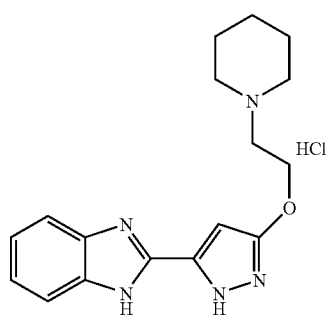 | 196 | 2-[5-(2-Piperidin-1-yl-ethoxy)-2H-pyrazol-3-yl]-1H-benzoimidazole |
| 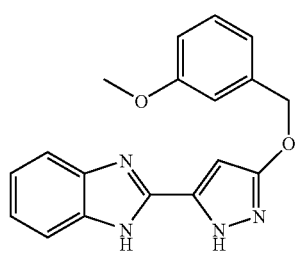 | 197 | 2-[5-(3-Methoxy-benzyloxy)-2H-pyrazol-3-yl]-1H-benzoimidazole |

TABLE 4-continued
| CHEMISTRY | | |
|---|---|---|
| 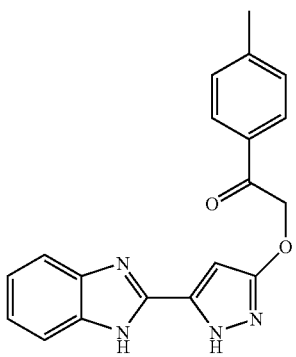 | 198 | 2-[5-(1H-Benzoimidazol-2-yl)-1H-pyrazol-3-yloxy]-1-p-tolyl-ethanone |
| 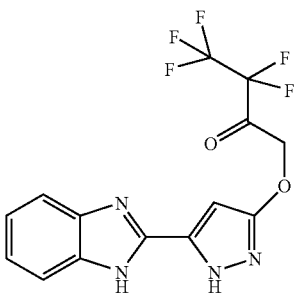 | 199 | 1-[5-(1H-Benzoimidazol-2-yl)-1H-pyrazol-3-yloxy]-3,3,4,4,4-pentafluoro-butan-2-one |
| 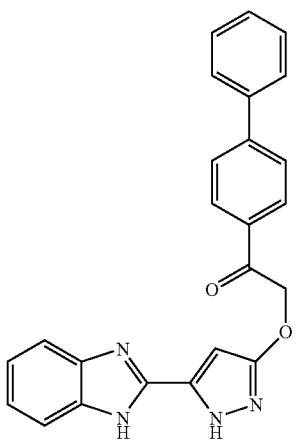 | 200 | 2-[5-(1H-Benzoimidazol-2-yl)-1H-pyrazol-3-yloxy]-1-biphenyl-4-yl-ethanone |
| 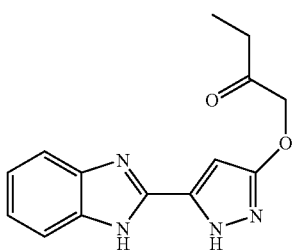 | 201 | 1-[5-(1H-Benzoimidazol-2-yl)-1H-pyrazol-3-yloxy]-butan-2-one |

TABLE 4-continued
| CHEMISTRY | | |
|---|---|---|
| 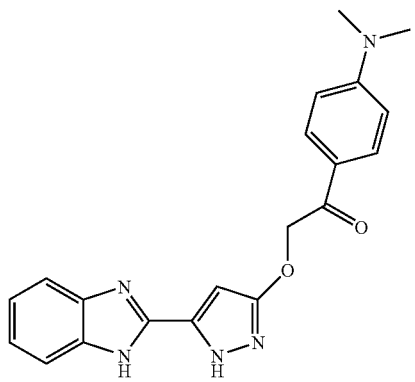 | 202 | 2-[5-(1H-Benzoimidazol-2-yl)-1H-pyrazol-3-yloxy]-1-(4-dimethylamino-phenyl)-ethanone |
| 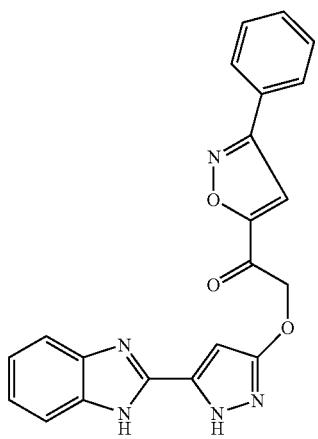 | 203 | 2-[5-(1H-Benzoimidazol-2-yl)-1H-pyrazol-3-yloxy]-1-(3-phenyl-isoxazol-5-yl)-ethanone |
| 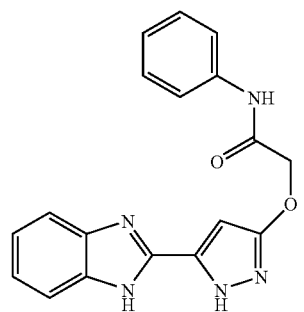 | 204 | 2-[5-(1H-Benzoimidazol-2-yl)-1H-pyrazol-3-yloxy]-N-phenyl-acetamide |
| 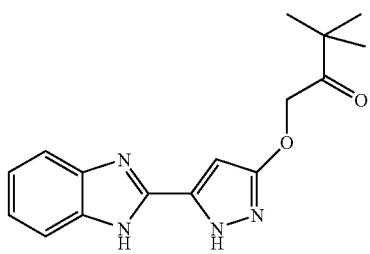 | 205 | 1-[5-(1H-Benzoimidazol-2-yl)-1H-pyrazol-3-yloxy]-3,3-dimethyl-butan-2-one |

TABLE 4-continued
CHEMISTRY
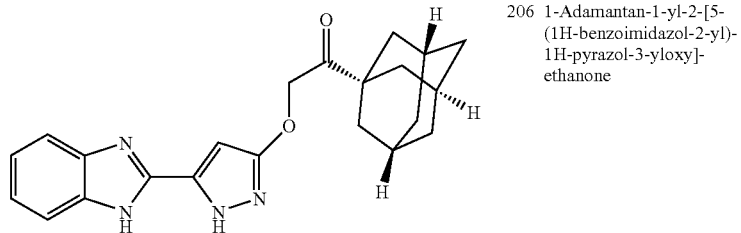
206  1-Adamantan-1-yl-2-[5-(1H-benzoimidazol-2-yl)-1H-pyrazol-3-yloxy]-ethanone
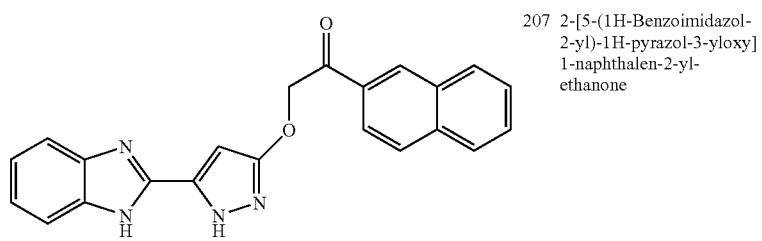
207  2-[5-(1H-Benzoimidazol-2-yl)-1H-pyrazol-3-yloxy]-1-naphthalen-2-yl-ethanone
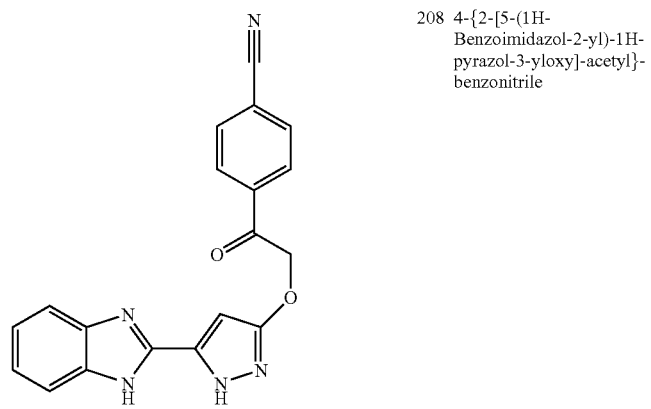
208  4-{2-[5-(1H-Benzoimidazol-2-yl)-1H-pyrazol-3-yloxy]-acetyl}-benzonitrile
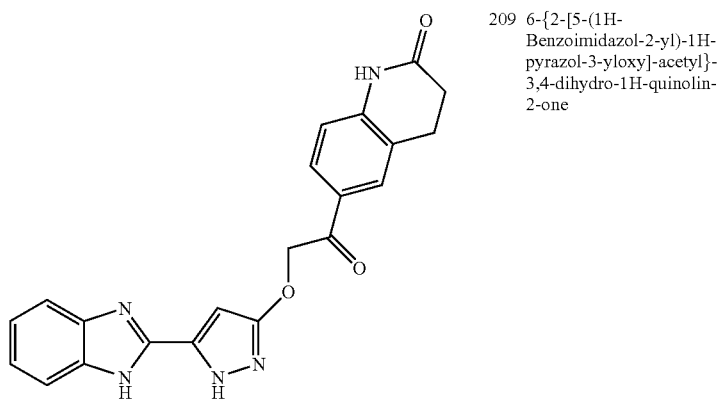
209  6-{2-[5-(1H-Benzoimidazol-2-yl)-1H-pyrazol-3-yloxy]-acetyl}-3,4-dihydro-1H-quinolin-2-one TABLE 4-continued
| CHEMISTRY | | |
|---|---|---|
| 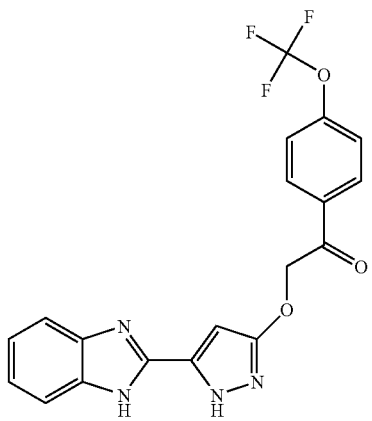 | 210 | 2-[5-(1H-Benzoimidazol-2-yl)-1H-pyrazol-3-yloxy]-1-(4-trifluoromethoxy-phenyl)-ethanone |
| 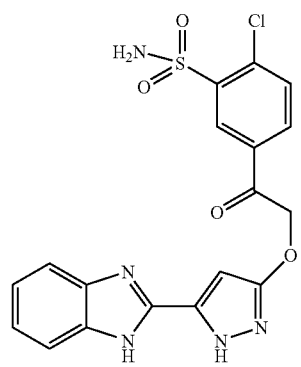 | 211 | 5-{2-[5-(1H-Benzoimidazol-2-yl)-1H-pyrazol-3-yloxy]-acetyl}-2-chloro benzenesulfonamide |
| 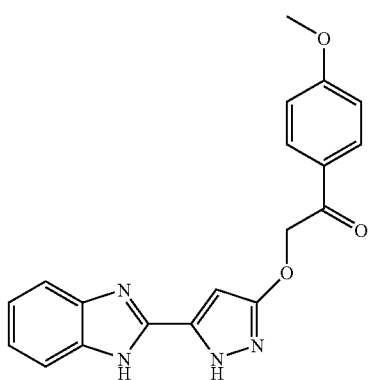 | 212 | 2-[5-(1H-Benzoimidazol-2-yl)-1H-pyrazol-3-yloxy]-1-(4-methoxy-phenyl)-ethanone |
| 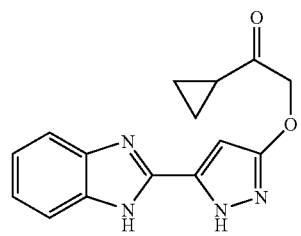 | 213 | 2-[5-(1H-Benzoimidazol-2-yl)-1H-pyrazol-3-yloxy]-1-cyclopropyl-ethanone |

TABLE 4-continued

| CHEMISTRY | |
|---|---|
| 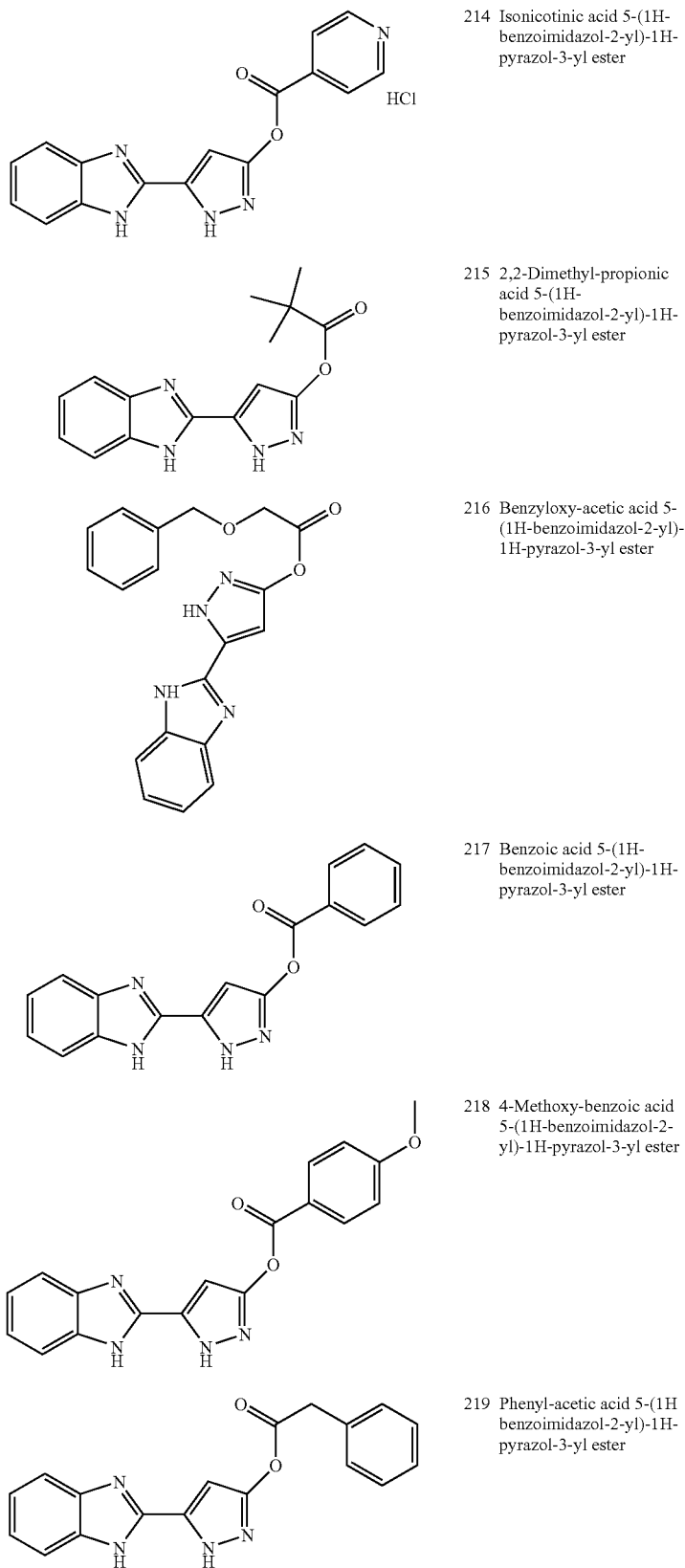 | 214 Isonicotinic acid 5-(1H-benzoimidazol-2-yl)-1H-pyrazol-3-yl ester |
| | 215 2,2-Dimethyl-propionic acid 5-(1H-benzoimidazol-2-yl)-1H-pyrazol-3-yl ester |
| | 216 Benzyloxy-acetic acid 5-(1H-benzoimidazol-2-yl)-1H-pyrazol-3-yl ester |
| | 217 Benzoic acid 5-(1H-benzoimidazol-2-yl)-1H-pyrazol-3-yl ester |
| | 218 4-Methoxy-benzoic acid 5-(1H-benzoimidazol-2-yl)-1H-pyrazol-3-yl ester |
| | 219 Phenyl-acetic acid 5-(1H-benzoimidazol-2-yl)-1H-pyrazol-3-yl ester |

TABLE 4-continued

| CHEMISTRY | | |
|---|---|---|
| 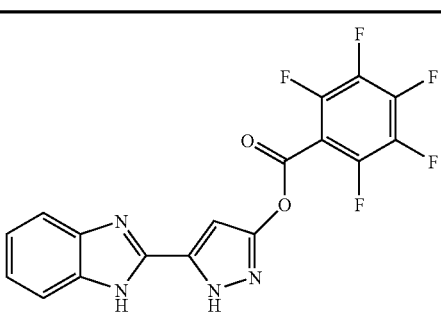 | 220 | 2,3,4,5,6-Pentafluoro-benzoic acid 5-(1H benzoimidazol-2-yl)-1H-pyrazol-3-yl ester |
| 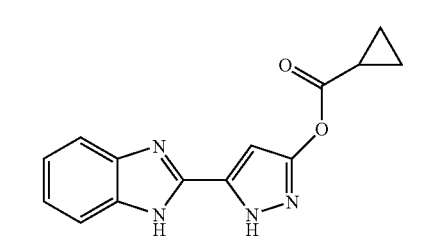 | 221 | Cyclopropanecarboxylic acid 5-(1H-benzoimidazol-2-yl)-1H-pyrazol-3-yl ester |
| 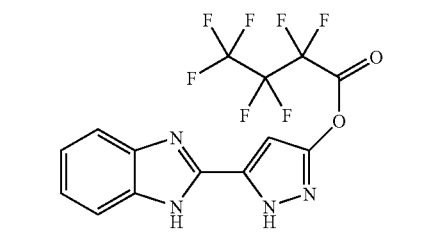 | 222 | 2,2,3,3,4,4,4-Heptafluoro-butyric acid 5-(1H-benzoimidazol-2-yl)-1H-pyrazol-3-yl ester |
| 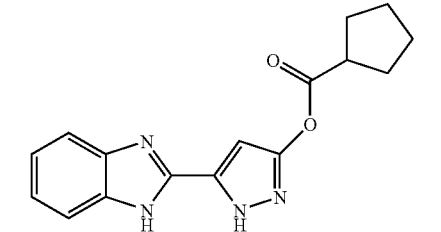 | 223 | Cyclopentanecarboxylic acid 5-(1H-benzoimidazol-2-yl)-1H-pyrazol-3-yl ester |
| 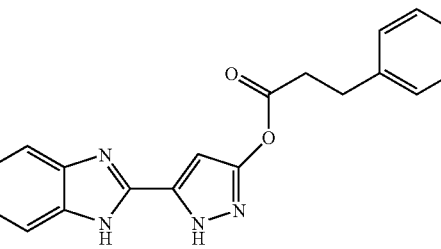 | 224 | 3-Phenyl-propionic acid 5-(1H-benzoimidazol-2-yl)-1H-pyrazol-3-yl ester |
| 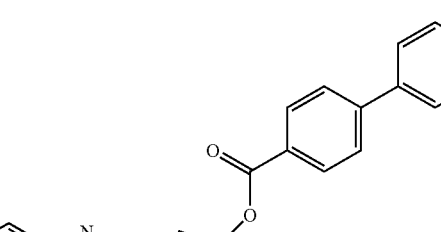 | 225 | Biphenyl-4-carboxylic acid 5-(1H-benzoimidazol-2-yl)-1H-pyrazol-3-yl ester |

TABLE 4-continued

| | CHEMISTRY | | |
|---|---|---|---|
| | 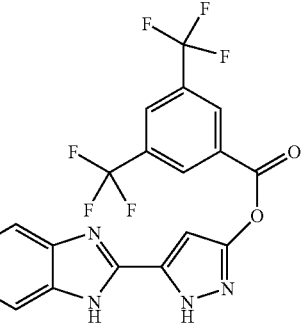 | 226 | 3,5-Bis-trifluoromethyl-benzoic acid 5-(1H-benzoimidazol-2-yl)-1H-pyrazol-3-yl ester |
| | 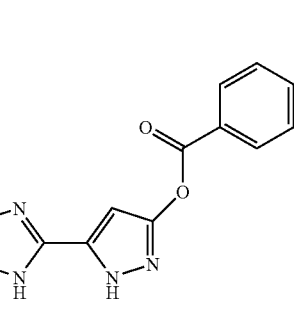 | 227 | 4-Trifluoromethyl-benzoic acid 5-(1H-benzoimidazol-2-yl)-1H-pyrazol-3-yl ester |
| | 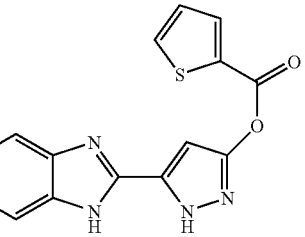 | 228 | Thiophene-2-carboxylic acid 5-(1H-benzoimidazol-2-yl)-1H-pyrazol-3-yl ester |

EXAMPLE 229

Pharmaceutical Composition

Tablets corresponding to the formula below were prepared:
Product of Example 1 . . . 0.2 g
Excipient for a finished tablet containing . . . 1 g
(details of the excipient: lactose, talc, starch, magnesium stearate).

Example 1 is taken as pharmaceutical preparation example, it being possible for this preparation to be produced, if desired, with other products in examples in the present application.

EXAMPLE 230

(a) 5,6-Dimethyl-2-(5-methylsulfanyl-1H-pyrazol-3-yl)-1H-benzoimidazole

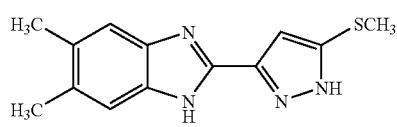

A mixture of 5,6-dimethyl-2-(5-methylsulfanyl-1H-pyrazol-3-yl)-1-(2-trimethylsilanyl-ethoxymethyl)-1H-benzoimidazole [90 mg, Reference Example 1(a)], hydrochloric acid (2 mL, 4N) and ethanol (4 mL) was heated at reflux temperature for 16 hours then cooled to room temperature. The pH of the reaction mixture was adjusted to 7 by addition of saturated sodium bicarbonate solution. The resulting solid was filtered, then washed with water and then dried in a vacuum oven to give 5,6-dimethyl-2-(5-methylsulfanyl-1H-pyrazol-3-yl)-1H-benzoimidazole (38 mg). LC-MS (METHOD A): $R_T$=2.22 minutes; 259 (M+H)$^+$.

(b) 6-Chloro-5-methyl-2-(5-methylsulfanyl-1H-pyrazol-3-yl)-1H-benzoimidazole

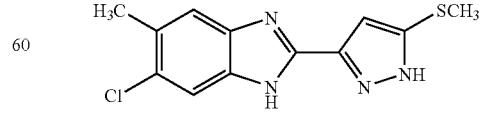

By proceeding in a similar manner to Example 230(a) above but using 6-chloro-5-methyl-2-(5-methylsulfanyl-1H-pyrazol-3-yl)-1-trimethylsilanyl-ethoxymethyl)-1H-benzoimidazole [Reference Example 1(b)] there was prepared 6-chloro-5-methyl-2-(5-methylsulfanyl-1H-pyrazol-3-yl)-1H-benzoimidazole.

(c) 6-Chloro-2-(5-ethylsulfanyl-1H-pyrazol-3-yl)-5-methyl-1H-benzoimidazole

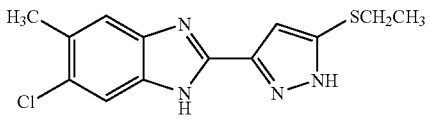

By proceeding in a similar manner to Example 230(a) above but using 6-chloro-2-(5-ethylsulfanyl-1H-pyrazol-3-yl)-5-methyl-1-(2-trimethylsilanyl-ethoxymethyl)-1H-benzoimidazole [Reference Example 1(c)] there was prepared 6-chloro-2-(5-ethylsulfanyl-1H-pyrazol-3-yl)-5-methyl-1H-benzoimidazole.

(d) 2-(5-methylsulfanyl-1H-pyrazol-3-yl)-5-trifluoromethyl-1H-benzoimidazole

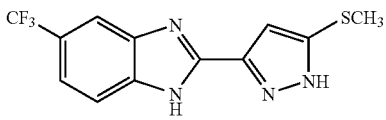

By proceeding in a similar manner to Example 230(a) above but using 2-(5-methylsulfanyl-1H-pyrazol-3-yl)-5-trifluoromethyl-1-(2-trimethylsilanyl-ethoxymethyl)-1H-benzoimidazole [Reference Example 1(d)] there was prepared 2-(5-methylsulfanyl-1H-pyrazol-3-yl-5-trifluoromethyl-1H-benzoimidazole.

(e) 2-(5-Cyclopropylmethylsulfanyl-1H-pyrazol-3-yl)-5,6-dimethyl-1H-benzoimidazole

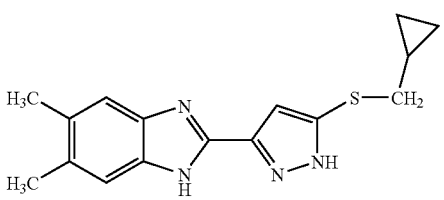

By proceeding in a similar manner to Example 230(a) above but using 2-(5-cyclopropylmethylsulfanyl-1H-pyrazol-3-yl)-5,6-dimethyl-1-(2-trimethylsilanyl-ethoxymethyl)-1H-benzoimidazole [Reference Example 1(e)] there was prepared 2-(5-cyclopropylmethylsulfanyl-1-pyrazol-3-yl)-5,6-dimethyl-1H-benzoimidazole. LC-MS (METHOD A): $R_T$=2.47 minutes; 299 (M+H)$^+$.

(f) 2-(5-Ethylsulfanyl-1H-pyrazol-3-yl)-5,6-dimethyl-1H-benzoimidazole

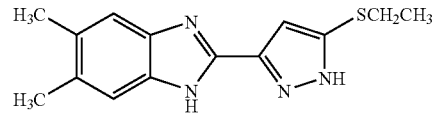

By proceeding in a similar manner to Example 230(a) above but using 5,6-dimethyl-2-(5-ethylsulfanyl-1H-pyrazol-3-yl)-1-(2-trimethylsilanyl-ethoxymethyl)-1H-benzoimidazole [Reference Example 1(f)] there was prepared 2:5-ethylsulfanyl-1H-pyrazol-3-yl)-5,6-dimethyl-1H-benzoimidazole. LC-MS (METHOD A): $R_T$=2.32 minutes; 273 (M+H)$^+$.

(g) 5,6-Dimethyl-2-[5-(pyridin-3-ylmethylsulfanyl)-1H-pyrazol-3-yl]-1H-benzoimidazole

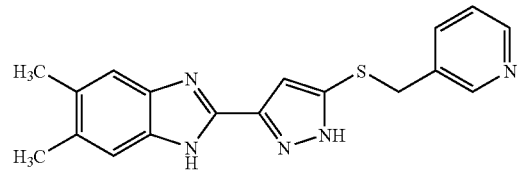

By proceeding in a similar manner to Example 230(a) above but using 5,6-dimethyl-2-[5-(pyridin-3-yl)methylsulfanyl-1H-pyrazol-3-yl]-1-(2-trimethylsilanyl-ethoxymethyl)-1H-benzoimidazole [Reference Example 1(g)] there was prepared 5,6-dimethyl-2-[5-(pyridin-3-ylmethylsulfanyl)-1H-pyrazol-3-yl]-1H-benzoimidazole as a colourless solid.

(h) 5-Fluoro-2-[5-methylsulfanyl)-1H-pyrazol-3-yl]-1H-benzoimidazole

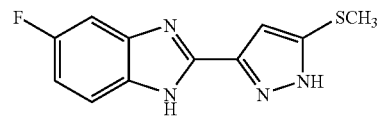

By proceeding in a similar manner to Example 230(a) above but using 5-fluoro-2-(5-methylsulfanyl-1H-pyrazol-3-yl)-1-(2-trimethylsilanyl-ethoxymethyl)-1H-benzoimidazole [Reference Example 1(h)] there was prepared 5-fluoro-2-[5-methylsulfanyl)-1H-pyrazol-3-yl]-1H-benzoimidazole. MS: 249 (M+H)$^+$.

(i) 5,6-Dimethyl-2-(5-phenethylsulfanyl-1H-pyrazol-3-yl)-1H-benzoimidazole

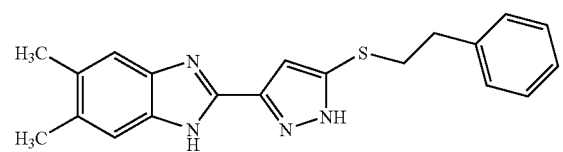

By proceeding in a similar manner to Example 230(a) above but using 5,6-dimethyl-2-(5-phenethylsulfanyl-1H-pyrazol-3-yl)-1-(2-trimethylsilanyl-ethoxymethyl)-1H-benzoimidazole [Reference Example 1(i)] there was prepared 5,6-dimethyl-2-(5-phenethylsulfanyl-1H-pyrazol-3-yl)-1H-benzoimidazole.

(j) 4-Methyl-2-(5-methylsulfanyl-1H-pyrazol-3-yl)-1H-benzoimidazole

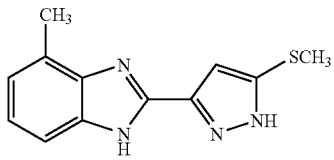

By proceeding in a similar manner to Example 230(a) above but using 4-methyl-2-(5-methylsulfanyl-1H-pyrazol-3-yl)-1-(2-trimethylsilanyl-ethoxymethyl)-1H-benzoimidazole [Reference Example 1(j)] there was prepared 4-methyl-2-(5-methylsulfanyl-1H-pyrazol-3-yl)-1H-benzoimidazole. MS: 245 (M+H)⁺.

(k) 5,6-Dimethyl-2-(5-benzylsulfanyl-1H-pyrazol-3-yl)-1H-benzoimidazole

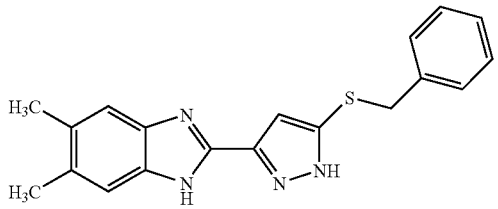

By proceeding in a similar manner to Example 230(a) above but using 2-(5-benzylsulfanyl-1H-pyrazol-3-yl)-5,6-dimethyl-1-(2-trimethylsilanyl-ethoxymethyl)-1H-benzoimidazole [Reference Example 1(k)] there was prepared 5,6-dimethyl-2-(5-benzylsulfanyl-1H-pyrazol-3-yl)-1H-benzoimidazole.

(l) 6-Chloro-5-methyl-2-(5-morpholin-4-yl-1H-pyrazol-3-yl)-1H-benzoimidazole

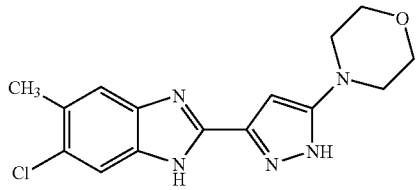

By proceeding in a similar manner to Example 230(a) above but using 6-chloro-5-methyl-2-(5-morpholin-4-yl-1H-pyrazol-3-yl)-1-(2-trimethylsilanyl-ethoxymethyl)-1H-benzoimidazole [Reference Example 1(l)] there was prepared 6-chloro-5-methyl-2-(5-morpholin-4-yl-1H-pyrazol-3-yl)-1H-benzoimidazole.

(m) 5,6-Dimethyl-2-[5-(thiophen-2-ylmethylsulfanyl)-1H-pyrazol-3-yl]-1H-benzoimidazole

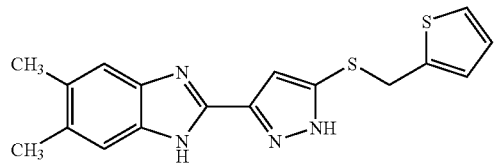

By proceeding in a similar manner to Example 230(a) above but using 5,6-dimethyl-2-[5-(thiophen-2-ylmethylsulfanyl)-1H-pyrazol-3-yl]-1-(2-trimethylsilanyl-ethoxymethyl)-1H-benzoimidazole [Reference Example 1(m)] there was prepared 5,6-dimethyl-2-[5-(thiophen-2-ylmethylsulfanyl)-1H-pyrazol-3-yl]-1H-benzoimidazole.

EXAMPLE 231

(2-(5-Ethylsulfanyl-1H-pyrazol-3-yl)-5-methoxy-1H-benzoimidazole hydrochloride

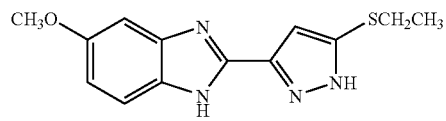

A mixture of 3,3-bis-ethylsulfanyl-1-[5-methoxy-1-(2-trimethylsilanyl-ethoxymethyl)-1H-benzoimidazol-2-yl]-propenone [~0.78 mmole, Reference Example 2(j)] and hydrazine hydrate (500 µL) in ethanol (6 mL) was heated at reflux temperature for 18 hours, then evaporated. The residue was purified on the Flashmaster to give 2-(5-ethylsulfanyl-1H-pyrazol-3-yl)-5-methoxy-1-(2-trimethylsilanyl-ethoxymethyl)-1H-benzoimidazole which was treated with ethanol (6 mL) and hydrochloric acid (3 mL). This mixture was heated at reflux temperature for 18 hours and then evaporated to give 2-(5-ethylsulfanyl-1H-pyrazol-3-yl)-5-methoxy-1H-benzoimidazole hydrochloride. LC-MS (METHOD A): R$_T$=2.17 minutes; 275 (M+H)⁺.

EXAMPLE 232

(a) 5-Methyl-2-(5-methylsulfanyl-4-propyl-1H-pyrazol-3-yl)-1H-benzoimidazole

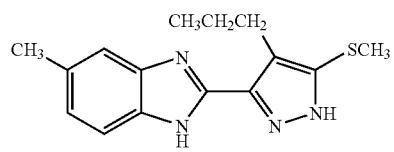

A mixture of 2-(bis-methylsulfanyl-methylene)-1-(5-methyl-1H-benzoimidazol-2-yl)-pentan-1-one [~0.49 mmole, Reference Example 2(l)] and hydrazine hydrate (200 µL) in ethanol (6 mL) was heated at reflux temperature for 2 days, then evaporated. The mixture was then treated with hydrochloric acid (4 mL, 4N) and heating was continued at reflux temperature for a further 24 hours. The reaction mixture was cooled, then neutralised by addition of sodium hydroxide solution (4N) and then extracted with dichloromethane. The extract was evaporated to give 5-methyl-2-(5-methylsulfanyl-4-propyl-1H-pyrazol-3-yl)-1H-benzoimidazole. MS: 287 (M+H)+.

(b) 2-(5-(4-methoxy-benzylsulfanyl)-4-propyl-1H-pyrazol-3-yl)-5-methyl-1H-benzoimidazole

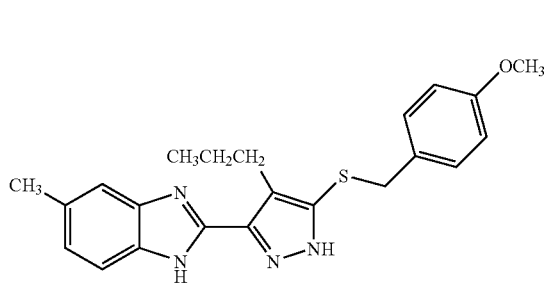

By proceeding in a similar manner to Example 233(a) above but using 2-[bis-(4-methoxy-benzylsulfanyl)-methylene]-1-(5-methyl-1H-benzoimidazol-2-yl)-pentan-1-one [Reference Example 2(m)] there was prepared 2-(5-(4-methoxy-benzylsulfanyl)-4-propyl-1H-pyrazol-3-yl)-5-methyl-1H-benzoimidazole. MS: 393 (M+H)+.

(c) 2-(5-Benzylsulfanyl-4-isopropyl-1H-pyrazol-3-yl)-5-methyl-1H-benzoimidazole

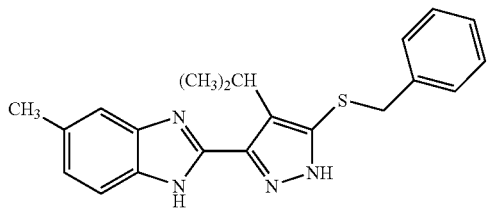

By proceeding in a similar manner to Example 232(a) above but using 2-(bis-benzylsulfanyl-methylene)-3-methyl-1-[5-methyl-1-(2-trimethylsilanyl-ethoxymethyl)-1H-benzoimidazol-2-yl]-butan-1-one [Reference Example (2n)] there was prepared 2-(5-benzylsulfanyl-4-isopropyl-1H-pyrazol-3-yl)-5-methyl-1H-benzoimidazole. MS: 363 (M+H)+.

(d) 2-(5-Methylsulfanyl-4-methyl-1H-pyrazol-3-yl)-5-methoxy-1H-benzoimidazole

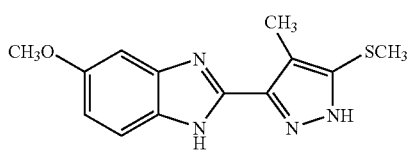

By proceeding in a similar manner to Example 232(a) above but using 1-[5-methoxy-1-(2-trimethylsilanyl-ethoxymethyl)-1H-benzoimidazol-2-yl]-2-methyl-3-(bis-methanesulfanyl)-1-propenone [Reference Example 2(r)] there was prepared 2-(5-methylsulfanyl-4-methyl-1H-pyrazol-3-yl)-5-methoxy-1H-benzoimidazole.

(e) 2-(5-Methylsulfanyl-4-methyl-1H-pyrazol-3-yl)-5-methyl-1H-benzoimidazole

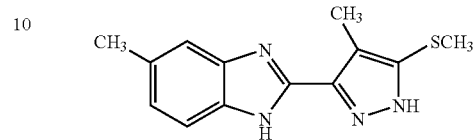

By proceeding in a similar manner to Example 232(a) above but using 1-[5-methyl-1-(2-trimethylsilanyl-ethoxymethyl)-1H-benzoimidazol-2-yl]-2-methyl-3-bis-methanesulfanyl)-1-propenone [Reference Example 2(t)] there was prepared 2-(5-methylsulfanyl-4-methyl-1H-pyrazol-3-yl)-5-methyl-1H-benzoimidazole.

EXAMPLE 233

(a) 3-(5-Chloro-1H-benzoimidazol-2-yl)-1H-pyrazol-4-ylamine

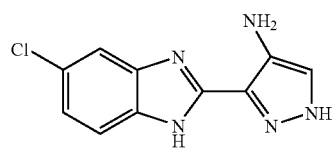

A solution of 5-chloro-2-(4-nitro-1H-pyrazol-3-yl)-1H-benzoimidazole [91 mg, Example 239(a)] in ethanol (40 mL), under nitrogen, was treated with palladium on carbon (spatula tip, 5%). The mixture was stirred under hydrogen for 3 hours and then filtered through Celite. The filter pad was washed well with dichloromethane. The combined filtrate and washings were evaporated to give 3-(5-chloro-1H-benzoimidazol-2-yl)-1H-pyrazol-4-ylamine (116 mg). LC-MS (METHOD A): $R_T$=2 minutes; 234 (M+H)+.

(b) 3-(5,6-Dichloro-1H-benzoimidazol-2-yl)-1H-pyrazol-4-ylamine

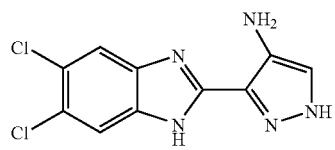

By proceeding in a similar manner to Example 233(a) above but using 5,6-dichloro-2-(4-nitro-1H-pyrazol-3-yl)-1H-benzoimidazole [Example 239(b)] there was prepared 3-(5,6-dichloro-1H-benzoimidazol-2-yl)-1H-pyrazol-4-ylamine. LC-MS (METHOD A): $R_T$=2.37 minutes; 268 (M+H)+.

(c) 3-(5,6-Dimethyl-1H-benzoimidazol-2-yl)-1H-pyrazol-4-ylamine

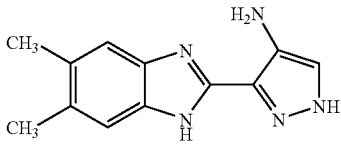

By proceeding in a similar manner to Example 233(a) above but using 5,6-dimethyl-2-(4-nitro-1H-pyrazol-3-yl)-1H-benzoimidazole [Example 249(a)] there was prepared 3-(5,6-dimethyl-1H-benzoimidazol-2-yl)-1H-pyrazol-4-ylamine as a brown solid. LC-MS (METHOD B): $R_T$=2.29 minutes; 228.25 (M+H)$^+$.

(d) 3-(5-Ethyl-6-methyl-1H-benzoimidazol-2-yl)-1H-pyrazol-4-ylamine

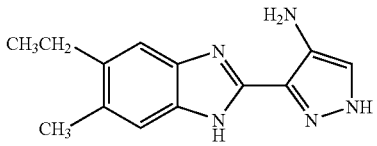

By proceeding in a similar manner to Example 233(a) above but using 5-ethyl-6-methyl-2-(4-nitro-1H-pyrazol-3-yl)-1H-benzoimidazole [Example 249(b)] there was prepared 3-(5-ethyl-6-methyl-1H-benzoimidazol-2-yl)-1H-pyrazol-4-ylamine as a brown solid. LC-MS (METHOD B): $R_T$=2.14 minutes, 242.20 (M+H)$^+$.

(e) 3-(6-chloro-5-methoxy-1H-benzoimidazol-2-yl)-1H-pyrazol-4-ylamine

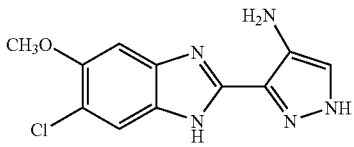

By proceeding in a similar manner to Example 233(a) above but using 6-chloro-5-methoxy-2-(4-nitro-1H-pyrazol-3-yl)-1H-benzoimidazole [0.7 g, Example 249(c)] there was prepared 3-(6-chloro-5-methoxy-1H-benzoimidazol-2-yl)-1H-pyrazol-4-ylamine (0.54 g) as a brown foam. MS 264 (M+H)$^+$.

(f) 3-(5-Methoxy-1H-benzoimidazol-2-yl)-1H-pyrazol-4-ylamine

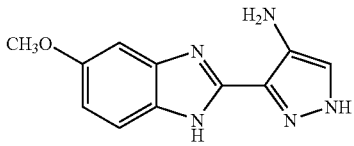

By proceeding in a similar manner to Example 233(a) above but using 5-methoxy-2-(4-nitro-1H-pyrazol-3-yl)-1H-benzoimidazole [373 mg, Example 257(f)] there was prepared 3-(5-methoxy-1H-benzoimidazol-2-yl)-1H-pyrazol-4-ylamine (257 mg) as a dark brown solid. LC-MS (Method H): $R_T$=1.23 minutes, 230.25 (M+H)$^+$, 228.25 (M−H)$^-$.

(g) 3-(5-Ethoxy-1H-benzoimidazol-2-yl)-1H-pyrazol-4-ylamine

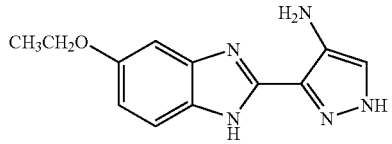

By proceeding in a manner similar to Example 233(a) above but using 5-ethoxy-2-(4-nitro-1H-pyrazol-3-yl)-1H-benzoimidazole [407 mg, Example 252(c)] there was prepared 3-(5-ethoxy-1H-benzoimidazol-2-yl)-1H-pyrazol-4-ylamine (375 mg) as a dark brown oil. LC-MS (Method H): $R_T$=1.43 minutes, 244.26 (M+H)$^+$, 242.28 (M−H)$^-$.

(h) 3-(5-Fluoro-6-methyl-1H-benzoimidazol-2-yl)-1H-pyrazol-4-ylamine

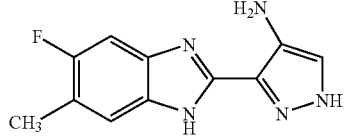

By proceeding in a manner similar to Example 233(a) above but using 5-fluoro-6-methyl-2-(4-nitro-1H-pyrazol-3-yl)-1H-benzoimidazole [Example 249(d)] there was prepared 3-(5-fluoro-6-methyl-1H-benzoimidazol-2-yl)-1H-pyrazol-4-ylamine (0.590 g) as a brown solid. LC-MS (METHOD J): $R_T$=2.25 minutes, MS: 232.29 (M+H)$^+$.

(i) 3-(5-Trifluoromethoxy-1H-benzoimidazol-2-yl)-1H-pyrazol-4-ylamine

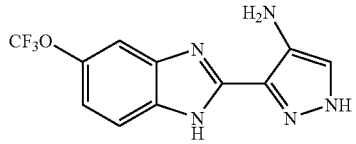

By proceeding in a manner similar to Example 233(a) above but using 5-trifluoromethoxy-2-(4-nitro-1H-pyrazol-3-yl)-1H-benzoimidazole [Example 249(e)] there was prepared 3-(5-trifluoromethoxy-1H-benzoimidazol-2-yl)-1H-pyrazol-4-ylamine (0.920 g) as a brown solid. LC-MS (METHOD J): $R_T$=2.76 minutes, 284.23 (M+H)$^+$.

(j) 3-(5-Trifluoromethyl-1H-benzoimidazol-2-yl)-1H-pyrazol-4-ylamine

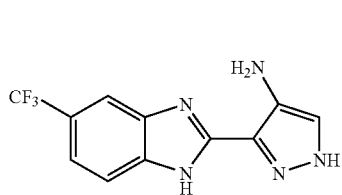

By proceeding in a manner similar to Example 233(a) above but using 5-trifluoromethyl-2-(4-nitro-1H-pyrazol-3-yl)-1H-benzoimidazole [Example 249(f)] there was prepared 3-(5-trifluoromethyl-1H-benzoimidazol-2-yl)-1H-pyrazol- 4-ylamine (0.150 g) as a brown solid. LC-MS (METHOD B): $R_T$=3.00 minutes, 268.16 (M+H)$^+$.

(k) 2-(4-Amino-1H-pyrazol-3-yl)-1H-benzoimidazole-5-carboxylic acid methyl ester

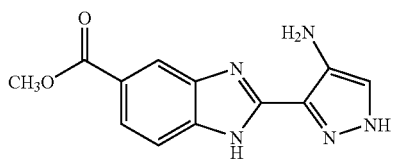

By proceeding in a manner similar to Example 233(a) above but using 2-(4-nitro-1H-pyrazol-3-yl)-1H-benzoimidazole-5-carboxylic acid methyl ester [Example 249(h)] there was prepared 2-(4-amino-1H-pyrazol-3-yl)-1H-benzoimidazole-5-carboxylic acid methyl ester (1.10 g) as an off-white solid. LC-MS (METHOD B): $R_T$=2.40 minutes, 258.17 (M+H)$^+$.

EXAMPLE 234

(a) 3-(1H-Benzoimidazol-2-yl)-1H-indazole

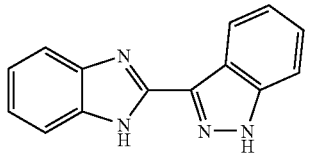

A mixture of 1,2-diaminobenzene (108 mg), indazole-3-carboxylic acid (118 mg) and polyphosphoric acid (1 mL) was heated at 150-160° C. for 24 hours. The mixture was cooled, then diluted with ice water (10 mL) and then treated with ethyl acetate (10 mL). The aqueous layer was basified by addition of solid potassium carbonate. The layers were separated and the aqueous layer was extracted with ethyl acetate (10 mL). The combined organic phases were dried and then evaporated. The residue was subjected to chromatography on silica eluting with a mixture of heptane and ethyl acetate to give 3-(1H-benzoimidazol-2-yl)-1H-indazole (78 mg). LC-MS (METHOD A): $R_T$=1.28 minutes; 235 (M+H)$^+$.

(b) 3-(5-Methoxy-1H-benzoimidazol-2-yl)-1H-indazole

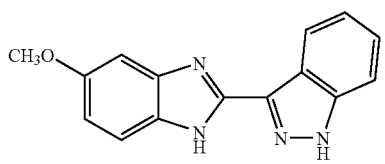

By proceeding in a similar manner to Example 234(a) above but using 4-methoxy-1,2-diaminobenzene hydrochloride there was prepared 3-(5-methoxy-1H-benzoimidazol-2-yl)-1H-indazole as a solid.
LC-MS (METHOD A): $R_T$=1.28 minutes; 265 (M+H)$^+$.

(c) [2-(Indazol-3-yl)-1H-benzoimidazol-5-yl]-phenyl-methanone

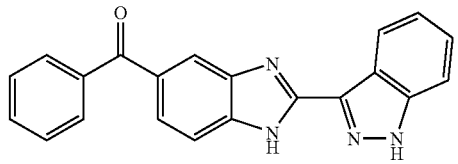

By proceeding in a similar manner to Example 234(a) above but using 3,4-diaminobenzophenone there was prepared [2-(indazol-3-yl)-1H-benzoimidazol-5-yl]-phenyl-methanone as a solid.
LC-MS (METHOD A): $R_T$=1.73 minutes; 339 (M+H)$^+$.

(d) 2-(1H-Indazol-3-yl)-3H-benzoimidazol-4-ol

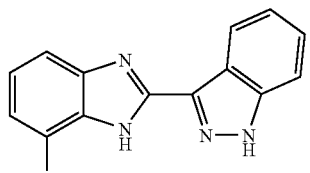

By proceeding in a similar manner to Example 234(a) above but using 2,3-diaminophenol there was prepared 2-(1H-indazol-3-yl)-3H-benzoimidazol-4-ol as a solid. LC-MS (METHOD A): $R_T$=1.63 minutes; 251 (M+H)$^+$.

(e) 2-Phenyl-1H-imidazol[4,5-b]pyrazine

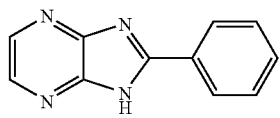

By proceeding in a similar manner to Example 234(a) above but using 2,3-diaminopyrazine [Reference Example 9] and benzoic acid there was prepared 2-phenyl-1H-imidazol[4,5-b]pyrazine as a pale brown solid, mp 239-240° C. HPLC (METHOD A1): $R_T$=10.18 minutes.

(f) 3-(5,6-Dimethyl-1H-benzoimidazol-2-yl)-1H-indazole

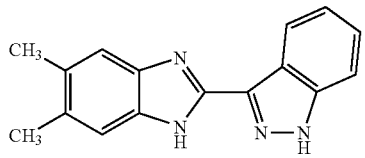

By proceeding in a similar manner to Example 234(a) above but using 1,2-diamino-4,5-dimethylbenzene there was prepared 3-(5,6-dimethyl-1H-benzoimidazol-2-yl)-1H-indazole (28 mg). LC-MS (METHOD A): $R_T$=1.34 minutes; 263 (M+H)$^+$.

(g) 2-(1H-indazol-3-yl)-3H-imidazo[4,5-c]pyridine

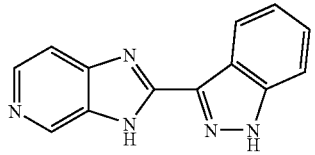

By proceeding in a similar manner to Example 234(a) above but using 3,4-diaminopyridine there was prepared 2-(1H-indazol-3-yl)-3H-imidazo[4,5-c]pyridine as a solid. MS: 236 (M+H)$^+$. HPLC (METHOD A): $R_T$=2.48 minutes.

(h) 2-(1H-indazole-3-yl)-3H-imidazo[4,5-b]pyridine

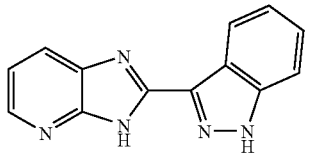

By proceeding in a similar manner to Example 234(a) above but using 2,3-diaminopyridine there was prepared 2-(1H-indazole-3-yl)-3H-imidazo[4,5-b]pyridine as a solid. MS: 236 (M+H)$^+$. HPLC (METHOD A): $R_T$=2.49 minutes.

EXAMPLE 235

(a) 2-(1H-Pyrazol-3yl)-1H-benzoimidazole

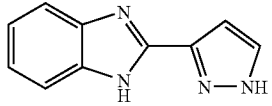

A mixture of 1H-pyrazole-3-carbaldehyde (0.961 g, Reference Example 10), o-phenylenediamine (0.973 g), sodium bisulfite (1.898 g) and dry dimethylformamide (10 mL) was stirred at reflux for 2 hours, then cooled to room temperature and then poured onto cracked ice (35 g). The mixture was filtered and the solid was washed with aqueous sodium bicarbonate and then with water. The solid was vacuum dried at 70° C. and then recrystallised from ethanol to give 2-(1H-pyrazol-3yl)-1H-benzoimidazole (0.645 g) as a pale yellowish solid, mp 335-338° C. [Elemental analysis:—C, 62.56%; H, 4.04%; N, 29.14%. Calculated for $C_{10}H_8N_4$:—C, 65.19%; H, 4.39%; N, 30.42%].

(b) 3-(5,6-Dimethyl-1H-benzoimidazol-2-yl)-5-methoxy-1H-indazole

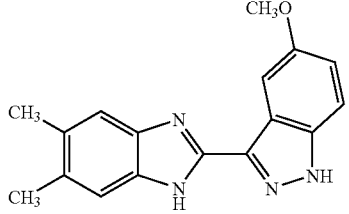

By proceeding in a similar manner to Example 235(a) above but using 3-formyl-5-methoxy-indazole-1-carboxylic acid tert-butyl ester [Reference Example 20(a)] and 4,5-dimethylbenzene-1,2-diamine there was prepared 3-(5,6-dimethyl-1H-benzoimidazol-2-yl)-5-methoxy-1H-indazole as a white solid.
LC-MS (METHOD B): $R_T$=2.35 minutes; 289 (M+H)$^+$.

(c) 3-(5-Ethyl-6-methyl-1H-benzoimidazol-2-yl)-5-methoxy-1H-indazole

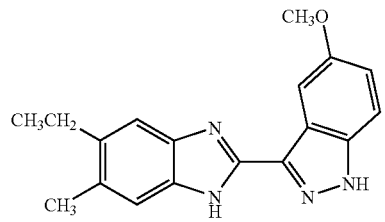

By proceeding in a manner similar to Example 235(a) above but using 3-formyl-5-methoxy-indazole-1-carboxylic acid tert-butyl ester [Reference Example 20(a)] and 4-ethyl-5-methyl phenylene diamine [Reference Example 30], and subjecting the reaction product to flash column chromatography on silica eluting with a mixture of ethyl acetate and 40-60 petrol (1:1, v/v), there was prepared, 3-(5-ethyl-6-methyl-1H-benzoimidazol-2-yl)-5-methoxy-1H-indazole as a pale yellow solid.
LC-MS (METHOD B): $R_T$=2.48 minutes; 307 (M+H)$^+$.

(d) 3-(5,6-Dimethyl-1H-benzoimidazol-2-yl)-5-fluoro-1H-indazole

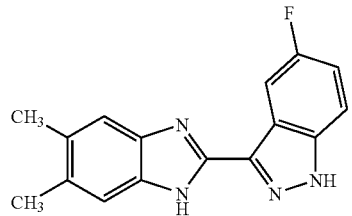

By proceeding in a manner similar to Example 235(a) above but using 5-fluoro-1H-indazole-3-carbaldehyde [Reference Example 6(c)] and 4,5-dimethylbenzene-1,2-diamine there was prepared 3-(5,6-dimethyl-1H-benzoimidazol-2-yl)-5-fluoro-1H-indazole as a brown solid.
LC-MS (METHOD B): $R_T$=2.41 minutes; 281 (M+H).

(e) 3-(5,6-Dimethyl-1H-benzoimidazol-2-yl)-6-fluoro-1H-indazole

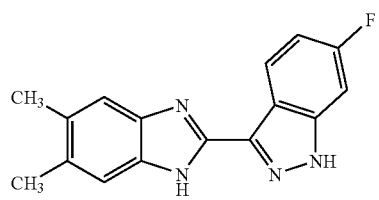

By proceeding in a manner similar to Example 235(a) above but using 6-fluoro-1H-indazole-3-carbaldehyde [Reference Example 6(d)] and 4,5-dimethylbenzene-1,2-diamine there was prepared 3-(5,6-dimethyl-1H-benzoimidazol-2-yl)-6-fluoro-1H-indazole (0.104 g) as a brown solid. MS: 281 (M+H)⁺. HPLC (METHOD B1): R$_T$=23.6 minutes.

(f) 3-(5,6-Dimethyl-1H-benzoimidazol-2-yl)-5-methyl-1H-indazole

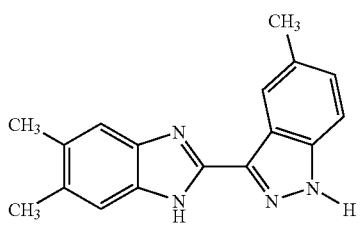

By proceeding in a manner similar to Example 235(a) above but using 5-methyl-1H-indazole-3-carbaldehyde [Reference Example 6(e)] there was prepared 3-(5,6-dimethyl-1H-benzoimidazol-2-yl)-5-methyl-1H-indazole as a brown solid. LC-MS (METHOD B): R$_T$=2.35 minutes; 277 (M+H)⁺.

(g) 3-(5,6-Dimethyl-1H-benzoimidazol-2-yl)-6-methoxy-1H-indazole

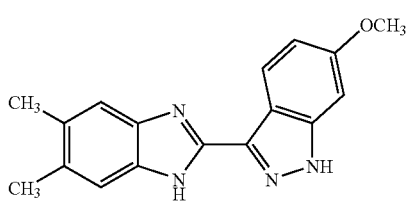

By proceeding in a manner similar to Example 235(a) above but using 6-methoxy-1H-indazole-3-carbaldehyde [Reference Example 6(f)] there was prepared 3-(5,6-dimethyl-1H-benzoimidazol-2-yl)-6-methoxy-1H-indazole as a pale orange solid. LC-MS (METHOD B): R$_T$=2.52 minutes; 293 (M+H)⁺.

(h) 5,6-Dimethyl-2-(4-phenyl-1H-pyrazol-3-yl)-1H-benzoimidazole

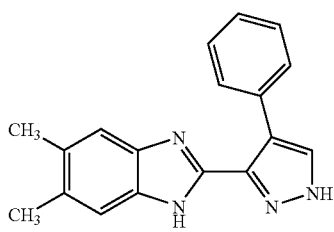

By proceeding in a manner similar to Example 235(a) above but using 4-phenyl-1H-pyrazole-3-carbaldehyde [Reference Example 6(g)] there was prepared 5,6-dimethyl-2-(4-phenyl-1H-pyrazol-3-yl)-1H-benzoimidazole as a white solid. LC-MS (METHOD B): R$_T$=2.35 minutes; 289 (M+H)⁺.

(i) 3-(5-Ethyl-1H-benzoimidazol-2-yl)-1H-indazole

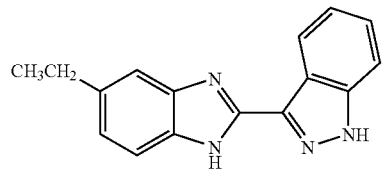

By proceeding in a manner similar to Example 235(a) above but using 4-ethyl-phenylene diamine [Reference Example 29(a)], a reaction temperature of 160° C. and subjecting the reaction product to flash column chromatography on silica eluting with a mixture of ethyl acetate and hexane (2:1) there was prepared 3-(5-ethyl-1H-benzoimidazol-2-yl)-1H-indazole as an off-white solid. LC-MS (Method D): R$_T$=23.13 minutes, 263.3 (M+H)⁺.

(j) 3-(5-Ethyl-6-methyl-1H-benzoimidazol-2-yl)-1H-indazole

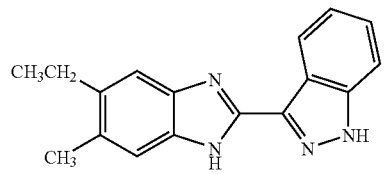

By proceeding in a manner similar to Example 235(i) above but using 4-ethyl-5-methyl-phenylene diamine [Reference Example 30(a)] there was prepared 3-(5-ethyl-6-methyl-1H-benzoimidazol-2-yl-1H-indazole as an off-white solid. LC-MS (Method D): R$_T$=23.79 minutes, 277.3 (M+H)⁺.

(k) 3-(5-Isopropyl-6-methyl-1H-benzoimidazol-2-yl)-1H-indazole

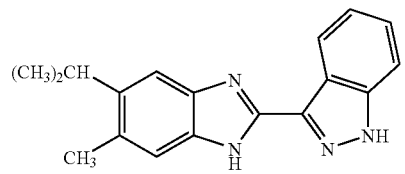

By proceeding in a manner similar to Example 235(i) above but using 4-isopropyl-5-methyl-phenylene diamine [Reference Example 30(b)] there was prepared 3-(5-isopropyl-6-methyl-1H-benzoimidazol-2-yl)-1H-indazole as an off-white solid. MS: 291.03 (N+H)⁺. HPLC (METHOD B1): R$_T$=23.39 minutes.

(l) 3-(5-Bromo-6-methyl-1H-benzoimidazol-2-yl)-1H-indazole

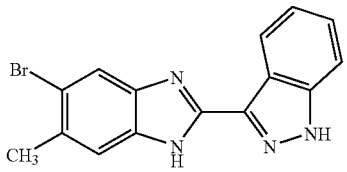

By proceeding in a manner similar to Example 235(i) above but using 4-bromo-5-methyl-phenylene diamine [Reference Example 30(c)] there was prepared 3-(5-bromo-6-methyl-1H-benzoimidazol-2-yl)-1H-indazole as an off-white solid. MS: 329.09 (M+H)⁺. HPLC (METHOD B1): $R_T$=22.74 minutes.

(m) 3-(5-Bromo-1H-benzoimidazol-2-yl)-1H-indazole

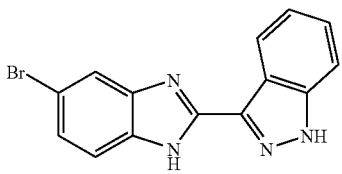

By proceeding in a manner similar to Example 235(i) above but using 4-bromo-phenylene diamine [Reference Example 30(e)] there was prepared 3-(5-bromo-1H-benzoimidazol-2-yl)-1H-indazole as a brown solid. LC-MS (Method D): $R_T$=23.46 minutes, 315.15 (M+1)⁺.

(n) 3-(5-(3-Cyano)phenyl-1H-benzoimidazol-2-yl)-1H-indazole

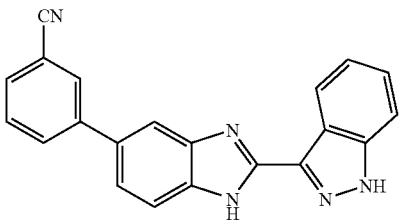

By proceeding in a manner similar to Example 235(i) above but using 3',4'-diaminobiphenyl-3-carbonitrile [Reference Example 30(f)] there was prepared 3-(5-(3-cyano)phenyl-1H-benzoimidazol-2-yl)-1H-indazole as a white solid. MS: 335.3 (M+H)⁺. HPLC (METHOD B1): $R_T$=21.47 minutes.

(o) 3-(5-(Pyrid-3-yl)-1H-benzoimidazol-2-yl)-1H-indazole

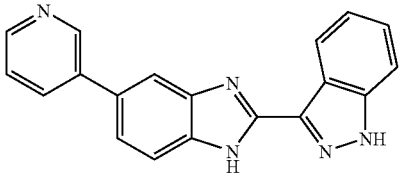

By proceeding in a manner similar to Example 235(i) above but using 4-(pyridine-3-yl) benzene-1,2-diamine [Reference Example 30(g)] there was prepared 3-(5-(pyrid-3-yl)-1H-benzoimidazol-2-yl)-1H-indazole as a white solid. MS: 312.2 (M+H)⁺. HPLC (METHOD B1): $R_T$=8.58 minutes.

(p) 3-(6-Methyl-5-phenyl-1H-benzoimidazol-2-yl)-1H-indazole

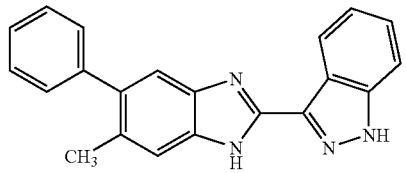

By proceeding in a manner similar to Example 235(i) above but using 6-methylbiphenyl-3,4-diamine [Reference Example 30(h)] there was prepared 3-(6-methyl-5-phenyl-1H-benzoimidazol-2-yl)-1H-indazole as a white solid. MS: 325.3 (M+H)⁺. HPLC (METHOD B1): $R_T$ 14.48 minutes.

(q) 3-(5-Phenyl-1H-benzoimidazol-2-yl)-1H-indazole

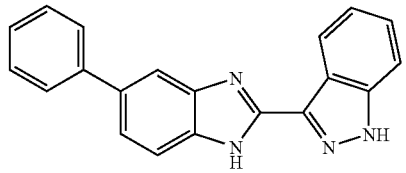

By proceeding in a manner similar to Example 235(i) above but using 4-biphenyl-3,4-diamine [Reference Example 30(i)] there was prepared 3-(5-phenyl-1H-benzoimidazol-2-yl)-1H-indazole as a white solid. MS: 311.2 (M+H)⁺. HPLC (Method D): $R_T$=24.54 minutes.

(r) 3-(5-(2-Fluoro)phenyl-1H-benzoimidazol-2-yl)-1H-indazole

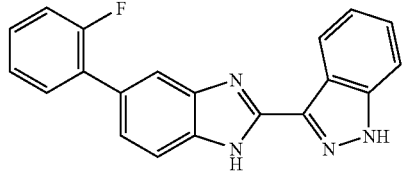

By proceeding in a manner similar to Example 235(i) above but using 2'-fluorobiphenyl-3,4-diamine diamine [Reference Example 30(j)] there was prepared 3-(5-(2-fluoro)phenyl-1H-benzoimidazol-2-yl)-1H-indazole as a white solid. MS: 329.2 (M+H)⁺. HPLC (METHOD B1): $R_T$=22.54 minutes.

(s) 3-(5-(3,4-methylenedioxy)phenyl-1H-benzoimidazol-2-yl)-1H-indazole

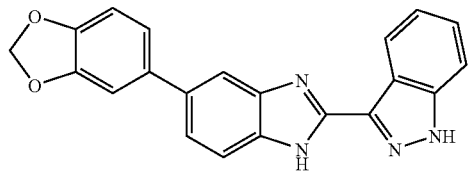

By proceeding in a manner similar to Example 235(i) above but using 4-benzo[1,3]dioxol-5-ylbenzene-1,2-diamine [Reference Example 30(k)] there was prepared 3-(5-

(5,6-methylenedioxy)phenyl-1H-benzoimidazol-2-yl)-1H-indazole as a white solid. MS: 355.2 (M+H)⁺. HPLC (METHOD B1): R_T=22.04 minutes.

(t) 3-(5-(2-Methoxy)phenyl-1H-benzoimidazol-2-yl)-1H-indazole

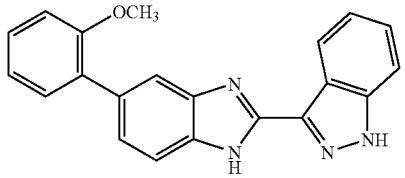

By proceeding in a manner similar to Example 235(i) above but using 2'-methoxybiphenyl-3,4-diamine [Reference Example 30(l)] there was prepared 3-(5-(2-methoxy)phenyl-1H-benzoimidazol-2-yl)-1H-indazole as a white solid. MS: 341.2 (M+H)⁺. HPLC (METHOD B1): R_T=22.09 minutes.

(u) 3-(5-(4-Chlorophenyl-1H-benzoimidazol-2-yl)-1H-indazole

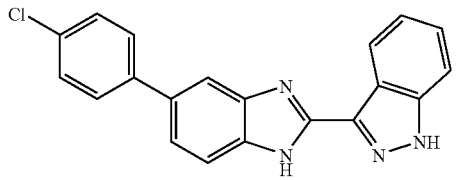

By proceeding in a manner similar to Example 235(i) above but using 4'-chlorobiphenyl-3,4-diamine [Reference Example 30(m)] there was prepared 3-(5-(4-chloro)phenyl-1H-benzoimidazol-2-yl)-1H-indazole as a white solid. MS: 345.2 (M+H)⁺. HPLC (METHOD B1): R_T=23.71 minutes.

(v) 3-(5-(4-Methyl)phenyl-1H-benzoimidazol-2-yl)-1H-indazole

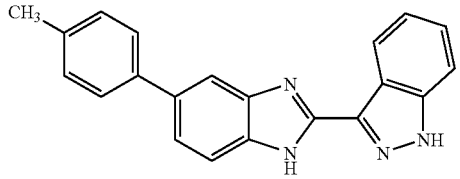

By proceeding in a manner similar to Example 235(i) above but using 4'-methylbiphenyl-3,4-diamine diamine [Reference Example 30(n)] there was prepared 3-(5-(4-methyl)phenyl-1H-benzoimidazol-2-yl)-1H-indazole as a white solid. MS: 325.1 (M+H)⁺. HPLC (METHOD C1): R_T=15.22 minutes.

(w) 3-(5-Benzyloxy-1H-benzoimidazol-2-yl)-1H-indazole

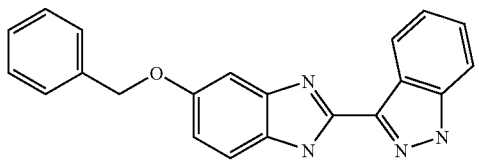

By proceeding in a manner similar to Example 235(i) above but using 4-benzyloxybenzene-1,2-diamine [Reference Example 30(o)] there was prepared 3-(5-benzyloxy-1H-benzoimidazol-2-yl)-1H-indazole as a white solid. MS: 339.3 (M+H)⁺. HPLC (METHOD B1): R_T=22.32 minutes.

(x) 3-(5,6-Methylenedioxy-1H-benzoimidazol-2-yl)-1H-indazole

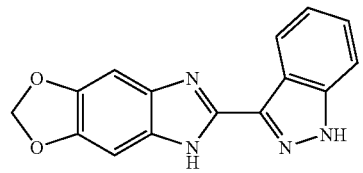

By proceeding in a manner similar to Example 235(i) above but using benzo[1,3]dioxole-5,6-diamine [Reference Example 30(p)] there was prepared 3-(5,6-methylenedioxy-1H-benzoimidazol-2-yl)-1H-indazole as a white solid. LC-MS (METHOD B): R_T=2.25 minutes; 279.22 (M+H)⁺.

(y) 3-(5,6-Dimethoxy-1H-benzoimidazol-2-yl)-1H-indazole

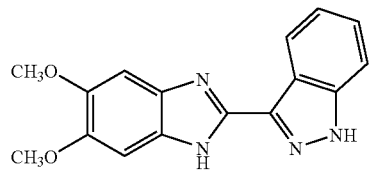

By proceeding in a manner similar to Example 235(i) above but using 4,5-dimethoxybenzene-1,2-diamine [Reference Example 30(q)] there was prepared 3-(5,6-dimethoxy-1H-benzoimidazol-2-yl)-1H-indazole as a white solid. LC-MS (METHOD B): R_T=2.16 minutes; 295.26 (M+H)⁺.

(z) 3-(5,6-Diethyl-1H-benzoimidazol-2-yl)-1H-indazole

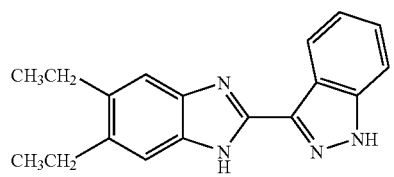

By proceeding in a manner similar to Example 235(i) above but using 4,5-diethylbenzene-1,2-diamine [Reference Example 30(r)] there was prepared 3-(5,6-diethyl-1H-benzoimidazol-2-yl)-1H-indazole as a white solid. LC-MS (METHOD B): R_T=2.49 minutes; 291.32 (M+H)⁺.

(aa) 3-(4,5-Dimethyl-1H-benzoimidazol-2-yl)-1H-indazole

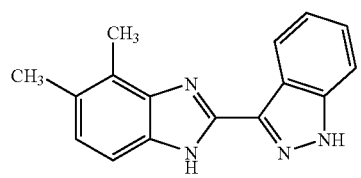

By proceeding in a manner similar to Example 235(i) above but using 3,4-dimethylbenzene-1,2-diamine there was prepared 3-(4,5-dimethyl-1H-benzoimidazol-2-yl)-1H-indazole as a white solid. LC-MS (METHOD B): $R_T$=2.31 minutes; 263.24 (M+H)$^+$.

(ab) 2-(1H-Indazol-3-yl)-1H-benzoimidazole-5-carbonitrile

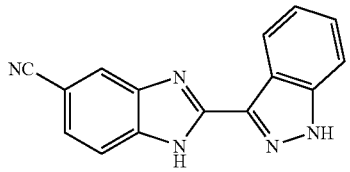

By proceeding in a manner similar to Example 235(i) above but using 3,4-diaminobenzonitrile amine there was prepared 2-(1H-indazol-3-yl)-1H-benzoimidazole-5-carbonitrile as a white solid.

LC-MS (Method D): $R_T$=21.81 minutes, MS: 260.10 (M+H)$^+$.

(ac) 3-(5-methoxycarbonyl-1H-benzoimidazol-2-yl)-1H-indazole

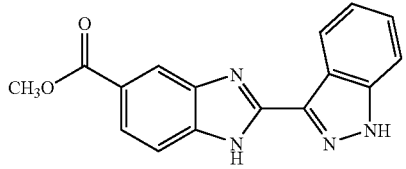

By proceeding in a manner similar to Example 235(i) above but using 3,4-diaminobenzoic acid, methyl ester there was prepared 3-(5-methoxycarbonyl-1H-benzoimidazol-2-yl)-1H-indazole as a white solid. LC-MS (Method D): $R_T$=22.13 minutes, 293.16 (M+H)$^+$.

(ad) 3-(5,6-Dimethyl-1H-benzoimidazol-2-yl)-5-ethoxy-1H-indazole

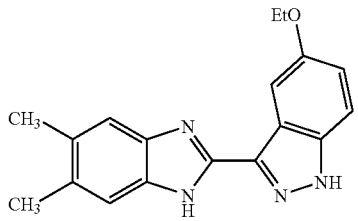

By proceeding in a manner similar to Example 235(a) above but using 5-ethoxy-3-formyl-indazole-1-carboxylic acid tert-butyl ester [Reference Example 20(d)] there was prepared 3-(5,6-dimethyl-1H-benzoimidazol-2-yl)-5-ethoxy-1H-indazole as a pale orange solid. MS: 307 (M+H)$^+$. HPLC (METHOD B1): $R_T$=13.58 minutes.

(ae) 3-(5,6-Dimethyl-1H-benzoimidazol-2-yl)-pyrazole-4-carboxylic acid ethyl ester

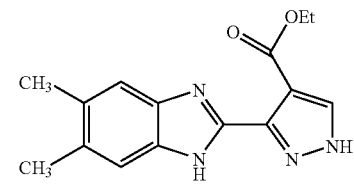

By proceeding in a manner similar to Example 235(a) above but using 3-formyl-pyrazole-4-carboxylic acid ethyl ester [Reference Example 6(i)] there was prepared 3-(5,6-dimethyl-1H-benzoimidazol-2-yl-pyrazole-4-carboxylic acid ethyl ester as a pale brown solid. LC-MS (METHOD B): 2.56 minutes; 285 (M+H)$^+$.

(af) 2-(4-Isopropylcarbamoyl-1H-pyrazol-3-yl)-1H-benzoimidazole-5-carboxylic acid methyl ester

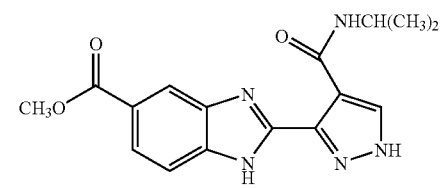

By proceeding in a manner similar to Example 235(a) above but using 3-formyl-pyrazole-4-carboxylic acid isopropylamide [Reference Example 6(j)] and methyl-3,4-diamino benzoate there was prepared 2-(4-isopropylcarbamoyl-1H-pyrazol-3-yl)-1H-benzoimidazole-5-carboxylic acid methyl ester as a yellow solid. LC-MS (METHOD B): 2.99 minutes; 328 (M+H)$^+$.

(ag) 3-(5,6-Dimethyl-1H-benzoimidazol-2-yl)-5-methyl-pyrazole-4-carboxylic acid ethyl ester

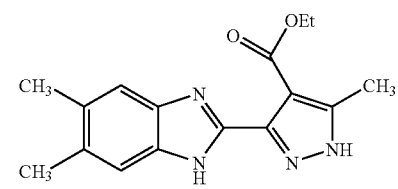

By proceeding in a manner similar to Example 235(a) above but using 3-formyl-5-methyl-pyrazole-4-carboxylic acid ethyl ester [Reference Example 6(k)] there was prepared 3-(5,6-dimethyl-1H-benzoimidazol-2-yl)-5-methyl-pyrazole-4-carboxylic acid ethyl ester as a white solid. LC-MS (METHOD B): $R_T$=2.59 minutes; 299 (M+H)$^+$.

(ah) 3-(1,5,6,7-Tetrahydro-1,3-diaza-s-indacen-2-yl)-1H-pyrazole-4-carboxylic acid cyclopropylamide

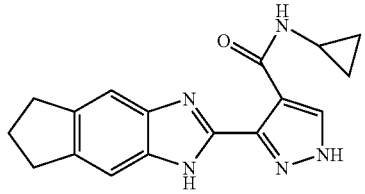

By proceeding in a manner similar to Example 235(a) above but using indane-5,6-diamine (130 mg) and 3-formyl-1H-pyrazole-4-carboxylic acid cyclopropylamide [150 mg, Reference Example 6(q)] and subjecting the reaction product to chromatography on silica [eluting with ethyl acetate/gradient 75 to 0% heptane] followed by trituration with acetone, there was prepared 3-(1,5,6,7-tetrahydro-1,3-diaza-s-indacen-2-yl)-1H-pyrazole-4-carboxylic acid cyclopropylamide (31 mg) as a white solid. LC-MS (Method A): $R_T$=2.85 minutes, 308 (M+H)$^+$.

(ai) 3-(5-Methoxy-6-methyl-1H-benzoimidazol-2-yl)-1H-pyrazole-4-carboxylic acid isopropylamide

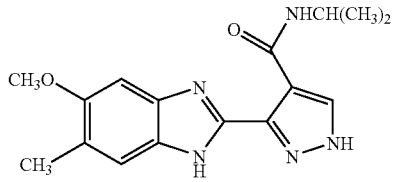

By proceeding in a manner similar to Example 235(a) above but using 3-formyl-pyrazole-4-carboxylic acid-isopropylamide [198 mg, Reference Example 60] and 4-methoxy-5-methyl-benzene-1,2-diamine [166 mg, Reference Example 29(b)] and subjecting the reaction product to flash chromatography on silica eluting with dichloromethane/methanol (95:5) followed by recrystallisation from a mixture of ethyl acetate and n-pentane there was prepared 3-(5-methoxy-6-methyl-1H-benzoimidazol-2-yl)-1H-pyrazole-4-carboxylic acid isopropylamide (145 mg) as a white solid. LC-MS (Method H): $R_T$=2.09 minutes, 314.27 (M+H)$^+$, 312.29 (M−H)$^−$.

(aj) 3-[5-(2-Morpholin-4-yl-ethoxy)-1H-benzoimidazol-2-yl]-1H-indazole

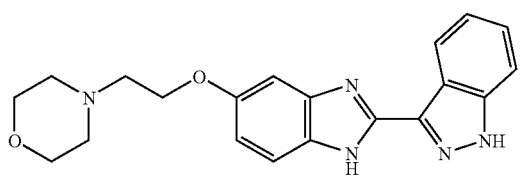

By proceeding in a manner similar to Example 235(i) above but using 4-(2-morpholin-4-yl-ethoxy)-benzene-1,2-diamine [Reference Example 29(c)] and subjecting the reaction product to preparative LC-MS there was prepared 3-[5-(2-morpholin-4-yl-ethoxy)-1H-benzoimidazol-2-yl]-1H-indazole (25 mg) as a white solid. MS: 364 (M+H)$^+$. HPLC (METHOD B1): $R_T$=19.38 minutes.

(ak) 3-(5,6-dimethyl-1H-benzoimidazol-2-yl)-1H-pyrazole-4-carboxylic acid (2-methoxy-ethyl)-amide

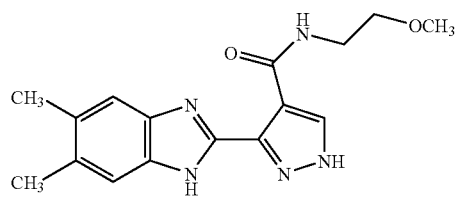

By proceeding in a manner similar to Example 235(i) above but using 4,5-dimethylbenzene-1,2-diamine and 3-formyl-1H-pyrazole-4-carboxylic acid (2-methoxy-ethyl)-amide [Reference Example 6(n)] there was prepared 3-(5,6-dimethyl-1H-benzoimidazol-2-yl)-1H-pyrazole-4-carboxylic acid (2-methoxy-ethyl)-amide (87 mg) as a cream solid. LC-MS (METHOD L): $R_T$=4.23 minutes, 314.2 (M+H)$^+$.

(al) 3-(5,6-dimethyl-1H-benzoimidazol-2-yl)-1H-pyrazole-4-carboxylic acid propylamide

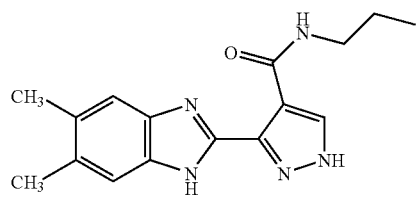

By proceeding in a manner similar to Example 6(i) above but using 4,5-dimethylbenzene-1,2-diamine and 3-formyl-1H-pyrazole-4-carboxylic acid propylamide [Reference Example 6(o)] there was prepared 3-(5,6-dimethyl-1H-benzoimidazol-2-yl)-1H-pyrazole-4-carboxylic acid propylamide (73 mg) as a pale yellow solid. LC-MS (METHOD L): $R_T$=4.94 minutes, 298.29 (M+H)$^+$.

(am) 3-(5,6-dimethyl-1H-benzoimidazol-2-yl)-1H-pyrazole-4-carboxylic acid (tetrahydro-pyran-4-yl)-amide

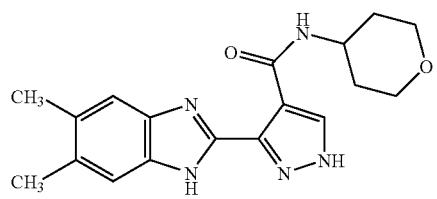

By proceeding in a manner similar to Example 235(i) above but using 4,5-dimethyl-1,2-phenylenediamine and 3-formyl-1H-pyrazole-4-carboxylic acid (tetrahydro-pyran-4-yl)-amide [Reference Example 6(p)] and recrystallising the reaction product from methanol there was prepared 3-(5,6-dimethyl-1H-benzoimidazol-2-yl)-1H-pyrazole-4-carboxylic acid (tetrahydro-pyran-4-yl)-amide (228 mg) as a white solid. LC-MS (METHOD R): $R_T$=9.40 minutes, 360 (M+H)$^+$.

(an) 3-(5-Ethyl-6-methyl-1H-benzoimidazol-2-yl)-1H-indazole-5-carbonitrile

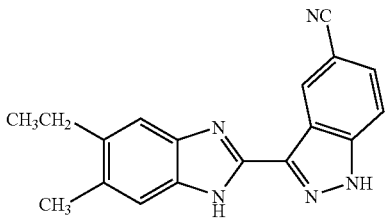

By proceeding in a manner similar to Example 235(i) above but using 4-ethyl-5-methyl-phenylene diamine [Reference Example 30(a)] and 3-formyl-1H-indazole-5-carbonitrile [Reference Example 68] there was prepared 3-(5-ethyl-6-methyl-1H-benzoimidazol-2-yl)-1H-indazole-5-carbonitrile (133 mg) as a pale yellow solid. MS: 302 (M+H)$^+$. HPLC (METHOD B1): $R_T$=16.45 minutes.

(ao) 3-(5-Difluoromethoxy-1H-benzoimidazol-2-yl)-1H-pyrazole-4-carboxylic acid isopropylamide

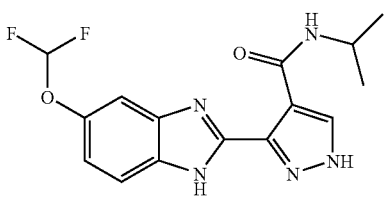

By proceeding in a manner similar to Example 235(i) above but using 4-difluormethoxy-benzene-1,2-diamine [Reference Example 30(y)] and 3-formyl-pyrazole-4-carboxylic acid isopropylamide [Reference Example 6(j)] there was prepared 3-(5-difluoromethoxy-1H-benzoimidazol-2-yl)-1H-pyrazole-4-carboxylic acid isopropylamide (118 mg) as a white solid. LC-MS (METHOD L): $R_T$=10.46 minutes, 336.19 (M+H)$^+$.

(ap) 3-(5-Difluoromethoxy-1H-benzoimidazol-2-yl)-1H-pyrazole-4-carboxylic acid cyclopropylamide

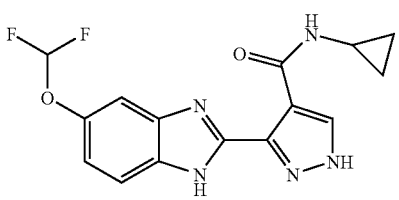

By proceeding in a manner similar to Example 235(ao) above but using 3-formyl-1H-pyrazole-4-carboxylic acid cyclopropylamide [Reference Example 6(q)] there was prepared 3-(5-difluoromethoxy-1H-benzoimidazol-2-yl)-1H-pyrazole-4-carboxylic acid cyclopropylamide (63 mg) as a white solid. LC-MS (METHOD L): $R_T$=10.18 minutes, 334.17 (M+H)$^+$.

(aq) 3-(6-Ethyl-5-methoxy-1H-benzoimidazol-2-yl)-1H-pyrazole-4-carboxylic acid isopropylamide

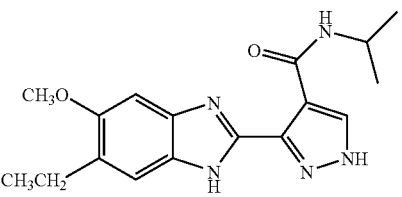

By proceeding in a manner similar to Example 235(i) but using 4-ethyl-5-methoxy-benzene-1,2-diamine [200 mg, Reference Example 30(z)] and 3-formyl-pyrazole-4-carboxylic acid isopropylamide [Reference Example 6(j)] there was prepared 3-(6-ethyl-5-methoxy-1H-benzoimidazol-2-yl)-1H-pyrazole-4-carboxylic acid isopropylamide (115 mg) as an off-white solid. LC-MS (METHOD L): $R_T$=11.34 minutes, 328.24 (M+H)$^+$.

(ar) 3-(5,6-Dimethyl-1H-benzoimidazol-2-yl)-1H-indazole-5-carbonitrile dihydrochloride

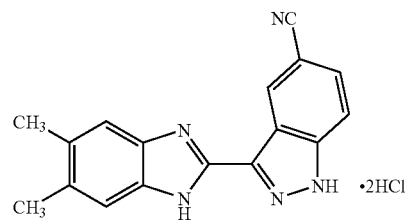

By proceeding in a manner similar to Example 235(i) above but (i) using 4,5-dimethyl-phenylene diamine and 3-formyl-1H-indazole-5-carbonitrile [Reference Example 68] (ii) treating a suspension of the reaction product in methanol with a solution of hydrochloric acid (4M) in 1,4-dioxane followed by evaporation of the mixture (iii) trituration of the residue with methanol and (iv) recrystallisation from diethyl ether, there was prepared 3-(5,6-dimethyl-1H-benzoimidazol-2-yl)-1H-indazole-5-carbonitrile dihydrochloride (133 mg) as an off-white solid. LC-MS (METHOD B): $R_T$=2.32 minutes. MS: 288 (M+H)$^+$.

(as) 3-(5-nitro-1H-benzoimidazol-2-yl)-1H-indazole

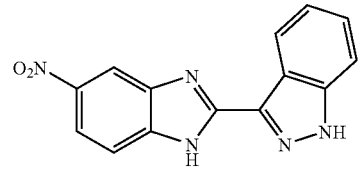

By proceeding in a manner similar to Example 235(a) above but using 4-nitrophenylenediamine there was prepared 3-(5-nitro-1H-benzoimidazol-2-yl)-1H-indazole as red solid. MS: 280.17 (M+H)$^+$. HPLC (Method B1): $R_T$=3.00 minutes.

EXAMPLE 236

2-(5-Methyl-1H-pyrazol-3-yl)-1H-benzoimidazole

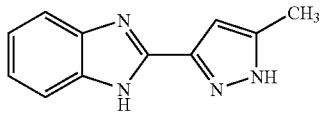

A mixture of o-phenylenediamine (1.08 g) and 5-methylpyrazole-3-carboxylic acid (1.266 g) was finely ground and the finely ground material was heated at 160° C. for 3 hours and then cooled to ambient temperature. The reaction mixture was recrystallised from ethyl alcohol (50 mL) to give a light blue solid (0.27 g). The filtrate gave another crop (0.1 g) on standing. The combined solids were recrystallised from ethyl alcohol to give 2-(5-methyl-1H-pyrazol-3-yl)-1H-benzoimidazole (223 mg) as a lilac coloured solid, mp 322-324° C. [Elemental analysis:—C, 66.54%; H, 4.80%; N, 28.14%. Calculated for $C_{11}H_{10}N_4$:—C, 66.64%; H, 5.09%; N, 28.27%].

EXAMPLE 237

2-(5-Ethoxy-1H-pyrazol-3-yl)-1H-benzoimidazole

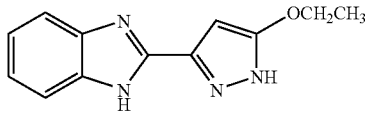

A mixture of trifluoroacetic acid (6 mL) and 2-(5-ethoxy-1H-pyrazol-3-yl)-1-(2-trimethylsilanyl-ethoxymethyl)-1H-benzoimidazole (300 mg, Reference Example 11) was stirred at 50° C. for 1.5 hours. The reaction mixture was evaporated and the residue was partitioned between ethyl acetate and water (pH 10). The organic layer was dried and then evaporated. The residue was subjected to chromatography on silica eluting with a mixture of dichloromethane and methanol (9:1, v/v) and then recrystallised from toluene to give 2-(5-ethoxy-1H-pyrazol-3-yl)-1H-benzoimidazole (0.1 g) as a colourless solid, mp 217-219.5° C. [Elemental analysis:—C, 62.26%; H, 5.23%; N, 23.44%. Calculated for $C_{12}H_{12}N_4O$:—C, 63.15%; H, 5.30%; N, 24.55%].

EXAMPLE 238

2-(5-Methylsulfanyl-isoxazol-3-yl)-1H-benzoimidazole

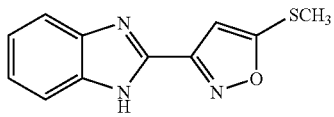

A mixture of 2-(5-methylsulfanyl-isoxazol-3-yl)-1-(2-trimethylsilanyl-ethoxymethyl)-1H-benzoimidazole (160 mg, Reference Example 12), methanol (12 mL) and concentrated aqueous hydrochloric acid (2.45 mL) were heated at reflux for four hours, then cooled and then evaporated. The residue was treated with aqueous sodium bicarbonate and the mixture was extracted with ethyl acetate. The extracts were dried and then evaporated to give 2-(5-methylsulfanyl-isoxazol-3-yl)-1H-benzoimidazole (96 mg) as an off white solid, mp 179-181° C. $^1$H-NMR [$(CD_3)_2SO$]: δ 4.65 (s, 3H), 9.00 (s, 1H), 9.15-9.6 (m, 4H).

EXAMPLE 239

(a) 5-Chloro-2-(4-nitro-1H-pyrazol-3-yl)-1H-benzoimidazole

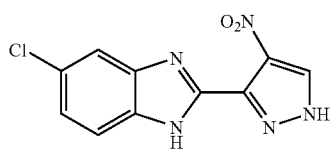

A solution of 4-chloro-benzene-1,2-diamine (500 mg) in hydrochloric acid (4N) was treated with 4-nitro-pyrazole-3-carboxylic acid (826 mg) then heated at reflux temperature, under nitrogen. The reaction mixture was cooled to room temperature when the pH was adjusted to 8 by addition of ammonium hydroxide and the mixture was extracted with ethyl acetate. The extracts were evaporated to give 5-chloro-2-(4-nitro-1H-pyrazol-3-yl)-1H-benzoimidazole.

(b) 5,6-dichloro-2-(4-nitro-1H-pyrazol-3-yl)-1H-benzoimidazole

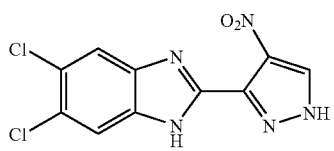

By proceeding in a similar manner to Example 239(a) above but using 4,5-dichloro-1,2-diaminobenzene there was prepared 5,6-dichloro-2-(4-nitro-1H-pyrazol-3-yl)-1H-benzoimidazole.

EXAMPLE 240

(Benzoimidazol-2-yl)-5-methylthio-3-pyrazole

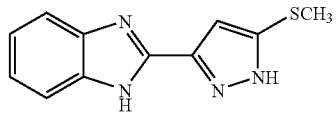

A mixture of 1-[(3,3-bis(methylthio))benzoimidazol-2-yl] propen-2-one [5.5 g, Reference Example 15], hydrazine hydrate (1.02 g) and acetonitrile (50 mL) was stirred at reflux for 18 hours. The reaction mixture was cooled, and the precipitate was isolated by filtration. Recrystallisation from aqueous ethanol provided (benzoimidazol-2-yl)-5-methylthio-3-pyrazole (3.36 g) as a beige crystalline solid, m.p.

242° C. [Elemental analysis: Found: C, 57.8; H, 4.5; N, 24.0. Calculated for $C_{11}H_{10}N_4S$: C, 57.37; H, 4.38; N, 24.33].

EXAMPLE 241

(a) 3-(5,6-Dimethyl-1H-benzoimidazol-2-yl)-4,5,6,7-tetrahydro-1H-indazole

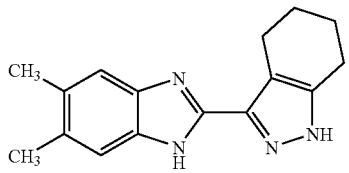

4,5-Dimethylbenzene-1,2-diamine (90 mg) and 4,5,6,7-tetrahydro-1H-indazole-3-carboxylic acid [110 mg, Reference Example 17(a)] were mixed in a glass vial then subjected to microwave radiation (900 W, domestic oven) twice for two minutes. The resulting solid was subjected to flash column chromatography on silica eluting with a mixture of ethyl acetate and hexane (85:15, v/v) to give 3-(5,6-dimethyl-1H-benzoimidazol-2-yl)-4,5,6,7-tetrahydro-1H-indazole (30 mg) as a pale brown solid. LC-MS (METHOD B): $R_T$=2.28 minutes; 267 (M+H)$^+$.

(b) 2-(5-Isopropyl-1H-pyrazol-3-yl)-5,6-dimethyl-1H-benzoimidazole

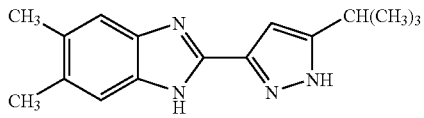

By proceeding in a manner similar to Example 241 (a) above, but using 5-isopropyl-1H-pyrazole-3-carboxylic acid [Reference Example 17(b)] there was prepared 2-(5-isopropyl-1H-pyrazol-3-yl)-5,6-dimethyl-1H-benzoimidazole (80 mg) as a brown solid. LC-MS (METHOD B): $R_T$=2.27 minutes; 255 (M+H)$^+$.

(c) 2-(5-Ethyl-1H-pyrazol-3-yl)-5,6-dimethyl-1H-benzoimidazole

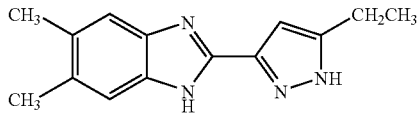

By proceeding in a manner similar to Example 241(a) above but using 5-ethyl-1H-pyrazole-3-carboxylic acid [Reference Example 17(c)], and triturating the brown solid reaction product with a mixture of ethyl acetate and hexane (1:1, v/v), there was prepared 2-(5-ethyl-1H-pyrazol-3-yl)-5,6-dimethyl-1H-benzoimidazole as a light brown solid. LC-MS (METHOD B): $R_T$=2.22 minutes; 241 (M+H)$^+$.

(d) 5,6-Dimethyl-2-(1,4,5,6-tetrahydro-cyclopentapyrazol-3-yl)-1H-benzoimidazole

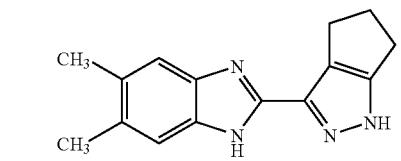

By proceeding in a manner similar to Example 214(a) above but using 1,4,5,6-tetrahydro-cyclopentapyrazole-3-carboxylic acid [Reference Example 17(f)] and triturating the reaction product with ethyl acetate, ether and methanol, there was prepared 5,6-dimethyl-2-(1,4,5,6-tetrahydro-cyclopentapyrazol-3-yl)-1H-benzoimidazole (50 mg) as an off-white solid. MS: 253 (M+H)$^+$. HPLC (METHOD B1): $R_T$=11.17 minutes.

EXAMPLE 242

(a) 3-(5,6-Dimethyl-1H-benzoimidazol-2-yl)-4-fluoro-1H-indazole

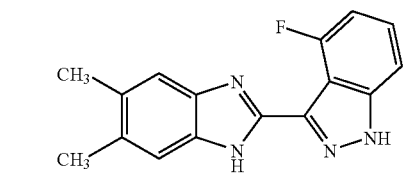

A mixture of 4,5-dimethylbenzene-1,2-diamine (70 mg) and 4-fluoro-1H-indazole-3-carbaldehyde [80 mg, Reference Example 20(b)] in dimethylformamide (8 ml) was heated to 120° C. for 30 minutes and then at 100° C. for 16 hours. The reaction mixture was cooled, then diluted with ethyl acetate and then washed five times with brine. The organic phase was dried over magnesium sulfate and then evaporated. The residue was subjected to flash column chromatography on silica eluting with a mixture of 40/60 petrol and ethyl acetate (1:5, v/v) to give 3-(5,6-dimethyl-1H-benzoimidazol-2-yl)-4-fluoro-1H-indazole (104 mg) as a light brown solid. MS: 281 (M+H)$^+$. HPLC (METHOD B1): $R_T$=10.08 minutes.

(b) 4-Chloro-3-(5,6-dimethyl-1H-benzoimidazol-2-yl)-1H-indazole

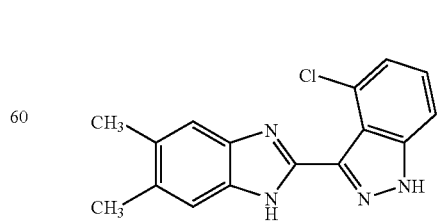

By proceeding in a manner similar to Example 242(a) above but using 4-chloro-3-formyl-indazole-1-carboxylic acid tert-butyl ester [Reference Example 20(c)] there was prepared 4-chloro-3-(5,6-dimethyl-1H-benzoimidazol-2-yl)-1H-indazole (25 mg) as an off-white solid. MS: 299 (M+H)+. HPLC (METHOD B1): $R_T$=10.59 minutes.

(c) 3-(5,6-Dimethyl-1H-benzoimidazol-2-yl)-5-chloro-1H-indazole

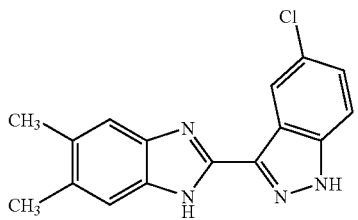

By proceeding in a manner similar to Example 242(a) above but using 5-chloro-1H-indazole-3-carbaldehyde [Reference Example 6(h)] there was prepared 3-(5,6-dimethyl-1H-benzoimidazol-2-yl)-5-chloro-1H-indazole (25 mg) as a pale brown solid. LC-MS (METHOD D): $R_T$=24.24 minutes, 299 (M+H)+.

EXAMPLE 243

3-(5,6-Dimethyl-1H-benzoimidazol-2-yl)-1H-indazol-5-ol

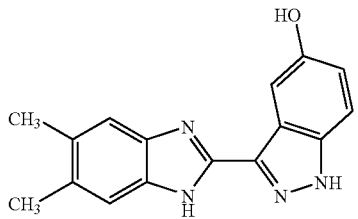

A solution of 3-(5,6-dimethyl-1H-benzoimidazol-2-yl)-5-methoxy-1H-indazole [34 mg, Example 235(b)] at 0° C. was treated with a solution of boron tribromide in dichloromethane (0.30 mL, 1M). The mixture was then heated at reflux temperature for 4 hours, then cooled and then treated dropwise with water. The pH was adjusted to between 7 and 8 by the addition of saturated aqueous sodium bicarbonate solution and this mixture was then extracted twice with ethyl acetate. The combined extracts were washed with brine, then dried over magnesium sulfate and then evaporated. The pale yellow solid residue was subjected to flash column chromatography on silica eluting with a mixture of ethyl acetate and triethylamine (99:1, v/v) to yield 3-(5,6-dimethyl-1H-benzoimidazol-2-yl)-1H-indazol-5-ol (23 mg) as a white solid. LC-MS (METHOD B): $R_T$=2.19 minutes; 279 (M+H)+.

EXAMPLE 244

(a) 3-(5-n-Propyl-1H-benzoimidazol-2-yl)-1H-indazole

A stirred solution of 4-propyl-benzene-1,2-diamine [57 mg, Reference Example 30(d)] and sodium bisulfite (40 mg) in dimethylformamide (2 ml) was treated with indazole-3-carboxaldehyde [Reference Example 6(l)]. The reaction mixture was heated in a Smith Creator microwave at 200° C. for 13 minutes then partitioned between ethyl acetate and water. The organic layer was washed with brine, then dried over magnesium sulfate and then evaporated. The residue was subjected to flash column chromatography on silica eluting with a mixture of ethyl acetate and hexane (3:1) to give 3-(5-n-propyl-1H-benzoimidazol-2-yl)-1H-indazole (74 mg) as a pale brown solid. MS: 277.3 (M+H)+. HPLC (METHOD B1): $R_T$=12.81 minutes.

(b) 2-(1H-Indazol-3-yl)-1H-benzoimidazole-5-sulfonic acid benzylamide

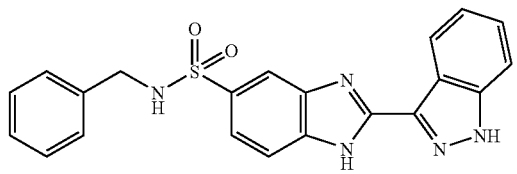

By proceeding in a manner similar to Example 244(a) above but using 3,4-diamino-N-benzyl-benzenesulfonamide [Reference Example 30(x)] and heating at 230° C. there was prepared 2-(1H-indazol-3-yl)-1H-benzoimidazole-5-sulfonic acid benzylamide (235 mg) as a white solid. LC-MS (METHOD L): $R_T$=6.35 minutes, 404.20 (M+H)+.

(c) 3-(5-Methanesulfonyl-1H-benzoimidazol-2-yl)-1H-indazole

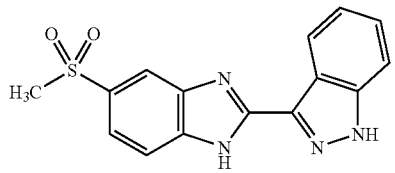

By proceeding in a manner similar to Example 244(a) above but using 4-methanesulfonyl-benzene-1,2-diamine [Reference Example 49(f)] and heating at 210° C. there was prepared 3-(5-methanesulfonyl-1H-benzoimidazol-2-yl)-1H-indazole (105 mg) as a white solid. LC-MS (METHOD L): $R_T$=5.71 minutes, 313.23 (M+H)+.

EXAMPLE 245

[2-(indazol-3-yl)-1H-benzoimidazol-5-yl]-phenyl-methanol

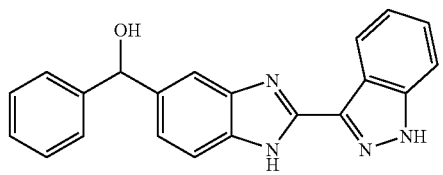

A stirred solution of [2-(indazol-3-yl)-1H-benzoimidazol-5-yl]-phenyl-methanone [200 mg, Example 234(c)] in tetrahydrofuran (10 mL), at −78° C. and under an atmosphere of nitrogen, was treated dropwise with a solution of diisobutylaluminium hydride in tetrahydrofuran (1.18 mL, 1N). The reaction mixture was warmed to ambient temperature, then stirred for 16 hours and then partitioned between ether and sodium hydroxide solution (2N). The organic phase was washed with water, then with brine, then dried over magnesium sulfate and then evaporated. The residue was subjected to flash column chromatography on silica eluting with a mixture of ethyl acetate and hexane (3:1, v/v) to give [2-(indazol-3-yl)-1H-benzoimidazol-5-yl]-phenyl-methanol (161 mg) as a white solid. LC-MS (Method D): $R_T$=21.89 minutes, 341.3 (M+H)$^+$.

EXAMPLE 246

(a) [2-(Indazol-3-yl)-1H-benzoimidazol-5-yl]-carboxylic acid, ethylamide

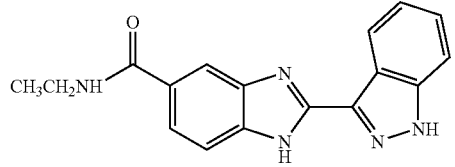

A stirred solution of [2-(indazol-3-yl)-1H-benzoimidazol-5-yl]-carboxylic acid [130 mg, Example 247(a)], hydroxybenzatriazole (189 mg) and diisopropyl ethylamine (732 µL) in dimethylformamide (3 mL) was treated with ethylamine and 1-(3-dimethylaminopropyl)-3-ethylcarbodiimide hydrochloride (267 mg). The reaction mixture was heated at 80° C. overnight and then partitioned between ethyl acetate and 5% citric acid. The aqueous layer was re-extracted with ethyl acetate. The combined organic layers were washed with saturated aqueous sodium hydrogen carbonate solution, then with brine, then dried over magnesium sulfate and then evaporated. The residual oil was subjected to preparative HPLC to give [2-(indazol-3-yl)-1H-benzoimidazol-5-yl]-carboxylic acid, ethylamide as a white solid. LC-MS (METHOD B): $R_T$=2.37 minutes; 306.27 (M+H)$^+$.

(b) [2-(Indazol-3-yl)-1H-benzoimidazol-5-yl]-carboxylic acid, methylamide

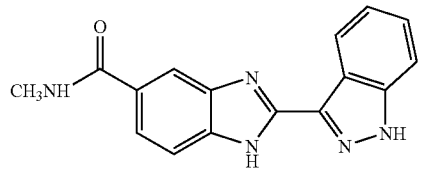

By proceeding in a manner similar to Example 246(a) above but using methylamine, there was prepared [2-(indazol-3-yl)-1H-benzoimidazol-5-yl]-carboxylic acid, methylamide as a white solid.

LC-MS (METHOD B): $R_T$=2.28 minutes; 292.30 (M+H)$^+$.

(c) [2-(Indazol-3-yl)-1H-benzoimidazol-5-yl]-carboxylic acid, dimethylamide

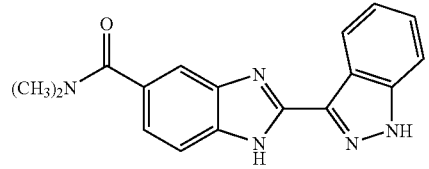

By proceeding in a manner similar to Example 246(a) above but using dimethylamine, there was prepared [2-(indazol-3-yl)-1H-benzoimidazol-5-yl]-carboxylic acid, dimethylamide as a white solid. LC-MS (METHOD B): $R_T$=2.38 minutes; 306.27 (M+H)$^+$.

(d) [2-(Indazol-3-yl)-1H-benzoimidazol-5-yl]-carboxylic acid, isopropylamide

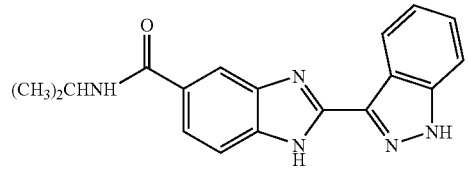

By proceeding in a manner similar to Example 246(a) above but using isopropylamine, there was prepared [2-(indazol-3-yl)-1H-benzoimidazol-5-yl]-carboxylic acid, isopropylamide as a white solid.

LC-MS (METHOD B): $R_T$=2.48 minutes; 320.30 (M+H)$^+$.

(e) [2-(Indazol-3-yl)-1H-benzoimidazol-5-yl]-carboxylic acid, benzylamide

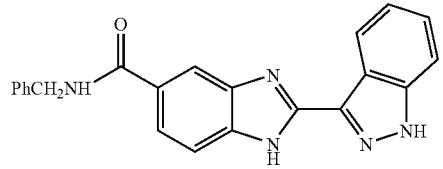

By proceeding in a manner similar to Example 246(a) above but using benzylamine, there was prepared [2-(indazol-3-yl)-1H-benzoimidazol-5-yl]-carboxylic acid, benzylamide as a white solid.

LC-MS (METHOD B): $R_T$=2.68 minutes; 368.27 (M+H)$^+$.

(f) [2-(Indazol-3-yl-1H-benzoimidazol-5-yl]-carboxylic acid, benzamide

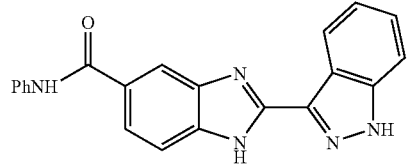

By proceeding in a manner similar to Example 246 (a) above but using aniline, there was prepared [2-(indazol-3-yl)-1H-benzoimidazol-5-yl]-carboxylic acid, benzamide as a white solid.

LC-MS (METHOD B): $R_T$=2.73 minutes; 354.26 (M+H)$^+$.

(g) 3-(5,6-Dimethyl-1H-benzoimidazol-2-yl)-1H-pyrazole-4-carboxylic acid isopropylamide

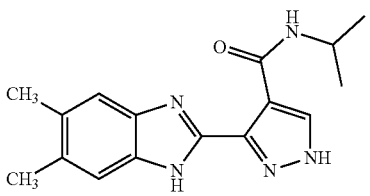

By proceeding in a manner similar to Example 246(a) above but using 3-(5,6-dimethyl-1H-benzoimidazol-2-yl)-pyrazole-4-carboxylic acid [Example 247(b)] and isopropylamine, and subjecting the reaction product to flash chromatography on silica eluting with a mixture of dichloromethane and methanol (19:1, v/v), there was prepared 3-(5,6-dimethyl-1H-benzoimidazol-2-yl)-1H-pyrazole-4-carboxylic acid isopropylamide as an off-white solid. LC-MS (METHOD B): $R_T$=2.67 minutes; 298 (M+H)$^+$.

(h) 3-(5,6-Dimethyl-1H-benzoimidazol-2-yl)-1H-pyrazole-4-carboxylic acid (2-hydroxy-1,1-dimethyl-ethyl)-amide

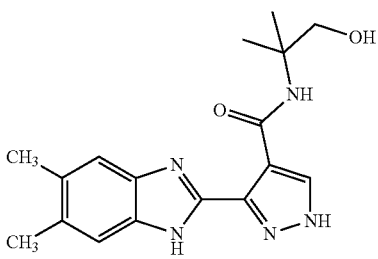

By proceeding in a manner similar to Example 246(a) above but using 3-(5,6-dimethyl-1H-benzoimidazol-2-yl)-pyrazole-4-carboxylic acid [Example 247(b)] and 2-amino-2-methyl-1-propanol, and subjecting the reaction product to flash chromatography on silica eluting with a mixture of dichloromethane and methanol (19:1, v/v), there was prepared 3-(5,6-dimethyl-1H-benzoimidazol-2-yl)-1H-pyrazole-4-carboxylic acid (2-hydroxy-1,1-dimethyl-ethyl)-amide as a pale yellow solid.
LC-MS (METHOD B): $R_T$=2.63 minutes; 328 (M+H)$^+$.

(i) 2-(4-Isopropylcarbamoyl-1H-pyrazol-3-yl)-1H-benzoimidazole-5-carboxylic acid (pyridin-3-ylmethyl)-amide

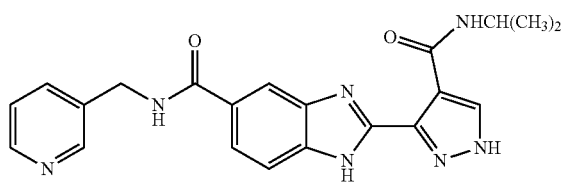

By proceeding in a manner similar to Example 246(a) above but using 2-(4-isopropylcarbamoyl-1H-pyrazol-3-yl)-1H-benzoimidazole-5-carboxylic acid [Example 247(c)] and 3-aminomethyl)pyridine there was prepared 2-(4-isopropylcarbamoyl-1H-pyrazol-3-yl)-1H-benzoimidazole-5-carboxylic acid (pyridin-3-ylmethyl)-amide as a white solid.
LC-MS (METHOD B): $R_T$=2.49 minutes; 404 (M+H)$^+$.

(j) 3-(5,6-Dimethyl-1H-benzoimidazol-2-yl)-5-methyl-1H-pyrazole-4-carboxylic acid cyclopropylamide

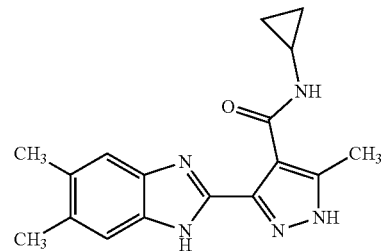

By proceeding in a manner similar to Example 246(a) above but using 3-(5,6-dimethyl-1H-benzoimidazol-2-yl)-5-methyl-pyrazole-4-carboxylic acid [Example 247(d)] and cyclopropylamine, and subjecting the reaction product to flash chromatography on silica eluting with a mixture of dichloromethane and methanol (119:1, v/v), there was prepared 3-(5,6-dimethyl-1H-benzoimidazol-2-yl)-5-methyl-1H-pyrazole-4-carboxylic acid cyclopropylamide as a white solid. LC-MS (METHOD B): $R_T$=2.67 minutes; 310 (M+H)$^+$.

(k) 2-(4-Isopropylcarbamoyl-1H-pyrazol-3-yl)-1H-benzoimidazole-5-carboxylic acid phenylmethyl-amide

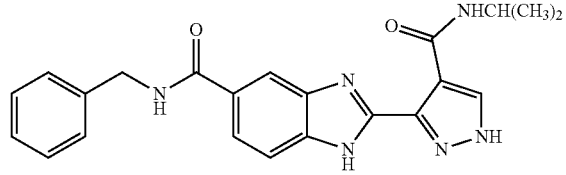

By proceeding in a manner similar to Example 246(a) above but using 2-(4-isopropylcarbamoyl-1H-pyrazol-3-yl)-1H-benzoimidazole-5-carboxylic acid [Example 247(c)] and benzylamine there was prepared 2-(4-isopropylcarbamoyl-1H-pyrazol-3-yl)-1H-benzoimidazole-5-carboxylic acid phenylmethyl-amide as a pale yellow solid. LC-MS (METHOD B): $R_T$=3.17 minutes; 403 (M+H)$^+$.

(l) 2-(4-Isopropylcarbamoyl-1H-pyrazol-3-yl)-1H-benzoimidazole-5-carboxylic acid (pyridin-2-ylmethyl)-amide

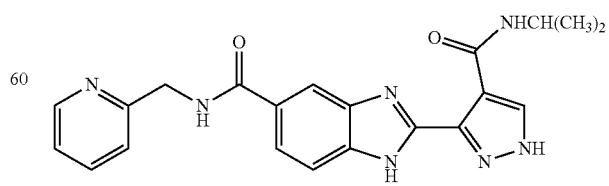

By proceeding in a manner similar to Example 246(a) above but using 2-(4-isopropylcarbamoyl-1H-pyrazol-3-yl)-

1H-benzoimidazole-5-carboxylic acid [Example 247(c)] and 2-(aminomethyl)pyridine there was prepared 2-(4-isopropylcarbamoyl-1H-pyrazol-3-yl)-1H-benzoimidazole-5-carboxylic acid (pyridin-2-ylmethyl)-amide as an off-white solid. LC-MS (Method D): $R_T$=9.33 minutes, 367.28 (M+H)⁺.

(m) 2-(1H-Indazol-3-yl)-1H-benzoimidazole-5-carboxylic acid (pyridin-3-ylmethyl)-amide

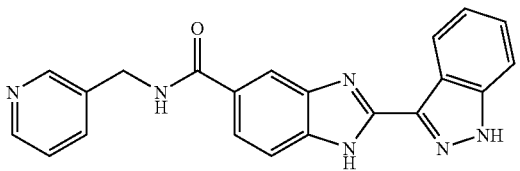

By proceeding in a manner similar to Example 246(a) above but using 3-(aminomethyl)pyridine there was prepared 2-(1H-indazol-3-yl)-1H-benzoimidazole-5-carboxylic acid (pyridin-3-ylmethyl)-amide (42.2 mg) as an off white solid. LC-MS (Method L): $R_T$=4.96 minutes, 367.19 (M−H)⁻.

(n) 2-(1H-Indazol-3-yl)-1H-benzoimidazole-5-carboxylic acid 3-methyl-benzylamide

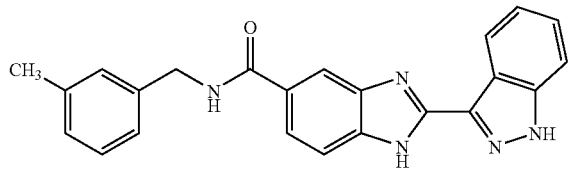

By proceeding in a manner similar to Example 246(a) above but using 3-methylbenzylamine there was prepared 2-(1H-indazol-3-yl)-1H-benzoimidazole-5-carboxylic acid 3-methyl-benzylamide (33.4 mg) as a white solid. MS: 382.52 (M+H)⁺. HPLC (Method B1): $R_T$=16.22 minutes.

(o) 2-(1H-Indazol-3-yl)-1H-benzoimidazole-5-carboxylic acid 4-methyl-benzylamide

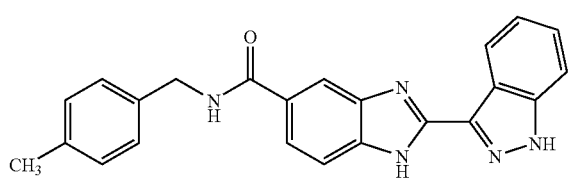

By proceeding in a manner similar to Example 246(a) above but using 4-methylbenzylamine there was prepared 2-(1H-indazol-3-yl)-1H-benzoimidazole-5-carboxylic acid 4-methyl-benzylamide (63.5 mg) as a white solid. MS: 382.54 (M+H)⁺. HPLC (Method B1): $R_T$=16.14 minutes.

(p) 2-(1H-Indazol-3-yl)-1H-benzoimidazole-5-carboxylic acid [3-(2-oxo-pyrrolidin-1-yl)-propyl]-amide

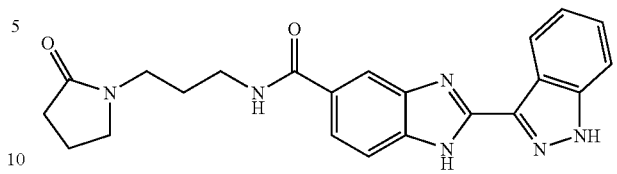

By proceeding in a manner similar to Example 246(a) above but using 1-(3-aminopropyl)-2-pyrrolidinone there was prepared 2-(1H-indazol-3-yl)-1H-benzoimidazole-5-carboxylic acid [3-(2-oxo-pyrrolidin-1-yl)-propyl]-amide (68.1 mg) as a white solid. MS: 401.13 (M−H)⁻. HPLC (Method B1): $R_T$=11.29 minutes.

(q) 2-(1H-Indazol-3-yl)-1H-benzoimidazole-5-carboxylic acid (2-morpholin-4-yl-ethyl)-amide

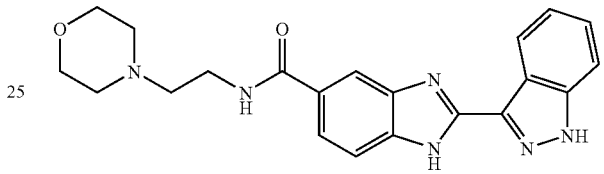

By proceeding in a manner similar to Example 246(a) above but using 4-(2-aminoethyl)morpholine there was prepared 2-(1H-indazol-3-yl)-1H-benzoimidazole-5-carboxylic acid (2-morpholin-4-yl-ethyl)-amide (70.8 mg) as a white solid. MS: 389.12 (M−H)⁻. HPLC (Method B1): $R_T$=8.51 minutes.

(r) 2-(1H-Indazol-3-yl)-1H-benzoimidazole-5-carboxylic acid (2-methoxy-ethyl)-amide

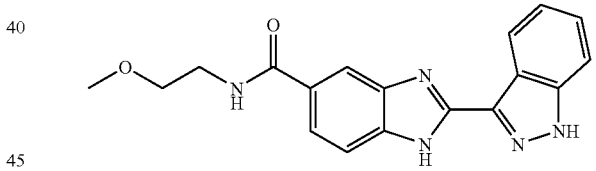

By proceeding in a manner similar to Example 246(a) above but using 2-methoxyethylamine there was prepared 2-(1H-indazol-3-yl)-1H-benzoimidazole-5-carboxylic acid (2-methoxy-ethyl)-amide (55.2 mg) as a white solid. MS: 336.52 (M+H)⁺. HPLC (Method B1): $R_T$=11.30 minutes.

(s) 2-(1H-Indazol-3-yl)-1H-benzoimidazole-5-carboxylic acid (2-cyano-ethyl)-amide

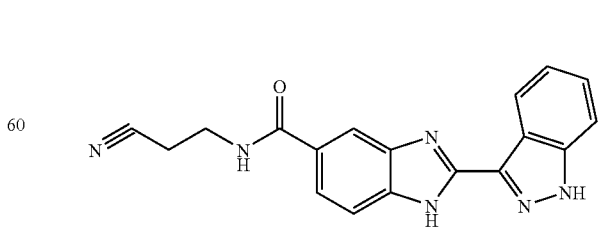

By proceeding in a manner similar to Example 246(a) above but heating the reaction at 50° C. and using 3-aminopropionitrile there was prepared 2-(1H-indazol-3-yl)-1H-benzoimidazole-5-carboxylic acid (2-cyano-ethyl)-amide (15.4 mg) as a white solid. MS: 331.15 (M+H)+, 329.17 (M−H)−. HPLC (Method B1): $R_T$=12.72 minutes.

(t) 2-(1H-Indazol-3-yl)-1H-benzoimidazole-5-carboxylic acid (2-hydroxy-1,1-dimethyl-ethyl)-amide

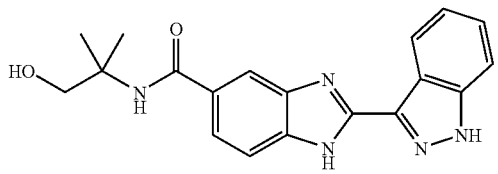

By proceeding in a manner similar to Example 246(a) above but heating the reaction at 50° C. and using 2-amino-2-methyl-1-propanol there was prepared 2-(1H-indazol-3-yl)-1H-benzoimidazole-5-carboxylic acid (2-hydroxy-1,1-dimethyl-ethyl)-amide (29.6 mg) as a brown oil. LC-MS (Method L): $R_T$=10.57 minutes, 350.16 (M+H)+, 348.18 (M−H)−.

(u) 2-(1H-Indazol-3-yl)-1H-benzoimidazole-5-carboxylic acid (3-imidazol-1-yl-propyl)-amide

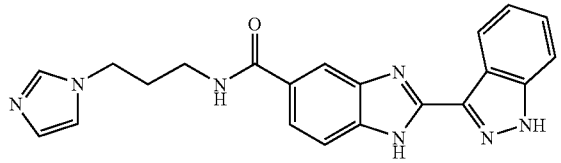

By proceeding in a manner similar to Example 246(a) above but using 1-(3-aminopropyl)imidazole there was prepared 2-(1H-Indazol-3-yl)-1H-benzoimidazole-5-carboxylic acid (3-imidazol-1-yl-propyl)-amide (31.9 mg) as a white solid. LC-MS (Method B): $R_T$=8.45 minutes, 386.22 (M+H)+, 384.26 (M−H)−.

(v) 3-(5,6-dimethyl-1H-benzoimidazol-2-yl)-1H-pyrazole-4-carboxylic acid isobutyl-amide

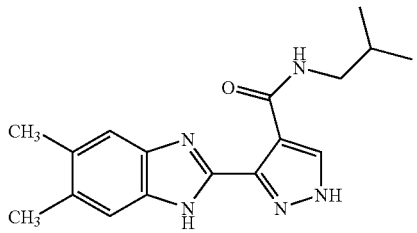

By proceeding in a manner similar to Example 246(g) above but using isobutylamine there was prepared 3-(5,6-dimethyl-1H-benzoimidazol-2-yl)-1H-pyrazole-4-carboxy-lic acid isobutyl-amide (101 mg) as a white solid. LC-MS (METHOD M): $R_T$=9.38 minutes, 312 (M+H)+.

(w) 3-(5,6-dimethyl-1H-benzoimidazol-2-yl)-1H-pyrazole-4-carboxylic acid isopropylamide

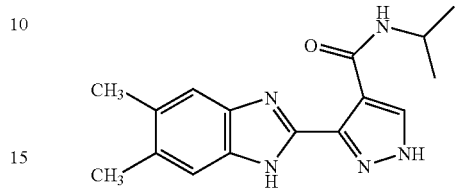

By proceeding in a manner similar to Example 246(g) above but using isopropylamine there was prepared 3-(5,6-dimethyl-1H-benzoimidazol-2-yl)-1H-pyrazole-4-carboxy-lic acid isopropylamide (100 mg) as a white solid. LC-MS (METHOD L): $R_T$=7.21 minutes, 298 (M+H)+.

(x) 3-(5,6-dimethyl-1H-benzoimidazol-2-yl)-1H-pyrazole-4-carboxylic acid cyclopropylmethyl-amide

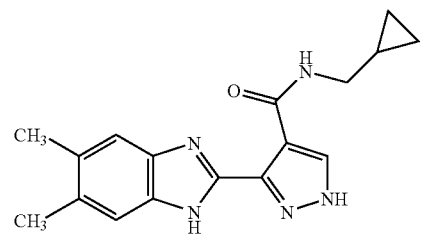

By proceeding in a manner similar to Example 246(g) above but using (aminomethyl)cyclopropane there was prepared 3-(5,6-dimethyl-1H-benzoimidazol-2-yl)-1H-pyrazole-4-carboxylic acid cyclopropylmethyl-amide (105 mg) as a white solid. LC-MS (METHOD M): $R_T$=8.77 minutes, 310 (M+H)+.

(y) 3-(5,6-dimethyl-1H-benzoimidazol-2-yl)-5-methyl-1H-pyrazole-4-carboxylic acid tert-butylamide

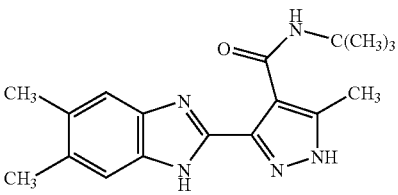

By proceeding in a manner similar to Example 246(j) above but using tert-butylamine there was prepared 3-(5,6-dimethyl-1H-benzoimidazol-2-yl)-5-methyl-1H-pyrazole-4-carboxylic acid tert-butylamide (57 mg) as an off-white solid. LC-MS (METHOD M): $R_T$=13.86 minutes, 326 (M+H)+.

(z) 3-(5,6-Dimethyl-1H-benzoimidazol-2-yl)-1H-indazole-5-carboxylic acid dimethylamide dihydrochloride

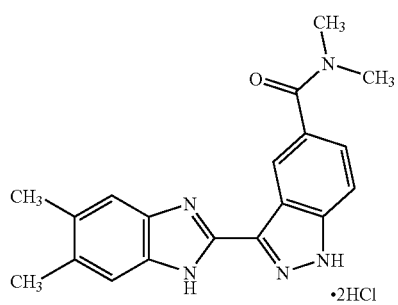

By proceeding in a manner similar to Example 246(j) above, but (i) using 3-(5,6-dimethyl-1H-benzoimidazol-2-yl)-1H-indazole-5-carboxylic acid [97 mg, Example 263] and dimethylamine hydrochloride (23 mg), (ii) carrying out the reaction at ambient temperature overnight, and (iii) subjecting the reaction product to flash column chromatography [eluting with ethyl acetate to ethyl acetate/methanol (97:3, v/v)] followed by treatment with 4M hydrogen chloride in 1,4-dioxane and trituration with dichloromethane and diethyl ether there was prepared 3-(5,6-dimethyl-1H-benzoimidazol-2-yl)-1H-indazole-5-carboxylic acid dimethylamide dihydrochloride (8 mg) as a white solid. LC-MS (METHOD M): $R_T$=9.37 minutes, 320 $(M+H)^+$.

(aa) 2-(4-Isobutyrylamino-1H-pyrazol-3-yl)-1H-benzoimidazole-5-carboxylic acid benzylamide

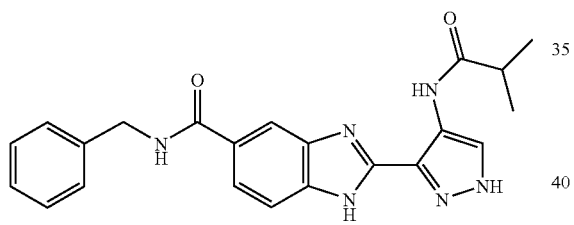

By proceeding in a manner similar to Example 246(a) above but using 2-(4-isobutylamino-1H-pyrazol-3-yl)-1H-benzoimidazole-5-carboxylic acid [Reference Example 35] and benzylamine there was prepared 2-(4-Isobutyrylamino-1H-pyrazol-3-yl)-1H-benzoimidazole-5-carboxylic acid benzylamide (17 mg) as a white solid. LC-MS (METHOD L): $R_T$=11.00 minutes, 403 $(M+H)^+$.

(ab) 2-(1H-Indazol-3-yl)-1H-benzoimidazole-5-carboxylic acid (2-piperidin-1-yl-ethyl)-amide

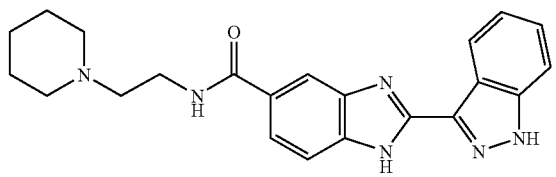

By proceeding in a manner similar to Example 246(a) above but using 1-(2-aminoethyl)piperidine, and heating the reaction mixture at 50° C. for 6 hours, there was prepared 2-(1H-indazol-3-yl)-1H-benzoimidazole-5-carboxylic acid (2-piperidin-1-yl-ethyl)-amide as an oil. MS: 387.22 (M–H)⁻. HPLC (Method L): $R_T$=5.03 minutes.

(ac) 2-(1H-Indazol-3-yl)-1H-benzoimidazole-5-carboxylic acid (pyridin-2-ylmethyl)-amide

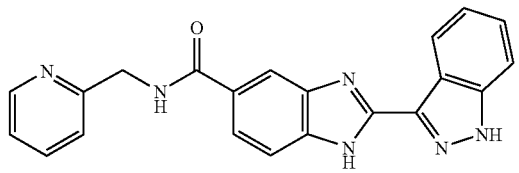

By proceeding in a manner similar to Example 246(ab) above but using (2-aminomethyl)pyridine there was prepared 2-(1H-indazol-3-yl)-1H-benzoimidazole-5-carboxylic acid (pyridin-2-ylmethyl)-amide as an off-white solid. MS: 367.28 $(M+H)^+$. HPLC (Method B1): $R_T$=9.33 minutes.

(ad) 2-(1H-Indazol-3-yl)-1H-benzoimidazole-5-carboxylic acid [3-(4-methyl-piperazin-1-yl)-propyl]-amide

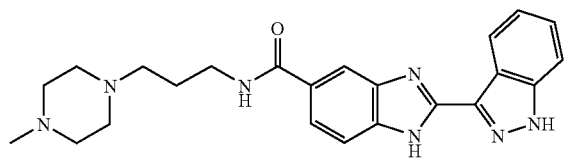

By proceeding in a manner similar to Example 246(ab) above but using 443-(aminopropyl))-1-methyl piperazine there was prepared 2-(4H-indazol-3-yl)-1H-benzoimidazole-5-carboxylic acid [3-(4-methyl-piperazin-1-yl)-propyl]-amide as an oil. MS: 416.21 $(M+H)^+$. HPLC (Method L): $R_T$=4.46 minutes.

(ae) N-[2-(1H-Indazol-3-yl)-1H-benzoimidazol-5-yl]-isobutyramide

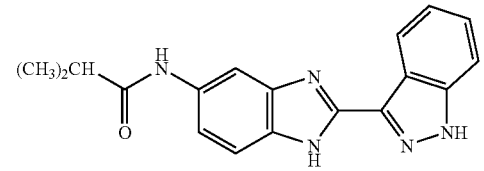

By proceeding in a manner similar to Example 246(ab) above but using isobutyric acid and 2-(1H-indazol-3-yl)-3H-benzoimidazol-5-amine [Example 265] there was prepared N-[2-(1H-Indazol-3-yl)-1H-benzoimidazol-5-yl]-isobutyramide as an off-white solid. MS: 320.23 $(M+H)^+$. HPLC (Method B1): $R_T$=19.28 minutes.

EXAMPLE 247

(a) [2-(Indazol-3-yl)-1H-benzoimidazol-5-yl]-carboxylic acid

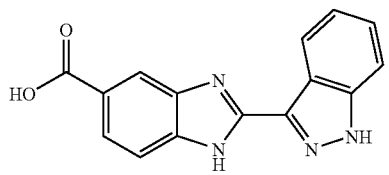

A stirred solution of 3-(5-methoxycarbonyl-1H-benzoimidazol-2-yl)-1H-indazole [84.5 mg, Example 235(ac)] and sodium hydroxide (74 mg) in tetrahydrofuran (4 mL) and water (2 mL) was heated at 75° C. overnight. The reaction mixture was evaporated and the oily residue was partitioned between ethyl acetate and water. The aqueous layer was acidified to pH 6 and extracted with ethyl acetate. The organic layers was dried over magnesium sulfate and then evaporated to give [2-(indazol-3-yl)-1H-benzoimidazol-5-yl]-carboxylic acid (80 mg) as an oil. MS: 279.14 (M+H)$^+$. HPLC (METHOD H): R$_T$=2.81 minutes.

(b) 3-(5,6-Dimethyl-1H-benzoimidazol-5-yl)-pyrazole-4-carboxylic acid

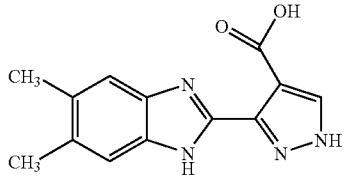

By proceeding in a manner similar to Example 247(a) above but using 3-(5,6-dimethyl-1H-benzoimidazol-2-yl)-pyrazole-4-carboxylic acid ethyl ester [Example 235(ae)] and carrying out the reaction at 60° C. there was prepared 3-(5,6-dimethyl-1H-benzoimidazol-5-yl)-pyrazole-4-carboxylic acid as a white solid. LC-MS (METHOD B): R$_T$=2.17 minutes; 257 (M+H)$^+$.

(c) 2-(4-Isopropylcarbamoyl-1H-pyrazol-3-yl)-1H-benzoimidazole-5-carboxylic acid

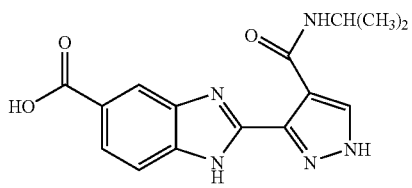

By proceeding in a manner similar to Example 247(a) above but using 2-(4-isopropylcarbamoyl-1H-pyrazol-3-yl)-1H-benzoimidazole-5-carboxylic acid methyl ester [Example 235(af)], replacing the tetrahydrofuran with methanol and carrying out the reaction at 65° C., there was prepared 2-(4-isopropylcarbamoyl-1H-pyrazol-3-yl)-1H-benzoimidazole-5-carboxylic acid as a pale brown solid which was used without further purification. LC-MS (METHOD B): R$_T$=2.67 minutes; 314 (M+H)$^+$.

(d) 3-(5,6-Dimethyl-1H-benzoimidazol-2-yl)-5-methyl-pyrazole-4-carboxylic acid

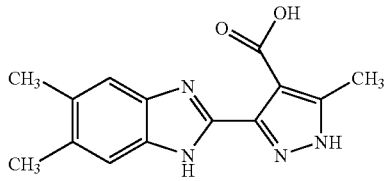

By proceeding in a manner similar to Example 247(a) above but using 3-(5,6-dimethyl-1H-benzoimidazol-2-yl)-5-methyl-pyrazole-4-carboxylic acid ethyl ester [Example 235 (ag)], replacing the tetrahydrofuran with methanol and carrying out the reaction at 65° C., there was prepared 3-(5,6-dimethyl-1H-benzoimidazol-2-yl)-5-methyl-pyrazole-4-carboxylic acid as a white solid. LC-MS (METHOD B): R$_T$=2.75 minutes; 271 (M+H)$^+$.

EXAMPLE 248

(a) N-[3-(5,6-Dimethyl-1H-benzoimidazol-2-yl)-1H-pyrazol-4-yl]-isobutyramide

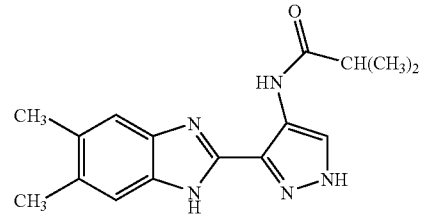

A stirred solution of 5,6-dimethyl-1H-benzoimidazol-2-yl)-1H-pyrazol-4-ylamine [83 mg, Example 233(c)] and diisopropylethylamine (256 µL) in dichloromethane (4 mL) was treated with isobutyryl chloride (115 µL). The reaction mixture was stirred for 30 minutes at room temperature then treated with piperidine (500 µL) and stirring was continued for a further hour. The reaction mixture was partitioned between 5% citric acid. The organic layer was dried over magnesium sulfate and then evaporated. The residue was subjected to flash chromatography on silica eluting with a mixture of hexane and ethyl acetate to give N-[3-(5,6-dimethyl-1H-benzoimidazol-2-yl)-1H-pyrazol-4-yl]-isobutyramide (49 mg) as a white solid. MS: 298.28 (M+H)$^+$. HPLC (METHOD B1): R$_T$=14.66 minutes.

(b) N-[3-(5,6-Dimethyl-1H-benzoimidazol-2-yl)-1H-pyrazol-4-yl]-3-methyl-butyramide

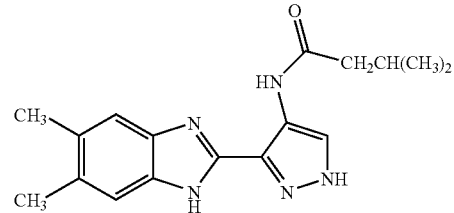

By proceeding in a manner similar to Example 248(a) above but using isovaleryl chloride there was prepared N-[3-(5,6-dimethyl-1H-benzoimidazol-2-yl)-1H-pyrazol-4-yl]-3-methyl-butyramide as a white solid. MS: 312.28 (M+H)$^+$. HPLC (METHOD B1): R$_T$=15.28 minutes.

(c) N-[3-(5,6-Dimethyl-1H-benzoimidazol-2-yl)-1H-pyrazol-4-yl]-2-phenyl-acetamide

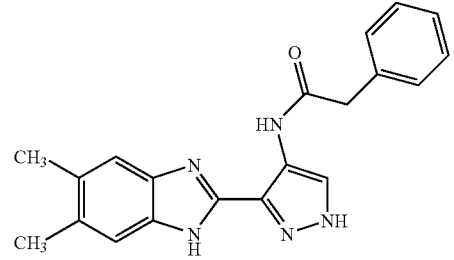

By proceeding in a manner similar to Example 248(a) above but using phenylacetyl chloride there was prepared N-[3-(5,6-dimethyl-1H-benzoimidazol-2-yl)-1H-pyrazol-4-yl]-2-phenyl-acetamide as a white solid. LC-MS (METHOD B): $R_T$=2.83 minutes, 346.18 (M+H)$^+$.

(d) Cyclopropanecarboxylic acid [3-(5,6-dimethyl-1H-benzoimidazol-2-yl)-1H-pyrazol-4-yl]-amide

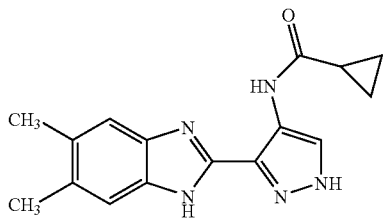

By proceeding in a manner similar to Example 248(a) above but using cyclopropanecarbonyl chloride, there was prepared cyclopropanecarboxylic acid [3-(5,6-dimethyl-1H-benzoimidazol-2-yl)-1H-pyrazol-4-yl]-amide as a white solid. MS: 296.28 (M+H)$^+$. HPLC (METHOD B1): $R_T$=13.50 minutes.

(e) Methoxyacetic acid [3-(5,6-dimethyl-1H-benzoimidazol-2-yl)-1H-pyrazol-4-yl]-amide

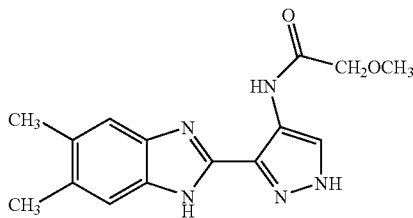

By proceeding in a manner similar to Example 248(a) above but using methoxyacetyl chloride, there was prepared methoxyacetic acid [3-(5,6-dimethyl-1H-benzoimidazol-2-yl)-1H-pyrazol-4-yl]-amide as a white solid. MS: 300.33 (M+H)$^+$. HPLC (METHOD C1): $R_T$=14.25 minutes.

(f) Cyclopentanecarboxylic acid [3-(5,6-dimethyl-1H-benzoimidazol-2-yl)-1H-pyrazol-4-yl]-amide

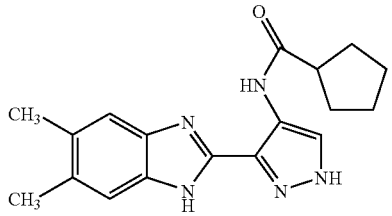

By proceeding in a manner similar to Example 248(a) above but using cyclopentylcarbonyl chloride, there was prepared cyclopentanecarboxylic acid [3-(5,6-dimethyl-1H-benzoimidazol-2-yl)-1H-pyrazol-4-yl]-amide as a white solid. MS: 324.39 (M+H)$^+$. HPLC (METHOD B1): $R_T$=17.64 minutes.

(g) Trimethylacetic acid [3-(5,6-dimethyl-1H-benzoimidazol-2-yl)-1H-pyrazol-4-yl]-amide

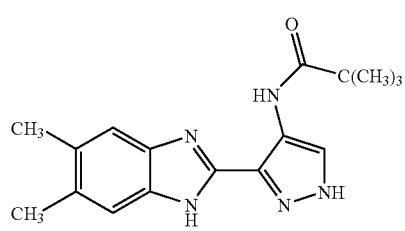

By proceeding in a manner similar to Example 248(a) above but using trimethylacetyl chloride, there was prepared trimethylacetic acid [3-(5,6-dimethyl-1H-benzoimidazol-2-yl)-1H-pyrazol-4-yl]-amide as a white solid. MS: 312.39 (M+H)$^+$. HPLC (METHOD B1): $R_T$=19.52 minutes.

(h) tert-Butylacetic acid [3-(5,6-dimethyl-1H-benzoimidazol-2-yl)-1H-pyrazol-4-yl]-amide

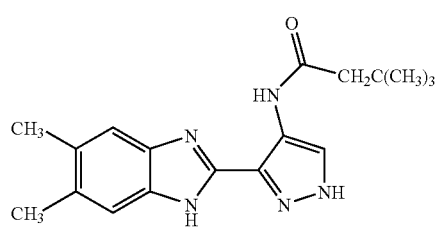

By proceeding in a manner similar to Example 248(a) above but using tert-butylacetyl chloride, there was prepared tert-butylacetic acid [3-(5,6-dimethyl-1H-benzoimidazol-2-yl)-1H-pyrazol-4-yl]-amide as a white solid. MS: 326.29 (M+H)$^+$. HPLC (METHOD B1): $R_T$=19.52 minutes.

(i) Butanoic acid [3-(5,6-dimethyl-1H-benzoimidazol-2-yl-1H-pyrazol-4-yl]-amide

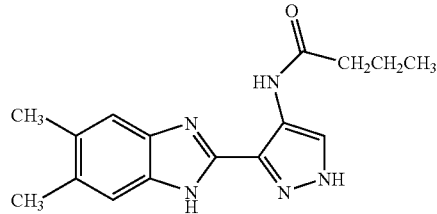

By proceeding in a manner similar to Example 248(a) above but using butyryl chloride, there was prepared butanoic acid [3-(5,6-dimethyl-1H-benzoimidazol-2-yl)-1H-pyrazol- 4-yl]-amide as a white solid. MS: 298.34 (M+H)⁺. HPLC (METHOD B1): R$_T$=15.07 minutes.

(j) Isoxazole-5-carboxylic acid [3-(5,6-dimethyl-1H-benzoimidazol-2-yl)-1H-pyrazol-4-yl]-amide

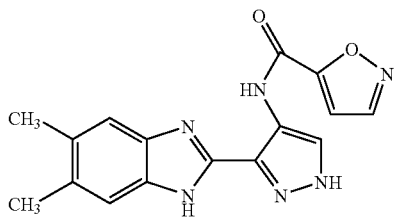

By proceeding in a manner similar to Example 248(a) above but using isoxazole-5-carbonyl chloride, there was prepared isoxazole-5-carboxylic acid [3-(5,6-dimethyl-1H-benzoimidazol-2-yl)-1H-pyrazol-4-yl]-amide as a white solid. MS: 323.16 (M+H)⁺. HPLC (METHOD B1): R$_T$=10.01 minutes.

(k) S(+)-2-Methylbutanoic acid [3-(5,6-dimethyl-1H-benzoimidazol-2-yl)-1H-pyrazol-4-yl]-amide

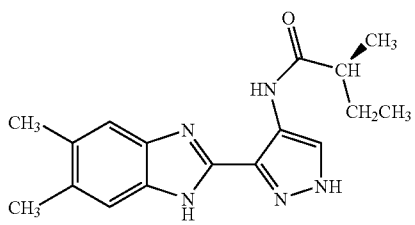

By proceeding in a manner similar to Example 248(a) above but using S(+)-2-methyl butyryl chloride, there was prepared S(+)-2-methylbutanoic acid [3-(5,6-dimethyl-1H-benzoimidazol-2-yl)-1H-pyrazol-4-yl]-amide as a white solid. MS: 312.18 (M+H)⁺. HPLC (METHOD B1): R$_T$=11.15 minutes.

(l) Cyclopropanecarboxylic acid [3-(5-ethyl-6-methyl-1H-benzoimidazol-2-yl)-1H-pyrazol-4-yl]-amide

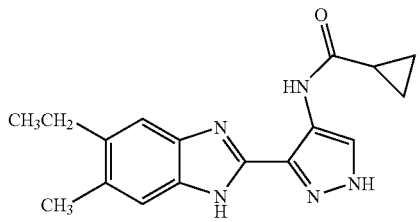

By proceeding in a manner similar to Example 248(a) above but using 3-(5-ethyl-6-methyl-1H-benzoimidazol-2-yl)-1H-pyrazol-4-ylamine [Example 233(d)] and cyclopropanecarbonyl chloride, there was prepared cyclopropanecarboxylic acid [3-(5-ethyl-6-methyl-1H-benzoimidazol-2-yl)-1H-pyrazol-4-yl]-amide as a white solid. MS: 310.32 (M+H)⁺. HPLC (METHOD B1): R$_T$=8.88 minutes.

(m) Piperidine-1-carboxylic acid[3-(6-chloro-5-methoxy-1H-benzoimidazol-2-yl)-1H-pyrazol-4-yl]-amide

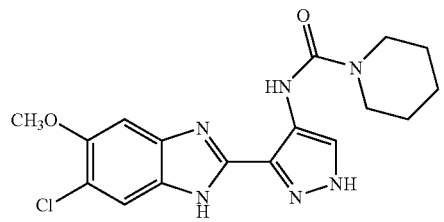

By proceeding in a manner similar to Example 248(a) above but (i) treating a solution of 3-(6-chloro-5-methoxy-1H-benzoimidazol-2-yl)-1H-pyrazol-4-ylamine [0.2 g, Example 233(e)] and diisopropylethylamine (392 mg, 4 eq) in tetrahydrofuran (25 mL) with piperidinecarbonyl chloride (450 mg, 4 eq), stirring overnight at ambient temperature, and evaporating the reaction mixture, (ii) triturating the reaction product with water (30 mL) and ethyl acetate (50 mL) and extracting with aqueous layer with ethyl acetate, (iii) combining the organic phases, drying over magnesium sulfate, then evaporating (iv) chromatographing the residue on silica gel (ethyl acetate), (v) triturating the partially purified material with ethyl acetate (15 mL) for 1.5 hours and filtering, and (vi) evaporating the filtrate and chromatographing the residue on silica gel (ethyl acetate/heptane gradient of 20-0%) there was prepared piperidine-1-carboxylic acid[3-(6-chloro-5-methoxy-1H-benzoimidazol-2-yl)-1H-pyrazol-4-yl]-amide (50 mg) as a yellow solid, mp>310° C. LC-MS (Method E) R$_T$=3.25 minutes, 374 (M+H)⁺.

(n) 3-[3-(6-Chloro-5-methoxy-1H-benzoimidazol-2-yl)-1H-pyrazol-4-yl]-1,1-dimethylurea

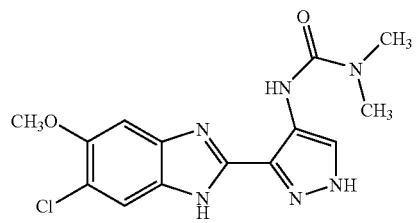

By proceeding in a similar manner to Example 248(m) above but using N,N-dimethylcarbamyl chloride there was prepared 3-[3-(6-chloro-5-methoxy-1H-benzoimidazol-2-yl)-1H-pyrazol-4-yl]-1,1-dimethylurea as a yellow solid, mp>300° C. LC-MS (Method E): R$_T$=2.4 minutes, 335 (M+H)⁺.

(o) Cyclopropanecarboxylic acid [3-(5-methoxy-1H-benzoimidazol-2-yl)-1H-pyrazol-4-yl]-amide

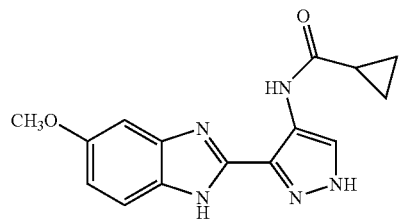

By proceeding in a manner similar to Example 248(a) above but using 3-(5-methoxy-1H-benzoimidazol-2-yl)-1H- pyrazol-4-ylamine [282 mg, Example 233(f)] and cyclopropanecarbonyl chloride (0.558 ml) there was prepared cyclopropanecarboxylic acid [3-(5-methoxy-1H-benzoimidazol-2-yl)-1H-pyrazol-4-yl]-amide (76 mg) as an off-white solid. LC-MS (Method L): $R_T$=5.25 minutes, 298.26 (M+H)$^+$.

(p) Cyclopropanecarboxylic acid [3-(5-ethoxy-1H-benzoimidazol-2-yl)-1H-pyrazol-4-yl]-amide

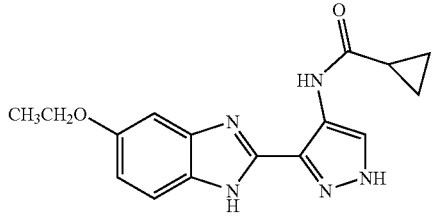

By proceeding in a manner similar to Example 248(o) above but using 3-(5-ethoxy-1H-benzoimidazol-2-yl)-1H-pyrazol-4-ylamine [187 mg, Example 233(g)] there was prepared cyclopropanecarboxylic acid [3-(5-ethoxy-1H-benzoimidazol-2-yl)-1H-pyrazol-4-yl]-amide (112 mg) as a pale yellow solid. LC-MS (Method H): $R_T$=2.26 minutes, 312.23 (M+H)$^+$, 310.30 (M−H)$^−$.

(q) Cyclopropanecarboxylic acid [3-(5-fluoro-6-methyl-1H-benzoimidazol-2-yl)-1H-pyrazol-4-yl]-amide

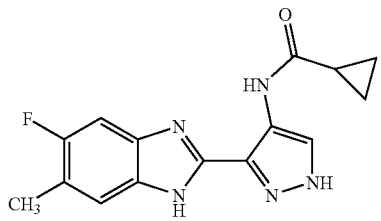

By proceeding in a manner similar to Example 248(a) above but using 3-(5-fluoro-6-methyl-1H-benzoimidazol-2-yl)-1H-pyrazol-4-ylamine [Example 233(h)] and cyclopropanecarbonyl chloride there was prepared cyclopropanecarboxylic acid [3-(5-fluoro-6-methyl-1H-benzoimidazol-2-yl)-1H-pyrazol-4-yl]-amide (135 mg) as a white solid. LC-MS (METHOD M): $R_T$=11.31 minutes, 300.31 (M+H)$^+$.

(r) Cyclopropanecarboxylic acid [3-(5-trifluoromethoxy-1H-benzoimidazol-2-yl)-1H-pyrazol-4-yl]-amide

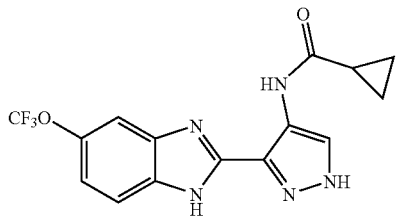

By proceeding in a manner similar to Example 248(a) above but using 3-(5-trifluoromethoxy-1H-benzoimidazol-2-yl)-1H-pyrazol-4-ylamine [Example 233(i)] and cyclopropanecarbonyl chloride there was prepared cyclopropanecarboxylic acid [3-(5-trifluoromethoxy-1H-benzoimidazol-2-yl)-1H-pyrazol-4-yl]-amide (275 mg) as a white solid. LC-MS (METHOD M): $R_T$=13.57 minutes, 352.22 (M+H)$^+$.

(s) Cyclopropanecarboxylic acid [3-(5-trifluoromethyl-1H-benzoimidazol-2-yl)-1H-pyrazol-4-yl]-amide

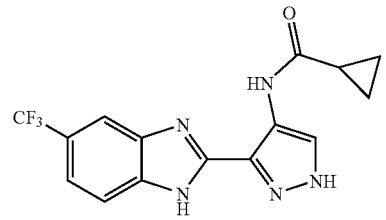

By proceeding in a manner similar to Example 248(a) above but using 3-(5-trifluoromethyl-1H-benzoimidazol-2-yl)-1H-pyrazol-4-ylamine [Example 233(j)] and cyclopropanecarbonyl chloride there was prepared cyclopropanecarboxylic acid [3-(5-trifluoromethyl-1H-benzoimidazol-2-yl)-1H-pyrazol-4-yl]-amide (88 mg) as a white solid. LC-MS (METHOD M): $R_T$=13.62 minutes, 338.12 (M+H)$^+$.

(t) N-[3-(5-Trifluoromethyl-1H-benzoimidazol-2-yl)-1H-pyrazol-4-yl]-isobutyramide

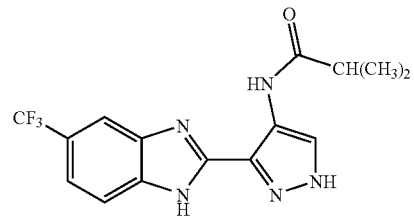

By proceeding in a manner similar to Example 248(s) above but using isobutyryl chloride there was prepared N-[3-(5-trifluoromethyl-1H-benzoimidazol-2-yl)-1H-pyrazol-4-yl]-isobutyramide (71 mg) as a white solid. LC-MS (METHOD M): $R_T$=10.11 minutes, 336.12 (M+H)$^+$.

(u) Cyclopropanecarboxylic acid [3-(5-chloro-6-methyl-1H-benzoimidazol-2-yl)-1H-pyrazol-4-yl]-amide

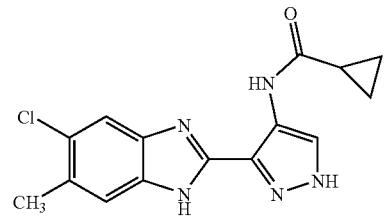

By proceeding in a manner similar to Example 248(a) above but using 3-(5-chloro-6-methyl-1H-benzoimidazol-2-yl)-1H-pyrazol-4-ylamine [Example 261] and cyclopropanecarbonyl chloride there was prepared cyclopropanecarboxylic acid [3-(5-chloro-6-methyl-1H-benzoimidazol-2-yl)-1H- pyrazol-4-yl]-amide (46 mg) as a white solid. LC-MS (METHOD L): $R_T$=7.06 minutes, MS: 316.26 (M+H)⁺.

(v) 3,5-Dimethyl-isoxazole-4-carboxylic acid [3-(5,6-dimethyl-1H-benzoimidazol-2-yl)-1H-pyrazol-4-yl]-amide

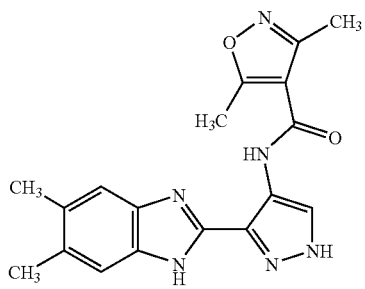

By proceeding in a manner similar to Example 248(a) above but using 3,5-dimethylisoxazole-4-carbonyl chloride there was prepared 3,5-dimethyl-isoxazole-4-carboxylic acid [3-(5,6-dimethyl-1H-benzoimidazol-2-yl)-1H-pyrazol-4-yl]-amide (62 mg) as a white solid. LC-MS (METHOD L): $R_T$=8.45 minutes, 351.32 (M+H)⁺.

(w) N-[3-(5,6-dimethyl-1H-benzoimidazol-2-yl)-1H-pyrazol-4-yl]-acetamide

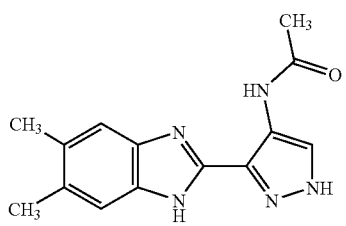

By proceeding in a manner similar to Example 248(a) above but using acetyl chloride there was prepared N-[3-(5,6-dimethyl-1H-benzoimidazol-2-yl)-1H-pyrazol-4-yl]-acetamide (25 mg) as a white solid. LC-MS (METHOD L): $R_T$=6.34 minutes, 270.14 (M+H)⁺.

(x) Furan-3-carboxylic acid [3-(5,6-dimethylmethyl-1H-benzoimidazol-2-yl)-1H-pyrazol-4-yl]-amide

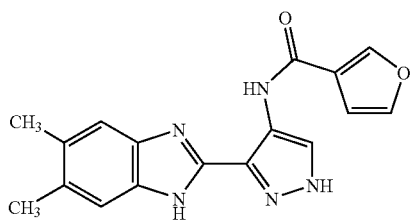

By proceeding in a manner similar to Example 248 (a) above but using 3-furoylchloride there was prepared furan-3-carboxylic acid [3-(5,6-dimethyl-1H-benzoimidazol-2-yl)-1H-pyrazol-4-yl]-amide (80 mg) as a white solid. LC-MS (METHOD L): $R_T$=7.10 minutes, 322.31 (M+H)⁺.

(y) N-[3-(5,6-Dimethyl-1H-benzoimidazol-2-yl)-1H-pyrazol-4-yl]-4-methyl-benzamide

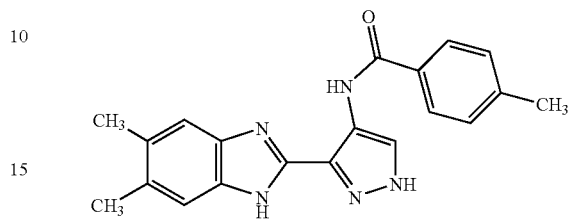

By proceeding in a manner similar to Example 248(a) above but using p-toluoyl chloride there was prepared N-[3-(5,6-dimethyl-1H-benzoimidazol-2-yl)-1H-pyrazol-4-yl]-4-methyl-benzamide (42 mg) as a white solid. LC-MS (METHOD L): $R_T$=12.24 minutes, 346 (M+H)⁺.

EXAMPLE 249

(a) 5,6-Dimethyl-2-(4-nitro-1H-pyrazol-3-yl)-1H-benzoimidazole

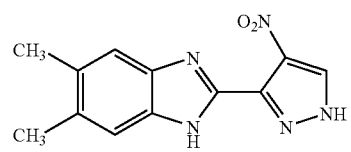

A stirred solution of 4-nitro-1H-pyrazole-3-carboxylic acid (2-amino-4,5-dimethylphenyl)amide [5.7 g, Reference Example 36(a)] in acetic acid (100 mL) was heated at 120° C. for 1 hour, then cooled to ambient temperature and then evaporated. The oily residue was partitioned between ethyl acetate and water. The organic layer was dried over magnesium sulfate and then evaporated to give 5,6-dimethyl-2-(4-nitro-1H-pyrazol-3-yl)-1H-benzoimidazole (5.70 g) as an orange solid. LC-MS (METHOD B): $R_T$=2.30 minutes, 258.11 (M+H)⁺.

(b) 5-Ethyl-6-methyl-2-(4-nitro-1H-pyrazol-3-yl)-1H-benzoimidazole

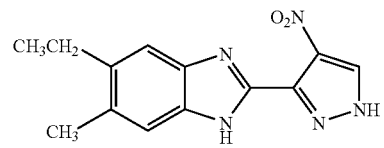

By proceeding in a manner similar to Example 249(a) above but using 4-nitro-1H-pyrazole-3-carboxylic acid (2-amino-4-ethyl-5-methylphenyl)amide [Reference Example 36(b)] there was prepared 5-ethyl-6-methyl-2-(4- nitro-1H-pyrazol-3-yl)-1H-benzoimidazole as a yellow solid. LC-MS (METHOD B): $R_T$=2.61 minutes, 272.23 (M+H)$^+$.

(c) 6-Chloro-5-methoxy-2-(4-nitro-1H-pyrazol-3-yl)-1H-benzoimidazole

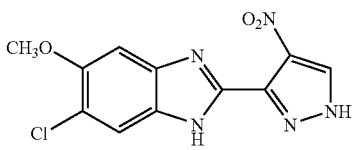

By proceeding in a manner similar to Example 249(a) above but using 4-nitro-1H-pyrazole-3-carboxylic acid (2-amino-5-chloro-4-methoxyphenyl)amide [1.5 g, Reference Example 36(c)] there was prepared 6-chloro-5-methoxy-2-(4-nitro-1H-pyrazol-3-yl)-1H-benzoimidazole (0.7 g) as a dark solid. MS: 294 (M+H)$^+$.

(d) 5-Fluoro-6-methyl-2-(4-nitro-1H-pyrazol-3-yl)-1H-benzoimidazole

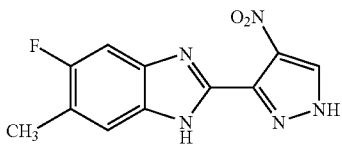

By proceeding in a manner similar to Example 249(a) above but using 4-Nitro-1H-pyrazole-3-carboxylic acid (2-amino-4-fluoro-5-methyl-phenyl)-amide [Reference Example 36(f)] there was prepared 5-fluoro-6-methyl-2-(4-nitro-1H-pyrazol-3-yl)-1H-benzoimidazole (0.730 g) as a red solid. LC-MS (METHOD J): $R_T$=2.76 minutes, 262.21 (M+H)$^+$.

(e) 2-(4-Nitro-1H-pyrazol-3-yl)-5-trifluoromethoxy-1H-benzoimidazole

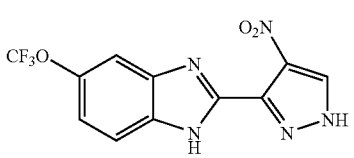

By proceeding in a manner similar to Example 249(a) above but using 4-nitro-1H-pyrazole-3-carboxylic acid (2-amino-4-trifluoromethoxy-phenyl)-amide [Reference Example 36(g)] there was prepared 2-(4-nitro-1H-pyrazol-3-yl)-5-trifluoromethoxy-1H-benzoimidazole (1.02 g) as a red solid. LC-MS (METHOD J): $R_T$=3.32 minutes, 314.19 (M+H)$^+$.

(f) 2-(4-Nitro-1H-pyrazol-3-yl)-5-trifluoromethyl-1H-benzoimidazole

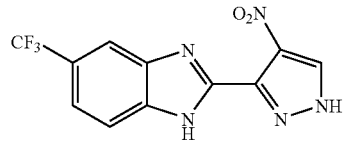

By proceeding in a manner similar to Example 249(a) above but using 4-nitro-1H-pyrazole-3-carboxylic acid (2-amino-4-trifluoromethyl-phenyl)-amide [Reference Example 36(h)] there was prepared 2-(4-nitro-1H-pyrazol-3-yl)-5-trifluoromethyl-1H-benzoimidazole (0.195 g) as an orange solid. MS: 298.07 (M+H)$^+$. HPLC (METHOD B): $R_T$=3.50 minutes.

(g) 5-Chloro-6-methyl-2-(4-nitro-1H-pyrazol-3-yl)-1H-benzoimidazole

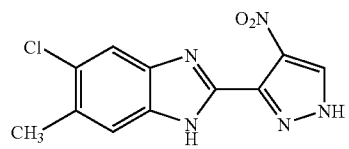

By proceeding in a manner similar to Example 249(a) above but using 4-nitro-1H-pyrazole-3-carboxylic acid (2-amino-4-chloro-5-methyl-phenyl)-amide [Reference Example 36(i)] there was prepared 5-chloro-6-methyl-2-(4-nitro-1H-pyrazol-3-yl)-1H-benzoimidazole (0.320 g) as an orange solid. LC-MS (METHOD C): $R_T$=3.36 minutes, 314.19 (M+H)$^+$.

(h) 2-(4-Nitro-1H-pyrazol-3-yl)-1H-benzoimidazole-5-carboxylic acid methyl ester

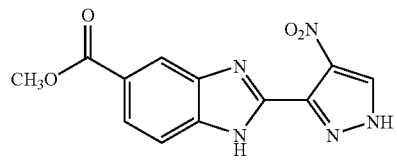

By proceeding in a manner similar to Example 249(a) above but using 3-amino-4-[(4-nitro-1H-pyrazole-3-carbonyl)-amino]-benzoic acid methyl ester [Reference Example 36(j)] there was prepared 2-(4-nitro-1H-pyrazol-3-yl)-1H-benzoimidazole-5-carboxylic acid methyl ester (2.50 g) as a yellow solid. LC-MS (METHOD B): $R_T$=2.76 minutes, 288.12 (M+H)$^+$.

EXAMPLE 250

(a) 3-(5,6-Dimethyl-1H-benzoimidazol-2-yl)-1,4,6,7-tetrahydro-pyrazolo[4,3-c]pyridine-5-carboxylic acid isopropylamide

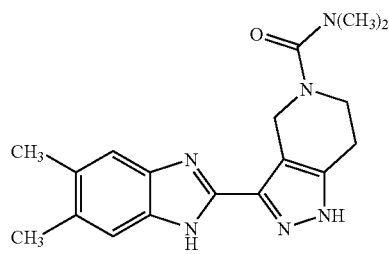

A solution of 3-(5,6-dimethyl-1H-benzoimidazol-2-yl)-4,5,6,7-tetrahydro-1H-pyrazolo[4,3-c]pyridine [0.150 g, Example 251(a)] in dimethyl formamide (4 ml) was treated with diisopropylethylamine (0.54 ml) and then with dimethyl carbamyl chloride (0.122 ml). After stirring for 1 hour the reaction mixture was quenched by the addition of methanol (0.1 ml) and then diluted with ethyl acetate. This mixture was washed five times with brine and then evaporated. The residue was treated with tetrahydrofuran (9 ml) and methanol (3 ml) and the resulting solution was then treated with potassium hydroxide (50 mg). This mixture was stirred for 1 hour, then acidified by addition of hydrochloric acid (1M) and then extracted three times with ethyl acetate. The aqueous layer was basified by addition of sodium carbonate and the resulting suspension was filtered, then washed with water, then dried in air and then azeotroped with toluene to yield 3-(5,6-dimethyl-1H-benzoimidazol-2-yl)-1,4,6,7-tetrahydro-pyrazolo[4,3-c]pyridine-5-carboxylic acid isopropylamide as a pale brown solid. MS: 339 (M+H)$^+$. HPLC (METHOD F1): R$_T$=8.67 minutes.

(b) Cyclopropyl-[3-(5,6-dimethyl-1H-benzoimidazol-2-yl)-1,4,6,7-tetrahydro-pyrazolo[4,3-c]pyridin-5-yl]-methanone

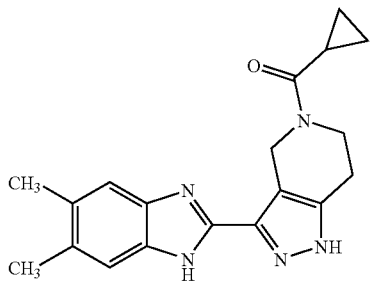

By proceeding in a manner similar to Example 250(a) above, but using cyclopropanecarbonylchloride and stirring the reaction mixture for 16 hours, there was prepared cyclopropyl-[3-(5,6-dimethyl-1H-benzoimidazol-2-yl)-1,4,6,7-tetrahydro-pyrazolo[4,3-c]pyridin-5-yl]-methanone (68 mg) as a pale yellow solid. LC-MS (METHOD M): R$_T$=10.57 minutes, 336 (M+H)$^+$.

(c) Isopropyl-[3-(5,6-dimethyl-1H-benzoimidazol-2-yl)-1,4,6,7-tetrahydro-pyrazolo[4,3-c]pyridin-5-yl]-methanone

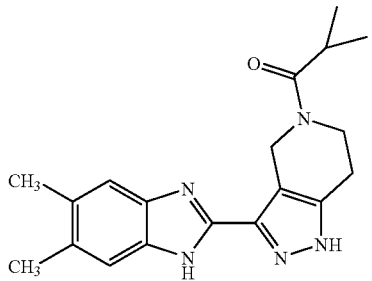

By proceeding in a manner similar to Example 250(b) above, but using isopropylcarbonyl chloride, cyclopropylcarbonylchloride there was prepared isopropyl-[3-(5,6-dimethyl-1H-benzoimidazol-2-yl)-1,4,6,7-tetrahydro-pyrazolo[4,3-c]pyridin-5-yl]-methanone (68 mg) as a white solid. LC-MS (METHOD M): R$_T$=9.28 minutes, 338 (M+H)$^+$.

(d) 1-[3-(5,6-Dimethyl-1H-benzoimidazol-2-yl)-1,4,6,7-tetrahydro-pyrazolo[4,3-c]pyridin-5-yl]-2,2-dimethyl-propan-1-one

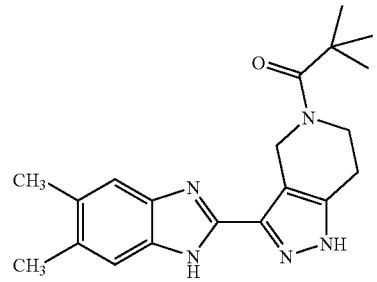

By proceeding in a manner similar to Example 250(b) above, but using trimethylacetyl chloride and filtering the precipitate formed upon basification with sodium carbonate, followed by azeotroping with toluene there was prepared 1-[3-(5,6-dimethyl-1H-benzoimidazol-2-yl)-1,4,6,7-tetrahydro-pyrazolo[4,3-c]pyridin-5-yl]-2,2-dimethyl-propan-1-one (49 mg) as a pale yellow solid. LC-MS (METHOD M): R$_T$=11.39 minutes, 352 (M+H)$^+$.

(e) 3-(5,6-Dimethyl-1H-benzoimidazol-2-yl)-1,4,6,7-tetrahydro-pyrazolo[4,3-c]pyridine-5-carboxylic acid methyl ester

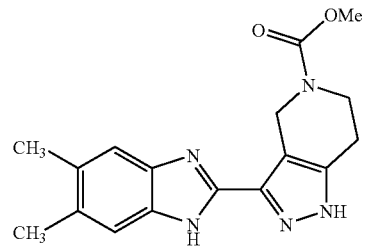

By proceeding in a manner similar to Example 250(b) above but using methylchloroformate there was prepared 3-(5,6-dimethyl-1H-benzoimidazol-2-yl)-1,4,6,7-tetrahydro-pyrazolo[4,3-c]pyridine-5-carboxylic acid methyl ester (89 mg) as a pale brown solid. LC-MS (METHOD M): R$_T$=8.95 minutes, 326 (M+H)$^+$.

EXAMPLE 251

(a) 3-(5,6-Dimethyl-1H-benzoimidazol-2-yl)-4,5,6,7-tetrahydro-1H-pyrazolo[4,3-c]pyridine

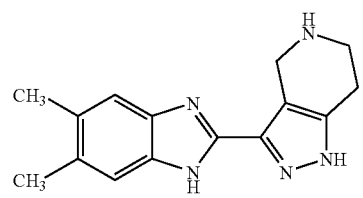

A solution of 3-(5,6-dimethyl-1H-benzoimidazol-2-yl)-1,4,6,7-tetrahydro-pyrazolo[4,3-c]pyridine-5-carboxylic acid tert-butyl ester [1.014 g, Example 252(a)] in methanol (20 ml)

was treated with a solution of hydrogen chloride in dioxane (5 ml, 4M). After stirring for 16 hours the reaction mixture was evaporated. The resulting beige solid was triturated with methanol to yield 3-(5,6-dimethyl-1H-benzoimidazol-2-yl)-4,5,6,7-tetrahydro-1H-pyrazolo[4,3-c]pyridine (0.523 g) as a pale yellow solid. LC-MS (METHOD B): $R_T$=0.63 minutes; 268 (M+H)$^+$.

(b) 3-(5-Chloro-6-methyl-1H-benzoimidazol-2-yl)-4,5,6,7-tetrahydro-1H-pyrazolo[4,3-c]pyridine

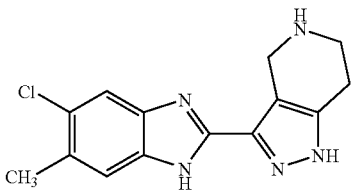

By proceeding in a manner similar to Example 251(a) above, but using 3-(5-chloro-6-methyl-1H-benzoimidazol-2-yl)-1,4,6,7-tetrahydro-pyrazolo[4,3-c]pyridine-5-carboxylic acid tert-butyl ester [Example 252(d)] there was prepared 3-(5-chloro-6-methyl-1H-benzoimidazol-2-yl)-4,5,6,7-tetrahydro-1H-pyrazolo[4,3-c]pyridine (223 mg) as a white solid. LC-MS (METHOD K): $R_T$=3.91 minutes, 288/290 (M+H)$^+$.

(c) 3-[5-(2-Morpholin-4-yl-ethoxy)-1H-benzoimidazol-2-yl]-4,5,6,7-tetrahydro-1H-pyrazolo[4,3-c]pyridine

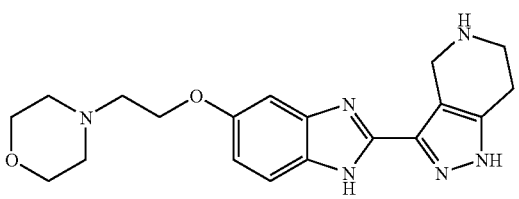

By proceeding in a manner similar to Example 251(a) above, but using 3-[5-(2-morpholin-4-yl-ethoxy)-1H-benzoimidazol-2-yl]-1,4,6,7-tetrahydro-pyrazolo[4,3-c]pyridine-5-carboxylic acid tert-butyl ester [Example 252(e)] there was prepared 3-[5-(2-morpholin-4-yl-ethoxy)-1H-benzoimidazol-2-yl]-4,5,6,7-tetrahydro-1H-pyrazolo[4,3-c]pyridine (200 mg) as an off-white solid. LC-MS (METHOD N): $R_T$=2.55 minutes, 369.19 (M+H)$^+$.

(d) 3-(5-trifluoromethyl-1H-benzoimidazol-2-yl)-4,5,6,7-tetrahydro-1H-pyrazolo[4,3-c]pyridine

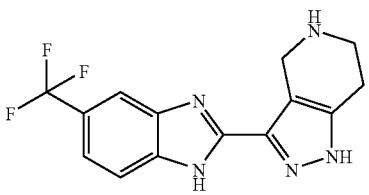

By proceeding in a manner similar to Example 251(a) above but using 3-(5-trifluoromethyl-1H-benzoimidazol-2-yl)-1,4,6,7-tetrahydro-pyrazolo[4,3-c]pyridine-5-carboxylic acid tert-butyl ester [Example 252(g)] there was prepared 3-(5-trifluoromethyl-1H-benzoimidazol-2-yl)-4,5,6,7-tetrahydro-1H-pyrazolo[4,3-c]pyridine (500 mg) as an off-white solid. LC-MS (METHOD N): $R_T$=3.21 minutes, 308.17 (M+H)$^+$.

EXAMPLE 252

(a) 3-(5,6-Dimethyl-1H-benzoimidazol-2-yl)-1,4,6,7-tetrahydro-pyrazolo[4,3-c]pyridine-5-carboxylic acid tert-butyl ester

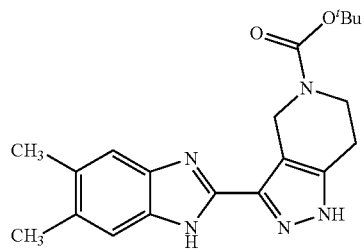

A suspension of 1,4,6,7-tetrahydro-pyrazolo[4,3-c]pyridine-3,5-dicarboxylic acid, 3-(2-amino-4,5-dimethylphenyl)amide, 5-tert-butyl ester [1.091 g, Reference Example 39(a)] in acetic acid (5 ml) was heated to 100° C. for 12 minutes in a Smith Creator Microwave. The mixture was neutralised with care by addition of solid sodium hydrogen carbonate and then extracted twice with ethyl acetate. The combined extracts were evaporated to yield 3-(5,6-dimethyl-1H-benzoimidazol-2-yl)-1,4,6,7-tetrahydro-pyrazolo[4,3-c]pyridine-5-carboxylic acid tert-butyl ester. LC-MS (METHOD B): $R_T$=2.79 minutes; 368 (M+H)$^+$.

(b) 5-Methoxy-2-(4-nitro-1H-pyrazol-3-yl)-1H-benzoimidazole

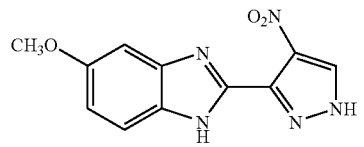

By proceeding in a manner similar to Example 252(a) above but (i) using 4-nitro-1H-pyrazole-3-carboxylic acid (2-amino-4-methoxy-phenyl)-amide [410 mg, Reference Example 36(d)] and heating at 120° C. for 5 minutes, (ii) pouring the reaction mixture into water, adjusting to pH14 with 2N sodium hydroxide and filtering, and (iii) adjusting the pH of the filtrate to 6 with 2N hydrochloric acid and collecting the precipitate by filtration, there was prepared 5-methoxy-2-(4-nitro-1H-pyrazol-3-yl)-1H-benzoimidazole (327 mg) as a yellow powder. LC-MS (Method H): $R_T$=1.61 minutes, 260.25 (M+H)$^+$, 258.26 (M−H)$^-$.

(c) 5-Ethoxy-2-(4-nitro-1H-pyrazol-3-yl)-1H-benzoimidazole

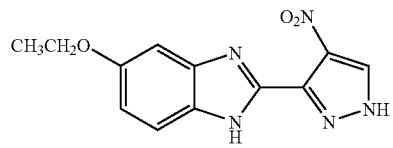

By proceeding in a manner similar to Example 252(b) above but using 4-nitro-1H-pyrazole-3-carboxylic acid (2-amino-4-ethoxy-phenyl)-amide [824 mg, Reference Example 36(e)] there was prepared 5-ethoxy-2-(4-nitro-1H- pyrazol-3-yl-1H-benzoimidazole (407 mg) as a light brown powder. LC-MS (Method H): R$_T$=1.82 minutes, 274.26 (M+H)$^+$, 272.30 (M–H)$^-$.

(d) 3-(5-Chloro-6-methyl-1H-benzoimidazol-2-yl)-1,4,6,7-tetrahydro-pyrazolo[4,3-c]pyridine-5-carboxylic acid tert-butyl ester

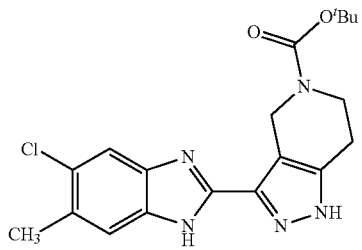

By proceeding in a manner similar to Example 252(b) above, but using 3-(2-amino-4-chloro-5-methyl-phenylcarbamoyl)-1,4,6,7-tetrahydro-pyrazolo[4,3-c]pyridine-5-carboxylic acid tert-butyl ester [Reference Example 39(c)] and heating at 110° C. for 15 minutes, there was prepared 3-(5-chloro-6-methyl-1H-benzoimidazol-2-yl)-1,4,6,7-tetrahydro-pyrazolo[4,3-c]pyridine-5-carboxylic acid tert-butyl ester (391 mg) as a brown solid. LC-MS (METHOD J): R$_T$=3.53 minutes, 388 (M+H)$^+$.

(e) 3-[5-(2-Morpholin-4-yl-ethoxy)-1H-benzoimidazol-2-yl]-1,4,6,7-tetrahydro-pyrazolo[4,3-c]pyridine-5-carboxylic acid tert-butyl ester

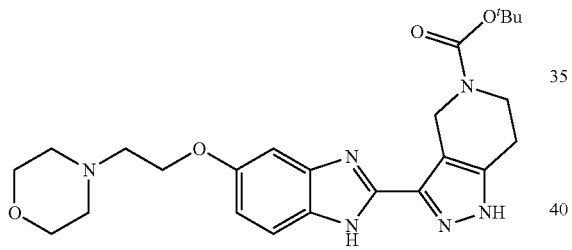

By proceeding in a manner similar to Example 252(b) above, but using 3-[2-amino-4-(2-morpholin-4-yl-ethoxy)-phenylcarbamoyl]-1,4,6,7-tetrahydro-pyrazolo[4,3-c]pyridine-5-carboxylic acid tert-butyl ester [Reference Example 39(d)] there was prepared 3-[5-(2-morpholin-4-yl-ethoxy)-1H-benzoimidazol-2-yl]-1,4,6,7-tetrahydro-pyrazolo[4,3-c]pyridine-5-carboxylic acid tert-butyl ester (350 mg) as a brown solid. LC-MS (METHOD N): R$_T$=3.53 minutes, 469.24 (M+H)$^+$.

(f) 3-(5,6-Dimethyl-1H-benzoimidazol-2-yl)-1,4,6,7-tetrahydro-pyrano[4,3-c]pyrazole

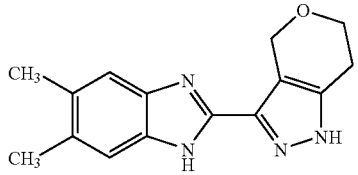

By proceeding in a manner similar to Example 252(a) above but using 1,4,6,7-tetrahydro-pyrano[4,3-c]pyrazole-3-carboxylic acid (2-amino-4,5-dimethyl-phenyl)-amide [Reference Example 39(e)] and beating at 120° C. for 3 minutes there was prepared 3-(5,6-dimethyl-1H-benzoimidazol-2-yl)-1,4,6,7-tetrahydro-pyrano[4,3-c]pyrazole (49 mg) as a pale brown solid. MS: 269 (M+H)$^+$. HPLC (METHOD C1): R$_T$=19.68 minutes.

(g) 3-(5-trifluoromethyl-1H-benzoimidazol-2-yl)-1,4,6,7-tetrahydro-pyrazolo[4,3-c]pyridine-5-carboxylic acid tert-butyl ester

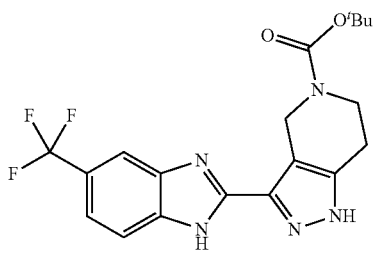

By proceeding in a manner similar to Example 252(a) above but using 3-(2-amino-4-trifluoromethyl-phenylcarbamoyl)-1,4,6,7-tetrahydro-pyrazolo[4,3-c]pyridine-5-carboxylic acid tert-butyl ester [Reference Example 39(f)] there was prepared 3-(5-trifluoromethyl-1H-benzoimidazol-2-yl)-1,4,6,7-tetrahydro-pyrazolo[4,3-c]pyridine-5-carboxylic acid tert-butyl ester (950 mg) was prepared as a brown solid. LC-MS (METHOD N): R$_T$=3.90 minutes, 408 (M+H)$^+$.

EXAMPLE 253

(a) N-[3-(5,6-Dimethyl-1H-benzoimidazol-2-yl)-1H-pyrazol-4-yl]-2-morpholin-4-yl-acetamide

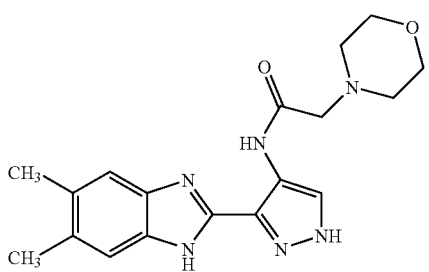

A stirred solution of 3-(5,6-dimethyl-1H-benzoimidazol-2-yl)-1H-pyrazol-4-ylamine [100 mg, Example 233(c)] and diisopropylethylamine (307 µl) in dichloromethane (10 ml) was treated with chloroacetyl chloride (105 µl). The reaction mixture was stirred for 30 minutes at room temperature, then treated with morpholine (575 µl), then kept at room temperature overnight and then evaporated. The oily residue was partitioned between ethyl acetate and water and the organic phase was washed with water, then dried over magnesium sulfate and then evaporated. The residue was subjected to flash chromatography on silica eluting with ethyl acetate to give the N-[3-(5,6-dimethyl-1H-benzoimidazol-2-yl)-1H-pyrazol-4-yl]-2-morpholin-4-yl-acetamide (49.9 mg) as an off-white solid. MS: 355.68 (M+H)$^+$. HPLC (METHOD B1): R$_T$=8.28 minutes.

(b) 2-Dimethylamino-N-[3-(5,6-dimethyl-1H-ben-zoimidazol-2-yl)-1H-pyrazol-4-yl]-acetamide

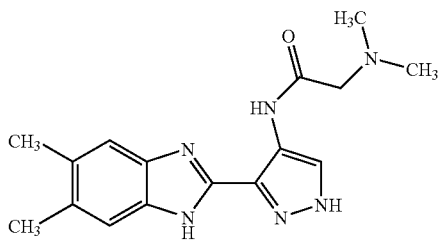

By proceeding in a manner similar to Example 253(a) above but using dimethylamine hydrochloride there was prepared 2-dimethylamino-N-[3-(5,6-dimethyl-1H-benzoimidazol-2-yl)-1H-pyrazol-4-yl]-acetamide (52 mg) as a white solid. LC-MS (METHOD M): $R_T$=8.28 minutes, 355.68 (M+H)$^+$.

(c) N-[3-(5,6-Dimethyl-1H-benzoimidazol-2-yl)-1H-pyrazol-4-yl]-2-piperidin-1-yl-acetamide

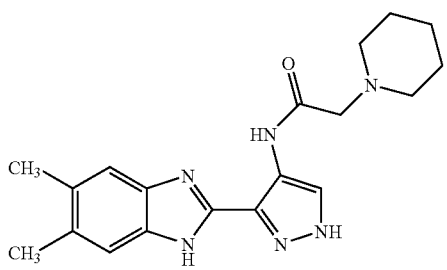

By proceeding in a manner similar to Example 253(a) above but using piperidine there was prepared N-[3-(5,6-dimethyl-1H-benzoimidazol-2-yl)-1H-pyrazol-4-yl]-2-piperidin-1-yl-acetamide (4 mg) as a white solid. LC-MS (METHOD M): $R_T$=7.69 minutes, 353.68 (M+H)$^+$.

EXAMPLE 254

(a) N-[3-(5,6-Dimethyl-1H-benzoimidazol-2-yl)-1H-pyrazol-4-yl]-2-(1H-1,2,3,4-tetraazol-1-yl)-acetamide

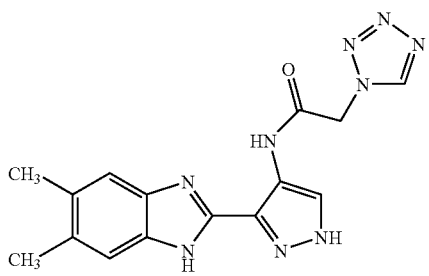

A stirred solution of 1-(3-dimethylaminopropyl)-3-ethylcarbodiimide hydrochloride (295.7 mg) and diisopropylethylamine (269 µl) in dimethylformamide (10 ml) were treated with 3-(5,6-dimethyl-1H-benzoimidazol-2-yl)-1H-pyrazol-4-ylamine [100 mg, Example 233(c)] and 2-(1H-1,2,3,4-tetraazol-1-yl) acetic acid (197.8 mg). The reaction mixture was stirred for 72 hours then treated further with 1-(3-dimethylaminopropyl)-3-ethylcarbodiimide hydrochloride (295.7 mg), diisopropylethylamine (269 µl) and 2-(1H-1,2,3,4-tetraazol-1-yl) acetic acid (197.8 mg). Stirring was continued for a further 48 hours then the reaction mixture was partitioned between ethyl acetate and water. The organic phase was evaporated and the residue was treated with 1N potassium hydroxide in a mixture of methanol and tetrahydrofuran (1:4, 8 ml). After 1 hour this mixture was extracted with ethyl acetate. The extract was washed with brine, then dried over magnesium sulfate and then evaporated to dryness. The residue was subjected to preparative HPLC to give N-[3-(5,6-dimethyl-1H-benzoimidazol-2-yl)-1H-pyrazol-4-yl]-2-(1H-1,2,3,4-tetraazol-1-yl)-acetamide (13.7 mg) as an off-white solid. MS: 338.14 (M+H)$^+$. HPLC (METHOD B1): $R_T$=7.26 minutes.

(b) N-[3-(5,6-Dimethyl-1H-benzoimidazol-2-yl)-1H-pyrazol-4-yl]-isonicotinamide

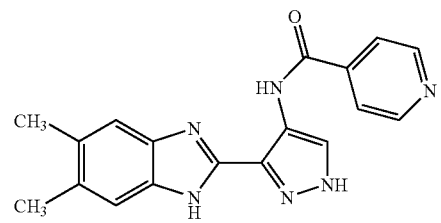

By proceeding in a manner similar to Example 254(a) above but using isonicotinic acid there was prepared N-[3-(5,6-dimethyl-1H-benzoimidazol-2-yl)-1H-pyrazol-4-yl]-isonicotinamide (9 mg) as a white solid. LC-MS (METHOD L): $R_T$=8.71 minutes, 331.21 (M+H)$^+$.

(c) 2-Cyclopropyl-N-[3-(5,6-dimethyl-1H-benzoimidazol-2-yl)-1H-pyrazol-4-yl]-acetamide

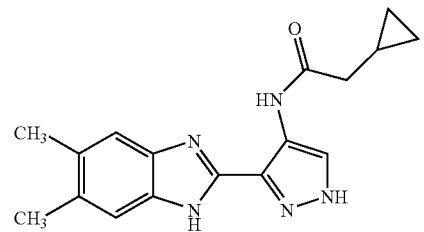

By proceeding in a manner similar to Example 254(a) above but using cyclopropylacetic acid there was prepared 2-cyclopropyl-N-[3-(5,6-dimethyl-1H-benzoimidazol-2-yl)-1H-pyrazol-4-yl]-acetamide (98 mg) as a light pink solid. LC-MS (METHOD M): $R_T$=11.04 minutes, MS: 310 (M+H)$^+$.

EXAMPLE 255

(a) 1-[3-(5,6-Dimethyl-1H-benzoimidazol-2-yl)-1H-pyrazol-4-yl]-3-methyl-urea

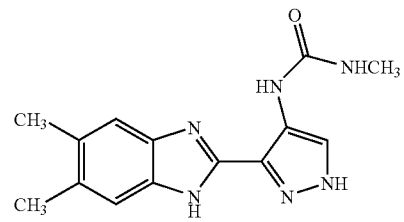

A solution of 3-(5,6-dimethyl-1H-benzoimidazol-2-yl)-1H-pyrazol-4-ylamine [0.500 g, Example 233(c)] in tetrahydrofuran (5 ml) was treated with methyl isocyanate (0.502 ml) and the mixture stirred at ambient temperature for 16 hours. The mixture was then concentrated in vacuo and the residue was redissolved in 1N potassium hydroxide in a mixture of methanol and tetrahydrofuran (1:3, 5 ml). The mixture was stirred for a further 1 hour, then concentrated and then partitioned between ethyl acetate and water. The aqueous layer was extracted three times with ethyl acetate and the combined organic extracts were washed with brine, then dried over magnesium sulfate, and then evaporated. The residue was subjected to flash column chromatography on silica eluting initially with a mixture of ethyl acetate and hexane (1:1, v/v) and then with ethyl acetate to afford 1-[3-(5,6-dimethyl-1H-benzoimidazol-2-yl-1H-pyrazol-4-yl]-3-methyl-urea (230 mg) as a white solid. MS: 269 (M+H)$^+$. HPLC (METHOD D1): R$_T$=5.97 minutes.

(b) 1-[3-(5,6-Dimethyl-1H-benzoimidazol-2-yl)-1H-pyrazol-4-yl]-3-isopropyl-urea

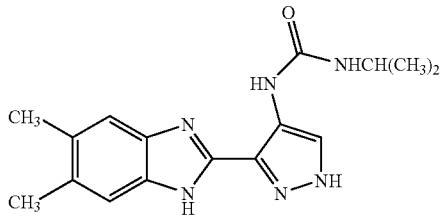

By proceeding in a manner similar to Example 255(a) above but using isopropyl isocyanate there was prepared 1-[3-(5,6-dimethyl-1H-benzoimidazol-2-yl)-1H-pyrazol-4-yl]-3-isopropyl-urea as a white solid. MS: 313 (M+H)$^+$. HPLC (METHOD D1): R$_T$=10.94 minutes.

(c) 1-[3-(5,6-Dimethyl-1H-benzoimidazol-2-yl)-1H-pyrazol-4-yl]-3-phenyl-urea

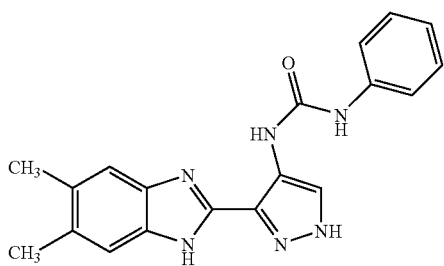

By proceeding in a manner similar to Example 255(a) above but using phenyl isocyanate there was prepared 1-[3-(5,6-dimethyl-1H-benzoimidazol-2-yl)-1H-pyrazol-4-yl]-3-phenyl-urea as a white solid. MS: 347 (M+H)$^+$. HPLC (METHOD B1): R$_T$=16.16 minutes.

(d) 1-Benzyl-3-[3-(5,6-dimethyl-1H-benzoimidazol-2-yl)-1H-pyrazol-4-yl]-urea

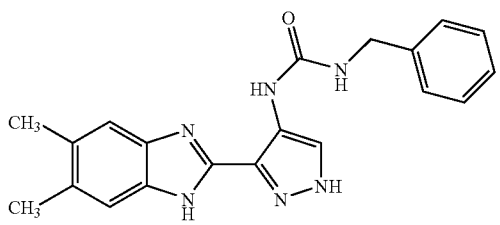

By proceeding in a manner similar to Example 255(a) above but using benzyl isocyanate there was prepared 1-benzyl-3-[3-(5,6-dimethyl-1H-benzoimidazol-2-yl)-1H-pyrazol-4-yl]-urea as a white solid. MS: 361 (M+H)$^+$. HPLC (METHOD D1): R$_T$=7.78 minutes.

(e) 3-(5,6-Dimethyl-1H-benzoimidazol-2-yl)-1,4,6,7-tetrahydro-pyrazolo[4,3-c]pyridine-5-carboxylic acid isopropylamide

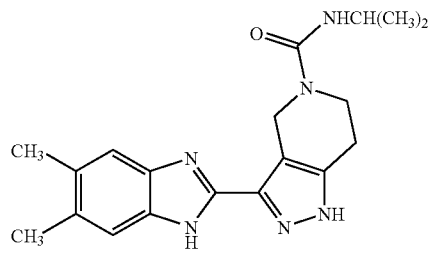

By proceeding in a manner similar to Example 255(a) above but using 3-(5,6-dimethyl-1H-benzoimidazol-2-yl)-4,5,6,7-tetrahydro-1H-pyrazolo[4,3-c]pyridine [Example 251(a)] and isopropylisocyanate, and subjecting the reaction product to flash column chromatography eluting with ethyl acetate/methanol (19:1, v/v), there was prepared 3-(5,6-dimethyl-1H-benzoimidazol-2-yl)-1,4,6,7-tetrahydro-pyrazolo[4,3-c]pyridine-5-carboxylic acid isopropylamide (93.3 mg) as an off-white solid. LC-MS (METHOD M): R$_T$=10.15 minutes, 353 (M+H)$^+$.

EXAMPLE 256

(a) Cyclopropanecarboxylic acid[3-(5-ethoxy-6-ethyl-1H-benzoimidazol-2-yl)-1H-pyrazol-4-yl] amide

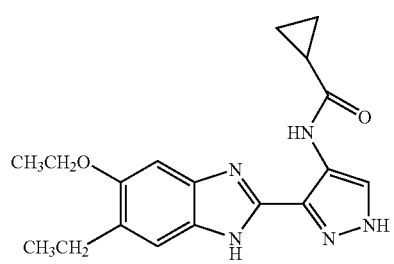

A solution of cyclopropanecarboxylic acid [3-(5-ethoxy-6-ethyl-1H-benzoimidazol-2-yl)-1-(tetrahydropyran-2-yl)-1H-pyrazol-4-yl]amide [0.3 g, Reference Example 48(a)] and p-toluenesulfonic acid hydrate (1.2 g) in ethanol (25 mL) was heated in an 80° C. in an oil bath for 1 hour, then cooled, and then poured into aqueous sodium bicarbonate solution. The aqueous mixture was extracted twice with ethyl acetate (75 mL). The combined extracts were evaporated and the residue was redissolved in a mixture of methylene chloride (100 mL) and methanol (10 mL). This solution was washed with aqueous sodium bicarbonate, to remove some residual p-toluenesulfonic acid, then evaporated to give cyclopropanecarboxylic acid[3-(5-ethoxy-6-ethyl-1H-benzoimidazol-2-yl)-1H-pyrazol-4-yl]amide (120 mg) as a white solid. LC-MS (Method E): R$_T$=2.36 minutes, 340 (M+H)$^+$.

(b) 3-(1,5,6,7-Tetrahydro-1,3-diaza-s-indacen-2-yl)-1H-pyrazol-4-ylamine

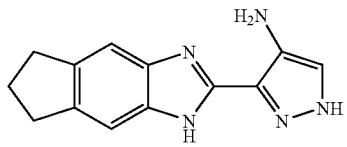

By proceeding in a similar manner to Example 256(a) but using 3-(1,5,6,7-tetrahydro-1,3-diaza-s-indacen-2-yl)-1-(tetrahydropyran-2-yl)-1H-pyrazol-4-ylamine [0.9 g, Reference Example 49(d)] and p-toluenesulfonic acid (1.0 g) in ethanol (100 mL) and carrying out the reaction at 55° C. for 2 hours, there was prepared 3-(1,5,6,7-tetrahydro-1,3-diaza-s-indacen-2-yl)-1H-pyrazol-4-ylamine (800 mg) as a brown solid. LC-MS (Method G): $R_T$=2.68 minutes, 240 (M+H)$^+$.

(c) 4-Methylpiperazine-1-carboxylic acid [3-(1,5,6,7-tetrahydro-1,3-diaza-s-indacen-2-yl)-1H-pyrazol-4-yl]amide

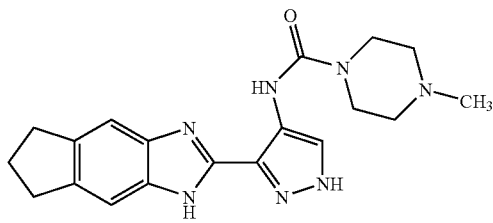

By proceeding in a similar manner to Example 256(a) but (i) using 4-methylpiperazine-1-carboxylic acid [3-(1,5,6,7-tetrahydro-1,3-diaza-s-indacen-2-yl)-1-(tetrahydropyran-2-yl)-1H-pyrazol-4-yl]amide [171 mg, Reference Example 48(b)], (ii) carrying out the reaction at 55° C. for 1.5 hours, then at 70° C. for 1 hour, and (iii) subjecting the reaction product to chromatography on silica gel (ethyl acetate/gradient 0 to 20% methanol), there was prepared 4-methylpiperazine-1-carboxylic acid [3-(1,5,6,7-tetrahydro-1,3-diaza-s-indacen-2-yl)-1H-pyrazol-4-yl]amide (55 mg) as a white solid. LC-MS (Method E): $R_T$=1.53 minutes, 366 (M+H)$^+$.

(d) 1,1-Dimethyl-3-[3-(1,5,6,7-tetrahydro-s-indacen-2-yl)-1H-pyrazol-4-yl]urea

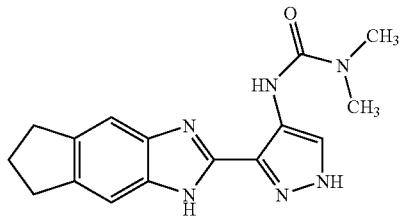

By proceeding in a similar manner to Example 256(c) but using 1,1-dimethyl-3-[3-(1,5,6,7-tetrahydro-s-indacen-2-yl)-1-(tetrahydropyran-2-yl)-1H-pyrazol-4-yl]urea (230 mg) and p-toluenesulfonic acid hydrate [40 mg, Reference Example 48(c)] there was prepared 1,1-dimethyl-3-[3-(1,5,6,7-tetrahydro-s-indacen-2-yl)-1H-pyrazol-4-yl]urea (106 mg) as a tan solid. LC-MS (Method E): $R_T$=1.97 minutes, 311 (M+H)$^+$.

EXAMPLE 257

(a) Cyclopropanecarboxylic acid [3-(6-ethoxy-5-fluoro-1H-benzimidazol-2-yl)-1H-pyrazol-4-yl]amide

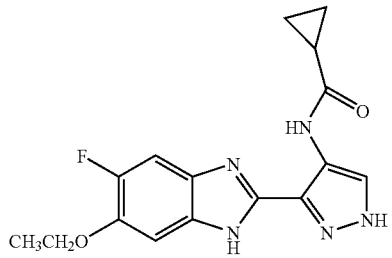

A solution of cyclopropanecarboxylic acid [3-(6-ethoxy-5-fluoro-1H-benzimidazol-2-yl)-1-(tetrahydropyran-2-yl)-1H-pyrazol-4-yl]amide [90 mg, Reference Example 48(d)] in a 1/1 mixture of trifluoroacetic acid and dichloromethane (30 mL) was stirred for 5 hours and then evaporated. The residue was mixed with ethyl acetate (30 mL) and aqueous sodium bicarbonate (30 mL). The organic layer was evaporated to give cyclopropanecarboxylic acid [3-(6-ethoxy-5-fluoro-1H-benzimidazol-2-yl)-1H-pyrazol-4-yl]amide (44 mg). LC-MS (Method E): $R_T$=2.34 minutes, 330 (M+H)$^+$.

(b) Tetrahydropyran-4-carboxylic acid [3-(6-ethoxy-5-fluoro-1H-benzimidazol-2-yl)-1H-pyrazole-4-yl]amide

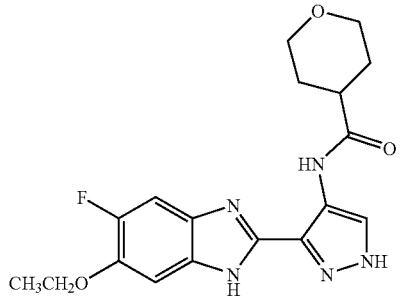

By proceeding in a similar manner to Example 257(a) but using tetrahydropyran-4-carboxylic acid [3-(6-ethoxy-5-fluoro-1H-benzimidazol-2-yl)-1-(tetrahydropyran-2-yl)-1H-pyrazole-4-yl]amide [120 mg, Reference Example 48(e)] there was prepared tetrahydropyran-4-carboxylic acid [3-(6-ethoxy-5-fluoro-1H-benzimidazol-2-yl)-1H-pyrazole-4-yl]amide (65 mg). LC-MS (Method E) $R_T$=2.17 minutes, 374 (M+H)$^+$.

(c) Morpholine-4-carboxylic acid[3-(6-ethoxy-5-fluoro-1H-benzimidazol-2-yl)-1H-pyrazol-4-yl]amide

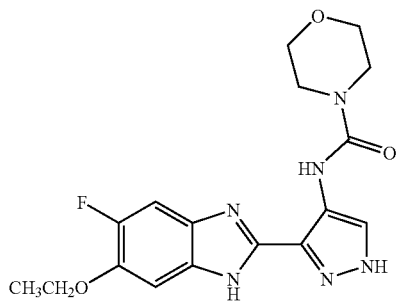

By proceeding in a similar manner to Example 257(a) but using morpholine-4-carboxylic acid[3-(6-ethoxy-5-fluoro-1H-benzimidazol-2-yl)-1-(tetrahydropyran-2-yl)-1H-pyrazol-4-yl]amide [140 mg, Reference Example 48(f)] there was prepared morpholine-4-carboxylic acid[3-(6-ethoxy-5-fluoro-1H-benzimidazol-2-yl)-1H-pyrazol-4-yl]amide (65 mg). LC-MS (Method E): $R_T$=2.62 minutes, 375 (M+H)$^+$.

(d) Piperidine-4-carboxylic acid[3-(6-ethoxy-5-fluoro-1H-benzimidazol-2-yl)-1H-pyrazol-4-yl]amide

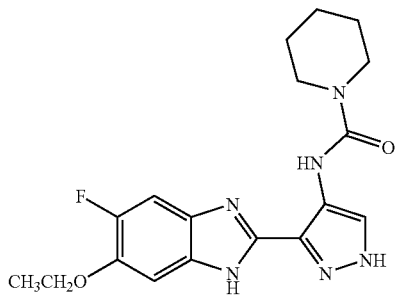

By proceeding in a similar manner to Example 257(a) but using piperidine-4-carboxylic acid[3-(6-ethoxy-5-fluoro-1H-benzimidazol-2-yl)-1-(tetrahydropyran-2-yl)-1H-pyrazol-4-yl]amide [127 mg, Reference Example 48(g)] there was prepared piperidine-4-carboxylic acid[3-(6-ethoxy-5-fluoro-1H-benzimidazol-2-yl)-1H-pyrazol-4-yl]amide (65 mg). LC-MS (Method E): $R_T$=3.15 minutes. MS 373 (M+H)$^+$.

(e) 3-[6-Ethoxy-5-fluoro-1H-benzimidazol-2-yl-1H-pyrazol-4-yl]-1-diethylurea

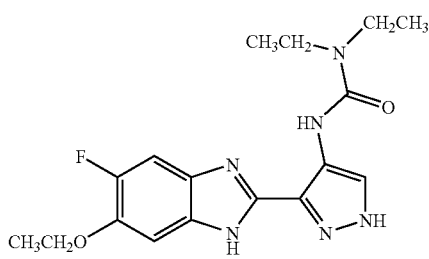

By proceeding in a similar manner to Example 257(a) but using 3-[6-ethoxy-5-fluoro-1H-benzimidazol-2-yl)-1-(tetrahydropyran-2-yl)-1H-pyrazol-4-yl]-1,1-diethylurea (110 mg, Reference Example 48(h)] there was prepared 3-[6-ethoxy-5-fluoro-1H-benzimidazol-2-yl)-1H-pyrazol-4-yl]-1H-diethylurea (65 mg). LC-MS (Method E): $R_T$=3.13 minutes, 361 (M+H)$^+$.

(f) 5-Methoxy-2-(4-nitro-1H-pyrazol-3-yl)-1H-benzoimidazole

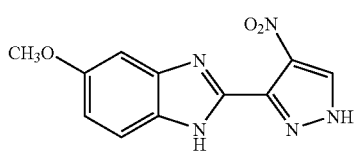

By proceeding in a similar manner to Example 257(a) but using 5-methoxy-2-[4-nitro-1-(tetrahydro-pyran-2-yl)-1H-pyrazol-3-yl]-1H-benzoimidazole (282 mg, Reference Example 50(d) there was prepared 5-methoxy-2-(4-nitro-1H-pyrazol-3-yl)-1H-benzoimidazole (373 mg) as a red powder. LC-MS (Method H): $R_T$=1.60 minutes, 260.22 (M+H)$^+$, 258.23 (M−H)$^-$.

(g) Morpholine-4-carboxylic acid [3-(5,6-dimethyl-1H-benzoimidazol-2-yl)-1H-pyrazol-4-ylmethyl]-amide

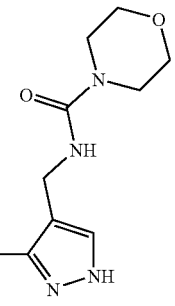

By proceeding in a similar manner to Example 257(a) but using morpholine-4-carboxylic acid (2,4-dimethoxy-benzyl)-[3-(5,6-dimethyl-1H-benzoimidazol-2-yl)-1-(tetrahydro-pyran-2-yl)-1H-pyrazol-4-ylmethyl]-amide (Reference Example 59), subjecting the reaction product to flash chromatography on silica [eluting with dichloromethane to dichloromethane/methanol (9:1)] and recrystallising from water/acetonitrile followed by trituration with diethyl ether there was prepared morpholine-4-carboxylic acid [3-(5,6-dimethyl-1H-benzoimidazol-2-yl)-1H-pyrazol-4-ylmethyl]-amide (16.5 mg) as a white solid. LC-MS (Method M): $R_T$=6.97 minutes, MS: 355.36 (M+H)$^+$, 353.39 (M−H)$^-$.

(h) 3-[3-(5-Difluoromethoxy-1H-benzoimidazol-2-yl)-1H-pyrazol-4-yl]-1,1-diethyl-urea

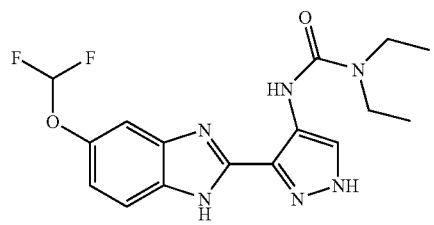

By proceeding in a manner similar to Example 257(a) above but using 3-[3-(5-difluoromethoxy-1H-benzoimidazol-2-yl)-1-(tetrahydro-pyran-2-yl)-1H-pyrazol-4-yl]-1,1-diethyl-urea [Reference Example 48(j)] there was prepared 3-[3-(5-difluoromethoxy-1H-benzoimidazol-2-yl)-1H-pyrazol-4-yl]-1,1-diethyl-urea (60 mg) as a white solid. LC-MS (METHOD L): $R_T$=10.61 minutes. $^1$H NMR(CD$_3$OD): δ 1.24 (t, 6H), 3.43 (q, 4H), 6.72 (bt, 1H), 6.98 (d, 1H), 7.26 (s, 1H), 7.47 (d, 1H), 7.91 (s, 1H).

(i) Piperidine-1-carboxylic acid [3-(5-difluoromethoxy-1H-benzoimidazol-2-yl)-1H-pyrazol-4-yl]-amide

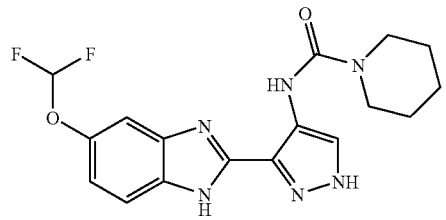

By proceeding in a manner similar to Example 257(a) above but using piperidine-1-carboxylic acid [3-(5-difluoromethoxy-1H-benzoimidazol-2-yl)-1-(tetrahydro-pyran-2-yl)-1H-pyrazol-4-yl]-amide [Reference Example 48(k)], there was prepared piperidine-1-carboxylic acid [3-(5-difluoromethoxy-1H-benzoimidazol-2-yl)-1H-pyrazol-4-yl]-amide (52 mg) as a white solid. HPLC (METHOD E1): $R_T$=10.78 minutes. $^1$H NMR(CD$_3$OD): δ 1.69 (bm, 6H), 3.64 (bm, 4H), 6.82 (bt, 1H), 7.09 (bm, 1H), 7.39 (bm, 1H), 7.61 (bm, 1H), 8.05 (bm, 1H).

EXAMPLE 258

(a) Cyclopropanecarboxylic acid [3-(6-chloro-5-methoxy-1H-benzoimidazol-2-yl)-1H-pyrazol-4-yl]-amide

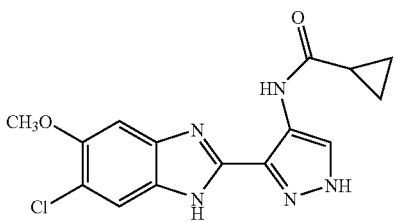

A solution of 3-(6-chloro-5-methoxy-1H-benzoimidazol-2-yl)-1H-pyrazol-4-ylamine [50 mg, Example 233(e)] and diisopropylethylamine (40 μL) in dichloromethane (20 mL), stirred at room temperature, was treated with cyclopropanecarbonyl chloride (51 μL, 3 eq). After stirring for a further 20 hours the reaction mixture was evaporated and the residue was subjected to chromatography on silica gel (ethyl acetate/heptane 1/1) to give the bis-acylated product (60 mg) as an orange solid. MS 400 (M+H)$^+$. The bis-acylated product was dissolved in methanol (5 mL), then treated with potassium hydroxide solution (0.5 mL, 5N), then stirred at 60° C. for 1 hour, then cooled and then evaporated. The residue was treated with water (15 mL) and the pH of the aqueous mixture was adjusted to 5 and then extracted twice with ethyl acetate (25 mL). The combined extracts were dried with magnesium sulfate, then evaporated and the residue was triturated with diisopropyl ether, filtered and the precipitate was vacuum dried at 60° C. to give cyclopropanecarboxylic acid [3-(6-chloro-5-methoxy-1H-benzoimidazol-2-yl-1H-pyrazol-4-yl]-amide (11 mg) as an off-white solid, mp 225-226° C. LC-MS (Method E): $R_T$=2.92 minutes, 332 (M+H)$^+$.

(b) Cyclopropanecarboxylic acid [3-(1,5,6,7-tetrahydro-1,3-diaza-s-indacen-2-yl)-1H-pyrazol-4-yl] amide

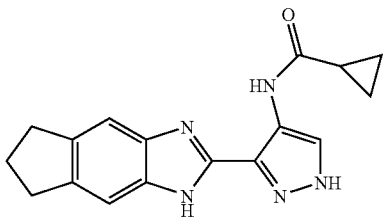

By proceeding in a similar manner to Example 258(a) above but (i) treating a solution of 3-(1,5,6,7-tetrahydro-1,3-diaza-s-indacen-2-yl)-1H-pyrazol-4-ylamine [310 mg, Example 256(b)] and triethylamine (4 eq) in tetrahydrofuran (15 mL) with cyclopropanecarbonyl chloride (4 eq), (ii) stirring the reaction mixture at 60° C. for 2 hours, (iii) treating the resulting bis-acylated product with methanolic potassium hydroxide (20 mL, 10.05 g KOH) at 40° C. for 1 hour followed by treatment with aqueous ammonium chloride (200 mL), (iii) extracting this mixture three times with ethyl acetate (100 mL), (iv) evaporating the combined extracts and (v) chromatographing the residue on silica gel (ethyl acetate/gradient of 50-0% heptane) there was prepared cyclopropanecarboxylic acid [3-(1,5,6,7-tetrahydro-1,3-diaza-s-indacen-2-yl)-1H-pyrazol-4-yl]amide (50 mg) as a yellow solid. LC-MS (Method E) $R_T$=2.05 minutes, 308 (M+H)$^+$.

(c) Morpholine-4-carboxylic acid[3-(1,5,6,7-tetrahydro-1,3-diaza-s-indacen-2-yl)-1H-pyrazol-4-yl]-amide

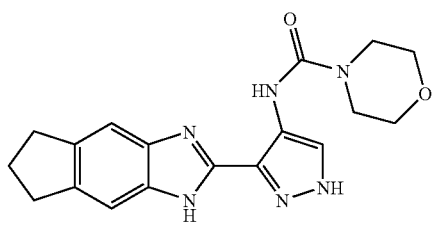

By proceeding in a similar manner to Example 258(b) above but using morpholine-4-carbonyl chloride there was prepared morpholine-4-carboxylic acid[3-(1,5,6,7-tetrahydro-1,3-diaza-s-indacen-2-yl)-1H-pyrazol-4-yl]-amide as an orange solid. LC-MS (Method E) $R_T$=2.45 minutes, 353 (M+H)$^+$.

(d) Piperidine-1-carboxylic acid [3-(5-methoxy-1H-benzoimidazol-2-yl)-1H-pyrazol-4-yl]-amide

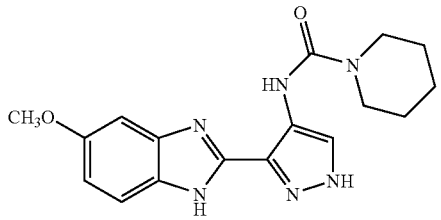

By proceeding in a similar manner to Example 258(a) above treating 3-(5-methoxy-1H-benzoimidazol-2-yl)-1H-pyrazol-4-ylamine [257 mg, Example 233(f)] with 1-piperidine-carbonyl chloride in the presence of diisopropylethylamine and using tetrahydrofuran as the solvent there was prepared piperidine-1-carboxylic acid [3-(5-methoxy-1H-benzoimidazol-2-yl)-1H-pyrazol-4-yl]-amide (46.1 mg) as a white solid. LC-MS (Method L) $R_T$=6.43 minutes, 341.28 (M+H)$^+$.

(e) 3-[3-(5-Methoxy-1H-benzoimidazol-2-yl)-1H-pyrazol-4-yl]-1,1-dimethyl-urea

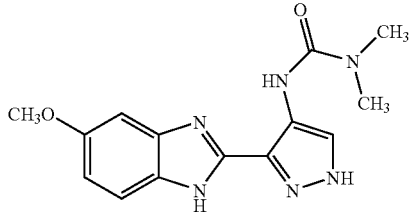

By proceeding in a manner similar to Example 258(d) above but using dimethylcarbamyl chloride there was prepared 3-[3-(5-methoxy-1H-benzoimidazol-2-yl)-1H-pyrazol-4-yl]-1,1-dimethyl-urea as a white solid. LC-MS (Method M): $R_T$=7.64 minutes, 301.35 (M+H)$^+$.

(f) Piperidine-1-carboxylic acid [3-(5-ethyl-6-methyl-1H-benzoimidazol-2-yl)-1H-pyrazol-4-yl]-amide

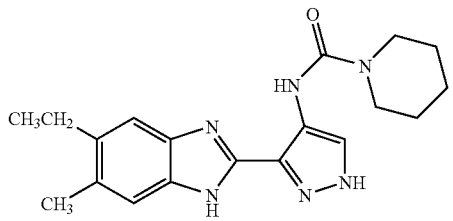

By proceeding in a manner similar to Example 258(d) above but (i) using 3-(5-ethyl-6-methyl-1H-benzoimidazol-2-yl)-1H-pyrazol-4-ylamine [400 mg, Example 233(d)], 1-piperidinecarbonyl chloride (1.25 ml) and diisopropylethylamine (1.74 ml) with tetrahydrofuran (20 ml) as the solvent and, stirring the reaction mixture at ambient temperature for 48 hours, then at 50° C. for 24 hours, (ii) treating the bis-acylated product with 1M potassium hydroxide in methanol/tetrahydrofuran (1:3, 20 ml) at room temperature, and (iii) subjecting the product to flash column chromatography on silica [eluting with ethyl acetate/hexane (1:1 v/v) to ethyl acetate/hexane (3:1 v/v)], there was prepared piperidine-1-carboxylic acid [3-(5-ethyl-6-methyl-1H-benzoimidazol-2-yl)-1H-pyrazol-4-yl]-amide (425 mg) as a white solid. LC-MS (METHOD L): $R_T$=7.55 minutes, 353.34 (M+H)$^+$.

(g) 3-[3-(5-Fluoro-6-methyl-1H-benzoimidazol-2-yl)-1H-pyrazol-4-yl]-1,1-dimethyl-urea

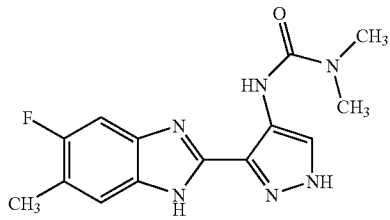

By proceeding in a manner similar to Example 258(f) above but using 3-(5-fluoro-6-methyl-1H-benzoimidazol-2-yl)-1H-pyrazol-4-ylamine [Example 233(h)] and N,N'-dimethylcarbamylchloride there was prepared 3-[3-(5-fluoro-6-methyl-1H-benzoimidazol-2-yl)-1H-pyrazol-4-yl]-1,1-dimethyl-urea (32 mg) as a white solid. LC-MS (METHOD M): $R_T$=10.40 minutes, 303.34 (M+H)$^+$.

(h) Morpholine-4-carboxylic acid [3-(5-trifluoromethyl-1H-benzoimidazol-2-yl)-1H-pyrazol-4-yl]-amide

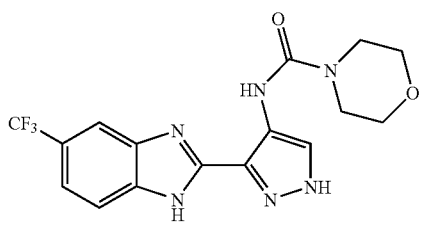

By proceeding in a manner similar to Example 258(f) above but using 3-(5-trifluoromethyl-1H-benzoimidazol-2-yl)-1H-pyrazol-4-ylamine [Example 233(j)] and morpholine-1-carbonyl chloride there was prepared morpholine-4-carboxylic acid [3-(5-trifluoromethyl-1H-benzoimidazol-2-yl)-1H-pyrazol-4-yl]-amide (131 mg) was prepared as a white solid. MS: 379.08 (M−H)$^−$. HPLC (METHOD E1): $R_T$=10.61 minutes.

(i) 3-(5,6-Dimethyl-1H-benzoimidazol-2-yl)-1,4,6,7-tetrahydro-pyrazolo[4,3-c]pyridine-5-carboxylic acid diethylamide

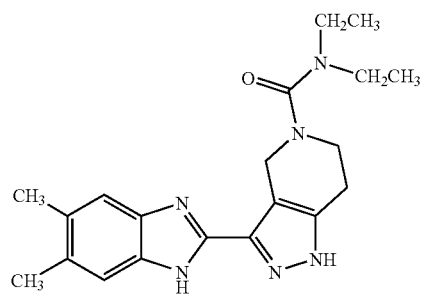

By proceeding in a manner similar to Example 258(f) above, but using 3-(5,6-dimethyl-1H-benzoimidazol-2-yl)-4,5,6,7-tetrahydro-1H-pyrazolo[4,3-c]pyridine [Example 251 (a)] and diethylcarbamyl chloride, and subjecting the reaction product to flash column chromatography eluting with ethyl acetate to ethyl acetate/methanol (49:1, v/v), there was prepared 3-(5,6-dimethyl-1H-benzoimidazol-2-yl)-1,4,6,7-tetrahydro-pyrazolo[4,3-c]pyridine-5-carboxylic acid diethylamide (20.9 mg) as an off-white solid. LC-MS (METHOD J): $R_T$=3.44 minutes, 367 (M+H)$^+$.

(j) [3-(5,6-Dimethyl-1H-benzoimidazol-2-yl)-1,4,6,7-tetrahydro-pyrazolo[4,3-c]pyridin-5-yl]pyrrolidin-1-yl-methanone

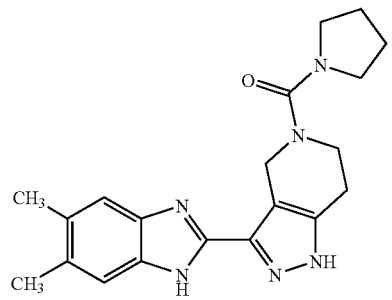

By proceeding in a manner similar to Example 258(i) above, but using 1-pyrollidincarbonyl chloride and triturating the reaction product with ethyl acetate, methanol and dichloromethane, there was prepared [3-(5,6-dimethyl-1H-benzoimidazol-2-yl)-1,4,6,7-tetrahydro-pyrazolo[4,3-c]pyridin-5-yl]-pyrrolidin-1-yl-methanone (68 mg) as an off-white solid. MS: 365 (M+H)$^+$. HPLC (METHOD E1): $R_T$=10.32 minutes.

(k) [3-(5,6-Dimethyl-1H-benzoimidazol-2-yl)-1,4,6,7-tetrahydro-pyrazolo[4,3-c]pyridin-5-yl]-piperidin-1-yl-methanone

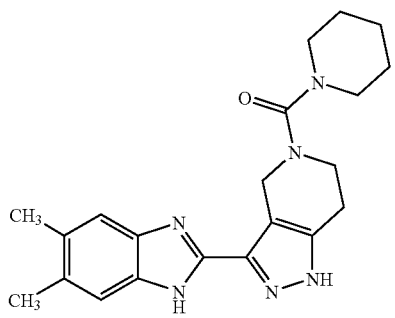

By proceeding in a manner similar to Example 258(f) above, but using 3-(5,6-dimethyl-1H-benzoimidazol-2-yl)-4,5,6,7-tetrahydro-1H-pyrazolo[4,3-c]pyridine [Example 251(a)] and subjecting the reaction product to flash column chromatography eluting with ethyl acetate/petrol (5:1, v/v) to 100% ethyl acetate to ethyl acetate/methanol (19:1, v/v), there was prepared [3-(5,6-dimethyl-1H-benzoimidazol-2-yl)-1,4,6,7-tetrahydro-pyrazolo[4,3-c]pyridin-5-yl]-piperidin-1-yl-methanone (93.3 mg) as an off-white solid. LC-MS (METHOD L): $R_T$=6.77 minutes, 379 (M+H)$^+$.

(l) [3-(5,6-Dimethyl-1H-benzoimidazol-2-yl)-1,4,6,7-tetrahydro-pyrazolo[4,3-c]pyridin-5-yl]-morpholin-4-yl-methanone

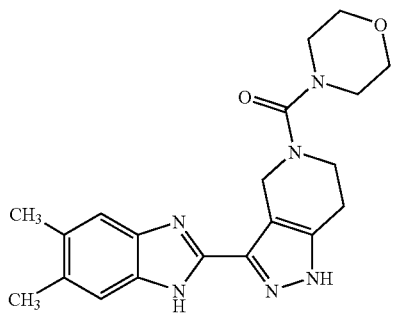

By proceeding in a manner similar to Example 258(k) above, but using 1-morpholinecarbonyl chloride and azeotroping the reaction product with toluene and dichloromethane, there was prepared [3-(5,6-dimethyl-1H-benzoimidazol-2-yl)-1,4,6,7-tetrahydro-pyrazolo[4,3-c]pyridin-5-yl]-morpholin-4-yl-methanone (32 mg) as an off-white solid. MS: 381 (M+H)$^+$. HPLC (METHOD E1): $R_T$=9.39 minutes.

(m) 3-(5-Chloro-6-methyl-1H-benzoimidazol-2-yl)-1,4,6,7-tetrahydro-pyrazolo[4,3-c]pyridine-5-carboxylic acid diethylamide

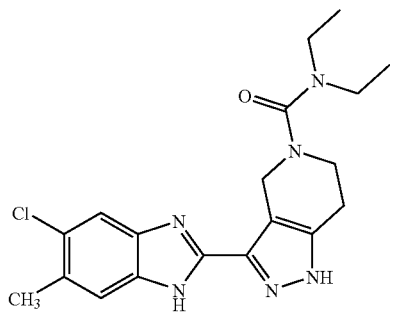

By proceeding in a manner similar to Example 258(a) above but (i) using 3-(5-chloro-6-methyl-1H-benzoimidazol-2-yl)-4,5,6,7-tetrahydro-1H-pyrazolo[4,3-c]pyridine [Example 251(b)] and diethylcarbamyl chloride, and (ii) subjecting the reaction product to flash column chromatography, eluting with ethyl acetate to ethyl acetate/methanol (47:3, v/v) followed by trituration with ethanol, there was prepared 3-(5-chloro-6-methyl-1H-benzoimidazol-2-yl)-1,4,6,7-tetrahydro-pyrazolo[4,3-c]pyridine-5-carboxylic acid diethylamide (35.6 mg) as a pale yellow solid. MS: 387/389 (M+H)$^+$. HPLC (METHOD E1): $R_T$=11.07 minutes.

(n) Morpholine-4-carboxylic acid [3-(5,6-dimethyl-1H-benzoimidazol-2-yl)-1H-pyrazol-4-yl]-amide

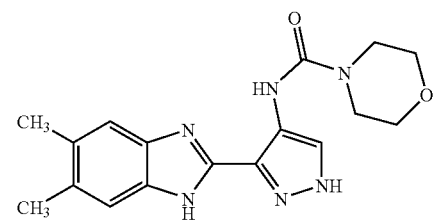

By proceeding in a manner similar to Example 258(p) above but using 3-(5,6-dimethyl-1H-benzoimidazol-2-yl)-1H-pyrazol-4-ylamine [Example 233(c)] and 1-morpholinecarbonyl chloride there was prepared morpholine-4-carboxylic acid [3-(5,6-dimethyl-1H-benzoimidazol-2-yl)-1H-pyrazol-4-yl]-amide (206 mg) as a white solid. LC-MS (METHOD L): $R_T$=7.36 minutes, 341 (M+H)$^+$.

(o) Piperidine-1-carboxylic acid [3-(5,6-dimethyl-1H-benzoimidazol-2-yl)-1H-pyrazol-4-yl]-amide

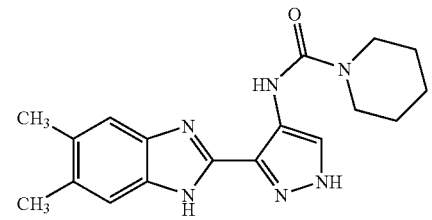

By proceeding in a manner similar to Example 258(p) above but using 1-piperidinecarbonyl chloride there was prepared piperidine-1-carboxylic acid [3-(5,6-dimethyl-1H-benzoimidazol-2-yl)-1H-pyrazol-4-yl]-amide (185 mg) as a white solid. LC-MS (METHOD M): $R_T$=10.79 minutes, 339 (M+H)$^+$.

(p) 3-[5-(2-Morpholin-4-yl-ethoxy)-1H-benzoimidazol-2-yl]-1,4,6,7-tetrahydro-pyrazolo[4,3-c]pyridine-5-carboxylic acid diethylamide

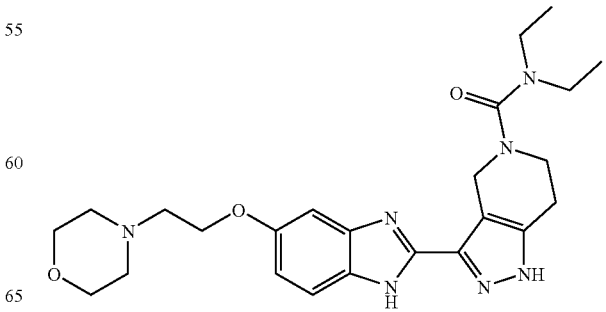

By proceeding in a manner similar to Example 258(a) above but using 3-[5-(2-morpholin-4-yl-ethoxy)-1H-benzoimidazol-2-yl]-4,5,6,7-tetrahydro-1H-pyrazolo[4,3-c]pyridine [Example 251 (c)] and diethylcarbamyl chloride there was prepared 3-[5-(2-morpholin-4-yl-ethoxy)-1H-benzoimidazol-2-yl]-1,4,6,7-tetrahydro-pyrazolo[4,3-c]pyridine-5-carboxylic acid diethylamide (28 mg) as a white solid. MS: 468.30 (M+H)$^+$. HPLC (METHOD E1): R$_T$=9.47 minutes.

(q) 3-(5-trifluoromethyl-1H-benzoimidazol-2-yl)-1,4,6,7-tetrahydro-pyrazolo[4,3-c]pyridine-5-carboxylic acid diethylamide

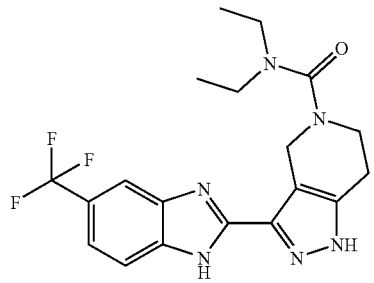

By proceeding in a manner similar to Example 258(a) above but using 3-(5-trifluoromethyl-1H-benzoimidazol-2-yl)-4,5,6,7-tetrahydro-1H-pyrazolo[4,3-c]pyridine [Example 251(d)] and diethylcarbamyl chloride there was prepared 3-(5-trifluoromethyl-1H-benzoimidazol-2-yl)-1,4,7-tetrahydro-pyrazolo[4,3-c]pyridine-5-carboxylic acid diethylamide (103 mg) as a white solid. MS: 407.17 (M+H)$^+$. HPLC (METHOD E1): R$_T$=10.81 minutes.

(r) 3-[3-(5,6-Dimethyl-1H-benzoimidazol-2-yl)-1H-pyrazol-4-yl]-1,1-dimethyl-urea

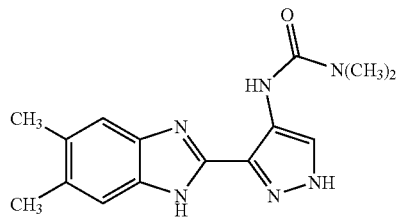

By proceeding in a manner similar to Example 258(p) above but using dimethylcarbamyl chloride there was prepared 3-[3-(5,6-dimethyl-1H-benzoimidazol-2-yl)-1H-pyrazol-4-yl]-1,1-dimethyl-urea. MS: 299 (M+H)$^+$. HPLC (Method E1): R$_T$=8.24 minutes.

EXAMPLE 259

2-(1H-Indazol-3-yl)-1H-benzoimidazole-5-carboxylic acid [2-(2H-tetrazol-5-yl)-ethyl]-amide

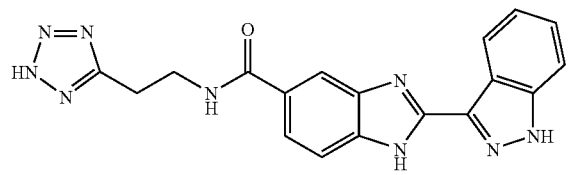

A stirred solution of 2-(1H-indazol-3-yl)-1H-benzoimidazole-5-carboxylic acid (2-cyano-ethyl)-amide [150 mg, Example 246(s)] and azidotributyltin (2 ml) was heated at 95° C. for 24 hours. The reaction was cooled to ambient temperature and stirred for 2 hours with acetonitrile (20 ml), tetrahydrofuran (10 ml) and acetic acid (20 ml). The reaction mixture was washed with iso-hexane (6×80 ml) and concentrated in vacuo. The residue was subjected to preparative HPLC to give 2-(1H-indazol-3-yl)-1H-benzoimidazole-5-carboxylic acid [2-(2H-tetrazol-5-yl)-ethyl]-amide (35.9 mg) as a brown solid.

LC-MS (Method L): R$_T$=9.80 minutes, 374.21 (M+H)$^+$.

EXAMPLE 260

(a) 1-Cyclopropyl-3-[3-(5-ethyl-6-methyl-1H-benzoimidazol-2-yl)-1H-pyrazol-4-yl]-urea

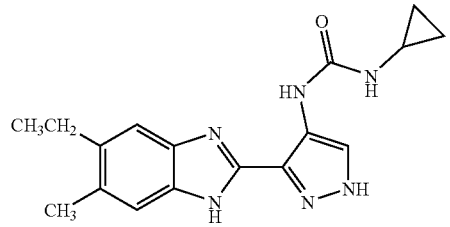

To a stirred solution of 3-(5-ethyl-6-methyl-1H-benzoimidazol-2-yl)-1H-pyrazol-4-ylamine [250 mg, Example 233(d)] in tetrahydrofuran (20 ml) was added 1,1-carbonyldiimidazole (740 mg) and the reaction heated at reflux for 60 hours. The reaction mixture was cooled to ambient temperature and the solvent removed in vacuo. The residue was added 2M cyclopropylamine in tetrahydrofuran (15 ml). The reaction mixture was transferred to a pressure tube and heated at reflux for 48 hours. The reaction mixture was cooled to ambient temperature and partitioned between ethyl acetate and water. The aqueous layer was extracted three times with ethyl acetate and the combined organic extracts washed with brine, dried over magnesium sulfate, and concentrated. The residue was subjected to flash column chromatography on silica eluting with ethyl acetate/hexane (1:1 v/v) to 100% ethyl acetate to afford 1-cyclopropyl-3-[3-(5-ethyl-6-methyl-1H-benzoimidazol-2-yl)-1H-pyrazol-4-yl]-urea (95 mg) as a white solid. LC-MS (METHOD M): R$_T$=9.40 minutes, 325.32 (M+H)$^+$.

(b) 1-[3-(5-Ethyl-6-methyl-1H-benzoimidazol-2-yl)-1H-pyrazol-4-yl]-3-methyl-urea

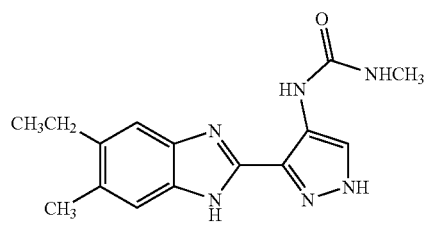

By proceeding in a manner similar to Example 260(a) above but using 2M methylamine in tetrahydrofuran there was prepared 1-[3-(5-ethyl-6-methyl-1H-benzoimidazol-2- yl)-1H-pyrazol-4-yl]-3-methyl-urea (36 mg) as a white solid. LC-MS (METHOD M): $R_T$=7.08 minutes, 299.34 (M+H)⁺.

(c) 4-Methyl-piperazine-1-carboxylic acid [3-(5-ethyl-6-methyl-1H-benzoimidazol-2-yl)-1H-pyrazol-4-yl]-amide

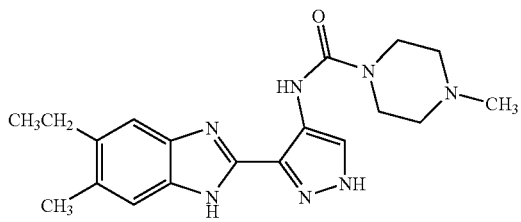

By proceeding in a manner similar to Example 260(a) above but using 2M 1-methylpiperazine in tetrahydrofuran there was prepared 4-methyl-piperazine-1-carboxylic acid [3-(5-ethyl-6-methyl-1H-benzoimidazol-2-yl)-1H-pyrazol-4-yl]-amide (247 mg) pared as a white solid. LC-MS (METHOD M): $R_T$=5.21 minutes, 368.32 (M+H)⁺.

(d) Piperidine-1-carboxylic acid [3-(5-fluoro-6-methyl-1H-benzoimidazol-2-yl)-1H-pyrazol-4-yl]-amide

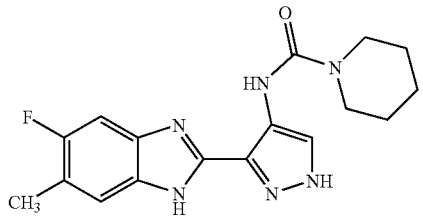

By proceeding in a manner similar to Example 260(a) above but using 3-(5-fluoro-6-methyl-1H-benzoimidazol-2-yl)-1H-pyrazol-4-ylamine [Example 233(h)] and 2M piperidine in tetrahydrofuran there was prepared piperidine-1-carboxylic acid [3-(5-fluoro-6-methyl-1H-benzoimidazol-2-yl)-1H-pyrazol-4-yl]-amide (140 mg) as a white solid. LC-MS (METHOD L): $R_T$=8.29 minutes, 343.26 (M+H)⁺.

(e) 1-[3-(5-Fluoro-6-methyl-1H-benzoimidazol-2-yl)-1H-pyrazol-4-yl]-3-methyl-urea

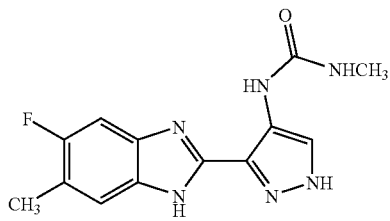

By proceeding in a manner similar to Example 260(d) above but using 2M methylamine in tetrahydrofuran there was prepared 1-[3-(5-fluoro-6-methyl-1H-benzoimidazol-2- yl)-1H-pyrazol-4-yl]-3-methyl-urea (61 mg) as a white solid. LC-MS (METHOD L): $R_T$=4.85 minutes, 289.26 (M+H)⁺.

(f) Morpholine-4-carboxylic acid [3-(5-fluoro-6-methyl-1H-benzoimidazol-2-yl)-1H-pyrazol-4-yl]-amide

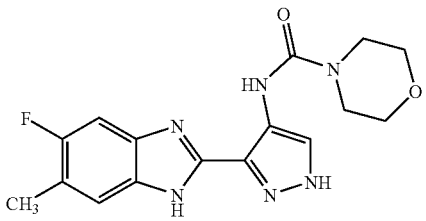

By proceeding in a manner similar to Example 260(d) above but using 2M morpholine in tetrahydrofuran there was prepared morpholine-4-carboxylic acid [3-(5-fluoro-6-methyl-1H-benzoimidazol-2-yl)-1H-pyrazol-4-yl]-amide (49 mg) as a white solid. LC-MS (METHOD L): $R_T$=6.26 minutes, 345.33 (M+H)⁺.

(g) 4-Methyl-piperazine-1-carboxylic acid [3-(5-fluoro-6-methyl-1H-benzoimidazol-2-yl)-1H-pyrazol-4-yl]-amide

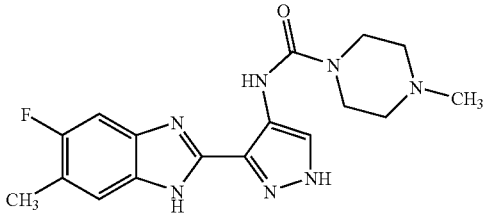

By proceeding in a manner similar to Example 31(d) above but using 2M 1-methylpiperazine in tetrahydrofuran there was prepared 4-methyl-piperazine-1-carboxylic acid [3-(5-fluoro-6-methyl-1H-benzoimidazol-2-yl)-1H-pyrazol-4-yl]-amide (58 mg) as a white solid. LC-MS (METHOD P): $R_T$=7.72 minutes, 358.19 (M+H)⁺.

(h) 1-Methyl-3-[3-(5-trifluoromethyl-1H-benzoimidazol-2-yl)-1H-pyrazol-4-yl]-urea

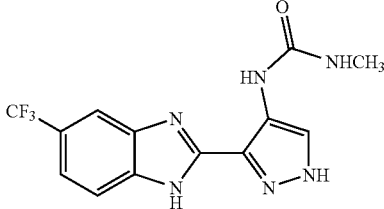

By proceeding in a manner similar to Example 260(a) above but using 3-(5-trifluoromethyl-1H-benzoimidazol-2-yl)-1H-pyrazol-4-ylamine [Example 2330)] and 2M methylamine in tetrahydrofuran there was prepared 1-methyl-3-[3-

(5-trifluoromethyl-1H-benzoimidazol-2-yl)-1H-pyrazol-4-yl]-urea (99 mg) as a white solid. LC-MS (METHOD L): $R_T$=6.51 minutes, 325 (M+H)$^+$.

(i) 1-[3-(5-Chloro-6-methyl-1H-benzoimidazol-2-yl)-1H-pyrazol-4-yl]-3-methyl-urea

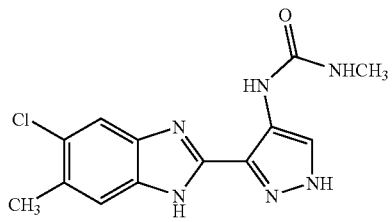

By proceeding in a manner similar to Example 260(a) above but using 3-(5-chloro-6-methyl-1H-benzoimidazol-2-yl)-1H-pyrazol-4-ylamine [Example 261] and 2M methylamine in tetrahydrofuran there was prepared 1-[3-(5-chloro-6-methyl-1H-benzoimidazol-2-yl)-1H-pyrazol-4-yl]-3-methyl-urea (45 mg) as a white solid. LC-MS (METHOD L): $R_T$=5.85 minutes, 305/307 (M+H)$^+$.

(j) 4-Methyl-piperazine-1-carboxylic acid [3-(5-chloro-6-methyl-1H-benzoimidazol-2-yl)-1H-pyrazol-4-yl]-amide

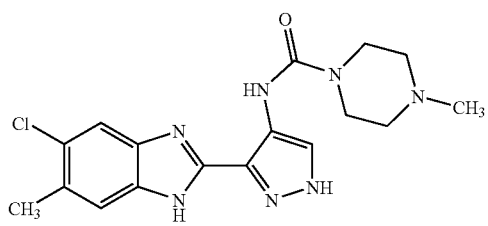

By proceeding in a manner similar to Example 260(i) above but using 2M 1-methylpiperazine in tetrahydrofuran there was prepared 4-methyl-piperazine-1-carboxylic acid [3-(5-chloro-6-methyl-1H-benzoimidazol-2-yl)-1H-pyrazol-4-yl]-amide (60 mg) as a pale yellow solid. LC-MS (METHOD M): $R_T$=6.35 minutes, 374 (M+H)$^+$.

(k) 1-tert-Butyl-3-[3-(5,6-dimethyl-1H-benzoimidazol-2-yl)-1H-pyrazol-4-yl]-urea

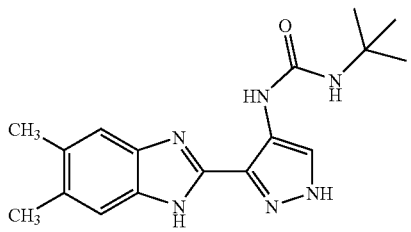

By proceeding in a manner similar to Example 260(a) above but using 3-(5,6-dimethyl-1H-benzoimidazol-2-yl)-1H-pyrazol-4-ylamine [Example 233(c)] and tert-butylamine there was prepared 1-tert-butyl-3-[3-(5,6-dimethyl-1H-benzoimidazol-2-yl)-1H-pyrazol-4-yl]-urea (21 mg) as a white solid. LC-MS (METHOD L): $R_T$=5.38 minutes, 327 (M+H)$^+$.

(l) 1-[3-(5,6-Dimethyl-1H-benzoimidazol-2-yl)-1H-pyrazol-4-yl]-3-ethyl-urea

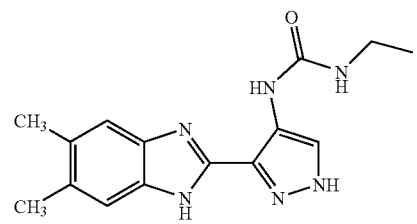

By proceeding in a manner similar to Example 260(k) above but using 2M ethylamine in tetrahydrofuran there was prepared 1-[3-(5,6-dimethyl-1H-benzoimidazol-2-yl)-1H-pyrazol-4-yl]-3-ethyl-urea (39 mg) as a white solid. LC-MS (METHOD L): $R_T$=3.95 minutes, 299 (M+H)$^+$.

(m) 4-Methyl-piperazine-1-carboxylic acid [3-(5,6-dimethyl-1H-benzoimidazol-2-yl)-1H-pyrazol-4-yl]-amide

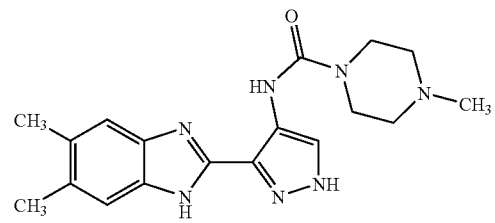

By proceeding in a manner similar to Example 260(k) above but using 2M 1-methylpiperazine in tetrahydrofuran there was prepared 4-methyl-piperazine-1-carboxylic acid [3-(5,6-dimethyl-1H-benzoimidazol-2-yl)-1H-pyrazol-4-yl]-amide (113 mg) as a white solid. MS: 354 (M+H)$^+$. HPLC (METHOD E1): $R_T$=10.21 minutes.

(n) 1-Cyclopropyl-3-[3-(5,6-dimethyl-1H-benzoimidazol-2-yl)-1H-pyrazol-4-yl]-urea

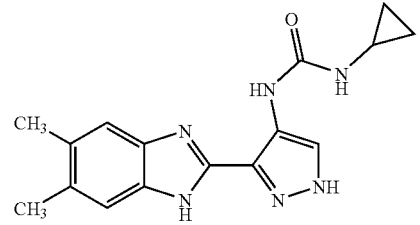

By proceeding in a manner similar to Example 260(k) above but using cyclopropylamine there was prepared 1-cyclopropyl-3-[3-(5,6-dimethyl-1H-benzoimidazol-2-yl)-1H- pyrazol-4-yl]-urea (80 mg) as a white solid. MS: 311 (M+H)⁺. HPLC (METHOD E1): $R_T$=10.36 minutes.

(o) 3-[3-(5,6-Dimethyl-1H-benzoimidazol-2-yl)-1H-pyrazol-4-yl]-1,1-diethyl-urea

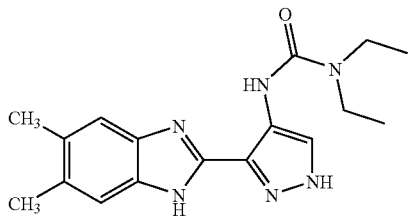

By proceeding in a manner similar to Example 260(k) above but using 2M diethylamine in tetrahydrofuran there was prepared 3-[3-(5,6-dimethyl-1H-benzoimidazol-2-yl)-1H-pyrazol-4-yl]-1,1-diethyl-urea (61 mg) as a white solid. MS: 327 (M+H)⁺. HPLC (METHOD E1): $R_T$=11.36 minutes.

(p) 1-[3-(5,6-Dimethyl-1H-benzoimidazol-2-yl)-1H-pyrazol-4-yl]-3-isobutyl-urea

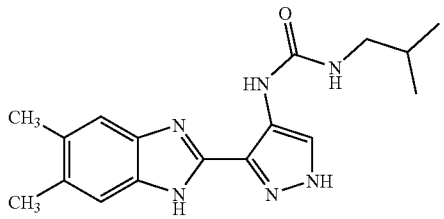

By proceeding in a manner similar to Example 2601(k) above but using 2M isobutylamine in tetrahydrofuran, there was prepared 1-[3-(5,6-dimethyl-1H-benzoimidazol-2-yl)-1H-pyrazol-4-yl]-3-isobutyl-urea (58 mg) as a white solid. MS: 327 (M+H)⁺. HPLC (METHOD E1): $R_T$=10.95 minutes.

(q) 1-Cyclopropylmethyl-3-[3-(5,6-dimethyl-1H-benzoimidazol-2-yl)-1H-pyrazol-4-yl]-urea

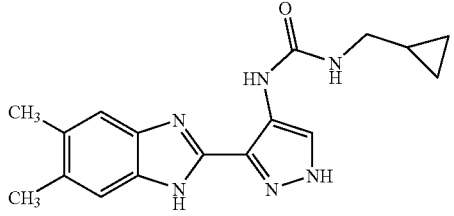

By proceeding in a manner similar to Example 260(k) above but using 2M (aminomethyl)cyclopropane in tetrahydrofuran, there was prepared 1-cyclopropylmethyl-3-[3-(5,6-dimethyl-1H-benzoimidazol-2-yl)-1H-pyrazol-4-yl]-urea (29 mg) as a white solid. MS: 325 (M+H)⁺. HPLC (METHOD E1): $R_T$=10.63 minutes.

EXAMPLE 261

3-(5-Chloro-6-methyl-1H-benzoimidazol-2-yl)-1H-pyrazol-4-ylamine

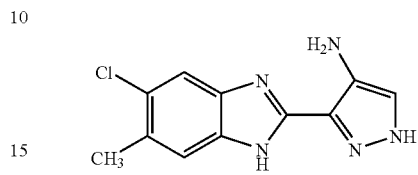

A stirred solution of 5-chloro-6-methyl-2-(4-nitro-1H-pyrazol-3-yl)-1H-benzoimidazole [0.320 g, Example 249(g)] and tin-chloride (1.10 g) in ethanol (5 ml) was heated in a Smith Creator microwave at 140° C. for 10 minutes. The reaction mixture was basified using saturated sodium hydrogen carbonate solution to pH 8 and extracted with ethyl acetate. The organic layer was dried over magnesium sulfate and concentrated to give 3-(5-chloro-6-methyl-1H-benzoimidazol-2-yl)-1H-pyrazol-4-ylamine as a pale brown solid. LC-MS (METHOD B): $R_T$=2.28 minutes, 248.13 (M+H)⁺.

EXAMPLE 262

3-(5-Ethyl-6-methyl-1H-benzoimidazol-2-yl)-1H-indazole-5-carboxylic acid amide dihydrochloride

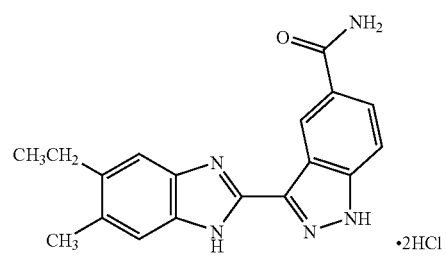

A stirred suspension of 3-(5-ethyl-6-methyl-1H-benzoimidazol-2-yl)-1H-indazole-5-carbonitrile [100 mg, Example 235(an)] in acetic acid (1 ml) and concentrated hydrochloric acid (1 ml) was heated at 80° C. for 30 minutes and then at 100° C. for 4 hours. The reaction was cooled to ambient temperature and stirred for 16 hours. The reaction was then heated at 80° C. for 2.5 hours and then at 100° C. for 2 hours. The reaction mixture was cooled to ambient temperature and neutralized with aqueous sodium carbonate solution. The resulting white precipitate was collected by filtration and the aqueous layer was extracted with ethyl acetate, combined with the precipitate and concentrated in vacuo. The residue was taken up in methanol, transferred to a solid phase cartridge containing MP-carbonate resin (100 mg) and shaken for 16 hours. The reaction was then filtered, the resin washed with methanol and the combined organic layers concentrated in vacuo. The residue was triturated with diethyl ether, taken up in methanol and acidified with 4M hydrogen chloride in 1,4-dioxane. The solvent was removed in vacuo to give 3-(5-ethyl-6-methyl-1H-benzoimidazol-2-yl)-1H-indazole-5-carboxylic acid amide dihydrochloride (58 mg) as a pale brown solid. LC-MS (METHOD M): $R_T$=9.40 minutes, 320 (M+H)$^+$.

EXAMPLE 263

3-(5,6-Dimethyl-1H-benzoimidazol-2-yl)-1H-indazole-5-carboxylic acid

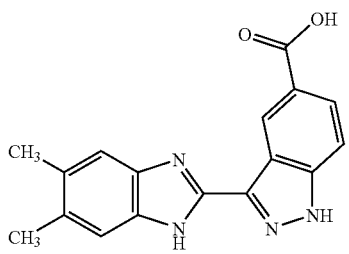

A stirred suspension of 3-(5,6-dimethyl-1H-benzoimidazol-2-yl)-1H-indazole-5-carbonitrile dihydrochloride [200 mg, Reference Example 6(aq)] in acetic acid/concentrated hydrochloric acid (4 ml, 1:1 v/v) was heated at 100° C. for 16 hours. The reaction mixture was cooled to ambient temperature and filtered. The precipitate was washed with water and dried in vacuo to give 3-(5,6-dimethyl-1H-benzoimidazol-2-yl)-1H-indazole-5-carboxylic acid (195 mg) as a white solid. LC-MS (METHOD B): $R_T$=2.52 minutes, 307 (M+H)$^+$.

EXAMPLE 264

2-(4-Isobutyrylamino-1H-pyrazol-3-yl)-1H-benzoimidazole-5-carboxylic acid

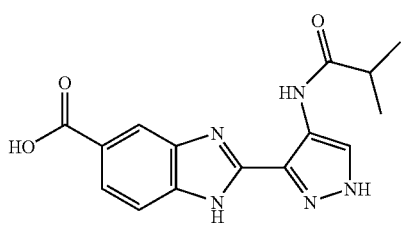

To a stirred solution of 2-(4-amino-1H-pyrazol-3-yl)-1H-benzoimidazole-5-carboxylic acid methyl ester [200 mg, Example 233(k)] in tetrahydrofuran (5 ml) was added diisopropylethylamine (545 µl) and isobutyryl chloride (327 µl) dropwise and the reaction stirred for 30 minutes. The reaction mixture was concentrated in vacuo and the residue was taken up in 1M potassium hydroxide in tetrahydrofuran/methanol (1:3, v/v) (5 ml) and stirred for 1 hour. The reaction mixture was concentrated in vacuo and the residue was taken up in 1M sodium hydroxide in water/methanol (5 ml) and stirred for 1 hour. The solvent was removed in vacuo and the residue was partitioned between ethyl acetate and water and the layers separated. The aqueous layer was acidified to pH 3-4 with 5% citric acid solution, extracted with ethyl acetate and the organic layer washed with brine. The organic layer was then dried over magnesium sulfate, filtered and the filtrate concentrated in vacuo to give 2-(4-isobutyrylamino-1H-pyrazol-3-yl)-1H-benzoimidazole-5-carboxylic acid (140 mg) as a white solid. LC-MS (METHOD C): $R_T$=2.87 minutes, 313.33 (M+H)$^+$.

EXAMPLE 265

2-(1H-Indazol-3-yl)-3H-benzoimidazol-5-amine

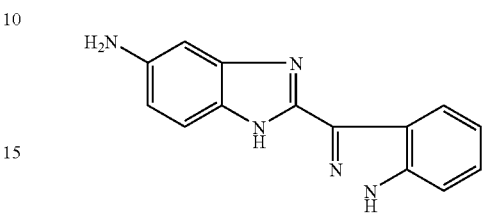

A stirred solution of 3-(5-nitro-1H-benzoimidazol-2-yl)-1H-indazole [90.8 mg, Reference Example 233(as)] in methanol (1 ml) was treated with tin chloride (616 mg). The reaction was heated at reflux for 16 hours and then cooled to ambient temperature. The pH of the reaction mixture was adjusted to pH 8 by addition of aqueous sodium bicarbonate and then this mixture was extracted with ethyl acetate. The organic extracts were dried over magnesium sulfate and then evaporated to yield an oil. The crude product was subjected to flash column chromatography on silica eluting with ethyl acetate and 10% triethylamine to give 2-(1H-indazol-3-yl)-3H-benzoimidazol-5-amine (826 mg). MS: 250.31 (M+H)$^+$, 248.31 (M−H)$^-$. HPLC (Method B): $R_T$=2.03 minutes.

REFERENCE EXAMPLE 1

(a) 5,6-Dimethyl-2-(5-methylsulfanyl-1H-pyrazol-3-yl)-1-(2-trimethylsilanyl-ethoxymethyl-1H-benzoimidazole

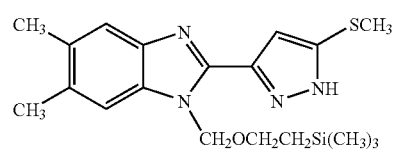

A mixture of 1-[5,6-dimethyl-1-(2-trimethylsilanyl-ethoxymethyl)-1H-benzoimidazol-2-yl]-3,3-bis-methylsulfanyl-propenone [318 mg, Reference Example 2(a)], hydrazine (2 mL) and ethanol (12 mL) was heated at reflux temperature for 1 hour. The reaction mixture was then cooled to room temperature, then stirred at room temperature overnight, then heated at 60° C. for 2 hours, then heated at reflux temperature for 3 hours, then stood at room temperature for 3 days and then evaporated. The residue was dissolved in dichloromethane and this solution was washed with water plus a little brine to facilitate separation and the aqueous phase was washed with dichloromethane and then with ethyl acetate. The combined organics were dried over magnesium sulfate and then evaporated to give 5,6-dimethyl-2-(5-methylsulfanyl-1H-pyrazol-3-yl)-1-(2-trimethylsilanyl-ethoxymethyl)-1H-benzoimidazole (90 mg) as a colourless solid.

(b) By proceeding in a similar manner to Reference Example 1(a) above but using 1-[6-chloro-5-methyl-1-(2-trimethylsilanyl-ethoxymethyl)-1H-benzoimidazol-2-yl]-3,3-bis-methylsulfanyl-propenone [Reference Example 2(b)]

there was prepared 6-chloro-5-methyl-2-(5-methylsulfanyl-1H-pyrazol-3-yl)-1-(2-trimethylsilanyl-ethoxymethyl)-1H-benzoimidazole.

(c) By proceeding in a similar manner to Reference Example 1(a) above but using 1-[6-chloro-5-methyl-1-(2-trimethylsilanyl-ethoxymethyl)-1H-benzoimidazol-2-yl]-3,3-bis-ethylsulfanyl-propenone [Reference Example 2(c)] there was prepared 6-chloro-5-methyl-2-(5-ethylsulfanyl-1H-pyrazol-3-yl)-1-(2-trimethylsilanyl-ethoxymethyl)-1H-benzoimidazole (d) By proceeding in a similar manner to Reference Example 1(a) above but using 3,3-bis-methylsulfanyl-1-[5-trifluoromethyl-1-(2-trimethylsilanyl-ethoxymethyl)-1H-benzoimidazol-2-yl]-propenone [Reference Example 2(d)] there was prepared 2-(5-methylsulfanyl-1H-pyrazol-3-yl)-5-trifluoromethyl-1-(2-trimethylsilanyl-ethoxymethyl)-1H-benzoimidazole (e) By proceeding in a similar manner to Reference Example 1(a) above but using 3,3-bis-cyclopropylmethylsulfanyl-1-[5,6-dimethyl-(2-trimethylsilanyl-ethoxymethyl)-1H-benzoimidazol-2-yl]-propenone [Reference Example 2(e)] there was prepared 2-(5-cyclopropylmethylsulfanyl-1H-pyrazol-3-yl)-5,6-dimethyl-1-(2-trimethylsilanyl-ethoxymethyl)-1H-benzoimidazole.

(f) By proceeding in a similar manner to Reference Example 1(a) above but using 1-[5,6-dimethyl-1-(2-trimethylsilanyl-ethoxymethyl)-1H-benzoimidazol-2-yl]-3,3-bis-ethylsulfanyl propenone [Reference Example 2(f)] there was prepared 5,6-dimethyl-2-(5-ethylsulfanyl-1H-pyrazol-3-yl)-1-(2-trimethylsilanyl-ethoxymethyl)-1H-benzoimidazole.

(g) By proceeding in a similar manner to Reference Example 1(a) above but using 1-[5,6-dimethyl-1-(2-trimethylsilanyl-ethoxymethyl)-1H-benzoimidazol-2-yl]-3,3-bis-(pyridin-3-ylmethylsulfanyl)-propenone [Reference Example 2(g)] there was prepared 5,6-dimethyl-2-(5-(pyridin-3-yl)methylsulfanyl-1H-pyrazol-3-yl)-1-(2-trimethylsilanyl-ethoxymethyl)-1H-benzoimidazole.

(h) By proceeding in a similar manner to Reference Example 1(a) above but using 1-[5-fluoro-1-(2-trimethylsilanyl-ethoxymethyl)-1H-benzoimidazol-2-yl]-3,3-bis-methylsulfanyl-propenone [Reference Example 2(h)] there was prepared 5-fluoro-2-(5-methylsulfanyl-1H-pyrazol-3-yl)-1-(2-trimethylsilanyl-ethoxymethyl)-1H-benzoimidazole.

(i) By proceeding in a similar manner to Reference Example 1(a) above but using 1-[5,6-dimethyl-1-(2-trimethylsilanyl-ethoxymethyl)-1H-benzoimidazol-2-yl]-3,3-bis-phenethylsulfanyl-propenone [Reference Example 2(i)] there was prepared 5,6-dimethyl-2-(5-phenethylsulfanyl-1H-pyrazol-3-yl)-1-(2-trimethylsilanyl-ethoxymethyl)-1H-benzoimidazole.

(j) By proceeding in a similar manner to Reference Example 1(a) above but using 3,3-bis-methylsulfanyl-1-[4-methyl-1-(2-trimethylsilanyl-ethoxymethyl)-1H-benzoimidazol-2-yl]-propenone [Reference Example 2(k)] there was prepared 4-methyl-2-(5-methylsulfanyl-1H-pyrazol-3-yl)-1-(2-trimethylsilanyl-ethoxymethyl)-1H-benzoimidazole.

(k) By proceeding in a similar manner to Reference Example 1(a) above but using 3,3-bis-benzylsulfanyl-1-[5,6-dimethyl-1-(2-trimethylsilanyl-ethoxymethyl)-1H-benzoimidazol-2-yl]-propenone [Reference Example 2(o)] there was prepared 2-(5-benzylsulfanyl-1H-pyrazol-3-yl)-5,6-dimethyl-1-(2-trimethylsilanyl-ethoxymethyl)-1H-benzoimidazole.

(l) By proceeding in a similar manner to Reference Example 1(a) above but using 1-[6-chloro-5-methyl-1-(2-trimethylsilanyl-ethoxymethyl)-1H-benzoimidazol-2-yl]-3-methylsulfanyl-3-morpholin-1-yl-propenone [Reference Example 13] there was prepared 6-chloro-5-methyl-2-(5-morpholin-4-yl-1H-pyrazol-3-yl)-1-(2-trimethylsilanyl-ethoxymethyl)-1H-benzoimidazole.

(m) By proceeding in a similar manner to Reference Example 1(a) above but using 1-[5,6-dimethyl-1-(2-trimethylsilanyl-ethoxymethyl)-1H-benzoimidazol-2-yl]-3,3-bis-(thiophen-2-ylmethylsulfanyl) propenone [Reference Example 2(s)] there was prepared 5,6-dimethyl-2-[5-(thiophen-2-ylmethylsulfanyl)-1H-pyrazol-3-yl]-1-(2-trimethylsilanyl-ethoxymethyl)-1H-benzoimidazole.

REFERENCE EXAMPLE 2

(a) 1-[5,6-Dimethyl-1-(2-trimethylsilanyl-ethoxymethyl)-1H-benzoimidazol-2-yl]-3,3-bis-methylsulfanyl-propenone

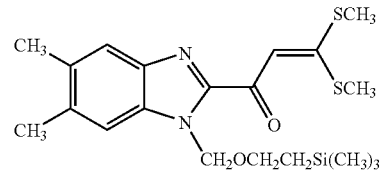

A stirred suspension of sodium tert-butoxide (350 mg) in benzene (6 mL), at −5° C., was treated with a solution of 1-[5,6-dimethyl-1-(2-trimethylsilanyl-ethoxymethyl)-1H-benzoimidazol-2-yl]-ethanone [240 mg, Reference Example 3(a)] in benzene (5 mL) followed by carbon disulfide (230 µL). The resulting orange solution was stirred for 1 hour at −5° C., then treated with methyl iodide (180 µL), then allowed to warm to room temperature and then stirred at room temperature overnight. An orange precipitate was formed. The reaction mixture was poured into ice-water and this mixture was then extracted with dichloromethane. The combined organic extracts were washed with water, then dried over sodium sulfate and then evaporated to give 1-[5,6-dimethyl-1-(2-trimethylsilanyl-ethoxymethyl)-1H-benzoimidazol-2-yl]-3,3-methylsulfanyl-propenone (318 mg) as an orange oil which was used without further purification.

(b) By proceeding in a similar manner to Reference Example 2(a) above but using 1-[6-chloro-5-methyl-1-(2-trimethylsilanyl-ethoxymethyl)-1H-benzoimidazol-2-yl]-ethanone [Reference Example 3(b)] there was prepared 1-[6-chloro-5-methyl-1-(2-trimethylsilanyl-ethoxymethyl)-1H-benzoimidazol-2-yl]-3,3-bis-methylsulfanyl-propenone.

(c) By proceeding in a similar manner to Reference Example 2(a) above but using 1-[6-chloro-5-methyl-1-(2-trimethylsilanyl-ethoxymethyl)-1H-benzoimidazol-2-yl]-ethanone [Reference Example 3(b)] and ethyl iodide there was prepared 1-[6-chloro-5-methyl-1-(2-trimethylsilanyl-ethoxymethyl)-1H-benzoimidazol-2-yl]-3,3-bis-ethylsulfanyl-propenone.

(d) By proceeding in a similar manner to Reference Example 2(a) above but using 1-[5-trifluoromethyl-1-(2-trimethylsilanyl-ethoxymethyl)-1H-benzoimidazol-2-yl]-ethanone [Reference Example 3(c)] there was prepared 3,3-bis-methylsulfanyl-1-[5-trifluoromethyl-1-(2-trimethylsilanyl-ethoxymethyl)-1H-benzoimidazol-2-yl]-propenone.

(e) By proceeding in a similar manner to Reference Example 2(a) above but using bromomethylcyclopropane there was prepared 3,3-bis-cyclopropylmethylsulfanyl-1-[5,6-dimethyl-1-(2-trimethylsilanyl-ethoxymethyl)-1H-benzoimidazol-2-yl]-propenone.

(f) By proceeding in a similar manner to Reference Example 2(a) above but using ethyl iodide there was prepared 1-[5,6-dimethyl-1-(2-trimethylsilanyl-ethoxymethyl)-1H-benzoimidazol-2-yl]-3,3-bis-ethylsulfanyl-propenone.

(g) By proceeding in a similar manner to Reference Example 2(a) above but using 3-picolyl chloride there was prepared 1-[5,6-dimethyl-1-(2-trimethylsilanyl-ethoxymethyl)-1H-benzoimidazol-2-yl]-3,3-bis-(pyridin-3-ylmethylsulfanyl)-propenone.

(h) By proceeding in a similar manner to Reference Example 2(a) above but using 1-[5-fluoro-1-(2-trimethylsilanyl-ethoxymethyl)-1H-benzoimidazol-2-yl]-ethanone [Reference Example 3(d)] there was prepared 1-[5-fluoro-1-(2-trimethylsilanyl-ethoxymethyl)-1H-benzoimidazol-2-yl]-3,3-bis-methylsulfanyl-propenone.

(i) By proceeding in a similar manner to Reference Example 2(a) above but using phenethyl bromide there was prepared 1-[5,6-dimethyl-1-(2-trimethylsilanyl-ethoxymethyl)-1H-benzoimidazol-2-yl]-3,3-bis-phenethylsulfanyl-propenone.

(j) By proceeding in a similar manner to Reference Example 2(a) above but using 1-[5-methoxy-1-(2-trimethylsilanyl-ethoxymethyl)-1H-benzoimidazol-2-yl]-ethanone [Reference Example 4(g)] and ethyl bromide there was prepared 3,3-bis-ethylsulfanyl-1-[5-methoxy-2-(trimethylsilanylethoxymethyl)-1H-benzoimidazol-2-yl]-propenone.

(k) By proceeding in a similar manner to Reference Example 2(a) above but using 1-[4-methyl-1-(2-trimethylsilanyl-ethoxymethyl)-1H-benzoimidazol-2-yl]-ethanone [Reference Example 3(e)] there was prepared 3,3-bis-methylsulfanyl-1-[4-methyl-1-(2-trimethylsilanyl-ethoxymethyl)-1H-benzoimidazol-2-yl]-propenone.

(l) By proceeding in a similar manner to Reference Example 2(a) above but using 1-[5-methyl-1-(2-trimethylsilanyl-ethoxymethyl)-1H-benzoimidazol-2-yl]-pentan-1-one [Reference Example 3(f)] there was prepared 2-(bis-methylsulfanyl-methylene)-1-(5-methyl-1H-benzoimidazol-2-yl)-pentan-1-one.

(m) By proceeding in a similar manner to Reference Example 2(a) above but using 1-[5-methyl-1-(2-trimethylsilanyl-ethoxymethyl)-1H-benzoimidazol-2-yl]-pentan-1-one [Reference Example 3(f)] and 4-methoxybenzyl chloride there was prepared 2-[bis-(4-methoxy-benzylsulfanyl)-methylene]-1-(5-methyl-1H-benzoimidazol-2-yl)-pentan-1-one.

(n) By proceeding in a similar manner to Reference Example 2(a) above but using 3-methyl-1-[5-methyl-1-(2-trimethylsilanyl-ethoxymethyl)-1H-benzoimidazol-2-yl]-butan-1-one [Reference Example 3(g)] and benzyl chloride there was prepared 2-(bis-benzylsulfanyl-methylene)-3-methyl-1-[5-methyl-1-(2-trimethylsilanyl-ethoxymethyl)-1H-benzoimidazol-2-yl]-butan-1-one.

(o) By proceeding in a similar manner to Reference Example 2(a) above but using benzyl chloride there was prepared 3,3-bis-benzylsulfanyl-1-[5,6-dimethyl-1-(2-trimethylsilanyl-ethoxymethyl)-1H-benzoimidazol-2-yl]-propenone.

(p) By proceeding in a similar manner to Reference Example 2(a) above but using 1-[1-(2-trimethylsilanyl-ethoxymethyl)-1H-benzoimidazol-2-yl]-ethanone [Reference Example 4(h)] with tetrahydrofuran as the solvent and carrying out the reaction at room temperature and then subjecting the reaction product to flash chromatography on silica under gradient elution conditions (20 to 33% ethyl acetate in pentane) there was prepared 3,3-bis-methanesulfanyl-1-[1-(2-trimethylsilanyl-ethoxymethyl)-1H-benzoimidazol-2-yl]-propenone as an oil which slowly solidified on standing at room temperature.

(q) By proceeding in a similar manner to Reference Example 2(a) above but using 1-[6-chloro-5-methyl-1-(2-trimethylsilanyl-ethoxymethyl)-1H-benzoimidazol-2-yl]-ethanone [Reference Example 3(b)] and methyl iodide there was prepared 1-[6-chloro-5-methyl-1-(2-trimethylsilanyl-ethoxymethyl)-1H-benzoimidazol-2-yl]-3,3-bis-methylsulfanyl-propenone.

(r) By proceeding in a similar manner to Reference Example 2(a) above but using 1-[5-methoxy-1-(2-trimethylsilanyl-ethoxymethyl)-1H-benzoimidazol-2-yl]-propan-1-one [Reference Example 4(i)] and methyl iodide there was prepared 1-[5-methoxy-1-(2-trimethylsilanyl-ethoxymethyl)-1H-benzoimidazol-2-yl]-2-methyl-3-(bis-methanesulfanyl)-1-propenone.

(s) By proceeding in a similar manner to Reference Example 2(a) above but using of 1-[5,6-dimethyl-1-(2-trimethylsilanyl-ethoxymethyl)-1H-benzoimidazol-2-yl]-ethanone [Reference Example 3(a)] and 2-chloromethylthiophene [Reference Example 14]) there was prepared 1-[5,6-dimethyl-1-(2-trimethylsilanyl-ethoxymethyl)-1H-benzoimidazol-2-yl]-3,3-bis-(thiophen-2-ylmethylsulfanyl)-propenone.

(t) By proceeding in a similar manner to Reference Example 2(a) above but using 1-[5-methyl-1-(2-trimethylsilanyl-ethoxymethyl)-1H-benzoimidazol-2-yl]-propan-1-one [Reference Example 3(h)] there was prepared 1-[5-methyl-1-(2-trimethylsilanyl-ethoxymethyl)-1H-benzoimidazol-2-yl]-2-methyl-3-(bis-methanesulfanyl)-1-propenone.

REFERENCE EXAMPLE 3

(a) 1-[5,6-Dimethyl-1-(2-trimethylsilanyl-ethoxymethyl)-1H-benzoimidazol-2-yl]-ethanone

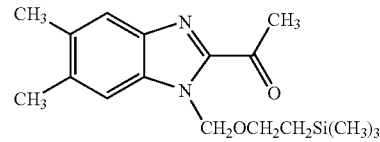

A solution of 5,6-dimethyl-1-(2-trimethylsilanyl-ethoxymethyl)-1H-benzoimidazole [5.01 g, Reference Example 4(a)] in dry tetrahydrofuran (55 mL), at −78° C., was treated with a solution of lithium diisopropylamide in a mixture of tetrahydrofuran and heptane (11.9 mL, 2M) over 10 minutes. The mixture was stirred for 15 minutes then treated dropwise with dimethylacetamide (2.15 mL) over 10 minutes. After stirring at −78° C. for a further 30 minutes the reaction mixture was poured into ice (50 g) and then left until all the ice had melted. This mixture was extracted with dichloromethane and the extracts were washed with brine, then with water, then dried over magnesium sulfate and then evaporated. The residual orange oil (5.91 g) was subjected to column chromatography on silica eluting with a mixture of petroleum ether and ethyl acetate (4:1, v/v) to give 1-[5,6-dimethyl-1-(2-trimethylsilanyl-ethoxymethyl)-1H-benzoimidazol-2-yl]-ethanone (3.93 g) as a yellow crystalline solid.

(b) By proceeding in a similar manner to Reference Example 3(a) above but using 6-chloro-5-methyl-1-(2-trimethylsilanyl-ethoxymethyl)-1H-benzoimidazole [Reference Example 4(b)] there was prepared 1-[6-chloro-5-methyl-1-(2-trimethylsilanyl-ethoxymethyl)-1H-benzoimidazol-2-yl]-ethanone.

(c) By proceeding in a similar manner to Reference Example 3(a) above but using 5-trifluoromethyl-1-(2-trimethylsilanyl-ethoxymethyl)-1H-benzoimidazole [Reference Example 4(c)] there was prepared 1-[5-trifluoromethyl-1-(2-trimethylsilanyl-ethoxymethyl)-1H-benzoimidazol-2-yl]-ethanone.

(d) By proceeding in a similar manner to Reference Example 3(a) above but using 5-fluoro-1-(2-trimethylsilanyl-ethoxymethyl)-1H-benzoimidazole [Reference Example 4(d)] there was prepared 1-[5-fluoro-1-(2-trimethylsilanyl-ethoxymethyl)-1H-benzoimidazol-2-yl]-ethanone.

(e) By proceeding in a similar manner to Reference Example 3(a) above but using 4-methyl-1-(2-trimethylsilanyl-ethoxymethyl)-1H-benzoimidazole [Reference Example 4(e)] there was prepared 1-[4-methyl-1-(2-trimethylsilanyl-ethoxymethyl)-1H-benzoimidazol-2-yl]-ethanone.

(f) By proceeding in a similar manner to Reference Example 3(a) above but using 5-methyl-1-(2-trimethylsilanyl-ethoxymethyl)-1H-benzoimidazole [Reference Example 4(f)] and dimethylvaleramide [Reference Example 8(a)] there was prepared 1-[5-methyl-1-(2-trimethylsilanyl-ethoxymethyl)-1H-benzoimidazol-2-yl]-pentan-1-one.

(g) By proceeding in a similar manner to Reference Example 3(a) above but using 5-methyl-1-(2-trimethylsilanyl-ethoxymethyl)-1H-benzoimidazole [Reference Example 4(f)] and dimethylisovalerylamide [Reference Example 8(b)] there was prepared 3-methyl-1-[5-methyl-1-(2-trimethylsilanyl-ethoxymethyl)-1H-benzoimidazol-2-yl]-butan-1-one.

(h) By proceeding in a similar manner to Reference Example 3(a) above but using 5-methyl-1-(2-trimethylsilanyl-ethoxymethyl)-1H-benzoimidazole [Reference Example 4(f)] and dimethylpropionamide there was prepared 1-[5-methyl-1-(2-trimethylsilanyl-ethoxymethyl)-1H-benzoimidazol-2-yl]-propan-1-one.

REFERENCE EXAMPLE 4

(a) 5,6-Dimethyl-1-(2-trimethylsilanyl-ethoxymethyl)-1H-benzoimidazole

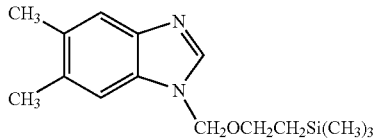

A stirred mixture of sodium hydride (1.08 g) in dimethylformamide (80 mL) was treated with a solution of 5,6-dimethyl-1H-benzoimidazole (4.95 g) in dimethylformamide (50 mL) at room temperature over 10 minutes. After stirring for a further 1 hour the mixture was then treated with 2-(trimethylsilanyl)ethoxymethyl) chloride (6.4 mL) over 15 minutes and then stirring was continued for 18 hours. The reaction mixture was treated with methanol (15 mL) and water (1 mL) and then evaporated. The residue was treated with water (50 mL) and this mixture was then extracted twice with diethyl ether (80 mL then 50 mL). The combined extracts were washed three times with water (50 mL), then dried over magnesium sulfate and then evaporated. The residual brown oil (10.3 g) was purified by Flashmaster using mixtures of ethyl acetate in hexane (20% to 80%) at 40 ml/minute to give 5,6-dimethyl-1-(2-trimethylsilanyl-ethoxymethyl)-1H-benzoimidazole (7.54 g) as an orange oil.

(b) By proceeding in a similar manner to Reference Example 4(a) above but using 6-chloro-5-methyl-1H-benzoimidazole [Reference Example 5(a)] there was prepared 6-chloro-5-methyl-1-(2-trimethylsilanyl-ethoxymethyl)-1H-benzoimidazole.

(c) By proceeding in a similar manner to Reference Example 4(a) above but using 5-trifluoromethyl-1H-benzoimidazole [Reference Example 5(b)] there was prepared 5-trifluoromethyl-1-(2-trimethylsilanyl-ethoxymethyl)-1H-benzoimidazole.

(d) By proceeding in a similar manner to Reference Example 4(a) above but using 5-fluoro-1H-benzoimidazole [Reference Example 5(c)] there was prepared 5-fluoro-1-(2-trimethylsilanyl-ethoxymethyl)-1H-benzoimidazole.

(e) By proceeding in a similar manner to Reference Example 4(a) above but using 4-methyl-1H-benzoimidazole [Reference Example 5(d)] there was prepared 4-methyl-1-(2-trimethylsilanyl-ethoxymethyl)-1H-benzoimidazole.

(f) By proceeding in a similar manner to Reference Example 4(a) above but using 5-methyl-1H-benzoimidazole there was prepared 5-methyl-1-(2-trimethylsilanyl-ethoxymethyl)-1H-benzoimidazole.

(g) By proceeding in a similar manner to Reference Example 4(a) above but using 1-(5-methoxy-1H-benzoimidazol-2-yl)-ethanone [Reference Example 6(a)] there was prepared 1-[5-methoxy-1-(2-trimethylsilanyl-ethoxymethyl)-1H-benzoimidazol-2-yl]-ethanone.

(h) By proceeding in a similar manner to Reference Example 4(a) above but using (1H-benzoimidazol-2-yl)-1-ethanone and carrying out the reaction in tetrahydrofuran there was prepared 1-[1-(2-trimethylsilanyl-ethoxymethyl)-1H-benzoimidazol-2-yl]-ethanone as a colourless oil.

(i) By proceeding in a similar manner to Reference Example 4(a) above but using 1-(5-methoxy-1H-benzoimidazol-2-yl)-propan-1-one [Reference Example 6(b)] there was prepared 1-[5-methoxy-1-(2-trimethylsilanyl-ethoxymethyl)-1H-benzoimidazol-2-yl]-propan-1-one

REFERENCE EXAMPLE 5

(a) 6-chloro-5-methyl-1H-benzoimidazole

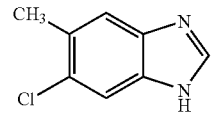

A solution of 5-chloro-4-methyl-1,2-phenylenediamine (7.8 g) in a mixture of formic acid (35 mL) and hydrochloric acid (300 mL) was heated at 50° C. for 3 hours then treated with ammonium hydroxide solution until the solution was basic. The reaction mixture was then extracted with dichloromethane. The extracts were evaporated to give 6-chloro-5-methyl-1H-benzoimidazole (7 g).

(b) By proceeding in a similar manner to Reference Example 5(a) above but using 4-trifluoromethyl-1,2-phenylenediamine there was prepared 5-trifluoromethyl-1H-benzoimidazole.

(c) By proceeding in a similar manner to Reference Example 5(a) above but using 4-fluoro-o-phenylenediamine there was prepared 5-fluoro-1H-benzoimidazole.

(d) By proceeding in a similar manner to Reference Example 5(a) above but using 2,3-diaminotoluene there was prepared 4-methyl-1H-benzoimidazole.

REFERENCE EXAMPLE 6

(a) 1-(5-Methoxy-1H-benzoimidazol-2-yl)-ethanone

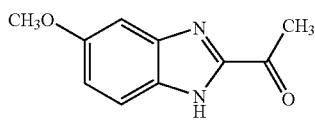

A stirred mixture of 1-(5-methoxy-1-benzoimidazole)-1-ethanol [5.14 g, Reference Example 7(a)] and manganese dioxide (9 g) in chloroform (80 mL) was heated at 60° C. for 18 hours, then cooled to room temperature and then filtered. The filtrate was evaporated to give 1-(5-methoxy-1H-benzoimidazol-2-yl)-ethanone (4.28 g).

(b) 1-(5-Methoxy-1H-benzoimidazol-2-yl)-propan-1-one

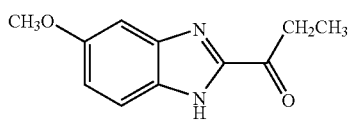

By proceeding in a similar manner to Reference Example 6(a) above but using 1-(5-methoxy-1-benzoimidazole)-1-propanol [Reference Example 7(b)] there was prepared 1-(5-methoxy-1H-benzoimidazol-2-yl)-propan-1-one.

(c) 5-Fluoro-1H-indazole-3-carbaldehyde

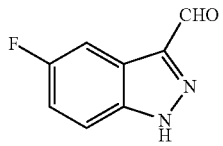

By proceeding in a similar manner to Reference Example 6(a) above but using (5-fluoro-1H-indazol-3-yl)-methanol [Reference Example 25(a)] with acetone as the solvent, a reaction temperature of 55° C. and subjecting the reaction product to flash column chromatography on silica eluting with a mixture of 40/60 petrol and ethyl acetate (1:1 v/v) there was prepared 5-fluoro-1H-indazole-3-carbaldehyde as a light brown solid. LC-MS (METHOD B): $R_T$=2.74 minutes, 165 (M+H)$^+$.

(d) 6-Fluoro-1H-indazole-3-carbaldehyde

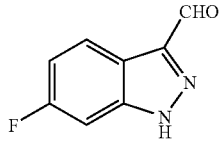

By proceeding in a similar manner to Reference Example 6(a) above but using (6-fluoro-1H-indazol-3-yl)-methanol [Reference Example 25(b)] with acetone as the solvent, a reaction temperature of 55° C. and subjecting the reaction product to flash column chromatography on silica eluting with a mixture of 40/60 petrol and ethyl acetate (1:1 v/v) there was prepared 6-fluoro-1H-indazole-3-carbaldehyde as a light brown solid. LC-MS (METHOD B): $R_T$=2.74 minutes, 165 (M+H)$^+$.

(e) 5-Methyl-1H-indazole-3-carbaldehyde

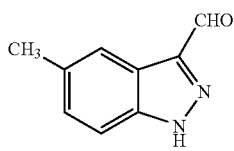

By proceeding in a manner similar to Reference Example 6(a) above but using (5-methyl-1H-indazol-3-yl)-methanol [Reference Example 25(c)] with dichloromethane as solvent, a reaction temperature of 40° C. and subjecting the reaction product to flash column chromatography on silica eluting with a mixture of hexane and ethyl acetate (1:1, v/v) there was prepared 5-methyl-1H-indazole-3-carbaldehyde as a pale brown solid. LC-MS (METHOD B): $R_T$=2.79 minutes, 161 (M+H)$^+$.

(f) 6-Methoxy-1H-indazole-3-carbaldehyde

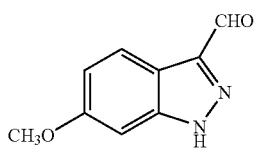

By proceeding in a manner similar to Reference Example 6(a) above but using (6-methoxy-1H-indazol-3-yl)-methanol [Reference Example 25(e)] with acetone as the solvent, a reaction temperature of 55° C. and subjecting the reaction product to flash column chromatography on silica eluting with a mixture of 40/60 petrol and ethyl acetate (1:1 v/v) there was prepared 6-methoxy-1H-indazole-3-carbaldehyde as a light brown solid. LC-MS (METHOD B): $R_T$=2.76 minutes, 177 (M+H)$^+$.

(g) 4-Phenyl-1H-pyrazole-3-carbaldehyde

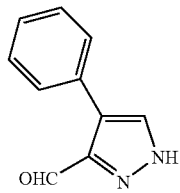

By proceeding in a similar manner to Reference Example 6(a) above but using (4-phenyl-1H-pyrazol-3-yl)-methanol [Reference Example 25(f)] with acetone as the solvent, a reaction temperature of 60° C. for 2 hours, and subjecting the reaction product to flash column chromatography on silica eluting with a mixture of dichloromethane and methanol (49:1, v/v) there was prepared 4-phenyl-1H-pyrazole-3-carbaldehyde as a white solid. LC-MS (METHOD B): $R_T$ 2.76 minutes; 213 (M+H)$^+$.

(h) 5-Chloro-1H-indazole-3-carbaldehyde

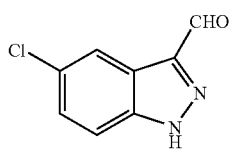

By proceeding in a similar manner to Reference Example 6(a) above but using (5-chloro-1H-indazol-3-yl)-methanol [Reference Example 25(d)] with a mixture of dichloromethane and tetrahydrofuran as solvent, heating at reflux temperature and subjecting the reaction product to flash column chromatography on silica eluting with a mixture of hexane and ethyl acetate (1:1, v/v) there was prepared 5-chloro-1H-indazole-3-carbaldehyde as a pale brown solid. LC-MS (METHOD B): $R_T$=2.89 minutes, 181 $(M+H)^+$.

(i) 3-Formyl-pyrazole-4-carboxylic acid ethyl ester

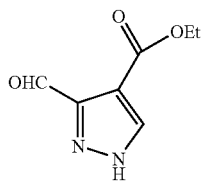

By proceeding in a manner similar to Reference Example 6(a) above but using 3-hydroxymethyl-1H-pyrazole-4-carboxylic acid ethyl ester [Reference Example 41 (a)] there was prepared 3-formyl-pyrazole-4-carboxylic acid ethyl ester as a brown solid. LC-MS (METHOD B): $R_T$=2.65 minutes; 169 $(M+H)^+$.

(j) 3-Formyl-pyrazole-4-carboxylic acid isopropylamide

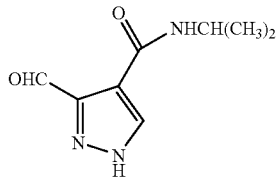

By proceeding in a manner similar to Reference Example 6(a) above but using 3-hydroxymethyl-1H-pyrazole-4-carboxylic acid isopropylamide [Reference Example 41(b)] there was prepared 3-formyl-pyrazole-4-carboxylic acid isopropylamide as a waxy orange solid. LC-MS (METHOD B): $R_T$=2.73 minutes; 182 $(M+H)^+$.

(k) 3-Formyl-5-methyl-pyrazole-4-carboxylic acid ethyl ester

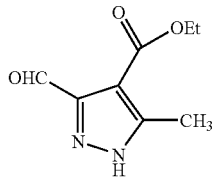

By proceeding in a manner similar to Reference Example 6(a) above but using 3-hydroxymethyl-5-methyl-1H-pyrazole-4-carboxylic acid ethyl ester [Reference Example 41(c)] there was prepared 3-formyl-5-methyl-pyrazole-4-carboxylic acid ethyl ester as a white solid. LC-MS (METHOD B): $R_T$=2.80 minutes; 183 $(M+H)^+$.

(l) 1H-indazole-3-carbaldehyde

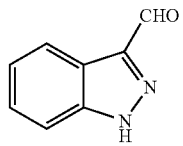

By proceeding in a manner similar to Reference Example 6(a) above but using (1H-indazol-3-yl)-methanol [Reference Example 25(g)] with acetone as the solvent and carrying out the reaction at reflux temperature for 16 hours there was prepared 1H-indazole-3-carbaldehyde as a yellow solid. LC-MS [METHOD B]; $R_T$=2.63 minutes; 147.26 $(M+H)^+$; 145.26 $(M-H)^-$.

(m) 4-Nitro-1-(tetrahydro-pyran-2-yl)-1H-pyrazole-3-carbaldehyde

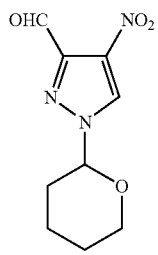

By proceeding in a manner similar to Reference Example 6(a) above but (i) using [4-nitro-1-(tetrahydro-pyran-2-yl)-1H-pyrazol-3-yl]-methanol (663 mg, Reference Example 53) and manganese (IV) oxide (2.54 g) with acetone as the solvent, (ii) carrying out the reaction at 65° C. for 2 hours and (iii) subjecting the reaction product to flash silica chromatography eluting with a mixture of pentane and ethyl acetate (70:30, v/v), there was prepared 4-nitro-1-(tetrahydro-pyran-2-yl)-1H-pyrazole-3-carbaldehyde (191 mg) as a pale yellow oil. LC-MS (Method H): $R_T$=2.19 minutes, 248.24 $(M+H+Na)^+$.

(n) 3-Formyl-1H-pyrazole-4-carboxylic acid (2-methoxy-ethyl)-amide

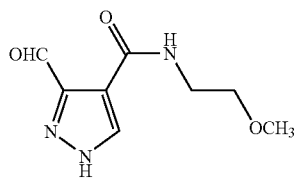

By proceeding in a manner similar to Reference Example 6(a) above but using 3-hydroxymethyl-1H-pyrazole-4-carboxylic acid (2-methoxy-ethyl)-amide [Reference Example 41 (d)] there was prepared 3-formyl-1H-pyrazole-4-carboxylic acid (2-methoxy-ethyl)-amide (325 mg) as a yellow oil. LC-MS (METHOD B): $R_T$=2.13 minutes, 198 (M+H)⁺.

(o) 3-Formyl-1H-pyrazole-4-carboxylic acid propylamide

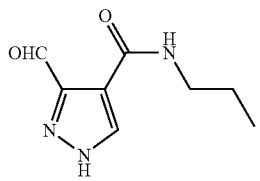

By proceeding in a manner similar to Reference Example 6(a) above but using 3-hydroxymethyl-1H-pyrazole-4-carboxylic acid propylamide [Reference Example 41(e)] there was prepared 3-formyl-1H-pyrazole-4-carboxylic acid propylamide (414 mg) as an orange oil. LC-MS (METHOD B): $R_T$=2.42 minutes, 182 (M+H)⁺.

(p) 3-Formyl-1H-pyrazole-4-carboxylic acid (tetrahydro-pyran-4-yl)-amide

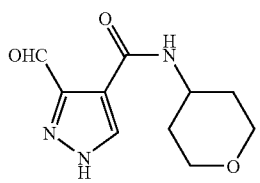

By proceeding in a manner similar to Reference Example 6(a) above but using 3-hydroxymethyl-1H-pyrazole-4-carboxylic acid (tetrahydro-pyran-4-yl)-amide [Reference Example 41(f)] there was prepared 3-formyl-1H-pyrazole-4-carboxylic acid (tetrahydro-pyran-4-yl)-amide (400 mg) as a brown oil. LC-MS (METHOD N): $R_T$=2.34 minutes, 224.31 (M+H)⁺.

(q) 3-Formyl-1H-pyrazole-4-carboxylic acid cyclopropylamide

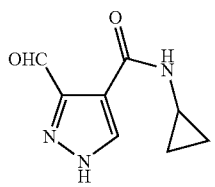

By proceeding in a manner similar to Reference Example 6(a) above but using 3-hydroxymethyl-1H-pyrazole-4-carboxylic acid cyclopropylamide [Reference Example 41(f)] there was prepared 3-formyl-1H-pyrazole-4-carboxylic acid cyclopropylamide (125 mg) as a yellow oil. LC-MS (METHOD H): $R_T$=1.87 minutes, 178.31 (M−H)⁻.

REFERENCE EXAMPLE 7

(a) 1-(5-Methoxy-1H-benzoimidazol-2-yl)-ethanol

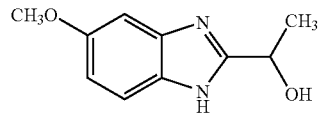

A mixture of 4-methoxy-phenylenediamine dihydrochloride (10 g), sodium L-lactate (10 g) and hydrochloric acid (60 mL, 4M) was heated at 70° C. for 48 hours. The reaction mixture was cooled to room temperature, then treated with ammonium hydroxide. The resulting precipitate was filtered and dried to give 1-(5-methoxy-1H-benzoimidazol-2-yl)-ethanol (5.14 g).

(b) 1-(5-Methoxy-1-benzoimidazole)-1-propanol

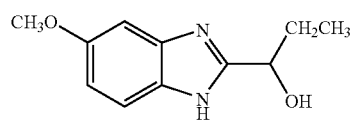

By proceeding in a similar manner to Reference Example 7(a) above but using 2-hydroxybutyric acid there was prepared 1-(5-methoxy-1-benzoimidazole)-1-propanol.

REFERENCE EXAMPLE 8

(a) Dimethylvaleramide

A solution of dimethylamine hydrochloride (6.76 g) and triethylamine (30 mL) in dichloromethane (100 mL), under nitrogen and at 0° C. was treated dropwise with valeryl chloride (10 g). After stirring at room temperature overnight the reaction mixture was treated with hydrochloric acid (2N) and dichloromethane. The organic phase was separated, dried over magnesium sulfate and then evaporated to give dimethylvaleramide as a clear oil.

(b) By proceeding in a similar manner to Reference Example 8(a) above but using isovaleryl chloride there was prepared dimethylisovalerylamide.

REFERENCE EXAMPLE 9

2,3-Diaminopyrazine

Liquid ammonia (50 mL) was introduced into a pressure reaction vessel containing a small lump of ice. To this was added copper bronze (1.17 g), copper (II) iodide (0.224 g) and 2,3-dichloropyrazine (4 g). The sealed reaction vessel was heated at 170° C. for 48 hours, then cooled to ambient temperature and then vented. The reaction mixture was treated with water (75 mL) and this mixture was extracted four times with diethyl ether (400 mL). The combined extracts were evaporated to give 2,3-diaminopyrazine as a white solid (0.3 g). The aqueous layer was continuously extracted with diethyl ether for 18 hours to yield a further quantity of 2,3-diaminopyrazine (1.24 g). ¹H-NMR [(CD₃)₂SO]: δ 5.87 (s, 4H), 7.15 (s, 2H).

REFERENCE EXAMPLE 10

1H-Pyrazole-3-carbaldehyde (i) Dry dimethylformamide (77.6 mL) was stirred at 80° C. while cyanuric chloride (26.6 g) was added in portions, whilst keeping the reaction temperature between 80 and 110° C. The reaction mixture was stirred at 100° C. for another 30 minutes then cooled and then allowed to stand at room temperature overnight. The reaction mixture was filtered to give dimethylvinylamine.

(ii) The dimethylvinylamine from (i) was added to dry methanol (260 mL) and the mixture was then treated with pyruvic aldehyde dimethylacetal (51 mL), followed by a solution of sodium methoxide in methanol (30%, 81 mL), then stirred for 2 hours at ambient temperature, then heated at reflux temperature for another hour, then cooled and then filtered. The filtrate was evaporated to give 1,1-dimethoxy-but-3-en-2-one as a brown oil (96.8 g).

(iii) A stirred solution of 1,1-dimethoxy-but-3-en-2-one in water (300 µL) was treated dropwise with hydrazine hydrate (21 mL). After standing at room temperature overnight the reaction mixture was treated with sodium chloride (108 g) and the mixture was then extracted with methyl-t-butylether (200 mL then 100 mL). The combined extracts were dried with magnesium sulfate and then evaporated to give 1H-pyrazol-3-carbaldehyde dimethyl acetal as a light brown oil (18.47 g).

(iv) A solution of 1H-pyrazol-3-carbaldehyde dimethyl acetal in water (85 mL) was treated with glacial acetic acid (3.7 mL). After two days the mixture was filtered to give 1H-pyrazole-3-carbaldehyde (1.3 g) as a light brown solid.

REFERENCE EXAMPLE 11

2-(5-Ethoxy-1H-pyrazol-3-yl)-1-(2-trimethylsilanyl-ethoxymethyl)-1H-benzoimidazole

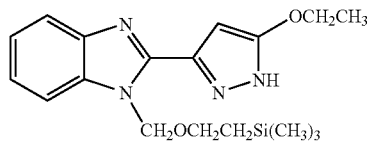

Sodium hydride (0.1 g) was added to ethanol (5 mL) and the mixture was stirred for ten minutes, then treated with 3,3-bis-methanesulfanyl-1-[1-(2-trimethylsilanyl-ethoxymethyl)-1H-benzoimidazol-2-yl]-propenone [0.5 g, Reference Example 2(p)] and then heated at reflux temperature for six hours. The reaction mixture was cooled, then treated with hydrazine hydrate (1.27 mmol) and then heated at reflux temperature for four hours. The mixture was then evaporated and the residue was triturated with water and filtered. The solid was subjected to chromatography on silica gel eluting with ethyl acetate to give 2-(5-ethoxy-1H-pyrazol-3-yl)-1-(2-trimethylsilanyl-ethoxymethyl)-1H-benzoimidazole as a yellow oil.

REFERENCE EXAMPLE 12

2-(5-Methylsulfanyl-isoxazol-3-yl)-1-(trimethylsilanyl-ethoxymethyl)-1H-benzoimidazole

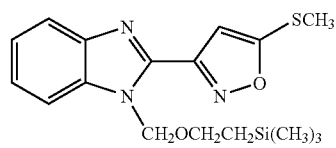

Hydroxylamine hydrochloride (168 mg) was added to a solution of sodium methoxide in methanol [prepared by the addition of sodium hydride (122 mg) to methanol (5 mL)]. The mixture was stirred for ten minutes, then treated with 3,3-bis-methanesulfanyl-1-[1-(2-trimethylsilanyl-ethoxymethyl)-1H-benzoimidazol-2-yl]-propenone [500 mg, Reference Example 2(p)], then heated at reflux for six hours, then cooled and then evaporated. The residue was taken up in water and the aqueous mixture was extracted with ethyl acetate. The extracts were dried and evaporated. The residue was subjected to chromatography on silica eluting with methylene chloride to give 2-(5-methylsulfanyl-isoxazol-3-yl)-1-(trimethylsilanyl-ethoxymethyl)-1H-benzoimidazole (0.16 g) as a colourless oil.

REFERENCE EXAMPLE 13

1-[6-Chloro-5-methyl-1-(2-trimethylsilanyl-ethoxymethyl)-1H-benzoimidazol-2-yl]-3-methylsulfanyl-3-morpholin-1-yl-propenone

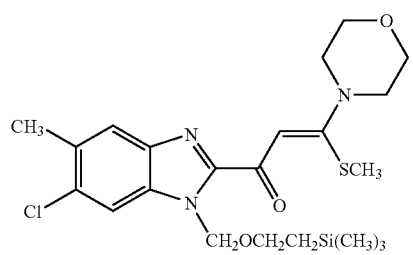

A solution of 1-[6-chloro-5-methyl-1-(2-trimethylsilanyl-ethoxymethyl)-1H-benzoimidazol-2-yl]-3,3-bis-methanesulfanyl-propenone [800 mg, Reference Example 2(q)] in morpholine (3 mL) was heated at 95° C. for 2 hours and then evaporated to give 1-[6-chloro-5-methyl-1-(2-trimethylsilanyl-ethoxymethyl)-1H-benzoimidazol-2-yl]-3-methylsulfanyl-3-morpholin-1-yl-propenone.

REFERENCE EXAMPLE 14

2-Chloromethyl-thiophene

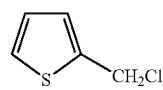

To a three-necked flask fitted with stirrer bar, pressure equalizing dropping funnel and inlet/outlet adapter was added thiophene (10 mL) and aqueous hydrochloric acid (5.5 mL). Hydrogen chloride gas [generated by dropping sulfuric acid (30 mL) onto dry sodium chloride (50 g)] was bubbled through the reaction mixture with vigorous stirring at 0° C. This mixture was then treated dropwise with formaldehyde solution (37%, 12.5 mL) and stirring was continued for 45 minutes. The phases were separated and the aqueous phase was extracted three times with diethyl ether (10 mL). The organic phases were then washed twice with water (10 mL), then twice with saturated sodium hydrogen carbonate (10 mL), then dried over magnesium sulfate and then evaporated. The residue was distilled at 20 mmHg using a heat gun to give 2-chloromethyl-thiophene which was used immediately without further purification.

REFERENCE EXAMPLE 15

Bis(methylthio)-3,3-(benzoimidazol-2-yl)-1-prop-2-en-2-one

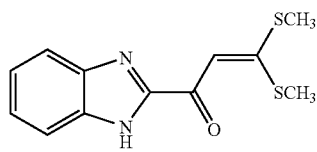

A mixture of sodium hydride (19.2 g) and toluene (400 mL), at 80° C., was treated portionwise with tertiary-butanol (30.8 g). After 2 hours the reaction mixture was cooled to room temperature and treated dropwise with a mixture of dimethylformamide (40 mL), carbon disulfide (12 mL) and 2-acetyl-1-(tetrahydropyran-2-yl)-benzoimidazole (51 g, Reference Example 16) over 90 minutes. After addition the red reaction mixture was stirred at 80° C. for 30 minutes, then cooled to room temperature and then treated with methyl iodide (50 mL). This mixture was stirred at 80° C. for 30 minutes when a precipitate started to form. The reaction mixture was cooled to room temperature and then filtered. The filtrate was concentrated to give a viscous red oil, which was dissolved in methanol (300 mL). This solution was treated with p-toluenesulfonic acid (2 g) and water (4 mL), then heated at reflux temperature for 13 hours and then cooled in an ice-bath. The resulting solid was filtered and then washed with isopropyl ether to give bis(methylthio)-3,3-(benzoimidazol-2-yl)-1-prop-2-en-2-one (11.2 g), m.p. 224° C.

REFERENCE EXAMPLE 16

2-Acetyl-1-(tetrahydropyran-2-yl)-benzoimidazole

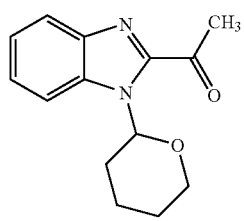

Dihydropyran (20.5 mL) as added dropwise to a solution of 2-acetylbenzoimidazole (32 g) and p-toluenesulfonic acid (2 g) in dichloromethane (280 mL) at reflux. The reaction mixture was stirred at this temperature for 24 hours, then cooled and the insoluble materials were filtered off. The filtrate was concentrated to give 2-acetyl-1-(tetrahydropyran-2-yl)-benzoimidazole as an amber oil (51.8 g). TLC: (dichloromethane:methanol, 97:3) $R_F$=0.80.

REFERENCE EXAMPLE 17

(a) 4,5,6,7-Tetrahydro-1H-indazole-3-carboxylic acid

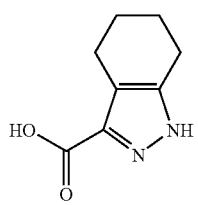

A solution of 4,5,6,7-tetrahydro-1H-indazole-3-carboxylic acid ethyl ester [0.606 g, Reference Example 18(a)] in methanol (50 ml) was treated with sodium hydroxide (0.500 g). The mixture was refluxed for 16 hours, then cooled and then evaporated. The residual white solid was treated with hydrochloric acid (30 ml, 2N) and the resulting solution was extracted three times with ethyl acetate (50 ml). The combined organic extracts were dried over sodium sulfate and then evaporated to yield 4,5,6,7-tetrahydro-1H-indazole-3-carboxylic acid (0.424 g) as a white solid. LC-MS (METHOD B): $R_T$=2.44 minutes; 167 (M+H)$^+$.

(b) 5-Isopropyl-1H-pyrazole-3-carboxylic acid

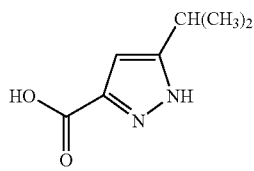

By proceeding to a manner similar to Example 17(a) above but using 5-isopropyl-1H-pyrazole-3-carboxylic acid ethyl ester [Reference Example 18(b)], there was prepared 5-isopropyl-1H-pyrazole-3-carboxylic acid as a white solid (0.973 g) which was used without further purification.
LC-MS (METHOD B): $R_T$=2.43 minutes; 155 (M+H)$^+$.

(c) 5-Ethyl-1H-pyrazole-3-carboxylic acid

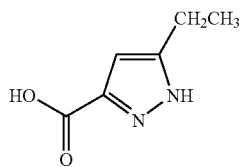

By proceeding in a manner similar to Reference Example 17(a) above, but using 5-ethyl-1H-pyrazole-3-carboxylic acid ethyl ester [Reference Example 18(c)], there was prepared 5-ethyl-1H-pyrazole-3-carboxylic acid as a white solid. LC-MS (METHOD B): $R_T$=2.34 minutes; 141 (M+H)$^+$.

(d) 3-tert-Butyloxymethyl-1H-pyrazole-4-carboxylic acid

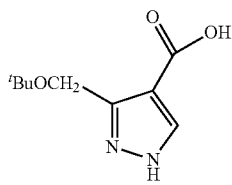

By proceeding in a manner similar to Reference Example 17(a) above, but using 3-tert-butyloxymethyl-1H-pyrazole-4-carboxylic acid ethyl ester [Reference Example 42], there was prepared 3-tert-butyloxymethyl-1H-pyrazole-4-carboxylic acid as a white solid which was used without further purification. LC-MS (METHOD B): $R_T$=2.75 minutes; 199 (M+H)$^+$.

(e) 1,4,6,7-Tetrahydro-pyrano[4,3-c]pyrazole-3-carboxylic acid

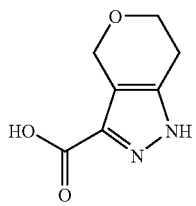

By proceeding in a manner similar to Reference Example 17(a) above but using 1,4,6,7-tetrahydro-pyrano[4,3-c]pyrazole-3-carboxylic acid ethyl ester [Reference Example 18(e)] there was prepared 1,4,6,7-tetrahydro-pyrano[4,3-c]pyrazole-3-carboxylic acid (261 mg) as a white solid. LC-MS (METHOD B): $R_T$ 1.98 minutes, 169 (M+H)$^+$.

(f) 1,4,5,6-Tetrahydro-cyclopentapyrazole-3-carboxylic acid

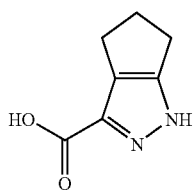

By proceeding in a manner similar to Reference Example 17(a) above but using 1,4,5,6-tetrahydro-cyclopentapyrazole-3-carboxylic acid ethyl ester [Reference Example 18(f)] there was prepared 1,4,5,6-tetrahydro-cyclopentapyrazole-3-carboxylic acid (0.641 g) as a white solid. LC-MS (METHOD B): $R_T$=2.13 minutes, 153.22 (M+H)$^+$.

REFERENCE EXAMPLE 18

(a) 4,5,6,7-Tetrahydro-1H-indazole-3-carboxylic acid ethyl ester

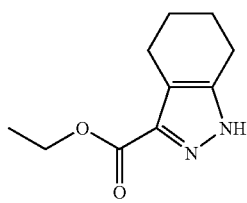

A solution of oxo-(2-oxo-cyclohexyl)-acetic acid ethyl ester [7.5 g, Reference Example 19(a)] in acetic acid (150 ml) was treated dropwise with hydrazine monohydrate (1.65 ml). The mixture was refluxed for 8 hours, then cooled and then evaporated. The residue was partitioned between ethyl acetate (200 ml) and saturated sodium bicarbonate solution (200 ml) and the organic layer was dried over sodium sulfate and then evaporated. The residual orange oil was subjected to flash column chromatography on silica eluting with a mixture of ethyl acetate and hexane (1:1, v/v) to give 4,5,6,7-tetrahydro-1H-indazole-3-carboxylic acid ethyl ester (606 mg) as an orange oil which solidified on standing. LC-MS (METHOD B): $R_T$=2.79 minutes; 195 (M+H)$^+$.

(b) 5-Isopropyl-1H-pyrazole-3-carboxylic acid ethyl ester

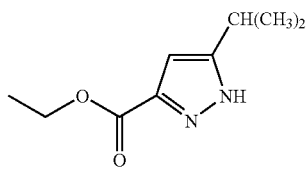

By proceeding to a manner similar to Reference Example 18(a) above but using 5-methyl-2,4-dioxo-hexanoic acid ethyl ester [2.00 g, Reference Example 19(b)] there was prepared 5-isopropyl-1H-pyrazole-3-carboxylic acid ethyl ester as a light yellow oil which was used without further purification. LC-MS (METHOD B): $R_T$=2.79 minutes; 183 (M+H)$^+$.

(c) 5-Ethyl-1H-pyrazole-3-carboxylic acid ethyl ester

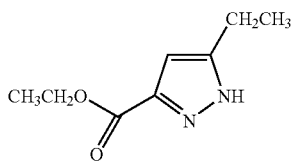

By proceeding in a manner similar to Reference Example 18(a) above, but using 2,4-dioxo-hexanoic acid ethyl ester [Reference Example 19(c)], and subjecting the reaction product, an orange oil, to flash chromatography on silica eluting with a mixture of ethyl acetate and hexane (8:1, v/v), there was prepared 5-ethyl-1H-pyrazole-3-carboxylic acid ethyl ester as a yellow oil. LC-MS (METHOD B): $R_T$=2.64 minutes; 169 $(M+H)^+$.

(d) 1,4,6,7-Tetrahydro-pyrazolo[4,3-c]pyridine-3,5-dicarboxylic acid 5-tert-butyl ester 3-ethyl ester

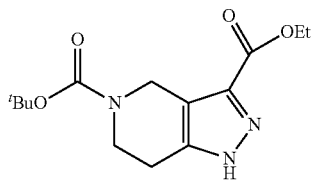

By proceeding in a manner similar to Reference Example 18(a) above, but using 3-ethoxyoxalyl-4-oxo-piperidine-1-carboxylic acid tert-butyl ester [Reference Example 19(d)], there was prepared 1,4,6,7-tetrahydro-pyrazolo[4,3-c]pyridine-3,5-dicarboxylic acid 5-tert-butyl ester 3-ethyl ester as a yellow oil. LC-MS (METHOD B): $R_T$=2.73 minutes; 296 $(M+H)^+$.

(e) 1,4,6,7-Tetrahydro-pyrano[4,3-c]pyrazole-3-carboxylic acid ethyl ester

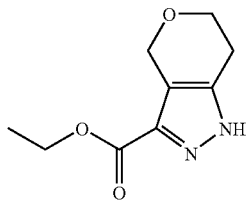

By proceeding in a manner similar to Reference Example 18(a) above but using tetrahydro-4H-pyran-4-one there was prepared 1,4,6,7-tetrahydro-pyrano[4,3-c]pyrazole-3-carboxylic acid ethyl ester (385 mg) as a white solid. LC-MS (METHOD B): $R_T$=2.43 minutes, 197 $(M+H)^+$.

(f) 1,4,5,6-Tetrahydro-cyclopentapyrazole-3-carboxylic acid ethyl ester

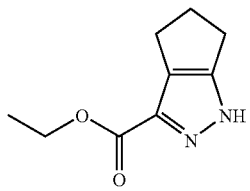

By proceeding in a manner similar to Reference Example 18(a) above but using oxo-(2-oxo-cyclopentyl)-acetic acid ethyl ester [Reference Example 19(e)] there was prepared 1,4,5,6-tetrahydro-cyclopentapyrazole-3-carboxylic acid ethyl ester (2.06 g) as a yellow solid. LC-MS (METHOD B): $R_T$=2.56 minutes, 185 $(M+H)^+$.

REFERENCE EXAMPLE 19

(a) Oxo-(2-oxo-cyclohexyl-acetic acid ethyl ester

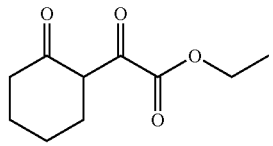

A solution of sodium (1.75 g) in ethanol (100 ml) was treated with a mixture of diethyl oxalate (9.41 ml) and cyclohexanone (7.18 ml). The mixture was heated to 60° C. for 5 hours then cooled and then evaporated to yield oxo-(2-oxo-cyclohexyl)-acetic acid ethyl ester as a brown foam (16.635 g). LC-MS (METHOD B): $R_T$ 3.10 minutes; 197 $(M-H)^-$.

(b) 5-Methyl-2,4-dioxo-hexanoic acid ethyl ester

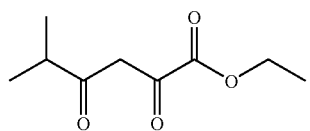

By proceeding to a manner similar to Example 19(a) above but using 3-methyl-2-butanone there was prepared 5-methyl-2,4-dioxo-hexanoic acid ethyl ester as a white solid. LC-MS (METHOD B): $R_T$=3.47 minutes; 187 $(M+H)^+$.

(c) 2,4-Dioxo-hexanoic acid ethyl ester

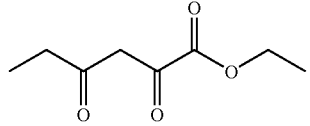

By proceeding in a manner similar to Reference Example 19(a) above, but using 2-butanone, there was prepared 2,4-dioxo-hexanoic acid ethyl ester as a brown oil which was used without further purification. LC-MS (METHOD B): $R_T$=3.28 minutes; 173 $(M+H)^+$.

(d) 3-Ethoxyoxalyl-4-oxo-piperidine-1-carboxylic acid tert-butyl ester

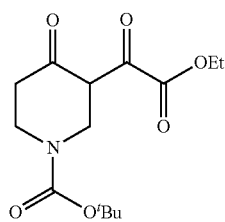

By proceeding in a manner similar to Reference Example 19(a) above, but using N-Boc piperidone, there was prepared 3-ethoxyoxalyl-4-oxo-piperidine-1-carboxylic acid tert-butyl ester as a brown oil which was used without further purification. LC-MS (METHOD B): $R_T$=3.43 minutes; 244 (M–tBu)$^+$.

(e) Oxo-(2-oxo-cyclopentyl)-acetic acid ethyl ester

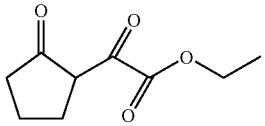

By proceeding in a manner similar to Reference Example 19(a) above but using cyclopentanone there was prepared oxo-(2-oxo-cyclopentyl)-acetic acid ethyl ester (9.99 g) as a yellow solid. LC-MS (METHOD B): $R_T$=3.12 minutes, 185 (M+H)$^+$.

REFERENCE EXAMPLE 20

(a) 3-Formyl-5-methoxy-indazole-1-carboxylic acid tert-butyl ester

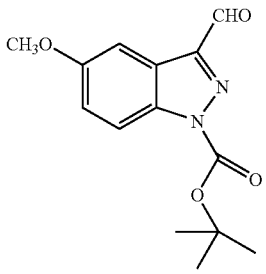

A solution of 5-methoxy-3-(2-methoxycarbonyl-vinyl)-indazole-1-carboxylic acid tert-butyl ester [282 mg, Reference Example 21(a)] in tetrahydrofuran (4 ml) and water (1.5 ml) was treated with a solution of osmium tetroxide in water (54 µL, 4 wt %) and sodium periodate (400 mg). The reaction mixture was stirred at ambient temperature for 16 hours and then filtered. The filtrate was evaporated and the residue was partitioned between ethyl acetate and water. The organic layer was dried over magnesium sulfate and then evaporated. The residue was subjected to flash column chromatography on silica eluting with a mixture of ethyl acetate and petrol (1:9, v/v) to yield 3-formyl-5-methoxy-indazole-1-carboxylic acid tert-butyl ester (162 mg) as a white solid. LC-MS (METHOD B): $R_T$=2.97 minutes; 277 (M+H)$^+$.

(b) 4-Fluoro-1H-indazole-3-carbaldehyde

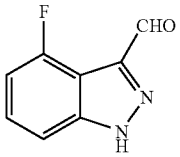

By proceeding in a manner similar to Reference Example 20(a) but using 4-fluoro-3-(2-methoxycarbonyl-vinyl)-indazole-1-carboxylic acid tert-butyl ester [Reference Example 21(b)] there was prepared 4-fluoro-1H-indazole-3-carbaldehyde as a light brown solid. LC-MS (METHOD B): $R_T$=2.63 minutes; 165 (M+H)$^+$.

(c) 4-Chloro-3-formyl-indazole-1-carboxylic acid tert-butyl ester

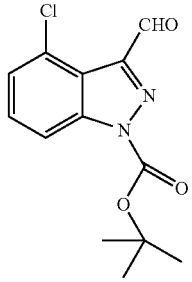

By proceeding in a manner similar to Reference Example 20(a) but using 4-chloro-3-(2-methoxycarbonyl-vinyl)-indazole-1-carboxylic acid tert-butyl ester [Reference Example 21(c)] there was prepared 4-chloro-3-formyl-indazole-1-carboxylic acid tert-butyl ester (0.217 g) as a brown oil. LC-MS (METHOD B): $R_T$=3.49 minutes; 283 (M+H)$^+$.

(d) 5-Ethoxy-3-formyl-indazole-1-carboxylic acid tert-butyl ester

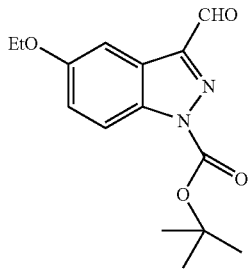

By proceeding in a manner similar to Reference Example 20(a) but using 5-ethoxy-3-(2-methoxycarbonyl-vinyl)-indazole-1-carboxylic acid tert-butyl ester [Reference Example 21(d)] there was prepared 5-ethoxy-3-formyl-indazole-1-carboxylic acid tert-butyl ester as a brown oil. TLC (ethyl acetate:hexane, 1:9, v/v): $R_F$=0.25. $^1$HNMR (400 MHz, CDCl$_3$): δ 1.38 (3H, t), 1.67 (9H, s), 4.05 (2H, q), 7.12 (1H, d), 7.60 (1H, s), 7.98 (1H, d), 10.20 (1H, s).

REFERENCE EXAMPLE 21

(a) 5-Methoxy-3-(2-methoxycarbonyl-vinyl)-indazole-1-carboxylic acid tert-butyl ester

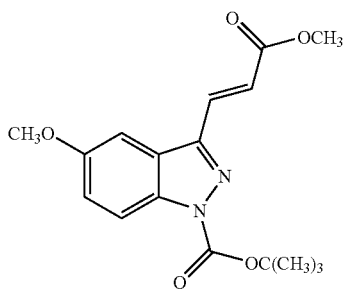

A solution of 3-iodo-5-methoxy-indazole-1-carboxylic acid tert-butyl ester [0.500 g, Reference Example 22(a)] in dioxane (15 ml) and under an atmosphere of nitrogen was treated with triethylamine (1.86 ml) followed by methyl acrylate (1.20 ml), triphenylphosphine (0.105 g), and palladium (II) acetate (60 mg). The resulting mixture was heated at 50° C. for 16 hours, then cooled to ambient temperature and then evaporated. The residue was partitioned between ethyl acetate and water. The organic layer was washed with brine, then dried over magnesium sulfate and then evaporated. The residue was subjected to flash column chromatography on silica eluting with a mixture of ethyl acetate and 40/60 petrol (1:9, v/v) to yield 5-methoxy-3-(2-methoxycarbonyl-vinyl)-indazole-1-carboxylic acid tert-butyl ester (282 mg). LC-MS (METHOD B): $R_T$=3.33 minutes; 333 $(M+H)^+$.

(b) By proceeding in a manner similar to Reference Example 21(a) but using 4-fluoro-3-iodo-indazole-1-carboxylic acid tert-butyl ester [Reference Example 22(b)] there was prepared 4-fluoro-3-(2-methoxycarbonyl-vinyl)-indazole-1-carboxylic acid tert-butyl ester as a light brown solid.

LC-MS (METHOD B): $R_T$=3.39 minutes; 321 $(M+H)^+$.

(c) By proceeding in a manner similar to Reference Example 21 (a) but using 4-chloro-3-iodo-indazole-1-carboxylic acid tert-butyl ester [Reference Example 22(c)] there was prepared 4-chloro-3-(2-methoxycarbonyl-vinyl)-indazole-1-carboxylic acid tert-butyl ester as a brown solid.

LC-MS (METHOD B): $R_T$=3.48 minutes; 339 $(M+H)^+$.

(d) By proceeding in a manner similar to Reference Example 21(a) but using 5-ethoxy-3-iodo-indazole-1-carboxylic acid tert-butyl ester [Reference Example 22(d)] there was prepared 5-ethoxy-3-(2-methoxycarbonyl-vinyl)-indazole-1-carboxylic acid tert-butyl ester as an off-white solid. LC-MS (METHOD B): $R_T$=3.41 minutes; 347 $(M+H)^+$.

REFERENCE EXAMPLE 22

(a) 3-Iodo-5-methoxy-indazole-1-carboxylic acid tert-butyl ester

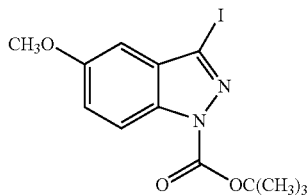

A solution of 3-iodo-5-methoxy-1H-indazole [1.48 g, Reference Example 23(a)] in acetonitrile (6 ml) was treated with triethylamine (0.98 ml) and N,N-dimethylaminopyridine (0.132 g). The mixture was cooled to 0° C. then treated with a solution of di-tert-butyl dicarbonate (1.41 g) in acetonitrile (6 ml). After stirring for 1 hour at ambient temperature the reaction mixture was evaporated and the residue was partitioned between ethyl acetate and water. The pH was adjusted to 2 and the organic layer was dried over magnesium sulfate and then evaporated. The residual orange oil was subjected to flash column chromatography on silica eluting with a mixture of ethyl acetate and petrol (1:4, v/v) to yield 3-iodo-5-methoxy-indazole-1-carboxylic acid tert-butyl ester (1.72 g) as a yellow solid.

LC-MS (METHOD B): $R_T$=3.45 minutes; 375 $(M+H)^+$.

(b) 4-Fluoro-3-iodo-indazole-1-carboxylic acid tert-butyl ester

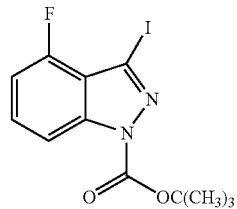

By proceeding in a manner similar to Reference Example 22(a) above but using 4-fluoro-3-iodo-1H-indazole [Reference Example 23(b)] there was prepared 4-fluoro-3-iodo-indazole-1-carboxylic acid tert-butyl ester as a light brown solid. LC-MS (METHOD B): $R_T$=3.48 minutes; 363 $(M+H)^+$.

(c) 4-Chloro-3-iodo-indazole-1-carboxylic acid tert-butyl ester

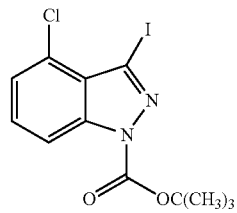

By proceeding in a manner similar to Reference Example 22(a) above but using 4-chloro-3-iodo-1H-indazole [Reference Example 23(c)] there was prepared 4-chloro-3-iodo-indazole-1-carboxylic acid tert-butyl ester as a brown solid. LC-MS (METHOD B): $R_T$=3.39 minutes; 381 $(M+H)^+$.

(d) 5-Ethoxy-3-iodo-indazole-1-carboxylic acid tert-butyl ester

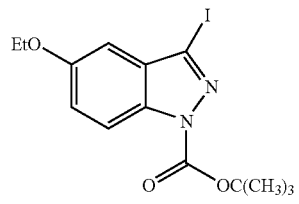

By proceeding in a manner similar to Reference Example 22(a) above but using 5-ethoxy-3-iodo-1H-indazole [Reference Example 23(d)] there was prepared 5-ethoxy-3-iodo-indazole-1-carboxylic acid tert-butyl ester as an off-white solid. LC-MS (METHOD B): $R_T$=3.49 minutes; 389 $(M+H)^+$.

REFERENCE EXAMPLE 23

(a) 3-Iodo-5-methoxy-1H-indazole

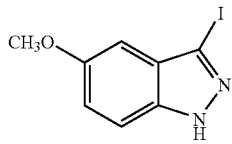

A solution of 5-methoxy-1H-indazole [0.815 g, Reference Example 24(a)] in dimethyl formamide (8 ml) was treated with iodine (2.80 g) and potassium hydroxide (1.16 g). The mixture was stirred at ambient temperature for 1 hour then poured into 10% aqueous sodium bisulfite solution (200 ml) and then extracted three times with ethyl acetate. The combined organic extracts were washed with water, then with brine, then dried over magnesium sulfate and then evaporated to yield 3-iodo-5-methoxy-1H-indazole (1.48 g) as a yellow solid. LC-MS (METHOD B): $R_T$=2.96 minutes; 275 (M+H)$^+$.

(b) 4-Fluoro-3-iodo-1H-indazole

By proceeding in a manner similar to Reference Example 23(a) above but using 4-fluoro-1H-indazole [Reference Example 24(b)] there was prepared 4-fluoro-3-iodo-1H-indazole as a red solid.

LC-MS (METHOD B): $R_T$=3.06 minutes; 281 (M+H)$^+$.

(c) 4-Chloro-3-iodo-1H-indazole

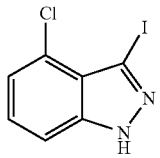

By proceeding in a manner similar to Reference Example 23(a) above but using 4-chloro-1H-indazole [Reference Example 24(c)] there was prepared 4-chloro-3-iodo-1H-indazole as a light brown solid. LC-MS (METHOD B): $R_T$=2.97 minutes; 263 (M+H)$^+$.

(d) 5-Ethoxy-3-iodo-1H-indazole

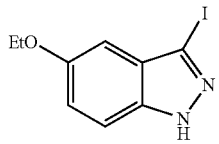

By proceeding in a manner similar to Reference Example 23(a) above but using 5-ethoxy-1H-indazole [Reference Example 37] there was prepared 5-ethoxy-3-iodo-1H-indazole as a light brown solid. LC-MS (METHOD B): $R_T$=2.97 minutes; 263 (M+H)$^+$.

REFERENCE EXAMPLE 24

(a) 5-Methoxy-1H-indazole

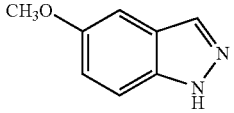

A solution of 4-methoxy-2-methylaniline (2 ml) in dichloromethane (10 ml) was treated with triethylamine (3.27 ml). The mixture was cooled to 0° C. then treated with acetic anhydride (2.38 ml), then stirred at ambient temperature for 1 hour, then cooled to 0° C. when a pink solid precipitated. This solid was filtered, then washed with cold dichloromethane and then dissolved in acetic acid (55 ml) and concentrated hydrochloric acid (20 ml). This solution was cooled to −5° C., then treated with a solution of sodium nitrite (2.68 g) in water (20 ml), then stirred at that temperature for 1 hour and then treated with water (100 ml). This mixture was stirred vigorously at 0° C. for 10 minutes after which a yellow solid precipitated. This solid was filtered, then washed with water and then dissolved in toluene (13 ml). This solution was heated to 80° C. for 1.5 hours, then cooled and then washed with aqueous 1N sodium carbonate solution. The organic phase was extracted three times with aqueous 2N hydrochloric acid and the acid extracts chilled and then made alkaline by addition of aqueous 5N sodium hydroxide solution. The aqueous layers were extracted three times with ethyl acetate and the combined organic layers were dried over magnesium sulfate and then evaporated to yield 5-methoxy-1H-indazole (0.410 g) as a yellow solid. LC-MS (METHOD B): $R_T$=1.32 minutes; 149 (M+H)$^+$.

(b) 4-Fluoro-1H-indazole

To tetrafluoroboric acid (8.2 ml, 48 wt % in water) was added 3-fluoro-2-methylaniline (2.27 ml). The mixture was cooled to 0° C. when a precipitate formed which was redissolved by the addition of water (8 ml). A solution of sodium nitrite (1.38 g) in water (2.7 ml) was then added dropwise and the mixture was then allowed to warm to ambient temperature and then stirred for a further 1 hour. The precipitated solid was filtered, then washed with diethyl ether, and then dried under suction for 30 minutes. The resulting tetrafluoroborate salt was added to a suspension of potassium acetate (3.92 g) and 18-crown-6 (0.264 g) in chloroform (45 ml). After stirring for 3 hours at ambient temperature the bright orange mixture was filtered and the insoluble material was washed with dichloromethane, then subjected to flash column chromatography on silica eluting with a mixture of 40/60 petrol and ethyl acetate (3:1 v/v) to give 4-fluoro-1H-indazole (0.675 g) as an off-white solid. LC-MS (METHOD B): $R_T$=2.70 minutes; 137 (M+H)$^+$.

(c) 4-Chloro-1H-indazole

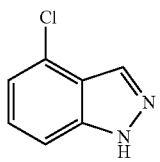

By proceeding to a manner similar to Reference Example 24(a) above but using 3-chloro-2-methylaniline, there was prepared 4-chloro-1H-indazole as a red solid (0.807 g) which was used without further purification. LC-MS (METHOD B): $R_T$=2.90 minutes; 155 (M+H)$^+$.

REFERENCE EXAMPLE 25

(a) (5-fluoro-1H-indazol-3-yl)-methanol

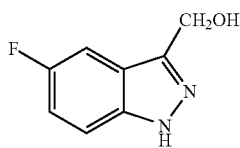

A solution of 5-fluoro-1H-indazole-3-carboxylic acid [0.680 g, Reference Example 26(a)] in anhydrous tetrahydrofuran (15 ml), at 0° C., was treated portionwise with lithium aluminium hydride (0.716 g), then stirred for 2 hours at ambient temperature and then treated with saturated aqueous sodium sulfate. The reaction mixture was acidified by addition of hydrochloric acid (1N) and then extracted three times with ethyl acetate (30 ml). The combined organic extracts were dried over magnesium sulfate and then evaporated. The residual dark brown oil was subjected to flash column chromatography on silica eluting with a mixture of 40/60 petrol and ethyl acetate (1:1 to 1:3 v/v) to yield (5-fluoro-1H-indazol-3-yl)-methanol (0.144 g) as a brown solid. LC-MS (METHOD B): $R_T$=2.40 minutes; 167 (M+H)$^+$.

(b) (6-Fluoro-1H-indazol-3-yl)-methanol

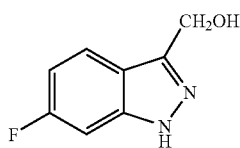

By proceeding in a manner similar to Reference Example 25(a) above but using 6-fluoro-1H-indazole-3-carboxylic acid [Reference Example 26(b)] there was prepared (6-fluoro-1H-indazol-3-yl)-methanol (0.265 g) as a dark grey solid. LC-MS (METHOD B): $R_T$=2.40 minutes, 165 (M−H).

(c) (5-Methyl-1H-indazol-3-yl)-methanol

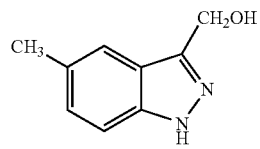

By proceeding in a manner similar to Reference Example 25(a) above but using 5-methyl-1H-indazole-3-carboxylic acid [Reference Example 26(c)] there was prepared (5-methyl-1H-indazol-3-yl)-methanol (0.511 g) as a brown oil. LC-MS (METHOD B): $R_T$=2.45 minutes; 163 (M+H)$^+$.

(d) (5-Chloro-1H-indazol-3-yl)-methanol

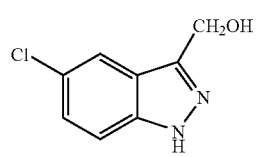

By proceeding in a manner similar to Reference Example 25(a) above but using 5-chloro-1H-indazole-3-carboxylic acid [Reference Example 26(d)] there was prepared (5-chloro-1H-indazol-3-yl)-methanol as a dark brown oil which solidified on standing. LC-MS (METHOD B): $R_T$=2.51 minutes; 185 (M+H)$^+$.

(e) (6-Methoxy-1H-indazol-3-yl)-methanol

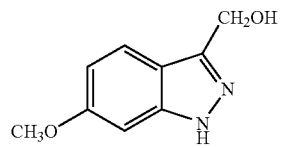

By proceeding in a manner similar to Reference Example 25(a) above but using 6-methoxy-1H-indazole-3-carboxylic acid [Reference Example 26(e)] there was prepared (6-methoxy-1H-indazol-3-yl)-methanol (0.265 g) as a brown solid. LC-MS (METHOD B): $R_T$=2.37 minutes; 179 (M+H)$^+$.

(f) (4-Phenyl-1H-pyrazol-3-yl)-methanol

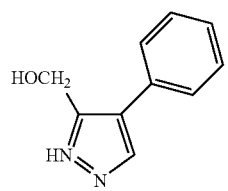

By proceeding in a manner similar to Reference Example 25(a) above but using 4-phenyl-1H-pyrazole-3-carboxylic acid [Reference Example 47] and subjecting the reaction product to flash column chromatography on silica eluting with a mixture of dichloromethane and methanol (9:1, v/v) there was prepared (4-phenyl-1H-pyrazol-3-yl)-methanol. LC-MS (METHOD B): $R_T$=2.51 minutes; 175 (M+H)$^+$.

(g) (1H-indazol-3-yl)-methanol

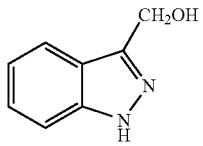

By proceeding in a manner similar to Reference Example 25(a) above but using indazole-3-carboxylic acid and subjecting the reaction product to column chromatography on silica eluting with a mixture of a mixture of n-hexane and ethyl acetate (1:1) to ethyl acetate there was prepared (1H-indazol-3-yl-methanol as a pale yellow solid. LC-MS (METHOD B): $R_T$=3.17 minutes; 149.21 ([M+H]$^+$.

REFERENCE EXAMPLE 26

(a) 5-Fluoro-1H-indazole-3-carboxylic acid

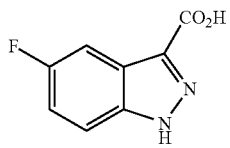

A solution of 5-fluoroisatin (2 g) and sodium hydroxide (0.509 g) in water (20 ml) was heated to 50° C. for 30 minutes, then cooled and then treated with sodium nitrite (0.836 g). This mixture was added over 10 minutes to a solution of concentrated sulfuric acid (2.26 g) in water (200 ml), at 0° C., whilst maintaining the temperature below 5° C. After a further 15 minutes a solution of tin (II) chloride (5.51 g) in concentrated hydrochloric acid (10.5 ml) was added and the resulting mixture maintained at 5° C. for a further 30 minutes. The mixture was then stirred for a further 1 hour whilst warming to ambient temperature then filtered. The light brown paste was dissolved in ethyl acetate and the solution was dried over magnesium sulfate and then evaporated to yield 5-fluoro-1H-indazole-3-carboxylic acid (0.863 g) as a light brown solid which was used without further purification.

LC-MS (METHOD B): $R_T$=2.51 minutes; 181 (M+H)$^+$.

(b) 6-Fluoro-1H-indazole-3-carboxylic acid

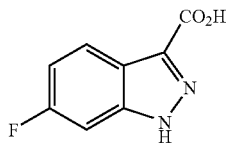

By proceeding in a manner similar to Reference Example 26(a) above but using 6-fluoro-1H-indole-2,3-dione [Reference Example 27(a)] there was prepared 6-fluoro-1H-indazole-3-carboxylic acid (1.962 g) as a light brown solid. LC-MS (METHOD B): $R_T$=2.50 minutes; 181 (M+H)$^+$.

(c) 5-Methyl-1H-indazole-3-carboxylic acid

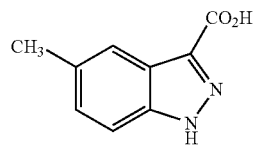

By proceeding in a manner similar to Reference Example 26(a) above but using 5-methyl isatin there was prepared 5-methyl-1H-indazole-3-carboxylic acid as a light brown solid. LC-MS (METHOD B): $R_T$=2.53 minutes; 177 (M+H)$^+$.

(d) 5-Chloro-1H-indazole-3-carboxylic acid

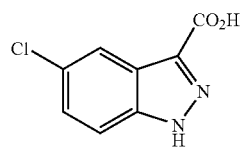

By proceeding in a manner similar to Reference Example 26(a) above but using 5-chloro isatin there was prepared 5-chloro-1H-indazole-3-carboxylic acid as a light brown solid. LC-MS (METHOD B): $R_T$=2.58 minutes; 171 (M+H)$^+$.

(e) 6-Methoxy-1H-indazole-3-carboxylic acid

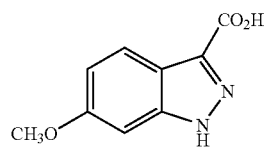

By proceeding in a manner similar to Reference Example 26(a) above but using 6-methoxy-1H-indole-2,3-dione [2.50 g, Reference Example 27(b)] there was prepared 6-methoxy-1H-indazole-3-carboxylic acid as a light brown solid. LC-MS (METHOD B): $R_T$=2.45 minutes; 193 (M+H)$^+$.

REFERENCE EXAMPLE 27

(a) 6-Fluoro-1H-indole-2,3-dione

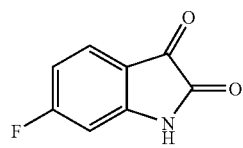

To vigorously stirring polyphosphoric acid (10 g) at 75° C. was added N-(3-fluoro-phenyl)-2-hydroxyimino-acetamide [10.304 g, Reference Example 28(a)] portionwise over 30 minutes. The resulting mixture was stirred at 80° C. for 15 minutes, then poured into ice, then left to stand for 16 hours and then filtered to give a brown paste. The filtrate was extracted four times with ethyl acetate. The combined organic fractions were dried over magnesium sulfate and then evaporated. The residue and the brown paste from the filtration above were combined and treated with aqueous sodium hydroxide (1N). The mixture was filtered and the filtrate was acidified by addition of aqueous hydrochloric acid (2N). The resulting brown solid was filtered and then treated with aqueous sodium hydroxide (1N). This mixture was filtered and the filtrate was acidified by addition of aqueous hydrochloric acid (2N) and then filtered. The combined acidic aqueous filtrates were extracted four times with ethyl acetate, then dried over magnesium sulfate, and then evaporated to give 6-fluoro-1H-indole-2,3-dione (1.861 g) as a pale orange solid. LC-MS (METHOD B): $R_T$=2.49 minutes; 166 $(M+H)^+$.

(b) 6-Methoxy-1H-indole-2,3-dione

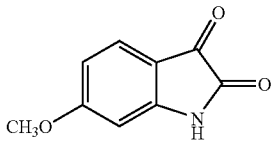

By proceeding in a manner similar to Reference Example 27(a) above but using 2-hydroxyimino-N-(3-methoxy-phenyl)-acetamide [7.20 g, Reference Example 28(b)] there was prepared 6-methoxy-1H-indole-2,3-dione as a brown solid. LC-MS (METHOD B): $R_T$=2.49 minutes; 178 $(M+H)^+$.

REFERENCE EXAMPLE 28

(a) N-(3-Fluoro-phenyl)-2-hydroxyimino-acetamide

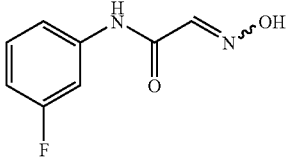

A mixture of chloral hydrate (0.819 g) in water (25 ml) was treated with sodium sulfate (5.10 g), 3-fluoroaniline (0.43 ml), concentrated hydrochloric acid (0.3 ml), and hydroxylamine hydrochloride (0.938 g). The mixture was warmed to 80° C. for 2 hours then allowed to cool and then filtered. The solid was washed with water and then dried in air for 16 hours to afford N-(3-fluoro-phenyl)-2-hydroxyimino-acetamide (0.756 g) as a buff solid. LC-MS (METHOD B): $R_T$=2.51 minutes; 181 $(M+H)^+$.

(b) 2-Hydroxyimino-N-(3-methoxy-phenyl)-acetamide

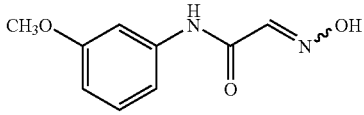

By proceeding in a manner similar to Reference Example 28(a) above but using m-anisidine (0.5 ml) there was prepared 2-hydroxyimino-N-(3-methoxy-phenyl)-acetamide as a brown solid. LC-MS (METHOD B): $R_T$=2.44 minutes; 195 $(M+H)^+$.

REFERENCE EXAMPLE 29

(a) 4-Ethyl-phenylene diamine

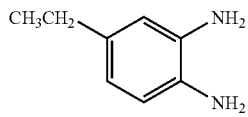

A stirred solution of 5-ethyl-2-nitro-aniline [200 mg, Reference Example 30(a)] and tin chloride (2.75 g) in ethanol (5 ml) was heated in a Smith Creator microwave at 140° C. for 10 minutes. The reaction mixture was basified to pH 8 by addition of saturated sodium hydrogen carbonate solution and then extracted with ethyl acetate. The organic extracts were dried over magnesium sulfate and then evaporated to give 4-ethyl-phenylene diamine (140 mg) as a pale orange solid, which was used without future purification. MS: 137.2 $(M+H)^+$. HPLC (METHOD H): $R_T$=2.91 minutes.

(b) 4-Methoxy-5-methyl-benzene-1,2-diamine

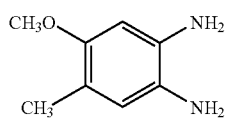

By proceeding in a manner similar to Reference Example 29(a) above but using 4-methoxy-5-methyl-2-nitro-phenylamine [582 mg, Reference Example 31(i)] there was prepared 4-methoxy-5-methyl-benzene-1,2-diamine (454 mg) as a light brown solid. LC-MS (Method K): $R_T$=2.39 minutes, 153.20 $(M+H)^+$.

(c) 4-(2-Morpholin-4-yl-ethoxy)-benzene-1,2-diamine

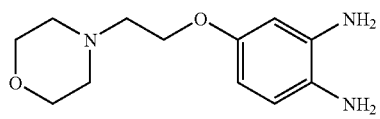

By proceeding in a manner similar to Reference Example 29(a) above but using 4-[2-(3,4-dinitro-phenoxy)-ethyl]-morpholine [Reference Example 67] there was prepared 4-(2-morpholin-4-yl-ethoxy)-benzene-1,2-diamine (170 mg) as a pale brown oil. LC-MS (METHOD N): $R_T$=2.2 minutes, 238.21 $(M+H)^+$.

REFERENCE EXAMPLE 30

(a) 4-Ethyl-5-methyl-phenylene diamine

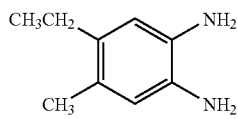

A stirred solution of 4-ethyl-5-methyl-2-nitro-aniline [484 mg, Reference Example 31(b)] in methanol (20 ml) was treated with tin chloride (5.09 g), then heated at reflux for 16 hours and then cooled to ambient temperature. The pH of the reaction mixture was adjusted to pH 8 by addition of aqueous sodium bicarbonate and then this mixture was extracted with ethyl acetate. The organic extracts were dried over magnesium sulfate and then evaporated to give 4-ethyl-5-methyl-phenylene diamine (374 mg) as an off-white solid. LC-MS (METHOD B): $R_T$=1.80 minutes; 151.25 (M+H)$^+$.

(b) 4-Isopropyl-5-methyl-phenylene diamine

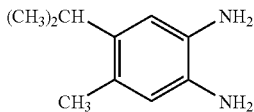

By proceeding in a manner similar to Reference Example 30(a) above but using 4-isopropyl-5-methyl-2-nitro-aniline [Reference Example 31(c)] there was prepared 4-isopropyl-5-methyl-phenylene diamine as a light brown solid. LC-MS (Method C): $R_T$=3.30 minutes; 165.16 (M+H)$^+$.

(c) 4-Bromo-5-methyl-phenylene diamine

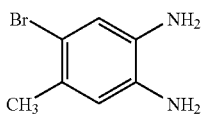

By proceeding in a manner similar to Reference Example 30(a) above but using 4-bromo-5-methyl-2-nitro-aniline [Reference Example 31 (d)] there was prepared 4-bromo-5-methyl-phenylene diamine as an off-white solid. LC-MS (METHOD B): $R_T$=2.63 minutes; 203.22 (M+H)$^+$.

(d) 4-n-propyl-phenylene diamine

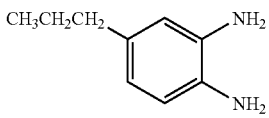

By proceeding in a manner similar to Reference Example 30(a) above but using 4-n-propyl-2-nitro-aniline [Reference Example 31 (e)] there was prepared 4-n-propyl-phenylene diamine as an off-white solid. LC-MS (METHOD B): $R_T$=2.07 minutes, 151.30 (M+H)$^+$.

(e) 4-Bromo-phenylene diamine

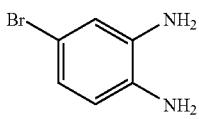

By proceeding in a manner similar to Reference Example 30(a) above but using 4-bromo-2-nitro-aniline there was prepared 4-bromo-phenylene diamine as a yellow solid. LC-MS (METHOD B): $R_T$=1.77 minutes; 187.22 (M+H)$^+$.

(f) 3',4'-diaminobophenyl-3-carbonitrile

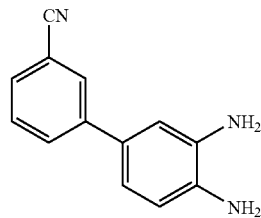

By proceeding in a manner similar to Reference Example 30(a) above but using 4'-amino-3'-nitro-biphenyl-3-carbonitrile [Reference Example 34(a)] there was prepared 3',4'-diaminobophenyl-3-carbonitrile as an off-white solid. LC-MS (METHOD B): $R_T$=2.72 minutes; 210.3 (M+H)$^+$.

(g) 4-(pyridine-3-yl)benzene-1,2-diamine

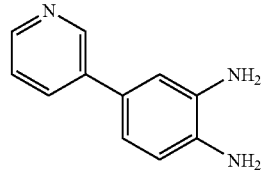

By proceeding in a manner similar to Reference Example 30(a) above but using 2-nitro-4-pyridine-3-yl-phenylamine [Reference Example 34(b)] there was prepared 4-(pyridine-3-yl)benzene-1,2-diamine as an off-white solid. LC-MS (METHOD B): $R_T$=0.37 minutes; 186.3 (M+H)$^+$.

(h) 6-methylbiphenyl-3,4-diamine

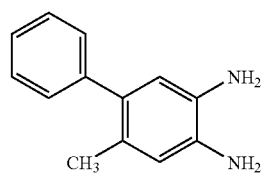

By proceeding in a manner similar to Reference Example 30(a) above but using 2-methyl-5-nitro-biphenyl-4-ylamine [Reference Example 34(c)] there was prepared 6-methylbiphenyl-3,4-diamine as an off-white solid. LC-MS (METHOD B): $R_T$=2.36 minutes; 199.25 (M+H)$^+$.

(i) biphenyl-3,4-diamine

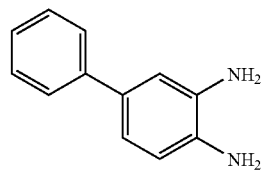

By proceeding in a manner similar to Reference Example 30(a) above but using 3-nitrobiphenyl-4-ylamine [Reference Example 34(d)] there was prepared biphenyl-3,4-diamine as a yellow solid.

LC-MS (METHOD B): $R_T$=2.25 minutes; 185.3 (M+H)$^+$.

(j) 2'-fluorobiphenyl-3,4-diamine

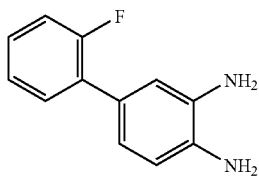

By proceeding in a manner similar to Reference Example 30(a) above but using 2'-fluoro-3-nitro-biphenyl-4-ylamine [Reference Example 34(e)] there was prepared 2'-fluorobiphenyl-3,4-diamine as a white solid. LC-MS (METHOD B): $R_T$=2.73 minutes; 203.31 (M+H)$^+$.

(k) 4-benzo[1,3]dioxol-5-ylbenzene-1,2-diamine

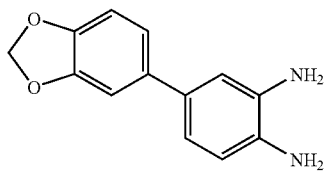

By proceeding in a manner similar to Reference Example 30(a) above but using 4-benzo[1,3]dioxo-5-yl-2-nitrophenylamine [Reference Example 34(f)] there was prepared 4-benzo[1,3]dioxol-5-ylbenzene-1,2-diamine as a white solid. LC-MS (METHOD B): $R_T$=2.66 minutes; 229.3 (M+H)$^+$.

(l) 2'-methoxybiphenyl-3,4-diamine

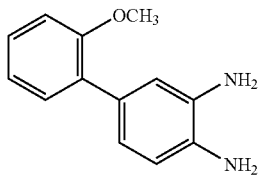

By proceeding in a manner similar to Reference Example 30(a) above but using 2'-methoxy-3-nitro-biphenyl-4-ylamine [Reference Example 34(g)] there was prepared 2'-methoxybiphenyl-3,4-diamine as a white solid. LC-MS (METHOD B): $R_T$=2.74 minutes; 215.33 (M+H)$^+$.

(m) 4'-chlorobiphenyl-3,4-diamine

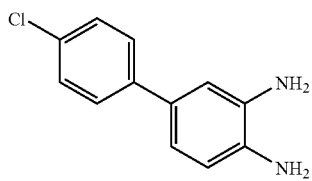

By proceeding in a manner similar to Reference Example 30(a) above but using 4'-chloro-3-nitro-biphenyl-4-yl-amine [Reference Example 34(h)] there was prepared 4'-chlorobiphenyl-3,4-diamine diamine as a white solid. LC-MS (METHOD B): $R_T$=2.85 minutes; 219.3 (M+H)$^+$.

(n) 4'-methylbiphenyl-3,4-diamine

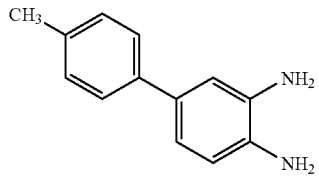

By proceeding in a manner similar to Reference Example 30(a) above but using 4'-methyl-3-nitro-biphenyl-4-yl-amine [Reference Example 34(i)] there was prepared 4'-methylbiphenyl-3,4-diamine as a white solid. LC-MS (METHOD B): $R_T$=2.39 minutes, 199.25 (M+H)$^+$.

(o) 4-benzyloxybenzene-1,2-diamine

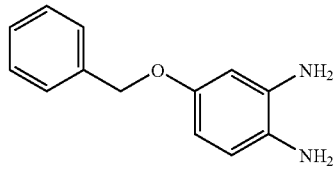

By proceeding in a manner similar to Reference Example 30(a) above but using 4-benzyloxy-1,2-dinitrobenzene [Reference Example 35(a)] there was prepared 4-benzyloxybenzene-1,2-diamine as a white solid. LC-MS (METHOD B): $R_T$=2.34 minutes, 215.33 (M+H)$^+$.

(p) benzo[1,3]dioxole-5,6-diamine

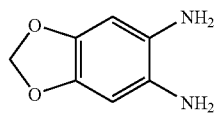

By proceeding in a manner similar to Reference Example 30(a) above but using 5,6-dinitro-benzo[1,3]dioxole [Reference Example 56(b)] there was prepared benzo[1,3]dioxole-5,6-diamine as an oily solid. LC-MS (METHOD B): $R_T$=0.43 minutes, 153.18 (M+H)$^+$.

(q) 4,5-dimethoxybenzene-1,2-diamine

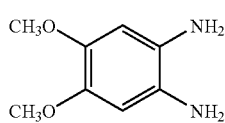

By proceeding in a manner similar to Reference Example 30(a) above but using 4,5-dimethoxy-2-nitroaniline there was prepared 4,5-dimethoxybenzene-1,2-diamine as an oily solid. LC-MS (METHOD B): $R_T$=0.43 minutes, 169.24 (M+H)$^+$.

(r) 4,5-diethylbenzene-1,2-diamine

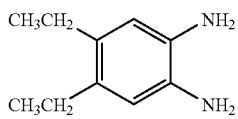

By proceeding in a manner similar to Reference Example 30(a) above but using 4,5-diethyl-2-nitroaniline [Reference Example 31(f)] there was prepared 4,5-diethylbenzene-1,2-diamine which was used without future purification. LC-MS (METHOD B): $R_T$=2.21 minutes, 165.24 $(M+H)^+$.

(s) 4-ethoxy-5-ethyl-benzene-1,2-diamine

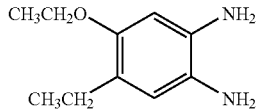

By proceeding in a manner similar to Reference Example 30(a) above but using 4-ethoxy-5-ethyl-2-nitrophenylamine [Reference Example 31(g)] there was prepared 4-ethoxy-5-ethyl-benzene-1,2-diamine.

(t) 4-Ethoxy-3-ethyl-phenylamine

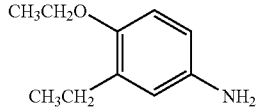

By proceeding in a manner similar to Reference Example 30(a) above but using 1-ethoxy-2-ethyl-4-nitrobenzene [Reference Example 32(h)] and subjecting the reaction product to chromatography on silica gel (heptane, ethyl acetate gradient 25-35%) there was prepared 4-ethoxy-3-ethyl-phenylamine (0.6 g) as an oil. GS-MS one peak, $R_T$=7.17 minutes. MS 165 $(M)^+$.

(u) 4-Methoxy-3-methyl-phenylamine

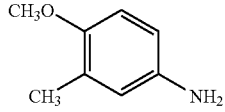

By proceeding in a manner similar to Reference Example 30(a) above but using 1-methoxy-2-methyl-4-nitrobenzene [2.7 g, Reference Example 56(a)] there was prepared 4-methoxy-3-methyl-phenylamine (2.07 g). $R_F$=0.5 [ethyl acetate/n-pentane, 1:1, v/v].

(v) 4-Ethoxy-benzene-1,2-diamine

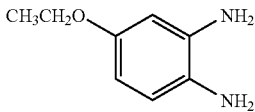

By proceeding in a manner similar to Reference Example 30(a) above but using 4-ethoxy-2-nitroaniline (1.5 g) 4-ethoxy-benzene-1,2-diamine (1.02 g) as a brown oil. LC-MS (Method J): $R_T$=0.50 and 3.88 minutes, 153.30 $(M+H)^+$.

(w) 4-Fluoro-5-methyl-benzene-1,2-diamine

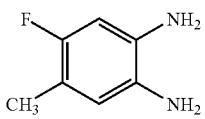

By proceeding in a manner similar to Reference Example 30(a) above but using 4-fluoro-5-methyl-2-nitro-phenylamine [Reference Example 31(j)] there was prepared 4-fluoro-5-methyl-benzene-1,2-diamine (1.27 g) as a yellow solid. LC-MS (METHOD J): $R_T$=1.93 minutes, 141.25 $(M+H)^+$.

(x) 3,4-Diamino-N-benzyl-benzenesulfonamide

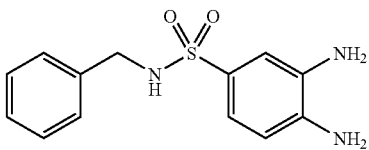

By proceeding in a manner similar to Reference Example 30(a) above but using 4-amino-N-benzyl-3-nitro-benzenesulfonamide [Reference Example 61] there was prepared 3,4-diamino-N-benzyl-benzenesulfonamide (0.350 g) as a yellow film. LC-MS (METHOD K): $R_T$=2.87 minutes, 278.28 $(M+H)^+$.

(y) 4-Difluoromethoxy-benzene-1,2-diamine

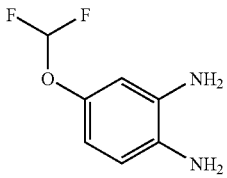

By proceeding in a manner similar to Reference Example 30(a) above but using 4-difluoromethoxy-2-nitro-phenylamine [Reference Example 31(k)] there was prepared 4-difluoromethoxy-benzene-1,2-diamine (2.70 g) as a pale brown solid LC-MS (METHOD N): $R_T$=2.45 minutes, 175 $(M+H)^+$.

(z) 4-Ethyl-5-methoxy-benzene-1,2-diamine [200 mg, Reference Example 30(z)]

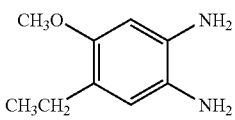

By proceeding in a manner similar to Reference Example 30(a) but using 5-ethyl-4-methoxy-2-nitro-phenylamine [2.4 g, Reference Example 31(l)] there was prepared 4-ethyl-5-methoxy-benzene-1,2-diamine (1.6 g) as a black solid. LC-MS (METHOD 1, AMMONIUM ACETATE, 5 min): $R_T$=3.50 minutes, 167.17 $(M+H)^+$.

(aa) 3-Ethyl-4-methoxy-phenylamine

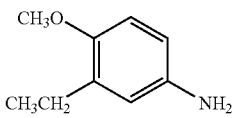

By proceeding in a manner similar to Reference Example 30(a) but using 5-ethyl-4-methoxy-2-nitro-phenylamine [3.6 g, Reference Example 31 (l)] and carrying out the reaction for 24 hours, there was prepared 3-ethyl-4-methoxy-phenylamine (2.5 g) as a brown oil. LC-MS (METHOD J): $R_T$=2.04 minutes, 152.2 $(M+H)^+$.

REFERENCE EXAMPLE 31

(a) 5-Ethyl-2-nitro-aniline

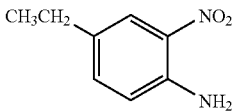

A stirred solution of sodium methoxide (0.35 g) in methanol (15 ml) was treated with a solution of 4-ethyl-2-nitro-N-acetyl-aniline [1 g, Reference Example 32(a)] in methanol (15 ml). The reaction mixture was stirred at room temperature for 24 hours and then poured onto ice-water. The resulting precipitate was filtered and then dried to give 5-ethyl-2-nitro-aniline (650 mg). LC-MS (METHOD B): $R_T$=3.11 minutes; 167.2 $(M+H)^+$.

(b) 4-Ethyl-5-methyl-2-nitro-aniline

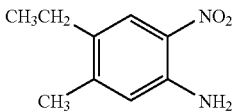

By proceeding in a manner similar to Reference Example 31 (a) above but using 4-ethyl-5-methyl-2-nitro-N-acetyl-aniline [1 g, Reference Example 32(b)] there was prepared 4-ethyl-5-methyl-2-nitro-aniline as a orange solid. LC-MS (METHOD B): $R_T$=3.16 minutes; 181.14 $(M+H)^+$.

(c) 4-isopropyl-5-methyl-2-nitro-aniline

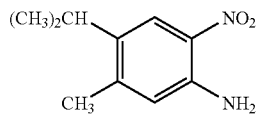

By proceeding in a manner similar to Reference Example 31(a) above but using 4-isopropyl-5-methyl-2-nitro-N-acetyl-aniline [1 g, Reference Example 32(c)] there was prepared 4-isopropyl-5-methyl-2-nitro-aniline as an orange solid. LC-MS (METHOD B): $R_T$=3.26 minutes; 195.3 $(M+H)^+$.

(d) 4-bromo-5-methyl-2-nitro-aniline

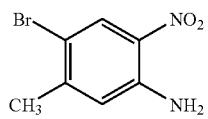

By proceeding in a manner similar to Reference Example 31 (a) above but using 4-bromo-5-methyl-2-nitro-N-acetyl-aniline [1 g, Reference Example 32(d)] there was prepared 4-bromo-5-methyl-2-nitro-aniline as a brown solid. LC-MS (METHOD B): $R_T$=3.24 minutes; 231.2 $(M+H)^+$.

(e) 4-n-Propyl-2-nitro-aniline

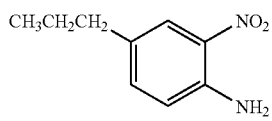

By proceeding in a manner similar to Reference Example 31 (a) above but using 2-nitro-4-propyl-N-acetyl-aniline there was prepared 4-n-propyl-2-nitro-aniline as an orange solid.
LC-MS (Method C): $R_T$=3.46 minutes; 181.2 $(M+H)^+$.

(f) 4,5-diethyl-2-nitro-aniline

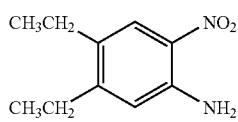

By proceeding in a manner similar to Reference Example 31 (a) above but using 4,5-diethyl-2-nitro-N-acetyl-aniline [Reference Example 32(f)] there was prepared 4,5-diethyl-2-nitro-aniline.
LC-MS (METHOD B): $R_T$=3.27 minutes; 195.22 $(M+H)^+$.

(g) 4-Ethoxy-5-ethyl-2-nitrophenylamine

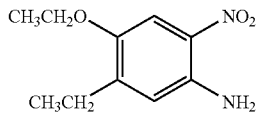

N-4-Ethoxy-5-ethyl-2-nitrophenyl)acetamide [0.2 g, Reference Example 32(g)] was dissolved in ethanol (25 mL) and sodium hydride (100 mg, 50% dispersion in mineral oil, 2 mmol) was added. Mixture was stirred overnight at ambient temperature, aq ammonium chloride (3 mL) was added and the mixture was evaporated. The residue was chromatographed on silica gel (heptane with gradient of 25-50% ethyl acetate) to give 4-ethoxy-5-ethyl-2-nitrophenylamine (0.1 g) as a red solid. LC-MS (Method E): $R_T$=3.4 minutes, 211 (M+H)$^+$.

(h) 5-Chloro-4-methoxy-2-nitrophenylamine

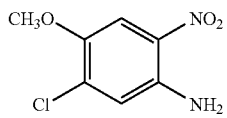

N-(5-Chloro-4-methoxy-2-nitrophenyl)acetamide (8.0 g, Reference Example 32(i) was added to a solution of sodium methoxide (2.0 g, 0.037 mole) in methanol (150 mL) and the mixture was stirred at ambient temperature for 4 hours. The reaction mixture was added to ice water (750 mL), stirred for 15 minutes and the aqueous mixture was filtered. The precipitate was washed with water and dried at 60° C. under vacuum to give 5-chloro-4-methoxy-2-nitrophenylamine (6.52 g) as an orange solid, mp 128-129° C.

(i) 4-Methoxy-5-methyl-2-nitro-phenylamine

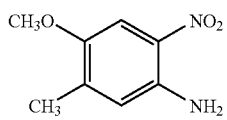

By proceeding in a manner similar to Reference Example 31 (a) above but using N-(4-methoxy-5-methyl-2-nitro-phenyl)-acetamide [2.53 g, Reference Example 32(j)] there was prepared 4-methoxy-5-methyl-2-nitro-phenylamine (2.05 g) as a bright orange solid. LC-MS (Method J): $R_T$=3.46 minutes, 183.29 (M+H)$^+$.

(j) 4-Fluoro-5-methyl-2-nitro-phenylamine

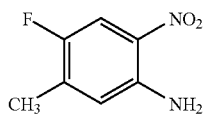

By proceeding in a manner similar to Reference Example 31 (a) above but using N-(4-fluoro-5-methyl-2-nitro-phenyl)-acetamide [2.53 g, Reference Example 32(k)] there was prepared 4-fluoro-5-methyl-2-nitro-phenylamine (2.25 g) as an orange solid. LC-MS (METHOD J): $R_T$=3.53 minutes, 171.28 (M+H)$^+$.

(k) 4-difluoromethoxy-2-nitro-phenylamine

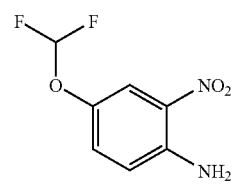

By proceeding in a manner similar to Reference Example 31 (a) above but using N-(4-difluoromethoxy-2-nitro-phenyl)-acetamide [Reference Example 32(l)] there was prepared 4-difluoromethoxy-2-nitro-phenylamine (10 g) as an orange solid. LC-MS (METHOD N): $R_T$=3.86 minutes, 205 (M+H)$^+$.

(l) 5-Ethyl-4-methoxy-2-nitro-phenylamine

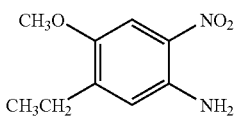

By proceeding in a manner similar to Reference Example 31(a) but using N-(5-ethyl-4-methoxy-2-nitro-phenyl)-acetamide [2.4 g, Reference Example 32(m)] there was prepared 5-ethyl-4-methoxy-2-nitro-phenylamine (1.9 g) as a brown solid. LC-MS (METHOD K): $R_T$=4.14 minutes, 197.09 (M+H)$^+$.

REFERENCE EXAMPLE 32

(a) 4-Ethyl-2-nitro-N-acetyl-aniline

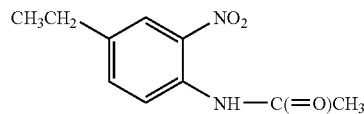

A stirred solution of 4-ethyl-N-acetyl-aniline [3 g, Reference Example 33(a)] in acetic anhydride (8 mL) and acetic acid (4 mL), at −5° C., was treated dropwise with a mixture of acetic acid (1.75 mL) and concentrated nitric acid (1.22 mL). The mixture was warmed to 0° C., then stirred at 0° C. for 2 hours and then poured onto water. This mixture was evaporated and the resulting oil was partitioned between ethyl acetate and water. The organic layer was dried over magnesium sulfate and then evaporated. The residual oil was subjected to flash column chromatography on silica eluting with a mixture of ethyl acetate and petroleum ether (2:5) to give 4-ethyl-2-nitro-N-acetyl-aniline (1.4 g) as an orange solid. LC-MS (METHOD B): $R_T$=2.95 minutes; 209.2 (M+H)$^+$.

(b) 4-Ethyl-5-methyl-2-nitro-N-acetyl-aniline

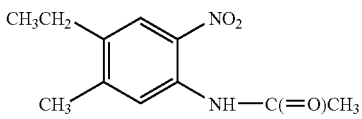

By proceeding in a manner similar to Reference Example 32(a) above but using 3-methyl-4-ethyl-N-acetyl aniline there was prepared 4-ethyl-5-methyl-2-nitro-N-acetyl-aniline as a orange solid.
LC-MS (METHOD B): $R_T$=3.03 minutes; 223.25 (M+H)$^+$.

(c) 4-isopropyl-5-methyl-2-nitro-N-acetyl-aniline

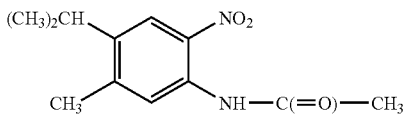

By proceeding in a manner similar to Reference Example 32(a) above but using 3-methyl-4-isopropyl-N-acetyl aniline [Reference Example 33(b))] there was prepared 4-isopropyl-5-methyl-2-nitro-N-acetyl-aniline as an orange solid. LC-MS (METHOD B): $R_T$=3.15 minutes; 231.36 (M+H)$^+$.

(d) 4-Bromo-5-methyl-2-nitro-N-acetyl-aniline

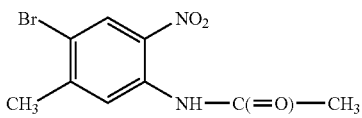

By proceeding in a manner similar to Reference Example 32(a) above but using 3-methyl-4-bromo-N-acetyl aniline [Reference Example 33(c)] there was prepared 4-bromo-5-methyl-2-nitro-N-acetyl-aniline as an orange solid. LC-MS (METHOD B): $R_T$=3.06 minutes; 274.2 (M+H)$^+$.

(f) 4,5-Diethyl-2-nitro-N-acetyl-aniline

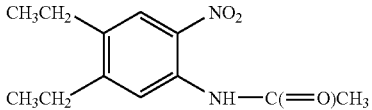

By proceeding in a manner similar to Reference Example 32(a) above but using 3,4-diethyl-N-acetyl aniline [Reference Example 33(d)] there was prepared 4,5-diethyl-2-nitro-N-acetyl-aniline as an orange solid. LC-MS (METHOD B): $R_T$=3.18 minutes; 237.4 (M+H)$^+$.

(g) N-(4-Ethoxy-5-ethyl-2-nitrophenyl)acetamide

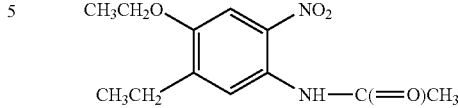

N-(4-Ethoxy-3-ethyl-phenyl) acetamide [3.1 g, Reference Example 33(e)] was dissolved in acetic anhydride (5 mL), a solution of nitric acid in acetic acid (0.5 mL of 95% nitric acid, in 4 mL) was added and the mixture was stirred overnight at ambient temperature. The mixture was diluted with water (100 mL) and the aqueous mixture was extracted twice with ethyl acetate (100 mL). The combined extracts were evaporated and the residue was chromatographed on silica gel (heptane/ethyl acetate 9/1) to give N-(4-ethoxy-5-ethyl-2-nitrophenyl)acetamide (3.0 g) as a bright yellow solid. LC-MS (Method E): $R_T$=3.27 minutes, 253 (M+H)$^+$.

(h) 1-Ethoxy-2-ethyl-4-nitrobenzene

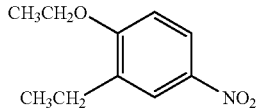

A solution of 1-ethoxy-2-ethyl benzene (3.5 g, Reference Example 51) in acetic anhydride (30 mL) was chilled in an ice-water bath. A solution of nitric acid (1.4 mL of 90%-30% excess) in acetic acid (25 mL) was added dropwise and the mixture was stirred overnight at ambient temperature. The reaction mixture was poured into ice water (300 mL) and the aqueous mixture was extracted with ethyl acetate (2×200 mL). The combined extracts were evaporated and the residue was chromatographed on silica gel (heptane with gradient of 5 to 10% ethyl acetate) to give 1-ethoxy-2-ethyl-4-nitrobenzene (1.4 g) as a clear liquid. LC-MS (Method E) $R_T$=3.75 minutes, 196 (M+H)$^+$.

(i) N-(5-Chloro-4-methoxy-2-nitrophenyl)acetamide

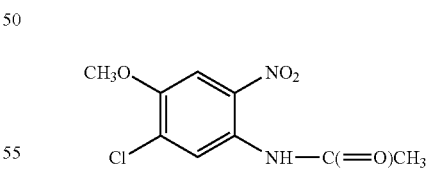

A solution of N-3-chloro-4-methoxyphenyl)acetamide (6.85 g, Reference Example) in a mixture of acetic acid (20 mL) and acetic anhydride (35 mL) was cooled to −5° C. and a solution of fuming nitric acid (3 mL) in acetic acid (4 mL) was added dropwise keeping the reaction temperature below 0° C. The mixture was stirred at 0° C. for 30 minutes at which point a yellow precipitate developed. After another 1.5 h at 0° C., the mixture was poured into water (100 mL) and the aqueous mixture was vigorously stirred for 15 minutes and filtered. The yellow precipitate was washed with water and (j) N-(4-Methoxy-5-methyl-2-nitro-phenyl)-acetamide

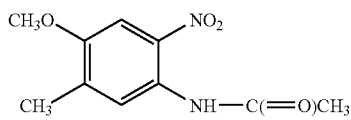

By proceeding in a manner similar to Reference Example 32(a) but using N-(4-methoxy-3-methyl-phenyl)-acetamide [2.65 g, Reference Example 33(f)] there was prepared N-(4-methoxy-5-methyl-2-nitro-phenyl)-acetamide (2.53 g) as a orange solid. LC-MS (Method J): $R_T$=3.30 minutes, 225.29 $(M+H)^+$, 223.29 $(M-H)^-$.

(k) N-(4-Fluoro-5-methyl-2-nitro-phenyl)-acetamide

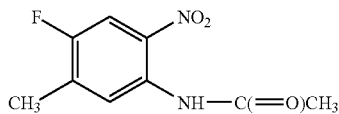

By proceeding in a manner similar to Reference Example 32(a) above but using N-(4-fluoro-3-methyl-phenyl)-acetamide [2.65 g, Reference Example 33(g)] there was prepared N-(4-fluoro-5-methyl-2-nitro-phenyl)-acetamide (2.25 g) as a yellow solid. LC-MS (METHOD J): $R_T$=3.31 minutes, 211.26 $(M-H)^-$ (l) N-(4-Difluoromethoxy-2-nitro-phenyl)-acetamide

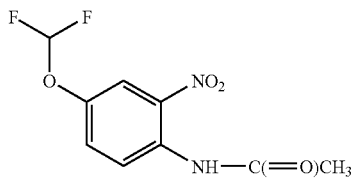

By proceeding in a manner similar to Reference Example 32(a) above but using N-4-diflluoromethoxy-phenyl)-acetamide [Reference Example 33(h)] there was prepared N-(4-difluoromethoxy-2-nitro-phenyl)acetamide (450 mg) as a yellow solid. LC-MS (METHOD K): $R_T$=3.72 minutes, MS: 245 $(M-H)^-$.

(m) N-(5-Ethyl-4-methoxy-2-nitro-phenyl)-acetamide

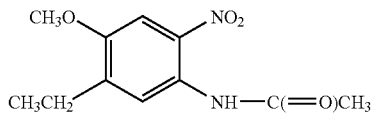

By proceeding in a manner similar to Reference Example 32(a) but using N-(3-ethyl-4-methoxy-phenyl)-acetamide [2.9 g, Reference Example 33(i)] there was prepared N-(5-Ethyl-4-methoxy-2-nitro-phenyl)-acetamide (2.4 g) as a yellow solid. LC-MS (METHOD K): $R_T$=4.04 minutes, MS: 239.16 $(M+H)^+$.

REFERENCE EXAMPLE 33

(a) 4-Ethyl-N-acetyl-aniline

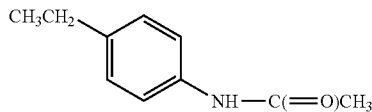

A stirred solution of 4-ethylaniline (2 g) and triethylamine (13.91 mL) in dichloromethane (40 mL) at 0° C. under nitrogen was treated dropwise with acetic anhydride (4.67 mL). The mixture was warmed to ambient temperature, then stirred for 16 hours at room temperature, then washed with (i) 10% citric acid (40 mL), (ii) water (40 mL) and (iii) brine (40 mL). The organic phase was dried over magnesium sulfate and then evaporated to give 4-ethyl-N-acetyl-aniline (2.36 g) as a pale orange solid which was used without further purification. LC-MS (METHOD B): $R_T$=2.80 minutes; 164.2 $(M+H)^+$.

(b) 3-Methyl-4-isopropyl-N-acetyl aniline

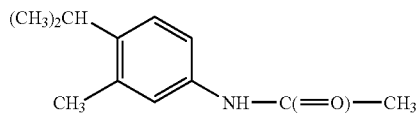

By proceeding in a manner similar to Reference Example 33(a) above but using 3-methyl-4-isopropylaniline there was prepared 3-methyl-4-isopropyl-N-acetyl aniline as an orange solid. LC-MS (METHOD B): $R_T$=2.97 minutes; 192.3 $(M+H)^+$.

(c) 3-Methyl-4-bromo-N-acetyl aniline

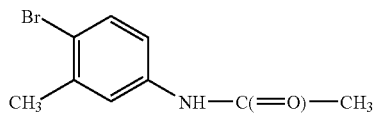

By proceeding in a manner similar to Reference Example 33(a) above but using 3-methyl-4-bromoaniline there was prepared 3-methyl-4-bromo-N-acetyl aniline as a brown solid.

LC-MS (METHOD B): $R_T$=2.88 minutes; 228.12 $(M+H)^+$.

(d) 3,4-Diethyl-N-acetyl aniline

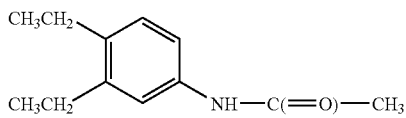

By proceeding in a manner similar to Reference Example 33(a) above but using 3,4-diethylaniline there was prepared 3,4-diethyl-N-acetyl aniline which was used without further purification.
LC-MS (METHOD B): $R_T$=3.03 minutes; 192.30 (M+H)$^+$.

(e) N-(4-Ethoxy-3-ethyl-phenyl) acetamide

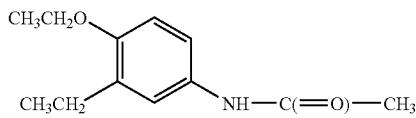

To a solution of 4-ethoxy-3-ethyl-phenylamine [0.6 g, Reference Example 30(t)] in pyridine (5 mL) was added acetic anhydride (1 mL) and the mixture was stirred 18 hours at ambient temperature. The reaction mixture was diluted with water (1000 mL) and the aqueous mixture was extracted twice with ethyl acetate (100 mL). The combined extracts were evaporated to give N-(4-ethoxy-3-ethyl-phenyl) acetamide (0.6 g) as a pink foam. GC-MS one peak, $R_T$=9.16 minutes, MS 207 (M)$^+$.

(f) N-(4-Methoxy-3-methyl-phenyl)-acetamide

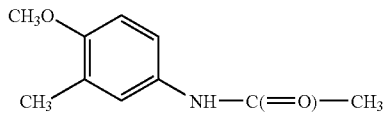

By proceeding in a manner similar to Reference Example 33(a) above but using 4-methoxy-3-methyl-phenylamine (2.07 g, Reference Example 30(u)) and subjecting the reaction product to flash chromatography on silica eluting with a mixture of ethyl acetate and n-pentane (1:1, v/v) there was prepared N-4-methoxy-3-methyl-phenyl)-acetamide (2.65 g) as a pale pink crystalline solid. LC-MS (Method J): $R_T$=2.94 minutes, 180.30 (M+H)$^+$.

(g) N-(4-Fluoro-3-methyl-phenyl)-acetamide

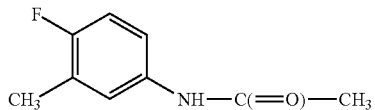

By proceeding in a manner similar to Reference Example 33(a) above but using 4-fluoro-3-methylaniline there was prepared N-(4-fluoro-3-methyl-phenyl)-acetamide (3.82 g) as an orange solid. LC-MS (METHOD J): $R_T$=3.08 minutes, 168.24 (M+H)$^+$.

(h) N-(4-Difluoromethoxy-phenyl)-acetamide

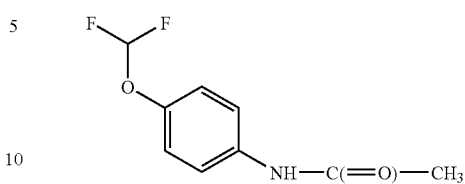

By proceeding in a manner similar to Reference Example 33(a) above but using 4-difluoromethoxyaniline there was prepared N-(4-difluoromethoxy-phenyl)-acetamide (5.90 g) as an orange solid. LC-MS (METHOD K): $R_T$=3.62 minutes, 202 (N+H)$^+$.

(i) N-(3-Ethyl-4-methoxy-phenyl)-acetamide

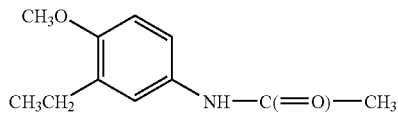

By proceeding in a manner similar to Reference Example 33(a) but using 3-ethyl-4-methoxy-phenylamine [2.5 g, Reference Example 30(aa)] there was prepared N-(3-ethyl-4-methoxy-phenyl-acetamide (2.9 g) was prepared as a light brown solid. LC-MS (METHOD K): $R_T$=3.92 minutes, 194.16 (M+H)$^+$.

REFERENCE EXAMPLE 34

(a) 4'-Amino-3'-nitro-biphenyl-3-carbonitrile

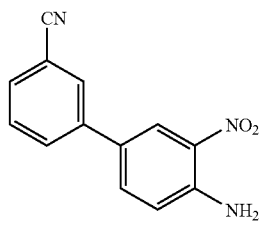

A stirred solution of 3-cyanophenyl boronic acid (812 mg) and tetrakis(triphenylphosphine) palladium (150 mg) in tetrahydrofuran (4 mL) under at atmosphere of nitrogen was treated with 4-bromo-2-nitroaniline in tetrahydrofuran (10 mL). The reaction mixture was heated at 85° C. for 48 hours, then cooled to ambient temperature and then partitioned between ethyl acetate and water. The organic layer was washed with brine, then dried over magnesium sulfate and then evaporated. The residue was subjected to flash column chromatography on silica eluting with a mixture of ethyl acetate and hexane (1:2, v/v) to give 4'-amino-3'-nitro-biphenyl-3-carbonitrile (224 mg) as a yellow solid. LC-MS (METHOD B): $R_T$=3.21 minutes, 240.3 (M+H)$^+$.

(b) 2-nitro-4-pyridine-3-yl-phenylamine

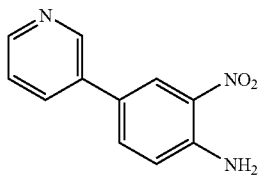

By proceeding in a manner similar to Reference Example 34(a) above but using pyridine-3-boronic acid there was prepared 2-nitro-4-pyridine-3-yl-phenylamine as a yellow solid. LC-MS (METHOD B): $R_T$=2.09 minutes, 216.24 (M+H)$^+$.

(c) 2-methyl-5-nitro-biphenyl-4-yl amine

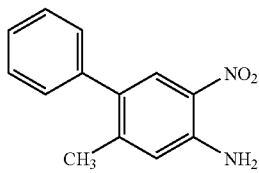

By proceeding in a manner similar to Reference Example 34(a) above but using phenyl boronic acid and 4-bromo-5-methyl-2-nitro-aniline [Reference Example 31(d)] there was prepared 2-methyl-5-nitro-biphenyl-4-yl amine as an orange solid. LC-MS (METHOD B): $R_T$=3.30 minutes, MS: 229.23 (M+H)$^+$.

(d) 3-nitrophenyl-4-ylamine

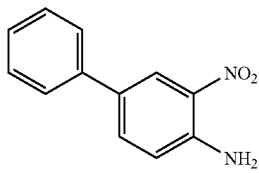

By proceeding in a manner similar to Reference Example 34(a) above but using phenyl boronic acid there was prepared 3-nitrophenyl-4-ylamine as a red solid. LC-MS (METHOD B): $R_T$=3.43 minutes, 215.06 (M+H)$^+$.

(e) 2'-fluoro-3-nitro-biphenyl-4-ylamine

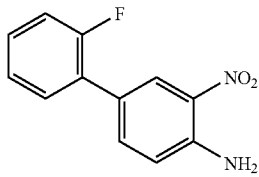

By proceeding in a manner similar to Reference Example 34(a) above but using 2-fluorophenyl boronic acid there was prepared 2'-fluoro-3-nitro-biphenyl-4-ylamine as a red solid. LC-MS (METHOD B): $R_T$=3.33 minutes, 233.3 (M+H)$^+$.

(f) 4'-benzo[1,3]dioxo-5-yl-2-nitrophenylamine

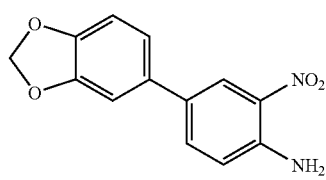

By proceeding in a manner similar to Reference Example 34(a) above but using 3,4-methylenedioxyphenyl boronic acid there was prepared 4'-benzo[1,3]dioxo-5-yl-2-nitrophenylamine as a orange solid. LC-MS (METHOD B): $R_T$=3.23 minutes, 259.3 (M+H)$^+$.

(g) 2'-methoxy-3-nitro-biphenyl-4-ylamine

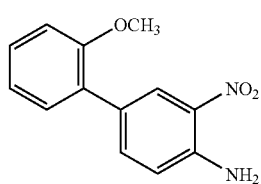

By proceeding in a manner similar to Reference Example 34(a) above but using 2-methoxyphenyl boronic acid there was prepared 2'-methoxy-3-nitro-biphenyl-4-ylamine as an orange solid. LC-MS (METHOD B): $R_T$=3.30 minutes, 245.3 (M+H)$^+$.

(h) 4'-chloro-3-nitro-biphenyl-4-ylamine

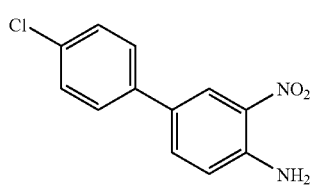

By proceeding in a manner similar to Reference Example 34(a) above but using 4-chlorophenyl boronic acid there was prepared 4'-chloro-3-nitro-biphenyl-4-ylamine as an orange solid. LC-MS (METHOD B): $R_T$=3.45 minutes, 249.27 (M+H)$^+$.

(i) 4'-methyl-3-nitro-biphenyl-4-ylamine

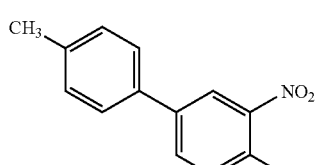

By proceeding in a manner similar to Reference Example 34(a) above but using 4-methylphenyl boronic acid there was prepared 4'-methyl-3-nitro-biphenyl-4-ylamine as an orange solid. LC-MS (METHOD B): $R_T$=3.33 minutes, 229.2 $(M+H)^+$.

REFERENCE EXAMPLE 35

(a) 4-benzyloxy-1,2-dinitrobenzene

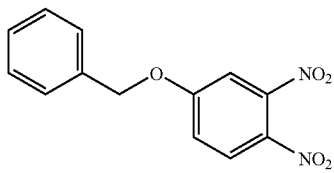

A stirred solution of 3,4-dinitrophenol (1 g) in dimethylformamide (30 mL) was treated with benzyl bromide (723 µL) and potassium carbonate (1.13 g). The reaction mixture was stirred at ambient temperature for 24 hours and then partitioned between ethyl acetate and water. The organic layer was washed with brine, then dried over magnesium sulfate and then evaporated. The residue was subjected to flash column chromatography on silica eluting with a mixture of ethyl acetate and hexane (1:4, v/v) to give 4-benzyloxy-1,2-dinitrobenzene (1.30 g) as a yellow solid. LC-MS (METHOD B): $R_T$=3.31 minutes. $^1$HNMR [$(CD_3)_2CO$, ppm): δ 5.28 (s, 2H), 7.26-7.42 (m, 61), 7.57 (d, 1H), 8.12 (d, 1H).

(b) 1-Ethyl-2-methoxy-benzene

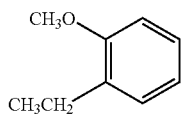

By proceeding in a manner similar to Reference Example 35(a) above, but using 2-ethylphenol (5 ml) and iodomethane (2.6 ml) with acetone as solvent and heating at 70° C. for 24 hours in a sealed pressure vessel, there was prepared 1-ethyl-2-methoxy-benzene (5.6 g) as a yellow oil which was used without future purification. LC-MS (METHOD K): $R_T$=3.83 minutes. $^1$H NMR ($d_6$ acetone): δ 6.95 (m, 2H), 6.75 (d, 1H), 6.68 (t, 1H), 3.67 (s, 3H), 2.44 (q, 2H) 0.95 (t, 3H).

REFERENCE EXAMPLE 36

(a) 4-Nitro-1H-pyrazole-3-carboxylic acid (2-amino-4,5-dimethylphenyl)amide

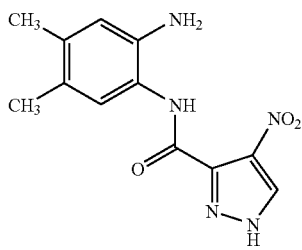

Method A A stirred solution of 4,5-dimethylphenylenediamine (4.32 g) and diisopropylethylamine (30 ml) in dichloromethane (200 ml) was treated with 4-nitropyrazole-3-carboxylic chloride (5 g) portionwise at 0° C. The reaction mixture was warmed to ambient temperature and stirred for 30 minutes. The solvent was removed in vacuo and the oily residue was partitioned between ethyl acetate and water. The organic layer was dried over magnesium sulfate and concentrated. The residual oil was re-crystallised from ethyl acetate and methanol (10%) to give 4-nitro-1H-pyrazole-3-carboxylic acid (2-amino-4,5-dimethylphenyl)amide (6.58 g) as an orange solid. LC-MS (METHOD B): $R_T$=2.36 minutes, 276.09 $(M+H)^+$.

Method B Polyphosphoric acid (500 g) was added to a 1 L flask equipped with an overhead stirrer and heated to 70° C. under nitrogen. A blended mixture of 4-nitro-3-pyrazole carboxylic acid (50 g) and 1,2-diamino-4,5-dimethylbenzene (43.4 g) was added and the mixture was heated to 180° C. After 1 hour at this temperature the reaction mixture was cooled to 130° C. and poured into ice water (2.5 kg). This mixture was stirred with an overhead stirrer and then treated with aqueous ammonium hydroxide (350 mL, 30%) until the pH was 2.1. After stirring for a further 15 minutes the mixture was filtered and the filtered solid was washed three times with water (200 mL) then dried under vacuum to give 4-nitro-1H-pyrazole-3-carboxylic acid (2-amino-4,5-dimethylphenyl) amide as a brown solid.

(b) 4-Nitro-1H-pyrazole-3-carboxylic acid (2-amino-4-ethyl-5-methylphenyl)amide

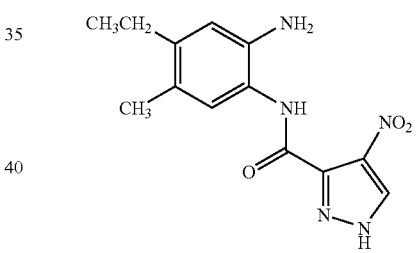

By proceeding in a manner similar to Reference Example 36(a), Method A, above but using 4-ethyl-5-methyl-phenylene diamine [Reference Example 30(a)] there was prepared 4-nitro-1H-pyrazole-3-carboxylic acid (2-amino-4-ethyl-5-methylphenyl)amide as a dark red solid. LC-MS (METHOD B): $R_T$ 2.89 minutes, 290.24 $(M+H)^+$.

(c) 4-Nitro-1H-pyrazole-3-carboxylic acid (2-amino-5-chloro-4-methoxyphenyl)amide

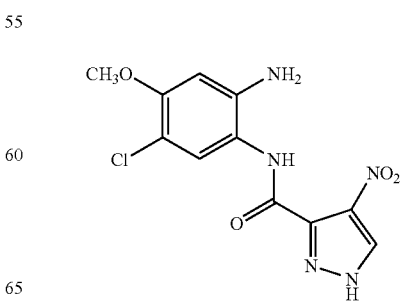

By proceeding in a manner similar to Reference Example 36(a), Method A, above but using 4-chloro-5-methoxybenzene-1,2-diamine [1 g, Reference Example 49(b)], diisopropylethylamine (4.1 mL, 4 eq), dichloromethane (50 mL) and a solution of 4-nitropyrazole-3-carbonyl chloride (1 g, 5.8 mmol) in dichloromethane (25 mL) and stirring the reaction mixture at ambient temperature for 18 hours there was prepared a mixture of 4-nitro-1H-pyrazole-3-carboxylic acid (2-amino-5-chloro-4-methoxyphenyl)amide and the bis-acylated material, MS 310 (M⁻) and 449 (M⁻). This material was used without further purification in Example 20(c).

(d) 4-Nitro-1H-pyrazole-3-carboxylic acid (2-amino-4-methoxy-phenyl)-amide

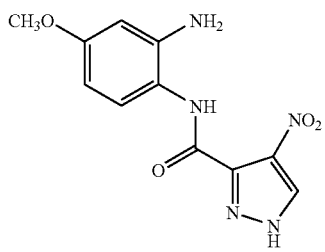

By proceeding in a manner similar to Reference Example 36(a), Method A, above but using 4-methoxy-1,2-phenylenediamine (880 mg) and 4-nitropyrazole-3-carboxylic chloride [prepared by treating a solution of 4-nitropyrazole-3-carboxylic acid (1 g) in dry dichloromethane (70 ml) under nitrogen with oxalyl chloride (1.11 ml) and dimethylformamide and after stirring overnight evaporating the reaction mixture then azeotroping three times with toluene (10 ml)] there was prepared 4-nitro-1H-pyrazole-3-carboxylic acid (2-amino-4-methoxy-phenyl)-amide (800 mg). LC-MS (Method J): $R_T$=2.67 minutes, 278.25 (M+H)⁺, 276.28 (M−H)⁻.

(e) 4-Nitro-1H-pyrazole-3-carboxylic acid (2-amino-4-ethoxy-phenyl)-amide

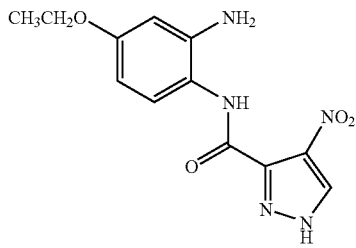

By proceeding in a manner similar to Reference Example 36(d) above but using 4-ethoxy-benzene-1,2-diamine [1.25 g, Reference Example 30(v)] and subjecting the reaction product to flash chromatography on silica, eluting initially with ethyl acetate and then with a mixture of ethyl acetate and methanol (9:1, v/v), there was prepared 4-nitro-1H-pyrazole-3-carboxylic acid (2-amino-4-ethoxy-phenyl)-amide (824 mg) a black solid. LC-MS (Method J): $R_T$=2.90 minutes, 292.27 (M+H)⁺, 290.30 (M−H)⁻.

(f) 4-Nitro-1H-pyrazole-3-carboxylic acid (2-amino-4-fluoro-5-methyl-phenyl)-amide

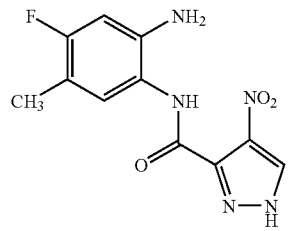

By proceeding in a manner similar to Reference Example 36(d) above but using 4-fluoro-5-methyl-benzene-1,2-diamine [Reference Example 30(w)] there was prepared 4-nitro-1H-pyrazole-3-carboxylic acid (2-amino-4-fluoro-5-methyl-phenyl)-amide (20.12 g) as a red oil. LC-MS (METHOD J): $R_T$=3.02 minutes, 280.25 (M+H)⁺.

(g) 4-Nitro-1H-pyrazole-3-carboxylic acid (2-amino-4-trifluoromethoxy-phenyl)-amide

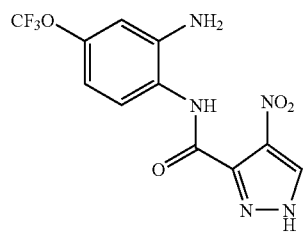

By proceeding in a manner similar to Reference Example 36(d) above but using 4-trifluoromethoxy-benzene-1,2-diamine [Reference Example 30(x)] there was prepared 4-nitro-1H-pyrazole-3-carboxylic acid (2-amino-4-trifluoromethoxy-phenyl)-amide (0.850 g) as a red solid. LC-MS (METHOD J): $R_T$=3.34 minutes, 332.21 (M+H)⁺.

(h) 4-Nitro-1H-pyrazole-3-carboxylic acid (2-amino-4-trifluoromethyl-phenyl)-amide

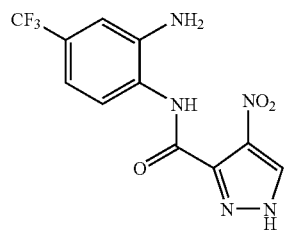

By proceeding in a manner similar to Reference Example 36(d) above but using 4-trifluoromethyl-benzene-1,2-diamine [Reference Example 30(y)] there was prepared 4-nitro-1H-pyrazole-3-carboxylic acid (2-amino-4-trifluoromethyl-phenyl)-amide (0.250 g) as an red solid. LC-MS (METHOD B): $R_T$=3.35 minutes, 316.14 (M+H)$^+$.

(i) 4-Nitro-1H-pyrazole-3-carboxylic acid (2-amino-4-chloro-5-methyl-phenyl)-amide

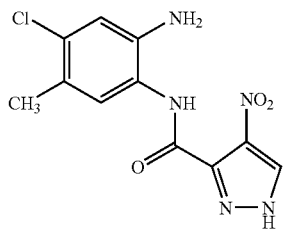

By proceeding in a manner similar to Reference Example 36(d) above but using 4-chloro-5-methyl-benzene-1,2-diamine there was prepared 4-nitro-1H-pyrazole-3-carboxylic acid (2-amino-4-chloro-5-methyl-phenyl)-amide (0.300 g) as a yellow solid. LC-MS (METHOD B): $R_T$=2.72 minutes, 296.10 (M+H)$^+$.

(j) 3-Amino-4-[(4-nitro-1H-pyrazole-3-carbonyl)-amino]-benzoic acid methyl ester

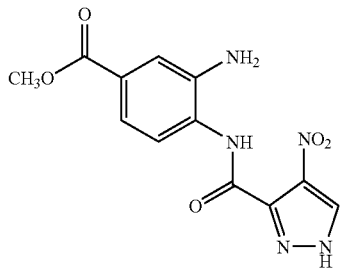

By proceeding in a manner similar to Reference Example 36(d) above but using methyl-3,4-diaminobenzoate there was prepared 3-amino-4-[(4-nitro-1H-pyrazole-3-carbonyl)-amino]-benzoic acid methyl ester (2.51 g) as a tan foam solid. LC-MS (METHOD B): $R_T$=2.83 minutes, 306.21 (M+H)$^+$.

REFERENCE EXAMPLE 37

5-Ethoxy-1H-indazole

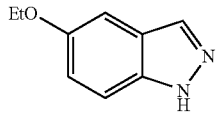

A solution of 5-hydroxy-1H-indazole [0.5 g, Reference Example 38] in acetone (10 ml) was treated with potassium carbonate (2.56 g) then with iodoethane (0.296 ml). The mixture was refluxed for 4 hours then cooled and then evaporated. The residue was partitioned between ethyl acetate and water and the aqueous layer was further extracted twice with ethyl acetate. The combined organic fractions were dried over magnesium sulfate and then evaporated to yield a brown residue which was subjected to flash column chromatography on silica eluting with a mixture of ethyl acetate and hexane (1:1, v/v) to give 5-ethoxy-1H-indazole (0.38 g) as an off-white solid. LC-MS (METHOD B): $R_T$=2.68 minutes; 163 (M+H)$^+$.

REFERENCE EXAMPLE 38

5-Hydroxy-1H-indazole

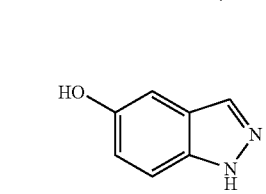

A solution of 5-methoxy-1H-indazole [0.410 g, Reference Example 24(a)] in dichloromethane (7.5 ml) was treated with a solution of boron tribromide in dichloromethane (7.5 ml, 1M). The mixture was then heated to reflux for 4 hours, then cooled to 0° C. and then treated dropwise with water (2 ml). The pH of this mixture was adjusted to 7-8 by addition of 10% aqueous sodium hydrogen carbonate. The mixture was then extracted three times with ethyl acetate. The combined extracts were dried over magnesium sulfate and then evaporated. The residual brown oil was subjected to flash column chromatography on silica eluting with a mixture of ethyl acetate and hexane (1:1, v/v) to give 5-hydroxy-1H-indazole (0.310 g) as a yellow solid. LC-MS (METHOD B): $R_T$=1.96 minutes; 135 (M+H)$^+$.

REFERENCE EXAMPLE 39

(a) 1,4,6,7-tetrahydro-pyrazolo[4,3-c]pyridine-3,5-dicarboxylic acid, 3-(2-amino-4,5-dimethylphenyl) amide, 5-tert-butyl ester

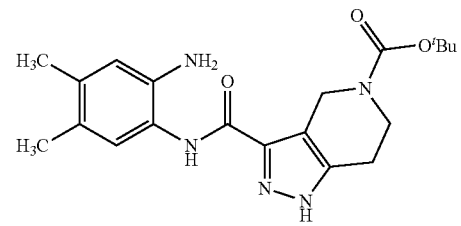

To a solution of 4,5-dimethylbenzene-1,2-diamine (0.841 g) and 1,4,6,7-tetrahydro-pyrazolo[4,3-c]pyridine-3,5-dicarboxylic acid 5-tert-butyl ester [1.5 g, Reference Example 40(a)] in dimethyl formamide (100 ml) was added diisopropylethylamine (1.08 ml) and 2-(1H-9-azabenzotriazole-1-yl)-1,1,3,3-tetramethyluronium hexafluorophosphate (2.35 g). The mixture was stirred for 1.5 hours and diluted with ethyl acetate then washed six times with brine. The organic layer was dried over magnesium sulfate and concentrated in vacuo to yield a pale brown solid. The solid was then triturated with methanol to yield 1,4,6,7-tetrahydro-pyrazolo[4,3-c]pyridine-3,5-dicarboxylic acid, 3-(2-amino-4,5-dimethylphenyl)amide, 5-tert-butyl ester (0.99 g) as an off-white solid.

LC-MS (METHOD B): $R_T$ 2.94 minutes; 386 (M+H)$^+$.

(b) Morpholine-4-carboxylic acid [3-(2-amino-4,5-dimethyl-phenylcarbamoyl)-1-(tetrahydropyran-2-yl)-1H-pyrazol-4-ylmethyl]-(2,4-dimethoxy-benzyl)-amide

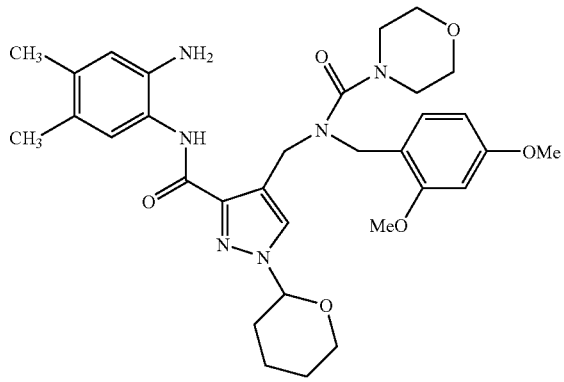

By proceeding in a manner similar to Reference Example 39(a) above but using 4-{[(2,4-dimethoxy-benzyl)-morpholine-4-carbonyl)-amino]-methyl}-1-(tetrahydro-pyran-2-yl)-1H-pyrazole-3-carboxylic acid [534 mg, Reference Example 40(b)] there was prepared morpholine-4-carboxylic acid [3-(2-amino-4,5-dimethyl-phenylcarbamoyl)-1-(tetrahydro-pyran-2-yl)-1H-pyrazol-4-ylmethyl]-(2,4-dimethoxy-benzyl)-amide (1.66 g) as a yellow oil. LC-MS (METHOD B): $R_T$=2.81 minutes, 607.71 (M+H)$^+$.

(c) 3-(2-Amino-4-chloro-5-methyl-phenylcarbamoyl)-1,4,6,7-tetrahydro-pyrazolo[4,3-c]pyridine-5-carboxylic acid tert-butyl ester

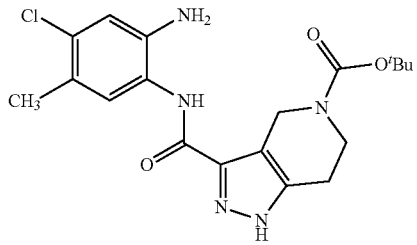

By proceeding in a manner similar to Reference Example 39(a) above but using 4-chloro-5-methyl-1,2-phenylenediamine there was prepared 3-(2-amino-4-chloro-5-methyl-phenylcarbamoyl)-1,4,6,7-tetrahydro-pyrazolo[4,3-c]pyridine-5-carboxylic acid tert-butyl ester (411 mg) as a brown solid. LC-MS (METHOD 3): $R_T$=3.66 minutes, 406/408 (M+H)$^+$.

(d) 3-[2-Amino-4-(2-morpholin-4-yl-ethoxy)-phenylcarbamoyl]-1,4,6,7-tetrahydro-pyrazolo[4,3-c]pyridine-5-carboxylic acid tert-butyl ester

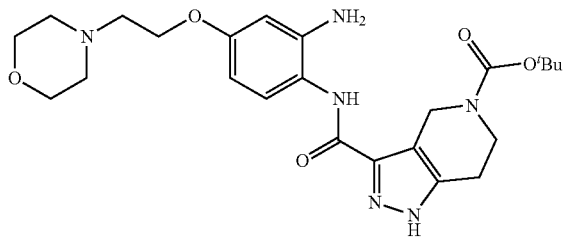

By proceeding in a manner similar to Reference Example 39(a) above but using 4-(2-morpholin-4-yl-ethoxy)-benzene-1,2-diamine [Reference Example 29(c)] there was prepared 3-[2-amino-4-(2-morpholin-4-yl-ethoxy)-phenylcarbamoyl]-1,4,6,7-tetrahydro-pyrazolo[4,3-c]pyridine-5-carboxylic acid tert-butyl ester (400 mg) as a brown solid. LC-MS (METHOD N): $R_T$=3.33 minutes, 485.18 (M–H)$^-$.

(e) 1,4,6,7-Tetrahydro-pyrano[4,3-c]pyrazole-3-carboxylic acid (2-amino-4,5-dimethyl-phenyl)-amide

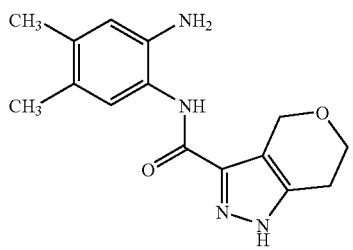

By proceeding in a manner similar to Reference Example 39(a) above but using 1,4,6,7-tetrahydro-pyrano[4,3-c]pyrazole-3-carboxylic acid [Reference Example 17(e)] there was prepared 1,4,6,7-tetrahydro-pyrano[4,3-c]pyrazole-3-carboxylic acid (2-amino-4,5-dimethyl-phenyl)-amide (116 mg) as a cream solid. LC-MS (METHOD B): $R_T$=2.32 minutes, 287 (M+H)$^+$.

(f) 3-(2-Amino-4-trifluoromethyl-phenylcarbamoyl)-1,4,6,7-tetrahydro-pyrazolo[4,3-c]pyridine-5-carboxylic acid tert-butyl ester

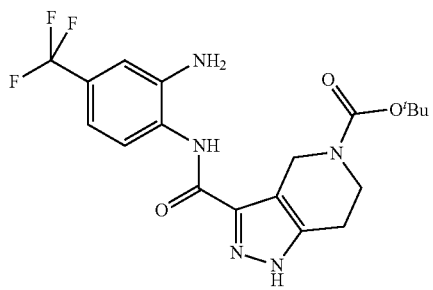

By proceeding in a manner similar to Reference Example 39(a) above but using 4-trifluoromethyl-1,2-phenylenediamine there was prepared 3-(2-amino-4-trifluoromethyl-phenylcarbamoyl)-1,4,6,7-tetrahydro-pyrazolo[4,3-c]pyridine-5-carboxylic acid tert-butyl ester (1.00 g) as a brown solid. LC-MS (METHOD N): $R_T$=3.75 minutes, 424.10 (M–H)$^-$.

REFERENCE EXAMPLE 40

(a) 1,4,6,7-Tetrahydro-pyrazolo[4,3-c]pyridine-3,5-dicarboxylic acid 5-tert-butyl ester

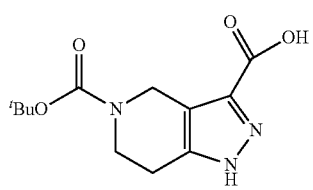

A solution of 1,4,6,7-tetrahydro-pyrazolo[4,3-c]pyridine-3,5-dicarboxylic acid 5-tert-butyl ester 3-ethyl ester [5.105 g, Reference Example 18(d)] and lithium hydroxide monohydrate (0.870 g) in methanol (30 ml) and water (10 ml) was stirred at 55° C. for 2.5 hours. The mixture was acidified with saturated aqueous potassium hydrogen sulfate solution and extracted three times with ethyl acetate. The organic extracts were combined, dried over magnesium sulfate and concentrated in vacuo to yield 1,4,6,7-tetrahydro-pyrazolo[4,3-c]pyridine-3,5-dicarboxylic acid 5-tert-butyl ester (4.442 g) as a pale yellow solid. MS: 268 (M+H)$^+$. HPLC (METHOD G): $R_T$=2.86 minutes.

(b) 4-{[(2,4-dimethoxy-benzyl)-(morpholine-4-carbonyl)-amino]-methyl}-1-(tetrahydro-pyran-2-yl)-1H-pyrazole-3-carboxylic acid

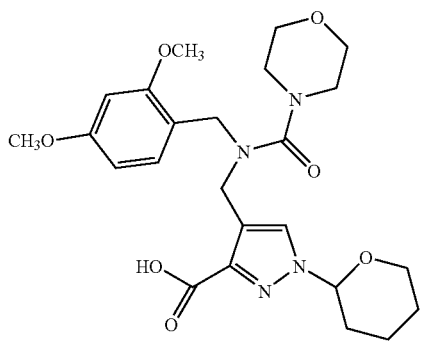

By proceeding in a manner similar to Reference Example 40(a) above but using 4-{[(2,4-dimethoxy-benzyl)-(morpholine-4-carbonyl)-amino]-methyl}-1-(tetrahydro-pyran-2-yl)-1H-pyrazole-3-carboxylic acid ethyl ester [594 mg, Reference Example 48(i)] there was prepared 4-{[(2,4-dimethoxy-benzyl)-(morpholine-4-carbonyl)-amino]-methyl}-1-(tetrahydro-pyran-2-yl)-1H-pyrazole-3-carboxylic acid (534 mg) as a white fluffy solid. LC-MS (Method B): $R_T$=2.71 minutes, 489.21 (M+H)$^+$.

REFERENCE EXAMPLE 41

(a) 3-Hydroxymethyl-1H-pyrazole-4-carboxylic acid ethyl ester

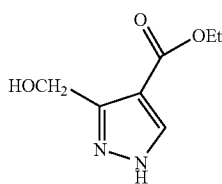

A solution of 3-tert-butyloxymethyl-1H-pyrazole-4-carboxylic acid ethyl ester [3.46 g, Reference Example 42] in dichloromethane (25 ml) was treated with trifluoroacetic acid (25 ml). The mixture was stirred for 1.5 hours and then concentrated. The residue was partitioned between saturated sodium carbonate solution and ethyl acetate. The organic layer was dried over magnesium sulfate and then evaporated to give 3-hydroxymethyl-1H-pyrazole-4-carboxylic acid ethyl ester (2.49 g) as a brown solid which was used without further purification. LC-MS (METHOD B): $R_T$=2.54 minutes; 171 (M+H)$^+$.

(b) 3-Hydroxymethyl-1H-pyrazole-4-carboxylic acid isopropylamide

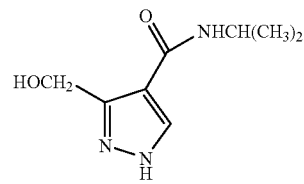

By proceeding in a manner similar to Reference Example 41 (a) above but using 3-tert-butyloxymethyl-1H-pyrazole-4-carboxylic acid isopropylamide [Reference Example 44(a)] there was prepared 3-hydroxymethyl-1H-pyrazole-4-carboxylic acid isopropylamide as a pale yellow solid, which was used without further purification. LC-MS (METHOD B): $R_T$=2.43 minutes; 184 (M+H)$^+$.

(c) 3-Hydroxymethyl-5-methyl-1H-pyrazole-4-carboxylic acid ethyl ester

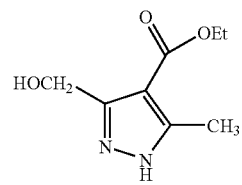

By proceeding in a manner similar to Reference Example 41 (a) above but using 3-tert-butyloxymethyl-5-methyl-1H-pyrazole-4-carboxylic acid ethyl ester [Reference Example 43] there was prepared 3-hydroxymethyl-5-methyl-1H-pyrazole-4-carboxylic acid ethyl ester as a orange solid which was used without further purification. LC-MS (METHOD B): $R_T$=2.58 minutes; 185 (M+H)$^+$.

(d) 3-Hydroxymethyl-1H-pyrazole-4-carboxylic acid (2-methoxy-ethyl)-amide

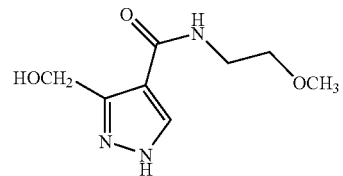

By proceeding in a manner similar to Reference Example 41(a) above but using 3-tert-butyloxymethyl-1H-pyrazole-4-carboxylic acid (2-methoxy-ethyl)-amide [Reference Example 44(b)] there was prepared 3-hydroxymethyl-1H- pyrazole-4-carboxylic acid (2-methoxy-ethyl)-amide (398 mg) as an orange oil. LC-MS (METHOD B): $R_T$=1.66 minutes, 222 (M+Na)$^+$.

(e) 3-Hydroxymethyl-1H-pyrazole-4-carboxylic acid propylamide

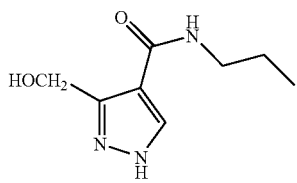

By proceeding in a manner similar to Reference Example 41(a) above but using 3-tert-butyloxymethyl-1H-pyrazole-4-carboxylic acid propylamide [Reference Example 44(c)] there was prepared 3-hydroxymethyl-1H-pyrazole-4-carboxylic acid propylamide (731 mg) as an orange oil. LC-MS (METHOD B): $R_T$=2.09 minutes, 206 (M+Na)$^+$.

(f) 3-Hydroxymethyl-1H-pyrazole-4-carboxylic acid (tetrahydro-pyran-4-yl)-amide

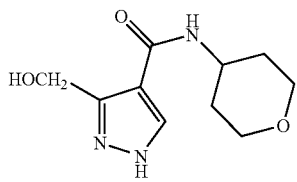

By proceeding in a manner similar to Reference Example 41(a) above but using 3-tert-butyloxymethyl-1H-pyrazole-4-carboxylic acid (tetrahydro-pyran-4-yl)-lamide [Reference Example 44(d)] there was prepared 3-hydroxymethyl-1H-pyrazole-4-carboxylic acid (tetrahydro-pyran-4-yl)-amide (4.10 g) as an orange oil. LC-MS (METHOD N): $R_T$=1.89 minutes, 226 (M+H)$^+$.

(g) 3-Hydroxymethyl-1H-pyrazole-4-carboxylic acid cyclopropylamide

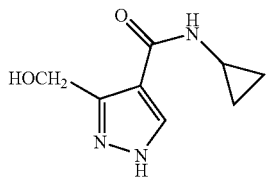

By proceeding in a manner similar to Reference Example 41(a) above but using 3-tert-butyloxymethyl-1H-pyrazole-4-carboxylic acid cyclopropylamide [Reference Example 44(e)] there was prepared 3-hydroxymethyl-1H-pyrazole-4-carboxylic acid cyclopropylamide (2.48 g) as a white foam. LC-MS (METHOD N): $R_T$=1.85 minutes, 180.15 (M−H)$^-$.

REFERENCE EXAMPLE 42

3-tert-Butyloxymethyl-1H-pyrazole-4-carboxylic acid ethyl ester

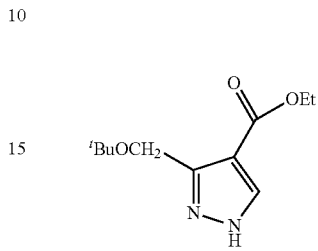

A solution of dimethyl formamide acetal (3.47 ml) and 4-tert-butoxy-3-oxo-butyric acid ethyl ester [3.52 g, Reference Example 43] in toluene (50 ml) was heated at 65° C. for 2 hours. The mixture was then concentrated and the residue redissolved in acetic acid (3 ml). To the mixture was added hydrazine hydrate (0.93 ml) and the whole allowed to stir at ambient temperature for 2 hours. The mixture was again concentrated in vacuo and the residue partitioned between ethyl acetate and 5% aqueous sodium hydrogen carbonate solution. The organic layer was dried over magnesium sulfate and then concentrated to yield a brown oil which was subjected to flash column chromatography on silica eluting with a mixture of ethyl acetate and petrol (3:7, v/v) to give 3-tert-butyloxymethyl-1H-pyrazole-4-carboxylic acid ethyl ester (3.46 g) as a yellow solid. LC-MS (METHOD B): $R_T$=2.79 minutes; 227 (M+H)$^+$.

REFERENCE EXAMPLE 43

4-tert-Butoxy-3-oxo-butyric acid ethyl ester

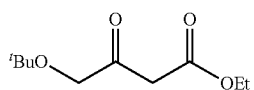

A suspension of sodium hydride (4.44 g, 60% dispersion in mineral oil) in dimethyl formamide (50 ml), at 0° C., was treated dropwise with ethyl-4-chloroacetoacetate (5 ml) and then with tert-butyl alcohol (7.08 ml). This mixture was maintained at 0° C. for 2 hours, then a further 2 hours at ambient temperature and then poured onto 2N hydrochloric acid/ice and then extracted four times with ethyl acetate. The combined extracts were washed with saturated aqueous sodium hydrogen carbonate solution, then with water, then with brine, then dried over magnesium sulfate and then evaporated. The resulting yellow oil was subjected to flash column chromatography on silica eluting with a mixture of ethyl acetate and petrol (1:9, v/v) to give 4-tert-butoxy-3-oxo-butyric acid ethyl ester (5.20 g) as a yellow oil. TLC (silica, 1:4, v/v ethyl acetate/petrol): $R_F$=0.51. NMR (400 MHz, CDCl$_3$): δ 1.21 (9H, s), 1.28 (3H, t), 3.55 (2H, s), 4.19 (2H, q).

REFERENCE EXAMPLE 44

(a) 3-tert-Butyloxymethyl-1H-pyrazole-4-carboxylic acid isopropylamide

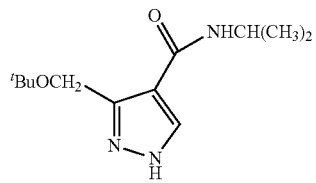

To a solution of 3-tert-butyloxymethyl-1H-pyrazole-4-carboxylic acid [1.520 g, Reference Example 17(d)], hydroxybenzatriazole (3.110 g) and diisopropyl ethylamine (4.010 ml) in dimethyl formamide (130 ml) was added isopropylamine (1.960 ml) followed by 1-(3-dimethylaminopropyl)-3-ethylcarbodiimide hydrochloride (4.420 g). The mixture was heated at 70° C. for 2.5 hours, then diluted with ethyl acetate, then washed with water, then with brine, then dried over magnesium sulfate and then evaporated. The residue was triturated with a mixture of ethyl acetate and petrol to yield 3-tert-butyloxymethyl-1H-pyrazole-4-carboxylic acid isopropylamide (652 mg) as an off-white solid.

LC-MS (METHOD B): 2.99 minutes; 240 (M+H)$^+$.

(b) 3-tert-Butyloxymethyl-1H-pyrazole-4-carboxylic acid (2-methoxy-ethyl)-amide

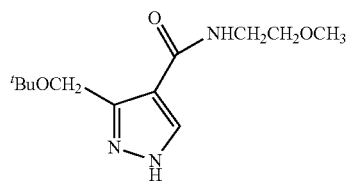

By proceeding in a manner similar to Reference Example 44(a) above but using 2-methoxyethylamine, there was prepared 3-tert-butyloxymethyl-1H-pyrazole-4-carboxylic acid (2-methoxy-ethyl)-amide (811 mg) as an orange oil. LC-MS (METHOD B): $R_T$=2.43 minutes, 278 (M+Na)$^+$.

(c) 3-tert-Butyloxymethyl-1H-pyrazole-4-carboxylic acid propylamide

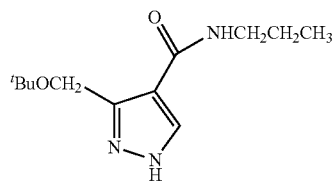

By proceeding in a manner similar to Reference Example 44(a) above but using n-propylamine there was prepared 3-tert-butyloxymethyl-1H-pyrazole-4-carboxylic acid propylamide (1.12 g) as an orange oil. LC-MS (METHOD B): $R_T$=2.65 minutes, 262 (M+Na)$^+$.

(d) 3-tert-Butyloxymethyl-1H-pyrazole-4-carboxylic acid (tetrahydro-pyran-4-yl)-lamide

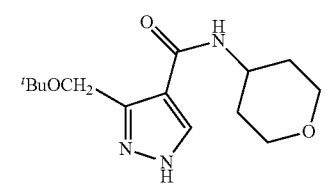

By proceeding in a manner similar to Reference Example 44(a) above but using tetrahydropyran-4-ylamine there was prepared 3-tert-butyloxymethyl-1H-pyrazole-4-carboxylic acid (tetrahydro-pyran-4-yl)-lamide (5.50 g) as an orange oil. LC-MS (METHOD N): $R_T$=3.05 minutes, 282 (M+H)$^+$.

(e) 3-tert-Butyloxymethyl-1H-pyrazole-4-carboxylic acid cyclopropylamide

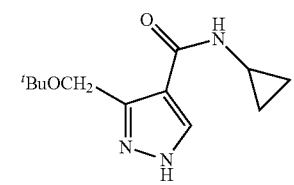

By proceeding in a manner similar to Reference Example 44(a) above but using cyclopropylamine there was prepared 3-tert-butyloxymethyl-1H-pyrazole-4-carboxylic acid cyclopropylamide (3.27 g) as an orange oil. LC-MS (METHOD H): $R_T$=2.24 minutes, 238.38 (M+H)$^+$.

REFERENCE EXAMPLE 45

3-tert-Butyloxymethyl-5-methyl-1H-pyrazole-4-carboxylic acid ethyl ester

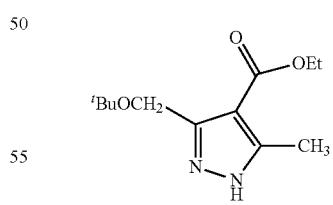

To a solution of 2-acetyl-4-tert-butoxy-3-oxo-butyric acid ethyl ester [0.325 g, Reference Example 46] in acetic acid (3 ml) was added hydrazine hydrate (71 μL). The mixture was stirred at ambient temperature for 16 hours and then evaporated to remove the acetic acid. The residue was dissolved in ethyl acetate and the solution was washed with 5% sodium hydrogen carbonate solution, then with water, then dried over magnesium sulfate, and then evaporated to yield 3-tert-butyloxymethyl-5-methyl-1H-pyrazole-4-carboxylic acid ethyl ester (0.258 g) as a yellow oil which was used without further purification. LC-MS (METHOD B): $R_T$=3.22 minutes; 241 (M+H)⁺.

REFERENCE EXAMPLE 46

2-Acetyl-4-tert-butoxy-3-oxo-butyric acid ethyl ester

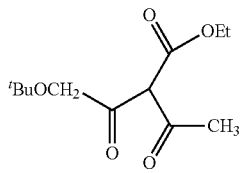

A suspension of dry magnesium chloride (0.471 g) in dichloromethane (6 ml) was treated with 4-tert-butoxy-3-oxo-butyric acid ethyl ester [1.00 g, Reference Example 43]. This mixture was cooled to 0° C., then treated with pyridine (0.80 ml), then stirred for 15 minutes at 0° C. and then treated with acetyl chloride (0.352 ml). After stirring for a further 15 minutes at 0° C. and then for 1 hour at ambient temperature the reaction mixture was treated with saturated aqueous ammonium chloride solution and then extracted twice with ethyl acetate. The combined extracts were dried over magnesium sulfate and then evaporated to yield 2-acetyl-4-tert-butoxy-3-oxo-butyric acid ethyl ester (1.15 g) as a yellow oil which was used without further purification. LC-MS (METHOD B): $R_T$=3.16 minutes; 243 (M−H)⁻.

REFERENCE EXAMPLE 47

4-Phenyl-1H-pyrazole-3-carboxylic acid

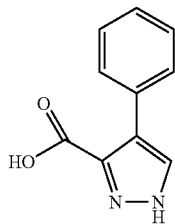

A solution of 3-methyl-4-phenylpyrazole (1.00 g) in tert-butanol (15 ml) and water (25 ml), at 60° C., was treated portionwise potassium permanganate (5.47 g). The temperature was then slowly elevated to 90° C. and maintained at that temperature for 5 hours. The mixture was then cooled and filtered through a pad of celite. The filtrate was concentrated and the pH was adjusted to 10 to 14 by addition of 5N aqueous sodium hydroxide solution. This mixture was washed twice with ethyl acetate. The aqueous layer was then acidified to pH 3 to 5 and then extracted four times with ethyl acetate. The combined extracts were dried over magnesium sulfate and then evaporated to yield 4-phenyl-1H-pyrazole-3-carboxylic acid (0.512 g) as a white solid, which was used without further purification. MS: 189 (M+H)⁺. HPLC (METHOD B): $R_T$=2.48 minutes.

REFERENCE EXAMPLE 48

(a) Cyclopropanecarboxylic acid [3-(5-ethoxy-6-ethyl-1H-benzoimidazol-2-yl)-1-(tetrahydropyran-2-yl)-1H-pyrazol-4-yl]amide

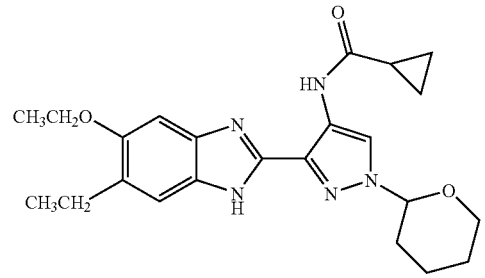

A solution of 3-(5-ethoxy-6-ethyl-1H-benzoimidazol-2-yl)-1-(tetrahydropyran-2-yl)-1H-pyrazol-4-ylamine [0.3 g, Reference Example 49(a)] and triethylamine (0.8 mL, excess) in tetrahydrofuran (20 mL) was treated dropwise with cyclopropanecarbonyl chloride (0.3 g, 2.4 mmol). This mixture was stirred for 48 hours then diluted with aqueous sodium bicarbonate solution (100 mL) and then extracted twice with ethyl acetate (100 mL). The combined extracts were evaporated and the residue was dissolved in tetrahydrofuran (50 mL). This solution was treated with a solution of potassium hydroxide (1.1 g) in ethanol (10 mL) and the mixture was stirred for 2 hours, then poured into water (100 mL) and then extracted twice with ethyl acetate (100 mL). The combined extracts were evaporated and the residue was chromatographed on silica gel eluting with a mixture of heptane and ethyl acetate (1/1, v/v) to give cyclopropanecarboxylic acid [3-(5-ethoxy-6-ethyl-1H-benzoimidazol-2-yl)-1-(tetrahydropyran-2-yl)-1H-pyrazol-4-yl]amide (0.3 g) as an off-white solid. LC-MS (Method E): $R_T$ 2.99 minutes, 424 (M+H)⁺.

(b) 4-Methylpiperazine-1-carboxylic acid [3-(1,5,6,7-tetrahydro-1,3-diaza-s-indacen-2-yl)-1-(tetrahydropyran-2-yl)-1H-pyrazol-4-yl]amide

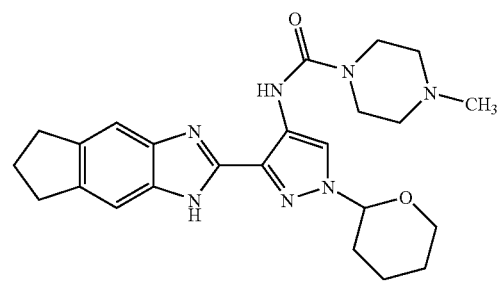

By proceeding in a similar manner to Reference Example 48(a) above but (i) treating a solution of 3-(1,5,6,7-tetrahydro-1,3-diaza-s-indacen-2-yl)-1-(tetrahydropyran-2-yl)-1H-pyrazol-4-ylamine [302 mg, Reference Example 49(d)] and triethylamine (0.94 g, 10 eq) in tetrahydrofuran (10 mL) with 4-methylpiperazine-1-carbonyl chloride (930 mg, 4.67 mmol), (ii) stirring the mixture at 45° C. for 4 hours, then at 55° C. for 1 hour, (iii) treating the cooled reaction mixture with aqueous sodium bicarbonate (200 mL) and extracting this mixture three times with ethyl acetate (100 mL), and (iv) evaporating the combined extracts and chromatographing the residue on silica gel (ethyl acetate/gradient 5-20% methanol) there was prepared 4-methylpiperazine-1-carboxylic acid [3-(1,5,6,7-tetrahydro-1,3-diaza-s-indacen-2-yl)-1-(tetrahydropyran-2-yl)-1H-pyrazol-4-yl]amide (189 mg) as a purple solid. LC-MS (Method F): $R_T$=2.28 minutes, 450 (M+H)$^+$.

(c) 1,1-Dimethyl-3-[3-(1,5,6,7-tetrahydro-s-indacen-2-yl)-1-(tetrahydropyran-2-yl)-1H-pyrazol-4-yl]urea

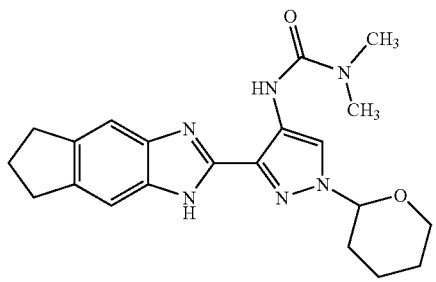

By proceeding in a similar manner to Reference Example 48(b) above but using dimethylcarbamyl chloride (4 eq) there was prepared 1,1-dimethyl-3-[3-(1,5,6,7-tetrahydro-s-indacen-2-yl)-1-(tetrahydropyran-2-yl)-1H-pyrazol-4-yl]urea as a beige foam. LC-MS (Method F): $R_T$=3.22 minutes, 395 (M+H)$^+$.

(d) Cyclopropanecarboxylic acid [3-(6-ethoxy-5-fluoro-1H-benzimidazol-2-yl)-1-(tetrahydropyran-2-yl)-1H-pyrazol-4-yl]amide

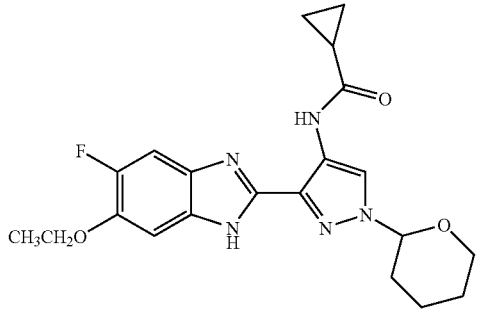

By proceeding in a similar manner to Reference Example 48(a) above but using 6-ethoxy-5-fluoro-2[4-amino-1-(tetrahydropyran-2-yl)-1H-pyrazole-3-yl]-1H-benzimidazole [0.45 g, Reference Example 49(e)] and subjecting the reaction product to chromatography on silica gel (heptane/ethyl acetate, 7/3, v/v) there was prepared cyclopropanecarboxylic acid [3-(6-ethoxy-5-fluoro-1H-benzimidazol-2-yl)-1-(tetrahydropyran-2-yl)-1H-pyrazol-4-yl]amide (90 mg). LC-MS (Method G): $R_T$=8.1 minutes, 414 (M+H)$^+$.

(e) Tetrahydropyran-4-carboxylic acid [3-(6-ethoxy-5-fluoro-1H-benzimidazol-2-yl)-1-(tetrahydropyran-2-yl)-1H-pyrazole-4-yl]amide

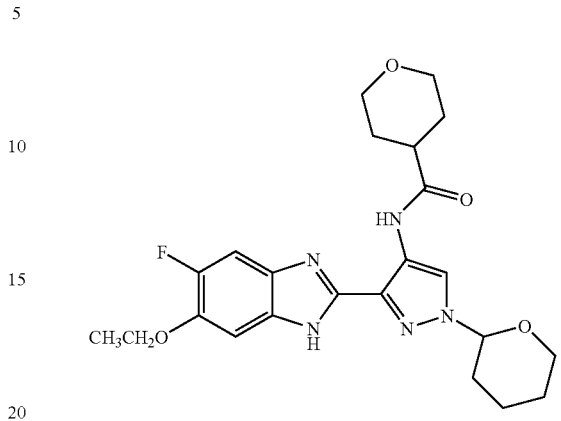

By proceeding in a similar manner to Reference Example 48(a) above but using 6-ethoxy-5-fluoro-2[4-amino-1-(tetrahydropyran-2-yl)-1H-pyrazole-3-yl]-1H-benzimidazole [0.45 g, Reference Example 49(e)] and tetrahydropyran-4-carbonyl chloride (0.135 g) and subjecting the reaction product to chromatography on silica gel (heptane/ethyl acetate, 7/3, v/v) there was prepared tetrahydropyran-4-carboxylic acid [3-(6-ethoxy-5-fluoro-1H-benzimidazol-2-yl)-1-(tetrahydropyran-2-yl)-1H-pyrazole-4-yl]amide (120 mg). LC-MS (Method G): $R_T$=8.05 minutes, 458 (M+H)$^+$.

(f) Morpholine-4-carboxylic acid[3-(6-ethoxy-5-fluoro-1H-benzimidazol-2-yl)-1-(tetrahydropyran-2-yl)-1H-pyrazol-4-yl]amide

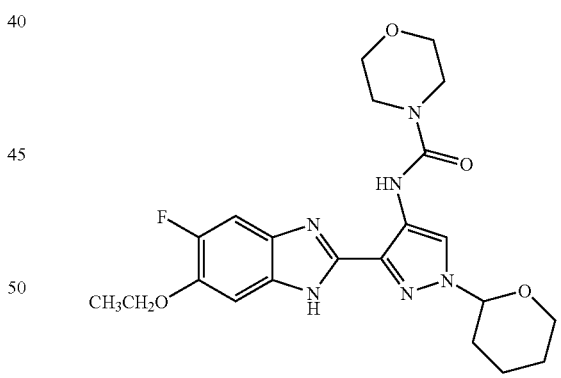

By proceeding in a similar manner to Reference Example 48(a) above but (i) treating 6-ethoxy-5-fluoro-2[4-amino-1-(tetrahydropyran-2-yl)-1H-pyrazole-3-yl]-1H-benzimidazole [90 mg, Reference Example 49(e)] and diisopropylethylamine (168 mg) in tetrahydrofuran (4 mL) with morpholine-4-carbonyl chloride (194 mg) for 2 days at ambient temperature, and (ii) subjecting the reaction product to chromatography on silica gel (heptane/ethyl acetate, 2/1, v/v), there was prepared morpholine-4-carboxylic acid[3-(6-ethoxy-5-fluoro-1H-benzimidazol-2-yl)-1-(tetrahydropyran-2-yl)-1H-pyrazol-4-yl]amide (140 mg). LC-MS (Method G): $R_T$=7.85 minutes, 459 (M+H)$^+$.

(g) Piperidine-4-carboxylic acid[3-(6-ethoxy-5-fluoro-1H-benzimidazol-2-yl)-1-(tetrahydropyran-2-yl)-1H-pyrazol-4-yl]amide

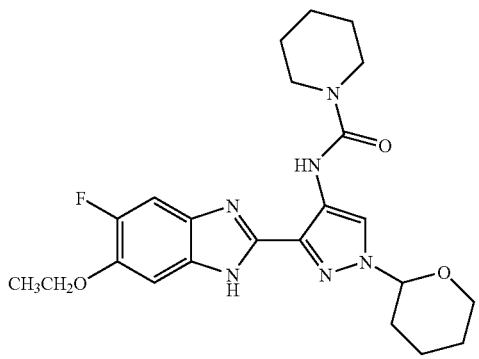

By proceeding in a similar manner to Reference Example 48(f) above but using piperidine-1-carbonyl chloride (191 mg) there was prepared piperidine-4-carboxylic acid[3-(6-ethoxy-5-fluoro-1H-benzimidazol-2-yl)-1-(tetrahydropyran-2-yl)-1H-pyrazol-4-yl]amide (127 mg). LC-MS (Method G): $R_T$=8.2 minutes, 457 (M+H)$^+$.

(h) 3-[6-Ethoxy-5-fluoro-1H-benzimidazol-2-yl)-1-(tetrahydropyran-2-yl)-1H-pyrazol-4-yl]-1,1-diethyl-urea

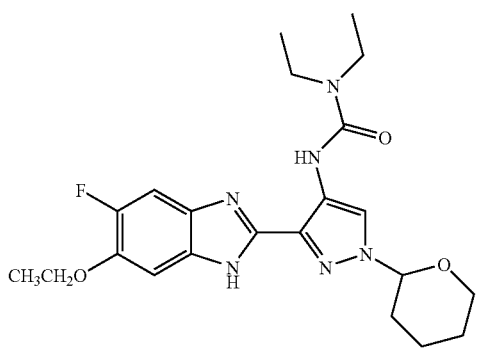

By proceeding in a similar manner to Reference Example 48(f) above but using diethylcarbamyl chloride (175 mg) there was prepared 3-[6-ethoxy-5-fluoro-1H-benzimidazol-2-yl)-1-(tetrahydropyran-2-yl)-1H-pyrazol-4-yl]-1,1-diethyl-urea (110 mg). LC-MS (Method G) $R_T$=7-9 minutes, 445 (M+H)$^+$.

(i) 4-{[(2,4-Dimethoxy-benzyl)-(morpholine-4-carbonyl)-amino]-methyl}-1-(tetrahydro-pyran-2-yl)-1H-pyrazole-3-carboxylic acid

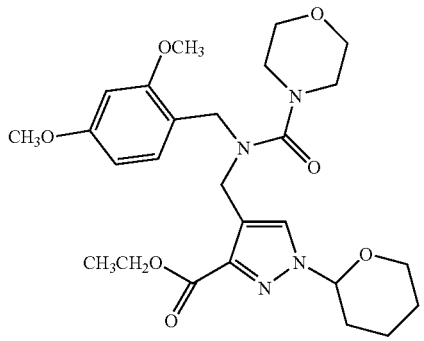

By proceeding in a similar manner to Reference Example 48(a) above but (i) using 4-[(2,4-dimethoxy-benzylamino]-methyl}-1-(tetrahydro-pyran-2-yl)-1H-pyrazole-3-carboxylic acid ethyl ester (829 mg, Reference Example 60) and 4-morpholinecarbonyl chloride (0.96 ml), and (ii) subjecting the reaction product to flash chromatography on silica eluting with ethyl acetate, there was prepared 4-{[(2,4-dimethoxy-benzyl)-(morpholine-4-carbonyl)-amino]-methyl}-1-(tetrahydro-pyran-2-yl)-1H-pyrazole-3-carboxylic acid (595 mg) as a colourless oil. LC-MS (Method B): $R_T$=2.96 minutes, 517.30 (M+H)$^+$.

(j) 3-[3-(5-Difluoromethoxy-1H-benzoimidazol-2-yl)-1-(tetrahydro-pyran-2-yl)-1H-pyrazol-4-yl]-1,1-diethyl-urea

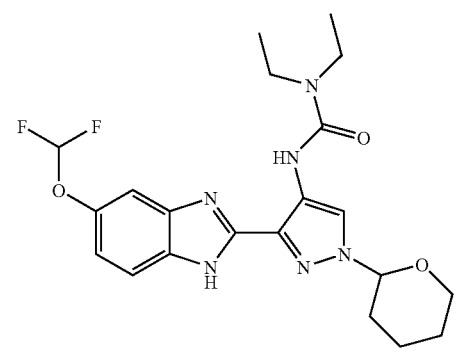

By proceeding in a manner similar to Reference Example 48(a) above but using 3-(5-difluoromethoxy-1H-benzoimidazol-2-yl)-1-(tetrahydro-pyran-2-yl)-1H-pyrazol-4-ylamine [Reference Example 49(g)] and diethylcarbamyl chloride, there was prepared 3-[3-(5-difluoromethoxy-1H-benzoimidazol-2-yl)-1-(tetrahydro-pyran-2-yl)-1H-pyrazol-4-yl]-1,1-diethyl-urea (220 mg) as a pale brown solid. LC-MS (METHOD K): $R_T$=4.02 minutes, 447.27 (M−H)$^-$.

(k) Piperidine-1-carboxylic acid [3-(5-difluoromethoxy-1H-benzoimidazol-2-yl)-1-(tetrahydro-pyran-2-yl)-1H-pyrazol-4-yl]-amide

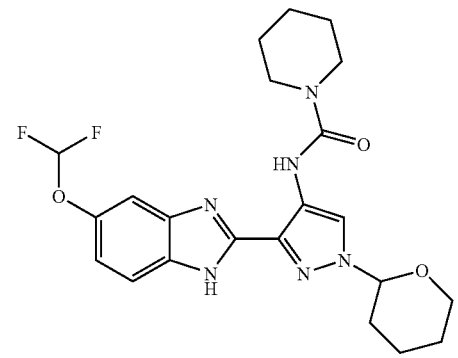

By proceeding in a manner similar to Reference Example 48(a) above but using piperidine-1-carbonyl chloride there was prepared piperidine-1-carboxylic acid [3-(5-difluoromethoxy-1H-benzoimidazol-2-yl)-1-(tetrahydro-pyran-2-yl)-1H-pyrazol-4-yl]-amide (220 mg) as a pale brown solid. LC-MS (METHOD N): $R_T$=4.07 minutes, 459.28 (M−H)$^-$.

REFERENCE EXAMPLE 49

(a) 3-(5-Ethoxy-6-ethyl-1H-benzoimidazol-2-yl)-1-(tetrahydropyran-2-yl)-1H-pyrazol-4-ylamine

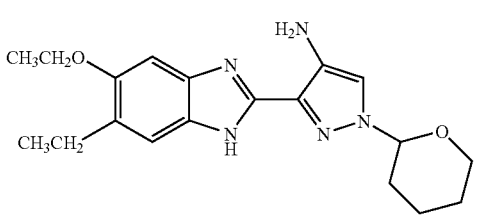

A solution of 5-ethoxy-6-ethyl-2-[4-nitro-1-(tetrahydropyran-2-yl)-1H-pyrazol-3-yl]-1H-benzoimidazole [0.8 g, Reference Example 50(a)] in ethanol (100 mL) was treated with palladium on carbon (0.1 g, 10%) and mixture was hydrogenated at atmospheric pressure (balloon) for 4 days. The catalyst was filtered off, the filtrate was evaporated and the residue was chromatographed on silica gel (ethyl acetate with gradient of 0-10% methanol) to give 3-(5-ethoxy-6-ethyl-1H-benzoimidazol-2-yl)-1-(tetrahydropyran-2-yl)-1H-pyrazol-4-ylamine (0.3 g) as a solid. LC-MS (Method E): $R_T$=2.15 minutes, 356 (M+H)$^+$.

(b) 4-chloro-5-methoxybenzene-1,2-diamine

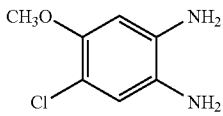

By proceeding in a similar manner to Reference Example 49 (a) above, but using 5-chloro-4-methoxy-2-nitrophenylamine [Reference Example 31 (h)] and subjecting the reaction product to chromatography on silica gel (ethyl acetate with gradient of 40% to 0% heptane) there was prepared 4-chloro-5-methoxybenzene-1,2-diamine (1.0 g) as an orange solid. MS: 173 (M+H)$^+$.

(c) 4-ethoxy-5-ethyl-benzene-1,2-diamine

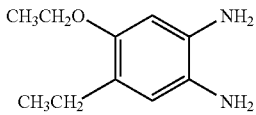

By proceeding in a similar manner to Reference Example 49(a) above, but using 4-ethoxy-5-ethyl-2-nitrophenylamine [Reference Example 31 (g)] and subjecting the reaction product to chromatography on silica gel eluting with ethyl acetate there was prepared 4-ethoxy-5-ethyl-benzene-1,2-diamine as a dark solid. LC-MS (Method E): $R_T$=8.434 minutes, 180 (M+H)$^+$.

(d) 3-(1,5,6,7-tetrahydro-1,3-diaza-s-indacen-2-yl)-1-(tetrahydropyran-2-yl)-1H-pyrazol-4-ylamine

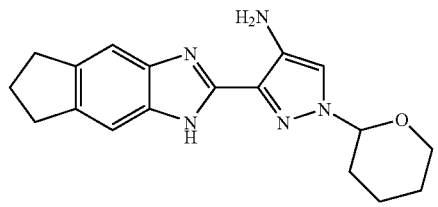

By proceeding in a similar manner to Reference Example 49(a) above, but (i) using a solution of 2-[4-nitro-1-(tetrahydropyran-2-yl)-1H-pyrazol-3-yl]-1,5,6,7-tetrahydro-1,3-diaza-s-indacene [4.1 g, Reference Example 50(b)] in ethanol (120 mL) and 5% palladium on carbon (320 mg), and (ii) using a Parr hydrogenation apparatus at 60 psi for 18 hours there was prepared 3-(1,5,6,7-tetrahydro-1,3-diaza-s-indacen-2-yl)-1-(tetrahydropyran-2-yl)-1H-pyrazol-4-ylamine (368 mg) as a brown solid. LC (Method G): $R_T$=3.079 minutes, 324 (M+H)+ and 346 (M+Na)$^+$.

(e) 6-Ethoxy-5-fluoro-2[4-amino-1-(tetrahydropyran-2-yl)-1H-pyrazole-3-yl]-1H-benzimidazole

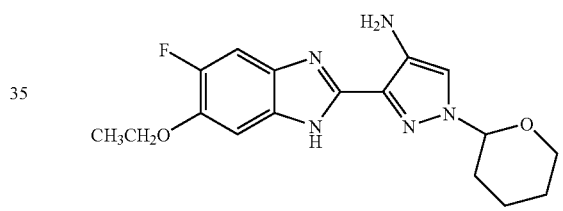

By proceeding in a similar manner to Reference Example 49(a) above, but using 6-ethoxy-5-fluoro-2-[4-nitro-1-(tetrahydropyran-2-yl)-1H-benzimidazole [1.2 g, Reference Example 50(c)] there was prepared 6-ethoxy-5-fluoro-2[4-amino-1-(tetrahydropyran-2-yl)-1H-pyrazole-3-yl]-1H-benzimidazole (1.2 g). LC-MS (Method G): $R_T$=6.74 minutes, 346 (M+H)$^+$.

(f) 4-Methanesulfonyl-benzene-1,2-diamine

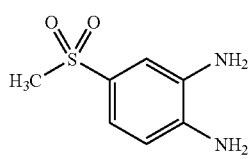

By proceeding in a similar manner to Reference Example 49(a) above, but using N*1*-benzyl-4-methanesulfonyl-benzene-1,2-diamine [Reference Example 65] there was prepared 4-methanesulfonyl-benzene-1,2-diamine as a white solid. LC-MS (METHOD J): $R_T$=0.98 minutes, 187.32 (M+H)$^+$.

(g) 3-(5-Difluoromethoxy-1H-benzoimidazol-2-yl-1-(tetrahydro-pyran-2-yl)-1H-pyrazol-4-ylamine

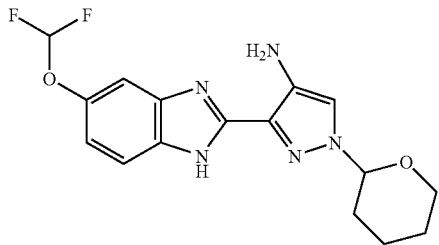

By proceeding in a manner similar to Reference Example 49(a) above but using 5-difluoromethoxy-2-[4-nitro-1-(tetrahydro-pyran-2-yl)-1H-pyrazol-3-yl]-1H-benzoimidazole [Reference Example 50(e)], there was prepared 3-(5-difluoromethoxy-1H-benzoimidazol-2-yl)-1-(tetrahydro-pyran-2-yl)-1H-pyrazol-4-ylamine (730 mg) as a pale brown solid. LC-MS (METHOD N): $R_T$=3.27 minutes, 350.29 $(M+H)^+$.

REFERENCE EXAMPLE 50

(a)-5-Ethoxy-6-ethyl-2-[4-nitro-1-(tetrahydropyran-2-yl)-1H-pyrazol-3-yl]-1H-benzoimidazole

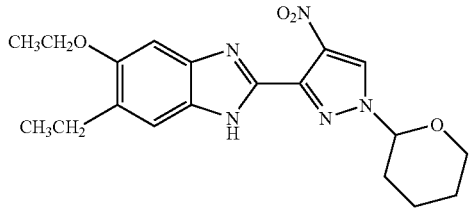

A mixture of 4-ethoxy-5-ethyl-benzene-1,2-diamine [0.18 g, Reference Example 30(s)], 4-nitro-1-(tetrahydro-pyran-2-yl)-1H-pyrazole-3-carbaldehyde [0.225 g, Reference Example 6(m)] and sodium bisulfite (0.12 g, 1.2 mmol) in dimethylformamide (10 mL) was heated at 120° C. for 1 hour. The mixture was cooled, water (100 mL) was added and the aqueous mixture was extracted with twice ethyl acetate (50 mL). The combined extracts were evaporated and the residue was chromatographed on silica gel (ethyl acetate with gradient of 20-0% heptane) to give 5-ethoxy-6-ethyl-2-[4-nitro-1-(tetrahydropyran-2-yl)-1H-pyrazol-3-yl]-1H-benzoimidazole (200 mg) as a solid. LC-MS (Method E) $R_T$=2.85 minutes, 386 $(M+H)^+$.

(b) 2-[4-nitro-1-(tetrahydropyran-2-yl)-1H-pyrazol-3-yl]-1,5,6,7-tetrahydro-1,3-diaza-s-indacene

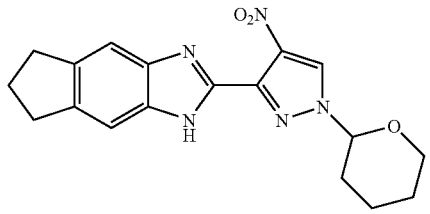

By proceeding in a similar manner to Reference Example 50(a) but using indane-5,6-diamine (1.05 g, prepared as described by Sui Xiong Cai et el., J. Med. Chem., 1997, 40, pages 730-738) and 4-nitro-1-(tetrahydro-pyran-2-yl)-1H-pyrazole-3-carbaldehyde [2.5 g, Reference Example 6(m)] there was prepared 2-[4-nitro-1-(tetrahydropyran-2-yl)-1H-pyrazol-3-yl]-1,5,6,7-tetrahydro-1,3-diaza-s-indacene which was used without father purification.

(c) 6-Ethoxy-5-fluoro-2-[4-nitro-1-(tetrahydropyran-2-yl]-1H-benzimidazole

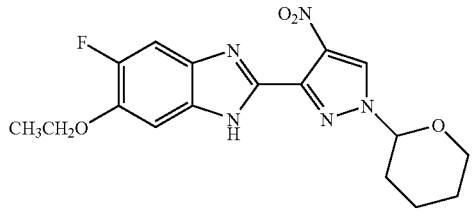

By proceeding in a similar manner to Reference Example 50(a) but using 4-ethoxy-5-fluoro-benzene-1,2-diamine (2.2 g, prepared according to the method of Uchida, et al, Chem. Pharm. Bull. 1989, volume 37, pages 1517 to 1523) there was prepared 6-ethoxy-5-fluoro-2-[4-nitro-1-(tetrahydropyran-2-yl]-1H-benzimidazole. LC-MS (Method G): $R_T$=8.1 minutes, 376 $(M+H)^+$.

(d) 5-Methoxy-2-[4-nitro-1-(tetrahydro-pyran-2-yl)-1H-pyrazol-3-yl]-1H-benzoimidazole

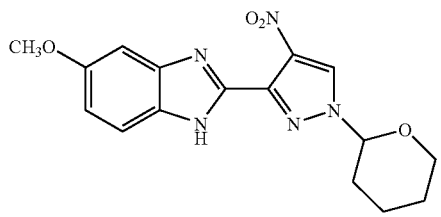

By proceeding in a similar manner to Reference Example 50(a) but using 4-methoxy-1,2-phenylenediamine (117 mg) there was prepared 5-methoxy-2-[4-nitro-1-(tetrahydro-pyran-2-yl)-1H-pyrazol-3-yl]-1H-benzoimidazole (282 mg) as a deep red oil. LC-MS (Method H): $R_T$=2.02 minutes, 344.21 $(M+H)^+$, 342.24 $(M-H)^-$.

(e) 5-Difluoromethoxy-2-[4-nitro-1-(tetrahydro-pyran-2-yl)-1H-pyrazol-3-yl]-1H-benzoimidazole

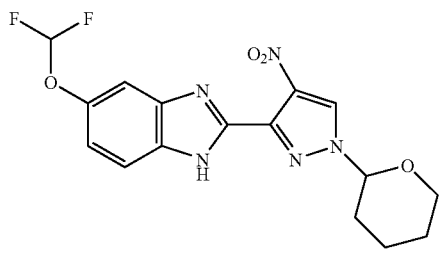

By proceeding in a manner similar to Reference Example 50(a) above but using difluoromethoxy-benzene-1,2-diamine [Reference Example 30(y)] and 4-nitro-1-(tetrahydropyran-2-yl)-1H-pyrazole-3-carbaldehyde [Reference Example 6(m)], there was prepared 5-difluoromethoxy-2-[4-nitro-1-(tetrahydro-pyran-2-yl)-1H-pyrazol-3-yl]-1H-benzoimidazole (910 mg) as a pale brown solid. LC-MS (METHOD N): $R_T$=3.40 minutes, 380.22 $(M+H)^+$.

REFERENCE EXAMPLE 51

1-Ethoxy-2-ethyl benzene

To a solution of 2-ethylphenol (6.9 g, 56.5 mmol), triphenylphosphine (15.7 g, 60 mmol) and ethanol (6 mL, excess) in tetrahydrofuran (100 mL) was added dropwise DIAD (12.1 g, 60 mmol). After stirring for 18 hours, mixture was evaporated and the residue was chromatographed on silica gel (heptane/ethyl acetate 9/1) to give 1-ethoxy-2-ethyl benzene (7.2 g) as a clear liquid. GC-MS shows one peak, $R_T$=5.6 minutes. MS 150 (M+).

REFERENCE EXAMPLE 52

N-(3-Chloro-4-methoxyphenyl)acetamide

A solution of 3-chloro-4-methoxyphenylamine (6.3 g) and triethylamine (4.04 g) in dichloromethane (100 mL) was chilled in an ice bath, acetyl chloride (3.45 g) was added dropwise and the mixture was stirred at ambient temperature overnight. The reaction mixture was extracted with water (2×30 mL) and brine (2×30 mL) and the organic layer was dried with magnesium sulfate. The drying agent was removed by filtration and the filtrate was evaporated to give N-(3-chloro-4-methoxyphenyl)acetamide (7.45 g) as a dark oil, which solidified on standing. MS: 200 (M+H)$^+$.

REFERENCE EXAMPLE 53

[4-Nitro-1-(tetrahydro-pyran-2-yl)-1H-pyrazol-3-yl]-methanol

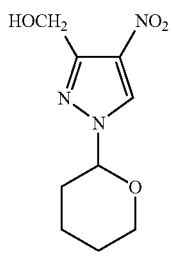

A stirred solution of 4-nitro-1-(tetrahydro-pyran-2-yl)-1H-pyrazole-3-carboxylic acid methyl ester [500 mg, Reference Example 54(a)] in tetrahydrofuran (20 ml) under nitrogen at −78° C. was treated dropwise with a solution of diisobutylaluminium hydride in tetrahydrofuran (8.82 ml, 1M). The reaction mixture was stirred at room temperature for 1.5 hours. The reaction mixture was taken up in diethyl ether (100 ml) and quenched with water (150 ml). The resulting suspension was filtered through celite and the organic layer was collected from the filtrate, then dried over magnesium sulfate and then evaporated to yield [4-nitro-1-(tetrahydro-pyran-2-yl)-1H-pyrazol-3-yl]-methanol (349 mg) as a peach oil. LC-MS (Method H): $R_T$=2.08 minutes, 250.29 (M+H+ Na)$^+$.

REFERENCE EXAMPLE 54

(a) 4-Nitro-1-(tetrahydro-pyran-2-yl)-1H-pyrazole-3-carboxylic acid methyl ester

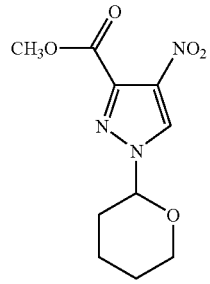

A suspension of 4-nitro-1H-pyrazole-3-carboxylic acid methyl ester (1.3 g, Reference Example 55) and p-toluene sulfonic acid (144 mg) in chloroform (30 ml) at 0° C. was treated with 3,4-dihydropyran (1.04 ml) dropwise. The reaction mixture was allowed to warm to room temperature overnight. The reaction mixture was washed with saturated sodium bicarbonate (40 ml) and water (3×40 ml). The combined aqueous layers were extracted with dichloromethane (3×60 ml). The organic layers were combined, dried over magnesium sulfate and concentrated to yield 4-nitro-1-(tetrahydro-pyran-2-yl)-1H-pyrazole-3-carboxylic acid methyl ester (2.23 g) as a viscous brown oil. LC-MS (Method H): $R_T$=2.79 minutes, 278.21 (M+H+ Na)$^+$.

(b) 4-Formyl-1-(tetrahydro-pyran-2-yl)-1H-pyrazole-3-carboxylic acid ethyl ester

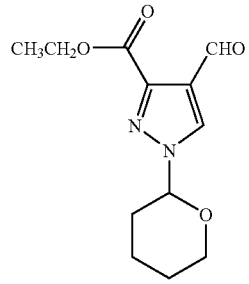

By proceeding in a manner similar to Reference Example 54(a) above but using 4-formyl-1H-pyrazole-3-carboxylic acid ethyl ester (100 mg, Reference Example 57) there was prepared 4-formyl-1-(tetrahydro-pyran-2-yl)-1H-pyrazole-3-carboxylic acid ethyl ester (170 mg) was prepared as a viscous yellow oil. LC-MS (Method J): $R_T$=3.29 minutes, 275.30 (M+H+ Na)$^+$.

REFERENCE EXAMPLE 55

4-Nitro-1H-pyrazole-3-carboxylic acid methyl ester

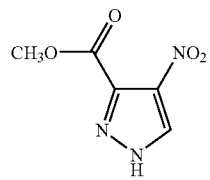

A stirred suspension of 4-nitro-3-pyrazolecarboxylic acid (1 g) in dichloromethane under nitrogen at 0° C. was treated with oxalyl chloride (1.11 ml) followed by dimethylformamide (5 drops). The reaction mixture was warmed to room temperature and stirred overnight. Methanol (10 ml) was added and the reaction mixture was stirred overnight. The solvent was removed under reduced pressure and azeotroped with toluene twice to yield 4-nitro-1H-pyrazole-3-carboxylic acid methyl ester (1.3 g) as a pale green solid. LC-MS (Method H): $R_T$=1.94 minutes, 170.23 (M–H)⁻.

REFERENCE EXAMPLE 56

(a) 1-Methoxy-2-methyl-4-nitrobenzene

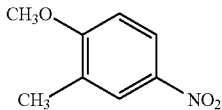

2-Methylanisole (2.5 ml) in acetic acid (140 ml) and dichloromethane (150 ml) was cooled to 15° C. Concentrated nitric acid (20 ml) was added slowly keeping the temperature of the reaction below 40° C. The reaction was stirred at ambient temperature for 30 minutes and cooled to 0° C. before adding fuming nitric acid (50 ml) dropwise. The reaction mixture was allowed to warm to ambient temperature slowly and stirred for a further 4 days. The reaction mixture was poured onto ice water (600 ml) and the organic layer was washed with water (2×40 ml) and saturated sodium hydrogencarbonate (2×40 ml), dried over magnesium sulfate and concentrated. The residual deep red solid was subjected to flash silica chromatography on silica eluting with isohexane/ethyl acetate (9:1) to (7:3) to yield 1-methoxy-2-methyl-4-nitrobenzene (2.70 g) as an off white solid. LC-MS (Method J): $R_T$ 3.74 minutes, 168.27 (M+H)⁺.

(b) 5,6-Dinitro-benzo[1,3]dioxole

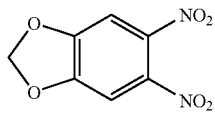

By proceeding in a manner similar to Reference Example 56(a) above but using 1,2-methylenedioxybenzene there was prepared 5,6-dinitro-benzo[1,3]dioxole as an orange solid. HPLC (Method C): $R_T$=2.99 minutes; 490.24 (2M+1).

REFERENCE EXAMPLE 57

4-Formyl-1H-pyrazole-3-carboxylic acid ethyl ester

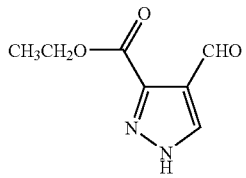

Phosphorus oxychloride (5.07 ml) was added dropwise to dimethylformamide (8.4 ml) at 0° C. under nitrogen. Ethyl pyruvate semicarbazide (4.3 g, Reference Example 58) was added portionwise to the stirring solution at 0° C. under a nitrogen positive pressure. The reaction mixture was heated at 60° C. for 2.5 hours and cooled to ambient temperature before pouring slowly onto ice (30 g). The pH of the reaction mixture was adjusted to pH12 with 6.25M sodium hydroxide solution whilst maintaining the temperature at 0° C. The aqueous reaction mixture was heated at 60° C. for 5 minutes and cooled to 0° C. The pH was re-adjusted to pH6 with 1M hydrochloric acid. The resulting precipitate which formed after 1 hour was collected by filtration to yield 4-formyl-1H-pyrazole-3-carboxylic acid ethyl ester (1.02 g) as a pale yellow solid. LC-MS (Method J): $R_T$=2.55 minutes, 169.27 (M+H)⁺, 167.30 (M–H)⁻

REFERENCE EXAMPLE 58

Ethyl Pyruvate Semicarbazide

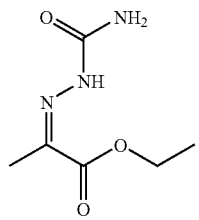

A stirred solution of semicarbazide hydrochloride (11.1 g) and sodium acetate (8.2 g) in water (250 ml) was treated with ethyl pyruvate (10.9 ml) in one portion. The resulting white precipitate was collected by filtration to yield ethyl pyruvate semicarbazide (16.59 g) as a white powder. LC-MS (Method J): $R_T$=2.38 minutes, 174.31 (M+H)⁺, 172.32 (M–H)⁻.

REFERENCE EXAMPLE 59

Morpholine-4-carboxylic acid (2,4-dimethoxy-benzyl)-[3-(5,6-dimethyl-1H-benzoimidazol-2-yl)-1-(tetrahydro-pyran-2-yl)-1H-pyrazol-4-ylmethyl]-amide

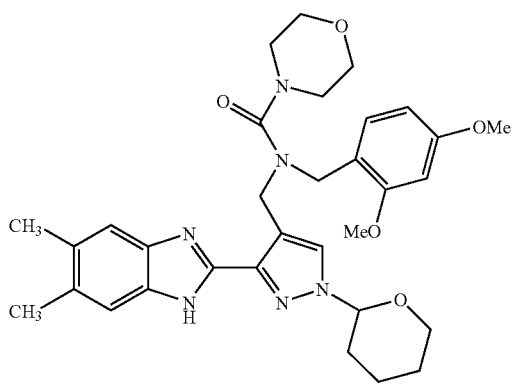

A stirred solution of [332 mg, Reference Example 39(b)] in acetic acid (5 ml) was heated at. 120° C. for 5 minutes in a Personal Chemistry Smith Creator microwave. The mixtures from five reactions were combined and the solvent removed in vacuo to yield morpholine-4-carboxylic acid (2,4-dimethoxy-benzyl)-[3-(5,6-dimethyl-1H-benzoimidazol-2-yl)-1-(tetrahydro-pyran-2-yl)-1H-pyrazol-4-ylmethyl]-amide (1.22 g) as a dark yellow oil. LC-MS (Method J): $R_T$=2.70 minutes, 589.63 (M+H)⁺.

REFERENCE EXAMPLE 60

4-{[(2,4-Dimethoxy-benzyl)-(morpholine-4-carbonyl)-amino]-methyl}-1-(tetrahydro-pyran-2-yl)-1H-pyrazole-3-carboxylic acid ethyl ester

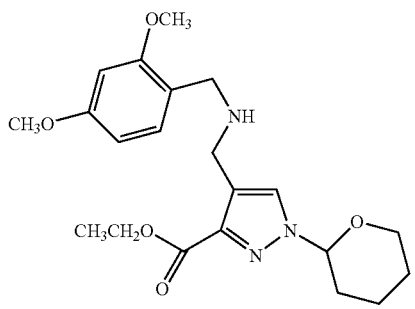

A stirred solution of 4-[(2,4-dimethoxy-benzylamino)-methyl]-1-(tetrahydro-pyran-2-yl)-1H-pyrazole-3-carboxylic acid ethyl ester [1 g, Reference Example 54(b)] in tetrahydrofuran (25 ml) was treated with 2,4-dimethyoxybenzylamine (0.596 ml). After stirring for 12 hours sodium triacetoxyborohydride (1.68 g) was added to the reaction mixture and the reaction mixture was stirred for a further 1 hour before partitioning between ethyl acetate (200 ml) and saturated sodium hydrogencarbonate (200 ml). The aqueous layer was extracted twice with ethyl acetate (100 ml) and the combined organic layers were dried over magnesium sulfate and then concentrated in vacuo to yield 4-{[(2,4-dimethoxy-benzyl)-(morpholine-4-carbonyl)-amino]-methyl}-1-(tetrahydro-pyran-2-yl)-1H-pyrazole-3-carboxylic acid ethyl ester (1.66 g) as a yellow oil. LC-MS (Method B): $R_T$=2.27 minutes, 404.17 (M+H)$^+$.

REFERENCE EXAMPLE 61

4-Amino-N-benzyl-3-nitro-benzenesulfonamide

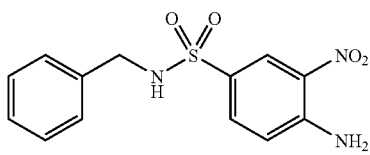

To a stirred suspension of (4-Benzylsulfamoyl-2-nitro-phenyl)-carbamic acid ethyl ester (1.50 g, Reference Example 62) in ethanol (30 ml) was added 2M sodium hydroxide solution (5.93 ml) and the reaction heated at 75° C. for 2 hours. The reaction mixture was cooled to ambient temperature, poured onto ice-water and acidified to pH3 with 2M hydrochloric acid (30 ml). The resultant precipitate was collected by filtration and dried in vacuo to give 4-amino-N-benzyl-3-nitro-benzenesulfonamide (1.01 g) as a yellow solid. LC-MS (METHOD J): $R_T$=3.41 minutes, 308.22 (M+H)$^+$.

REFERENCE EXAMPLE 62

(4-Benzylsulfamoyl-2-nitro-phenyl)-carbamic acid ethyl ester

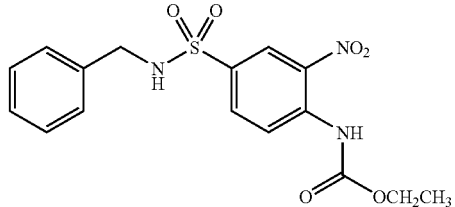

To a stirred solution of (4-chlorosulfonyl-2-nitro-phenyl)-carbamic acid ethyl ester (2 g, Reference Example 63) in dichloromethane (50 ml) at 0° C., under a nitrogen atmosphere, was added diisopropylethylamine (2.71 ml) and benzylamine (0.850 ml). The reaction was warmed to ambient temperature and stirred for 12 hours. The reaction mixture was then washed with water (2×20 ml) and brine (2×20 ml), dried over magnesium sulfate, filtered and the filtrate concentrated in vacuo to give the title compound (2.29 g) as a brown solid. LC-MS (METHOD J): $R_T$=3.83 minutes, 380.12 (M+H)$^+$.

REFERENCE EXAMPLE 63

(4-Chlorosulfonyl-2-nitro-phenyl)-carbamic acid ethyl ester

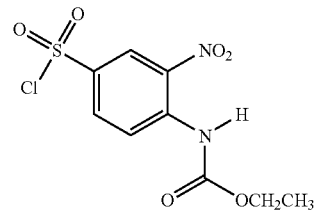

To a stirred suspension of (4-chlorosulfonyl-phenyl)-carbamic acid ethyl ester (5 g, Reference Example 64) in concentrated sulfuric acid (25 ml) at 0° C., was added dropwise a suspension of sodium nitrate (1.61 g) in concentrated sulfuric acid and the reaction stirred for 3 hours. The reaction mixture was then poured onto ice, the resultant precipitate collected by filtration and dried in vacuo to give (4-chlorosulfonyl-2-nitro-phenyl)-carbamic acid ethyl ester (4.80 g) as a yellow solid. LC-MS (METHOD B): $R_T$=3.32 minutes, 307.08 (M–H)$^-$.

REFERENCE EXAMPLE 64

(4-Chlorosulfonyl-phenyl)-carbamic acid ethyl ester

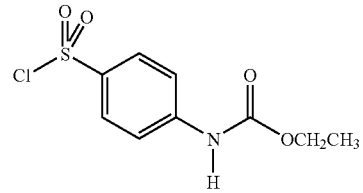

To a stirred solution of chlorosulfonic acid (20 ml) at 0° C., was added N-phenylurethane (9.90 g) at such a rate that the temperature did not exceed 20° C. The reaction was then heated at 60° C. for 3 hours, cooled to ambient temperature and poured carefully onto ice. The resultant precipitate was collected by filtration and dried in vacuo to give (4-chlorosulfonyl-phenyl)-carbamic acid ethyl ester (140.50 g) as an off-white solid. LC-MS (METHOD B): $R_T$=3.11 minutes, 284.23 (M+H)$^+$.

REFERENCE EXAMPLE 65

N*1*-Benzyl-4-methanesulfonyl-benzene-1,2-diamine

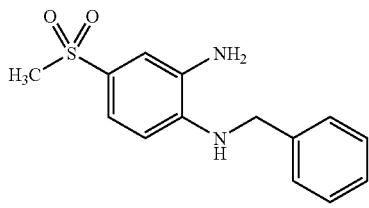

A stirred solution of benzyl-(4-methanesulfonyl-2-nitro-phenyl)-amine (0.300 g, Reference Example 66) and tin chloride (1.86 g) in ethanol (5 ml) was heated in a Smith Creator microwave at 140° C. for 10 minutes. The reaction mixture was basified using saturated sodium hydrogen carbonate solution to pH 8 and extracted with ethyl acetate. The organic layer was dried over magnesium sulfate and concentrated to give N*1*-benzyl-4-methanesulfonyl-benzene-1,2-diamine (0.255 g) as a pale brown solid. LC-MS (METHOD B): $R_T$=2.74 minutes, 275.20 (M–H)$^-$.

REFERENCE EXAMPLE 66

Benzyl-(4-methanesulfonyl-2-nitro-phenyl)-amine

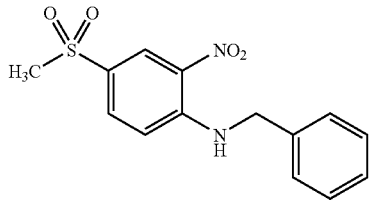

To a stirred suspension of (4-fluoro-2-nitrophenyl)methylsulfone (0.50 g) and sodium hydrogen carbonate (0.575 g) in ethanol and water (3:2) (30 ml) was added benzylamine (0.374 ml) and the reaction stirred for 16 hours. The reaction mixture was then poured onto ice water, the resultant precipitate collected by filtration and dried in vacuo to give benzyl-(4-methanesulfonyl-2-nitro-phenyl)-amine (0.660 g) as a yellow solid. LC-MS (METHOD B): $R_T$=2.97 minutes, 307.04 (M+H)$^+$.

REFERENCE EXAMPLE 67

4-[2-(3,4-Dinitro-phenoxy)ethyl]-morpholine

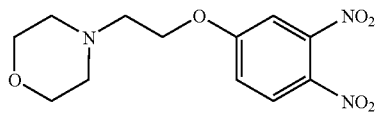

A mixture of 3,4-dinitrophenol (250 mg), 4-(2-chloroethyl)morpholine hydrochloride (252 mg) and potassium carbonate (375 mg) in dimethylformamide (3 ml) was heated at 120° C. for 20 minutes in a Personal Chemistry Smith Creator microwave. The reaction mixture was partitioned between ethyl acetate and water and the organic layer dried over magnesium sulfate, filtered and the filtrate concentrated in vacuo to give 4-[2-(3,4-dinitro-phenoxy)-ethyl]-morpholine (319 mg) as a yellow oil. LC-MS (METHOD B): $R_T$=2.13 minutes, 298 (M+H)$^+$.

REFERENCE EXAMPLE 68

3-Formyl-1H-indazole-5-carbonitrile

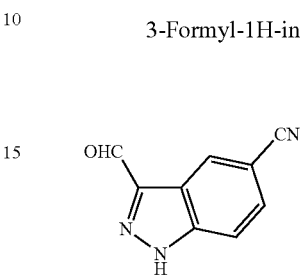

To a suspension of 5-cyanoindole (3.93 g) and sodium nitrite (19.07 g) in water was added 6M hydrochloric acid slowly until the pH was less than 2. The suspension was then stirred for 3 hours at ambient temperature. The mixture was then extracted with ethyl acetate, dried over magnesium sulfate, filtered and the filtrate concentrated in vacuo to give 3-formyl-1H-indazole-5-carbonitrile (4.5 g) as a pale brown solid. LC-MS (METHOD B): $R_T$=2.47 minutes, 172.29 (M+H)$^+$.

In Vitro Test Procedures

A. In Vitro Test Procedures for SYK

1. Inhibitory Effects of Compounds on SYK Kinase

Inhibitory effects of compounds on SYK kinase were determined using a time-resolved fluorescent assay.

The catalytic domain of SYK kinase (residues A340-N635) was expressed as a fusion protein in yeast cells and purified to homogeneity. Kinase activity was determined in 50 mM Tris-HCl buffer pH 7.0 containing 50 mM NaCl, 5 mM MgCl$_2$, 5 mM MnCl$_2$, 1 µM adenosine triphosphate and 10 µM synthetic peptide Biotin-(β-Alanine)$_3$-DEEDYEIPP-NH$_2$. Enzyme reactions were terminated by the addition of buffer containing 0.4M KF, 133 mM EDTA, pH 7.0, containing a streptavidin-XL665 conjugate and a monoclonal phosphospecfic antibody conjugated to a europium cryptate (Eu—K). Features of the two fluorophores, XL-665 and Eu—K are given in G. Mathis et al., Anticancer Research, 1997, 17, pages 3011-3014. The specific long time signal of XL-665, produced only when the synthetic peptide is phosphorylated by SYK, was measured on a Packard Discovery Microplate analyzer or on an LJL Biosystems Analyst AD microplate reader. Inhibition of SYK activity with compounds of the invention was expressed as percentage inhibition of control activity exhibited in the absence of test compounds. Particular compounds of the invention inhibit SYK activity with IC$_{50}$,s in the range 100 micromolar to 0.1 nanomolar. Preferred compounds of the invention inhibit SYK activity with IC$_{50}$,s in the range 5000 nanomolar to 0.1 nanomolar. Particularly preferred compounds of the invention inhibit SYK activity with IC$_{50}$,s in the range 1000 nanomolar to 0.1 nanomolar. Especially preferred compounds of the invention inhibit SYK activity with IC$_{50}$,s in the range 100 nanomolar to 0.1 nanomolar. More especially preferred compounds of the invention inhibit SYK activity with IC$_{50}$,s in the range 10 nanomolar to 0.1 nanomolar.

2. Antigen-Induced Degranulation of Rat Bosophilic Leukemia (RBL) Cells as Measured by [$^3$H]5-hydoxytryptamine (Serotonin) Release 2.1 Cell Culture, Labelling of RBL-2H3 Cells and Performance of Assay.

Method A: For each 24-well culture plate to be set up, $6 \times 10^6$ cells RBL-2H3 cells were washed and resuspended in 15 mL DMEM-10 containing 25 µl of 1 mCi/mL [$^3$H]-serotonin (0.5 µCi/mL final concentration) and 1 µg/mL (15 mL) of anti-DNP IgE. 0.5 mL of cell suspension was added into each well of a 24-well plate. Cells were incubated for 2 days at 37° C., until they have reached confluence. The medium was gently aspirated from each well and the cells were then washed with assay buffer. A final volume of 200 mL of assay buffer (+ or − the test compounds at the appropriate concentrations) was then added to each of three replicate wells. 100 ng/mL of DNP (antigen) was then added to all wells (excluding negative control wells i.e. to measure spontaneous [$^3$H]-serotonin release in the absence of receptor cross-linking). The cells were incubated for 30 minutes at 37° C. and the reaction was stopped by transferring 100 µl of the supernatant from each sample into a liquid scintillation microtitre plate kept on ice. 200 µl of scintillant-40 was then added to each well of the microtitre plate and the plate was read on a Topcount Liquid Scintillation Counter.

Method B: RBL-2H3 cells are maintained in T75 flasks at 37° C. and 5% $CO_2$, and passaged every 3-4 days. To harvest cells, 5 ml trypsin-EDTA is used to rinse the flask once, then 5 ml trypsin is added to each flask, and incubated at room temperature for 2 minutes. Cells are transferred to a tube with 14 ml medium, spun down at 1100 rpm $R_T$ for 5 minutes and resuspended at $2 \times 10^5$/ml. Cells are sensitized by adding 1 µl of DNP-specific IgE (1 mg/ml stock solution) to every 10 ml of cells. 200 µl of cells are added to each well of a flat-bottom 96 well plate (40,000 cells/well), and the plate incubated overnight at 37° C. and 5% $CO_2$. The next day compounds are prepared in 100% DMSO at 10 mM. Each compound is then diluted 1:100 in assay buffer and then diluted further in 1% DMSO-assay buffer to obtain final concentrations of 0.03-30 µM. 80 µl assay buffer (Hank's Balanced Salt Solution with $Ca^{++}/Mg^{++}$, 2 mg/ml glucose, 0.03% BSA) is added to each well, followed by 10 µl of diluted compound. Incubation follows for 5 minutes. 10 µl of DNP-HSA (100 ng/ml) is added to each well and incubated at 37° C. (no $CO_2$) for 30 minutes. As one control, 1% DMSO alone (no compound) is added to a set of wells to determine total release. As another control, buffer is added instead of DNP-HSA to another set of wells to determine the assay background. After 30 minutes incubation, the supernatants are transferred to a new 96-well plate. Add 50 µl supernatant to each well of an assay plate. Add 100 µl of substrate solution (5 mM PNAG in 0.4M citric acid, 0.2M $Na_2HPO_4$) to each well and incubate at 37° C. for 90 minutes. Add 50 µl of 0.4 M glycine solution to stop the reaction and the plate is read at 405 nm on a Molecular Devices SpectraMax 250 plate reader.

2.2 Calculation of Results

Method A (i) The mean±s.e.m. of each set of triplicate wells was calculated.
(ii) Maximum response was the positive control wells containing antigen (10 ng/mL) but no compound.
(iii) Minimum response was the control wells containing no antigen and no compound.
(iv) Using these values as the maximum (100%) and minimum (0%) values respectively, the data was normalised to give a percentage of the maximum response.
(v) A dose response curve was plotted and the $IC_{50}$ of the compound was calculated.

Method B (i) The mean±SD of each set of triplicate wells was calculated.
(ii) Maximum response was the positive control wells containing antigen (100 ng/mL) but no compound.
(iii) Minimum response was the control wells containing buffer (no antigen) and no compound.
(iv) Using these values as the maximum (100%) and minimum (0%) values respectively, the experimental data was calculated to yield a percentage of the maximum response (designated % control).
(v) A dose response curve was plotted and the $IC_{50}$ of the compound was calculated using Prism GraphPad software and nonlinear least squares regression analysis.

B. In Vitro Test Procedures for KDR

1. Inhibitory Effects of Compounds on KDR

The inhibitory effect of the compounds is determined in a test of phosphorylation of a substrate by the enzyme KDR in vitro by the flasplate technique (96-well plate, NEN).

The cytoplasmic domain of human KDR enzyme is cloned in the form of a GST fusion into the baculovirus expression vector pFastBac. The protein is expressed in the SF21 cells and purified to about 60% homogeneity.

The kinase activity of KDR is measured in 20 mM MOPS, 10 mM MgCl2, 10 mM MnCl2, 1 mM DTT, 2.5 mM EGTA, 10 mM β~glycerophosphate, pH 7.2 in the presence of 10 mM MgCl2, 100 µM Na3VO4, 1 mM NaF. 10 µl of the compound are added to 70 µl of kinase buffer containing 100 ng of KDR enzyme at 4° C. The reaction is initiated by adding 20 µl of solution containing 2 µg of substrate (fragment SH2-SH3 of PLCγ expressed in the form of a GST fusion protein), 2 µCi γ33P[ATP] and 2 µM cold ATP. After incubating for 1 hour at 37° C., the reaction is quenched by adding 1 volume (100 µl) of 200 mM EDTA. The incubation buffer is removed and the wells are washed three times with 300 µl of PBS. The radioactivity is measured in each well using a Top Count NXT instrument (Packard).

Background noise is determined by measuring the radioactivity in wells in quadruplet containing radioactive ATP and the substrate alone.

An activity control is measured in wells in quadruplet containing all the reagents (γ33P-[ATP], KDR and the substrate PLCγ) and in the absence of compound.

The inhibition of the KDR activity with the compound of the invention is expressed as a percentage of inhibition of the control activity determined in the absence of compound.

The compound SU5614 (Calbiochem) (1 µM) is included in each plate as inhibition control.

The $IC_{50}$ values for the compounds are calculated by plotting the dose-response curves. The $IC_{50}$ corresponds to the concentration of compound that induces a 50% inhibition of the kinase activity. Particular compounds of the invention inhibit KDR activity with $IC_{50}$,s in the range 100 micromolar to 10 nanomolar. Preferred compounds of the invention inhibit KDR activity with $IC_{50}$,s in the range 3000 nanomolar to 10 nanomolar. Particular preferred compounds of the invention inhibit KDR activity with $IC_{50}$,s in the range 300 nanomolar to 10 nanomolar.

II) Cellular Activity on Endothelial Cells

1) Inhibition of the VEGF-Dependent Proliferation of HDMECs

The anti-KDR activity of the molecules is assessed by incorporating [14C]-thymidine into HDMECs (Human Dermal Microvascular Endothelial Cells) in response to VEGF.

HDMECs (Promocell, passage 5 to 7) are inoculated in 100 µl at 5000 cells per well in Cytostar (Amersham) 96-well plates precoated with attachment factor (AF, Cascad Biologics) at 37° C., 5% $CO_2$, on day 1. On day 2, the complete medium (basal medium supplemented with 5% FCS and a mixture of growth factors) is replaced with minimum medium (basal medium supplemented with 5% FCS) and the cells are incubated for 24 hours. On day 3, the medium is replaced with 200 µl of fresh medium that has or has not been supplemented with 100 ng/ml of VEGF (R&D System) and containing or not containing the compound of the invention and 0.1 µCi [14C]-thymidine. The cells are incubated at 37° C. under 5% $CO_2$ for 4 days. The incorporation of [14C]-thymidine is then quantified by counting the radioactivity. The tests are performed in 3 wells. The final concentration of DMSO in the test is 0.1%. The % of inhibition is calculated as follows: [cpm(+VEGF)−cpm (+VEGF+cpd)/cpm(+VEGF)−cpm (BM5% FCS)]×100.

2) Inhibition of the Production of TF (Tissue Factor) by Endothelial Cells in Response to VEGF The endothelial cells are inoculated at 20 000 cells per well in a 96-well plate precoated with attachment factor. After culturing for 8 hours, the medium is changed and the cells are preincubated with the compounds (0.1% DMSO final) in basal medium for 16 hours. The synthesis of the TF (tissue factor) is induced by adding VEGF (100 ng/ml final). After incubating for 6 hours, the cells are rinsed and lysed. The tissue factor is then detected by means of the Imubind ELISA test.

3) Effect of the Molecules on the VEGF-Independent Growth of HDMECs

The HDMECs (5000 cells per well) are inoculated in complete medium in Cytostar (Amersham) 96-well plates precoated with attachment factor (AF, Cascad Biologics) at 37° C., 5% $CO_2$, on day 1. The whole medium is then removed and the cells are incubated in 200 µl of complete medium containing the molecules of the invention and [14C]-thymidine (0.1 µCi). The incorporation of the [14C]-thymidine is measured using a Wallac counter after incubating for 3 days. The % of inhibition is calculated as follows: [cpm(CM)−cpm (CM+cpd)/cpm(CM)]×100.

Table 5 below gives the results obtained in the above tests for the products indicated as examples in the present patent application.

TABLE 5

| Example No. | $IC_{50}$ (µM) on inhibition of the phosphorylation of PLCγ by KDR | % of inhibition of the phosphorylation of PLCγ by KDR (product tested at a concentration of 10 µM) |
|---|---|---|
| 14 | 1.2 | |
| 15 | 0.8 | |
| 16 | 2 | |
| 20 | 3.4 | |
| 21 | — | 35 |
| 1 | 0.47 | |
| 2 | 0.45 | |
| 3 | — | 91.8 |
| 4 | 0.45 | |
| 5 | — | 91.9 |
| 6 | 0.33 | |
| 7 | 0.72 | |
| 8 | 0.67 | |
| 9 | 0.35 | |
| 10 | 0.34 | |
| 11 | 0.26 | |

TABLE 5-continued

| Example No. | $IC_{50}$ (µM) on inhibition of the phosphorylation of PLCγ by KDR | % of inhibition of the phosphorylation of PLCγ by KDR (product tested at a concentration of 10 µM) |
|---|---|---|
| 12 | 0.16 | |
| 13 | 0.61 | |
| 18 | — | 91.2 |
| 23 | 2 | |

The pharmacological results obtained in the above tests for products indicated in examples in the present application are given in the table 6 below, the degrees of activities of the products being indicated by + signs according to the ranges of activity indicated in the table, i.e.:

TABLE 6

| Example No. | Molecular formula | Molecular weight | Activity<br>+: $IC_{50}$ > 3 µM<br>++: 0.3 µM < $IC_{50}$ < 3 µM<br>+++: $IC_{50}$ < 0.3 µM |
|---|---|---|---|
| 28 | C22H18N6O3S | 446.49 | +++ |
| 29 | C20H21N5O2 | 363.42 | ++ |
| 30 | C22H16BrN5O | 446.31 | +++ |
| 31 | C23H19N5O3S | 445.50 | +++ |
| 32 | C26H19N5O | 417.47 | ++ |
| 33 | C23H16F3N5O | 435.41 | ++ |
| 34 | C20H15N5OS | 373.44 | ++ |
| 35 | C24H22N6O | 410.48 | ++ |
| 36 | C26H30N6O3 | 474.56 | ++ |
| 37 | C22H16N6O3 | 412.41 | +++ |
| 38 | C21H16N6O | 368.40 | ++ |
| 39 | C22H16BrN5O | 446.31 | ++ |
| 40 | C23H19N5O2 | 397.44 | ++ |
| 41 | C23H17N5O3 | 411.42 | ++ |
| 42 | C24H17N5OS | 423.50 | ++ |
| 43 | C21H19N7O | 385.43 | ++ |
| 44 | C23H16F3N5O2 | 451.41 | ++ |
| 45 | C23H19N5O | 381.44 | +++ |
| 46 | C21H17N5OS | 387.46 | ++ |
| 47 | C23H16F3N5O | 435.41 | ++ |
| 48 | C28H21N5O2 | 459.51 | ++ |
| 49 | C23H16F3N5O2 | 451.41 | ++ |
| 50 | C21H23N5O2 | 377.45 | ++ |
| 51 | C20H17N7O | 371.40 | ++ |
| 52 | C25H23N5O | 409.49 | ++ |
| 53 | C22H19N5O2 | 385.43 | ++ |
| 54 | C24H17N5OS | 423.50 | ++ |
| 55 | C26H24N6O3 | 468.52 | ++ |
| 56 | C21H15C1N6O | 402.84 | +++ |
| 57 | C24H17N5OS2 | 455.56 | ++ |
| 58 | C24H19N5O2 | 409.45 | +++ |
| 59 | C23H16N6O | 392.42 | ++ |
| 60 | C24H16C1N5OS | 457.94 | + |
| 61 | C23H16F3N5O | 435.41 | + |
| 62 | C23H19N5OS | 413.50 | +++ |
| 63 | C24H17N5OS | 423.50 | +++ |
| 64 | C21H21N5O2 | 375.43 | ++ |
| 65 | C24H19N5O3 | 425.45 | ++ |
| 66 | C20H15N5O2 | 357.37 | ++ |
| 67 | C22H16N6O3 | 412.41 | ++ |
| 68 | C20H15N5OS | 373.44 | ++ |
| 69 | C24H21N5O | 395.47 | ++ |
| 70 | C24H19N7O | 421.46 | ++ |
| 71 | C23H19N5O | 381.44 | +++ |
| 72 | C22H16C1N5O | 401.86 | +++ |
| 73 | C22H18N6O3S | 446.49 | ++ |
| 74 | C20H21N5O2 | 363.42 | + |
| 75 | C22H16BrN5O | 446.31 | + |
| 76 | C26H19N5O | 417.47 | + |
| 77 | C20H15N5OS | 373.44 | + |
| 78 | C24H22N6O | 410.48 | + |
| 79 | C22H16N6O3 | 412.41 | + |
| 80 | C21H16N6O | 368.40 | ++ |
| 81 | C22H16BrN5O | 446.31 | + |

TABLE 6-continued

| Example No. | Molecular formula | Molecular weight | Activity +: IC$_{50}$ > 3 μM ++: 0.3 μM < IC$_{50}$ < 3 μM +++: IC$_{50}$ < 0.3 μM |
|---|---|---|---|
| 82 | C23H19N5O2 | 397.44 | ++ |
| 83 | C24H17N5OS | 423.50 | + |
| 84 | C28H21N5O2 | 459.51 | + |
| 85 | C23H16F3N5O2 | 451.41 | + |
| 86 | C21H15C1N6O | 402.84 | + |
| 87 | C24H19N5O2 | 409.45 | + |
| 88 | C23H16F3N5O | 435.41 | + |
| 89 | C23H19N5OS | 413.50 | +++ |
| 90 | C20H15N5O2 | 357.37 | ++ |
| 91 | C22H16N6O3 | 412.41 | ++ |
| 92 | C24H21N5O | 395.47 | ++ |
| 93 | C22H16C1N5O | 401.86 | + |
| 94 | C21H15N5O | 353.38 | ++ |
| 95 | C22H17N5O | 367.41 | + |
| 96 | C23H19N5O | 381.44 | + |
| 97 | C20H14N4 | 310.36 | + |
| 98 | C20H12C12N4 | 379.25 | + |
| 99 | C24H16N4 | 360.42 | + |
| 100 | C20H13FN4 | 328.35 | ++ |
| 101 | C20H13C1N4 | 344.80 | + |
| 102 | C21H16N4O | 340.39 | ++ |
| 103 | C20H12C1FN4 | 362.79 | ++ |
| 104 | C20H12C12N4 | 379.25 | + |
| 105 | C26H16N4S2 | 448.57 | + |
| 106 | C26H18N4 | 386.46 | + |
| 107 | C21H16N4 | 324.39 | + |
| 108 | C21H16N4 | 324.39 | ++ |
| 109 | C21H16N4 | 324.39 | ++ |
| 110 | C18H12N4S | 316.39 | ++ |
| 111 | C21H13F3N4 | 378.36 | + |
| 112 | C21H13F3N4 | 378.36 | + |
| 113 | C20H13C1N4 | 344.80 | ++ |
| 114 | C21H16N4O | 340.39 | ++ |
| 115 | C22H18N4 | 338.41 | ++ |
| 116 | C22H18N4 | 338.41 | + |
| 117 | C21H14N4O2 | 354.37 | ++ |
| 118 | C24H22N4 | 366.47 | + |
| 119 | C20H20N4 | 316.41 | ++ |
| 120 | C22H18N4O2 | 370.41 | ++ |
| 121 | C20H14N4O | 326.36 | ++ |
| 122 | C20H14N4O | 326.36 | ++ |
| 123 | C20H12C12N4 | 379.25 | + |
| 124 | C21H13F3N4O | 394.36 | + |
| 125 | C22H16N4O | 352.40 | + |
| 126 | C22H14N4S | 366.45 | + |
| 127 | C23H20N4O3 | 400.44 | ++ |
| 128 | C20H14N4OS | 358.42 | ++ |
| 129 | C22H16N4O | 352.40 | + |
| 130 | C27H20N4O | 416.48 | + |
| 131 | C26H17FN4 | 404.45 | + |
| 132 | C22H14N4S | 366.45 | + |
| 133 | C21H16N4O | 340.39 | ++ |
| 134 | C22H18N4S | 370.48 | + |
| 135 | C20H12F2N4 | 346.34 | ++ |
| 136 | C21H13F3N4O | 394.36 | + |
| 137 | C21H15FN4 | 342.38 | ++ |
| 138 | C22H15FN4 | 354.39 | + |
| 139 | C22H15C1N4 | 370.84 | + |
| 140 | C23H18N4O2 | 382.42 | + |
| 141 | C21H16N4O | 340.39 | ++ |
| 142 | C18H12N4O | 300.32 | ++ |
| 143 | C27H20N4O | 416.48 | + |
| 144 | C23H20N4 | 352.44 | ++ |
| 145 | C21H16N4O2S | 388.45 | + |
| 146 | | | ++ |
| 147 | | | ++ |
| 148 | | | ++ |
| 149 | | | ++ |
| 150 | | | ++ |
| 151 | | | ++ |
| 152 | | | ++ |
| 153 | | | ++ |
| 154 | | | ++ |
| 155 | | | ++ |
| 156 | | | ++ |
| 157 | | | +++ |
| 158 | | | ++ |
| 159 | | | ++ |
| 160 | | | ++ |
| 161 | | | ++ |
| 162 | | | + |
| 163 | | | + |
| 164 | | | + |
| 165 | | | + |
| 166 | | | ++ |
| 167 | | | +++ |
| 168 | | | +++ |
| 169 | | | +++ |
| 170 | | | ++ |
| 171 | | | ++ |
| 172 | | | ++ |
| 173 | | | ++ |
| 174 | | | ++ |
| 175 | | | ++ |
| 176 | | | +++ |
| 177 | | | +++ |
| 178 | | | +++ |
| 179 | | | +++ |
| 180 | | | +++ |
| 181 | | | ++ |
| 182 | | | ++ |
| 183 | | | + |
| 184 | | | ++ |
| 185 | | | ++ |
| 186 | | | + |
| 187 | | | + |
| 188 | | | ++ |
| 189 | | | + |
| 190 | | | + |
| 191 | | | ++ |
| 192 | | | + |
| 193 | | | ++ |
| 194 | | | + |
| 195 | | | + |
| 196 | | | + |
| 197 | | | ++ |
| 198 | | | + |
| 199 | | | + |
| 200 | | | + |
| 201 | | | + |
| 202 | | | + |
| 203 | | | + |
| 204 | | | + |
| 205 | | | + |
| 206 | | | + |
| 207 | | | + |
| 208 | | | + |
| 209 | | | + |
| 210 | | | + |
| 211 | | | + |
| 212 | | | + |
| 213 | | | + |
| 214 | | | ++ |
| 215 | | | + |
| 216 | | | + |
| 217 | | | ++ |
| 218 | | | + |
| 219 | | | + |
| 220 | | | + |
| 221 | | | + |
| 222 | | | + |
| 223 | | | + |
| 224 | | | ++ |
| 225 | | | + |
| 226 | | | + |
| 227 | | | + |
| 228 | | | + |

C. In Vitro Test Procedures for ITK
1. Inhibitory Effects of Compounds on ITK Kinase Inhibitory effects of compounds on ITK kinase were determined using a Fluorescence Polarization assay.

ITK kinase was produced with Baculovirus expression system.

1.1 Assay Technology

The assay measures the autophosphorylation of the ITK kinase. The assay is configured based on Fluorescence Polarization method. The enzyme is incubated with ATP and compound. After incubation, a mixture containing fluorescence labeled phospho-peptide tracer and anti-phospho-tyrosine antibody (CoreHTS tyrosine kinase assay kit, P2837, Panvera) is added in order to generate the specific signal that is reversely proportional to the phosphorylation of the enzyme. The phosphorylated ITK generated from the kinase reaction will compete specifically for the antibody and release the fluorescence labeled tracer. Inhibition of ITK kinase activity will result in increased FP value.

1.2 Assay Conditions

The assay is run in BD black 384-shallow well plate. For enzyme reaction, the final reagent concentration/well: 16.5 nM ITK enzyme, 50 µM ATP, 20 mM Hepes (pH 7.5), 0.15M NaCl, 3 mM MgCl$_2$, 1 mM MnCl$_2$, 0.01% Triton X-100, 1 mM DTT, 5% glycerol and 0.1% γ-globulin. Incubation time: 45 minutes. Temperature: 25° C. Reaction volume: 10 µL. For immuno-reaction, add 10 µL of Stop-Detection mixture containing 10 mM EDTA, 1:2 dilution of antibody and 1:4 dilution of tracer in 1× dilution buffer (Panvera). Incubation time: 90 minutes at 37° C. followed by room temperature 60 minutes.

1.3 Assay Procedure:
1. Add 5.0 µL ATP solution to each well of the black 384-shallow well plate.
2. Add 1.0 µL compounds or 1% DMSO in TBS buffer.
3. Start Reaction by adding 5.0 µL enzyme solution.
4. Incubate at 25° C. for 45 minutes.
5. Add 10 µL of stop-detection solution.
6. Incubate for 90 minutes at 37° C. followed by incubation at room temperature for 60 minutes.
7. Read by LJL Acquest at FP mode using a fluorescence filter set ($E_x$=485 nm, $E_m$=535 nm) with FL dichroic mirror. Integration Time: 200,000 µs. G factor instrument dependent $$\left[G \text{ factor} = \frac{(S_{TracerOnly} - S_{Buffer})}{(S_{TracerOnly} + S_{Buffer})}\right]$$

Inhibition of ITK activity with compounds of the invention was expressed as percentage inhibition of control activity determined in the absence of test compounds.

The IC$_{50}$ values for the compounds are calculated by plotting the dose-response curves. The IC$_{50}$ corresponds to the concentration of compound that induces a 50% inhibition of the kinase activity. Particular compounds of the invention inhibit ITK activity with IC$_{50}$,s in the range 100 micromolar to 1 micromolar.

In Vivo Test Procedures
A. In Vivo Test Procedures for SYK
1. Inhibition of Antigen-Dependent Passive Cutaneous Anaphylaxis.

Compounds of the invention were assessed in the Balb/c mouse passive cutaneous anaphylaxis (PCA) model. The model used in these in vivo studies mimics relevant features of mast cell-driven antigen-dependent activation and functional responses. These studies demonstrated that compounds of the invention inhibit the increase in edema observed in the sensitized mouse ear following antigen exposure.

Protocol for Sensitization and Challenge

Balb/c mice were sensitized in the right ear on day 0 with monoclonal anti-DNP IgE (25 µg) administered intradermally in the ear pinnae. The left ear was injected with PBS to serve as a control. Sixteen to twenty hours after sensitization, mice were antigen challenged with 150 µg DNP-albumin administered i.v.

Protocol for Dosing and Calculation of Results

Test drug was administered orally 15-60 minutes before DNP-albumin antigen challenge. Doses of compound were administered at half log divisions between 3 and 100 mg/kg. A control set of mice was administered vehicle alone, and thereafter treated identically. Ear thickness was measured at t=0, 15, 30 or 60 minutes after DNP-albumin antigen challenge, in both ears, by digital calipers and expressed in units of mm×0.01. Ear thickness at t=0 was recorded to serve as a baseline. The net increase in both the right and left ear was calculated by subtracting the values at t=0 from those at t=15, 30 or 60 minutes. Percent inhibition of ear edema was then calculated as [ear thickness of control-(ear thickness of right ear-ear thickness of left ear)]/ear thickness of control×100 for each time point measured.

Results (i) The compound demonstrated dose-dependent inhibition of ear edema following oral administration of 3-100 mg/kg. Inhibition of ear edema was observed at t=15, 30 and 60 minutes after antigen challenge.

These results indicate that compounds of the invention inhibit mast cell activation and functional responses when given orally in a mouse model of passive cutaneous anaphylaxis.

2. Antigen-Induced Degranulation of Rat Bosophilic Leukemia (RBL) Cells as Measured by [$^3$H]5-hydoxytryptamine (Serotonin) Release 2.1 Cell Culture, Labelling of RBL-2H3 Cells and Performance of Assay.

Method A: For each 24-well culture plate to be set up, 6×10$^6$ cells RBL-2H3 cells were washed and resuspended in 15 mL DMEM-10 containing 25 µl of 1 mCi/mL [$^3$H]-serotonin (0.5 µCi/mL final concentration) and 1 µg/mL (15 mL) of anti-DNP IgE. 0.5 mL of cell suspension was added into each well of a 24-well plate. Cells were incubated for 2 days at 37° C., until they have reached confluence. The medium was gently aspirated from each well and the cells were then washed with assay buffer. A final volume of 200 mL of assay buffer (+ or − the test compounds at the appropriate concentrations) was then added to each of three replicate wells. 100 ng/mL of DNP (antigen) was then added to all wells (excluding negative control wells i.e. to measure spontaneous [$^3$H]-serotonin release in the absence of receptor cross-linking). The cells were incubated for 30 minutes at 37° C. and the reaction was stopped by transferring 100 µl of the supernatant from each sample into a liquid scintillation microtitre plate kept on ice. 200 µl of scintillant-40 was then added to each well of the microtitre plate and the plate was read on a Topcount Liquid Scintillation Counter.

Method B: RBL-2H3 cells are maintained in T75 flasks at 37° C. and 5% CO$_2$, and passaged every 3-4 days. To harvest cells, 5 ml trypsin-EDTA is used to rinse the flask once, then 5 ml trypsin is added to each flask, and incubated at room temperature for 2 minutes. Cells are transferred to a tube with 14 ml medium, spun down at 1100 rpm R$_T$ for 5 minutes and resuspended at 2×10$^5$/ml. Cells are sensitized by adding 1 µl of DNP-specific IgE (1 mg/ml stock solution) to every 10 ml of cells. 200 μl of cells are added to each well of a flat-bottom 96 well plate (40,000 cells/well), and the plate incubated overnight at 37° C. and 5% $CO_2$. The next day compounds are prepared in 100% DMSO at 10 mM. Each compound is then diluted 1:100 in assay buffer and then diluted further in 1% DMSO-assay buffer to obtain final concentrations of 0.03-30 μM. 80 μl assay buffer (Hank's Balanced Salt Solution with $Ca^{++}/Mg^{++}$, 2 mg/ml glucose, 0.03% BSA) is added to each well, followed by 10 μl of diluted compound. Incubation follows for 5 minutes. 10 μl of DNP-HSA (100 ng/ml) is added to each well and incubated at 37° C. (no $CO_2$) for 30 minutes. As one control, 1% DMSO alone (no compound) is added to a set of wells to determine total release. As another control, buffer is added instead of DNP-HSA to another set of wells to determine the assay background. After 30 minutes incubation, the supernatants are transferred to a new 96-well plate. Add 50 μl supernatant to each well of an assay plate. Add 100 μl of substrate solution (5 mM PNAG in 0.4M citric acid, 0.2M $Na_2HPO_4$) to each well and incubate at 37° C. for 90 minutes. Add 50 μl of 0.4 M glycine solution to stop the reaction and the plate is read at 405 nm on a Molecular Devices SpectraMax 250 plate reader.

2.2 Calculation of Results

Method A (i) The mean±s.e.m. of each set of triplicate wells was calculated.
(ii) Maximum response was the positive control wells containing antigen (10 ng/mL) but no compound.
(iii) Minimum response was the control wells containing no antigen and no compound.
(iv) Using these values as the maximum (100%) and minimum (0%) values respectively, the data was normalised to give a percentage of the maximum response.
(v) A dose response curve was plotted and the $IC_{50}$ of the compound was calculated.

Method B (i) The mean±SD of each set of triplicate wells was calculated.
(ii) Maximum response was the positive control wells containing antigen (100 ng/mL) but no compound.
(iii) Minimum response was the control wells containing buffer (no antigen) and no compound.
(iv) Using these values as the maximum (100%) and minimum (0%) values respectively, the experimental data was calculated to yield a percentage of the maximum response (designated % control).
(v) A dose response curve was plotted and the $IC_{50}$ of the compound was calculated using Prism GraphPad software and nonlinear least squares regression analysis.

What is claimed is:

1. A compound according to formula IAb:

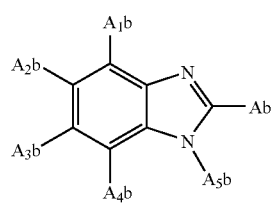

(IAb)

wherein
Ab represents a pyrazolyl radical substituted with a radical chosen from —NH—C(=O)$NY^1bY^2b$, acylamino (NH—CO—$R^6b$), and —NH—C(=O)$R^6b$, with $NY^1bY^2b$ such that either $Y^1b$ and $Y^2b$, which may be identical or different, are chosen from hydrogen and optionally substituted alkyl, cycloalkyl, cycloalkylalkyl, phenyl, naphthyl, phenoxy, phenylalkyl, phenylalkylthio and naphthylalkyl or $Y^1b$ and $Y^2b$ form, together with the nitrogen atom to which they are attached, a piperidyl, hexahydrofuran, morpholinyl or morpholinylalkyl radical;

$A_1b$ and $A_4b$ are hydrogen;

$A_2b$ and $A_3b$, which may be identical or different, are chosen from a hydrogen atom, halogen atoms, hydroxyl, alkyl, alkenyl, alkoxy, nitro, cyano, furyl, thienyl, benzothienyl, naphthyl, thianthrenyl, phenyl and phenoxy radicals and a carboxyl radical which is free, salified, esterified with an alkyl radical or amidated with a radical $NA^6bA^7b$ such that either $A^6b$ and $A^7b$, which may be identical or different, are chosen from hydrogen and alkyl, alkoxyalkyl, phenoxyalkyl, phenyl, phenylalkyl, cycloalkylalkyl, cycloalkyl, furylalkyl, naphthylalkyl, thienylalkyl, piperidylalkyl, pyridylalkyl, benzothienylalkyl, pyrazolylalkyl, dihydrobenzofuranylalkyl, hexahydropyranylalkyl, ethylenedioxyphenylalkyl and benzimidazolylalkyl radicals, all these radicals being optionally substituted, or $A^6b$ and $A^7b$ form, together with the nitrogen atom to which they are attached, a pyrrolidinyl, morpholino or piperazinyl radical, the piperazinyl radical being optionally substituted on the second nitrogen atom with an alkyl radical itself optionally substituted, it being understood that $A_2b$ and $A_3b$ can form, with the benzimidazole radical to which they are attached, an optionally substituted 4,5-ethylenedioxybenzimidazole radical or an optionally substituted 4,5-methylenedioxybenzimidazole radical;

$A_5b$ represents a hydrogen atom;

all the above radicals containing alkyl, alkenyl, phenyl, phenoxy, furyl, thienyl, piperidyl, pyridyl, pyrazolyl and benzimidazolyl being optionally substituted with one or more radicals chosen from halogen atoms and hydroxyl, cyano, alkyl, alkoxy, amino, alkylamino, dialkylamino, phenylamino, phenylalkylamino, acylamino(NH—COR$^6$b), —C(=O)OR$^6$b, acyl —C(=O)R$^6$b, hydroxyalkyl, carboxyalkyl, phenoxyalkyl, S(O)$_n$-alk, S(O)$_n$—$NH_2$, S(O)$_n$—NH(alk), S(O)$_n$—N(alk)$_2$, $CF_3$, $OCF_3$, $NO_2$, CN, phenyl, itself optionally substituted with one or more halogen atoms, thienyl, phenoxy, phenylalkoxy, —C(=O)—$NH_2$, —C(=O)—NH(alk) or C(=O)—N(alk)$_2$ radicals;

with n representing an integer from 0 to 2,
and $R^6b$ representing hydrogen,
all the phenyl radicals of the above radicals furthermore being optionally substituted with a dioxole radical; or
a racemic, enantiomeric or diastereoisomeric isomer form of such compound, or an addition salt with a mineral or an organic acid or with a mineral base of such compound.

2. A compound according to claim 1 wherein when one of $A_2b$ and $A_3b$ represents a carboxyl radical amidated with a radical $NA^6bA^7b$, then either one of $A^6b$ and $A^7b$ represents a hydrogen atom or an alkyl radical and the other of $A^6b$ and $A^7b$ is chosen from the values defined for $A^6b$ and $A^7b$, or $A^6b$ and $A^7b$ form, together with the nitrogen atom to which they are attached, a 5- or 6-membered cyclic radical; or a racemic, enantiomeric or diastereoisomeric isomer form of such compound, or an addition salt with a mineral or an organic acid or with a mineral base of such compound.

3. A compound according to claim 1 wherein $A_2b$ and $A_3b$ optionally form a dioxole radical;

or a racemic, enantiomeric or diastereoisomeric isomer form of such compound, or an addition salt with a mineral or an organic acid or with a mineral base of such compound.

4. A pharmaceutical composition comprising a pharmaceutically effective amount of a compound according to claim 1, together with one or more pharmaceutically acceptable carriers or excipients.

5. A pharmaceutical composition comprising a pharmaceutically effective amount of a compound according to claim 2, together with one or more pharmaceutically acceptable carriers or excipients.

6. A pharmaceutical composition comprising a pharmaceutically effective amount of a compound according to claim 3, together with one or more pharmaceutically acceptable carriers or excipients.

7. A compound of claim 1, wherein said compound is according to formula Ixa:

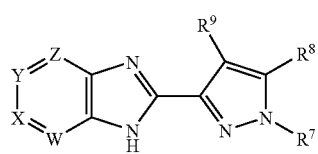

(Ixa)

wherein
W represents CH;
X represents CH or $CR^2$;
Y represents CH or $CR^3$;
Z represents CH;

$R^2$ and $R^3$ each represents, independently, H, carboxy, cyano, halo, haloalkyl, hydroxy, nitro, $R^4$, —C(=O)$R^4$, —C(=O)$NY^1Y^2$, —C(=O)$OR^4$, —$NY^1Y^2$, —N($R^6$)C(=O)$R^4$, —N($R^6$)C(=O)$NY^1Y^2$, —N($R^6$)C(=O)$OR^4$, —N($R^6$)$SO_2R^4$, —N($R^6$)$SO_2NY^1Y^2$, —$OR^4$, —$OCF_2H$, —$OCF_3$, —OC(=O)$R^4$, —OC(=O)$NY^1Y^2$, —S(O)$_nR^4$, —S(O)$_nNY^1Y^2$ or —S(O)$_nOR^4$; or $R^2$ represents H, carboxy, cyano, halo, haloalkyl, hydroxy, nitro, $R^4$, —C(=O)$R^4$, —C(=O)$NY^1Y^2$, —C(=O)$OR^4$, —$NY^1Y^2$, —N($R^6$)C(=O)$R^4$, —N($R^6$)C(=O)$NY^1Y^2$, —N($R^6$)C(=O)$OR^4$, —N($R^6$)$SO_2R^4$, —N($R^6$)$SO_2NY^1Y^2$, —$OR^4$, —$OCF_2H$, —$OCF_3$, —OC(=O)$R^4$, —OC(=O)$NY^1Y^2$, —S(O)$_nR^4$, —S(O)$_nNY^1Y^2$ or —S(O)$_nOR^4$ and $R^3$ represents alkyl, haloalkyl, halogen or $OR^6$; or $R^2$ and $R^3$ form a group selected from —O—$CH_2$—O—, —O—$CH_2$—$CH_2$—O—; —$CH_2$—O—$CH_2$—, —$CH_2$—$CH_2$—$CH_2$—, —$CH_2$—C($CH_3$)$_2$—$CH_2$—, —$CH_2$—O—$CH_2$—$CH_2$—, —$CH_2$—$CH_2$—$CH_2$—$CH_2$—, and —$CH_2$—C($CH_3$)$_2$—$CH_2$—$CH_2$—;

$R^4$ is alkyl, alkenyl, alkynyl, cycloalkyl, heterocycloalkyl, aryl or heteroaryl, each optionally substituted with one or more substituents selected from alkyl, aryl, cycloalkyl, heteroaryl, heterocycloalkyl, halo, hydroxy, hydroxyalkyl, —C(=O)$NY^3Y^4$, —C(=O)$OR^6$, —N($R^6$)C(=O)$NY^1Y^2$, —$NY^1Y^2$, —$OR^5$ or alkyl substituted by —$NY^3Y^4$;

$R^5$ and $R^6$ each is, independently, alkyl, alkenyl, aryl, arylalkyl, cycloalkyl, cycloalkylalkyl, heteroaryl, heteroarylalkyl, heterocycloalkyl or heterocycloalkylalkyl;

n is zero or an integer 1 or 2;

$Y^1$ and $Y^2$ are independently hydrogen, alkenyl, aryl, cycloalkyl, heteroaryl, heterocycloalkyl, heterocycloalkylalkyl or alkyl optionally substituted by one or more groups selected from cyano, aryl, heteroaryl, hydroxy, —C(=O)$OR^6$, —C(=O)$NY^3Y^4$, —$NY^3Y^4$ or —$OR^5$, or the group —$NY^1Y^2$ may form a cyclic amine;

$Y^3$ and $Y^4$ are independently hydrogen, alkenyl, alkyl, aryl, arylalkyl, cycloalkyl, heteroaryl or heteroarylalkyl; or the group —$NY^3Y^4$ may form a cyclic amine;

R7 represents hydrogen;
R8 represents hydrogen; and
R9 represents —NHC(=O)$R^{4'}$, in which said —NHC(=O)$R^{4'}$ is:

—NH—C(=O)—$CH_3$, —NH—C(=O)—$(CH_2)_2CH_3$,

—NH—C(=O)—$CH(CH_3)_2$,

—NH—C(=O)—$C(CH_3)_3$,

—NH—C(=O)—$CH_2CH(CH_3)_2$,

—NH—C(=O)—$CH(CH_3)CH_2CH_3$,

—NH—C(=O)—$CH_2C(CH_3)_3$,

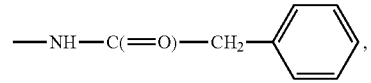

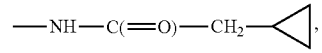

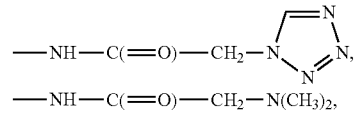

—NH—C(=O)—$CH_2$—N($CH_3$)$_2$,

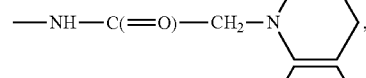

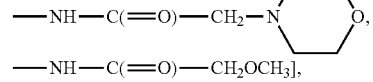

—NH—C(=O)—$CH_2OCH_3$],

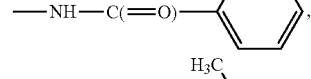

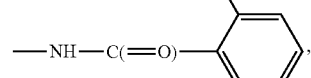

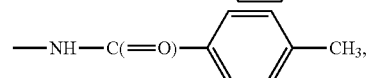

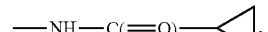

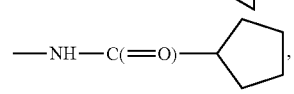

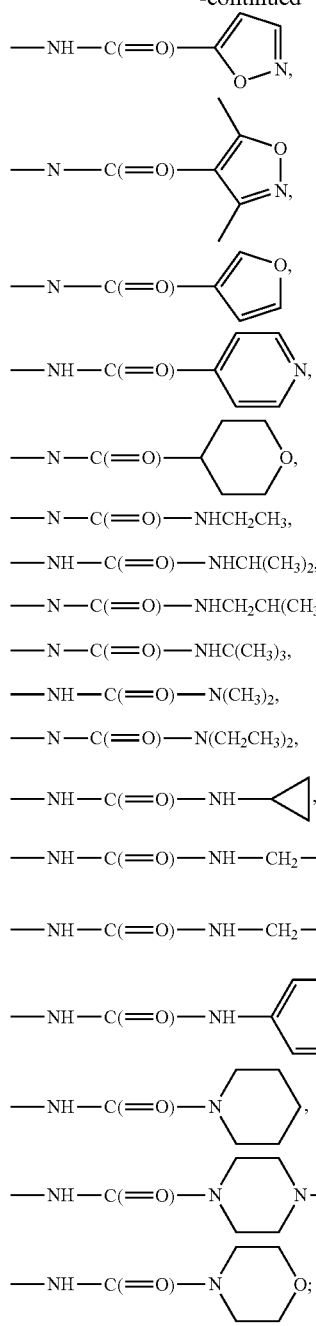
or a racemic, enantiomeric or diastereoisomeric isomer form of such compound, or an addition salt with a mineral or an organic acid or with a mineral base of such compound.
8. A compound of claim 7, wherein:
X represents CH; and
Y represents:
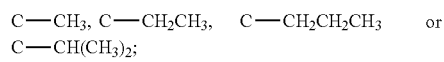
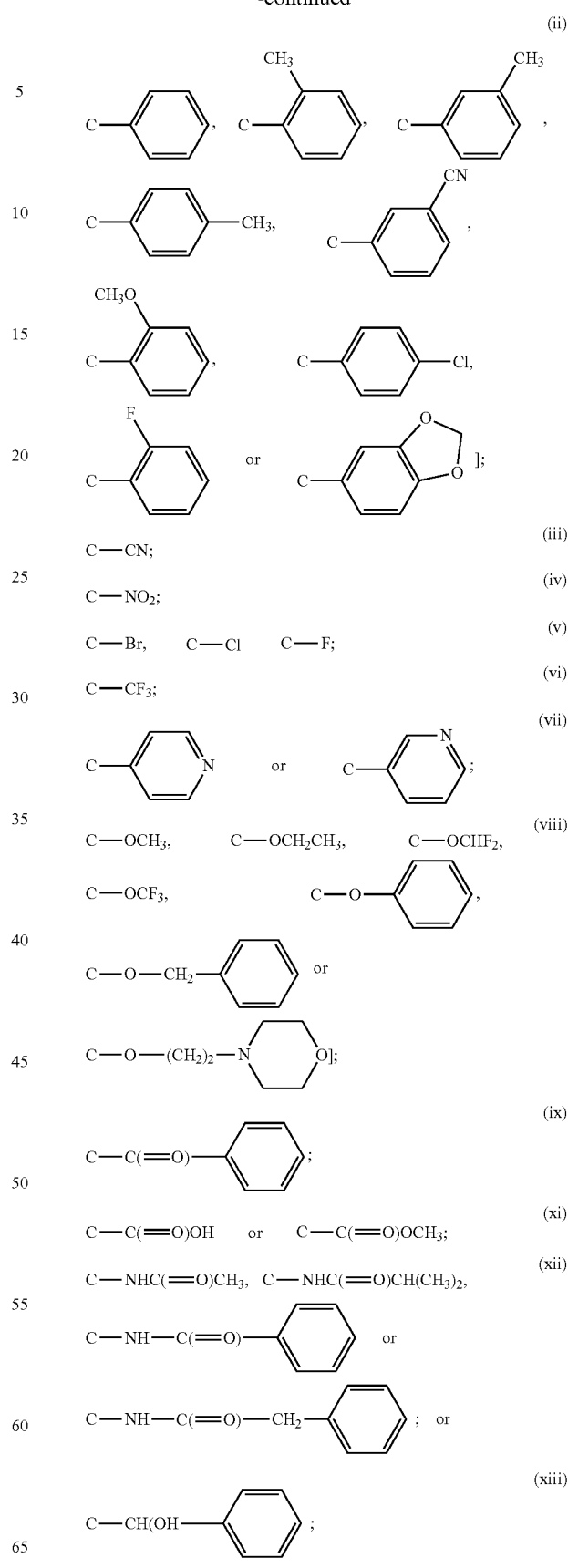

9. A compound of claim 7, wherein:

X represents C—CH₃, C—CH₂CH₃, C—CH(CH₃)₂, C—OCH₃, C—OCH₂CH₃, C—Br or C—Cl; and

Y represents C—CH₃, C—CH₂CH₃, C—OCH₃, C—Br, C—Cl, C—F,

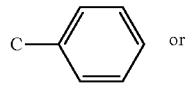 or

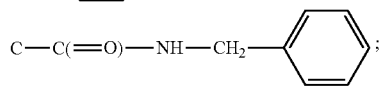;

or a racemic, enantiomeric or diastereoisomeric isomer form of such compound, or an addition salt with a mineral or an organic acid or with a mineral base of such compound.

10. A compound of claim 7, wherein:

X represents CR² and Y represents CR³, where R² and R³ form the group —CH₂—O—CH₂—;

or a racemic, enantiomeric or diastereoisomeric isomer form of such compound, or an addition salt with a mineral or an organic acid or with a mineral base of such compound.

11. A compound of claim 7, wherein:

X represents CR² and Y represents CR³, where R² and R³ form the group —CH₂—CH₂—CH₂—;

or a racemic, enantiomeric or diastereoisomeric isomer form of such compound, or an addition salt with a mineral or an organic acid or with a mineral base of such compound.

12. A compound of claim 7, wherein:

X represents CH; and

Y represents CH;

Or a racemic, enantiomeric or diastereoisomeric isomer form of such compound, or an addition salt with a mineral or an organic acid or with a mineral base of such compound.

13. A compound of claim 7, wherein said compound is:

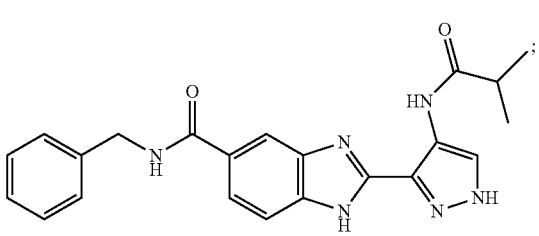

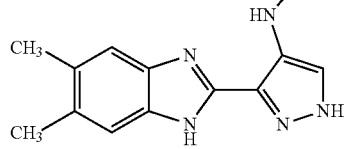

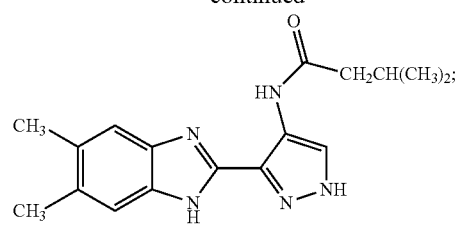

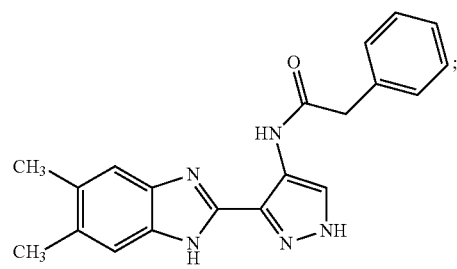

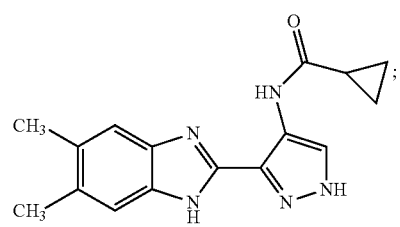

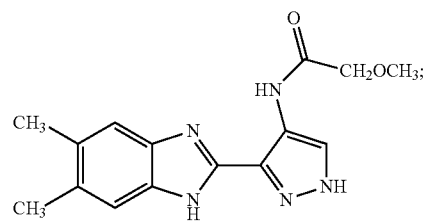

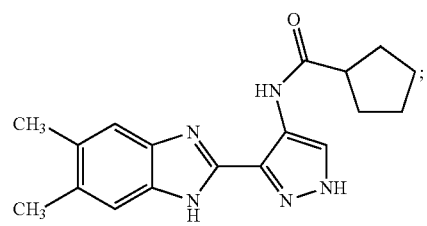

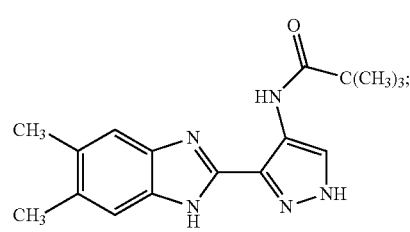

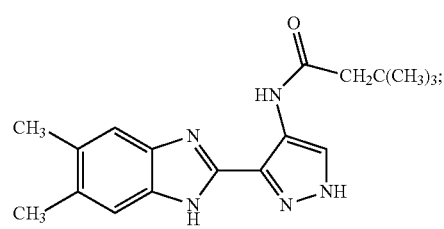

-continued
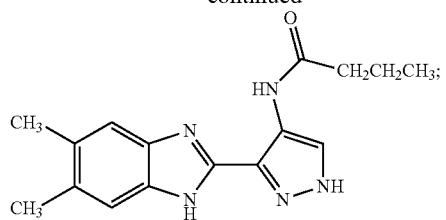
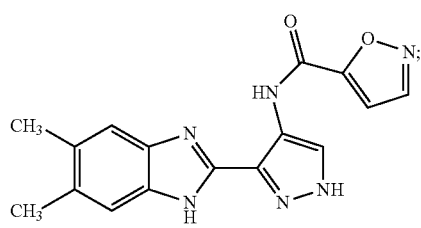
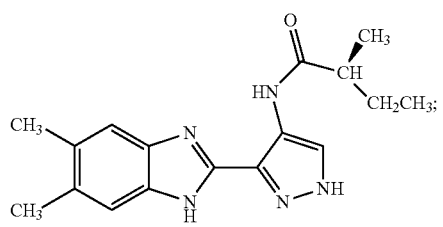
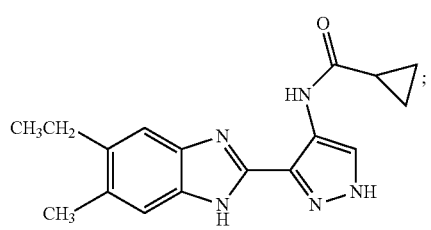
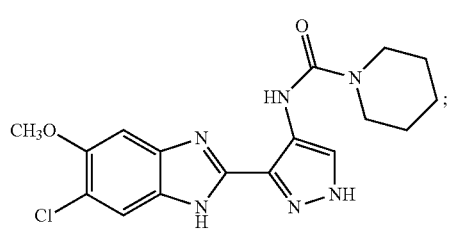
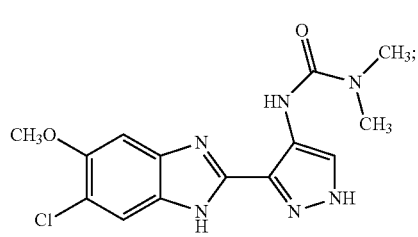
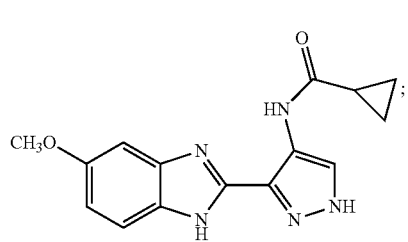
-continued
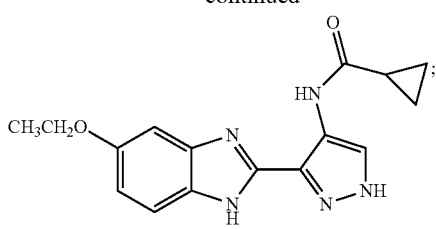
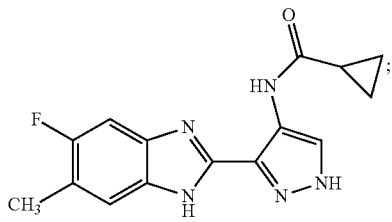
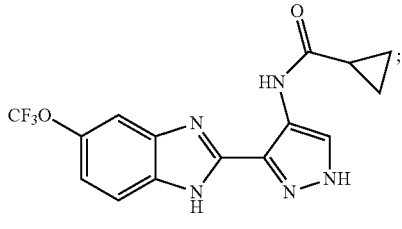
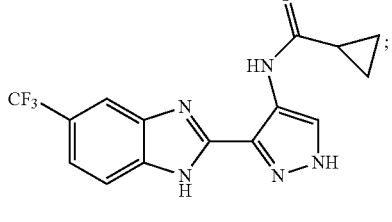
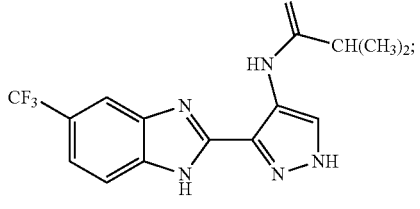
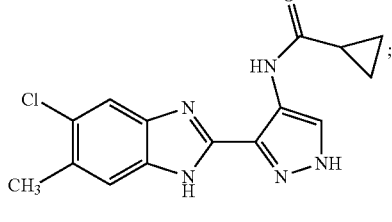
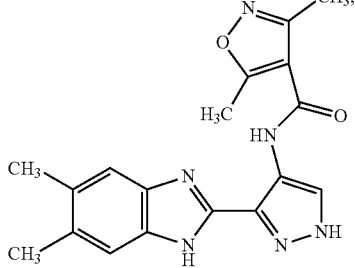

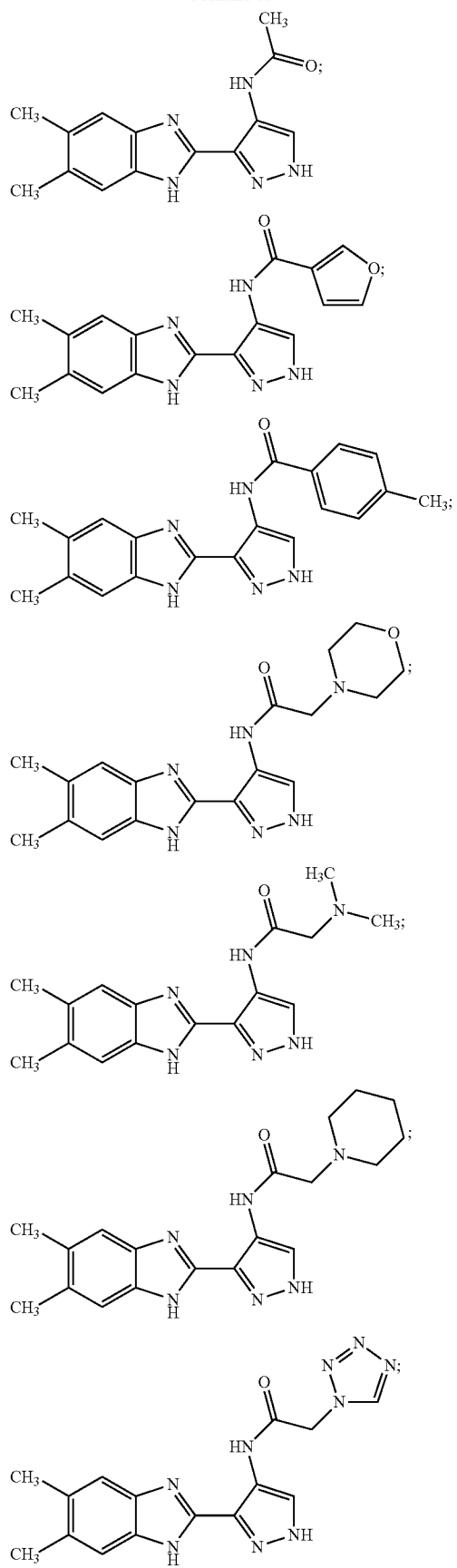
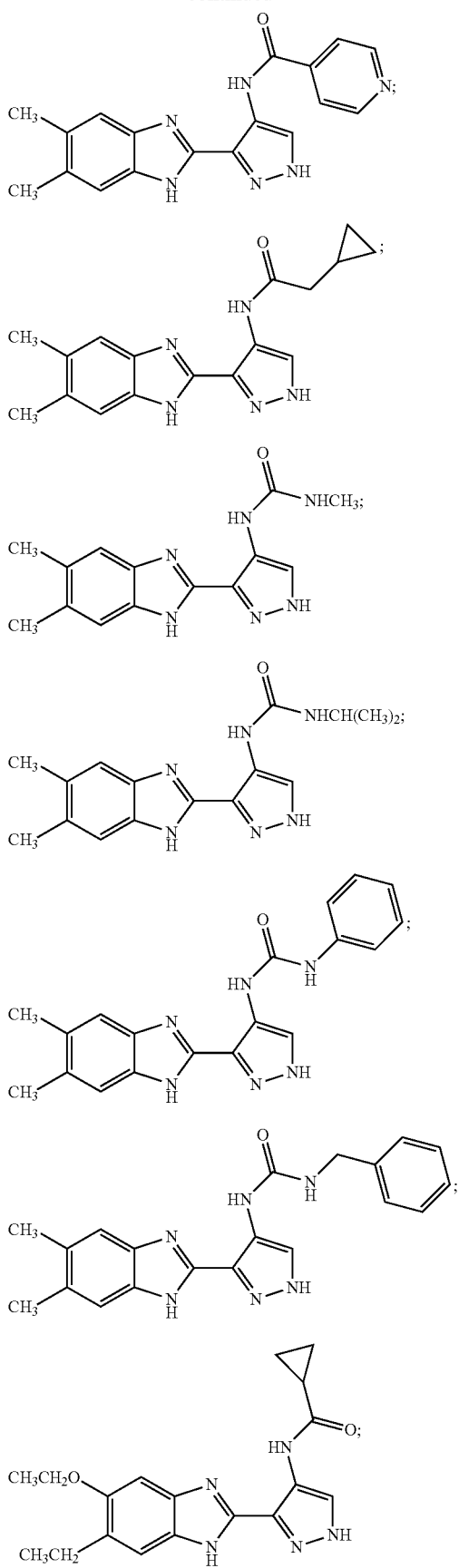

-continued
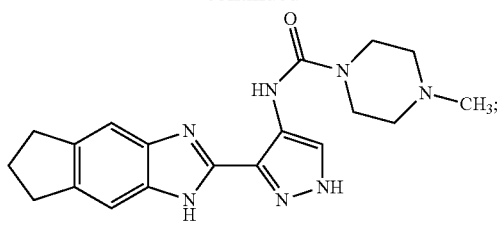
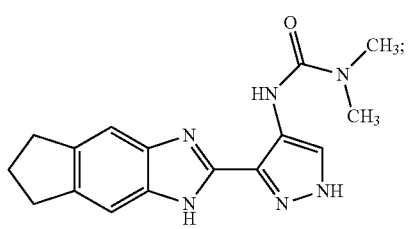
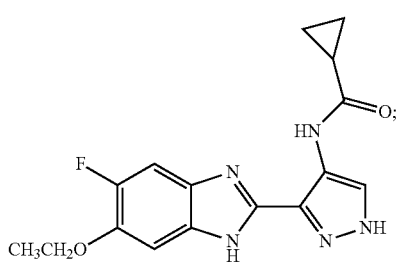
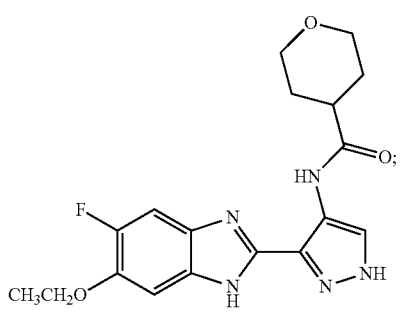
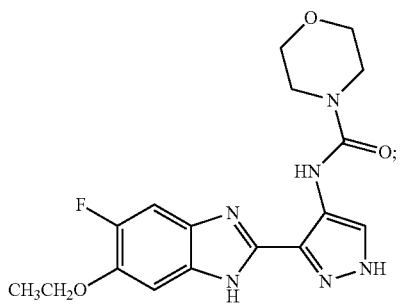
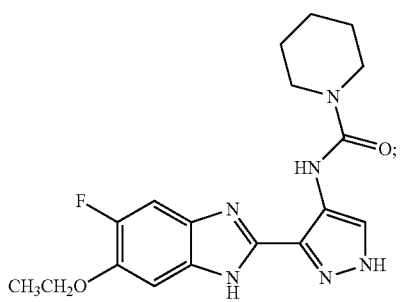
-continued
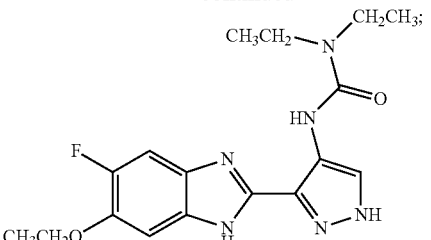
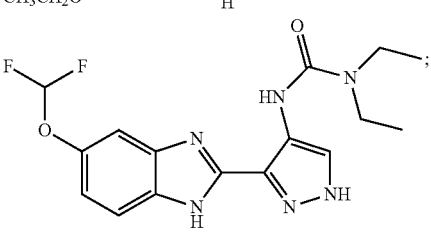
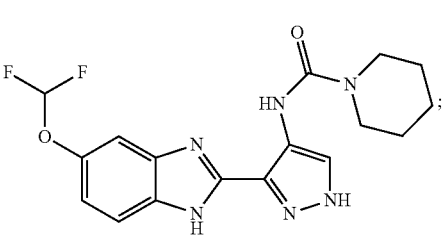
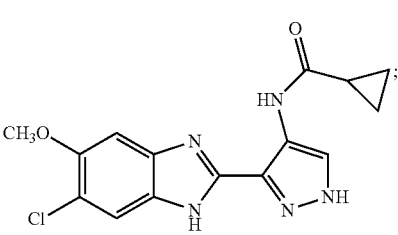
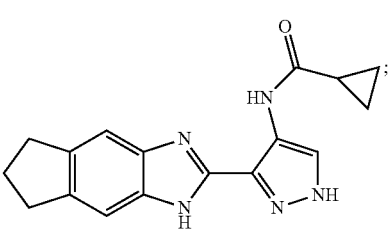
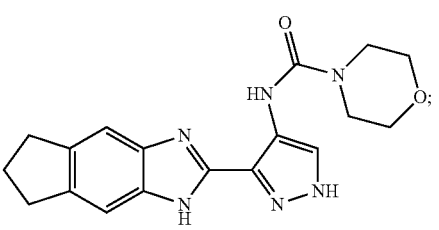
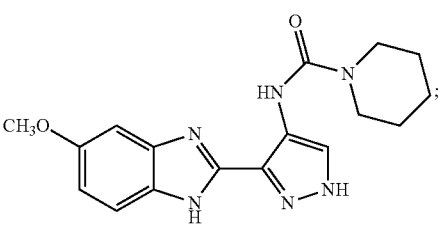

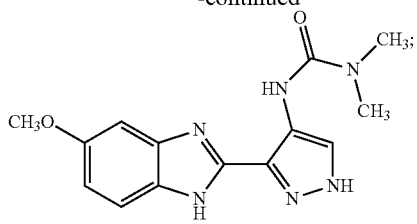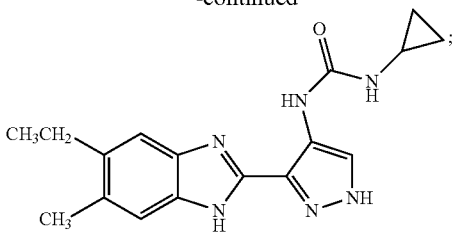

645

-continued

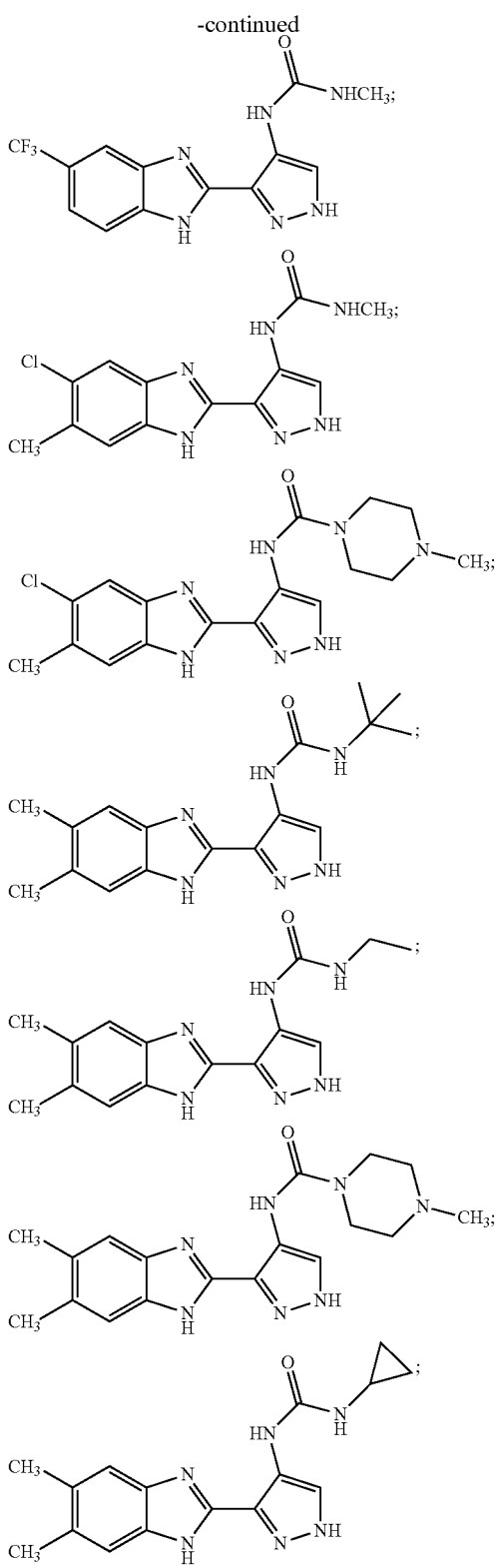

646

-continued

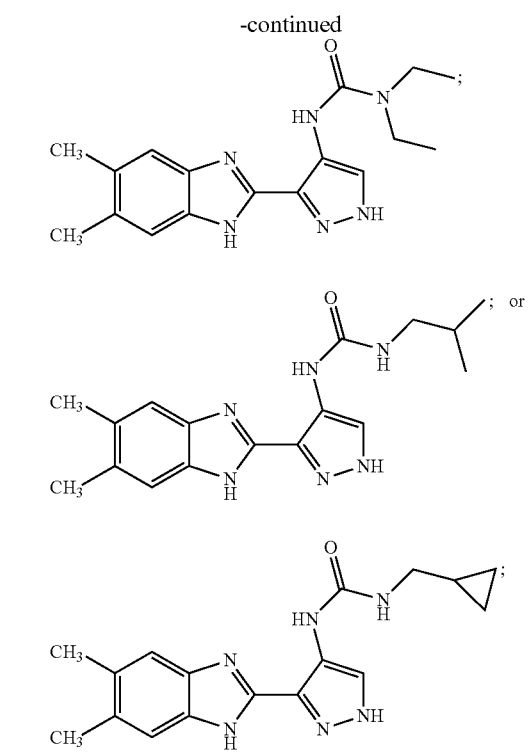

or a racemic, enantiomeric or diastereoisomeric isomer form of such compound, or an addition salt with a mineral or an organic acid or with a mineral base of such compound.

14. A pharmaceutical composition comprising a pharmaceutically effective amount of a compound according to claim 7, together with one or more pharmaceutically acceptable carriers or excipients.

15. A pharmaceutical composition comprising a pharmaceutically effective amount of a compound according to claim 8, together with one or more pharmaceutically acceptable carriers or excipients.

16. A pharmaceutical composition comprising a pharmaceutically effective amount of a compound according to claim 9, together with one or more pharmaceutically acceptable carriers or excipients.

17. A pharmaceutical composition comprising a pharmaceutically effective amount of a compound according to claim 12, together with one or more pharmaceutically acceptable carriers or excipients.

18. A pharmaceutical composition comprising a pharmaceutically effective amount of a compound according to claim 13, together with one or more pharmaceutically acceptable carriers or excipients.

* * * * *